US007262338B2

(12) United States Patent
McCourt et al.

(10) Patent No.: US 7,262,338 B2
(45) Date of Patent: Aug. 28, 2007

(54) STRESS TOLERANCE AND DELAYED SENESCENCE IN PLANTS

(75) Inventors: Peter McCourt, Toronto (CA); Majid Ghassemian, Carlsbad, CA (US); Sean Cutler, Toronto (CA); Dario Bonetta, Palo Alto, CA (US)

(73) Assignee: Performance Plants, Inc., Ontario (CA)

( * ) Notice: Subject to any disclaimer, the term of this patent is extended or adjusted under 35 U.S.C. 154(b) by 259 days.

(21) Appl. No.: 10/229,541

(22) Filed: Aug. 27, 2002

(65) Prior Publication Data

US 2004/0010821 A1 Jan. 15, 2004

Related U.S. Application Data

(63) Continuation-in-part of application No. 10/160,764, filed on May 31, 2002, and a continuation-in-part of application No. 10/210,760, filed on Aug. 1, 2002, and a continuation-in-part of application No. 09/191,687, filed on Nov. 13, 1998, now abandoned.

(60) Provisional application No. 60/337,084, filed on Dec. 4, 2001, provisional application No. 60/348,909, filed on Oct. 22, 2001, provisional application No. 60/309,396, filed on Aug. 1, 2001, provisional application No. 60/294,766, filed on May 31, 2001.

(51) Int. Cl.
*C12N 15/82* (2006.01)
*A01H 5/00* (2006.01)
*A01H 5/10* (2006.01)

(52) U.S. Cl. ...................... 800/289; 800/285; 800/286; 800/287; 800/298

(58) Field of Classification Search ................ 800/295, 800/285, 286, 298; 536/23.1; 435/320.1
See application file for complete search history.

(56) References Cited

U.S. PATENT DOCUMENTS 5,759,829 A * 6/1998 Shewmaker et al. ........ 800/286

FOREIGN PATENT DOCUMENTS

| | | |
|---|---|---|
| WO | WO99/06580 | 2/1999 |
| WO | WO 00/14207 | 3/2000 |
| WO | WO 00/18880 | 4/2000 |
| WO | WO 02/097097 A2 | 12/2002 |

OTHER PUBLICATIONS

Delauney et al. PNAS. USA. 1988. vol. 85, pp. 4300-4304.*
Ziegelhoffer et al. PNAS. USA. 2000. vol. 97(13), pp. 7633-7638.*
Guo et al. PNAS. USA. 2004. vol. 101, pp. 9205-9210.*
Hill et al. Biochem Biophys Res Comm. 1998. vol. 244, pp. 573-577.*
Lazar et al. Mol Cell Biol 1988. vol. 8, pp. 1247-1252.*
Sandler S.J. et al. Inhibition of gene expression in transformed plants by antisense RNA. Plant Molecular Biology, 1988, vol. 11, No. 3, pp. 301-310.*
van der Krol A.R. et al. Inhibition of flower pigmentation by antisense CHS genes: promoter and minimal sequence requirements for the antisense effect. Plant Mol Biol. Apr. 1990;14(4):457-66.*
Waterhouse et al. Virus resistance and gene silencing: killing the messenger. Trends Plant Sci. Nov. 1999;4(11):452-457.*
Mizukami Y. et al. Separation of AG function in floral meristem determinacy from that in reproductive organ identity by expressing antisense AG RNA. Plant Mol Biol. Aug. 1995;28(5):767-84.*
Tamura T et al. Osmotic stress tolerance of transgenic tobacco expressing a gene encoding a membrane-located receptor-like protein from tobacco plants. Plant Physiol. Feb. 2003;131(2):454-62.*
Cutler S. et al. A protein farnesyl transferase involved in abscisic acid signal transduction in Arabidopsis. Science. Aug. 30, 1996;273(5279):1239-41.*
Wang Y. et. al. Molecular tailoring of farnesylation for plant drought tolerance and yield protection. Plant J. Aug. 2005;43(3):413-24.*
Cutler, et al., *Science*, 273:1239-1241 (1996).
Pei, et al., *Science*, 282:287-290 (1998).
Partial International Search Report for PCT/US03/26894, date of mailing: Jan. 20, 2004.
Chen, et al., *Cell*, 66:327 (1991).
Cutler, et al., EMBL Sequence Data Library, XP002090869, Heidelberg, Germany, Accession No. U46574 (1996).
Cutler, et al., EMBL Sequence Data Library, XP002090870, Heidelberg, Germany, Accession No. Q38920 (1996).
Goodman, et al., *Yeast*, 4:271 (1988).
Koomneef, et al., Plant *Physiol*., 61:377-383 (1984).
Merlot, et al., *Plant Physiol*., 114:751-757 (1997).
Qian, et al., *The Plant Cell*, 8:2381-2394 (1996).
Schafer, et al., *Ann. Rev. Genet*., 30:209-237 (1992).
Smith, et al., *Nature*, 334:724-726 (1988).
Yang, et al., *Plant Physiol*., 101:667-674 (1993).

* cited by examiner

*Primary Examiner*—Cynthia Collins
(74) *Attorney, Agent, or Firm*—Mintz, Levin, Cohn, Ferris, Glovsky and Popeo, P.C.; Ivor R. Elrifi; Cynthia A. Kozakiewicz

(57) ABSTRACT

The novel constructs and methods of this invention improve tolerance in plants to environmental stresses and senescence. Nucleic acids encoding a plant farnesyl transferase are described, as are transgenic plants and seeds incorporating these nucleic acids and proteins. Also provided are inhibitors of naturally-occurring farnesyl transferase which, when expressed, will enhance drought tolerance in the plants, improve resistance to senescence and modify growth habit.

4 Claims, 42 Drawing Sheets

| | | | | | |
|---|---|---|---|---|---|
| 10 | 20 | 30 | 40 | 50 | 60 |
| ATGGAGATTC | AGCGAGATAA | GCAATTGGAT | TATCTGATGA | AAGGCTTAAG | GCAGCTTGGT |
| 70 | 80 | 90 | 100 | 110 | 120 |
| CCGCAGTTTT | CTTCCTTAGA | TGCTAAGTAA | GTGACATGAT | GCTTGGCTTC | TTGTTTTCAT |
| 130 | 140 | 150 | 160 | 170 | 180 |
| GAATTTCTTA | GTACATTTTG | TCCAGTGAGA | GAGTAAAGCT | TTGGAGCTTT | GCCAATAGAC |
| 190 | 200 | 210 | 220 | 230 | 240 |
| TTAGAAGTTT | GATTTTGGCT | TTTTGGATTT | TGGAACAGTC | GACCTTGGCT | TTGTTACTGG |
| 250 | 260 | 270 | 280 | 290 | 300 |
| ATTCTTCATT | CAATAGCTTT | GCTTGGGGAG | ACTGTGGATG | ATGAATTAGA | AAGCAATGCC |
| 310 | 320 | 330 | 340 | 350 | 360 |
| ATTGACTTCC | TTGGACGCTG | CCAGGTTAGT | CTCAATTCCT | TTTGCTTGTA | CCCAATCATG |
| 370 | 380 | 390 | 400 | 410 | 420 |
| AAAACTCTTC | ATATTTGCTC | TTGCATTCTT | CTTGATTTTC | TGCTCCTTTA | GTTCACGTTT |
| 430 | 440 | 450 | 460 | 470 | 480 |
| TCTTTTCCCG | TTGCTATTAG | TGTTATCTGT | TATTGTTCTT | TATGTACTTA | GTTTGCTTTC |
| 490 | 500 | 510 | 520 | 530 | 540 |
| TCATGTCGCT | TGTCAGGGCT | CTGAAGGTGG | ATACGGTGGT | GGTCCTGGCC | AAGTAAGTAT |
| 550 | 560 | 570 | 580 | 590 | 600 |
| ATGTCTGTTT | CTTTAAAGTG | TGTGGATCAC | TTTCATTTCA | TGCAATTGGA | GAATAAACAT |
| 610 | 620 | 630 | 640 | 650 | 660 |
| TGAGACCAGA | TTATTTTATT | CTGCCAGATC | TCTTTTAGGT | GTTTTTTTTA | TGCATCATCT |
| 670 | 680 | 690 | 700 | 710 | 720 |
| CATTGTTTGG | TTGTGATGCC | TTTAATTCAA | GCAGCACACG | TAGTTTAAGT | TTAAGTTTTT |
| 730 | 740 | 750 | 760 | 770 | 780 |
| TTCTGTGAAG | ACGTAAAATG | GTGTCTTTAG | TTCAAGCAGC | ATTTAGTTGT | TTAAGTTTGT |
| 790 | 800 | 810 | 820 | 830 | 840 |
| GGTTGTAAAT | TTTCCAAACA | TGGCAGAGAA | AGTTAGGATA | TATAACTTTT | GGTCTGCCTT |
| 850 | 860 | 870 | 880 | 890 | 900 |
| TTTCAGTTTC | CTTTTTTTTT | CTACTAGTAA | TGGAGATATT | TTTTCCCAGC | TTCCACATCT |
| 910 | 920 | 930 | 940 | 950 | 960 |
| TGCAACTACT | TATGCTGCAG | TGAATGCACT | TGTTACTTTA | GGAGGTGACA | AAGCCCTTTC |
| 970 | 980 | 990 | 1000 | 1010 | 1020 |
| TTCAATTAAT | AGGTGGTGCA | TTCTTTTTTC | TTTGTGGTCA | GTTTCTTTTA | TTAAGAGTCT |
| 1030 | 1040 | 1050 | 1060 | 1070 | 1080 |
| AGTGATGTTT | CCTCTAGAAT | ACTTACATGT | GACTCATTCT | TCTTTCAGAG | AAAAAATGTC |
| 1090 | 1100 | 1110 | 1120 | 1130 | 1140 |
| TTGTTTTTTA | AGACGGATGA | AGGATACAAG | TGGAGGTTTC | AGGTTTGATT | CTCTTTCTGC |
| 1150 | 1160 | 1170 | 1180 | 1190 | 1200 |
| TTGAACTTCT | TAAAGGCATC | ATTTTTACTG | ACAGCGCACT | CTTTATGCAT | TCGTATCGCT |
| 1210 | 1220 | 1230 | 1240 | 1250 | 1260 |
| GTTAATGCCA | TACCTTCAGT | CATGTTGTTT | TTTTAATTCT | TGCTTAATTC | TACTTACTCA |
| 1270 | 1280 | 1290 | 1300 | 1310 | 1320 |
| CTGATCGTTA | GGATGCATGA | TATGGGAGAA | ATTGATGTTC | GTGCATGCTA | CACTGCAATT |

FIGURE 1A 1330 1340 1350 1360 1370 1380
TCGGTGAGTT TTACCAACTT CTATTTTCCT TTTCTCTGTT TTTGTGGACA CCAAAACTTT
1390 1400 1410 1420 1430 1440
TTAGGATTAA TGAGATCAAC AAAGTCTGGA CCCATTATGC TATGTTTCTT CCGTTTTCAT
1450 1460 1470 1480 1490 1500
GGCTTAAACA TCACATTCAG ATTACGATAT GATCTTATTA TTTGCACACT TGCGCCCACC
1510 1520 1530 1540 1550 1560
AGGATACTTT GAATAGAGAT TACTCGTTTT GAGACTTACA CGTCTTGCAA ATGCATCCTA
1570 1580 1590 1600 1610 1620
TGGCTGGTTT TCTCCCTGAT ATGTTTGACT TCTCTCTTGT GACACAGGTT GCAAGCATCC
1630 1640 1650 1660 1670 1680
TAAATATTAT GGATGATGAA CTCACCCAGG GCCTAGGAGA TTACATCTTG AGGTAGCTTT
1690 1700 1710 1720 1730 1740
TCTTATTACT TTTATCTCGC ATTATATATA TATAGCTGAA CTACTGTTAT ACAGTTGTAA
1750 1760 1770 1780 1790 1800
ATTCAGGAAT TCATTAATTT CCCTGGGAAA GCTCTTTTAA CTCGATTTAT ATTGAGCAGT
1810 1820 1830 1840 1850 1860
TGCCAAACTT ATGAAGGTGG CATTGGAGGG GAACCTGGCT CCGAAGCTCA CGGTGGGTAT
1870 1880 1890 1900 1910 1920
GGTCTCCAAC TAACTTCCAT TATGTTGAGG CTTAGATAAA AATTGTGCTT TGCTTCCCTC
1930 1940 1950 1960 1970 1980
TTCCTTGATG ACATGGTTAT TGATGGTTAA GTATAATTAA TTTTCTGAAA TAGGATTTGT
1990 2000 2010 2020 2030 2040
CACCTGCAGC TTGCATGCCT GCCGCTTTGC TTATTACCAA GTTGTTTTTT GTTTAGGTAT
2050 2060 2070 2080 2090 2100
ACCTACTGTG GTTTGGCTGC TATGATTTTA ATCAATGAGG TCGACCCGTT TGAATTTGGA
2110 2120 2130 2140 2150 2160
TTCATTAATG GTAACATACA ATGCTGTTTG GAGATGATTA ATAATTTTCC CTGAGAGATA
2170 2180 2190 2200 2210 2220
TTTTCCTTAC CAAATAATTT CCTTATGATT CTAGAATTGG GCTGTACATC GACAAGGAGT
2230 2240 2250 2260 2270 2280
AGAAATGGGA TTTCAAGGTA GGACGAACAA ATTGGTCGAT GGTTGCTACA CATTTTGGCA
2290 2300 2310 2320 2330 2340
GGTTAACTTT CTATCTTTCA GGATTATTAT TGGCCCTACT TCTAAATTCT TCACCGTTGT
2350 2360 2370 2380 2390 2400
TGTCTTTTCT TATTTCCTTT GGGTATATGT TAAACAGGCA GCCCCTTGTG TTCTACTACA
2410 2420 2430 2440 2450 2460
AAGATTATAT TCAACCAATG ATCATGACGT TCATGGATCA TCACATATAT CAGAAGGGAC
2470 2480 2490 2500 2510 2520
AAATGAAGAA CATCATGCTC ATGATGAAGA TGACCTTGAA GACAGTGATG ATGATGATGA
2530 2540 2550 2560 2570 2580
TTCTGATGAG GACAACGATG AAGGTATTCA ATCAAATTTC TCAACCATCA AGTCCATCTG
2590 2600 2610 2620 2630 2640
ATAATTCAAA ACACAACGAA ATTTTAGTTA GCTTATATTT GCAGATTCAG TGAATGGTCA

FIGURE 1B

| | | | | | |
|---|---|---|---|---|---|
| 2650 | 2660 | 2670 | 2680 | 2690 | 2700 |
| CAGAATCCAT | CATACATCCA | CCTACATTAA | CAGGAGAATG | CAACTGGTTT | TTGATAGCCT |
| 2710 | 2720 | 2730 | 2740 | 2750 | 2760 |
| CGG?TTGCAG | AGATATGTAC | TCTTGTGCTC | TAAGGTCAGT | CCAGAACAAA | ACATCCAGTC |
| 2770 | 2780 | 2790 | 2800 | 2810 | 2820 |
| AAGTTAACAC | TTAACATTTG | TATAACACAA | GCACACACAC | TTGTATGCGC | AGATCCCTGA |
| 2830 | 2840 | 2850 | 2860 | 2870 | 2880 |
| CGGTGGATTC | AGAGACAAGC | CGAGGAAACC | CCGTGACTTC | TACCACACAT | GTTACTGCCT |
| 2890 | 2900 | 2910 | 2920 | 2930 | 2940 |
| GAGCGGCTTG | TCTGTGGCTC | AGCACGCTTG | GTTAAAAGAC | GAGGACACTC | CTCCTTTGAC |
| 2950 | 2960 | 2970 | 2980 | 2990 | 3000 |
| TCGCGACATT | ATGGGTGGCT | ACTCGAATCT | CCTTGAACCT | GTTCAACTTC | TTCACAACAT |
| 3010 | 3020 | 3030 | 3040 | 3050 | 3060 |
| TGTCATGGAT | CAGTATAATG | AAGCTATCGA | GTTCTTCTTT | AAAGCAGCAT | GACCCGTTGT |
| 3070 | 3080 | 3090 | 3100 | 3110 | 3120 |
| TGCTAATGTA | TGGGAAACCC | CAAACATAAG | AGTTTCCGTA | GTGTTGTAAC | TTGTAAGATT |
| 3130 | 3140 | 3150 | 3160 | 3170 | 3180 |
| TCAAAAGAAG | TTTCACTAAT | TTAACCTTAA | AACCTGTTAC | TTTTTATTAC | GTATA..... |

FIGURE 1C

MEIQRDKQLDYLMKGLRQLGPQFSSLDANRPWLCYWILHSIAL
LGETVDDELESNAIDFLGRCQGSEGGYGGGPGQLPHLA
TTYAAVNALVTLGGDKALSSINREKMSCFLRRMKDTSGGFR
MHDMGEIDVRACYTAISVASILNIMDDELTQGLGDYILS
CQTYEGGIGGEPGSEAHGGYTYCGLAAMILINEVDRLNLDSL
MNWAVHRQGVEMGFQGRTNKLVDGCYTFWQAAPCVLLQ
RLYSTNDHDVHGSSHISEGTNEEHHAHDEDDLEDSDDDDDSDE
DNDEDSVNGHRIHHTSTYINRRMQLVFDSLGLQRYVL
LCSEIPDGGFRDKPRKPRDFYHACYCLSGLSVAQHAWLKDED
TPPLTRDIMGGYSNLLEPVQLLHNIVMDQYNEAIEFFF
KAA

FIGURE 2

```
        10         20         30         40         50         60
CTCACTCATT AGCACCCCAG CTTTACACTT TATGCTTCCG CTCGTATGTT GTGTGGAATT
        70         80         90        100        110        120
GTGAGCGATA ACAATTTC?A CACAGGAAAC AGCTATGACA TGATTACGAA TTCAAAAAAA
       130        140        150        160        170        180
TAGAGATTGG CAATATTTTA GTGTGTGAAT AATATTCATC CCTAAAAAGA AGTCATCTTT
       190        200        210        220        230        240
CGACTTTGTG GCAACAGTTC TGTTATTAAA ATGTGTGAGC GTGACATATT TTGAAGAGGT
       250        260        270        280        290        300
ACCTCGACAA AATCGGAAGG TGTCTCATTT TCTTCTATCG GAAGGCTTTC TCGTTGAAGG
       310        320        330        340        350        360
TAGTCGTTGT AGCTGAAAAA TTAAGAAAAC CTAGTGAGCT CTTCATGTAT TCAAAAATTC
       370        380        390        400        410        420
AACCAGTGTA ATCAAACTCA AGAGGTAAAT AGTTAAAATC CCATACCAAA CCGTGTAATC
       430        440        450        460        470        480
TATGCAATAC CTAATTAACA AAGTTAAAAG CGTTAGTCTA GCAGTAATAT TGTATCAAAA
       490        500        510        520        530        540
GCTCTAACAG TAATTAATAA CCAGTGTCAC CAGAAACAAA TGTCAATAAC ATGGAAAATT
       550        560        570        580        590        600
GAATTTAGTT GAGTCCTGGA GGTCGTGGAC GTCGTGGAGG CTGTGGACGT CGTGAATACG
       610        620        630        640        650        660
CATAAAGAAA AATCTTATAA TCGTGCAAAT ATTCACCGTT CTTCTTATAC ATCACCTACG
       670        680        690        700        710        720
GTAATAAAAG AGTTTTATTT CAGCAATCGT ACATTCAAAT TGAAACTTAG ATACACTATA
       730        740        750        760        770        780
TATTTTTCAT CATAACTAAC TATAAACTAG TCTAAACCTT TTTTGCTTCG TTAGCAGAAG
       790        800        810        820        830        840
CAAAGTCAAC AGGCCATAGC ACCTATGGAT ACGCTTGGCG GTTACAAAAA GTCGAACACG
       850        860        870        880        890        900
AACAACTTCT CCAGCATCTT TGAAGAAATT GATGCTGTAA CAAACAGTGT AAGGTAAAAA
       910        920        930        940        950        960
TATCAGTCAT GCTCAGAGAA GGAAAGTGGA GATTGAAGAT GGTGCTACTT ACATATCTGA
       970        980        990       1000       1010       1020
TATTTTAGTT TGGGGAGGGA TATGGCCATT AAAGA?CGTC TTTTTTGTCA CCTGGATTTA
      1030       1040       1050       1060       1070       1080
ACAGCCAAGT GTGTTAGCAC AAGATTCTTA ATTGAACAGA AATTTGTACA AAATATCTAG
      1090       1100       1110       1120       1130       1140
CAAATCCGTT GGTTGTTTCC TCCTGTTACA TATGATACAA GATCAAAGAG TAGCCATTAG
      1150       1160       1170       1180       1190       1200
AAGAAGACAG TG?AAAGAAG ATTGTTTTGT CAAAGAAGAA GAGTAATACG AGGCCATCTT
      1210       1220       1230       1240       1250       1260
AGGGTTACCT TATTCTACTT ATGTCTCTTG AGAATGGAAT TGGTCACCAA ATCATCTTCT
      1270       1280       1290       1300       1310       1320
TCAGGGTTAC GCTTACCTAA AAGAAGAGCA ACAA??AAAA AACTCTTGAG ACAAGTTTAA
```

FIGURE 3A

```
      1330       1340       1350       1360       1370       1380
CACATTAGAT AAAAGAGAGA GAGAGAGAGG CAACCAAAAA CAAACCCAAT AAATTGCTAC
      1390       1400       1410       1420       1430       1440
TAGAAGTGGC CATGGAGAAG ATGAAACGAG GTTTATGTAT TTTTCCGTTA AGAGCAAGCA
      1450       1460       1470       1480       1490       1500
ATAATATAGC CCTAAAGAAA TATAGACCTA GCCTAGGAAG AAGTTTCTAA GACCATCCTT
      1510       1520       1530       1540       1550       1560
ATCAATGAAC TCTTACATAA AGTTCTAAAC AATTTTGATA TACAAAATAA TGTTTAAACA
      1570       1580       1590       1600       1610       1620
TTAGAATGGC TCTTACAAAA AAAGAGAATA AAGAAAAAAA AAACTTAGCT AAGAGCCATT
      1630       1640       1650       1660       1670       1680
TTTCATTTCT TAAGCACACT TTTTTATTTT TTTATTCTTA TTTTATTTAA TATAATATTT
      1690       1700       1710       1720       1730       1740
TGATAGTTCT TATGATATTG TTAACAACCT ATTGATAAGG ATGCTCTAAC TAATCTTATA
      1750       1760       1770       1780       1790       1800
AATAAAACAA TGAATCTGGT TTGGTCTGGG CGTAACAG?A ATTATACTCT TTTTTTTTTT
      1810       1820       1830       1840       1850       1860
TGTCAAGAGG AAATTATACT AAGAAGCAAC AGATTAAACA TTAAAGCGTA TAGTAAAATT
      1870       1880       1890       1900       1910       1920
AATTGTTTGA GAATCTTAAA CCAAACCGAA CCGGTATTAA ACCGGAACCA AATTGGCAAT
      1930       1940       1950       1960       1970       1980
GAAATTTAGA TGCCAGTAGT AACCCGCTTG ATTCGTTTGA AGTGTGTAGG GCTCAGACTT
      1990       2000       2010       2020       2030       2040
GACCGGAGTG GACTCAATCG GCGAATCTGT CACGGAGGAC ACGGGGAATC AACGCGGCGG
      2050       2060       2070       2080       2090       2100
AGAGTGATGG AAGAGTTTTC AAGCCTAACC GTGAGTCAGC GCGAGCAATT TCTGGTGGAG
      2110       21200      2130       2140       2150       2160
AACGATGTGT TCGGGATCTA TAATTACTTC GACGCCAGCG ACGTTTCTAC TCAAAAATAC
      2170       2180       2190       2200       2210       2220
ATGTAAGCTG ACGGATTGAT TTTCTAGTTT TCTTCATGAT CTGATGAATT TTAGTAGCGT
      2230       2240       2250       2260       2270       2280
CGTGAAAGAA TTATTTTCGT CGATAGATGA ATCTTACTGA TATGGAAGTT GTTCTATCCT
      2290       2300       2310       2320       2330       2340
AGGATG ... .......... .......... .......... .......... ..........
   └-First Codon
```

FIGURE 3B

```
                                                                   29
Arab.    MEIQRDKQLD YLMKGLRQLG PQFSSLDAN- ---------- ----------
Pea      ..ASTAAETP TPTVSQ.DQW IVE.QVFHIY QLFANIPPNA QSII------
Yeast    .RQRVGRSIA RAKFINTA.L GRKRPVMERV VDIAHVDSSK AIQPLMKELE
Rat      .ASSSSFTYY CPPSSSPVWS EPLY..RPEH ARERLQDDSV ETVTSIEQAK

Arab.    ---------- ---------- ---------- ---------- ----------
Pea      ---------- ---------- ---------- ---------- ----------
Yeast    TDTTEARYKV LQSVLEIYDD EKNIEPALTK EFHKMYLDVA FEISLPPQMT
Rat      VEEKIQEVFS SYKFNHLVPR LVLQREKHFH YLKRGLRQ-- ----LTDAYE
                                                                   73
Arab.    -----RPWLC YWILHSIALL G-ETVDDELE SNAIDFLGRC QGSEGGYGGG
Pea      -----..... ...I...... .-.SI..D.. D.TV...N.. .DPN...A..
Yeast    ALDASQ..ML ...AN.LKVM DRDWLS.DTK RKIV.K.FTI SP.G.PF...
Rat      CLDAS..... ......LE.. D-.PIPQIVA TDVCQ..EL. .SPD..F...
                                                                  122
Arab.    PGQLPHLATT YAAVNALVTL GGDKALSS-I NREKMSCFLR RMKDTSGG.R
Pea      ...M...... .....T.I.. ..E.S.A.-. ..N.LYG.M. ...QPN....
Yeast    ....S...S. ...I...SLC DNIDGCWDR. D.KGIYQW.I SL.EPN...K
Rat      ...Y....P. .......CII .TEE.YNV-. ....LLQY.Y SL.QPD.S.L
                                                                  171
Arab.    -MHDMGEIDV RACYTAISVA SILNIMDDEL TQGLGDYILS CQTYEGGIGG
Pea      -...E..... .......... .V...L.... IKNV..F... .......LA.
Yeast    TCLEV..V.T .GI.C.L.I. TL...LTE.. .E.VLN.LKN ..N....F.S
Rat      -..VG..V.. .SA.C.A... .LT..ITPD. FE.TAEW.AR ..NW......
                                                                  218
Arab.    EP-GSEAHGG YTYCGL.AM- ILINEVDRLN LDSLMNWAVH RQGV-EMGFQ
Pea      ..-....... ..F......- ...G..N..D .PR.LD.V.F ...K-.C...
Yeast    C.HVD..... ..F.AT.SLA ..RSM-.QI. VEK.LE.SSA ..LQE.R..C
Rat      V.-.M..... ..F.....LV ..KK.-RS.. .K..LQ.VTS ..MRF.G...
                                                                  267
Arab.    GRTNKLVDGC YTFWQAAPCV LLQR-LYSTN DHDVHGSSHI SEGTNEEHHA
Pea      .......... .S...GGAVA ....-.H.II .EQMAEA.QF VTVSDAPEEK
Yeast    ..S....... .S..VGGSAA I.EAFG.GQC ---------- ----------
Rat      ..C....... .S....GLLP ..H.A.HAQG .PALSM.--- ----------
                                                                  316
Arab.    HDEDDLEDSD DDDDSDEDND EDSVNGHRIH HTSTYINRRM -QLVFDSLGL
Pea      ECL.GTSSHA TSHIRH.GMN .SCSSDVKNI GYNFISEW.Q SEPL.H.IA.
Yeast    ---------- ---------- ---------- ---------- ----.NKHA.
Rat      ---------- ---------- ---------- ---------- -HWM.HQQA.
                                                                  364
Arab.    QRYVLLCSKI -PDGGFRDKP RKPRDFYHTC YCLSGLSVAQ HAWLKDE-DT
Pea      .Q.I....QE -Q...L.... G.R..H..S. .......LC. YS.S.RP-.S
Yeast    RD.I.Y.CQE KEQP.L.... GAHS.....N ...L..A..E SSYSCTPN.S
Rat      .E.I.M.CQC -.A..LL... G.S....... .......I.. -----HFGSG
                                                                  404
Arab.    PPLTRDIMGG YSNLLEPVQL LHNIVMDQYN EAIEFFFKAA ----------
Pea      ...PKVV..P .......IHP .F.V.L.R.R ..H...SQL- ----------
Yeast    .HNIKCTPDR LIGSSKLTDV NPVYGLPIE. VRKIIHYFKS NLSSPS----
Rat      AM.HDVV..V PE.V.Q.THP VY..GP.KVI Q.TTH.LQKP VPGFEECEDA

Arab.    ----------
Pea      ----------
Yeast    ----------
Rat      VTSDPATD--
```

FIGURE 4

Wild-type Columbia eral-2 mutant

Day 0

Wild-type Columbia eral-2 mutant

Day 3

Wild-type Columbia eral-2 mutant

Day 6

Wild-type Columbia eral-2 mutant

Day 9

Wild-type Columbia eral-2 mutant

Day 12

Wild-type eral-2
Day After Bolting 0 4 8 0 4 8
FIG.9A CAB
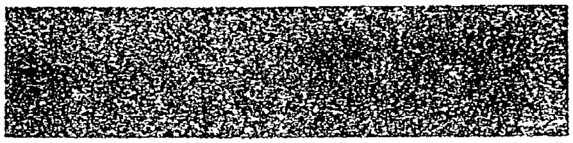
Wild-type eral-2
Day After Bolting 0 4 8 0 4 8
FIG.9B SAG12
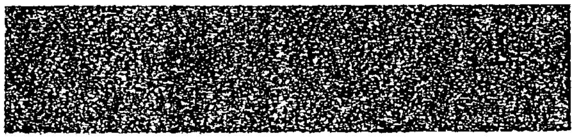
Wild-type eral-2
Day After Bolting 0 4 8 0 4 8
FIG.9C SAG 13
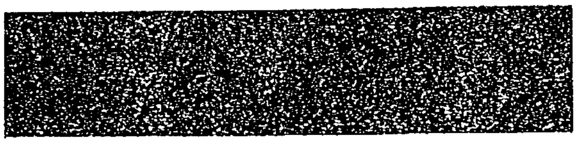

Day 8 of water stress

| DNA | Brassica napus | Arabidopsis thaliana | PPI Glycine max | Zea mays | Rice | Soy 1 | Soy 2 | Triticum | Tomato | Pea |
|---|---|---|---|---|---|---|---|---|---|---|
| Brassica napus | X | | | | | | | | | |
| Arabidopsis thaliana | 89 | X | | | | | | | | |
| PPI Glycine max | 61 | 55 | X | | | | | | | |
| Zea mays | 57 | 45 | 52 | X | | | | | | |
| Rice | 55 | 46 | 54 | 63 | X | | | | | |
| Soy 1 | 61 | 50 | 98 | 43 | 47 | X | | | | |
| Soy 2 | 61 | 50 | 99 | 41 | 46 | 99 | X | | | |
| Triticum | 58 | 45 | 52 | 56 | 66 | 43 | 41 | X | | |
| Tomato | 65 | 53 | 63 | 44 | 51 | 52 | 49 | 41 | X | |
| Pea | 66 | 55 | 78 | 46 | 50 | 70 | 69 | 44 | 49 | X |
| | | | | | | | | | | |
| | | | | | | | | | | |
| **PROTEIN** | Brassica napus | Arabidopsis thaliana | PPI Glycine max | Pea | Tomato | Rice | Zea mays | Soy 1 | Soy 2 | Triticum |
| Brassica napus | X | | | | | | | | | |
| Arabidopsis thaliana | 89 | X | | | | | | | | |
| PPI Glycine max | 65 | 63 | X | | | | | | | |
| Pea | 61 | 61 | 77 | X | | | | | | |
| Tomato | 60 | 59 | 57 | 58 | X | | | | | |
| Rice | 64 | 63 | 56 | 58 | 58 | X | | | | |
| Zea mays | 61 | 56 | 58 | 57 | 56 | 75 | X | | | |
| Soy 1 | 66 | 64 | 98 | 77 | 58 | 57 | 58 | X | | |
| Soy 2 | 66 | 64 | 98 | 78 | 58 | 57 | 58 | 99 | X | |
| Triticum | 61 | 60 | 57 | 59 | 60 | 80 | 73 | 58 | 58 | X |

Figure 17

| DNA | Brassica napus | Arabidopsis thaliana | Wiggum | PPI Glycine max | Glycine max | PPI Zea maize | Zea maize | Pea | Tomato | Tobacco |
|---|---|---|---|---|---|---|---|---|---|---|
| Brassica napus | X | | | | | | | | | |
| Arabidopsis thaliana | 88 | X | | | | | | | | |
| Wiggum | 88 | 99 | X | | | | | | | |
| PPI Glycine max | 60 | 64 | 65 | X | | | | | | |
| Glycine max | 60 | 64 | 65 | 99 | X | | | | | |
| PPI Zea maize | 38 | 54 | 59 | 63 | 63 | X | | | | |
| Zea maize | 54 | 54 | 59 | 62 | 62 | 99 | X | | | |
| Pea | 65 | 57 | 45 | 78 | 77 | 56 | 56 | X | | |
| Tomato | 68 | 62 | 52 | 70 | 70 | 64 | 64 | 51 | X | |
| Tobacco | 68 | 64 | 60 | 71 | 71 | 65 | 65 | 55 | 83 | X |
| | | | | | | | | | | |
| | | | | | | | | | | |
| **PROTEIN** | Brassica napus | Arabidopsis thaliana | Wiggum | PPI Glycine max | Glycine max | PPI Zea maize | Zea maize | Pea | Tomato | Tobacco |
| Brassica napus | X | | | | | | | | | |
| Arabidopsis thaliana | 84 | X | | | | | | | | |
| Wiggum | 84 | 99 | X | | | | | | | |
| PPI Glycine max | 54 | 58 | 59 | X | | | | | | |
| Glycine max | 53 | 58 | 58 | 99 | X | | | | | |
| PPI Zea maize | 52 | 50 | 52 | 58 | 58 | X | | | | |
| Zea maize | 51 | 50 | 52 | 58 | 58 | 99 | X | | | |
| Pea | 58 | 56 | 57 | 78 | 78 | 56 | 56 | X | | |
| Tomato | 60 | 62 | 55 | 63 | 63 | 58 | 58 | 62 | X | |
| Tobacco | 62 | 63 | 59 | 64 | 63 | 58 | 58 | 64 | 83 | X |

| Nucleic Acid | PPI-AtCPP | PPI-BnCPP | PPI-SoyCPP | BASF-AT1 | BASF-AT2 | BASF-Corn | BASF-Soy | AFC1 | AT4g01320 | AF007269 |
|---|---|---|---|---|---|---|---|---|---|---|
| PPI-AtCPP | X | | | | | | | | | |
| PPI-BnCPP | 92 | X | | | | | | | | |
| PPI-SoyCPP | 76 | 77 | X | | | | | | | |
| BASF-AT1 | 98 | 93 | 76 | X | | | | | | |
| BASF-AT2 | 99 | 93 | 76 | 99 | X | | | | | |
| BASF-Corn | 57 | 57 | 57 | 57 | 57 | X | | | | |
| BASF-Soy | 72 | 72 | 93 | 72 | 72 | 52 | X | | | |
| AFC1 | 99 | 93 | 77 | 99 | 99 | 57 | 72 | X | | |
| AT4g01320 | 99 | 92 | 70 | 99 | 99 | 50 | 64 | 99 | X | |
| AF007269 | 97 | 91 | 10 | 97 | 97 | 13 | 8 | 97 | 97 | X |

B

| Amino Acid | PPI-AtCPP | PPI-BnCPP | PPI-SoyCPP | BASF-AT1 | BASF-AT2 | BASF-Corn | BASF-Soy | AFC1 | AT4g01320 | AF007269 |
|---|---|---|---|---|---|---|---|---|---|---|
| PPI-AtCPP | X | | | | | | | | | |
| PPI-BnCPP | 94 | X | | | | | | | | |
| PPI-SoyCPP | 83 | 83 | X | | | | | | | |
| BASF-AT1 | 98 | 95 | 83 | X | | | | | | |
| BASF-AT2 | 99 | 95 | 83 | 99 | X | | | | | |
| BASF-Corn | 82 | 82 | 79 | 82 | 82 | X | | | | |
| BASF-Soy | 83 | 83 | 99 | 83 | 83 | 73 | X | | | |
| AFC1 | 98 | 95 | 83 | 99 | 99 | 82 | 83 | X | | |
| AT4g01320 | 95 | 93 | 82 | 96 | 96 | 72 | 76 | 96 | X | |
| AF007269 | 98 | 94 | 82 | 98 | 99 | 82 | 82 | 98 | 100 | X |

Figure 26

2 weeks old seedling on different [ABA]

35S-AtCPP 12 days old seedlings - toluidin blue

WT 23 97 35

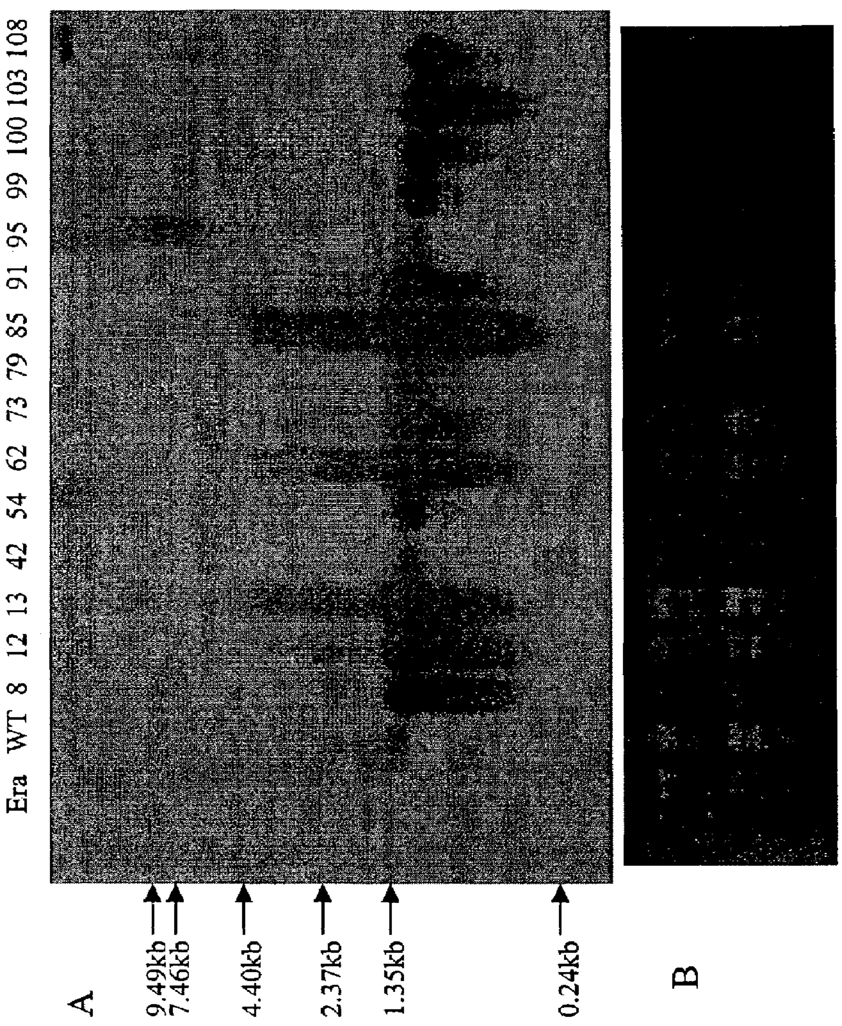
Figure 39 . Northern blot of ΔN90AtFTB arabidopsis plants
A. Northern blot probed with ΔN90AtFTB DNA probe
B. Ethidium bromide stain of agarose gel showing RNA loading per lane

SEQUENCE LISTING

```
<160> NUMBER OF SEQ ID NOS: 178

<210> SEQ ID NO 1
<211> LENGTH: 3174
<212> TYPE: DNA
<213> ORGANISM: Arabidopsis sp.
<220> FEATURE:
<221> NAME/KEY: misc_feature
<222> LOCATION: (2703)
<223> OTHER INFORMATION: Wherein n is a or t or c or g.

<400> SEQUENCE: 1

atggagattc agcgagataa gcaattggat tatctgatga aaggcttaag gcagcttggt     60
ccgcagtttt cttccttaga tgctaagtaa gtgacatgat gcttggcttc ttgttttcat    120
gaatttctta gtacattttg tccagtgaga gagtaaagct ttggagcttt gccaatagac    180
ttagaagttt gattttggct ttttggattt tggaacagtc gaccttggct ttgttactgg    240
attcttcatt caatagcttt gcttggggag actgtggatg atgaattaga aagcaatgcc    300
attgacttcc ttggacgctg ccaggttagt ctcaattcct tttgcttgta cccaatcatg    360
aaaactcttc atatttgctc ttgcattctt cttgattttc tgctccttta gttcacgttt    420
tcttttcccg ttgctattag tgttatctgt tattgttctt tatgtactta gtttgctttc    480
tcatgtcgct tgtcagggct ctgaaggtgg atacggtggt ggtcctggcc aagtaagtat    540
atgtctgttt ctttaaagtg tgtggatcac tttcatttca tgcaattgga gaataaacat    600
tgagaccaga ttattttatt ctgccagatc tcttttaggt gtttttttta tgcatcatct    660
cattgtttgg ttgtgatgcc tttaattcaa gcagcacacg tagtttaagt ttaagttttt    720
ttctgtgaag acgtaaaatg gtgtctttag ttcaagcagc atttagttgt ttaagtttgt    780
ggttgtaaat tttccaaaca tggcagagaa agttaggata tataactttt ggtctgcctt    840
tttcagtttc cttttttttt ctactagtaa tggagatatt ttttcccagc ttccacatct    900
tgcaactact tatgctgcag tgaatgcact tgttacttta ggaggtgaca aagccctttc    960
ttcaattaat aggtggtgca ttcttttttc tttgtggtca gtttctttta ttaagagtct   1020
agtgatgttt cctctagaat acttacatgt gactcattct tctttcagag aaaaaaatgtc  1080
ttgtttttta agacggatga aggatacaag tggaggtttc aggtttgatt ctctttctgc   1140
ttgaacttct taaaggcatc atttttactg acagcgcact ctttatgcat tcgtatcgct   1200
gttaatgcca taccttcagt catgttgttt ttttaattct tgcttaattc tacttactca   1260
ctgatcgtta ggatgcatga tatgggagaa attgatgttc gtgcatgcta cactgcaatt   1320
tcggtgagtt ttaccaactt ctattttcct tttctctgtt tttgtggaca ccaaaacttt   1380
ttaggattaa tgagatcaac aaagtctgga cccattatgc tatgtttctt ccgttttcat   1440
ggcttaaaca tcacattcag attacgatat gatcttatta tttgcacact tgcgcccacc   1500
aggatacttt gaatagagat tactcgtttt gagacttaca cgtcttgcaa atgcatccta   1560
```

-continued

```
tggctggttt tctccctgat atgtttgact tctctcttgt gacacaggtt gcaagcatcc   1620
taaatattat ggatgatgaa ctcacccagg gcctaggaga ttacatcttg aggtagcttt   1680
tcttattact tttatctcgc attatatata tatagctgaa ctactgttat acagttgtaa   1740
attcaggaat tcattaattt ccctgggaaa gctcttttaa ctcgatttat attgagcagt   1800
tgccaaactt atgaaggtgg cattggaggg gaacctggct ccgaagctca cggtgggtat   1860
ggtctccaac taacttccat tatgttgagg cttagataaa aattgtgctt tgcttccctc   1920
ttccttgatg acatggttat tgatggttaa gtataattaa ttttctgaaa taggatttgt   1980
cacctgcagc ttgcatgcct gccgctttgc ttattaccaa gttgtttttt gtttaggtat   2040
acctactgtg gtttggctgc tatgatttta atcaatgagg tcgaccgttt gaatttggat   2100
tcattaatgg taacatacaa tgctgtttgg agatgattaa taattttccc tgagagatat   2160
tttccttacc aaataatttc cttatgattc tagaattggg ctgtacatcg acaaggagta   2220
gaaatgggat ttcaaggtag gacgaacaaa ttggtcgatg gttgctacac attttggcag   2280
gttaactttc tatctttcag gattattatt ggccctactt ctaaattctt caccgttgtt   2340
gtcttttctt atttcctttg ggtatatgtt aaacaggcag ccccttgtgt tctactacaa   2400
agattatatt caaccaatga tcatgacgtt catggatcat cacatatatc agaagggaca   2460
aatgaagaac atcatgctca tgatgaagat gaccttgaag acagtgatga tgatgatgat   2520
tctgatgagg acaacgatga aggtattcaa tcaaatttct caaccatcaa gtccatctga   2580
taattcaaaa cacaacgaaa ttttagttag cttatatttg cagattcagt gaatggtcac   2640
agaatccatc atacatccac ctacattaac aggagaatgc aactggtttt tgatagcctc   2700
ggnttgcaga gatatgtact cttgtgctct aaggtcagtc cagaacaaaa catccagtca   2760
agttaacact taacatttgt ataacacaag cacacacact tgtatgcgca gatccctgac   2820
ggtggattca gagacaagcc gaggaaaccc cgtgacttct accacacatg ttactgcctg   2880
agcggcttgt ctgtggctca gcacgcttgg ttaaaagacg aggacactcc tcctttgact   2940
cgcgacatta tgggtggcta ctcgaatctc cttgaacctg ttcaacttct tcacaacatt   3000
gtcatggatc agtataatga agctatcgag ttcttcttta aagcagcatg acccgttgtt   3060
gctaatgtat gggaaacccc aaacataaga gtttccgtag tgttgtaact tgtaagattt   3120
caaaagaagt ttcactaatt taaccttaaa acctgttact ttttattacg tata         3174
```

<210> SEQ ID NO 2
<211> LENGTH: 400
<212> TYPE: PRT
<213> ORGANISM: Arabidopsis sp.

<400> SEQUENCE: 2

```
Met Glu Ile Gln Arg Asp Lys Gln Leu Asp Tyr Leu Met Lys Gly Leu
  1               5                  10                  15

Arg Gln Leu Gly Pro Gln Phe Ser Ser Leu Asp Ala Asn Arg Pro Trp
             20                  25                  30

Leu Cys Tyr Trp Ile Leu His Ser Ile Ala Leu Leu Gly Glu Thr Val
         35                  40                  45

Asp Asp Glu Leu Glu Ser Asn Ala Ile Asp Phe Leu Gly Arg Cys Gln
     50                  55                  60

Gly Ser Glu Gly Gly Tyr Gly Gly Gly Pro Gly Gln Leu Pro His Leu
 65                  70                  75                  80

Ala Thr Thr Tyr Ala Ala Val Asn Ala Leu Val Thr Leu Gly Gly Asp
```

```
                85                  90                  95

Lys Ala Leu Ser Ser Ile Asn Arg Glu Lys Met Ser Cys Phe Leu Arg
            100                 105                 110

Arg Met Lys Asp Thr Ser Gly Gly Phe Arg Met His Asp Met Gly Glu
        115                 120                 125

Ile Asp Val Arg Ala Cys Tyr Thr Ala Ile Ser Val Ala Ser Ile Leu
    130                 135                 140

Asn Ile Met Asp Asp Glu Leu Thr Gln Gly Leu Gly Asp Tyr Ile Leu
145                 150                 155                 160

Ser Cys Gln Thr Tyr Glu Gly Gly Ile Gly Gly Glu Pro Gly Ser Glu
                165                 170                 175

Ala His Gly Gly Tyr Thr Tyr Cys Gly Leu Ala Ala Met Ile Leu Ile
            180                 185                 190

Asn Glu Val Asp Arg Leu Asn Leu Asp Ser Leu Met Asn Trp Ala Val
        195                 200                 205

His Arg Gln Gly Val Glu Met Gly Phe Gln Gly Arg Thr Asn Lys Leu
    210                 215                 220

Val Asp Gly Cys Tyr Thr Phe Trp Gln Ala Ala Pro Cys Val Leu Leu
225                 230                 235                 240

Gln Arg Leu Tyr Ser Thr Asn Asp His Asp Val His Gly Ser Ser His
                245                 250                 255

Ile Ser Glu Gly Thr Asn Glu Glu His His Ala His Asp Glu Asp Asp
            260                 265                 270

Leu Glu Asp Ser Asp Asp Asp Asp Asp Ser Asp Glu Asp Asn Asp Glu
        275                 280                 285

Asp Ser Val Asn Gly His Arg Ile His His Thr Ser Thr Tyr Ile Asn
    290                 295                 300

Arg Arg Met Gln Leu Val Phe Asp Ser Leu Gly Leu Gln Arg Tyr Val
305                 310                 315                 320

Leu Leu Cys Ser Lys Ile Pro Asp Gly Gly Phe Arg Asp Lys Pro Arg
                325                 330                 335

Lys Pro Arg Asp Phe Tyr His Thr Cys Tyr Cys Leu Ser Gly Leu Ser
            340                 345                 350

Val Ala Gln His Ala Trp Leu Lys Asp Glu Asp Thr Pro Pro Leu Thr
        355                 360                 365

Arg Asp Ile Met Gly Gly Tyr Ser Asn Leu Leu Glu Pro Val Gln Leu
    370                 375                 380

Leu His Asn Ile Val Met Asp Gln Tyr Asn Glu Ala Ile Glu Phe Phe
385                 390                 395                 400
```

<210> SEQ ID NO 3
<211> LENGTH: 2286
<212> TYPE: DNA
<213> ORGANISM: Artificial Sequence
<220> FEATURE:
<223> OTHER INFORMATION: Description of Artificial Sequence: ERA1 promoter
<220> FEATURE:
<221> NAME/KEY: misc_feature
<222> LOCATION: (79)
<223> OTHER INFORMATION: Wherein n is a or t or c or g.
<220> FEATURE:
<221> NAME/KEY: misc_feature
<222> LOCATION: (996)
<223> OTHER INFORMATION: Wherein n is a or t or c or g.
<220> FEATURE:
<221> NAME/KEY: misc_feature
<222> LOCATION: (1153)
<223> OTHER INFORMATION: Wherein n is a or t or c or g.

-continued

<220> FEATURE:
<221> NAME/KEY: misc_feature
<222> LOCATION: (1295..1296)
<223> OTHER INFORMATION: Wherein n is a or t or c or g.
<220> FEATURE:
<221> NAME/KEY: misc_feature
<222> LOCATION: (1779)
<223> OTHER INFORMATION: Wherein n is a or t or c or g.

<400> SEQUENCE: 3
ctcactcatt agcaccccag ctttacactt tatgcttccg ctcgtatgtt gtgtggaatt 60
gtgagcgata acaatttcna cacaggaaac agctatgaca tgattacgaa ttcaaaaaaa 120
tagagattgg caatatttta gtgtgtgaat aatattcatc cctaaaaaga agtcatcttt 180
cgactttgtg gcaacagttc tgttattaaa atgtgtgagc gtgacatatt ttgaagaggt 240
acctcgacaa aatcggaagg tgtctcattt tcttctatcg gaaggctttc tcgttgaagg 300
tagtcgttgt agctgaaaaa ttaagaaaac ctagtgagct cttcatgtat tcaaaaattc 360
aaccagtgta atcaaactca agaggtaaat agttaaaatc ccataccaaa ccgtgtaatc 420
tatgcaatac ctaattaaca aagttaaaag cgttagtcta gcagtaatat tgtatcaaaa 480
gctctaacag taattaataa ccagtgtcac cagaaacaaa tgtcaataac atggaaaatt 540
gaatttagtt gagtcctgga ggtcgtggac gtcgtggagg ctgtggacgt cgtgaatacg 600
cataaagaaa aatcttataa tcgtgcaaat attcaccgtt cttcttatac atcacctacg 660
gtaataaaag agttttattt cagcaatcgt acattcaaat tgaaacttag atacactata 720
tatttttcat cataactaac tataaactag tctaaacctt ttttgcttcg ttagcagaag 780
caaagtcaac aggccatagc acctatggat acgcttggcg gttacaaaaa gtcgaacacg 840
aacaacttct ccagcatctt tgaagaaatt gatgctgtaa caaacagtgt aaggtaaaaa 900
tatcagtcat gctcagagaa ggaaagtgga gattgaagat ggtgctactt acatatctga 960
tattttagtt tggggaggga tatggccatt aaagancgtc ttttttgtca cctggattta 1020
acagccaagt gtgttagcac aagattctta attgaacaga aatttgtaca aaatatctag 1080
caaatccgtt ggttgtttcc tcctgttaca tatgatacaa gatcaaagag tagccattag 1140
aagaagacag tgnaaagaag attgttttgt caaagaagaa gagtaatacg aggccatctt 1200
agggttacct tattctactt atgtctcttg agaatggaat tggtcaccaa atcatcttct 1260
tcagggttac gcttacctaa aagaagagca acaannaaaa aactcttgag acaagtttaa 1320
cacattagat aaaagagaga gagagagagg caaccaaaaa caaacccaat aaattgctac 1380
tagaagtggc catggagaag atgaaacgag gtttatgtat ttttccgtta agagcaagca 1440
ataatatagc cctaaagaaa tatagaccta gcctaggaag aagtttctaa gaccatcctt 1500
atcaatgaac tcttacataa agttctaaac aattttgata tacaaaataa tgtttaaaca 1560
ttagaatggc tcttacaaaa aaagagaata aagaaaaaaa aaacttagct aagagccatt 1620
tttcatttct taagcacact tttttatttt tttattctta ttttatttaa tataatattt 1680
tgatagttct tatgatattg ttaacaacct attgataagg atgctctaac taatcttata 1740
aataaaacaa tgaatctggt ttggtctggg cgtaacagna attatactct tttttttttt 1800
tgtcaagagg aaattatact aagaagcaac agattaaaca ttaaagcgta tagtaaaatt 1860
aattgtttga gaatcttaaa ccaaaccgaa ccggtattaa accggaacca aattggcaat 1920
gaaatttaga tgccagtagt aacccgcttg attcgtttga agtgtgtagg gctcagactt 1980
gaccggagtg gactcaatcg gcgaatctgt cacggaggac acggggaatc aacgcggcgg 2040

-continued

```
agagtgatgg aagagttttc aagcctaacc gtgagtcagc gcgagcaatt tctggtggag   2100

aacgatgtgt tcgggatcta taattacttc gacgccagcg acgtttctac tcaaaaatac   2160

atgtaagctg acggattgat tttctagttt tcttcatgat ctgatgaatt ttagtagcgt   2220

cgtgaaagaa ttattttcgt cgatagatga atcttactga tatggaagtt gttctatcct   2280

aggatg                                                              2286


<210> SEQ ID NO 4
<211> LENGTH: 192
<212> TYPE: PRT
<213> ORGANISM: Pisum sativum

<400> SEQUENCE: 4

Ala Ser Thr Ala Ala Glu Thr Pro Thr Pro Thr Val Ser Gln Asp Gln
  1               5                  10                  15

Trp Ile Val Glu Gln Val Phe His Ile Tyr Gln Leu Phe Ala Asn Ile
             20                  25                  30

Pro Pro Asn Ala Gln Ser Ile Ile Ile Ser Ile Asp Asp Thr Val Asn
         35                  40                  45

Asp Pro Asn Ala Met Thr Ile Glu Ser Ala Asn Leu Tyr Gly Met Gln
     50                  55                  60

Pro Asn Glu Val Leu Ile Lys Asn Val Phe Leu Ala Phe Gly Asn Asp
 65                  70                  75                  80

Pro Arg Leu Asp Val Phe Lys Cys Asp Gly Gly Ala Val Ala His Ile
                 85                  90                  95

Ile Glu Gln Met Ala Glu Ala Gln Phe Val Thr Val Ser Asp Ala Pro
            100                 105                 110

Glu Glu Lys Glu Cys Leu Gly Thr Ser Ser His Ala Thr Ser His Ile
        115                 120                 125

Arg His Gly Met Asn Ser Cys Ser Ser Asp Val Lys Asn Ile Gly Tyr
    130                 135                 140

Asn Phe Ile Ser Glu Trp Gln Ser Glu Pro Leu His Ile Ala Gln Ile
145                 150                 155                 160

Gln Glu Gln Leu Gly Arg His Ser Leu Cys Tyr Ser Ser Arg Pro Ser
                165                 170                 175

Pro Lys Val Val Pro Ile His Pro Phe Val Leu Arg Arg His Ser Gln
            180                 185                 190


<210> SEQ ID NO 5
<211> LENGTH: 311
<212> TYPE: PRT
<213> ORGANISM: Saccharomyces sp.

<400> SEQUENCE: 5

Arg Gln Arg Val Gly Arg Ser Ile Ala Arg Ala Lys Phe Ile Asn Thr
  1               5                  10                  15

Ala Leu Gly Arg Lys Arg Pro Val Met Glu Arg Val Val Asp Ile Ala
             20                  25                  30

His Val Asp Ser Ser Lys Ala Ile Gln Pro Leu Met Lys Glu Leu Glu
         35                  40                  45

Thr Asp Thr Thr Glu Ala Arg Tyr Lys Val Leu Gln Ser Val Leu Glu
     50                  55                  60

Ile Tyr Asp Asp Glu Lys Asn Ile Glu Pro Ala Leu Thr Lys Glu Phe
 65                  70                  75                  80

His Lys Met Tyr Leu Asp Val Ala Phe Glu Ile Ser Leu Pro Pro Gln
                 85                  90                  95
```

-continued

```
Met Thr Ala Leu Asp Ala Ser Gln Met Leu Ala Asn Leu Lys Val Met
            100                 105                 110

Asp Arg Asp Trp Leu Ser Asp Thr Lys Arg Lys Ile Val Lys Phe Thr
        115                 120                 125

Ile Ser Pro Gly Pro Phe Ser Ser Ile Ser Leu Cys Asp Asn Ile Asp
    130                 135                 140

Gly Cys Trp Asp Arg Asp Lys Gly Ile Tyr Gln Trp Ile Ser Leu Glu
145                 150                 155                 160

Pro Asn Lys Thr Cys Leu Glu Val Val Thr Gly Ile Cys Leu Ile Thr
                165                 170                 175

Leu Leu Thr Glu Glu Val Leu Asn Leu Lys Asn Asn Phe Ser Cys His
            180                 185                 190

Val Asp Phe Ala Thr Ser Leu Ala Arg Ser Met Gln Ile Val Glu Lys
        195                 200                 205

Leu Glu Ser Ser Ala Leu Gln Glu Arg Cys Ser Ser Val Gly Gly Ser
    210                 215                 220

Ala Ala Ile Glu Ala Phe Gly Gly Gln Cys Asn Lys His Ala Arg Asp
225                 230                 235                 240

Ile Tyr Cys Gln Glu Lys Glu Gln Pro Leu Gly Ala His Ser Asn Leu
                245                 250                 255

Ala Glu Ser Ser Tyr Ser Cys Thr Pro Asn Ser His Asn Ile Lys Cys
            260                 265                 270

Thr Pro Asp Arg Leu Ile Gly Ser Ser Lys Leu Thr Asp Val Asn Pro
        275                 280                 285

Val Tyr Gly Leu Pro Ile Glu Val Arg Lys Ile Ile His Tyr Phe Lys
    290                 295                 300

Ser Asn Leu Ser Ser Pro Ser
305                 310


<210> SEQ ID NO 6
<211> LENGTH: 270
<212> TYPE: PRT
<213> ORGANISM: Rattus norvegicus

<400> SEQUENCE: 6

Ala Ser Ser Ser Ser Phe Thr Tyr Tyr Cys Pro Pro Ser Ser Ser Pro
  1               5                  10                  15

Val Trp Ser Glu Pro Leu Tyr Arg Pro Glu His Ala Arg Glu Arg Leu
             20                  25                  30

Gln Asp Asp Ser Val Glu Thr Val Thr Ser Ile Glu Gln Ala Lys Val
         35                  40                  45

Glu Glu Lys Ile Gln Glu Val Phe Ser Ser Tyr Lys Phe Asn His Leu
     50                  55                  60

Val Pro Arg Leu Val Leu Gln Arg Glu Lys His Phe His Tyr Leu Lys
 65                  70                  75                  80

Arg Gly Leu Arg Gln Leu Thr Asp Ala Tyr Glu Cys Leu Asp Ala Ser
                 85                  90                  95

Leu Glu Asp Pro Ile Pro Gln Ile Val Ala Thr Asp Val Cys Gln Glu
            100                 105                 110

Leu Ser Pro Asp Phe Tyr Pro Cys Ile Ile Thr Glu Glu Tyr Asn Val
        115                 120                 125

Leu Leu Gln Tyr Tyr Ser Leu Gln Pro Asp Ser Leu Val Gly Val Ser
    130                 135                 140

Ala Cys Ala Leu Thr Ile Thr Pro Asp Phe Glu Thr Ala Glu Trp Ala
```

-continued

```
145                 150                 155                 160

Arg Asn Trp Val Met Phe Leu Val Lys Lys Arg Ser Lys Leu Gln Val
                165                 170                 175

Thr Ser Met Arg Phe Gly Cys Ser Gly Leu Leu Pro His Ala His Ala
            180                 185                 190

Gln Gly Pro Ala Leu Ser Met His Trp Met His Gln Gln Ala Glu Ile
        195                 200                 205

Met Cys Gln Cys Ala Leu Leu Gly Ser Ile His Phe Gly Ser Gly Ala
    210                 215                 220

Met His Asp Val Val Val Pro Glu Val Gln Thr His Pro Val Tyr Gly
225                 230                 235                 240

Pro Lys Val Ile Gln Thr Thr His Leu Gln Lys Pro Val Pro Gly Phe
                245                 250                 255

Glu Glu Cys Glu Asp Ala Val Thr Ser Asp Pro Ala Thr Asp
            260                 265                 270
```

<210> SEQ ID NO 7
<211> LENGTH: 999
<212> TYPE: DNA
<213> ORGANISM: Arabidopsis thaliana

<400> SEQUENCE: 7

```
aaacccggga tgaatttcga cgagaccgtg ccactgagcc aacgattgga gtggtcagac     60

gtggtcccat tgactcagga cgatggtccg aatccagtgg tgccaattgc ctacaaggaa    120

gagttccgcg agactatgga ttacttccgt gcgatttact tttccgacga gcgatctcct    180

cgcgcactac gactcacgga agaaaccctc ctcttaaact ccggcaacta cacagtgtgg    240

catttcaggc gcctagtact cgaggccctt aatcacgact tgtttgaaga actcgagttc    300

atcgaacgca ttgctgagga taactctaag aactaccaac tgtggcatca tcggcgatgg    360

gttgcagaga aactgggtcc tgatgttgca gggagagaac ttgaatttac ccgtagagta    420

ctttcacttg atgccaaaca ttatcatgct tggtcacata ggcagtggac actacgggca    480

ttaggaggat gggaagatga gctcgattac tgtcacgagc tccttgaagc tgacgtcttt    540

aacaattccg cctggaatca gaggtattat gtcatcaccc aatctccttt gttgggaggc    600

ctagaagcca tgagagaatc tgaagtaagc tacacaatca aagccatttt aaccaatcct    660

gcaaacgaga gctcatggcg atacctaaaa gcgctttaca aagacgacaa agaatcctgg    720

attagtgatc caagtgtttc ctcagtctgt ttgaatgttc tatcccgcac agattgcttc    780

catggattcg ctctgagcac ccttttggat cttctatgtg atggactgag accaaccaac    840

gagcataaag actcagtgag agctctagct aatgaagaac cagagactaa cttggccaat    900

ttggtgtgta ctattcttgg tcgtgtagat cctataagag ctaactattg ggcatggagg    960

aagagcaaga ttacagtggc agcaatttga ggatccttt                           999
```

<210> SEQ ID NO 8
<211> LENGTH: 999
<212> TYPE: DNA
<213> ORGANISM: Artificial Sequence
<220> FEATURE:
<223> OTHER INFORMATION: Description of Artificial Sequence: Compliment
      to Seq ID:07

<400> SEQUENCE: 8

```
aaaggatcct caaattgctg ccactgtaat cttgctcttc ctccatgccc aatagttagc     60

tcttatagga tctacacgac caagaatagt acacaccaaa ttggccaagt tagtctctgg    120
```

-continued

```
ttcttcatta gctagagctc tcactgagtc tttatgctcg ttggttggtc tcagtccatc    180

acatagaaga tccaaaaggg tgctcagagc gaatccatgg aagcaatctg tgcgggatag    240

aacattcaaa cagactgagg aaacacttgg atcactaatc caggattctt tgtcgtcttt    300

gtaaagcgct tttaggtatc gccatgagct ctcgtttgca ggattggtta aaatggcttt    360

gattgtgtag cttacttcag attctctcat ggcttctagg cctcccaaca aaggagattg    420

ggtgatgaca taatacctct gattccaggc ggaattgtta aagacgtcag cttcaaggag    480

ctcgtgacag taatcgagct catcttccca tcctcctaat gcccgtagtg tccactgcct    540

atgtgaccaa gcatgataat gtttggcatc aagtgaaagt actctacggg taaattcaag    600

ttctctccct gcaacatcag gacccagttt ctctgcaacc catcgccgat gatgccacag    660

ttggtagttc ttagagttat cctcagcaat gcgttcgatg aactcgagtt cttcaaacaa    720

gtcgtgatta agggcctcga gtactaggcg cctgaaatgc cacactgtgt agttgccgga    780

gtttaagagg agggtttctt ccgtgagtcg tagtgcgcga ggagatcgct cgtcggaaaa    840

gtaaatcgca cggaagtaat ccatagtctc gcggaactct tccttgtagg caattggcac    900

cactggattc ggaccatcgt cctgagtcaa tgggaccacg tctgaccact ccaatcgttg    960

gctcagtggc acggtctcgt cgaaattcat cccgggttt                            999
```

<210> SEQ ID NO 9
<211> LENGTH: 989
<212> TYPE: DNA
<213> ORGANISM: Artificial Sequence
<220> FEATURE:
<223> OTHER INFORMATION: Description of Artificial Sequence: Compliment to SEQ ID NO: 7 ligated

<400> SEQUENCE: 9

```
gatcctcaaa ttgctgccac tgtaatcttg ctcttcctcc atgcccaata gttagctctt     60

ataggatcta cacgaccaag aatagtacac accaaattgg ccaagttagt ctctggttct    120

tcattagcta gagctctcac tgagtcttta tgctcgttgg ttggtctcag tccatcacat    180

agaagatcca aaagggtgct cagagcgaat ccatggaagc aatctgtgcg ggatagaaca    240

ttcaaacaga ctgaggaaac acttggatca ctaatccagg attctttgtc gtctttgtaa    300

agcgctttta ggtatcgcca tgagctctcg tttgcaggat tggttaaaat ggctttgatt    360

gtgtagctta cttcagattc tctcatggct tctaggcctc ccaacaaagg agattgggtg    420

atgacataat acctctgatt ccaggcggaa ttgttaaaga cgtcagcttc aaggagctcg    480

tgacagtaat cgagctcatc ttcccatcct cctaatgccc gtagtgtcca ctgcctatgt    540

gaccaagcat gataatgttt ggcatcaagt gaaagtactc tacgggtaaa ttcaagttct    600

ctccctgcaa catcaggacc cagtttctct gcaacccatc gccgatgatg ccacagttgg    660

tagttcttag agttatcctc agcaatgcgt tcgatgaact cgagttcttc aaacaagtcg    720

tgattaaggg cctcgagtac taggcgcctg aaatgccaca ctgtgtagtt gccggagttt    780

aagaggaggg tttcttccgt gagtcgtagt gcgcgaggag atcgctcgtc ggaaaagtaa    840

atcgcacgga agtaatccat agtctcgcgg aactcttcct tgtaggcaat tggcaccact    900

ggattcggac catcgtcctg agtcaatggg accacgtctg accactccaa tcgttggctc    960

agtggcacgg tctcgtcgaa attcatccc                                      989
```

<210> SEQ ID NO 10
<211> LENGTH: 5250

-continued

<212> TYPE: DNA
<213> ORGANISM: Artificial Sequence
<220> FEATURE:
<223> OTHER INFORMATION: Description of Artificial Sequence:plasmid
pBI121-35S-anti-AtFTA

<400> SEQUENCE: 10
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160

-continued

```
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcaaatt gctgccactg taatcttgct   3360
cttcctccat gcccaatagt tagctcttat aggatctaca cgaccaagaa tagtacacac   3420
caaattggcc aagttagtct ctggttcttc attagctaga gctctcactg agtctttatg   3480
ctcgttggtt ggtctcagtc catcacatag aagatccaaa agggtgctca gagcgaatcc   3540
atggaagcaa tctgtgcggg atagaacatt caaacagact gaggaaacac ttggatcact   3600
aatccaggat tctttgtcgt ctttgtaaag cgcttttagg tatcgccatg agctctcgtt   3660
tgcaggattg gttaaaatgg ctttgattgt gtagcttact tcagattctc tcatggcttc   3720
taggcctccc aacaaaggag attgggtgat gacataatac ctctgattcc aggcggaatt   3780
gttaaagacg tcagcttcaa ggagctcgtg acagtaatcg agctcatctt cccatcctcc   3840
taatgcccgt agtgtccact gcctatgtga ccaagcatga taatgtttgg catcaagtga   3900
aagtactcta cgggtaaatt caagttctct ccctgcaaca tcaggaccca gtttctctgc   3960
aacccatcgc cgatgatgcc acagttggta gttcttagag ttatcctcag caatgcgttc   4020
gatgaactcg agttcttcaa acaagtcgtg attaagggcc tcgagtacta ggcgcctgaa   4080
atgccacact gtgtagttgc cggagtttaa gaggagggtt tcttccgtga gtcgtagtgc   4140
gcgaggagat cgctcgtcgg aaaagtaaat cgcacggaag taatccatag tctcgcggaa   4200
ctcttccttg taggcaattg gcaccactgg attcggacca tcgtcctgag tcaatgggac   4260
cacgtctgac cactccaatc gttggctcag tggcacggtc tcgtcgaaat tcatcccctc   4320
gaatttcccc gatcgttcaa acatttggca ataaagtttc ttaagattga atcctgttgc   4380
cggtcttgcg atgattatca tataatttct gttgaattac gttaagcatg taataattaa   4440
catgtaatgc atgacgttat ttatgagatg ggtttttatg attagagtcc cgcaattata   4500
```

-continued

```
catttaatac gcgatagaaa acaaaatata gcgcgcaaac taggataaat tatcgcgcgc   4560

ggtgtcatct atgttactag atcgggaatt cactggccgt cgttttacaa cgtcgtgact   4620

gggaaaaccc tggcgttacc caacttaatc gccttgcagc acatccccct ttcgccagct   4680

ggcgtaatag cgaagaggcc cgcaccgatc gcccttccca acagttgcgc agcctgaatg   4740

gcgcccgctc ctttcgcttt cttcccttcc tttctcgcca cgttcgccgg ctttccccgt   4800

caagctctaa atcgggggct ccctttaggg ttccgattta gtgctttacg gcacctcgac   4860

cccaaaaaac ttgatttggg tgatggttca cgtagtgggc catcgccctg atagacggtt   4920

tttcgccctt tgacgttgga gtccacgttc tttaatagtg gactcttgtt ccaaactgga   4980

acaacactca accctatctc gggctattct tttgatttat aagggatttt gccgatttcg   5040

gaaccaccat caaacaggat tttcgcctgc tggggcaaac cagcgtggac cgcttgctgc   5100

aactctctca gggccaggcg gtgaagggca atcagctgtt gcccgtctca ctggtgaaaa   5160

gaaaaaccac cccagtacat taaaaacgtc cgcaatgtgt tattaagttg tctaagcgtc   5220

aatttgttta caccacaata tatcctgcca                                    5250
```

<210> SEQ ID NO 11
<211> LENGTH: 326
<212> TYPE: PRT
<213> ORGANISM: Arabidopsis thaliana

<400> SEQUENCE: 11

```
Met Asn Phe Asp Glu Thr Val Pro Leu Ser Gln Arg Leu Glu Trp Ser
  1               5                  10                  15

Asp Val Val Pro Leu Thr Gln Asp Asp Gly Pro Asn Pro Val Val Pro
             20                  25                  30

Ile Ala Tyr Lys Glu Glu Phe Arg Glu Thr Met Asp Tyr Phe Arg Ala
         35                  40                  45

Ile Tyr Phe Ser Asp Glu Arg Ser Pro Arg Ala Leu Arg Leu Thr Glu
     50                  55                  60

Glu Thr Leu Leu Leu Asn Ser Gly Asn Tyr Thr Val Trp His Phe Arg
 65                  70                  75                  80

Arg Leu Val Leu Glu Ala Leu Asn His Asp Leu Phe Glu Glu Leu Glu
                 85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Arg Glu Leu Glu Phe Thr Arg Arg Val Leu Ser Leu Asp Ala Lys His
    130                 135                 140

Tyr His Ala Trp Ser His Arg Gln Trp Thr Leu Arg Ala Leu Gly Gly
145                 150                 155                 160

Trp Glu Asp Glu Leu Asp Tyr Cys His Glu Leu Leu Glu Ala Asp Val
                165                 170                 175

Phe Asn Asn Ser Ala Trp Asn Gln Arg Tyr Tyr Val Ile Thr Gln Ser
            180                 185                 190

Pro Leu Leu Gly Gly Leu Glu Ala Met Arg Glu Ser Glu Val Ser Tyr
        195                 200                 205

Thr Ile Lys Ala Ile Leu Thr Asn Pro Ala Asn Glu Ser Ser Trp Arg
    210                 215                 220

Tyr Leu Lys Ala Leu Tyr Lys Asp Asp Lys Glu Ser Trp Ile Ser Asp
225                 230                 235                 240
```

-continued

```
Pro Ser Val Ser Ser Val Cys Leu Asn Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Lys Asp Ser Val Arg Ala Leu Ala Asn
        275                 280                 285

Glu Glu Pro Glu Thr Asn Leu Ala Asn Leu Val Cys Thr Ile Leu Gly
    290                 295                 300

Arg Val Asp Pro Ile Arg Ala Asn Tyr Trp Ala Trp Arg Lys Ser Lys
305                 310                 315                 320

Ile Thr Val Ala Ala Ile
                325


<210> SEQ ID NO 12
<211> LENGTH: 822
<212> TYPE: DNA
<213> ORGANISM: Brassica napus

<400> SEQUENCE: 12

atggattact tccgtgcgat ttacttctcc gacgagcgtt ctgctcgcgc gctgcgactc      60

acggaagaag ctctccgctt aaactcgggc aactacaccg tgtggcactt cgggcgctta     120

gtactcgagg agcttaataa cgacttgtat gaagagctca agttcatcga aagcattgct     180

gaggataact ctaagaacta ccagttgtgg catcatcgac gatgggtcgc agagaaactg     240

ggtcctgatg ttgcaggaaa ggaacttgag tttactcgga gggtactatc acttgatgcc     300

aagcattatc atgcttggtc acataggcag tgggcgctac aagcattagg aggatgggaa     360

aatgagctta actactgcca cgagctcctt gaagctgacg tctttaacaa ctctgcatgg     420

aatcagaggt attacgttat aactagatca ccttcgttgg gaggcctaga agccatgaga     480

gaatctgaag taagctacac agtcaaagcc attttagcaa atcccgggaa cgagagctct     540

tggaggtacc tgaaagccct ttacaaagac gacacagagt cttggattag tgatccaagt     600

gtttcctcag tctgtttgaa agttctctca cgcgcggact gcttccatgg attcgctctg     660

agcacccttt tggatcttct gtgcgatggg ttgagaccaa ccaacgagca tagagactcg     720

gtgaaagctc tagctaatga agaaccagag actaacttgg ccaatttggt gtgtaccatt     780

ctgtgtcgtg ttgatccaat aagagctaac tattgggcat gg                        822


<210> SEQ ID NO 13
<211> LENGTH: 276
<212> TYPE: PRT
<213> ORGANISM: Brassica napus

<400> SEQUENCE: 13

Met Asp Tyr Phe Arg Ala Ile Tyr Phe Ser Asp Glu Arg Ser Ala Arg
  1               5                  10                  15

Ala Leu Arg Leu Thr Glu Glu Ala Leu Arg Leu Asn Ser Gly Asn Tyr
             20                  25                  30

Thr Val Trp His Phe Gly Arg Leu Val Leu Glu Glu Leu Asn Asn Asp
         35                  40                  45

Leu Tyr Glu Glu Leu Lys Phe Ile Glu Ser Ile Ala Glu Asp Asn Ser
     50                  55                  60

Lys Asn Tyr Gln Leu Trp His His Arg Arg Trp Val Ala Glu Lys Leu
 65                  70                  75                  80

Gly Pro Asp Val Ala Gly Leu Glu Lys Glu Phe Thr Arg Arg Val Leu
                 85                  90                  95
```

-continued

Ser Leu Asp Ala Lys His Tyr His Ala Trp Ser His Arg Gln Trp Ala
100 105 110

Leu Gln Ala Leu Gly Gly Trp Glu Asn Glu Leu Asn Tyr Cys His Glu
115 120 125

Leu Leu Glu Ala Asp Val Phe Asn Asn Ser Ala Trp Asn Gln Arg Tyr
130 135 140

Tyr Val Ile Thr Arg Ser Pro Ser Leu Gly Gly Leu Glu Ala Met Arg
145 150 155 160

Glu Ser Glu Val Ser Tyr Thr Val Lys Ala Ile Leu Ala Asn Pro Gly
165 170 175

Asn Glu Ser Ser Trp Arg Tyr Leu Lys Ala Leu Tyr Lys Asp Asp Thr
180 185 190

Glu Ser Trp Ile Ser Asp Pro Ser Val Ser Ser Val Cys Leu Lys Val
195 200 205

Leu Ser Arg Ala Asp Cys Phe His Gly Phe Ala Leu Ser Thr Leu Leu
210 215 220

Asp Leu Leu Cys Asp Gly Leu Arg Pro Thr Asn Glu His Arg Asp Ser
225 230 235 240

Val Lys Ala Leu Ala Asn Glu Glu Pro Glu Thr Asn Leu Ala Asn Leu
245 250 255

Val Cys Thr Ile Leu Cys Arg Val Asp Pro Ile Arg Ala Asn Tyr Trp
260 265 270

Ala Trp Lys Leu
275

<210> SEQ ID NO 14
<211> LENGTH: 1110
<212> TYPE: DNA
<213> ORGANISM: Brassica napus

<400> SEQUENCE: 14
tggctttgtt actggattct tcattcaatt gctttgcttg gggagtctgt ggatgatgac 60
ttagaaaaca atgcaatcga ttttcttgga cgttgccagg gttctgatgg tggatatggt 120
ggtggtcctg gccaacttcc acatcttgca acaagttatg ctgcagtgaa tacacttgtt 180
actttaggag gtgagaaagc cttctcttca attaacagag aacaaatggc ttgtttctta 240
agacgaatga aggatacaaa tggaggtttc aggatgcata atatgggaga aatagatgtg 300
cgagcgtgct acactgcgat tttgattgca agcatcctga acattgtgga tgatgaactc 360
acccgcggct taggagatta cattttgagt tgccaaactt atgaaggtgg cattggaggg 420
gaacctggct ccgaagctca tggtgggtac acgtactgtg ggttggctac tatgatttta 480
atcaatgaag tcgaccgctt gaatttggat tcgttaatga attgggttgt acatcgacaa 540
ggagtagaaa tgggattcca aggtaggacg aacaaattgg tcgacggttg ctacacgttt 600
tggcaggcag ccccctgtgt tctactacag cgattttttt catcccagga tatggcacct 660
catggatcat catcacatat gtcacaaggg acagatgaag atcacgagga acatggtcat 720
gatgaagatg atcctgaaga cagtgatgaa gatgattctg atgaggatag cgatgaagat 780
tcagggaatg gtcaccaagt tcatcatacg tctacctaca ttgacaggag aattcaacct 840
gtttttgata gcctcggctt gcaaagatat gtgctcttgt gctctcaggt tgctgatggt 900
ggattcagag acaagctgag gaaaccccgt gacttctacc acacatgtta ctgcctaagc 960
ggtctttccg tggctcaaca cgcttggtca aaagacgagg acactcctcc tttgactcgt 1020

-continued

```
gacattttgg gtggctacgc aaaccacctt gaacctgttc acctcctcca caacattgtc   1080

ttggatcggt attatgaagc ttctagattt                                    1110


<210> SEQ ID NO 15
<211> LENGTH: 370
<212> TYPE: PRT
<213> ORGANISM: Brassica napus

<400> SEQUENCE: 15

Trp Leu Cys Tyr Trp Ile Leu His Ser Ile Ala Leu Leu Gly Glu Ser
  1               5                  10                  15

Val Asp Asp Asp Leu Glu Asn Asn Ala Ile Asp Phe Leu Gly Arg Cys
             20                  25                  30

Gln Gly Ser Asp Gly Gly Tyr Gly Gly Gly Pro Gly Gln Leu Pro His
         35                  40                  45

Leu Ala Thr Ser Tyr Ala Ala Val Asn Thr Leu Val Thr Leu Gly Gly
     50                  55                  60

Glu Lys Ala Phe Ser Ser Ile Asn Arg Glu Gln Met Ala Cys Phe Leu
 65                  70                  75                  80

Arg Arg Met Lys Asp Thr Asn Gly Gly Phe Arg Met His Asn Met Gly
                 85                  90                  95

Glu Ile Asp Val Arg Ala Cys Tyr Thr Ala Ile Leu Ile Ala Ser Ile
            100                 105                 110

Leu Asn Ile Val Asp Asp Glu Leu Thr Arg Gly Leu Gly Asp Tyr Ile
        115                 120                 125

Leu Ser Cys Gln Thr Tyr Glu Gly Gly Ile Gly Gly Glu Pro Gly Ser
    130                 135                 140

Glu Ala His Gly Gly Tyr Thr Tyr Cys Gly Leu Ala Thr Met Ile Leu
145                 150                 155                 160

Ile Asn Glu Val Asp Arg Leu Asn Leu Asp Ser Leu Met Asn Trp Val
                165                 170                 175

Val His Arg Gln Gly Val Glu Met Gly Phe Gln Gly Arg Thr Asn Lys
            180                 185                 190

Leu Val Asp Gly Cys Tyr Thr Phe Trp Gln Ala Ala Pro Cys Val Leu
        195                 200                 205

Leu Gln Arg Phe Phe Ser Ser Gln Asp Met Ala Pro His Gly Ser Ser
    210                 215                 220

Ser His Met Ser Gln Gly Thr Asp Glu Asp His Glu Glu His Gly His
225                 230                 235                 240

Asp Glu Asp Asp Pro Glu Asp Ser Asp Glu Asp Asp Ser Asp Glu Asp
                245                 250                 255

Ser Asp Glu Asp Ser Gly Asn Gly His Gln Val His His Thr Ser Thr
            260                 265                 270

Tyr Ile Asp Arg Arg Ile Gln Pro Val Phe Asp Ser Leu Gly Leu Gln
        275                 280                 285

Arg Tyr Val Leu Leu Cys Ser Gln Val Ala Asp Gly Gly Phe Arg Asp
    290                 295                 300

Lys Leu Arg Lys Pro Arg Asp Phe Tyr His Thr Cys Tyr Cys Leu Ser
305                 310                 315                 320

Gly Leu Ser Val Ala Gln His Ala Trp Ser Lys Asp Glu Asp Thr Pro
                325                 330                 335

Pro Leu Thr Arg Asp Ile Leu Gly Gly Tyr Ala Asn His Leu Glu Pro
            340                 345                 350

Val His Leu Leu His Asn Ile Leu Val Asp Arg Tyr Tyr Glu Ala Ser
```

-continued

```
        355                 360                 365

Arg Phe
    370


<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 16

gccgacagtg gtcccaaaga tgg                                              23


<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 17

aaaggatcct caaattgctg ccactgtaat                                       30


<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 18

aaacccggga tgaatttcga cgagaacgtg                                       30


<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 19

gcaagaccgg caacagga                                                    18


<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 20

tttaagcttg acagaaacag tcagcgagac                                       30


<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 21

gctcttcctc catgccca                                                    18


<210> SEQ ID NO 22
```

-continued

<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 22
tttaagcttg gagccataga tgcaattcaa 30

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 23
cgggcattag gaggatggga a 21

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 24
gtccggaatt cccgggtc 18

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 25
ggatccatgg attacttccg tgcgatttac ttctcc 36

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 26
aaaaagcttc catgcccaat agttagctct tattggatc 39

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 27
aaaaagcttt ggctttgtta ctggattctt cattcaat 38

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 28

-continued

```
aaatctagaa gcttcataat accgatccaa gacaatgtt                      39


<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 29

aaaggatcca tggaatctgg gtctagcga                                 29


<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 30

aaatctagaa ggaagtctgc tcttgcgc                                  28


<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 31

aaatctagag ccaccattcc tcgcaacg                                  28


<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 32

aaagagctcg tggtggagaa tctgggtgc                                 29


<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 33

ggcggatccc gacctaccga gg                                        22


<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 34

aaagagctcg tggatggatt ggctccagc                                 29


<210> SEQ ID NO 35
<211> LENGTH: 822
<212> TYPE: DNA
```

-continued

```
<213> ORGANISM: Artificial Sequence
<220> FEATURE:
<223> OTHER INFORMATION: Description of Artificial Sequence: Compiment
      to SEQ ID NO: 12

<400> SEQUENCE: 35

ccatgcccaa tagttagctc ttattggatc aacacgacac agaatggtac acaccaaatt     60

ggccaagtta gtctctggtt cttcattagc tagagctttc accgagtctc tatgctcgtt    120

ggttggtctc aacccatcgc acagaagatc caaaagggtg ctcagagcga atccatggaa    180

gcagtccgcg cgtgagagaa ctttcaaaca gactgaggaa acacttggat cactaatcca    240

agactctgtg tcgtctttgt aaagggcttt caggtacctc caagagctct cgttcccggg    300

atttgctaaa atggctttga ctgtgtagct tacttcagat tctctcatgg cttctaggcc    360

tcccaacgaa ggtgatctag ttataacgta atacctctga ttccatgcag agttgttaaa    420

gacgtcagct tcaaggagct cgtggcagta gttaagctca ttttcccatc ctcctaatgc    480

ttgtagcgcc cactgcctat gtgaccaagc atgataatgc ttggcatcaa gtgatagtac    540

cctccgagta aactcaagtt cctttcctgc aacatcagga cccagtttct ctgcgaccca    600

tcgtcgatga tgccacaact ggtagttctt agagttatcc tcagcaatgc tttcgatgaa    660

cttgagctct tcatacaagt cgttattaag ctcctcgagt actaagcgcc cgaagtgcca    720

cacggtgtag ttgcccgagt ttaagcggag agcttcttcc gtgagtcgca gcgcgcgagc    780

agaacgctcg tcggagaagt aaatcgcacg gaagtaatcc at                       822


<210> SEQ ID NO 36
<211> LENGTH: 1110
<212> TYPE: DNA
<213> ORGANISM: Artificial Sequence
<220> FEATURE:
<223> OTHER INFORMATION: Description of Artificial Sequence: Compliment
      to SEQ ID NO: 14

<400> SEQUENCE: 36

aaatctagaa gcttcataat accgatccaa gacaatgttg tggaggaggt gaacaggttc     60

aaggtggttt gcgtagccac ccaaaatgtc acgagtcaaa ggaggagtgt cctcgtcttt    120

tgaccaagcg tgttgagcca cggaaagacc gcttaggcag taacatgtgt ggtagaagtc    180

acggggtttc ctcagcttgt ctctgaatcc accatcagca acctgagagc acaagagcac    240

atatctttgc aagccgaggc tatcaaaaac aggttgaatt ctcctgtcaa tgtaggtaga    300

cgtatgatga acttggtgac cattccctga atcttcatcg ctatcctcat cagaatcatc    360

ttcatcactg tcttcaggat catcttcatc atgaccatgt tcctcgtgat cttcatctgt    420

cccttgtgac atatgtgatg atgatccatg aggtgccata tcctgggatg aaaaaaatcg    480

ctgtagtaga acacaggggg ctgcctgcca aaacgtgtag caaccgtcga ccaatttgtt    540

cgtcctacct tggaatccca tttctactcc ttgtcgatgt acaacccaat tcattaacga    600

atccaaattc aagcggtcga cttcattgat taaaatcata gtagccaacc cacagtacgt    660

gtacccacca tgagcttcgg agccaggttc ccctccaatg ccaccttcat aagtttggca    720

actcaaaatg taatctccta agccgcgggt gagttcatca tccacaatgt tcaggatgct    780

tgcaatcaaa atcgcagtgt agcacgctcg cacatctatt tctcccatat tatgcatcct    840

gaaacctcca tttgtatcct tcattcgtct taagaaacaa gccatttgtt ctctgttaat    900

tgaagagaag gctttctcac ctcctaaagt aacaagtgta ttcactgcag cataacttgt    960

tgcaagatgt ggaagttggc caggaccacc accatatcca ccatcagaac cctggcaacg   1020
```

tccaagaaaa tcgattgcat tgttttctaa gtcatcatcc acagactccc caagcaaagc 1080
aattgaatga agaatccagt aacaaagcca 1110

<210> SEQ ID NO 37
<211> LENGTH: 1041
<212> TYPE: DNA
<213> ORGANISM: Glycine max
<220> FEATURE:
<221> NAME/KEY: misc_feature
<222> LOCATION: (360)
<223> OTHER INFORMATION: Wherein n is a or t or c or g.

<400> SEQUENCE: 37
atggaatctg ggtctagcga aggagaagag gtgcagcaac gcgtgccgtt gagggagaga 60
gtggagtggt cagatgttac tccggttcct caaaacgacg gccctaaccc tgtcgttccg 120
atccagtaca ctgaagagtt ttccgaagtt atggattact ttcgcgccgt ttacctcacc 180
gatgaacgct cccctcgcgc cctcgctctc acagccgaag ccgttcaatt caactccggc 240
aactacactg tgtggcattt ccgacggttg ttacttgagt cgctaaaagt cgacttgaac 300
gatgaactgg agtttgtgga gcgtatggcc gctggaaatt ctaaaaatta tcagatgtgn 360
atgttctgta ggcatcctag acgatgggtt gccgagaagt taggtcctga agctagaaac 420
aatgagctcg agttcaccaa aaagatactg tccgttgatg ccaaacatta tcatgcatgg 480
tctcatagac agtgggctct tcaaacacta ggaggatggg aagatgaact taattattgc 540
acagaactac ttaaagaaga catttttaac aattctgctt ggaatcagag atattttgtc 600
ataacaaggt ctcctttctt ggggggccta aaagctatga gagagtctga agtgctttac 660
accatcgaag ccattatagc ctaccctgaa aatgaaagct cgtggagata tctacgagga 720
ctttataaag gtgaaactac ttcatgggta aatgatcctc aagtttcttc agtatgctta 780
aagattttga gaactaagag caactacgtg tttgctctta gcactatttt agatcttata 840
tgctttggtt atcaaccaaa tgaagacatt agagatgcca ttgacgcctt aaagaccgca 900
gatatggata aacaagattt agatgatgat gagaaagggg aacaacaaaa tttaaatata 960
gcacgaaata tttgttctat cctaaaacaa gttgatccaa ttagaaccaa ctattggatt 1020
tggcgcaaga gcagacttcc t 1041

<210> SEQ ID NO 38
<211> LENGTH: 1041
<212> TYPE: DNA
<213> ORGANISM: Artificial Sequence
<220> FEATURE:
<223> OTHER INFORMATION: Description of Artificial Sequence: Compliment
to SEQ ID NO: 37
<220> FEATURE:
<221> NAME/KEY: misc_feature
<222> LOCATION: (682)
<223> OTHER INFORMATION: Wherein n is a or t or c or g.

<400> SEQUENCE: 38
aggaagtctg ctcttgcgcc aaatccaata gttggttcta attggatcaa cttgttttag 60
gatagaacaa atatttcgtg ctatatttaa attttgttgt tccccttttct catcatcatc 120 taaatcttgt ttatccatat ctgcggtctt taaggcgtca atggcatctc taatgtcttc 180
atttggttga taaccaaagc atataagatc taaaatagtg ctaagagcaa acacgtagtt 240
gctcttagtt ctcaaaatct ttaagcatac tgaagaaact tgaggatcat ttacccatga 300
agtagtttca cctttataaa gtcctcgtag atatctccac gagctttcat tttcagggta 360

-continued

```
ggctataatg gcttcgatgg tgtaaagcac ttcagactct ctcatagctt ttaggccccc    420

caagaaagga gaccttgtta tgacaaaata tctctgattc caagcagaat tgttaaaaat    480

gtcttcttta agtagttctg tgcaataatt aagttcatct tcccatcctc ctagtgtttg    540

aagagcccac tgtctatgag accatgcatg ataatgtttg gcatcaacgg acagtatctt    600

tttggtgaac tcgagctcat tgtttctagc ttcaggacct aacttctcgg caacccatcg    660

tctaggatgc ctacagaaca tncacatctg ataattttta gaatttccag cggccatacg    720

ctccacaaac tccagttcat cgttcaagtc gacttttagc gactcaagta acaaccgtcg    780

gaaatgccac acagtgtagt tgccggagtt gaattgaacg gcttcggctg tgagagcgag    840

ggcgcgaggg gagcgttcat cggtgaggta aacggcgcga aagtaatcca taacttcgga    900

aaactcttca gtgtactgga tcggaacgac agggttaggg ccgtcgtttt gaggaaccgg    960

agtaacatct gaccactcca ctctctccct caacggcacg cgttgctgca cctcttctcc   1020

ttcgctagac ccagattcca t                                             1041
```

<210> SEQ ID NO 39
<211> LENGTH: 347
<212> TYPE: PRT
<213> ORGANISM: Glycine max
<220> FEATURE:
<221> NAME/KEY: VARIANT
<222> LOCATION: (120)
<223> OTHER INFORMATION: Wherein Xaa is any amino acid.

<400> SEQUENCE: 39

```
Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
             20                  25                  30

Asp Gly Pro Asn Pro Val Val Pro Ile Gln Tyr Thr Glu Glu Phe Ser
         35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Glu Phe Val Glu Arg Met Ala Ala Gly
            100                 105                 110

Asn Ser Lys Asn Tyr Gln Met Xaa Met Phe Cys Arg His Pro Arg Arg
        115                 120                 125

Trp Val Ala Glu Lys Leu Gly Pro Glu Ala Arg Asn Asn Glu Leu Glu
    130                 135                 140

Phe Thr Lys Lys Ile Leu Ser Val Asp Ala Lys His Tyr His Ala Trp
145                 150                 155                 160

Ser His Arg Gln Trp Ala Leu Gln Thr Leu Gly Gly Trp Glu Asp Glu
                165                 170                 175

Leu Asn Tyr Cys Thr Glu Leu Leu Lys Glu Asp Ile Phe Asn Asn Ser
            180                 185                 190

Ala Trp Asn Gln Arg Tyr Phe Val Ile Thr Arg Ser Pro Phe Leu Gly
        195                 200                 205

Gly Leu Lys Ala Met Arg Glu Ser Glu Val Leu Tyr Thr Ile Glu Ala
    210                 215                 220
```

-continued

```
Ile Ile Ala Tyr Pro Glu Asn Glu Ser Ser Trp Arg Tyr Leu Arg Gly
225                 230                 235                 240

Leu Tyr Lys Gly Glu Thr Thr Ser Trp Val Asn Asp Pro Gln Val Ser
                245                 250                 255

Ser Val Cys Leu Lys Ile Leu Arg Thr Lys Ser Asn Tyr Val Phe Ala
            260                 265                 270

Leu Ser Thr Ile Leu Asp Leu Ile Cys Phe Gly Tyr Gln Pro Asn Glu
        275                 280                 285

Asp Ile Arg Asp Ala Ile Asp Ala Leu Lys Thr Ala Asp Met Asp Lys
    290                 295                 300

Gln Asp Leu Asp Asp Asp Glu Lys Gly Glu Gln Gln Asn Leu Asn Ile
305                 310                 315                 320

Ala Arg Asn Ile Cys Ser Ile Leu Lys Gln Val Asp Pro Ile Arg Thr
                325                 330                 335

Asn Tyr Trp Ile Trp Arg Lys Ser Arg Leu Pro
            340                 345
```

<210> SEQ ID NO 40
<211> LENGTH: 1135
<212> TYPE: DNA
<213> ORGANISM: Glycine max

<400> SEQUENCE: 40

```
gccaccattc ctcgcaacgc ccaaaccctc atgttggagc ttcaacgcga taatcacatg      60

cagtatgtct ccaaaggcct tcgccatctc agttccgcat tttccgtttt ggacgctaat     120

cgaccctggc tctgctactg gatcttccac tccattgctt tgttgggaga atccgtcgat     180

gatgaactcg aagataacgc tatcgatttt cttaaccgtt gccaggatcc gaatggtgga     240

tatgccgggg gaccaggcca gatgcctcat attgccacaa cttatgctgc tgttaattca     300

cttattactt tgggtggtga gaaatccctg gcatcaatta atagagataa actgtatggg     360

tttctgcggc ggatgaagca accaaatggt ggattcagga tgcatgatga aggtgaaatt     420

gatgttcgag cttgctacac tgccatttct gttgcaagtg ttttgaacat tttggatgat     480

gagctgatcc agaatgttgg agactacatt ataagctgtc aaacatatga gggtggcatt     540

gctggtgagc ctggttctga ggctcatggt gggtacacct tttgtggatt agctacaatg     600

attctgattg gtgaggttaa tcacttggat ctgcctcgat tagttgactg ggtggtattc     660

cgacaaggta aggaatgtgg attccagggg agaacaaata aactggtgga tggatgctat     720

tccttttggc agggaggtgc tgttgctcta ttgcaaagat tatcttctat tatcaacaaa     780

cagatggaag agacatcaca gatttttgcg gtatcttatg tatctgaagc aaaagaaagt     840

ttggatggaa cctctagtca tgcaacatgc cgtggtgagc atgaaggcac cagtgaatcc     900

agttcatctg attttaaaaa tattgcctat aaatttatta atgagtggag agcacaagaa     960

ccactttttc acagtattgc tttacagcaa tatattctct tatgtgcaca ggagcaagag    1020

ggtggactga gagacaaacc gggtaaacgt agagatcatt atcacacatg ttactgttta    1080

agtggactct cattgtgcca gtatagttgg tcaaagcacc cagattctcc accac         1135
```

<210> SEQ ID NO 41
<211> LENGTH: 1135
<212> TYPE: DNA
<213> ORGANISM: Artificial Sequence
<220> FEATURE:
<223> OTHER INFORMATION: Description of Artificial Sequence: Compliment
      to SEQ ID NO: 40

-continued

```
<400> SEQUENCE: 41

gtggtggaga atctgggtgc tttgaccaac tatactggca caatgagagt ccacttaaac      60

agtaacatgt gtgataatga tctctacgtt tacccggttt gtctctcagt ccaccctctt     120

gctcctgtgc acataagaga atatattgct gtaaagcaat actgtgaaaa agtggttctt     180

gtgctctcca ctcattaata aatttatagg caatattttt aaaatcagat gaactggatt     240

cactggtgcc ttcatgctca ccacggcatg ttgcatgact agaggttcca tccaaacttt     300

cttttgcttc agatacataa gataccgcaa aaatctgtga tgtctcttcc atctgtttgt     360

tgataataga agataatctt tgcaatagag caacagcacc tccctgccaa aaggaatagc     420

atccatccac cagtttattt gttctcccct ggaatccaca ttccttacct tgtcggaata     480

ccacccagtc aactaatcga ggcagatcca agtgattaac ctcaccaatc agaatcattg     540

tagctaatcc acaaaaggtg tacccaccat gagcctcaga accaggctca ccagcaatgc     600

caccctcata tgtttgacag cttataatgt agtctccaac attctggatc agctcatcat     660

ccaaaatgtt caaaacactt gcaacagaaa tggcagtgta gcaagctcga acatcaattt     720

caccttcatc atgcatcctg aatccaccat ttggttgctt catccgccgc agaaacccat     780

acagtttatc tctattaatt gatgccaggg atttctcacc acccaaagta ataagtgaat     840

taacagcagc ataagttgtg gcaatatgag gcatctggcc tggtccccg gcatatccac      900

cattcggatc ctggcaacgg ttaagaaaat cgatagcgtt atcttcgagt tcatcatcga     960

cggattctcc caacaaagca atggagtgga agatccagta gcagagccag ggtcgattag    1020

cgtccaaaac ggaaaatgcg gaactgagat ggcgaaggcc tttggagaca tactgcatgt    1080

gattatcgcg ttgaagctcc aacatgaggg tttgggcgtt gcgaggaatg gtggc         1135

<210> SEQ ID NO 42
<211> LENGTH: 378
<212> TYPE: PRT
<213> ORGANISM: Glycine max

<400> SEQUENCE: 42

Ala Thr Ile Pro Arg Asn Ala Gln Thr Leu Met Leu Glu Leu Gln Arg
  1               5                  10                  15

Asp Asn His Met Gln Tyr Val Ser Lys Gly Leu Arg His Leu Ser Ser
             20                  25                  30

Ala Phe Ser Val Leu Asp Ala Asn Arg Pro Trp Leu Cys Tyr Trp Ile
         35                  40                  45

Phe His Ser Ile Ala Leu Leu Gly Glu Ser Val Asp Asp Glu Leu Glu
     50                  55                  60

Asp Asn Ala Ile Asp Phe Leu Asn Arg Cys Gln Asp Pro Asn Gly Gly
 65                  70                  75                  80

Tyr Ala Gly Gly Pro Gly Gln Met Pro His Ile Ala Thr Thr Tyr Ala
                 85                  90                  95

Ala Val Asn Ser Leu Ile Thr Leu Gly Gly Glu Lys Ser Leu Ala Ser
            100                 105                 110

Ile Asn Arg Asp Lys Leu Tyr Gly Phe Leu Arg Arg Met Lys Gln Pro
        115                 120                 125

Asn Gly Gly Phe Arg Met His Asp Glu Gly Glu Ile Asp Val Arg Ala
    130                 135                 140

Cys Tyr Thr Ala Ile Ser Val Ala Ser Val Leu Asn Ile Leu Asp Asp
145                 150                 155                 160

Glu Leu Ile Gln Asn Val Gly Asp Tyr Ile Ile Ser Cys Gln Thr Tyr
```

-continued

```
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240

Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270

Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375
```

<210> SEQ ID NO 43
<211> LENGTH: 1245
<212> TYPE: DNA
<213> ORGANISM: Zea mays

<400> SEQUENCE: 43

```
ggcggatccc gacctaccga ggctcacggt gacgcaggtg gagcagatga aggtggaggc     60

cagggttggc gacatctacc gctccctctt cggggccgcg cccaacacga aatccatcat    120

gctagagctg tggcgtgatc agcatatcga gtatctgacg cctgggctga ggcatatggg    180

accagccttt catgttctag atgccaatcg cccttggcta tgctactgga tggttcatcc    240

acttgctttg ctggatgaag cacttgatga tgatcttgag aatgatatca tagacttctt    300

agctcgatgt caggataaag atggtggata tagtggtgga cctggacagt tgcctcacct    360

agctacgact tatgctgctg taaatacact tgtgacaata gggagcgaaa gagcattgtc    420

atcaatcaat aggggcaacc tgtacaattt tatgctgcag atgaaagatg tatcaggtgc    480

tttcagaatg catgatggtg gcgaaattga tgtccgtgct tcctacaccg ctatatcggt    540

tgccagcctt gtgaatattc ttgattttaa actggcaaaa ggtgtaggcg actacatagc    600

aagatgtcaa acttatgaag gtggtattgc tggggagcct tatgctgaag cacatggtgg    660

gtatacattc tgtggattgg ctgctttgat cctgcttaat gaggcagaga aagttgactt    720

gcctagtttg attggctggg tggcttttcg tcaaggagtg gaatgcggat ttcaaggacg    780

aactaataaa ttggttgatg gttgctactc cttttggcag ggagctgcca ttgctttcac    840

acaaaagtta attacgattg ttgataagca attgaggtcc tcgtattcct gcaaaaggcc    900
```

-continued

```
atcaggagag gatgcctgca gcaccagttc atatgggtgc accgcgaata agtcttcctc    960

tgctgtggac tatgcgaagt ttggatttga ttttatacaa cagagcaacc aaattggccc   1020

actcttccat aacattgccc tgcaacaata catcctactt tgttctcagg tactagaggg   1080

aggcttgagg gataagcctg gaaagaacag agatcactat cattcatgct actgcctcag   1140

tggcctcgca gttagccagt acagtgccat gactgatact ggttcgtgcc cattacctca   1200

gcatgtgctt ggaccgtact ctaatttgct ggagccaatc catcc                   1245
```

<210> SEQ ID NO 44
<211> LENGTH: 1245
<212> TYPE: DNA
<213> ORGANISM: Artificial Sequence
<220> FEATURE:
<223> OTHER INFORMATION: Description of Artificial Sequence: Compliment to SEQ ID NO: 43

<400> SEQUENCE: 44

```
ggatggattg gctccagcaa attagagtac ggtccaagca catgctgagg taatgggcac     60

gaaccagtat cagtcatggc actgtactgg ctaactgcga ggccactgag gcagtagcat    120

gaatgatagt gatctctgtt ctttccaggc ttatccctca agcctccctc tagtacctga    180

gaacaaagta ggatgtattg ttgcagggca atgttatgga agagtgggcc aatttggttg    240

ctctgttgta taaaatcaaa tccaaacttc gcatagtcca cagcagagga agacttattc    300

gcggtgcacc catatgaact ggtgctgcag gcatcctctc ctgatggcct tttgcaggaa    360

tacgaggacc tcaattgctt atcaacaatc gtaattaact tttgtgtgaa agcaatggca    420

gctccctgcc aaaaggagta gcaaccatca accaatttat tagttcgtcc ttgaaatccg    480

cattccactc cttgacgaaa agccacccag ccaatcaaac taggcaagtc aactttctct    540

gcctcattaa gcaggatcaa agcagccaat ccacagaatg tatacccacc atgtgcttca    600

gcataaggct ccccagcaat accaccttca taagtttgac atcttgctat gtagtcgcct    660

acaccttttg ccagtttaaa atcaagaata ttcacaaggc tggcaaccga tatagcggtg    720

taggaagcac ggacatcaat ttcgccacca tcatgcattc tgaaagcacc tgatacatct    780

ttcatctgca gcataaaatt gtacaggttg cccctattga ttgatgacaa tgctctttcg    840

ctccctattg tcacaagtgt atttacagca gcataagtcg tagctaggtg aggcaactgt    900

ccaggtccac cactatatcc accatcttta tcctgacatc gagctaagaa gtctatgata    960

tcattctcaa gatcatcatc aagtgcttca tccagcaaag caagtggatg aaccatccag   1020

tagcatagcc aagggcgatt ggcatctaga acatgaaagg ctggtcccat atgcctcagc   1080

ccaggcgtca gatactcgat atgctgatca cgccacagct ctagcatgat ggatttcgtg   1140

ttgggcgcgg ccccgaagag ggagcggtag atgtcgccaa ccctggcctc caccttcatc   1200

tgctccacct gcgtcaccgt gagcctcggt aggtcgggat ccgcc                   1245
```

<210> SEQ ID NO 45
<211> LENGTH: 414
<212> TYPE: PRT
<213> ORGANISM: Zea mays

<400> SEQUENCE: 45

```
Ala Asp Pro Asp Leu Pro Arg Leu Thr Val Thr Gln Val Glu Gln Met
  1               5                  10                  15

Lys Val Glu Ala Arg Val Gly Asp Ile Tyr Arg Ser Leu Phe Gly Ala
             20                  25                  30
```

-continued

```
Ala Pro Asn Thr Lys Ser Ile Met Leu Glu Leu Trp Arg Asp Gln His
        35                  40                  45

Ile Glu Tyr Leu Thr Pro Gly Leu Arg His Met Gly Pro Ala Phe His
    50                  55                  60

Val Leu Asp Ala Asn Arg Pro Trp Leu Cys Tyr Trp Met Val His Pro
65                  70                  75                  80

Leu Ala Leu Leu Asp Glu Ala Leu Asp Asp Asp Leu Glu Asn Asp Ile
                85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn
        115                 120                 125

Thr Leu Val Thr Ile Gly Ser Glu Arg Ala Leu Ser Ser Ile Asn Arg
    130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190

Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Arg Ser Ser Tyr Ser Cys Lys Arg Pro Ser Gly Glu Asp
    290                 295                 300

Ala Cys Ser Thr Ser Ser Tyr Gly Cys Thr Ala Asn Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380

Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410
```

<210> SEQ ID NO 46
<211> LENGTH: 5247
<212> TYPE: DNA
<213> ORGANISM: Artificial Sequence
<220> FEATURE:
<223> OTHER INFORMATION: Description of Artificial Sequence: Plasmid -continued pBI121-35S-AtFTA

<400> SEQUENCE: 46

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
```

-continued ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tccatgaatt tcgacgagac cgtgccactg 3360
agccaacgat tggagtggtc agacgtggtc ccattgactc aggacgatgg tccgaatcca 3420
gtggtgccaa ttgcctacaa ggaagagttc cgcgagacta tggattactt ccgtgcgatt 3480
tacttttccg acgagcgatc tcctcgcgca ctacgactca cggaagaaac cctcctctta 3540
aactccggca actacacagt gtggcatttc aggcgcctag tactcgaggc ccttaatcac 3600
gacttgtttg aagaactcga gttcatcgaa cgcattgctg aggataactc taagaactac 3660
caactgtggc atcatcggcg atgggttgca gagaaactgg gtcctgatgt tgcagggaga 3720
gaacttgaat ttacccgtag agtactttca cttgatgcca aacattatca tgcttggtca 3780
cataggcagt ggacactacg ggcattagga ggatgggaag atgagctcga ttactgtcac 3840
gagctccttg aagctgacgt ctttaacaat tccgcctgga atcagaggta ttatgtcatc 3900
acccaatctc ctttgttggg aggcctagaa gccatgagag aatctgaagt aagctacaca 3960
atcaaagcca ttttaaccaa tcctgcaaac gagagctcat ggcgatacct aaaagctctt 4020
tacaaagacg acaaagaatc ctggattagt gatccaagtg tttcctcagt ctgtttgaat 4080
gttctatccc gcacagattg cttccatgga ttcgctctga gcaccctttt ggatcttcta 4140
tgtgatggac tgagaccaac caacgagcat aaagactcag tgagagctct agctaatgaa 4200
gaaccagaga ctaacttggc caatttggtg tgtactattc ttggtcgtgt agatcctgta 4260
agagctaact attgggcatg gaggaagagc aagattacag tggcagcaat ttgactcgaa 4320
tttccccgat cgttcaaaca tttggcaata aagtttctta agattgaatc ctgttgccgg 4380
tcttgcgatg attatcatat aatttctgtt gaattacgtt aagcatgtaa taattaacat 4440
gtaatgcatg acgttattta tgagatgggt ttttatgatt agagtcccgc aattatacat 4500
ttaatacgcg atagaaaaca aaatatagcg cgcaaactag gataaattat cgcgcgcggt 4560
gtcatctatg ttactagatc gggaattcac tggccgtcgt tttacaacgt cgtgactggg 4620

-continued aaaaccctgg cgttacccaa cttaatcgcc ttgcagcaca tccccctttc gccagctggc 4680
gtaatagcga agaggcccgc accgatcgcc cttcccaaca gttgcgcagc ctgaatggcg 4740
cccgctcctt tcgctttctt cccttccttt ctcgccacgt tcgccggctt tccccgtcaa 4800
gctctaaatc gggggctccc tttagggttc cgatttagtg ctttacggca cctcgacccc 4860
aaaaaacttg atttgggtga tggttcacgt agtgggccat cgccctgata gacggttttt 4920
cgccctttga cgttggagtc cacgttcttt aatagtggac tcttgttcca aactggaaca 4980
acactcaacc ctatctcggg ctattctttt gatttataag ggattttgcc gatttcggaa 5040
ccaccatcaa acaggatttt cgcctgctgg ggcaaaccag cgtggaccgc ttgctgcaac 5100
tctctcaggg ccaggcggtg aagggcaatc agctgttgcc cgtctcactg gtgaaaagaa 5160
aaaccacccc agtacattaa aaacgtccgc aatgtgttat taagttgtct aagcgtcaat 5220
ttgtttacac cacaatatat cctgcca 5247

<210> SEQ ID NO 47
<211> LENGTH: 5373
<212> TYPE: DNA
<213> ORGANISM: Artificial Sequence
<220> FEATURE:
<223> OTHER INFORMATION: Description of Artificial Sequence: Plasmid
pBI121-rd29A-anti-AtFTA

<400> SEQUENCE: 47
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380

-continued

```
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa agactctaga ggatcctcaa attgctgcca ctgtaatctt   3480
gctcttcctc catgcccaat agttagctct tataggatct acacgaccaa gaatagtaca   3540
caccaaattg gccaagttag tctctggttc ttcattagct agagctctca ctgagtcttt   3600
atgctcgttg gttggtctca gtccatcaca tagaagatcc aaaagggtgc tcagagcgaa   3660
tccatggaag caatctgtgc gggatagaac attcaaacag actgaggaaa cacttggatc   3720
actaatccag gattctttgt cgtctttgta aagcgctttt aggtatcgcc atgagctctc   3780
```

-continued

```
gtttgcagga ttggttaaaa tggctttgat tgtgtagctt acttcagatt ctctcatggc   3840

ttctaggcct cccaacaaag gagattgggt gatgacataa tacctctgat tccaggcgga   3900

attgttaaag acgtcagctt caaggagctc gtgacagtaa tcgagctcat cttcccatcc   3960

tcctaatgcc cgtagtgtcc actgcctatg tgaccaagca tgataatgtt tggcatcaag   4020

tgaaagtact ctacgggtaa attcaagttc tctccctgca acatcaggac ccagtttctc   4080

tgcaacccat cgccgatgat gccacagttg gtagttctta gagttatcct cagcaatgcg   4140

ttcgatgaac tcgagttctt caaacaagtc gtgattaagg gcctcgagta ctaggcgcct   4200

gaaatgccac actgtgtagt tgccggagtt taagaggagg gtttcttccg tgagtcgtag   4260

tgcgcgagga gatcgctcgt cggaaaagta aatcgcacgg aagtaatcca tagtctcgcg   4320

gaactcttcc ttgtaggcaa ttggcaccac tggattcgga ccatcgtcct gagtcaatgg   4380

gaccacgtct gaccactcca atcgttggct cagtggcacg gtctcgtcga aattcatccc   4440

ctcgaatttc cccgatcgtt caaacatttg gcaataaagt ttcttaagat tgaatcctgt   4500

tgccggtctt gcgatgatta tcatataatt tctgttgaat tacgttaagc atgtaataat   4560

taacatgtaa tgcatgacgt tatttatgag atgggttttt atgattagag tcccgcaatt   4620

atacatttaa tacgcgatag aaaacaaaat atagcgcgca aactaggata aattatcgcg   4680

cgcggtgtca tctatgttac tagatcggga attcactggc cgtcgtttta caacgtcgtg   4740

actgggaaaa ccctggcgtt acccaactta atcgccttgc agcacatccc cctttcgcca   4800

gctggcgtaa tagcgaagag gcccgcaccg atcgcccttc ccaacagttg cgcagcctga   4860

atggcgcccg ctcctttcgc tttcttccct tcctttctcg ccacgttcgc cggctttccc   4920

cgtcaagctc taaatcgggg gctcccttta gggttccgat ttagtgcttt acggcacctc   4980

gaccccaaaa aacttgattt gggtgatggt tcacgtagtg ggccatcgcc ctgatagacg   5040

gtttttcgcc ctttgacgtt ggagtccacg ttctttaata gtggactctt gttccaaact   5100

ggaacaacac tcaaccctat ctcgggctat tcttttgatt tataagggat tttgccgatt   5160

tcggaaccac catcaaacag gattttcgcc tgctggggca aaccagcgtg gaccgcttgc   5220

tgcaactctc tcagggccag gcggtgaagg gcaatcagct gttgcccgtc tcactggtga   5280

aaagaaaaac caccccagta cattaaaaac gtccgcaatg tgttattaag ttgtctaagc   5340

gtcaatttgt ttacaccaca atatatcctg cca                                5373


<210> SEQ ID NO 48
<211> LENGTH: 6285
<212> TYPE: DNA
<213> ORGANISM: Artificial Sequence
<220> FEATURE:
<223> OTHER INFORMATION: Description of Artificial Sequence: Plasmid
      pBI121-35A-DA-AtFTA

<400> SEQUENCE: 48

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420
```

-continued

```
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
```

-continued

```
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcgctct tcctccatgc ccaatagtta   3360
gctcttacag gatctacacg accaagaata gtacacacca aattggccaa gttagtctct   3420
ggttcttcat tagctagagc tctcactgag tctttatgct cgttggttgg tctcagtcca   3480
tcacatagaa gatccaaaag ggtgctcaga gcgaatccat ggaagcaatc tgtgcgggat   3540
agaacattca aacagactga ggaaacactt ggatcactaa tccaggattc tttgtcgtct   3600
ttgtaaagag cttttaggta tcgccatgag ctctcgtttg caggattggt taaaatggct   3660
ttgattgtgt agcttacttc agattctctc atggcttcta ggcctcccaa caaaggagat   3720
tgggtgatga cataatacct ctgattccag gcggaattgt taaagacgtc agcttcaagg   3780
agctcgtgac agtaatcgag ctcatcttcc catcctccta atgcccggag gatccccatc   3840
tacccgcttc gcgtcggcat ccggtcagtg gcagtgaagg gcgaacagtt cctgattaac   3900
cacaaaccgt tctactttac tggctttggt cgtcatgaag atgcggactt gcgtggcaaa   3960
ggattcgata acgtgctgat ggtgcacgac cacgcattaa tggactggat tggggccaac   4020
tcctaccgta cctcgcatta cccttacgct gaagagatgc tcgactgggc agatgaacat   4080
ggcatcgtgg tgattgatga aactgctgct gtcggctttt cgctctcttt aggcattggt   4140
ttcgaagcgg gcaacaagcc gaaagaactg tacagcgaag aggcagtcaa cggggaaact   4200
cagcaagcgc acttacaggc gattaaagag ctgatagcgc gtgacaaaaa ccacccaagc   4260
gtggtgatgt ggagtattgc caacgaaccg gatacccgtc cgcaaggtgc acgggaatat   4320
ttcgcgccac tggcggaagc aacgcgtaaa ctcgacccga cgcgtccgat cacctgcgtc   4380
aatgtaatgt tctgcgacgc tcacaccgat accatcagcg atctctttga tgtgctgtgc   4440
ctgaaccgtt attacggatg gtatgtccaa agcggcgatt tggaaacggc agagaaggta   4500
ctggaaaaag aacttctggc ctggcaggag aaactgtaca ccgacatgtg gagtgaagag   4560
tatcagtgtg catggctgga tatgtatcac cgcgtctttg atcgcgtcag cgccgtcgtc   4620
ggtgaacagg tatggaattt cgccgatttt gcgacctcgc aaggcatatt gcgcgttggc   4680
ggtaacaaga aagggatctt cactcgcgac cgcaaaccga agtcggcggc ttttctgctg   4740
caaaaacgct ggactggcat gaacttcggt gaaaaaccgc agcagggagg caaacaatga   4800
atcaacaact ctcctggcgc accatcgtcg gctacagcct cgggaattgc taccgagctc   4860
gctcttcctc catgcccaat agttagctct tacaggatct acacgaccaa gaatagtaca   4920
caccaaattg gccaagttag tctctggttc ttcattagct agagctctca ctgagtcttt   4980
atgctcgttg gttggtctca gtccatcaca tagaagatcc aaaagggtgc tcagagcgaa   5040
tccatggaag caatctgtgc gggatagaac attcaaacag actgaggaaa cacttggatc   5100
actaatccag gattctttgt cgtctttgta aagagctttt aggtatcgcc atgagctctc   5160
```

-continued gtttgcagga ttggttaaaa tggctttgat tgtgtagctt acttcagatt ctctcatggc 5220
ttctaggcct cccaacaaag gagattgggt gatgacataa tacctctgat tccaggcgga 5280
attgttaaag acgtcagctt caaggagctc gtgacagtaa tcgagctcat cttcccatcc 5340
tcctaatgcc cgctcgaatt tccccgatcg ttcaaacatt tggcaataaa gtttcttaag 5400
attgaatcct gttgccggtc ttgcgatgat tatcatataa tttctgttga attacgttaa 5460
gcatgtaata attaacatgt aatgcatgac gttatttatg agatgggttt ttatgattag 5520
agtcccgcaa ttatacattt aatacgcgat agaaaacaaa atatagcgcg caaactagga 5580
taaattatcg cgcgcggtgt catctatgtt actagatcgg gaattcactg gccgtcgttt 5640
tacaacgtcg tgactgggaa aaccctggcg ttacccaact taatcgcctt gcagcacatc 5700 ccccttttcgc cagctggcgt aatagcgaag aggcccgcac cgatcgccct tcccaacagt 5760
tgcgcagcct gaatggcgcc cgctcctttc gctttcttcc cttcctttct cgccacgttc 5820
gccggctttc cccgtcaagc tctaaatcgg gggctccctt tagggttccg atttagtgct 5880
ttacggcacc tcgaccccaa aaaacttgat ttgggtgatg gttcacgtag tgggccatcg 5940
ccctgataga cggtttttcg ccctttgacg ttggagtcca cgttctttaa tagtggactc 6000
ttgttccaaa ctggaacaac actcaaccct atctcgggct attcttttga tttataaggg 6060
attttgccga tttcggaacc accatcaaac aggattttcg cctgctgggg caaaccagcg 6120
tggaccgctt gctgcaactc tctcagggcc aggcggtgaa gggcaatcag ctgttgcccg 6180
tctcactggt gaaaagaaaa accaccccag tacattaaaa acgtccgcaa tgtgttatta 6240
agttgtctaa gcgtcaattt gtttacacca caatatatcc tgcca 6285

<210> SEQ ID NO 49
<211> LENGTH: 6409
<212> TYPE: DNA
<213> ORGANISM: Artificial Sequence
<220> FEATURE:
<223> OTHER INFORMATION: Description of Artificial Sequence: Plasmid pBI121-RD29A-DA-AtFTA

<400> SEQUENCE: 49
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900

-continued

```
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
```

-continued aaaagatcaa gccgacacag acacgcgtag agagcaaaat gactttgacg tcacaccacg 3300
aaaacagacg cttcatacgt gtccctttat ctctctcagt ctctctataa acttagtgag 3360
accctcctct gttttactca caaatatgca aactagaaaa caatcatcag gaataaaggg 3420
tttgattact tctattggaa aggactctag aggatcctcg ctcttcctcc atgcccaata 3480
gttagctctt acaggatcta cacgaccaag aatagtacac accaaattgg ccaagttagt 3540
ctctggttct tcattagcta gagctctcac tgagtcttta tgctcgttgg ttggtctcag 3600
tccatcacat agaagatcca aaagggtgct cagagcgaat ccatggaagc aatctgtgcg 3660
ggatagaaca ttcaaacaga ctgaggaaac acttggatca ctaatccagg attctttgtc 3720
gtctttgtaa agagctttta ggtatcgcca tgagctctcg tttgcaggat tggttaaaat 3780
ggctttgatt gtgtagctta cttcagattc tctcatggct tctaggcctc ccaacaaagg 3840
agattgggtg atgacataat acctctgatt ccaggcggaa ttgttaaaga cgtcagcttc 3900
aaggagctcg tgacagtaat cgagctcatc ttcccatcct cctaatgccc ggaggatccc 3960
catctacccg cttcgcgtcg gcatccggtc agtggcagtg aagggcgaac agttcctgat 4020
taaccacaaa ccgttctact ttactggctt tggtcgtcat gaagatgcgg acttgcgtgg 4080
caaaggattc gataacgtgc tgatggtgca cgaccacgca ttaatggact ggattggggc 4140
caactcctac cgtacctcgc attaccctta cgctgaagag atgctcgact gggcagatga 4200
acatggcatc gtggtgattg atgaaactgc tgctgtcggc ttttcgctct ctttaggcat 4260
tggtttcgaa gcgggcaaca agccgaaaga actgtacagc gaagaggcag tcaacgggga 4320
aactcagcaa gcgcacttac aggcgattaa agagctgata gcgcgtgaca aaaaccaccc 4380
aagcgtggtg atgtggagta ttgccaacga accggatacc cgtccgcaag gtgcacggga 4440
atatttcgcg ccactggcgg aagcaacgcg taaactcgac ccgacgcgtc cgatcacctg 4500
cgtcaatgta atgttctgcg acgctcacac cgataccatc agcgatctct ttgatgtgct 4560
gtgcctgaac cgttattacg gatggtatgt ccaaagcggc gatttggaaa cggcagagaa 4620
ggtactggaa aaagaacttc tggcctggca ggagaaactg tacaccgaca tgtggagtga 4680
agagtatcag tgtgcatggc tggatatgta tcaccgcgtc tttgatcgcg tcagcgccgt 4740
cgtcggtgaa caggtatgga atttcgccga ttttgcgacc tcgcaaggca tattgcgcgt 4800
tggcggtaac aagaaaggga tcttcactcg cgaccgcaaa ccgaagtcgg cggcttttct 4860
gctgcaaaaa cgctggactg gcatgaactt cggtgaaaaa ccgcagcagg gaggcaaaca 4920
atgaatcaac aactctcctg gcgcaccatc gtcggctaca gcctcgggaa ttgctaccga 4980
gctcgctctt cctccatgcc caatagttag ctcttacagg atctacacga ccaagaatag 5040
tacacaccaa attggccaag ttagtctctg gttcttcatt agctagagct ctcactgagt 5100
ctttatgctc gttggttggt ctcagtccat cacatagaag atccaaaagg gtgctcagag 5160
cgaatccatg gaagcaatct gtgcgggata gaacattcaa acagactgag gaaacacttg 5220
gatcactaat ccaggattct ttgtcgtctt tgtaaagagc ttttaggtat cgccatgagc 5280
tctcgtttgc aggattggtt aaaatggctt tgattgtgta gcttacttca gattctctca 5340
tggcttctag gcctcccaac aaaggagatt gggtgatgac ataatacctc tgattccagg 5400
cggaattgtt aaagacgtca gcttcaagga gctcgtgaca gtaatcgagc tcatcttccc 5460
atcctcctaa tgcccgctcg aatttccccg atcgttcaaa catttggcaa taaagtttct 5520
taagattgaa tcctgttgcc ggtcttgcga tgattatcat ataatttctg ttgaattacg 5580
ttaagcatgt aataattaac atgtaatgca tgacgttatt tatgagatgg gtttttatga 5640

-continued

```
ttagagtccc gcaattatac atttaatacg cgatagaaaa caaaatatag cgcgcaaact   5700

aggataaatt atcgcgcgcg gtgtcatcta tgttactaga tcgggaattc actggccgtc   5760

gttttacaac gtcgtgactg ggaaaaccct ggcgttaccc aacttaatcg ccttgcagca   5820

catccccctt tcgccagctg gcgtaatagc gaagaggccc gcaccgatcg cccttcccaa   5880

cagttgcgca gcctgaatgg cgcccgctcc tttcgctttc ttcccttcct ttctcgccac   5940

gttcgccggc tttccccgtc aagctctaaa tcgggggctc cctttagggt tccgatttag   6000

tgctttacgg cacctcgacc ccaaaaaact tgatttgggt gatggttcac gtagtgggcc   6060

atcgccctga tagacggttt ttcgcccttt gacgttggag tccacgttct ttaatagtgg   6120

actcttgttc caaactggaa caacactcaa ccctatctcg ggctattctt ttgatttata   6180

agggattttg ccgatttcgg aaccaccatc aaacaggatt ttcgcctgct ggggcaaacc   6240

agcgtggacc gcttgctgca actctctcag ggccaggcgg tgaagggcaa tcagctgttg   6300

cccgtctcac tggtgaaaag aaaaaccacc ccagtacatt aaaaacgtcc gcaatgtgtt   6360

attaagttgt ctaagcgtca atttgtttac accacaatat atcctgcca               6409
```

```
<210> SEQ ID NO 50
<211> LENGTH: 1254
<212> TYPE: DNA
<213> ORGANISM: Artificial Sequence
<220> FEATURE:
<223> OTHER INFORMATION: Description of Artificial Sequence: Plasmid
      MuA-anti-GmFTA

<400> SEQUENCE: 50
```

```
gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

aggaagtctg ctcttgcgcc aaatccaata gttggttcta attggatcaa cttgttttag    420

gatagaacaa atatttcgtg ctatatttaa attttgttgt tcccctttct catcatcatc    480

taaatcttgt ttatccatat ctgcggtctt taaggcgtca atggcatctc taatgtcttc    540

atttggttga taaccaaagc atataagatc taaaatagtg ctaagagcaa acacgtagtt    600

gctcttagtt ctcaaaatct ttaagcatac tgaagaaact tgaggatcat ttacccatga    660

agtagtttca cctttataaa gtcctcgtag atatctccac gagctttcat tttcagggta    720

ggctataatg gcttcgatgg tgtaaagcac ttcagactct ctcatagctt ttaggccccc    780

caagaaagga gaccttgtta tgacaaaata tctctgattc caagcagaat tgttaaaaat    840

gtcttcttta agtagttctg tgcaataatt aagttcatct tcccatcctc ctagtgtttg    900

aagagcccac tgtctatgag accatgcatg ataatgtttg gcatcaacgg acagtatctt    960

tttggtgaac tcgagctgag ctcgaatttc cccgatcgtt caaacatttg gcaataaagt   1020

ttcttaagat tgaatcctgt tgccggtctt gcgatgatta tcatataatt tctgttgaat   1080

tacgttaagc atgtaataat taacatgtaa tgcatgacgt tatttatgag atgggttttt   1140

atgattagag tcccgcaatt atacatttaa tacgcgatag aaaacaaaat atagcgcgca   1200

aactaggata aattatcgcg cgcggtgtca tctatgttac tagatcggga attc         1254
```

-continued

<210> SEQ ID NO 51
<211> LENGTH: 1822
<212> TYPE: DNA
<213> ORGANISM: Artificial Sequence
<220> FEATURE:
<223> OTHER INFORMATION: Description of Artificial Sequence: Plasmid RD29A-anti-GmFTA

<400> SEQUENCE: 51

```
ggagccatag atgcaattca atcaaactga aatttctgca agaatctcaa acacggagat     60
ctcaaagttt gaaagaaaat ttatttcttc gactcaaaac aaacttacga aatttaggta    120
gaacttatat acattatatt gtaatttttt gtaacaaaat gtttttatta ttattataga    180
attttactgg ttaaattaaa aatgaataga aaaggtgaat taagaggaga gaggaggtaa    240
acattttctt ctattttttc atattttcag gataaattat tgtaaaagtt tacaagattt    300
ccatttgact agtgtaaatg aggaatattc tctagtaaga tcattatttc atctacttct    360
tttatcttct accagtagag gaataaacaa tatttagctc ctttgtaaat acaaattaat    420
tttccttctt gacatcattc aattttaatt ttacgtataa aataaaagat catacctatt    480
agaacgatta aggagaaata caattcgaat gagaaggatg tgccgtttgt tataataaac    540
agccacacga cgtaaacgta aaatgaccac atgatgggcc aatagacatg gaccgactac    600
taataatagt aagttacatt ttaggatgga ataaatatca taccgacatc agttttgaaa    660
gaaaagggaa aaaaagaaaa aataaataaa agatatacta ccgacatgag ttccaaaaag    720
caaaaaaaaa gatcaagccg acacagacac gcgtagagag caaaatgact ttgacgtcac    780
accacgaaaa cagacgcttc atacgtgtcc ctttatctct ctcagtctct ctataaactt    840
agtgagaccc tcctctgttt tactcacaaa tatgcaaact agaaaacaat catcaggaat    900
aaagggtttg attacttcta ttggaaagag gaagtctgct cttgcgccaa atccaatagt    960
tggttctaat tggatcaact tgttttagga tagaacaaat atttcgtgct atatttaaat   1020
tttgttgttc ccctttctca tcatcatcta aatcttgttt atccatatct gcggtcttta   1080
aggcgtcaat ggcatctcta atgtcttcat ttggttgata accaaagcat ataagatcta   1140
aaatagtgct aagagcaaac acgtagttgc tcttagttct caaaatcttt aagcatactg   1200
aagaaacttg aggatcattt acccatgaag tagtttcacc tttataaagt cctcgtagat   1260
atctccacga gctttcattt tcagggtagg ctataatggc ttcgatggtg taaagcactt   1320
cagactctct catagctttt aggcccccca agaaaggaga ccttgttatg acaaaatatc   1380
tctgattcca agcagaattg ttaaaaatgt cttctttaag tagttctgtg caataattaa   1440
gttcatcttc ccatcctcct agtgtttgaa gagcccactg tctatgagac catgcatgat   1500
aatgtttggc atcaacggac agtatctttt tggtgaactc gagctgagct cgaatttccc   1560
cgatcgttca aacatttggc aataaagttt cttaagattg aatcctgttg ccggtcttgc   1620
gatgattatc atataatttc tgttgaatta cgttaagcat gtaataatta acatgtaatg   1680
catgacgtta tttatgagat gggtttttat gattagagtc ccgcaattat acatttaata   1740
cgcgatagaa aacaaaatat agcgcgcaaa ctaggataaa ttatcgcgcg cggtgtcatc   1800
tatgttacta gatcgggaat tc                                            1822
```

<210> SEQ ID NO 52
<211> LENGTH: 1570
<212> TYPE: DNA
<213> ORGANISM: Artificial Sequence -continued
<220> FEATURE:
<223> OTHER INFORMATION: Description of Artificial Sequence: Plasmid
MuA-HP-GmFTA-Nos-Term

<400> SEQUENCE: 52

```
gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

aggaagtctg ctcttgcgcc aaatccaata gttggttcta attggatcaa cttgttttag    420

gatagaacaa atatttcgtg ctatatttaa attttgttgt tccccttttct catcatcatc    480

taaatcttgt ttatccatat ctgcggtctt taaggcgtca atggcatctc taatgtcttc    540

atttggttga taaccaaagc atataagatc taaaatagtg ctaagagcaa acacgtagtt    600

gctcttagtt ctcaaaatct ttaagcatac tgaagaaact tgaggatcat ttacccatga    660

agtagtttca cctttataaa gtcctcgtag atatctccac gagctttcat tttcagggta    720

ggctataatg gcttcgatgg tgtaaagcac ttcagactct ctcatagctt ttaggccccc    780

caagaaagga gaccttgtta tgacaaaata tctctgattc caagcagaat tgttaaaaat    840

gtcttcttta agtagttctg tgcaataatt aagttcatct tcccatcctc ctagtgtttg    900

aagagcccac tgtctatgag accatgcatg ataatgtttg gcatcaacgg acagtatctt    960

tttggtgaac tcgagcttaa aggtgaaact acttcatggg taaatgatcc tcaagtttct   1020

tcagtatgct taaagatttt gagaactaag agcaactacg tgtttgctct tagcactatt   1080

ttagatctta tatgctttgg ttatcaacca aatgaagaca ttagagatgc cattgacgcc   1140

ttaaagaccg cagatatgga taaacaagat ttagatgatg atgagaaagg ggaacaacaa   1200

aatttaaata tagcacgaaa tatttgttct atcctaaaac aagttgatcc aattagaacc   1260

aactattgga tttggcgcaa gagcagactt cctgagctcg aatttccccg atcgttcaaa   1320

catttggcaa taaagtttct taagattgaa tcctgttgcc ggtcttgcga tgattatcat   1380

ataatttctg ttgaattacg ttaagcatgt aataattaac atgtaatgca tgacgttatt   1440

tatgagatgg gtttttatga ttagagtccc gcaattatac atttaatacg cgatagaaaa   1500

caaaatatag cgcgcaaact aggataaatt atcgcgcgcg gtgtcatcta tgttactaga   1560

tcgggaattc                                                          1570
```

<210> SEQ ID NO 53
<211> LENGTH: 2138
<212> TYPE: DNA
<213> ORGANISM: Artificial Sequence
<220> FEATURE:
<223> OTHER INFORMATION: Description of Artificial Sequence: Plasmid
RD29AP-HP-GmFTA-Nos-Term

<400> SEQUENCE: 53

```
ggagccatag atgcaattca atcaaactga aatttctgca agaatctcaa acacggagat     60

ctcaaagttt gaaagaaaat ttatttcttc gactcaaaac aaacttacga aatttaggta    120

gaacttatat acattatatt gtaatttttt gtaacaaaat gtttttatta ttattataga    180

attttactgg ttaaattaaa aatgaataga aaaggtgaat taagaggaga gaggaggtaa    240
```

-continued

```
acattttctt ctattttttc atattttcag gataaattat tgtaaaagtt tacaagattt    300

ccatttgact agtgtaaatg aggaatattc tctagtaaga tcattatttc atctacttct    360

tttatcttct accagtagag gaataaacaa tatttagctc ctttgtaaat acaaattaat    420

tttccttctt gacatcattc aattttaatt ttacgtataa aataaaagat catacctatt    480

agaacgatta aggagaaata caattcgaat gagaaggatg tgccgtttgt tataataaac    540

agccacacga cgtaaacgta aaatgaccac atgatgggcc aatagacatg gaccgactac    600

taataatagt aagttacatt ttaggatgga ataaatatca taccgacatc agttttgaaa    660

gaaaagggaa aaaaagaaaa aataaataaa agatatacta ccgacatgag ttccaaaaag    720

caaaaaaaaa gatcaagccg acacagacac gcgtagagag caaaatgact ttgacgtcac    780

accacgaaaa cagacgcttc atacgtgtcc ctttatctct ctcagtctct ctataaactt    840

agtgagaccc tcctctgttt tactcacaaa tatgcaaact agaaaacaat catcaggaat    900

aaagggtttg attacttcta ttggaaagag gaagtctgct cttgcgccaa atccaatagt    960

tggttctaat tggatcaact tgttttagga tagaacaaat atttcgtgct atatttaaat   1020

tttgttgttc ccctttctca tcatcatcta aatcttgttt atccatatct gcggtcttta   1080

aggcgtcaat ggcatctcta atgtcttcat ttggttgata accaaagcat ataagatcta   1140

aaatagtgct aagagcaaac acgtagttgc tcttagttct caaaatcttt aagcatactg   1200

aagaaacttg aggatcattt acccatgaag tagtttcacc tttataaagt cctcgtagat   1260

atctccacga gctttcattt tcagggtagg ctataatggc ttcgatggtg taaagcactt   1320

cagactctct catagctttt aggcccccca agaaaggaga ccttgttatg acaaaatatc   1380

tctgattcca agcagaattg ttaaaaatgt cttctttaag tagttctgtg caataattaa   1440

gttcatcttc ccatcctcct agtgtttgaa gagcccactg tctatgagac catgcatgat   1500

aatgtttggc atcaacggac agtatctttt tggtgaactc gagcttaaag gtgaaactac   1560

ttcatgggta aatgatcctc aagtttcttc agtatgctta aagattttga gaactaagag   1620

caactacgtg tttgctctta gcactatttt agatcttata tgctttggtt atcaaccaaa   1680

tgaagacatt agagatgcca ttgacgcctt aaagaccgca gatatggata aacaagattt   1740

agatgatgat gagaaagggg aacaacaaaa tttaaatata gcacgaaata tttgttctat   1800

cctaaaacaa gttgatccaa ttagaaccaa ctattggatt tggcgcaaga gcagacttcc   1860

tgagctcgaa tttccccgat cgttcaaaca tttggcaata aagtttctta agattgaatc   1920

ctgttgccgg tcttgcgatg attatcatat aatttctgtt gaattacgtt aagcatgtaa   1980

taattaacat gtaatgcatg acgttattta tgagatgggt ttttatgatt agagtcccgc   2040

aattatacat ttaatacgcg atagaaaaca aaatatagcg cgcaaactag gataaattat   2100

cgcgcgcggt gtcatctatg ttactagatc gggaattc                           2138
```

<210> SEQ ID NO 54
<211> LENGTH: 5511
<212> TYPE: DNA
<213> ORGANISM: Artificial Sequence
<220> FEATURE:
<223> OTHER INFORMATION: Description of Artificial Sequence: Plasmid
pBI121-35S-Anti-AtFTB

<400> SEQUENCE: 54

```
gtttacccgc caatatatcc tgtcaaacac tgatagttta aactgaaggc gggaaacgac     60

aatctgatca tgagcggaga attaagggag tcacgttatg acccccgccg atgacgcggg    120
```

-continued

```
acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740

tttaatacgc gatagaaaac aaaatatagc gcgcaaacta ggataaatta tcgcgcgcgg   1800

tgtcatctat gttactagat cgggcctcct gtcaatgctg gcggcggctc tggtggtggt   1860

tctggtggcg gctctgaggg tggtggctct gagggtggcg gttctgaggg tggcggctct   1920

gagggaggcg gttccggtgg tggctctggt tccggtgatt ttgattatga aaagatggca   1980

aacgctaata agggggctat gaccgaaaat gccgatgaaa acgcgctaca gtctgacgct   2040

aaaggcaaac ttgattctgt cgctactgat tacggtgctg ctatcgatgg tttcattggt   2100

gacgtttccg gccttgctaa tggtaatggt gctactggtg attttgctgg ctctaattcc   2160

caaatggctc aagtcggtga cggtgataat tcacctttaa tgaataattt ccgtcaatat   2220

ttaccttccc tccctcaatc ggttgaatgt cgcccttttg tctttggccc aatacgcaaa   2280

ccgcctctcc ccgcgcgttg gccgattcat taatgcagct ggcacgacag gtttcccgac   2340

tggaaagcgg gcagtgagcg caacgcaatt aatgtgagtt agctcactca ttaggcaccc   2400

caggctttac actttatgct tccggctcgt atgttgtgtg gaattgtgag cggataacaa   2460

tttcacacag gaaacagcta tgaccatgat tacgccaagc ttgcatgcct gcagcccaca   2520
```

-continued

```
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccgtccgga attcccgggt cgacccacgc   3360
gtccgggaga ttcagcgaga taagcaattg gattatctga tgaaaggctt aaggcagctt   3420
ggtccgcagt tttcttcctt agatgctaat cgaccttggc tttgttactg gattcttcat   3480
tcaatagctt tgcttgggga gactgtggat gatgaattag aaagcaatgc cattgacttc   3540
cttggacgct gccagggctc tgaaggtgga tacggtggtg gtcctggcca acttccacat   3600
cttgcaacta cttatgctgc agtgaatgca cttgttactt taggaggtga caaagccctt   3660
tcttcaatta atagagaaaa aatgtcttgt tttttaagac ggatgaagga tacaagtgga   3720
ggtttcagga tgcatgatat gggagaaatg gatgttcgtg catgctacac tgcaatttcg   3780
gttgcaagca tcctaaatat tatggatgat gaactcaccc agggcctagg agattacatc   3840
ttgagttgcc aaacttatga aggtggcatt ggaggggaac ctggctccga agctcacggt   3900
gggtatacct actgtggttt ggctgctatg attttaatca atgaggtcga ccgtttgaat   3960
ttggattcat taatgaattg ggctgtacat cgacaaggag tagaaatggg atttcaaggt   4020
aggacgaaca aattggtcga tggttgctac acattttggc aggcagcccc ttgtgttcta   4080
ctacaaagat tatattcaac caatgatcat gacgttcatg gatcatcaca tatatcagaa   4140
gggacaaatg aagaacatca tgctcatgat gaagatgacc ttgaagacag tgatgatgat   4200
gatgattctg atgaggacaa cgatgaagat tcagtgaatg gtcacagaat ccatcataca   4260
tccacctaca ttaacaggag aatgcaactg gtttttgata gcctcggctt gcagagatat   4320
gtactcttgt gctctaagat ccctgacggt ggattcagag acaagccgag gaaaccccgt   4380
gacttctacc acacatgtta ctgcctgagc ggcttgtctg tggctcagca cgcttggtta   4440
aaagacgagg acactcctcc tttgactcgc gacattatgg gtggctactc gaatctcctt   4500
gaacctgttc aacttcttca caacattgtc atggatcagt ataatgaagc tatcgagttc   4560
ttctttaaag cagcatgact cgaatttccc cgatcgttca aacatttggc aataaagttt   4620
cttaagattg aatcctgttg ccggtcttgc gatgattatc atataatttc tgttgaatta   4680
cgttaagcat gtaataatta acatgtaatg catgacgtta tttatgagat gggtttttat   4740
gattagagtc ccgcaattat acatttaata cgcgatagaa aacaaaatat agcgcgcaaa   4800
ctaggataaa ttatcgcgcg cggtgtcatc tatgttacta gatcgggaat tcactggccg   4860
```

-continued

```
tcgttttaca acgtcgtgac tgggaaaacc ctggcgttac ccaacttaat cgccttgcag   4920

cacatccccc tttcgccagc tggcgtaata gcgaagaggc ccgcaccgat cgcccttccc   4980

aacagttgcg cagcctgaat ggcgcccgct cctttcgctt tcttcccttc ctttctcgcc   5040

acgttcgccg gctttccccg tcaagctcta aatcgggggc tccctttagg gttccgattt   5100

agtgctttac ggcacctcga ccccaaaaaa cttgatttgg gtgatggttc acgtagtggg   5160

ccatcgccct gatagacggt ttttcgccct ttgacgttgg agtccacgtt ctttaatagt   5220

ggactcttgt tccaaactgg aacaacactc aaccctatct cgggctattc ttttgattta   5280

taagggattt tgccgatttc ggaaccacca tcaaacagga ttttcgcctg ctggggcaaa   5340

ccagcgtgga ccgcttgctg caactctctc agggccaggc ggtgaagggc aatcagctgt   5400

tgcccgtctc actggtgaaa agaaaaacca ccccagtaca ttaaaaacgt ccgcaatgtg   5460

ttattaagtt gtctaagcgt caatttgttt acaccacaat atatcctgcc a            5511
```

<210> SEQ ID NO 55
<211> LENGTH: 5635
<212> TYPE: DNA
<213> ORGANISM: Artificial Sequence
<220> FEATURE:
<223> OTHER INFORMATION: Description of Artificial Sequence: Plasmid
pBI12-RD29AP-Anti-AtFTB

<400> SEQUENCE: 55

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380
```

-continued

```
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccgtc cggaattccc gggtcgaccc   3480
acgcgtccgg gagattcagc gagataagca attggattat ctgatgaaag gcttaaggca   3540
gcttggtccg cagttttctt ccttagatgc taatcgacct tggctttgtt actggattct   3600
tcattcaata gctttgcttg gggagactgt ggatgatgaa ttagaaagca atgccattga   3660
cttccttgga cgctgccagg gctctgaagg tggatacggt ggtggtcctg gccaacttcc   3720
acatcttgca actacttatg ctgcagtgaa tgcacttgtt actttaggag gtgacaaagc   3780
```

-continued

```
cctttcttca attaatagag aaaaaatgtc ttgtttttta agacggatga aggatacaag   3840

tggaggtttc aggatgcatg atatgggaga aatggatgtt cgtgcatgct acactgcaat   3900

ttcggttgca agcatcctaa atattatgga tgatgaactc acccagggcc taggagatta   3960

catcttgagt tgccaaactt atgaaggtgg cattggaggg gaacctggct ccgaagctca   4020

cggtgggtat acctactgtg gtttggctgc tatgatttta atcaatgagg tcgaccgttt   4080

gaatttggat tcattaatga attgggctgt acatcgacaa ggagtagaaa tgggatttca   4140

aggtaggacg aacaaattgg tcgatggttg ctacacattt tggcaggcag ccccttgtgt   4200

tctactacaa agattatatt caaccaatga tcatgacgtt catggatcat cacatatatc   4260

agaagggaca aatgaagaac atcatgctca tgatgaagat gaccttgaag acagtgatga   4320

tgatgatgat tctgatgagg acaacgatga agattcagtg aatggtcaca gaatccatca   4380

tacatccacc tacattaaca ggagaatgca actggttttt gatagcctcg gcttgcagag   4440

atatgtactc ttgtgctcta agatccctga cggtggattc agagacaagc cgaggaaacc   4500

ccgtgacttc taccacacat gttactgcct gagcggcttg tctgtggctc agcacgcttg   4560

gttaaaagac gaggacactc ctcctttgac tcgcgacatt atgggtggct actcgaatct   4620

ccttgaacct gttcaacttc ttcacaacat tgtcatggat cagtataatg aagctatcga   4680

gttcttcttt aaagcagcat gactcgaatt tccccgatcg ttcaaacatt tggcaataaa   4740

gtttcttaag attgaatcct gttgccggtc ttgcgatgat tatcatataa tttctgttga   4800

attacgttaa gcatgtaata attaacatgt aatgcatgac gttatttatg agatgggttt   4860

ttatgattag agtcccgcaa ttatacattt aatacgcgat agaaaacaaa atatagcgcg   4920

caaactagga taaattatcg cgcgcggtgt catctatgtt actagatcgg gaattcactg   4980

gccgtcgttt tacaacgtcg tgactgggaa aaccctggcg ttacccaact taatcgcctt   5040

gcagcacatc ccccttttcgc cagctggcgt aatagcgaag aggcccgcac cgatcgccct   5100

tcccaacagt tgcgcagcct gaatggcgcc cgctcctttc gctttcttcc cttcctttct   5160

cgccacgttc gccggctttc cccgtcaagc tctaaatcgg gggctccctt tagggttccg   5220

atttagtgct ttacggcacc tcgaccccaa aaaacttgat ttgggtgatg gttcacgtag   5280

tgggccatcg ccctgataga cggtttttcg ccctttgacg ttggagtcca cgttctttaa   5340

tagtggactc ttgttccaaa ctggaacaac actcaaccct atctcgggct attcttttga   5400

tttataaggg attttgccga tttcggaacc accatcaaac aggattttcg cctgctgggg   5460

caaaccagcg tggaccgctt gctgcaactc tctcagggcc aggcggtgaa gggcaatcag   5520

ctgttgcccg tctcactggt gaaaagaaaa accaccccag tacattaaaa acgtccgcaa   5580

tgtgttatta agttgtctaa gcgtcaattt gtttacacca caatatatcc tgcca        5635
```

<210> SEQ ID NO 56
<211> LENGTH: 6299
<212> TYPE: DNA
<213> ORGANISM: Artificial Sequence
<220> FEATURE:
<223> OTHER INFORMATION: Description of Artificial Sequence: Plasmid
      pBI121-35S-HP-AtFTB

<400> SEQUENCE: 56

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180
```

-continued

```
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
```

-continued

```
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacgggggga ctctagagga tcctcctcct aggccctggg tgagttcatc   3360
atccataata tttaggatgc ttgcaaccga aattgcagtg tagcatgcac gaacatccat   3420
ttctcccata tcatgcatcc tgaaacctcc acttgtatcc ttcatccgtc ttaaaaaaca   3480
agacattttt tctctattaa ttgaagaaag ggctttgtca cctcctaaag taacaagtgc   3540
attcactgca gcataagtag ttgcaagatg tggaagttgg ccaggaccac caccgtatcc   3600
accttcagag ccctggcagc gtccaaggaa gtcaatggca ttgctttcta attcatcatc   3660
cacagtctcc ccaagcaaag ctattgaatg aagaatccag taacaaagcc aaggtcgatt   3720
agcatctaag gaagaaaact gcggaccaag ctgccttaag cctttcatca gataatccaa   3780
ttgcttatct cgctgaatct cccggacgcg tgggtcgacc cgggaattcc ggacgaggat   3840
ccccatctac ccgcttcgcg tcggcatccg gtcagtggca gtgaagggcg aacagttcct   3900
gattaaccac aaaccgttct actttactgg ctttggtcgt catgaagatg cggacttgcg   3960
tggcaaagga ttcgataacg tgctgatggt gcacgaccac gcattaatgg actggattgg   4020
ggccaactcc taccgtacct cgcattaccc ttacgctgaa gagatgctcg actgggcaga   4080
tgaacatggc atcgtggtga ttgatgaaac tgctgctgtc ggcttttcgc tctctttagg   4140
cattggtttc gaagcgggca acaagccgaa agaactgtac agcgaagagg cagtcaacgg   4200
ggaaactcag caagcgcact tacaggcgat taaagagctg atagcgcgtg acaaaaacca   4260
cccaagcgtg gtgatgtgga gtattgccaa cgaaccggat acccgtccgc aaggtgcacg   4320
ggaatatttc gcgccactgg cggaagcaac gcgtaaactc gacccgacgc gtccgatcac   4380
ctgcgtcaat gtaatgttct gcgacgctca caccgatacc atcagcgatc tctttgatgt   4440
gctgtgcctg aaccgttatt acggatggta tgtccaaagc ggcgatttgg aaacggcaga   4500
gaaggtactg gaaaaagaac ttctggcctg gcaggagaaa ctgtacaccg acatgtggag   4560
tgaagagtat cagtgtgcat ggctggatat gtatcaccgc gtctttgatc gcgtcagcgc   4620
cgtcgtcggt gaacaggtat ggaatttcgc cgattttgcg acctcgcaag gcatattgcg   4680
cgttggcggt aacaagaaag ggatcttcac tcgcgaccgc aaaccgaagt cggcggcttt   4740
tctgctgcaa aaacgctgga ctggcatgaa cttcggtgaa aaaccgcagc agggaggcaa   4800
acaatgaatc aacaactctc ctggcgcacc atcgtcggct acagcctcgg gaattgctac   4860
cgagctcgtc cggaattccc gggtcgaccc acgcgtccgg gagattcagc gagataagca   4920
```

-continued

```
attggattat ctgatgaaag gcttaaggca gcttggtccg cagttttctt ccttagatgc   4980
taatcgacct tggctttgtt actggattct tcattcaata gctttgcttg ggagactgt   5040
ggatgatgaa ttagaaagca atgccattga cttccttgga cgctgccagg gctctgaagg   5100
tggatacggt ggtggtcctg gccaacttcc acatcttgca actacttatg ctgcagtgaa   5160
tgcacttgtt actttaggag gtgacaaagc cctttcttca attaatagag aaaaaatgtc   5220
ttgtttttta agacggatga aggatacaag tggaggtttc aggatgcatg atatgggaga   5280
aatggatgtt cgtgcatgct acactgcaat ttcggttgca agcatcctaa atattatgga   5340
tgatgaactc acccagggcc taggagctcg aatttccccg atcgttcaaa catttggcaa   5400
taaagtttct taagattgaa tcctgttgcc ggtcttgcga tgattatcat ataatttctg   5460
ttgaattacg ttaagcatgt aataattaac atgtaatgca tgacgttatt tatgagatgg   5520
gtttttatga ttagagtccc gcaattatac atttaatacg cgatagaaaa caaaatatag   5580
cgcgcaaact aggataaatt atcgcgcgcg gtgtcatcta tgttactaga tcgggaattc   5640
actggccgtc gttttacaac gtcgtgactg ggaaaaccct ggcgttaccc aacttaatcg   5700
ccttgcagca catccccctt tcgccagctg gcgtaatagc gaagaggccc gcaccgatcg   5760
cccttcccaa cagttgcgca gcctgaatgg cgcccgctcc tttcgctttc ttcccttcct   5820
ttctcgccac gttcgccggc tttccccgtc aagctctaaa tcgggggctc cctttagggt   5880
tccgatttag tgctttacgg cacctcgacc ccaaaaaact tgatttgggt gatggttcac   5940
gtagtgggcc atcgccctga tagacggttt ttcgcccttt gacgttggag tccacgttct   6000
ttaatagtgg actcttgttc caaactggaa caacactcaa ccctatctcg ggctattctt   6060
ttgatttata agggattttg ccgatttcgg aaccaccatc aaacaggatt ttcgcctgct   6120
ggggcaaacc agcgtggacc gcttgctgca actctctcag ggccaggcgg tgaagggcaa   6180
tcagctgttg cccgtctcac tggtgaaaag aaaaaccacc ccagtacatt aaaaacgtcc   6240
gcaatgtgtt attaagttgt ctaagcgtca atttgtttac accacaatat atcctgcca    6299
```

```
<210> SEQ ID NO 57
<211> LENGTH: 6423
<212> TYPE: DNA
<213> ORGANISM: Artificial Sequence
<220> FEATURE:
<223> OTHER INFORMATION: Description of Artificial Sequence: Plasmid
      pBI121-RD29AP-HP-AtFTB

<400> SEQUENCE: 57
```

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
```

-continued

```
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
```

-continued attaaggaga aatacaattc gaatgagaag gatgtgccgt ttgttataat aaacagccac 3060
acgacgtaaa cgtaaaatga ccacatgatg ggccaataga catggaccga ctactaataa 3120
tagtaagtta cattttagga tggaataaat atcataccga catcagtttt gaaagaaaag 3180
ggaaaaaaag aaaaaataaa taaaagatat actaccgaca tgagttccaa aaagcaaaaa 3240
aaaagatcaa gccgacacag acacgcgtag agagcaaaat gactttgacg tcacaccacg 3300
aaaacagacg cttcatacgt gtccctttat ctctctcagt ctctctataa acttagtgag 3360
accctcctct gttttactca caaatatgca aactagaaaa caatcatcag gaataaaggg 3420
tttgattact tctattggaa aggactctag aggatcctcc tcctaggccc tgggtgagtt 3480
catcatccat aatatttagg atgcttgcaa ccgaaattgc agtgtagcat gcacgaacat 3540
ccatttctcc catatcatgc atcctgaaac ctccacttgt atccttcatc cgtcttaaaa 3600
aacaagacat tttttctcta ttaattgaag aaagggcttt gtcacctcct aaagtaacaa 3660
gtgcattcac tgcagcataa gtagttgcaa gatgtggaag ttggccagga ccaccaccgt 3720
atccaccttc agagccctgg cagcgtccaa ggaagtcaat ggcattgctt tctaattcat 3780
catccacagt ctccccaagc aaagctattg aatgaagaat ccagtaacaa agccaaggtc 3840
gattagcatc taaggaagaa aactgcggac caagctgcct taagcctttc atcagataat 3900
ccaattgctt atctcgctga atctcccgga cgcgtgggtc gacccgggaa ttccggacga 3960
ggatccccat ctacccgctt cgcgtcggca tccggtcagt ggcagtgaag ggcgaacagt 4020
tcctgattaa ccacaaaccg ttctacttta ctggctttgg tcgtcatgaa gatgcggact 4080
tgcgtggcaa aggattcgat aacgtgctga tggtgcacga ccacgcatta atggactgga 4140
ttggggccaa ctcctaccgt acctcgcatt acccttacgc tgaagagatg ctcgactggg 4200
cagatgaaca tggcatcgtg gtgattgatg aaactgctgc tgtcggcttt tcgctctctt 4260
taggcattgg tttcgaagcg ggcaacaagc cgaaagaact gtacagcgaa gaggcagtca 4320
acggggaaac tcagcaagcg cacttacagg cgattaaaga gctgatagcg cgtgacaaaa 4380
accacccaag cgtggtgatg tggagtattg ccaacgaacc ggatacccgt ccgcaaggtg 4440
cacgggaata tttcgcgcca ctggcggaag caacgcgtaa actcgacccg acgcgtccga 4500
tcacctgcgt caatgtaatg ttctgcgacg ctcacaccga taccatcagc gatctctttg 4560
atgtgctgtg cctgaaccgt tattacggat ggtatgtcca aagcggcgat ttggaaacgg 4620
cagagaaggt actggaaaaa gaacttctgg cctggcagga gaaactgtac accgacatgt 4680
ggagtgaaga gtatcagtgt gcatggctgg atatgtatca ccgcgtcttt gatcgcgtca 4740
gcgccgtcgt cggtgaacag gtatggaatt tcgccgattt tgcgacctcg caaggcatat 4800
tgcgcgttgg cggtaacaag aaagggatct tcactcgcga ccgcaaaccg aagtcggcgg 4860
cttttctgct gcaaaaacgc tggactggca tgaacttcgg tgaaaaaccg cagcagggag 4920
gcaaacaatg aatcaacaac tctcctggcg caccatcgtc ggctacagcc tcgggaattg 4980
ctaccgagct cgtccggaat tcccgggtcg acccacgcgt ccgggagatt cagcgagata 5040
agcaattgga ttatctgatg aaaggcttaa ggcagcttgg tccgcagttt tcttccttag 5100
atgctaatcg accttggctt tgttactgga ttcttcattc aatagctttg cttggggaga 5160
ctgtggatga tgaattagaa agcaatgcca ttgacttcct tggacgctgc cagggctctg 5220
aaggtggata cggtggtggt cctggccaac ttccacatct tgcaactact tatgctgcag 5280
tgaatgcact tgttacttta ggaggtgaca aagccctttc ttcaattaat agagaaaaaa 5340
tgtcttgttt tttaagacgg atgaaggata caagtggagg tttcaggatg catgatatgg 5400

-continued gagaaatgga tgttcgtgca tgctacactg caatttcggt tgcaagcatc ctaaatatta 5460
tggatgatga actcacccag ggcctaggag ctcgaatttc cccgatcgtt caaacatttg 5520
gcaataaagt ttcttaagat tgaatcctgt tgccggtctt gcgatgatta tcatataatt 5580
tctgttgaat tacgttaagc atgtaataat taacatgtaa tgcatgacgt tatttatgag 5640
atgggttttt atgattagag tcccgcaatt atacatttaa tacgcgatag aaaacaaaat 5700
atagcgcgca aactaggata aattatcgcg cgcggtgtca tctatgttac tagatcggga 5760
attcactggc cgtcgtttta caacgtcgtg actgggaaaa ccctggcgtt acccaactta 5820
atcgccttgc agcacatccc cctttcgcca gctggcgtaa tagcgaagag gcccgcaccg 5880
atcgcccttc ccaacagttg cgcagcctga atggcgcccg ctcctttcgc tttcttccct 5940
tcctttctcg ccacgttcgc cggctttccc cgtcaagctc taaatcgggg gctcccttta 6000
gggttccgat ttagtgcttt acggcacctc gaccccaaaa aacttgattt gggtgatggt 6060
tcacgtagtg ggccatcgcc ctgatagacg gtttttcgcc ctttgacgtt ggagtccacg 6120
ttctttaata gtggactctt gttccaaact ggaacaacac tcaaccctat ctcgggctat 6180
tcttttgatt tataagggat tttgccgatt tcggaaccac catcaaacag gattttcgcc 6240
tgctggggca aaccagcgtg gaccgcttgc tgcaactctc tcagggccag gcggtgaagg 6300
gcaatcagct gttgcccgtc tcactggtga aaagaaaaac caccccagta cattaaaaac 6360
gtccgcaatg tgttattaag ttgtctaagc gtcaatttgt ttacaccaca atatatcctg 6420
cca 6423

<210> SEQ ID NO 58
<211> LENGTH: 5715
<212> TYPE: DNA
<213> ORGANISM: Artificial Sequence
<220> FEATURE:
<223> OTHER INFORMATION: Description of Artificial Sequence: Plasmid pBI121-35S-AtFTB

<400> SEQUENCE: 58
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960

-continued

```
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
```

-continued

```
tttggagaga acacggggga ctctagagga tccatgccag tagtaacccg cttgattcgt   3360
ttgaagtgtg tagggctcag acttgaccgg agtggactca atcggcgaat ctgtcacgga   3420
ggacacgggg aatcaacgcg gcggagagtg atggaagagc tttcaagcct aaccgtgagt   3480
cagcgcgagc aatttctggt ggagaacgat gtgttcggga tctataatta cttcgacgcc   3540
agcgacgttt ctactcaaaa atacatgatg gagattcagc gagataagca attggattat   3600
ctgatgaaag gcttaaggca gcttggtccg cagttttctt ccttagatgc taatcgacct   3660
tggctttgtt actggattct tcattcaata gctttgcttg gggagactgt ggatgatgaa   3720
ttagaaagca atgccattga cttccttgga cgctgccagg gctctgaagg tggatacggt   3780
ggtggtcctg gccaacttcc acatcttgca actacttatg ctgcagtgaa tgcacttgtt   3840
actttaggag gtgacaaagc cctttcttca attaatagag aaaaaatgtc ttgtttttta   3900
agacggatga aggatacaag tggaggtttc aggatgcatg atatgggaga aatggatgtt   3960
cgtgcatgct acactgcaat ttcggttgca agcatcctaa atattatgga tgatgaactc   4020
acccagggcc taggagatta catcttgagt tgccaaactt atgaaggtgg cattggaggg   4080
gaacctggct ccgaagctca cggtgggtat acctactgtg gtttggctgc tatgatttta   4140
atcaatgagg tcgaccgttt gaatttggat tcattaatga attgggctgt acatcgacaa   4200
ggagtagaaa tgggatttca aggtaggacg aacaaattgg tcgatggttg ctacacattt   4260
tggcaggcag ccccttgtgt tctactacaa agattatatt caaccaatga tcatgacgtt   4320
catggatcat cacatatatc agaagggaca aatgaagaac atcatgctca tgatgaagat   4380
gaccttgaag acagtgatga tgatgatgat tctgatgagg acaacgatga agattcagtg   4440
aatggtcaca gaatccatca tacatccacc tacattaaca ggagaatgca actggttttt   4500
gatagcctcg gcttgcagag atatgtactc ttgtgctcta agatccctga cggtggattc   4560
agagacaagc cgaggaaacc ccgtgacttc taccacacat gttactgcct gagcggcttg   4620
tctgtggctc agcacgcttg gttaaaagac gaggacactc ctcctttgac tcgcgacatt   4680
atgggtggct actcgaatct ccttgaacct gttcaacttc ttcacaacat tgtcatggat   4740
cagtataatg aagctatcga gttcttcttt aaagcagcat gactcgaatt tccccgatcg   4800
ttcaaacatt tggcaataaa gtttcttaag attgaatcct gttgccggtc ttgcgatgat   4860
tatcatataa tttctgttga attacgttaa gcatgtaata attaacatgt aatgcatgac   4920
gttatttatg agatgggttt ttatgattag agtcccgcaa ttatacattt aatacgcgat   4980
agaaaacaaa atatagcgcg caaactagga taaattatcg cgcgcggtgt catctatgtt   5040
actagatcgg gaattcactg gccgtcgttt tacaacgtcg tgactgggaa aaccctggcg   5100
ttacccaact taatcgcctt gcagcacatc ccccttttcgc cagctggcgt aatagcgaag   5160
aggcccgcac cgatcgccct tcccaacagt tgcgcagcct gaatggcgcc cgctcctttc   5220
gctttcttcc cttcctttct cgccacgttc gccggctttc cccgtcaagc tctaaatcgg   5280
gggctccctt tagggttccg atttagtgct ttacggcacc tcgaccccaa aaaacttgat   5340
ttgggtgatg gttcacgtag tgggccatcg ccctgataga cggtttttcg ccctttgacg   5400
ttggagtcca cgttctttaa tagtggactc ttgttccaaa ctggaacaac actcaaccct   5460
atctcgggct attcttttga tttataaggg attttgccga tttcggaacc accatcaaac   5520
aggattttcg cctgctgggg caaaccagcg tggaccgctt gctgcaactc tctcagggcc   5580
aggcggtgaa gggcaatcag ctgttgcccg tctcactggt gaaaagaaaa accaccccag   5640
tacattaaaa acgtccgcaa tgtgttatta agttgtctaa gcgtcaattt gtttacacca   5700
```

-continued caatatatcc tgcca 5715

<210> SEQ ID NO 59
<211> LENGTH: 1772
<212> TYPE: DNA
<213> ORGANISM: Artificial Sequence
<220> FEATURE:
<223> OTHER INFORMATION: Description of Artificial Sequence: Plasmid
MuA-anti-GmFTB-Nos-Term

<400> SEQUENCE: 59
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
gtggtggaga atctgggtgc tttgaccaac tatactggca caatgagagt ccacttaaac 420
agtaacatgt gtgataatga tctctacgtt tacccggttt gtctctcagt ccaccctctt 480
gctcctgtgc acataagaga atatattgct gtaaagcaat actgtgaaaa agtggttctt 540
gtgctctcca ctcattaata aatttatagg caatattttt aaaatcagat gaactggatt 600
cactggtgcc ttcatgctca ccacggcatg ttgcatgact agaggttcca tccaaacttt 660
cttttgcttc agatacataa gataccgcaa aaatctgtga tgtctcttcc atctgtttgt 720
tgataataga agataatctt tgcaatagag caacagcacc tccctgccaa aaggaatagc 780
atccatccac cagtttattt gttctcccct ggaatccaca ttccttacct tgtcggaata 840
ccacccagtc aactaatcga ggcagatcca agtgattaac ctcaccaatc agaatcattg 900
tagctaatcc acaaaaggtg tacccaccat gagcctcaga accaggctca ccagcaatgc 960
caccctcata tgtttgacag cttataatgt agtctccaac attctggatc agctcatcat 1020
ccaaaatgtt caaaacactt gcaacagaaa tggcagtgta gcaagctcga acatcaattt 1080
caccttcatc atgcatcctg aatccaccat ttggttgctt catccgccgc agaaacccat 1140
acagtttatc tctattaatt gatgccaggg atttctcacc acccaaagta ataagtgaat 1200
taacagcagc ataagttgtg gcaatatgag gcatctggcc tggtccccccg gcatatccac 1260 cattcggatc ctggcaacgg ttaagaaaat cgatagcgtt atcttcgagt tcatcatcga 1320
cggattctcc caacaaagca atggagtgga agatccagta gcagagccag ggtcgattag 1380
cgtccaaaac ggaaaatgcg gaactgagat ggcgaaggcc tttggagaca tactgcatgt 1440
gattatcgcg ttgaagctcc aacatgaggg tttgggcgtt gcgaggaatg gtggcgagct 1500
cgaatttccc cgatcgttca aacatttggc aataaagttt cttaagattg aatcctgttg 1560
ccggtcttgc gatgattatc atataatttc tgttgaatta cgttaagcat gtaataatta 1620
acatgtaatg catgacgtta tttatgagat gggtttttat gattagagtc ccgcaattat 1680
acatttaata cgcgatagaa aacaaaatat agcgcgcaaa ctaggataaa ttatcgcgcg 1740
cggtgtcatc tatgttacta gatcgggaat tc 1772

<210> SEQ ID NO 60
<211> LENGTH: 2340
<212> TYPE: DNA
<213> ORGANISM: Artificial Sequence -continued
<220> FEATURE:
<223> OTHER INFORMATION: Description of Artificial Sequence: Plasmid
RD29AP-anti-GmFTB-Nos-Term

<400> SEQUENCE: 60

```
ggagccatag atgcaattca atcaaactga aatttctgca agaatctcaa acacggagat     60
ctcaaagttt gaaagaaaat ttatttcttc gactcaaaac aaacttacga aatttaggta    120
gaacttatat acattatatt gtaatttttt gtaacaaaat gtttttatta ttattataga    180
attttactgg ttaaattaaa aatgaataga aaaggtgaat taagaggaga gaggaggtaa    240
acattttctt ctattttttc atattttcag gataaattat tgtaaaagtt tacaagattt    300
ccatttgact agtgtaaatg aggaatattc tctagtaaga tcattatttc atctacttct    360
tttatcttct accagtagag gaataaacaa tatttagctc ctttgtaaat acaaattaat    420
tttccttctt gacatcattc aattttaatt ttacgtataa aataaaagat catacctatt    480
agaacgatta aggagaaata caattcgaat gagaaggatg tgccgtttgt tataataaac    540
agccacacga cgtaaacgta aaatgaccac atgatgggcc aatagacatg gaccgactac    600
taataatagt aagttacatt ttaggatgga ataaatatca taccgacatc agttttgaaa    660
gaaaagggaa aaaaagaaaa aataaataaa agatatacta ccgacatgag ttccaaaaag    720
caaaaaaaaa gatcaagccg acacagacac gcgtagagag caaaatgact ttgacgtcac    780
accacgaaaa cagacgcttc atacgtgtcc ctttatctct ctcagtctct ctataaactt    840
agtgagaccc tcctctgttt tactcacaaa tatgcaaact agaaaacaat catcaggaat    900
aaagggtttg attacttcta ttggaaaggt ggtggagaat ctgggtgctt tgaccaacta    960
tactggcaca atgagagtcc acttaaacag taacatgtgt gataatgatc tctacgttta   1020
cccggtttgt ctctcagtcc accctcttgc tcctgtgcac ataagagaat atattgctgt   1080
aaagcaatac tgtgaaaaag tggttcttgt gctctccact cattaataaa tttataggca   1140
atatttttaa aatcagatga actggattca ctggtgcctt catgctcacc acggcatgtt   1200
gcatgactag aggttccatc caaactttct tttgcttcag atacataaga taccgcaaaa   1260
atctgtgatg tctcttccat ctgtttgttg ataatagaag ataatctttg caatagagca   1320
acagcacctc cctgccaaaa ggaatagcat ccatccacca gtttatttgt tctcccctgg   1380
aatccacatt ccttaccttg tcggaatacc acccagtcaa ctaatcgagg cagatccaag   1440
tgattaacct caccaatcag aatcattgta gctaatccac aaaaggtgta cccaccatga   1500
gcctcagaac caggctcacc agcaatgcca ccctcatatg tttgacagct tataatgtag   1560
tctccaacat tctggatcag ctcatcatcc aaaatgttca aaacacttgc aacagaaatg   1620
gcagtgtagc aagctcgaac atcaatttca ccttcatcat gcatcctgaa tccaccattt   1680
ggttgcttca tccgccgcag aaacccatac agtttatctc tattaattga tgccagggat   1740
ttctcaccac ccaaagtaat aagtgaatta acagcagcat aagttgtggc aatatgaggc   1800
atctggcctg gtcccccggc atatccacca ttcggatcct ggcaacggtt aagaaaatcg   1860
atagcgttat cttcgagttc atcatcgacg gattctccca acaaagcaat ggagtggaag   1920
atccagtagc agagccaggg tcgattagcg tccaaaacgg aaaatgcgga actgagatgg   1980
cgaaggcctt tggagacata ctgcatgtga ttatcgcgtt gaagctccaa catgagggtt   2040
tgggcgttgc gaggaatggt ggcgagctcg aatttccccg atcgttcaaa catttggcaa   2100
taaagtttct taagattgaa tcctgttgcc ggtcttgcga tgattatcat ataatttctg   2160
ttgaattacg ttaagcatgt aataattaac atgtaatgca tgacgttatt tatgagatgg   2220
```

-continued gtttttatga ttagagtccc gcaattatac atttaatacg cgatagaaaa caaaatatag 2280
cgcgcaaact aggataaatt atcgcgcgcg gtgtcatcta tgttactaga tcgggaattc 2340

<210> SEQ ID NO 61
<211> LENGTH: 2298
<212> TYPE: DNA
<213> ORGANISM: Artificial Sequence
<220> FEATURE:
<223> OTHER INFORMATION: Description of Artificial Sequence: Plasmid
MuA-HP-GmFTB-Nos-Term

<400> SEQUENCE: 61
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
gtggtggaga atctgggtgc tttgaccaac tatactggca caatgagagt ccacttaaac 420
agtaacatgt gtgataatga tctctacgtt tacccggttt gtctctcagt ccaccctctt 480
gctcctgtgc acataagaga atatattgct gtaaagcaat actgtgaaaa agtggttctt 540
gtgctctcca ctcattaata aatttatagg caatattttt aaaatcagat gaactggatt 600
cactggtgcc ttcatgctca ccacggcatg ttgcatgact agaggttcca tccaaacttt 660
cttttgcttc agatacataa gataccgcaa aaatctgtga tgtctcttcc atctgtttgt 720
tgataataga agataatctt tgcaatagag caacagcacc tccctgccaa aaggaatagc 780
atccatccac cagtttattt gttctcccct ggaatccaca ttccttacct tgtcggaata 840
ccacccagtc aactaatcga ggcagatcca agtgattaac ctcaccaatc agaatcattg 900
tagctaatcc acaaaaggtg tacccaccat gagcctcaga accaggctca ccagcaatgc 960
caccctcata tgtttgacag cttataatgt agtctccaac attctggatc agctcatcat 1020
ccaaaatgtt caaaacactt gcaacagaaa tggcagtgta gcaagctcga acatcaattt 1080
caccttcatc atgcatcctg aatccaccat ttggttgctt catccgccgc agaaacccat 1140
acagtttatc tctattaatt gatgccaggg atttctcacc acccaaagta ataagtgaat 1200
taacagcagc ataagttgtg gcaatatgag gcatctggcc tggtcccccg gcatatccac 1260
cattcggatc ctggcaacgg ttaagaaaat cgatagcgtt atcttcgagt tcatcatcga 1320
cggattctcc caacaaagca atggagtgga agatccagta gcagagccag ggtcgattag 1380
cgtccaaaac ggaaaatgcg gaactgagat ggcgaaggcc tttggagaca tactgcatgt 1440
gattatcgcg ttgaagctcc aacatgaggg tttgggcgtt gcgaggaatg gtggcggtga 1500
ggttaatcac ttggatctgc ctcgattagt tgactgggtg gtattccgac aaggtaagga 1560
atgtggattc caggggagaa caaataaact ggtggatgga tgctattcct tttggcaggg 1620
aggtgctgtt gctctattgc aaagattatc ttctattatc aacaaacaga tggaagagac 1680
atcacagatt tttgcggtat cttatgtatc tgaagcaaaa gaaagtttgg atggaacctc 1740
tagtcatgca acatgccgtg gtgagcatga aggcaccagt gaatccagtt catctgattt 1800
taaaaatatt gcctataaat ttattaatga gtggagagca caagaaccac tttttcacag 1860
tattgcttta cagcaatata ttctcttatg tgcacaggag caagagggtg gactgagaga 1920

-continued caaaccgggt aaacgtagag atcattatca cacatgttac tgtttaagtg gactctcatt 1980
gtgccagtat agttggtcaa agcacccaga ttctccacca cgagctcgaa tttccccgat 2040
cgttcaaaca tttggcaata aagtttctta agattgaatc ctgttgccgg tcttgcgatg 2100
attatcatat aatttctgtt gaattacgtt aagcatgtaa taattaacat gtaatgcatg 2160
acgttattta tgagatgggt ttttatgatt agagtcccgc aattatacat ttaatacgcg 2220
atagaaaaca aaatatagcg cgcaaactag gataaattat cgcgcgcggt gtcatctatg 2280
ttactagatc gggaattc 2298

<210> SEQ ID NO 62
<211> LENGTH: 2866
<212> TYPE: DNA
<213> ORGANISM: Artificial Sequence
<220> FEATURE:
<223> OTHER INFORMATION: Description of Artificial Sequence: Plasmid RD29AP-HP-GmFTB-Nos-Term

<400> SEQUENCE: 62
ggagccatag atgcaattca atcaaactga aatttctgca agaatctcaa acacggagat 60
ctcaaagttt gaaagaaaat ttatttcttc gactcaaaac aaacttacga aatttaggta 120
gaacttatat acattatatt gtaatttttt gtaacaaaat gtttttatta ttattataga 180
attttactgg ttaaattaaa aatgaataga aaaggtgaat taagaggaga gaggaggtaa 240
acattttctt ctattttttc atattttcag gataaattat tgtaaaagtt tacaagattt 300
ccatttgact agtgtaaatg aggaatattc tctagtaaga tcattatttc atctacttct 360
tttatcttct accagtagag gaataaacaa tatttagctc ctttgtaaat acaaattaat 420
tttccttctt gacatcattc aattttaatt ttacgtataa aataaaagat catacctatt 480
agaacgatta aggagaaata caattcgaat gagaaggatg tgccgtttgt tataataaac 540
agccacacga cgtaaacgta aaatgaccac atgatgggcc aatagacatg gaccgactac 600
taataatagt aagttacatt ttaggatgga ataaatatca taccgacatc agttttgaaa 660
gaaaagggaa aaaaagaaaa aataaataaa agatatacta ccgacatgag ttccaaaaag 720
caaaaaaaaa gatcaagccg acacagacac gcgtagagag caaaatgact ttgacgtcac 780
accacgaaaa cagacgcttc atacgtgtcc ctttatctct ctcagtctct ctataaactt 840
agtgagaccc tcctctgttt tactcacaaa tatgcaaact agaaaacaat catcaggaat 900
aaagggtttg attacttcta ttggaaaggt ggtggagaat ctgggtgctt tgaccaacta 960
tactggcaca atgagagtcc acttaaacag taacatgtgt gataatgatc tctacgttta 1020
cccggtttgt ctctcagtcc accctcttgc tcctgtgcac ataagagaat atattgctgt 1080
aaagcaatac tgtgaaaaag tggttcttgt gctctccact cattaataaa tttataggca 1140
atatttttaa aatcagatga actggattca ctggtgcctt catgctcacc acggcatgtt 1200
gcatgactag aggttccatc caaactttct tttgcttcag atacataaga taccgcaaaa 1260
atctgtgatg tctcttccat ctgtttgttg ataatagaag ataatctttg caatagagca 1320
acagcacctc cctgccaaaa ggaatagcat ccatccacca gtttatttgt tctcccctgg 1380
aatccacatt ccttaccttg tcggaatacc acccagtcaa ctaatcgagg cagatccaag 1440
tgattaacct caccaatcag aatcattgta gctaatccac aaaaggtgta cccaccatga 1500
gcctcagaac caggctcacc agcaatgcca ccctcatatg tttgacagct tataatgtag 1560
tctccaacat tctggatcag ctcatcatcc aaaatgttca aaacacttgc aacagaaatg 1620

-continued gcagtgtagc aagctcgaac atcaatttca ccttcatcat gcatcctgaa tccaccattt 1680
ggttgcttca tccgccgcag aaacccatac agtttatctc tattaattga tgccagggat 1740
ttctcaccac ccaaagtaat aagtgaatta acagcagcat aagttgtggc aatatgaggc 1800
atctggcctg gtcccccggc atatccacca ttcggatcct ggcaacggtt aagaaaatcg 1860
atagcgttat cttcgagttc atcatcgacg gattctccca acaaagcaat ggagtggaag 1920
atccagtagc agagccaggg tcgattagcg tccaaaacgg aaaatgcgga actgagatgg 1980
cgaaggcctt tggagacata ctgcatgtga ttatcgcgtt gaagctccaa catgagggtt 2040
tgggcgttgc gaggaatggt ggcggtgagg ttaatcactt ggatctgcct cgattagttg 2100
actgggtggt attccgacaa ggtaaggaat gtggattcca ggggagaaca aataaactgg 2160
tggatggatg ctattccttt tggcagggag gtgctgttgc tctattgcaa agattatctt 2220
ctattatcaa caaacagatg gaagagacat cacagatttt tgcggtatct tatgtatctg 2280
aagcaaaaga aagtttggat ggaacctcta gtcatgcaac atgccgtggt gagcatgaag 2340
gcaccagtga atccagttca tctgatttta aaaatattgc ctataaattt attaatgagt 2400
ggagagcaca agaaccactt tttcacagta ttgctttaca gcaatatatt ctcttatgtg 2460
cacaggagca agagggtgga ctgagagaca aaccgggtaa acgtagagat cattatcaca 2520
catgttactg tttaagtgga ctctcattgt gccagtatag ttggtcaaag cacccagatt 2580
ctccaccacg agctcgaatt tccccgatcg ttcaaacatt tggcaataaa gtttcttaag 2640
attgaatcct gttgccggtc ttgcgatgat tatcatataa tttctgttga attacgttaa 2700
gcatgtaata attaacatgt aatgcatgac gttatttatg agatgggttt ttatgattag 2760
agtcccgcaa ttatacattt aatacgcgat agaaaacaaa atatagcgcg caaactagga 2820
taaattatcg cgcgcggtgt catctatgtt actagatcgg gaattc 2866

<210> SEQ ID NO 63
<211> LENGTH: 1882
<212> TYPE: DNA
<213> ORGANISM: Artificial Sequence
<220> FEATURE:
<223> OTHER INFORMATION: Description of Artificial Sequence: Plasmid MuA-anti-Zea maizeFTB-Nos-Term

<400> SEQUENCE: 63
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
ggatggattg gctccagcaa attagagtac ggtccaagca catgctgagg taatgggcac 420
gaaccagtat cagtcatggc actgtactgg ctaactgcga ggccactgag gcagtagcat 480
gaatgatagt gatctctgtt ctttccaggc ttatccctca agcctccctc tagtacctga 540
gaacaaagta ggatgtattg ttgcagggca atgttatgga agagtgggcc aatttggttg 600
ctctgttgta taaaatcaaa tccaaacttc gcatagtcca cagcagagga agacttattc 660
gcggtgcacc catatgaact ggtgctgcag gcatcctctc ctgatggcct tttgcaggaa 720
tacgaggacc tcaattgctt atcaacaatc gtaattaact tttgtgtgaa agcaatggca 780

-continued gctccctgcc aaaaggagta gcaaccatca accaatttat tagttcgtcc ttgaaatccg 840
cattccactc cttgacgaaa agccacccag ccaatcaaac taggcaagtc aactttctct 900
gcctcattaa gcaggatcaa agcagccaat ccacagaatg tatacccacc atgtgcttca 960
gcataaggct ccccagcaat accaccttca taagtttgac atcttgctat gtagtcgcct 1020
acaccttttg ccagtttaaa atcaagaata ttcacaaggc tggcaaccga tatagcggtg 1080
taggaagcac ggacatcaat ttcgccacca tcatgcattc tgaaagcacc tgatacatct 1140
ttcatctgca gcataaaatt gtacaggttg cccctattga ttgatgacaa tgctctttcg 1200
ctccctattg tcacaagtgt atttacagca gcataagtcg tagctaggtg aggcaactgt 1260
ccaggtccac cactatatcc accatcttta tcctgacatc gagctaagaa gtctatgata 1320
tcattctcaa gatcatcatc aagtgcttca tccagcaaag caagtggatg aaccatccag 1380
tagcatagcc aagggcgatt ggcatctaga acatgaaagg ctggtcccat atgcctcagc 1440
ccaggcgtca gatactcgat atgctgatca cgccacagct ctagcatgat ggatttcgtg 1500
ttgggcgcgg ccccgaagag ggagcggtag atgtcgccaa ccctggcctc caccttcatc 1560
tgctccacct gcgtcaccgt gagcctcggt aggtcgggat ccgccgagct cgaatttccc 1620
cgatcgttca aacatttggc aataaagttt cttaagattg aatcctgttg ccggtcttgc 1680
gatgattatc atataatttc tgttgaatta cgttaagcat gtaataatta acatgtaatg 1740
catgacgtta tttatgagat gggtttttat gattagagtc ccgcaattat acatttaata 1800
cgcgatagaa aacaaaatat agcgcgcaaa ctaggataaa ttatcgcgcg cggtgtcatc 1860
tatgttacta gatcgggaat tc 1882

<210> SEQ ID NO 64
<211> LENGTH: 2505
<212> TYPE: DNA
<213> ORGANISM: Artificial Sequence
<220> FEATURE:
<223> OTHER INFORMATION: Description of Artificial Sequence: Plasmid
MuA-HP-Zea MaizeFTB-Nos-Term

<400> SEQUENCE: 64
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
ggatggattg gctccagcaa attagagtac ggtccaagca catgctgagg taatgggcac 420
gaaccagtat cagtcatggc actgtactgg ctaactgcga ggccactgag gcagtagcat 480
gaatgatagt gatctctgtt ctttccaggc ttatccctca agcctccctc tagtacctga 540
gaacaaagta ggatgtattg ttgcagggca atgttatgga agagtgggcc aatttggttg 600
ctctgttgta taaaatcaaa tccaaacttc gcatagtcca cagcagagga agacttattc 660
gcggtgcacc catatgaact ggtgctgcag gcatcctctc ctgatggcct tttgcaggaa 720
tacgaggacc tcaattgctt atcaacaatc gtaattaact tttgtgtgaa agcaatggca 780
gctccctgcc aaaaggagta gcaaccatca accaatttat tagttcgtcc ttgaaatccg 840
cattccactc cttgacgaaa agccacccag ccaatcaaac taggcaagtc aactttctct 900

-continued

```
gcctcattaa gcaggatcaa agcagccaat ccacagaatg tatacccacc atgtgcttca    960
gcataaggct ccccagcaat accaccttca taagtttgac atcttgctat gtagtcgcct   1020
acaccttttg ccagtttaaa atcaagaata ttcacaaggc tggcaaccga tatagcggtg   1080
taggaagcac ggacatcaat ttcgccacca tcatgcattc tgaaagcacc tgatacatct   1140
ttcatctgca gcataaaatt gtacaggttg cccctattga ttgatgacaa tgctctttcg   1200
ctccctattg tcacaagtgt atttacagca gcataagtcg tagctaggtg aggcaactgt   1260
ccaggtccac cactatatcc accatcttta tcctgacatc gagctaagaa gtctatgata   1320
tcattctcaa gatcatcatc aagtgcttca tccagcaaag caagtggatg aaccatccag   1380
tagcatagcc aagggcgatt ggcatctaga acatgaaagg ctggtcccat atgcctcagc   1440
ccaggcgtca gatactcgat atgctgatca cgccacagct ctagcatgat ggatttcgtg   1500
ttgggcgcgg ccccgaagag ggagcggtag atgtcgccaa ccctggcctc caccttcatc   1560
tgctccacct gcgtcaccgt gagcctcggt aggtcgggat ccgccggatc cgctggggag   1620
ccttatgctg aagcacatgg tgggtataca ttctgtggat tggctgcttt gatcctgctt   1680
aatgaggcag agaaagttga cttgcctagt ttgattggct gggtggcttt tcgtcaagga   1740
gtggaatgcg gatttcaagg acgaactaat aaattggttg atggttgcta ctccttttgg   1800
cagggagctg ccattgcttt cacacaaaag ttaattacga ttgttgataa gcaattgagg   1860
tcctcgtatt cctgcaaaag gccatcagga gaggatgcct gcagcaccag ttcatatggg   1920
tgcaccgcga ataagtcttc ctctgctgtg gactatgcga agtttggatt tgattttata   1980
caacagagca accaaattgg cccactcttc cataacattg ccctgcaaca atacatccta   2040
ctttgttctc aggtactaga gggaggcttg agggataagc ctggaaagaa cagagatcac   2100
tatcattcat gctactgcct cagtggcctc gcagttagcc agtacagtgc catgactgat   2160
actggttcgt gcccattacc tcagcatgtg cttggaccgt actctaattt gctggagcca   2220
atccatccaa gcttgaattt ccccgatcgt tcaaacattt ggcaataaag tttcttaaga   2280
ttgaatcctg ttgccggtct tgcgatgatt atcatataat ttctgttgaa ttacgttaag   2340
catgtaataa ttaacatgta atgcatgacg ttatttatga gatgggtttt tatgattaga   2400
gtcccgcaat tatacattta atacgcgata gaaaacaaaa tatagcgcgc aaactaggat   2460
aaattatcgc gcgcggtgtc atctatgtta ctagatcgga agctt                   2505
```

<210> SEQ ID NO 65
<211> LENGTH: 1323
<212> TYPE: DNA
<213> ORGANISM: Pisum sativum

<400> SEQUENCE: 65

```
caacacctac ctagtgcttc tagttctggt tctaggactg agagtaaaca gaagtgaaga     60
agaatccaga acatggccgg gaatatcgaa gttgaagaag acgatcgtgt gccgctaaga    120
ttacgacctg agtggtcaga tgttactccg atcccacaag acgatggccc tagtcccgtc    180
gtgccgatca actactccga agagttttca gaagttatgg attactttcg tgctgtttac    240
ttcgccaaag aactttcctc tcgcgctctt gctctcaccg ccgaagctat cggtttaaac    300
gccggaaact acactgtgtg gcatttccgg cggttattac ttgagtcact gaaagttgac    360
ctacatgttg aacgggaatt cgtggagcgt gttgccagtg gcaattcaaa aaattatcag    420
atttggcatc atagacgatg ggttgctgag aaattaggac ctgaagctag aaacagtgaa    480
```

-continued

```
cttgagttca ccaaaaagat tctgtctgtt gacgccaaac actatcatgc atggtctcat    540

aggcagtggg ttcttcaaaa tctaggagga tgggaagatg aactcagtta ttgtagtgaa    600

ctgcttgcag aagacatatt taacaattct gcttggaatc agagatactt cgtcataaca    660

aggtctcccg tcttgggagg gctaaaagcc atgagagagt ctgaagtgct tttcaccgtt    720

gaagccatta tttcttaccc agaaaatgaa agctcatgga gatatcttcg aggacttttc    780

aaagatgaat ccacgttata tgtaaatgat gcccaagtat cttcattatg tttaaagatt    840

ttgaaaacta agagcaacta tttgtttgct ctaagtactc tgctggatct atctgcctcg    900

gttattcaac caaatgaaga tttcagagat gccattgagg ctttaagact tcagattttg    960

ataaaacaag attcagatat agcaataact atttgttcta ttttagaaca agttgatcca   1020

attagagtca actattgggt ctggcggaag agtagacttc ctcaggcagc gtaaaggaca   1080

aacttatgtc atatgtgtaa tttttagtct attggaattt gacgtcatgg ataacagggt   1140

ggttgttttt gttatgatat gttttccaga tgtatttcta tatttaacag caaagttgat   1200

ttaacattgg tgttaacaaa ccaatgatct ccaaaaaatc aatgttttat ttctcttcat   1260

ttgtctgatt ttgtggcata acattcttga tgattttgtg gtaaaaaaaa aaaaaaaaaa   1320

aaa                                                                 1323
```

<210> SEQ ID NO 66
<211> LENGTH: 1505
<212> TYPE: DNA
<213> ORGANISM: Lycopersicon esculentum

<400> SEQUENCE: 66

```
taccccgaag gcaattccag tattgaacta ccgccggcag ttttccgatc ggatcccgga     60

gccgagtatc aaatggacag ttgtgaggtg acgaaaacgc gaattccttt caaggaaagg    120

cccgactggg ccgatgtgaa gcccgttccg caagacgacg ggccctgccc ggttgttccc    180

atagcctaca cagaagactt ctctgaaacc atggactact tccgggcaat ttacgtagcc    240

gatgagcgat ctacacgcgc cctccagctt actggtgaag ctattcagct aaaccctgga    300

aattacactg tatggcaatt taggcgtgtt gtgctggagg cattgggtgt tgatttacgt    360

gaagaattga agtttgttga tcgcattgct ggggagaata ccaaaaatta tcaaatatgg    420

catcatagac ggtggcttgc tgagaagctg ggagctgatg ctgtgacaaa tgagctagaa    480

ttcaccaaga aaatattttc tcaggatgca aaaaattatc atgcttggtc ccatcggcag    540

tgggtccttc aagcacttgg aggatgggaa gatgagcttg cttattgtca acaactcctt    600

gaagatgata tttacaacaa ttctgcttgg aatcagagat actttgtcgt aacacgatca    660

cctctactag gggcctagt ggcaatgagg gaattggaag tgaattacac agttcaagcc    720

atcagagcta gtccagagaa tgaaagtcct tggaggtatc ttcgtggtct ttacaagaat    780

gatacacaat ctctagttca ggattctcaa gtagcatcag tactttggga cgtcttaacc    840

tcccaaaata gtcatgtgca cgctctgagg ttcttgttgg atcttctttg tcatgatttg    900

gaaccgagcc aagaattgaa aagtgctgta gatgttctta ctccccagtc atgctcacca    960

gatttagcac tgacaaagaa aatttgttcc atcttggaac atgctgatcc aatgagagta   1020

aaatattgga attggcgcaa gagcatggtt cgggttcaat tacttcagag tcagaatgca   1080

gagaggttgg ctaatttgag tgttcaagaa tgacttgtga gaatattgta ctgtgtttac   1140

gaaatacata cttgcatcta aggtgatcct tcgggcacat gtgctgggaa gtgactgaat   1200

atcacgaaga actaaaaaaa ctgtgattgg caacattgta ctactccaaa taggtcactt   1260
```

-continued

```
tcgatgactt tttgtactgc cttgagtttt ggctctgcta tgttttgtaa gttttggata   1320

tggatgcata gcttattgat acttttggtg acttaaaata ctctggaagg caggtagcat   1380

gtgtataatt cactgttact tcccatgtcg agttagatgc ttgaaaattt tagtaggtgt   1440

tcttttatga agcacacatt aatgtggaaa aaaaaaaaaa aaaaaaaaaa aaaaaaaaaa   1500

aaaaa                                                               1505
```

<210> SEQ ID NO 67
<211> LENGTH: 1218
<212> TYPE: DNA
<213> ORGANISM: Oryza sp.

<400> SEQUENCE: 67

```
gcacgaggtt ctaacgccgc cgccgccgcc gccgtctccg cagaatctga tcgatggcgc     60

cgtcgtcgac gtcgtcggag ggtgcctccg acgagtggtt gccacccagc cggcggccgg    120

agctggcgga cgtggtcccc gtgacgcagg acgacgggcc ccaccccgtg gtggccatcg    180

cctaccggga cgagttccgc gaggtcatgg actacttccg cgccctctac ttcgccggcg    240

agcgcagcgt ccgcgccctc cacctcaccg ccgaggtcat cgaccttaat cccggcaact    300

acacggtgtg gcattttagg cgtcttgttc tagaggcact ggatgctgat ctgcgtgagg    360

aaatggattt tgtggaccga attgtcgaat gtaacccaaa aaattatcaa atctggcatc    420

acaagagatg gcttgcggag aaattaggac cagatattgc aaataaagag cacgaattta    480

caaggaagat actttctatg gatgctaaaa attaccatgc ttggtctcat aggcagtggg    540

ttcttcaagc actgggtgga tgggagactg aactacagta ttgcaaccag ctgcttgagg    600

aagacgtctt caataattca gcttggaatc agagatacct tgtaataaca agttcaccac    660

ttcttggagg ccttgcagca atgcgtgact cggaagtgga ttacacagtt ggggctattc    720

tggctaaccc tcagaatgaa agcccctgga gatacctcaa aggcctgtac aagggtgaaa    780

ataacttgct gatggctgat gagcgcatct ctgatgtttg tctcaaggtc ctgaaacatg    840

attcgacctg cgtatttgct ttgagcttgc tgctcgatct tcttcaaatt ggtttacaac    900

cttcagatga actcaaagga actatcgaag caataaagaa ctctgatcct gaagcagatg    960

aagcagtaga tgctgatctt gcgactgcaa tctgctcaat attgcagaga tgtgatcccc   1020

tgcggataaa ttactggtcc tggtacagga ccactatttc ttctcaaacc tgaagcatgc   1080

agtggcctcc atgaggtcat aatggagata tcttctatct tcgtgtgatt ctgggcgttg   1140

aggtgcctag ctacatttgt tatgaacttt ccttgggcat aactgatcac tgatattact   1200

ccaatattgt gttctaaa                                                 1218
```

<210> SEQ ID NO 68
<211> LENGTH: 1426
<212> TYPE: DNA
<213> ORGANISM: Zea mays

<400> SEQUENCE: 68

```
gcacgagaca gcgcaattac ttaagctatt tgtattcgga tctgatccaa ccctggtggt     60

cagctggact catcgcccat ggagcacact aagtcaggcc ccagcagttg gccagaactg    120

gccgacgtgg tgccggtgcc gcaggacgat gggcctagcc ctgtggtgtc catcgcctat    180

cgagatgact ttcgtgaggt catggattac ttccgcgccc tctacctcac cggtgagcga    240

agccctcgcg ctctccgcct caccgccgag gccatcgagc tcaaccccgg caactacact    300
```

-continued

```
gtctggcatt tccggcgcct tattctggag tcactagatt ttgatttact agaggagatg    360

aaatttgtcg aaaaaattgc tgaatgcaat ccaaaaaatt accaaatctg gcaccataag    420

agatggcttg ctgagaaatt aggacctggt attgcaaaca aagagcatga attcacaatg    480

aagatacttg ctattgatgc aaaaaattat catgcttggt ctcataggca gtgggttctt    540

caagcgttgg ggggatggga gactgaatta gaatactgtg accacttact taaggaagac    600

gtcttcaata attcagcttg gaatcagaga tactttgtta taacaagatc accatttctt    660

ggtggccttg cggcaatgcg tgattcagaa gtagactaca caattgaagc tattctagca    720

aacgctcaga atgaaagccc ctggaggtac ctcaagggtc tatacaaggg tgagaataac    780

ctgctagtag aggacgagcg catctctgct gtttgtttca aggtcctgaa gaatgattgg    840

acttgtgtat ttgctttgag tttgctgctc gatcttctct gcactggttt gcagccttca    900

gatgaactta ggtccactct tgaaacaata aggagctccc atcctgaaac cgcggatgat    960

gatcctgcag ccgctgtttg ctgtatcctg cagaaatgtg atcccctgcg ggtaaattat   1020

tggtcttggt tcaaggacac tctttctcag atctcatgac ttcacatggg ttcacccctt   1080

gtccgcgctg gtccgggctc tgtgagatag acatgtttta gatagtttca ttggacaccc   1140

aaacagagcg gacagagtgt atggctgcta ccttctccgt gactgaaagc agtgcttgta   1200

acgattttgt ttagtaaaat ttgtgagtgt tactgctcca aacaacacct tatgcaacca   1260

tatttgaata tttcacatgt aagcttgaat ccaggtgtgt ttgttaatgt attacacttg   1320

ccatgggagc ctaaatgaga cccataatca cttccactag agtcggaaga ccgtgtcgag   1380

cagttcactc atatggtcac ttaaagcaaa aaaaaaaaaa aaaaaa                  1426
```

```
<210> SEQ ID NO 69
<211> LENGTH: 1261
<212> TYPE: DNA
<213> ORGANISM: Glycine max

<400> SEQUENCE: 69

gcacgaggat taacgaagga tggaatctgg gtctagcgaa ggagaagagg tgcagcaacg     60

cgtgccgttg agggagagag tggagtggtc agatgttact ccggttcctc aaaacgacgg    120

ccctaaccct gtcgttccga tccagtacac tgaagagttt tccgaagtta tggattactt    180

tcgcgccgtt tacctcaccg atgaacgctc ccctcgcgcc ctcgctctca cagccgaagc    240

cgttcaattc aactccggca actacactgt gtggcatttc cgacggttgt tacttgagtc    300

gctaaaagtc gacttgaacg atgaactgga ttttgtggag cgtatggccg ctggaaattc    360

taaaaattat cagatgtggc atcatagacg atgggttgcc gagaagttag gtcctgaagc    420

tagaaacaat gagctcgagt tcaccaaaaa gatactgtcc gttgatgcca aacattatca    480

tgcatggtct catagacagt gggctcttca aacactagga ggatgggaag atgaacttaa    540

ttattgcaca gaactactta aagaagacat ttttaacaat tctgcttgga atcagagata    600

ttttgtcata acaaggtctc ctttcttggg gggcctaaaa gctatgagag agtctgaagt    660

gctttacacc attgaagcca ttatagccta ccctgaaaat gaaagctcgt ggagatatct    720

acgaggactt tataaaggtg aaactacttc atgggtaaat gatcctcaag tttcttcagt    780

atgcttaaag attttgagaa ctaagagcaa ctacgtgttt gctcttagca ctattttaga    840

tcttatatgc tttggttatc aaccaaatga agacattaga gatgccattg acgccttaaa    900

gaccgcagat atggataaac aagatttaga tgatgatgag aaaggggaac aacaaaattt    960

aaatatagca cgaaatattt gttctatcct aaaacaagtt gatccaatta gaaccaacta   1020
```

-continued

```
ttggatttgg cgcaagagca gacttcctct atcagcttag taaccaaagt aattaaaggg   1080

caactctgtg ttatgtgtaa cctagtttat tgaaactgga tttttattta ttattatttt   1140

ttatgttgtc atgtatctgt ttgtgcaaat ttatcttttt gtcatgccat tactggcatt   1200

tgagtgtaag gattgaaagc catgcagaat aagaaattta agtttttttt tccgttgaaa   1260

a                                                                   1261
```

<210> SEQ ID NO 70
<211> LENGTH: 1333
<212> TYPE: DNA
<213> ORGANISM: Glycine max

<400> SEQUENCE: 70

```
gcacgagctt gcgtgtggag tgaagaagat taacgaagga tggaatctgg gtctagcgaa     60

ggagaagagg tgcagcaacg cgtgccgttg agggagagag tggagtggtc agatgttact    120

ccggttcctc aaaacgacgg ccctaaccct gtcgttccga tccagtacac tgaagagttt    180

tccgaagtta tggattactt tcgcgccgtt tacctcaccg atgaacgctc ccctcgcgcc    240

ctcgctctca cagccgaagc cgttcaattc aactccggca actacactgt gtggcatttc    300

cgacggttgt tacttgagtc gctaaaagtc gacttgaacg atgaactgga gtttgtggag    360

cgtatggccg ctggaaattc taaaaattat cagatgtggt gtgatgctct gctctgctct    420

ttcttccata ctttgcatca tagacgatgg gttgccgaga agttaggtcc tgaagctaga    480

aacaatgagc tcgagttcac caaaaagata ctgtccgttg atgccaaaca ttatcatgca    540

tggtctcata gacagtgggc tcttcaaaca ctaggaggat gggaagatga acttaattat    600

tgcacagaac tacttaaaga agacattttt aacaattctg cttggaatca gagatatttt    660

gtcataacaa ggtctccttt cttgggggc ctaaaagcta tgagagagtc tgaagtgctt    720

tacaccattg aagccattat agcctaccct gaaaatgaaa gctcgtggag atatctacga    780

ggactttata aaggtgaaac tacttcatgg gtaaatgatc ctcaagtttc ttcagtatgc    840

ttaaagattt tgagaactaa gagcaactac gtgtttgctc ttagcactat tttagatctt    900

atatgctttg gttatcaacc aaatgaagac attagagatg ccattgacgc cttaaagacc    960

gcagatatgg ataaacaaga tttagatgat gatgagaaag gggaacaaca aaatttaaat   1020

atagcacgaa atatttgttc tatcctaaaa caagttgatc caattagaac caactattgg   1080

atttggcgca agagcagact tcctctatca gcttagtaac caaagtaatt aaagggcaac   1140

tctgtgttat gtgtaaccta gtttattgaa actggatgtt tatttattat tattttttat   1200

gttgtcatgt atctgtttgt gcaaatttat ctttttgtca tgccattact ggcatttgag   1260

tgtaaggatt gaaagccatg cagaataaga aatttaagtt tttttttccg ttgaaaaaaa   1320

aaaaaaaaaa aaa                                                      1333
```

<210> SEQ ID NO 71
<211> LENGTH: 1339
<212> TYPE: DNA
<213> ORGANISM: Triticum sp.

<400> SEQUENCE: 71

```
cggacgtggc gccgctgccg caggccgacg ggccctgccc cgtcgtctcc atcgcttacc     60

gcggcgactt ccgcgaggtc atggactact tccgcgccct ctacgccgcc ggcgagcgca    120

gcccccgcgc cctccgcctc accgccgacg ccatccacct caaccccggc aactacactg    180
```

-continued

```
tatggcattt caggcgcgtt gttctagagg cactggatgc tgatttattg ctagaaatgc    240

attttgtgga ccaaattgct gaatctaatc caaaaaatta ccaagtctgg catcacaaga    300

gatggcttgc tgagaaaata ggaccagatg ctgcaaatag tgaacatgac ttcacaagga    360

agatacttgc tatggatgct aaaaactacc atgcttggtc ccataggcag tgggttcttc    420

aagcattggg tggatgggag agtgaactgc agtactgcaa ccagcttctt gaggaagatg    480

tcttcaataa ctcagcttgg aatcagagat accttgtggt aacacgatca ccaattcttg    540

ggggccttgc ggcaatgcgc gactcagaag tagattacac agttgaggcc attatggtga    600

accctcagaa tgaaagcccc tggagatacc tcagaggttt atataaggat gataacaatt    660

tgctggtggc tgataatcgc atttctgatg cttgcctcaa ggtcctgaat aaggattgga    720

catgcgtatt tgctttgagc ttcctgcttg atcttcttcg catgggtttg cagccttcga    780

atgaacttaa aggaaccatc gaagcaatgg agaactctga tcctgaaacg ggacatgctg    840

atattgcagt agctgtctgc tcaatcctgc agaaatgtga tcccctgcgg ataaactact    900

ggtcatggta ccagaccact ctttcttctt agacatctga aaattcagct gaagacagtt    960

ttagcagcat gatgtaaact caatcgaagg ggttgacgca gtgtatgaaa aacctttcct   1020

gtgatcttgg tgcggagcaa tttgtactga ttttactggg aaaaatcaat caatgacagc   1080

atgcccaaca atgtcttgtg tgaatatgtt actgcctgat attcacatgt tagcagaatg   1140

agaataacca atcaaactcc aacgagcaga ttgttacagt aacggccact ggtggtgtga   1200

aaatcctgaa atctgcttca gtcactttgc cttgtttaca gttgagtctg ttgttgtgat   1260

ctgtacctaa tgcatgtaca caatcatcaa attattagtt tttgtaccaa tgagtattcg   1320

atgaaaaaaa aaaaaaaaa                                                1339


<210> SEQ ID NO 72
<211> LENGTH: 333
<212> TYPE: PRT
<213> ORGANISM: Pisum sativum

<400> SEQUENCE: 72

Met Ala Gly Asn Ile Glu Val Glu Glu Asp Asp Arg Val Pro Leu Arg
  1               5                  10                  15

Leu Arg Pro Glu Trp Ser Asp Val Thr Pro Ile Pro Gln Asp Asp Gly
             20                  25                  30

Pro Ser Pro Val Val Pro Ile Asn Tyr Ser Glu Glu Phe Ser Glu Val
         35                  40                  45

Met Asp Tyr Phe Arg Ala Val Tyr Phe Ala Lys Glu Leu Ser Ser Arg
     50                  55                  60

Ala Leu Ala Leu Thr Ala Glu Ala Ile Gly Leu Asn Ala Gly Asn Tyr
 65                  70                  75                  80

Thr Val Trp His Phe Arg Arg Leu Leu Leu Glu Ser Leu Lys Val Asp
                 85                  90                  95

Leu His Val Glu Arg Glu Phe Val Glu Arg Val Ala Ser Gly Asn Ser
            100                 105                 110

Lys Asn Tyr Gln Ile Trp His His Arg Arg Trp Val Ala Glu Lys Leu
        115                 120                 125

Gly Pro Glu Ala Arg Asn Ser Glu Leu Glu Phe Thr Lys Lys Ile Leu
    130                 135                 140

Ser Val Asp Ala Lys His Tyr His Ala Trp Ser His Arg Gln Trp Val
145                 150                 155                 160

Leu Gln Asn Leu Gly Gly Trp Glu Asp Glu Leu Ser Tyr Cys Ser Glu
```

-continued

```
                165                 170                 175

Leu Leu Ala Glu Asp Ile Phe Asn Asn Ser Ala Trp Asn Gln Arg Tyr
            180                 185                 190

Phe Val Ile Thr Arg Ser Pro Val Leu Gly Gly Leu Lys Ala Met Arg
        195                 200                 205

Glu Ser Glu Val Leu Phe Thr Val Glu Ala Ile Ile Ser Tyr Pro Glu
    210                 215                 220

Asn Glu Ser Ser Trp Arg Tyr Leu Arg Gly Leu Phe Lys Asp Glu Ser
225                 230                 235                 240

Thr Leu Tyr Val Asn Asp Ala Gln Val Ser Ser Leu Cys Leu Lys Ile
                245                 250                 255

Leu Lys Thr Lys Ser Asn Tyr Leu Phe Ala Leu Ser Thr Leu Leu Asp
            260                 265                 270

Leu Ser Ala Ser Val Ile Gln Pro Asn Glu Asp Phe Arg Asp Ala Ile
        275                 280                 285

Glu Ala Leu Arg Leu Gln Ile Leu Ile Lys Gln Asp Ser Asp Ile Ala
    290                 295                 300

Ile Thr Ile Cys Ser Ile Leu Glu Gln Val Asp Pro Ile Arg Val Asn
305                 310                 315                 320

Tyr Trp Val Trp Arg Lys Ser Arg Leu Pro Gln Ala Ala
                325                 330


<210> SEQ ID NO 73
<211> LENGTH: 346
<212> TYPE: PRT
<213> ORGANISM: Lycopersicon esculentum

<400> SEQUENCE: 73

Met Asp Ser Cys Glu Val Thr Lys Thr Arg Ile Pro Phe Lys Glu Arg
  1               5                  10                  15

Pro Asp Trp Ala Asp Val Lys Pro Val Pro Gln Asp Asp Gly Pro Cys
            20                  25                  30

Pro Val Val Pro Ile Ala Tyr Thr Glu Asp Phe Ser Glu Thr Met Asp
        35                  40                  45

Tyr Phe Arg Ala Ile Tyr Val Ala Asp Glu Arg Ser Thr Arg Ala Leu
     50                  55                  60

Gln Leu Thr Gly Glu Ala Ile Gln Leu Asn Pro Gly Asn Tyr Thr Val
 65                  70                  75                  80

Trp Gln Phe Arg Arg Val Val Leu Glu Ala Leu Gly Val Asp Leu Arg
                 85                  90                  95

Glu Glu Leu Lys Phe Val Asp Arg Ile Ala Gly Glu Asn Thr Lys Asn
            100                 105                 110

Tyr Gln Ile Trp His His Arg Arg Trp Leu Ala Glu Lys Leu Gly Ala
        115                 120                 125

Asp Ala Val Thr Asn Glu Leu Glu Phe Thr Lys Lys Ile Phe Ser Gln
    130                 135                 140

Asp Ala Lys Asn Tyr His Ala Trp Ser His Arg Gln Trp Val Leu Gln
145                 150                 155                 160

Ala Leu Gly Gly Trp Glu Asp Glu Leu Ala Tyr Cys Gln Gln Leu Leu
                165                 170                 175

Glu Asp Asp Ile Tyr Asn Asn Ser Ala Trp Asn Gln Arg Tyr Phe Val
            180                 185                 190

Val Thr Arg Ser Pro Leu Leu Gly Gly Leu Val Ala Met Arg Glu Leu
        195                 200                 205
```

-continued

```
Glu Val Asn Tyr Thr Val Gln Ala Ile Arg Ala Ser Pro Glu Asn Glu
    210                 215                 220

Ser Pro Trp Arg Tyr Leu Arg Gly Leu Tyr Lys Asn Asp Thr Gln Ser
225                 230                 235                 240

Leu Val Gln Asp Ser Gln Val Ala Ser Val Leu Trp Asp Val Leu Thr
                245                 250                 255

Ser Gln Asn Ser His Val His Ala Leu Arg Phe Leu Leu Asp Leu Leu
            260                 265                 270

Cys His Asp Leu Glu Pro Ser Gln Glu Leu Lys Ser Ala Val Asp Val
        275                 280                 285

Leu Thr Pro Gln Ser Cys Ser Pro Asp Leu Ala Leu Thr Lys Lys Ile
    290                 295                 300

Cys Ser Ile Leu Glu His Ala Asp Pro Met Arg Val Lys Tyr Trp Asn
305                 310                 315                 320

Trp Arg Lys Ser Met Val Arg Val Gln Leu Leu Gln Ser Gln Asn Ala
                325                 330                 335

Glu Arg Leu Ala Asn Leu Ser Val Gln Glu
            340                 345
```

<210> SEQ ID NO 74
<211> LENGTH: 339
<212> TYPE: PRT
<213> ORGANISM: Oryza sp.

<400> SEQUENCE: 74

```
Met Ala Pro Ser Ser Thr Ser Ser Glu Gly Ala Ser Asp Glu Trp Leu
  1               5                  10                  15

Pro Pro Ser Arg Arg Pro Glu Leu Ala Asp Val Val Pro Val Thr Gln
             20                  25                  30

Asp Asp Gly Pro His Pro Val Val Ala Ile Ala Tyr Arg Asp Glu Phe
         35                  40                  45

Arg Glu Val Met Asp Tyr Phe Arg Ala Leu Tyr Phe Ala Gly Glu Arg
     50                  55                  60

Ser Val Arg Ala Leu His Leu Thr Ala Glu Val Ile Asp Leu Asn Pro
 65                  70                  75                  80

Gly Asn Tyr Thr Val Trp His Phe Arg Arg Leu Val Leu Glu Ala Leu
                 85                  90                  95

Asp Ala Asp Leu Arg Glu Glu Met Asp Phe Val Asp Arg Ile Val Glu
            100                 105                 110

Cys Asn Pro Lys Asn Tyr Gln Ile Trp His His Lys Arg Trp Leu Ala
        115                 120                 125

Glu Lys Leu Gly Pro Asp Ile Ala Asn Lys Glu His Glu Phe Thr Arg
    130                 135                 140

Lys Ile Leu Ser Met Asp Ala Lys Asn Tyr His Ala Trp Ser His Arg
145                 150                 155                 160

Gln Trp Val Leu Gln Ala Leu Gly Gly Trp Glu Thr Glu Leu Gln Tyr
                165                 170                 175

Cys Asn Gln Leu Leu Glu Glu Asp Val Phe Asn Asn Ser Ala Trp Asn
            180                 185                 190

Gln Arg Tyr Leu Val Ile Thr Ser Ser Pro Leu Leu Gly Gly Leu Ala
        195                 200                 205

Ala Met Arg Asp Ser Glu Val Asp Tyr Thr Val Gly Ala Ile Leu Ala
    210                 215                 220

Asn Pro Gln Asn Glu Ser Pro Trp Arg Tyr Leu Lys Gly Leu Tyr Lys
225                 230                 235                 240
```

-continued

```
Gly Glu Asn Asn Leu Leu Met Ala Asp Glu Arg Ile Ser Asp Val Cys
                245                 250                 255

Leu Lys Val Leu Lys His Asp Ser Thr Cys Val Phe Ala Leu Ser Leu
            260                 265                 270

Leu Leu Asp Leu Leu Gln Ile Gly Leu Gln Pro Ser Asp Glu Leu Lys
        275                 280                 285

Gly Thr Ile Glu Ala Ile Lys Asn Ser Asp Pro Glu Ala Asp Glu Ala
    290                 295                 300

Val Asp Ala Asp Leu Ala Thr Ala Ile Cys Ser Ile Leu Gln Arg Cys
305                 310                 315                 320

Asp Pro Leu Arg Ile Asn Tyr Trp Ser Trp Tyr Arg Thr Thr Ile Ser
                325                 330                 335

Ser Gln Thr


<210> SEQ ID NO 75
<211> LENGTH: 326
<212> TYPE: PRT
<213> ORGANISM: Zea mays

<400> SEQUENCE: 75

Met Glu His Thr Leu Ser Gly Pro Ser Ser Trp Pro Glu Leu Ala Asp
  1               5                  10                  15

Val Val Pro Val Pro Gln Asp Asp Gly Pro Ser Pro Val Val Ser Ile
             20                  25                  30

Ala Tyr Arg Asp Asp Phe Arg Gly Val Met Asp Tyr Phe Arg Ala Leu
         35                  40                  45

Tyr Leu Thr Gly Glu Arg Ser Pro Arg Ala Leu Arg Leu Thr Ala Glu
     50                  55                  60

Ala Ile Glu Leu Asn Pro Gly Asn Tyr Thr Val Trp His Phe Arg Arg
 65                  70                  75                  80

Leu Ile Leu Glu Ser Leu Asp Phe Asp Leu Leu Glu Glu Met Lys Phe
                 85                  90                  95

Val Glu Leu Ile Ala Glu Cys Asn Pro Lys Asn Tyr Gln Ile Trp His
            100                 105                 110

His Leu Arg Trp Leu Ala Glu Lys Leu Gly Pro Gly Ile Ala Asn Lys
        115                 120                 125

Glu His Glu Phe Thr Met Lys Ile Leu Ala Ile Asp Ala Leu Asn Tyr
    130                 135                 140

His Ala Trp Ser His Arg Gln Trp Val Leu Gln Ala Leu Gly Gly Trp
145                 150                 155                 160

Glu Thr Glu Leu Glu Tyr Cys Asp His Leu Leu Lys Glu Asp Val Phe
                165                 170                 175

Asn Asn Ser Ala Trp Asn Gln Arg Tyr Phe Val Ile Thr Arg Ser Pro
            180                 185                 190

Phe Leu Gly Gly Leu Ala Ala Met Arg Asp Ser Gly Val Asp Tyr Thr
        195                 200                 205

Ile Glu Ala Ile Leu Ala Asn Ala Gln Asn Gly Ser Pro Trp Arg Tyr
    210                 215                 220

Leu Lys Gly Leu Tyr Lys Gly Glu Asn Asn Leu Leu Val Glu Asp Gly
225                 230                 235                 240

Arg Ile Ser Ala Val Cys Phe Lys Val Leu Lys Asn Asp Trp Thr Cys
                245                 250                 255

Val Phe Ala Leu Ser Leu Leu Leu Asp Leu Leu Cys Thr Gly Leu Gln
            260                 265                 270
```

-continued

Pro Ser Asp Gly Leu Arg Ser Thr Leu Gly Thr Ile Arg Ser Ser His
        275                 280                 285

Pro Glu Thr Ala Asp Asp Asp Pro Ala Ala Ala Val Cys Cys Ile Leu
    290                 295                 300

Gln Lys Cys Asp Pro Leu Ala Val Asn Tyr Trp Ser Trp Phe Lys Asp
305                 310                 315                 320

Thr Leu Ser Gln Ile Ser
                325

<210> SEQ ID NO 76
<211> LENGTH: 346
<212> TYPE: PRT
<213> ORGANISM: Glycine max

<400> SEQUENCE: 76

Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
             20                  25                  30

Asp Gly Pro Asn Pro Val Val Pro Ile Gln Tyr Thr Glu Glu Phe Ser
         35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Asp Phe Val Glu Arg Met Ala Ala Gly
            100                 105                 110

Asn Ser Lys Asn Tyr Gln Met Trp His His Arg Arg Trp Val Ala Glu
        115                 120                 125

Lys Leu Gly Pro Glu Ala Arg Asn Asn Glu Leu Glu Phe Thr Lys Lys
    130                 135                 140

Ile Leu Ser Val Asp Ala Lys His Tyr His Ala Trp Ser His Arg Gln
145                 150                 155                 160

Trp Ala Leu Gln Thr Leu Gly Gly Trp Glu Asp Glu Leu Asn Tyr Cys
                165                 170                 175

Thr Glu Leu Leu Lys Glu Asp Ile Phe Asn Asn Ser Ala Trp Asn Gln
            180                 185                 190

Arg Tyr Phe Val Ile Thr Arg Ser Pro Phe Leu Gly Gly Leu Lys Ala
        195                 200                 205

Met Arg Glu Ser Glu Val Leu Tyr Thr Ile Glu Ala Ile Ile Ala Tyr
    210                 215                 220

Pro Glu Asn Glu Ser Ser Trp Arg Tyr Leu Arg Gly Leu Tyr Lys Gly
225                 230                 235                 240

Glu Thr Thr Ser Trp Val Asn Asp Pro Gln Val Ser Ser Val Cys Leu
                245                 250                 255

Lys Ile Leu Arg Thr Lys Ser Asn Tyr Val Phe Ala Leu Ser Thr Ile
            260                 265                 270

Leu Asp Leu Ile Cys Phe Gly Tyr Gln Pro Asn Glu Asp Ile Arg Asp
        275                 280                 285

Ala Ile Asp Ala Leu Lys Thr Ala Asp Met Asp Lys Gln Asp Leu Asp
    290                 295                 300

Asp Asp Glu Lys Gly Glu Gln Gln Asn Leu Asn Ile Ala Arg Asn Ile

-continued

```
305                 310                 315                 320

Cys Ser Ile Leu Lys Gln Val Asp Pro Ile Arg Thr Asn Tyr Trp Ile
                325                 330                 335

Trp Arg Lys Ser Arg Leu Pro Leu Ser Ala
            340                 345


<210> SEQ ID NO 77
<211> LENGTH: 358
<212> TYPE: PRT
<213> ORGANISM: Glycine max

<400> SEQUENCE: 77

Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
             20                  25                  30

Asp Gly Pro Asn Pro Val Val Pro Ile Gln Tyr Thr Glu Glu Phe Ser
         35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Glu Phe Val Glu Arg Met Ala Ala Gly
            100                 105                 110

Asn Ser Lys Asn Tyr Gln Met Trp Cys Asp Ala Leu Leu Cys Ser Phe
        115                 120                 125

Phe His Thr Leu His His Arg Arg Trp Val Ala Glu Lys Leu Gly Pro
    130                 135                 140

Glu Ala Arg Asn Asn Glu Leu Glu Phe Thr Lys Lys Ile Leu Ser Val
145                 150                 155                 160

Asp Ala Lys His Tyr His Ala Trp Ser His Arg Gln Trp Ala Leu Gln
                165                 170                 175

Thr Leu Gly Gly Trp Glu Asp Glu Leu Asn Tyr Cys Thr Glu Leu Leu
            180                 185                 190

Lys Glu Asp Ile Phe Asn Asn Ser Ala Trp Asn Gln Arg Tyr Phe Val
        195                 200                 205

Ile Thr Arg Ser Pro Phe Leu Gly Gly Leu Lys Ala Met Arg Glu Ser
    210                 215                 220

Glu Val Leu Tyr Thr Ile Glu Ala Ile Ile Ala Tyr Pro Glu Asn Glu
225                 230                 235                 240

Ser Ser Trp Arg Tyr Leu Arg Gly Leu Tyr Lys Gly Glu Thr Thr Ser
                245                 250                 255

Trp Val Asn Asp Pro Gln Val Ser Ser Val Cys Leu Lys Ile Leu Arg
            260                 265                 270

Thr Lys Ser Asn Tyr Val Phe Ala Leu Ser Thr Ile Leu Asp Leu Ile
        275                 280                 285

Cys Phe Gly Tyr Gln Pro Asn Glu Asp Ile Arg Asp Ala Ile Asp Ala
    290                 295                 300

Leu Lys Thr Ala Asp Met Asp Lys Gln Asp Leu Asp Asp Asp Glu Lys
305                 310                 315                 320

Gly Glu Gln Gln Asn Leu Asn Ile Ala Arg Asn Ile Cys Ser Ile Leu
                325                 330                 335
```

-continued

```
Lys Gln Val Asp Pro Ile Arg Thr Asn Tyr Trp Ile Trp Arg Lys Ser
            340                 345                 350

Arg Leu Pro Leu Ser Ala
        355
```

<210> SEQ ID NO 78
<211> LENGTH: 309
<212> TYPE: PRT
<213> ORGANISM: Triticum sp.

<400> SEQUENCE: 78

```
Asp Val Ala Pro Leu Pro Gln Ala Asp Gly Pro Cys Pro Val Val Ser
  1               5                  10                  15

Ile Ala Tyr Arg Gly Asp Phe Arg Glu Val Met Asp Tyr Phe Arg Ala
            20                  25                  30

Leu Tyr Ala Ala Gly Glu Arg Ser Pro Arg Ala Leu Arg Leu Thr Ala
        35                  40                  45

Asp Ala Ile His Leu Asn Pro Gly Asn Tyr Thr Val Trp His Phe Arg
     50                  55                  60

Arg Val Val Leu Gly Ala Leu Asp Ala Asp Leu Leu Leu Glu Met His
 65                  70                  75                  80

Phe Val Asp Gln Ile Ala Glu Ser Asn Pro Leu Asn Tyr Gln Val Trp
                 85                  90                  95

His His Lys Arg Trp Leu Ala Glu Lys Ile Gly Pro Asp Ala Ala Asn
            100                 105                 110

Ser Glu His Asp Phe Thr Arg Lys Ile Leu Ala Met Asp Ala Lys Asn
        115                 120                 125

Tyr His Ala Trp Ser His Arg Gln Trp Val Leu Gln Ala Leu Gly Gly
    130                 135                 140

Trp Glu Ser Glu Leu Gln Tyr Cys Asn Gln Leu Leu Glu Glu Asp Val
145                 150                 155                 160

Phe Asn Asn Ser Ala Trp Asn Gln Arg Tyr Leu Val Val Thr Arg Ser
                165                 170                 175

Pro Ile Leu Gly Gly Leu Ala Ala Met Arg Asp Ser Glu Val Asp Tyr
            180                 185                 190

Thr Val Glu Ala Ile Met Val Asn Pro Gln Asn Glu Ser Pro Trp Arg
        195                 200                 205

Tyr Leu Arg Gly Leu Tyr Lys Asp Asp Asn Asn Leu Leu Val Ala Asp
    210                 215                 220

Asn Arg Ile Ser Asp Ala Cys Leu Lys Val Leu Asn Lys Asp Trp Thr
225                 230                 235                 240

Cys Val Phe Ala Leu Ser Phe Leu Leu Asp Leu Leu Arg Met Gly Leu
                245                 250                 255

Gln Pro Ser Asn Glu Leu Lys Gly Thr Ile Glu Ala Met Glu Asn Ser
            260                 265                 270

Asp Pro Glu Thr Gly His Ala Asp Ile Ala Val Ala Val Cys Ser Ile
        275                 280                 285

Leu Gln Lys Cys Asp Pro Leu Arg Ile Asn Tyr Trp Ser Trp Tyr Gln
    290                 295                 300

Thr Thr Leu Ser Ser
305
```

<210> SEQ ID NO 79
<211> LENGTH: 5517
<212> TYPE: DNA
<213> ORGANISM: Artificial Sequence -continued
<220> FEATURE:
<223> OTHER INFORMATION: Description of Artificial Sequence: DN90AtFTB
vector

<400> SEQUENCE: 79
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220

-continued

```
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccgtccgga attcccgggt cgacccacgc   3360
gtccgggaga ttcagcgaga taagcaattg gattatctga tgaaaggctt aaggcagctt   3420
ggtccgcagt tttcttcctt agatgctaat cgaccttggc tttgttactg gattcttcat   3480
tcaatagctt tgcttgggga gactgtggat gatgaattag aaagcaatgc cattgacttc   3540
cttggacgct gccagggctc tgaaggtgga tacggtggtg gtcctggcca acttccacat   3600
cttgcaacta cttatgctgc agtgaatgca cttgttactt taggaggtga caaagccctt   3660
tcttcaatta atagagaaaa aatgtcttgt tttttaagac ggatgaagga tacaagtgga   3720
ggtttcagga tgcatgatat gggagaaatg gatgttcgtg catgctacac tgcaatttcg   3780
gttgcaagca tcctaaatat tatggatgat gaactcaccc agggcctagg agattacatc   3840
ttgagttgcc aaacttatga aggtggcatt ggaggggaac ctggctccga agctcacggt   3900
gggtatacct actgtggttt ggctgctatg attttaatca atgaggtcga ccgtttgaat   3960
ttggattcat taatgaattg ggctgtacat cgacaaggag tagaaatggg atttcaaggt   4020
aggacgaaca aattggtcga tggttgctac acattttggc aggcagcccc ttgtgttcta   4080
ctacaaagat tatattcaac caatgatcat gacgttcatg gatcatcaca tatatcagaa   4140
gggacaaatg aagaacatca tgctcatgat gaagatgacc ttgaagacag tgatgatgat   4200
gatgattctg atgaggacaa cgatgaagat tcagtgaatg gtcacagaat ccatcataca   4260
tccacctaca ttaacaggag aatgcaactg gtttttgata gcctcggctt gcagagatat   4320
gtactcttgt gctctaagat ccctgacggt ggattcagag acaagccgag gaaaccccgt   4380
gacttctacc acacatgtta ctgcctgagc ggcttgtctg tggctcagca cgcttggtta   4440
aaagacgagg acactcctcc tttgactcgc gacattatgg gtggctactc gaatctcctt   4500
gaacctgttc aacttcttca caacattgtc atggatcagt ataatgaagc tatcgagttc   4560
```

-continued ttctttaaag cagcatgagg atccctcgaa tttccccgat cgttcaaaca tttggcaata 4620
aagtttctta agattgaatc ctgttgccgg tcttgcgatg attatcatat aatttctgtt 4680
gaattacgtt aagcatgtaa taattaacat gtaatgcatg acgttattta tgagatgggt 4740
ttttatgatt agagtcccgc aattatacat ttaatacgcg atagaaaaca aaatatagcg 4800
cgcaaactag gataaattat cgcgcgcggt gtcatctatg ttactagatc gggaattcac 4860
tggccgtcgt tttacaacgt cgtgactggg aaaaccctgg cgttacccaa cttaatcgcc 4920
ttgcagcaca tccccctttc gccagctggc gtaatagcga agaggcccgc accgatcgcc 4980
cttcccaaca gttgcgcagc ctgaatggcg cccgctcctt tcgctttctt cccttccttt 5040
ctcgccacgt tcgccggctt tccccgtcaa gctctaaatc gggggctccc tttagggttc 5100
cgatttagtg ctttacggca cctcgacccc aaaaaacttg atttgggtga tggttcacgt 5160
agtgggccat cgccctgata gacggttttt cgccctttga cgttggagtc cacgttcttt 5220
aatagtggac tcttgttcca aactggaaca acactcaacc ctatctcggg ctattctttt 5280
gatttataag ggattttgcc gatttcggaa ccaccatcaa acaggatttt cgcctgctgg 5340
ggcaaaccag cgtggaccgc ttgctgcaac tctctcaggg ccaggcggtg aagggcaatc 5400
agctgttgcc cgtctcactg gtgaaaagaa aaaccacccc agtacattaa aaacgtccgc 5460
aatgtgttat taagttgtct aagcgtcaat ttgtttacac cacaatatat cctgcca 5517

<210> SEQ ID NO 80
<211> LENGTH: 1627
<212> TYPE: DNA
<213> ORGANISM: Unknown Organism
<220> FEATURE:
<223> OTHER INFORMATION: Description of Unknown Organism: Wiggum Gene

<400> SEQUENCE: 80
atgccagtag taacccgctt gattcgtttg aagtgtgtag ggctcagact tgaccggagt 60
ggactcaatc ggcgaatctg tcacggagga cacggggaat caacgcggcg gagagtgatg 120
gaagagcttt caagcctaac cgtgagtcag cgcgagcaat ttctggtgga gaacgatgtg 180
ttcgggatct ataattactt cgacgccagc gacgtttcta ctcaaaaata catgatggag 240
attcagcgag ataagcaatt ggattatctg atgaaaggct taaggcagct tggtccgcag 300
ttttcttcct tagatgctaa tcgaccttgg ctttgttact ggattcttca ttcaatagct 360
ttgcttgggg agactgtgga tgatgaatta gaaagcaatg ccattgactt ccttggacgc 420
tgccagggct ctgaaggtgg atacggtggt ggtcctggcc aacttccaca tcttgcaact 480
acttatgctg cagtgaatgc acttgttact ttaggaggtg acaaagccct ttcttcaatt 540
aatagagaaa aaatgtcttg ttttttaaga cggatgaagg atacaagtgg aggtttcagg 600
atgcatgata tgggagaaat ggatgttcgt gcatgctaca ctgcaatttc ggttgcaagc 660
atcctaaata ttatggatga tgaactcacc cagggcctag gagattacat cttgagttgc 720
caaacttatg aaggtggcat tggaggggaa cctggctccg aagctcacgg tgggtatacc 780
tactgtggtt tggctgctat gattttaatc aatgaggtcg accgtttgaa tttggattca 840
ttaatgaatt gggctgtaca tcgacaagga gtagaaatgg gatttcaagg taggacgaac 900
aaattggtcg atggttgcta cacattttgg caggcagccc cttgtgttct actacaaaga 960
ttatattcaa ccaatgatca tgacgttcat ggatcatcac atatatcaga agggacaaat 1020
gaagaacatc atgctcatga tgaagatgac cttgaagaca gtgatgatga tgatgattct 1080
gatgaggaca acgatgaaga ttcagtgaat ggtcacagaa tccatcatac atccacctac 1140

-continued

```
attaacagga gaatgcaact ggtttttgat agcctcggct tgcagagata tgtactcttg   1200
tgctctaaga tccctgacgg tggattcaga gacaagccga ggaaaccccg tgacttctac   1260
cacacatgtt actgcctgag cggcttgtct gtggctcagc acgcttggtt aaaagacgag   1320
gacactcctc ctttgactcg cgacattatg ggtggctact cgaatctcct tgaacctgtt   1380
caacttcttc acaacattgt catggatcag tataatgaag ctatcgagtt cttctttaaa   1440
gcagcatgac ccgttgttgc taatgtatgg gaaactccaa acataagagt tttcgtagtg   1500
ttgtaacttg taagatttca aaagaagttt cactaattta accttaaaac ctgttacttt   1560
tttattacgt atataccatt tatcatatct ttggtttacg acttaaagaa tttgatgatt   1620
gttgaaa                                                             1627
```

<210> SEQ ID NO 81
<211> LENGTH: 1135
<212> TYPE: DNA
<213> ORGANISM: Glycine max

<400> SEQUENCE: 81

```
gccaccattc ctcgcaacgc ccaaaccctc atgttggagc ttcaacgcga taatcacatg     60
cagtatgtct ccaaaggcct tcgccatctc agttccgcat tttccgtttt ggacgctaat    120
cgaccctggc tctgctactg gatcttccac tccattgctt tgtcgggaga atccgtcgat    180
gatgaactcg aagataacgc tatcgatttt cttaaccgtt gccaggatcc gaatggtgga    240
tatgccgggg gaccaggcca gatgcctcat attgccacaa cttatgctgc tgttaattca    300
cttattactt tgggtggtga gaaatccctg gcatcaatta atagagataa actgtatggg    360
tttctgcggc ggatgaagca accaaatggt ggattcagga tgcatgatga aggtgaaatt    420
gatgttcgag cttgctacac tgccatttct gttgcaagtg ttttgaacat tttggatgat    480
gagctgatcc agaatgttgg agactacatt ataagctgtc aaacatatga gggtggcatt    540
gctggtgagc ctggttctga ggctcatggt gggtacacct tttgtggatt agctacaatg    600
attctgattg gtgaggttaa tcacttggat ctgcctcgat tagttgactg ggtggtattc    660
cgacaaggta aggaatgtgg attccagggg agaacaaata aactggtgga tggatgctat    720
tccttttggc agggaggtgc tgttgctcta ttgcaaagat tatcttctat tatcaacaaa    780
cagatggaag agacatcaca gatttttgcg gtatcttatg tatctgaagc aaaagaaagt    840
ttggatggaa cctctagtca tgcaacatgc cgtggtgagc atgaaggcac cagtgaatcc    900
agttcatctg attttaaaaa tattgcctat aaatttatta atgagtggag agcacaagaa    960
ccactttttc acagtattgc tttacagcaa tatattctct tatgtgcaca ggagcaagag   1020
ggtggactga gagacaaacc gggtaaacgt agagatcatt atcacacatg ttactgttta   1080
agtggactct cattgtgcca gtatagttgg tcaaagcacc cagattctcc accac        1135
```

<210> SEQ ID NO 82
<211> LENGTH: 1245
<212> TYPE: DNA
<213> ORGANISM: Glycine max

<400> SEQUENCE: 82

```
ggcggatccc gacctaccga ggctcacggt gacgcaggtg gagcagatga aggtggaggc     60
cagggttggc gacatctacc gctccctctt cggggccgcg cccaacacga aatccatcat    120
gctagagctg tggcgtgatc agcatatcga gtatctgacg cctgggctga ggcatatggg    180
```

-continued

```
accagccttt catgttctag atgccaatcg cccttggcta tgctactgga tggttcatcc    240
acttgctttg ctggatgaag cacttgatga tgatcttgag aatgatatca tagacttctt    300
agctcgatgt caggataaag atggtggata tagtggtgga cctggacagt tgcctcacct    360
agctacgact tatgctgctg taaatacact tgtgacaata gggagccaaa gagcattgtc    420
atcaatcaat aggggcaacc tgtacaattt tatgctgcag atgaaagatg tatcaggtgc    480
tttcagaatg catgatggtg gcgaaattga tgtccgtgct tcctacaccg ctatatcggt    540
tgccagcctt gtgaatattc ttgattttaa actggcaaaa ggtgtaggcg actacatagc    600
aagatgtcaa acttatgaag gtggtattgc tggggagcct tatgctgaag cacatggtgg    660
gtatacattc tgtggattgg ctgctttgat cctgcttaat gaggcagaga aagttgactt    720
gcctagtttg attggctggg tggcttttcg tcaaggagtg gaatgcggat ttcaaggacg    780
aactaataaa ttggttgatg gttgctactc cttttggcag ggagctgcca ttgctttcac    840
acaaaagtta attacgattg ttgataagca attgaagtcc tcgtattcct gcaaaaggcc    900
atcaggagag gatgcctgca gcaccagttc atatgggtgc accgcgaaaa agtcttcctc    960
tgctgtggac tatgcgaagt ttggatttga ttttatacaa cagagcaacc aaattggccc   1020
actcttccat aacattgccc tgcaacaata catcctactt tgttctcagg tactagaggg   1080
aggcttgagg gataagcctg gaaagaacag agatcactac cattcatgct actgcctcag   1140
tggcctcgca gttagccagt acagtgccat gactgatact ggttcgtgcc cattacctca   1200
gcatgtgctt ggaccgtact ctaatttgct ggagccaatc catcc                   1245
```

<210> SEQ ID NO 83
<211> LENGTH: 1648
<212> TYPE: DNA
<213> ORGANISM: Pisum sativum

<400> SEQUENCE: 83

```
cggacccccc cgtccacaat cgtgatgatg acgtctccgc gagcatttca acaaccagtt     60
actcaaacca ccgcggagta acacatggaa gcttcaaccg cggcggagac accaactccg    120
acggtgagtc agagagatca atggatagta gaatcacagg tctttcatat ttatcaactc    180
ttcgccaata ttcctcctaa cgcccaatct atcattcgac cttggctgtg ttactggatt    240
attcattcaa ttgctttgtt gggagaatct attgatgatg atctcgaaga taacactgtc    300
gattttctta accgttgcca ggatccaaat ggtggatatg ctgggggacc tggtcagatg    360
cctcatcttg ccacaactta tgctgcagtc aatactctta ttactctggg tggtgagaaa    420
tctttggcat ctattaatag aaataagttg tacgggttta tgcggcggat gaaacagcca    480
aacggcggat tcaggatgca tgacgaggga gaaattgacg ttcgagcttg ctacactgcc    540
atctctgtgg caagtgttct gaacattttg gatgatgagc tgatcaagaa tgttggagac    600
ttcattttaa gctgtcaaac atatgaggga ggccttgctg gtgagcctgg gtctgaggct    660
catggcgggt ataccttttg tgggttagct gcaatgattc tgattggtga ggttaatcgc    720
ttggatctgc ctcgtttact tgattgggtt gtgtttcggc aaggtaaaga gtgtggattt    780
caggggagaa cgaataaatt ggtagatgga tgctactcgt tttggcaggg aggtgctgtt    840
gccctattgc aaagattaca ttctattatc gacgaacaaa tggcagaggc atcacagttt    900
gttacagtat ctgatgcacc tgaagaaaag gaatgtttgg acggaacctc aagtcatgca    960
acttcccata ttaggcatga aggcatgaat gaatcctgct catctgacgt taaaaatatt   1020
ggttataact ttattagtga gtggagacaa agtgaaccac tttttcacag cattgcctta   1080
```

-continued cagcaatata ttcttttatg ttcacaggag caagatggtg ggctcaggga caaaccgggt 1140
aaacgcaggg atcattatca ttcatgttac tgtttaagtg ggttgtcact gtgccagtat 1200
agttggtcga agcgcccaga ttctccaccg ctgcctaagg tagtaatggg cccatactcc 1260
aatctcttag aacccatcca tcctctcttt aatgttgttt tggatcgata tcgtgaagct 1320
catgaattct tttctcagtt gtgacggatg acaaggtttt agctaccaat agctcgatca 1380
ttagaatgta aaatgtaaac taaaatatga aatatgaaat accaaaaaga tattattgga 1440
tgaaattcac gtggatctaa tacaactgcg tggttttcat tcctgatttg attttgattt 1500
acatgagtta aaacgttaaa cccttcttat tcatacattt gttaagagct taaggcttaa 1560
tggttaagcc aatgatataa atatttatgc agaaagctgt tgcttatcac caacggtaat 1620
attaataagc aaacaagtat tctgtgat 1648

<210> SEQ ID NO 84
<211> LENGTH: 1832
<212> TYPE: DNA
<213> ORGANISM: Lycopersicon esculentum

<400> SEQUENCE: 84
gtaaacgagc gttgatttgt cgctgacgaa atttacagtc aagagtagta accggttgta 60
gtgaaaaaat ggagtcgagg aaagtgacga agacgctgga agatcaatgg gtggtggagc 120
gtcgagtccg agagatatac gattatttct acagcatttc ccccaactct ccgtccgacc 180
tcatagagat cgaacgtgac aaacacttcg gttatctaag ccaaggtctc agaaaacttg 240
gtccgtcgtt ttccgttttg gatgccagtc gaccatggct ttgctactgg acacttcatt 300
caatcgcttt gttgggagaa tctattggtg gcaaactgga aaatgatgca attgactttc 360
tgacccgttg ccaggataaa gatggtggct atggaggtgg acctggtcag atgcctcatc 420
ttgcaactac ttatgctgca gtcaattcac taataacttt gggcaaacct gaagctctgt 480
catcaattaa tagagaaaag ttgtacacat ttttgctgcg aatgaaagac gcaagtggtg 540
gattcaggat gcacgatggt ggagaagtag atgttcgtgc ctgttatact gccatttctg 600
ttgcaaatat attaaacatt gtggatgacg agctgattca tggtgttgga aattacatcc 660
taagttgtca gacttatgaa ggtggaattg ctggcgaacc aggttctgaa gctcatggtg 720
ggtatacttt ctgtgggttg gctgcaatga ttctgatcaa cgaagtagat cgattggact 780
tgccaggttt aattgattgg gtggtattta gacaaggggt cgaaggtgga tttcaaggca 840
ggacaaataa attagtcgat ggctgctatt cctttttggca gggcgcggta gtgtttctta 900
tacaaagact aaatttgata gtccatgaac aactagggct gtcaaatgac ctcagtacag 960
aaagtgctga tgattcttca gagtcagagt tatctgatga agaagagcat ttggaaggga 1020
tatcctctca tgttcaggat actttccctc ttggacaagc aggtgcttgt caagaaaatg 1080
cttctcatag cccaaaaata gcagatactg gatatgagtt tatcaaccga cccatagcta 1140
tgaggcctct ctttgacagc atgtatctgc agcaatatgt tcttctttgc tctcagattg 1200
aagttggtgg tttcagagac aaacctggga agggtagaga ctactaccat acctgttact 1260
gtttaagtgg tctttcaatt gctcagtata gctggaccga cgaagctgat tctacaccat 1320
tacccaggga tgtatttggt ccttattcca aatgtctgtt ggaacaggtt cacccactct 1380
tcaacgtagt gttggatcgg tattatgaag ctcgcgaata ctctcaggct tgtgagactg 1440
tttcaccact ttcattagca ccaacttttt cagaaactta gttgcaatcc agaagttaaa 1500

-continued

```
agtgtcattg ggttcaaaag agttgtgatc gtttatgtac atatccttgc atttgtatac   1560

gtgatacaag ttgagagaat aacgggtact ttctgaactt gctgaactag cacgtaaatt   1620

cgtctctggt ttagtgaggt ctgtaaacat caatgtgaaa ttgcgagata tgcatgtaat   1680

agtggctaag atttacaaat ctggataccg gttattagtg atcagaaatt tcattcaatt   1740

tcccaaacgg tcacctaagt ttaggatatt gctttaaaat attatttatt tttcatttaa   1800

gaatcaaaaa aaaaaaaaaa aaaaaaaaaa aa                                 1832
```

```
<210> SEQ ID NO 85
<211> LENGTH: 1449
<212> TYPE: DNA
<213> ORGANISM: Nicotiana sp.
<220> FEATURE:
<221> NAME/KEY: misc_feature
<222> LOCATION: (87)
<223> OTHER INFORMATION: Wherein n is a or t or c or g.
<220> FEATURE:
<221> NAME/KEY: misc_feature
<222> LOCATION: (1038)
<223> OTHER INFORMATION: Wherein n is a or t or c or g.

<400> SEQUENCE: 85

ggcacgagcg gcacgaggac actggaagat caatggatgg tggagcgtca agttcgggag     60

atatacaatt ttttctacag cattccnccc aattcccact tagagacttc aacagaaaag    120

cacttcgatt atctcactcg aggtctcaga aaacttggtc cgtcgttctc cgtcttggat    180

gctaatcgac catggctttg ctactggata cttcattcaa tcgctttgtt gggagaatct    240

attgatgccc aactggaaaa tgatgcaatt gactttctga gccgttgcca ggatgaagat    300

ggtggctatg gtggtggacc tggtcagatg cctcatcttg caactactta tgctgcagtc    360

aattcactca taactttggg cagccctaaa gctctgtcat caatcaatag agaaaaattg    420

tatacatttt ggctgcaaat gaaagacaca agtggtggct tcaggatgca tgatggtgga    480

gaagtagatg ttcgtgcctg ttatactgcc atttctgttg caagtatatt gcaaattgtg    540

gatgatgaac tgattaatga tgttgggaat tacatcctaa gttgtcagac ttatgaaggt    600

ggaattgctg gcgaaccagg ttctgaagct catggtgggt ataccttctg tgggttggct    660

gcaatgattc tgattaacga agcgaatcga ttggacttgc caagattaat tgattgggtg    720

gtatttagac aaggagtcga aggtggattt caaggcagga caaataaatt agtcgatggc    780

tgctattcct tttggcaggc cgcggtagct tttcttatac aaagattaaa atcgacagtc    840

catgaacaac tagggctgtc aaatgaactc agtacagaaa gtgctgatga ttcttcggag    900

tcagagttat ctgatgaaga gcatttgcaa gggacatcat ctcatgttca gaagacttgc    960

cctcttggac aagaaggaca ggaaaatgct tcagatccca caaagatagc agatactggt   1020

tatgattttg tcaatcgnac gatagctatg cgacctgtgt ttgacagctt ttatctgcag   1080

caatacgttc ttctctgctc ccagatagat ggaggtttca gagacaaacc tgggaagggt   1140

agagaccact accatacttg ctactgttta agtggtcttt caattgctca atatagctgg   1200

accaacgaag ctgatgcgcc accattaccc agggatgtat ttggtcctta ttctcaaaat   1260

cttttggaac agattcaccc actttacaac gtagtgttgg atcggtatta tgaagctcgt   1320

agcttcttct catgcttgtg ataatatttt acgcgatagc tgtagctgga atgttacctc   1380

tagttgttca gaatcagaga ctaatctatt attttgaggg attggattca aaaaaaaaaa   1440

aaaaaaaaa                                                           1449
```

-continued

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: FORWARD
Primer SacI site

<400> SEQUENCE: 86
aaacccggga tgccagtagt aaccccgc 27

<210> SEQ ID NO 87
<211> LENGTH: 482
<212> TYPE: PRT
<213> ORGANISM: Unknown Organism
<220> FEATURE:
<223> OTHER INFORMATION: Description of Unknown Organism: Wiggum gene

<400> SEQUENCE: 87

```
Met Pro Val Val Thr Arg Leu Ile Arg Leu Lys Cys Val Gly Leu Arg
  1               5                  10                  15

Leu Asp Arg Ser Gly Leu Asn Arg Arg Ile Cys His Gly Gly His Gly
             20                  25                  30

Glu Ser Thr Arg Arg Arg Val Met Glu Glu Leu Ser Ser Leu Thr Val
         35                  40                  45

Ser Gln Arg Glu Gln Phe Leu Val Glu Asn Asp Val Phe Gly Ile Tyr
     50                  55                  60

Asn Tyr Phe Asp Ala Ser Asp Val Ser Thr Gln Lys Tyr Met Met Glu
 65                  70                  75                  80

Ile Gln Arg Asp Lys Gln Leu Asp Tyr Leu Met Lys Gly Leu Arg Gln
                 85                  90                  95

Leu Gly Pro Gln Phe Ser Ser Leu Asp Ala Asn Arg Pro Trp Leu Cys
            100                 105                 110

Tyr Trp Ile Leu His Ser Ile Ala Leu Leu Gly Glu Thr Val Asp Asp
        115                 120                 125

Glu Leu Glu Ser Asn Ala Ile Asp Phe Leu Gly Arg Cys Gln Gly Ser
    130                 135                 140

Glu Gly Gly Tyr Gly Gly Gly Pro Gly Gln Leu Pro His Leu Ala Thr
145                 150                 155                 160

Thr Tyr Ala Ala Val Asn Ala Leu Val Thr Leu Gly Gly Asp Lys Ala
                165                 170                 175

Leu Ser Ser Ile Asn Arg Glu Lys Met Ser Cys Phe Leu Arg Arg Met
            180                 185                 190

Lys Asp Thr Ser Gly Gly Phe Arg Met His Asp Met Gly Glu Met Asp
        195                 200                 205

Val Arg Ala Cys Tyr Thr Ala Ile Ser Val Ala Ser Ile Leu Asn Ile
    210                 215                 220

Met Asp Asp Glu Leu Thr Gln Gly Leu Gly Asp Tyr Ile Leu Ser Cys
225                 230                 235                 240

Gln Thr Tyr Glu Gly Gly Ile Gly Gly Glu Pro Gly Ser Glu Ala His
                245                 250                 255

Gly Gly Tyr Thr Tyr Cys Gly Leu Ala Ala Met Ile Leu Ile Asn Glu
            260                 265                 270

Val Asp Arg Leu Asn Leu Asp Ser Leu Met Asn Trp Ala Val His Arg
        275                 280                 285

Gln Gly Val Glu Met Gly Phe Gln Gly Arg Thr Asn Lys Leu Val Asp
    290                 295                 300
```

-continued

Gly Cys Tyr Thr Phe Trp Gln Ala Ala Pro Cys Val Leu Leu Gln Arg
305 310 315 320

Leu Tyr Ser Thr Asn Asp His Asp Val His Gly Ser Ser His Ile Ser
325 330 335

Glu Gly Thr Asn Glu Glu His His Ala His Asp Glu Asp Asp Leu Glu
340 345 350

Asp Ser Asp Asp Asp Asp Asp Ser Asp Glu Asp Asn Asp Glu Asp Ser
355 360 365

Val Asn Gly His Arg Ile His His Thr Ser Thr Tyr Ile Asn Arg Arg
370 375 380

Met Gln Leu Val Phe Asp Ser Leu Gly Leu Gln Arg Tyr Val Leu Leu
385 390 395 400

Cys Ser Lys Ile Pro Asp Gly Gly Phe Arg Asp Lys Pro Arg Lys Pro
405 410 415

Arg Asp Phe Tyr His Thr Cys Tyr Cys Leu Ser Gly Leu Ser Val Ala
420 425 430

Gln His Ala Trp Leu Lys Asp Glu Asp Thr Pro Pro Leu Thr Arg Asp
435 440 445

Ile Met Gly Gly Tyr Ser Asn Leu Leu Glu Pro Val Gln Leu Leu His
450 455 460

Asn Ile Val Met Asp Gln Tyr Asn Glu Ala Ile Glu Phe Phe Phe Lys
465 470 475 480

Ala Ala

<210> SEQ ID NO 88
<211> LENGTH: 378
<212> TYPE: PRT
<213> ORGANISM: Glycine max

<400> SEQUENCE: 88

Ala Thr Ile Pro Arg Asn Ala Gln Thr Leu Met Leu Glu Leu Gln Arg
1 5 10 15

Asp Asn His Met Gln Tyr Val Ser Lys Gly Leu Arg His Leu Ser Ser
20 25 30

Ala Phe Ser Val Leu Asp Ala Asn Arg Pro Trp Leu Cys Tyr Trp Ile
35 40 45

Phe His Ser Ile Ala Leu Ser Gly Glu Ser Val Asp Asp Glu Leu Glu
50 55 60

Asp Asn Ala Ile Asp Phe Leu Asn Arg Cys Gln Asp Pro Asn Gly Gly
65 70 75 80

Tyr Ala Gly Gly Pro Gly Gln Met Pro His Ile Ala Thr Thr Tyr Ala
85 90 95

Ala Val Asn Ser Leu Ile Thr Leu Gly Gly Glu Lys Ser Leu Ala Ser
100 105 110

Ile Asn Arg Asp Lys Leu Tyr Gly Phe Leu Arg Arg Met Lys Gln Pro
115 120 125

Asn Gly Gly Phe Arg Met His Asp Glu Gly Glu Ile Asp Val Arg Ala
130 135 140

Cys Tyr Thr Ala Ile Ser Val Ala Ser Val Leu Asn Ile Leu Asp Asp
145 150 155 160

Glu Leu Ile Gln Asn Val Gly Asp Tyr Ile Ile Ser Cys Gln Thr Tyr
165 170 175

Glu Gly Gly Ile Ala Gly Glu Pro Gly Ser Glu Ala His Gly Gly Tyr
180 185 190

-continued

```
Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240

Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270

Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375
```

<210> SEQ ID NO 89
<211> LENGTH: 414
<212> TYPE: PRT
<213> ORGANISM: Zea mays

<400> SEQUENCE: 89

```
Ala Asp Pro Asp Leu Pro Arg Leu Thr Val Thr Gln Val Glu Gln Met
  1               5                  10                  15

Lys Val Glu Ala Arg Val Gly Asp Ile Tyr Arg Ser Leu Phe Gly Ala
             20                  25                  30

Ala Pro Asn Thr Lys Ser Ile Met Leu Glu Leu Trp Arg Asp Gln His
         35                  40                  45

Ile Glu Tyr Leu Thr Pro Gly Leu Arg His Met Gly Pro Ala Phe His
     50                  55                  60

Val Leu Asp Ala Asn Arg Pro Trp Leu Cys Tyr Trp Met Val His Pro
 65                  70                  75                  80

Leu Ala Leu Leu Asp Glu Ala Leu Asp Asp Asp Leu Glu Asn Asp Ile
                 85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn
        115                 120                 125

Thr Leu Val Thr Ile Gly Ser Gln Arg Ala Leu Ser Ser Ile Asn Arg
    130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190
```

-continued

```
Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Lys Ser Ser Tyr Ser Cys Lys Arg Pro Ser Gly Glu Asp
    290                 295                 300

Ala Cys Ser Thr Ser Ser Tyr Gly Cys Thr Ala Lys Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380

Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410
```

<210> SEQ ID NO 90
<211> LENGTH: 420
<212> TYPE: PRT
<213> ORGANISM: Pisum sativum

<400> SEQUENCE: 90

```
Met Glu Ala Ser Thr Ala Ala Glu Thr Pro Thr Pro Thr Val Ser Gln
  1               5                  10                  15

Arg Asp Gln Trp Ile Val Glu Ser Gln Val Phe His Ile Tyr Gln Leu
             20                  25                  30

Phe Ala Asn Ile Pro Pro Asn Ala Gln Ser Ile Ile Arg Pro Trp Leu
         35                  40                  45

Cys Tyr Trp Ile Ile His Ser Ile Ala Leu Leu Gly Glu Ser Ile Asp
     50                  55                  60

Asp Asp Leu Glu Asp Asn Thr Val Asp Phe Leu Asn Arg Cys Gln Asp
 65                  70                  75                  80

Pro Asn Gly Gly Tyr Ala Gly Gly Pro Gly Gln Met Pro His Leu Ala
                 85                  90                  95

Thr Thr Tyr Ala Ala Val Asn Thr Leu Ile Thr Leu Gly Gly Glu Lys
            100                 105                 110

Ser Leu Ala Ser Ile Asn Arg Asn Lys Leu Tyr Gly Phe Met Arg Arg
        115                 120                 125

Met Lys Gln Pro Asn Gly Gly Phe Arg Met His Asp Glu Gly Glu Ile
    130                 135                 140

Asp Val Arg Ala Cys Tyr Thr Ala Ile Ser Val Ala Ser Val Leu Asn
```

-continued

```
145                 150                 155                 160

Ile Leu Asp Asp Glu Leu Ile Lys Asn Val Gly Asp Phe Ile Leu Ser
                165                 170                 175

Cys Gln Thr Tyr Glu Gly Gly Leu Ala Gly Glu Pro Gly Ser Glu Ala
            180                 185                 190

His Gly Gly Tyr Thr Phe Cys Gly Leu Ala Ala Met Ile Leu Ile Gly
        195                 200                 205

Glu Val Asn Arg Leu Asp Leu Pro Arg Leu Leu Asp Trp Val Val Phe
    210                 215                 220

Arg Gln Gly Lys Glu Cys Gly Phe Gln Gly Arg Thr Asn Lys Leu Val
225                 230                 235                 240

Asp Gly Cys Tyr Ser Phe Trp Gln Gly Gly Ala Val Ala Leu Leu Gln
                245                 250                 255

Arg Leu His Ser Ile Ile Asp Glu Gln Met Ala Glu Ala Ser Gln Phe
            260                 265                 270

Val Thr Val Ser Asp Ala Pro Glu Glu Lys Glu Cys Leu Asp Gly Thr
        275                 280                 285

Ser Ser His Ala Thr Ser His Ile Arg His Glu Gly Met Asn Glu Ser
    290                 295                 300

Cys Ser Ser Asp Val Lys Asn Ile Gly Tyr Asn Phe Ile Ser Glu Trp
305                 310                 315                 320

Arg Gln Ser Glu Pro Leu Phe His Ser Ile Ala Leu Gln Gln Tyr Ile
                325                 330                 335

Leu Leu Cys Ser Gln Glu Gln Asp Gly Gly Leu Arg Asp Lys Pro Gly
            340                 345                 350

Lys Arg Arg Asp His Tyr His Ser Cys Tyr Cys Leu Ser Gly Leu Ser
        355                 360                 365

Leu Cys Gln Tyr Ser Trp Ser Lys Arg Pro Asp Ser Pro Pro Leu Pro
    370                 375                 380

Lys Val Val Met Gly Pro Tyr Ser Ser Asn Leu Leu Glu Pro Ile His
385                 390                 395                 400

Pro Leu Phe Asn Val Val Leu Asp Arg Tyr Arg Glu Ala His Glu Phe
                405                 410                 415

Phe Ser Gln Leu
            420


<210> SEQ ID NO 91
<211> LENGTH: 470
<212> TYPE: PRT
<213> ORGANISM: Lycopersicon esculentum

<400> SEQUENCE: 91

Met Glu Ser Arg Lys Val Thr Lys Thr Leu Glu Asp Gln Trp Val Val
  1               5                  10                  15

Glu Arg Arg Val Arg Glu Ile Tyr Asp Tyr Phe Tyr Ser Ile Ser Pro
             20                  25                  30

Asn Ser Pro Ser Asp Leu Ile Glu Ile Glu Arg Asp Lys His Phe Gly
         35                  40                  45

Tyr Leu Ser Gln Gly Leu Arg Lys Leu Gly Pro Ser Phe Ser Val Leu
     50                  55                  60

Asp Ala Ser Arg Pro Trp Leu Cys Tyr Trp Thr Leu His Ser Ile Ala
 65                  70                  75                  80

Leu Leu Gly Glu Ser Ile Gly Gly Lys Leu Glu Asn Asp Ala Ile Asp
                 85                  90                  95
```

-continued

```
Phe Leu Thr Arg Cys Gln Asp Lys Asp Gly Gly Tyr Gly Gly Gly Pro
            100                 105                 110

Gly Gln Met Pro His Leu Ala Thr Thr Tyr Ala Ala Val Asn Ser Leu
        115                 120                 125

Ile Thr Leu Gly Lys Pro Glu Ala Leu Ser Ser Ile Asn Arg Glu Lys
    130                 135                 140

Leu Tyr Thr Phe Leu Leu Arg Met Lys Asp Ala Ser Gly Gly Phe Arg
145                 150                 155                 160

Met His Asp Gly Gly Glu Val Asp Val Arg Ala Cys Tyr Thr Ala Ile
                165                 170                 175

Ser Val Ala Asn Ile Leu Asn Ile Val Asp Asp Glu Leu Ile His Gly
            180                 185                 190

Val Gly Asn Tyr Ile Leu Ser Cys Gln Thr Tyr Glu Gly Gly Ile Ala
        195                 200                 205

Gly Glu Pro Gly Ser Glu Ala His Gly Gly Tyr Thr Phe Cys Gly Leu
    210                 215                 220

Ala Ala Met Ile Leu Ile Asn Glu Val Asp Arg Leu Asp Leu Pro Gly
225                 230                 235                 240

Leu Ile Asp Trp Val Val Phe Arg Gln Gly Val Glu Gly Gly Phe Gln
                245                 250                 255

Gly Arg Thr Asn Lys Leu Val Asp Gly Cys Tyr Ser Phe Trp Gln Gly
            260                 265                 270

Ala Val Val Phe Leu Ile Gln Arg Leu Asn Leu Ile Val His Glu Gln
        275                 280                 285

Leu Gly Leu Ser Asn Asp Leu Ser Thr Glu Ser Ala Asp Asp Ser Ser
    290                 295                 300

Glu Ser Glu Leu Ser Asp Glu Glu Glu His Leu Glu Gly Ile Ser Ser
305                 310                 315                 320

His Val Gln Asp Thr Phe Pro Leu Gly Gln Ala Gly Ala Cys Gln Glu
                325                 330                 335

Asn Ala Ser His Ser Pro Lys Ile Ala Asp Thr Gly Tyr Glu Phe Ile
            340                 345                 350

Asn Arg Pro Ile Ala Met Arg Pro Leu Phe Asp Ser Met Tyr Leu Gln
        355                 360                 365

Gln Tyr Val Leu Leu Cys Ser Gln Ile Glu Val Gly Gly Phe Arg Asp
    370                 375                 380

Lys Pro Gly Lys Gly Arg Asp Tyr Tyr His Thr Cys Tyr Cys Leu Ser
385                 390                 395                 400

Gly Leu Ser Ile Ala Gln Tyr Ser Trp Thr Asp Glu Ala Asp Ser Thr
                405                 410                 415

Pro Leu Pro Arg Asp Val Phe Gly Pro Tyr Ser Lys Cys Leu Leu Glu
            420                 425                 430

Gln Val His Pro Leu Phe Asn Val Val Leu Asp Arg Tyr Tyr Glu Ala
        435                 440                 445

Arg Glu Tyr Ser Gln Ala Cys Glu Thr Val Ser Pro Leu Ser Leu Ala
    450                 455                 460

Pro Thr Phe Ser Glu Thr
465                 470
```

<210> SEQ ID NO 92
<211> LENGTH: 446
<212> TYPE: PRT
<213> ORGANISM: Nicotiana sp.

<400> SEQUENCE: 92

-continued

```
Gly Thr Ser Gly Thr Arg Thr Leu Glu Asp Gln Trp Met Val Glu Arg
  1               5                  10                  15

Gln Val Arg Glu Ile Tyr Asn Phe Phe Tyr Ser Ile Pro Pro Asn Ser
             20                  25                  30

His Leu Glu Thr Ser Thr Glu Lys His Phe Asp Tyr Leu Thr Arg Gly
         35                  40                  45

Leu Arg Lys Leu Gly Pro Ser Phe Ser Val Leu Asp Ala Asn Arg Pro
     50                  55                  60

Trp Leu Cys Tyr Trp Ile Leu His Ser Ile Ala Leu Leu Gly Glu Ser
 65                  70                  75                  80

Ile Asp Ala Gln Leu Glu Asn Asp Ala Ile Asp Phe Leu Ser Arg Cys
                 85                  90                  95

Gln Asp Glu Asp Gly Gly Tyr Gly Gly Gly Pro Gly Gln Met Pro His
            100                 105                 110

Leu Ala Thr Thr Tyr Ala Ala Val Asn Ser Leu Ile Thr Leu Gly Ser
        115                 120                 125

Pro Lys Ala Leu Ser Ser Ile Asn Arg Glu Lys Leu Tyr Thr Phe Trp
    130                 135                 140

Leu Gln Met Lys Asp Thr Ser Gly Gly Phe Arg Met His Asp Gly Gly
145                 150                 155                 160

Glu Val Asp Val Arg Ala Cys Tyr Thr Ala Ile Ser Val Ala Ser Ile
                165                 170                 175

Leu Gln Ile Val Asp Asp Glu Leu Ile Asn Asp Val Gly Asn Tyr Ile
            180                 185                 190

Leu Ser Cys Gln Thr Tyr Glu Gly Gly Ile Ala Gly Glu Pro Gly Ser
        195                 200                 205

Glu Ala His Gly Gly Tyr Thr Phe Cys Gly Leu Ala Ala Met Ile Leu
    210                 215                 220

Ile Asn Glu Ala Asn Arg Leu Asp Leu Pro Arg Leu Ile Asp Trp Val
225                 230                 235                 240

Val Phe Arg Gln Gly Val Glu Gly Gly Phe Gln Gly Arg Thr Asn Lys
                245                 250                 255

Leu Val Asp Gly Cys Tyr Ser Phe Trp Gln Ala Ala Val Ala Phe Leu
            260                 265                 270

Ile Gln Arg Leu Lys Ser Thr Val His Glu Gln Leu Gly Leu Ser Asn
        275                 280                 285

Glu Leu Ser Thr Glu Ser Ala Asp Asp Ser Ser Glu Ser Glu Leu Ser
    290                 295                 300

Asp Glu Glu His Leu Gln Gly Thr Ser Ser His Val Gln Lys Thr Cys
305                 310                 315                 320

Pro Leu Gly Gln Glu Gly Gln Glu Asn Ala Ser Asp Pro Thr Lys Ile
                325                 330                 335

Ala Asp Thr Gly Tyr Asp Phe Val Asn Arg Thr Ile Ala Met Arg Pro
            340                 345                 350

Val Phe Asp Ser Phe Tyr Leu Gln Gln Tyr Val Leu Leu Cys Ser Gln
        355                 360                 365

Ile Asp Gly Gly Phe Arg Asp Lys Pro Gly Lys Gly Arg Asp His Tyr
    370                 375                 380

His Thr Cys Tyr Cys Leu Ser Gly Leu Ser Ile Ala Gln Tyr Ser Trp
385                 390                 395                 400

Thr Asn Glu Ala Asp Ala Pro Pro Leu Pro Arg Asp Val Phe Gly Pro
                405                 410                 415
```

-continued

```
Tyr Ser Gln Asn Leu Leu Glu Gln Ile His Pro Leu Tyr Asn Val Val
            420                 425                 430

Leu Asp Arg Tyr Tyr Glu Ala Arg Ser Phe Phe Ser Cys Leu
        435                 440                 445
```

<210> SEQ ID NO 93
<211> LENGTH: 323
<212> TYPE: PRT
<213> ORGANISM: Artificial Sequence
<220> FEATURE:
<223> OTHER INFORMATION: Description of Artificial Sequence: Consensus
FTA
<220> FEATURE:
<221> NAME/KEY: VARIANT
<222> LOCATION: (1)..(6)
<223> OTHER INFORMATION: Wherein Xaa is any amino acid.
<220> FEATURE:
<221> NAME/KEY: VARIANT
<222> LOCATION: (10)..(11)
<223> OTHER INFORMATION: Wherein Xaa is any amino acid.
<220> FEATURE:
<221> NAME/KEY: VARIANT
<222> LOCATION: (13)
<223> OTHER INFORMATION: Wherein Xaa is any amino acid.
<220> FEATURE:
<221> NAME/KEY: VARIANT
<222> LOCATION: (19)
<223> OTHER INFORMATION: Wherein Xaa is any amino acid.
<220> FEATURE:
<221> NAME/KEY: VARIANT
<222> LOCATION: (21)..(22)
<223> OTHER INFORMATION: Wherein Xaa is any amino acid.
<220> FEATURE:
<221> NAME/KEY: VARIANT
<222> LOCATION: (24)
<223> OTHER INFORMATION: Wherein Xaa is any amino acid.
<220> FEATURE:
<221> NAME/KEY: VARIANT
<222> LOCATION: (34)
<223> OTHER INFORMATION: Wherein Xaa is any amino acid.
<220> FEATURE:
<221> NAME/KEY: VARIANT
<222> LOCATION: (36)
<223> OTHER INFORMATION: Wherein Xaa is any amino acid.
<220> FEATURE:
<221> NAME/KEY: VARIANT
<222> LOCATION: (40)
<223> OTHER INFORMATION: Wherein Xaa is any amino acid.
<220> FEATURE:
<221> NAME/KEY: VARIANT
<222> LOCATION: (42)
<223> OTHER INFORMATION: Wherein Xaa is any amino acid.
<220> FEATURE:
<221> NAME/KEY: VARIANT
<222> LOCATION: (68)
<223> OTHER INFORMATION: Wherein Xaa is any amino acid.
<220> FEATURE:
<221> NAME/KEY: VARIANT
<222> LOCATION: (86)
<223> OTHER INFORMATION: Wherein Xaa is any amino acid.
<220> FEATURE:
<221> NAME/KEY: VARIANT
<222> LOCATION: (89)
<223> OTHER INFORMATION: Wherein Xaa is any amino acid.
<220> FEATURE:
<221> NAME/KEY: VARIANT
<222> LOCATION: (92)
<223> OTHER INFORMATION: Wherein Xaa is any amino acid.
<220> FEATURE:
<221> NAME/KEY: VARIANT
<222> LOCATION: (92)
<223> OTHER INFORMATION: Wherein Xaa is any amino acid.
<220> FEATURE:
<221> NAME/KEY: VARIANT
<222> LOCATION: (129)
<223> OTHER INFORMATION: Wherein Xaa is any amino acid.
<220> FEATURE:

-continued

<221> NAME/KEY: VARIANT
<222> LOCATION: (194)
<223> OTHER INFORMATION: Wherein Xaa is any amino acid.
<220> FEATURE:
<221> NAME/KEY: VARIANT
<222> LOCATION: (218)
<223> OTHER INFORMATION: Wherein Xaa is any amino acid.
<220> FEATURE:
<221> NAME/KEY: VARIANT
<222> LOCATION: (284)
<223> OTHER INFORMATION: Wherein Xaa is any amino acid.
<220> FEATURE:
<221> NAME/KEY: VARIANT
<222> LOCATION: (304)
<223> OTHER INFORMATION: Wherein Xaa is any amino acid.
<220> FEATURE:
<221> NAME/KEY: VARIANT
<222> LOCATION: (320)..(323)
<223> OTHER INFORMATION: Wherein Xaa is any amino acid.

<400> SEQUENCE: 93

```
Xaa Xaa Xaa Xaa Xaa Xaa Val Pro Leu Xaa Xaa Arg Xaa Glu Trp Ser
  1               5                  10                  15

Asp Val Xaa Pro Xaa Xaa Gln Xaa Asp Gly Pro Asn Pro Val Val Pro
             20                  25                  30

Ile Xaa Tyr Xaa Glu Glu Phe Xaa Glu Xaa Met Asp Tyr Phe Arg Ala
         35                  40                  45

Ile Tyr Phe Ser Asp Glu Arg Ser Pro Arg Ala Leu Arg Leu Thr Glu
     50                  55                  60

Glu Ala Leu Xaa Leu Asn Ser Gly Asn Tyr Thr Val Trp His Phe Arg
 65                  70                  75                  80

Arg Leu Val Leu Glu Xaa Leu Asn Xaa Asp Leu Xaa Glu Glu Leu Glu
                 85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Xaa Glu Leu Glu Phe Thr Arg Arg Val Leu Ser Leu Asp Ala Lys His
    130                 135                 140

Tyr His Ala Trp Ser His Arg Gln Trp Ala Leu Gln Ala Leu Gly Gly
145                 150                 155                 160

Trp Glu Asp Glu Leu Asn Tyr Cys His Glu Leu Leu Glu Ala Asp Val
                165                 170                 175

Phe Asn Asn Ser Ala Trp Asn Gln Arg Tyr Tyr Val Ile Thr Arg Ser
            180                 185                 190

Pro Xaa Leu Gly Gly Leu Glu Ala Met Arg Glu Ser Glu Val Ser Tyr
        195                 200                 205

Thr Ile Lys Ala Ile Leu Ala Asn Pro Xaa Asn Glu Ser Ser Trp Arg
    210                 215                 220

Tyr Leu Lys Ala Leu Tyr Lys Asp Asp Thr Glu Ser Trp Ile Ser Asp
225                 230                 235                 240

Pro Ser Val Ser Ser Val Cys Leu Lys Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Arg Asp Ser Val Xaa Ala Leu Ala Asn
        275                 280                 285

Glu Glu Pro Glu Thr Asn Leu Ala Asn Leu Val Cys Thr Ile Leu Xaa
    290                 295                 300
```

-continued

```
Arg Val Asp Pro Ile Arg Ala Asn Tyr Trp Ala Trp Arg Lys Ser Xaa
305                 310                 315                 320

Xaa Xaa Xaa
```

<210> SEQ ID NO 94
<211> LENGTH: 394
<212> TYPE: PRT
<213> ORGANISM: Artificial Sequence
<220> FEATURE:
<223> OTHER INFORMATION: Description of Artificial Sequence: Consensus FTB
<220> FEATURE:
<221> NAME/KEY: VARIANT
<222> LOCATION: (1)
<223> OTHER INFORMATION: Wherein Xaa is any amino acid.
<220> FEATURE:
<221> NAME/KEY: VARIANT
<222> LOCATION: (3)..(5)
<223> OTHER INFORMATION: Wherein Xaa is any amino acid.
<220> FEATURE:
<221> NAME/KEY: VARIANT
<222> LOCATION: (7)..(10)
<220> FEATURE:
<221> NAME/KEY: VARIANT
<222> LOCATION: (15)
<223> OTHER INFORMATION: Wherein Xaa is any amino acid.
<220> FEATURE:
<221> NAME/KEY: VARIANT
<222> LOCATION: (18)
<223> OTHER INFORMATION: Wherein Xaa is any amino acid.
<220> FEATURE:
<221> NAME/KEY: VARIANT
<222> LOCATION: (20)..(21)
<223> OTHER INFORMATION: Wherein Xaa is any amino acid.
<220> FEATURE:
<221> NAME/KEY: VARIANT
<222> LOCATION: (23)..(25)
<223> OTHER INFORMATION: Wherein Xaa is any amino acid.
<220> FEATURE:
<221> NAME/KEY: VARIANT
<222> LOCATION: (30)..(32)
<223> OTHER INFORMATION: Wherein Xaa is any amino acid.
<220> FEATURE:
<221> NAME/KEY: VARIANT
<222> LOCATION: (35)
<223> OTHER INFORMATION: Wherein Xaa is any amino acid.
<220> FEATURE:
<221> NAME/KEY: VARIANT
<222> LOCATION: (49)
<223> OTHER INFORMATION: Wherein Xaa is any amino acid.
<220> FEATURE:
<221> NAME/KEY: VARIANT
<222> LOCATION: (72)
<223> OTHER INFORMATION: Wherein Xaa is any amino acid.
<220> FEATURE:
<221> NAME/KEY: VARIANT
<222> LOCATION: (77)
<223> OTHER INFORMATION: Wherein Xaa is any amino acid.
<220> FEATURE:
<221> NAME/KEY: VARIANT
<222> LOCATION: (82)
<223> OTHER INFORMATION: Wherein Xaa is any amino acid.
<220> FEATURE:
<221> NAME/KEY: VARIANT
<222> LOCATION: (116)
<223> OTHER INFORMATION: Wherein Xaa is any amino acid.
<220> FEATURE:
<221> NAME/KEY: VARIANT
<222> LOCATION: (117)
<223> OTHER INFORMATION: Wherein Xaa is any amino acid.
<220> FEATURE:
<221> NAME/KEY: VARIANT
<222> LOCATION: (120)
<223> OTHER INFORMATION: Wherein Xaa is any amino acid.
<220> FEATURE:
<221> NAME/KEY: VARIANT
<222> LOCATION: (128)

-continued

<223> OTHER INFORMATION: Wherein Xaa is any amino acid.
<220> FEATURE:
<221> NAME/KEY: VARIANT
<222> LOCATION: (137)
<223> OTHER INFORMATION: Wherein Xaa is any amino acid.
<220> FEATURE:
<221> NAME/KEY: VARIANT
<222> LOCATION: (154)
<223> OTHER INFORMATION: Wherein Xaa is any amino acid.
<220> FEATURE:
<221> NAME/KEY: VARIANT
<222> LOCATION: (163)..(164)
<223> OTHER INFORMATION: Wherein Xaa is any amino acid.
<220> FEATURE:
<221> NAME/KEY: VARIANT
<222> LOCATION: (171)
<223> OTHER INFORMATION: Wherein Xaa is any amino acid.
<220> FEATURE:
<221> NAME/KEY: VARIANT
<222> LOCATION: (207)..(208)
<223> OTHER INFORMATION: Wherein Xaa is any amino acid.
<220> FEATURE:
<221> NAME/KEY: VARIANT
<222> LOCATION: (215)..(216)
<223> OTHER INFORMATION: Wherein Xaa is any amino acid.
<220> FEATURE:
<221> NAME/KEY: VARIANT
<222> LOCATION: (248)
<223> OTHER INFORMATION: Wherein Xaa is any amino acid.
<220> FEATURE:
<221> NAME/KEY: VARIANT
<222> LOCATION: (255)
<223> OTHER INFORMATION: Wherein Xaa is any amino acid.
<220> FEATURE:
<221> NAME/KEY: VARIANT
<222> LOCATION: (258)
<223> OTHER INFORMATION: Wherein Xaa is any amino acid.
<220> FEATURE:
<221> NAME/KEY: VARIANT
<222> LOCATION: (262)..(264)
<223> OTHER INFORMATION: Wherein Xaa is any amino acid.
<220> FEATURE:
<221> NAME/KEY: VARIANT
<222> LOCATION: (267)..(269)
<223> OTHER INFORMATION: Wherein Xaa is any amino acid.
<220> FEATURE:
<221> NAME/KEY: VARIANT
<222> LOCATION: (271)..(276)
<223> OTHER INFORMATION: Wherein Xaa is any amino acid.
<220> FEATURE:
<221> NAME/KEY: VARIANT
<222> LOCATION: (278)..(280)
<223> OTHER INFORMATION: Wherein Xaa is any amino acid.
<220> FEATURE:
<221> NAME/KEY: VARIANT
<222> LOCATION: (285)..(287)
<223> OTHER INFORMATION: Wherein Xaa is any amino acid.
<220> FEATURE:
<221> NAME/KEY: VARIANT
<222> LOCATION: (289)..(296)
<223> OTHER INFORMATION: Wherein Xaa is any amino acid.
<220> FEATURE:
<221> NAME/KEY: VARIANT
<222> LOCATION: (300)..(301)
<223> OTHER INFORMATION: Wherein Xaa is any amino acid.
<220> FEATURE:
<221> NAME/KEY: VARIANT
<222> LOCATION: (303)..(304)
<223> OTHER INFORMATION: Wherein Xaa is any amino acid.
<220> FEATURE:
<221> NAME/KEY: VARIANT
<222> LOCATION: (306)..(309)
<223> OTHER INFORMATION: Wherein Xaa is any amino acid.
<220> FEATURE:
<221> NAME/KEY: VARIANT
<222> LOCATION: (312)..(314)
<223> OTHER INFORMATION: Wherein Xaa is any amino acid.
<220> FEATURE:
<221> NAME/KEY: VARIANT -continued
<222> LOCATION: (316)
<223> OTHER INFORMATION: Wherein Xaa is any amino acid.
<220> FEATURE:
<221> NAME/KEY: VARIANT
<222> LOCATION: (318)
<223> OTHER INFORMATION: Wherein Xaa is any amino acid.
<220> FEATURE:
<221> NAME/KEY: VARIANT
<222> LOCATION: (337)
<223> OTHER INFORMATION: Wherein Xaa is any amino acid.
<220> FEATURE:
<221> NAME/KEY: VARIANT
<222> LOCATION: (348)
<223> OTHER INFORMATION: Wherein Xaa is any amino acid.
<220> FEATURE:
<221> NAME/KEY: VARIANT
<222> LOCATION: (364)
<223> OTHER INFORMATION: Wherein Xaa is any amino acid.
<220> FEATURE:
<221> NAME/KEY: VARIANT
<222> LOCATION: (372)
<223> OTHER INFORMATION: Wherein Xaa is any amino acid.
<220> FEATURE:
<221> NAME/KEY: VARIANT
<222> LOCATION: (378)..(381)
<223> OTHER INFORMATION: Wherein Xaa is any amino acid.
<220> FEATURE:
<221> NAME/KEY: VARIANT
<222> LOCATION: (384)
<223> OTHER INFORMATION: Wherein Xaa is any amino acid.
<220> FEATURE:
<221> NAME/KEY: VARIANT
<222> LOCATION: (386)
<223> OTHER INFORMATION: Wherein Xaa is any amino acid.
<220> FEATURE:
<221> NAME/KEY: VARIANT
<222> LOCATION: (388)
<223> OTHER INFORMATION: Wherein Xaa is any amino acid.
<220> FEATURE:
<221> NAME/KEY: VARIANT
<222> LOCATION: (392)
<223> OTHER INFORMATION: Wherein Xaa is any amino acid.
<220> FEATURE:
<221> NAME/KEY: VARIANT
<222> LOCATION: (394)
<223> OTHER INFORMATION: Wherein Xaa is any amino acid.

<400> SEQUENCE: 94

```
Xaa Thr Xaa Xaa Xaa Asn Xaa Xaa Xaa Xaa Met Leu Glu Leu Xaa Arg
  1               5                  10                  15

Asp Xaa His Xaa Xaa Tyr Xaa Xaa Xaa Gly Leu Arg His Xaa Xaa Xaa
             20                  25                  30

Ala Phe Xaa Val Leu Asp Ala Asn Arg Pro Trp Leu Cys Tyr Trp Ile
         35                  40                  45

Xaa His Ser Ile Ala Leu Leu Gly Glu Ser Val Asp Asp Asp Leu Glu
     50                  55                  60

Asn Asn Ala Ile Asp Phe Leu Xaa Arg Cys Gln Asp Xaa Asp Gly Gly
 65                  70                  75                  80

Tyr Xaa Gly Gly Pro Gly Gln Leu Pro His Leu Ala Thr Thr Tyr Ala
                 85                  90                  95

Ala Val Asn Thr Leu Val Thr Leu Gly Gly Glu Lys Ala Leu Ser Ser
            100                 105                 110

Ile Asn Arg Xaa Xaa Leu Tyr Xaa Phe Leu Arg Arg Met Lys Asp Xaa
        115                 120                 125

Asn Gly Gly Phe Arg Met His Asp Xaa Gly Glu Ile Asp Val Arg Ala
    130                 135                 140

Cys Tyr Thr Ala Ile Ser Val Ala Ser Xaa Leu Asn Ile Leu Asp Asp
145                 150                 155                 160
```

-continued

```
Glu Leu Xaa Xaa Gly Val Gly Asp Tyr Ile Xaa Ser Cys Gln Thr Tyr
            165                 170                 175

Glu Gly Gly Ile Ala Gly Glu Pro Gly Ser Glu Ala His Gly Gly Tyr
        180                 185                 190

Thr Phe Cys Gly Leu Ala Thr Met Ile Leu Ile Asn Glu Val Xaa Xaa
    195                 200                 205

Leu Asp Leu Pro Ser Leu Xaa Xaa Trp Val Val Phe Arg Gln Gly Val
    210                 215                 220

Glu Cys Gly Phe Gln Gly Arg Thr Asn Lys Leu Val Asp Gly Cys Tyr
225                 230                 235                 240

Ser Phe Trp Gln Gly Ala Ala Xaa Ala Leu Leu Gln Arg Leu Xaa Ser
            245                 250                 255

Ile Xaa Asp Lys Gln Xaa Xaa Xaa Ser Ser Xaa Xaa Xaa Ser Xaa Xaa
        260                 265                 270

Xaa Xaa Xaa Xaa Glu Xaa Xaa Xaa Gly Thr Ser Ser Xaa Xaa Xaa Cys
    275                 280                 285

Xaa Xaa Xaa Xaa Xaa Xaa Xaa Xaa Glu Ser Ser Xaa Xaa Asp Xaa Xaa
    290                 295                 300

Asn Xaa Xaa Xaa Xaa Phe Ile Xaa Xaa Xaa Arg Xaa Ile Xaa Pro Leu
305                 310                 315                 320

Phe His Ser Ile Ala Leu Gln Gln Tyr Ile Leu Leu Cys Ser Gln Val
            325                 330                 335

Xaa Glu Gly Gly Leu Arg Asp Lys Pro Gly Lys Xaa Arg Asp His Tyr
        340                 345                 350

His Thr Cys Tyr Cys Leu Ser Gly Leu Ser Val Xaa Gln Tyr Ser Trp
    355                 360                 365

Ser Lys Asp Xaa Asp Ser Pro Pro Leu Xaa Xaa Xaa Xaa Leu Gly Xaa
    370                 375                 380

Tyr Xaa Asn Xaa Leu Glu Pro Xaa His Xaa
385                 390
```

<210> SEQ ID NO 95
<211> LENGTH: 1018
<212> TYPE: DNA
<213> ORGANISM: Artificial Sequence
<220> FEATURE:
<223> OTHER INFORMATION: Description of Artificial Sequence: Consensus FTA
<220> FEATURE:
<221> NAME/KEY: misc_feature
<222> LOCATION: (1)..(4)
<223> OTHER INFORMATION: Wherein n is a or t or c or g.
<220> FEATURE:
<221> NAME/KEY: misc_feature
<222> LOCATION: (7)..(8)
<223> OTHER INFORMATION: Wherein n is a or t or c or g.
<220> FEATURE:
<221> NAME/KEY: misc_feature
<222> LOCATION: (10)
<223> OTHER INFORMATION: Wherein n is a or t or c or g.
<220> FEATURE:
<221> NAME/KEY: misc_feature
<222> LOCATION: (12)
<223> OTHER INFORMATION: Wherein n is a or t or c or g.
<220> FEATURE:
<221> NAME/KEY: misc_feature
<222> LOCATION: (14)
<223> OTHER INFORMATION: Wherein n is a or t or c or g.
<220> FEATURE:
<221> NAME/KEY: misc_feature
<222> LOCATION: (17)..(18)
<223> OTHER INFORMATION: Wherein n is a or t or c or g.
<220> FEATURE:
<221> NAME/KEY: misc_feature -continued
<222> LOCATION: (20)
<223> OTHER INFORMATION: Wherein n is a or t or c or g.
<220> FEATURE:
<221> NAME/KEY: misc_feature
<222> LOCATION: (22)..(23)
<223> OTHER INFORMATION: Wherein n is a or t or c or g.
<220> FEATURE:
<221> NAME/KEY: misc_feature
<222> LOCATION: (25)
<223> OTHER INFORMATION: Wherein n is a or t or c or g.
<220> FEATURE:
<221> NAME/KEY: misc_feature
<222> LOCATION: (27)..(28)
<223> OTHER INFORMATION: Wherein n is a or t or c or g.
<220> FEATURE:
<221> NAME/KEY: misc_feature
<222> LOCATION: (35)..(36)
<223> OTHER INFORMATION: Wherein n is a or t or c or g.
<220> FEATURE:
<221> NAME/KEY: misc_feature
<222> LOCATION: (41)..(42)
<223> OTHER INFORMATION: Wherein n is a or t or c or g.
<220> FEATURE:
<221> NAME/KEY: misc_feature
<222> LOCATION: (44)..(45)
<223> OTHER INFORMATION: Wherein n is a or t or c or g.
<220> FEATURE:
<221> NAME/KEY: misc_feature
<222> LOCATION: (48)
<223> OTHER INFORMATION: Wherein n is a or t or c or g.
<220> FEATURE:
<221> NAME/KEY: misc_feature
<222> LOCATION: (62)
<223> OTHER INFORMATION: Wherein n is a or t or c or g.
<220> FEATURE:
<221> NAME/KEY: misc_feature
<222> LOCATION: (65)..(68)
<223> OTHER INFORMATION: Wherein n is a or t or c or g.
<220> FEATURE:
<221> NAME/KEY: misc_feature
<222> LOCATION: (71)..(72)
<223> OTHER INFORMATION: Wherein n is a or t or c or g.
<220> FEATURE:
<221> NAME/KEY: misc_feature
<222> LOCATION: (74)..(75)
<223> OTHER INFORMATION: Wherein n is a or t or c or g.
<220> FEATURE:
<221> NAME/KEY: misc_feature
<222> LOCATION: (80)..(81)
<223> OTHER INFORMATION: Wherein n is a or t or c or g.
<220> FEATURE:
<221> NAME/KEY: misc_feature
<222> LOCATION: (86)
<223> OTHER INFORMATION: Wherein n is a or t or c or g.
<220> FEATURE:
<221> NAME/KEY: misc_feature
<222> LOCATION: (89)
<223> OTHER INFORMATION: Wherein n is a or t or c or g.
<220> FEATURE:
<221> NAME/KEY: misc_feature
<222> LOCATION: (92)
<223> OTHER INFORMATION: Wherein n is a or t or c or g.
<220> FEATURE:
<221> NAME/KEY: misc_feature
<222> LOCATION: (95)
<223> OTHER INFORMATION: Wherein n is a or t or c or g.
<220> FEATURE:
<221> NAME/KEY: misc_feature
<222> LOCATION: (98)
<223> OTHER INFORMATION: Wherein n is a or t or c or g.
<220> FEATURE:
<221> NAME/KEY: misc_feature
<222> LOCATION: (101)
<223> OTHER INFORMATION: Wherein n is a or t or c or g.
<220> FEATURE:
<221> NAME/KEY: misc_feature
<222> LOCATION: (104)
<223> OTHER INFORMATION: Wherein n is a or t or c or g.
<220> FEATURE:

-continued

<221> NAME/KEY: misc_feature
<222> LOCATION: (107)
<223> OTHER INFORMATION: Wherein n is a or t or c or g.
<220> FEATURE:
<221> NAME/KEY: misc_feature
<222> LOCATION: (110)..(113)
<223> OTHER INFORMATION: Wherein n is a or t or c or g.
<220> FEATURE:
<221> NAME/KEY: misc_feature
<222> LOCATION: (118)..(119)
<223> OTHER INFORMATION: Wherein n is a or t or c or g.
<220> FEATURE:
<221> NAME/KEY: misc_feature
<222> LOCATION: (128)..(130)
<223> OTHER INFORMATION: Wherein n is a or t or c or g.
<220> FEATURE:
<221> NAME/KEY: misc_feature
<222> LOCATION: (134)..(136)
<223> OTHER INFORMATION: Wherein n is a or t or c or g.
<220> FEATURE:
<221> NAME/KEY: misc_feature
<222> LOCATION: (176)
<223> OTHER INFORMATION: Wherein n is a or t or c or g.
<220> FEATURE:
<221> NAME/KEY: misc_feature
<222> LOCATION: (188)
<223> OTHER INFORMATION: Wherein n is a or t or c or g.
<220> FEATURE:
<221> NAME/KEY: misc_feature
<222> LOCATION: (191)
<223> OTHER INFORMATION: Wherein n is a or t or c or g.
<220> FEATURE:
<221> NAME/KEY: misc_feature
<222> LOCATION: (214)
<223> OTHER INFORMATION: Wherein n is a or t or c or g.
<220> FEATURE:
<221> NAME/KEY: misc_feature
<222> LOCATION: (236)
<220> FEATURE:
<221> NAME/KEY: misc_feature
<222> LOCATION: (249)
<223> OTHER INFORMATION: Wherein n is a or t or c or g.
<220> FEATURE:
<221> NAME/KEY: misc_feature
<222> LOCATION: (276)
<223> OTHER INFORMATION: Wherein n is a or t or c or g.
<220> FEATURE:
<221> NAME/KEY: misc_feature
<222> LOCATION: (342)
<223> OTHER INFORMATION: Wherein n is a or t or c or g.
<220> FEATURE:
<221> NAME/KEY: misc_feature
<222> LOCATION: (395)
<223> OTHER INFORMATION: Wherein n is a or t or c or g.
<220> FEATURE:
<221> NAME/KEY: misc_feature
<222> LOCATION: (398)
<223> OTHER INFORMATION: Wherein n is a or t or c or g.
<220> FEATURE:
<221> NAME/KEY: misc_feature
<222> LOCATION: (416)
<223> OTHER INFORMATION: Wherein n is a or t or c or g.
<220> FEATURE:
<221> NAME/KEY: misc_feature
<222> LOCATION: (425)
<223> OTHER INFORMATION: Wherein n is a or t or c or g.
<220> FEATURE:
<221> NAME/KEY: misc_feature
<222> LOCATION: (473)
<223> OTHER INFORMATION: Wherein n is a or t or c or g.
<220> FEATURE:
<221> NAME/KEY: misc_feature
<222> LOCATION: (554)
<223> OTHER INFORMATION: Wherein n is a or t or c or g.
<220> FEATURE:
<221> NAME/KEY: misc_feature
<222> LOCATION: (581)
<223> OTHER INFORMATION: Wherein n is a or t or c or g.
<220> FEATURE:

-continued

<221> NAME/KEY: misc_feature
<222> LOCATION: (664)
<223> OTHER INFORMATION: Wherein n is a or t or c or g.
<220> FEATURE:
<221> NAME/KEY: misc_feature
<222> LOCATION: (677)
<223> OTHER INFORMATION: Wherein n is a or t or c or g.
<220> FEATURE:
<221> NAME/KEY: misc_feature
<222> LOCATION: (695)
<223> OTHER INFORMATION: Wherein n is a or t or c or g.
<220> FEATURE:
<221> NAME/KEY: misc_feature
<222> LOCATION: (716)
<223> OTHER INFORMATION: Wherein n is a or t or c or g.
<220> FEATURE:
<221> NAME/KEY: misc_feature
<222> LOCATION: (719)
<223> OTHER INFORMATION: Wherein n is a or t or c or g.
<220> FEATURE:
<221> NAME/KEY: misc_feature
<222> LOCATION: (758)
<223> OTHER INFORMATION: Wherein n is a or t or c or g.
<220> FEATURE:
<221> NAME/KEY: misc_feature
<222> LOCATION: (764)
<223> OTHER INFORMATION: Wherein n is a or t or c or g.
<220> FEATURE:
<221> NAME/KEY: misc_feature
<222> LOCATION: (767)
<223> OTHER INFORMATION: Wherein n is a or t or c or g.
<220> FEATURE:
<221> NAME/KEY: misc_feature
<222> LOCATION: (773)
<223> OTHER INFORMATION: Wherein n is a or t or c or g.
<220> FEATURE:
<221> NAME/KEY: misc_feature
<222> LOCATION: (776)
<223> OTHER INFORMATION: Wherein n is a or t or c or g.
<220> FEATURE:
<221> NAME/KEY: misc_feature
<222> LOCATION: (827)
<223> OTHER INFORMATION: Wherein n is a or t or c or g.
<220> FEATURE:
<221> NAME/KEY: misc_feature
<222> LOCATION: (857)
<223> OTHER INFORMATION: Wherein n is a or t or c or g.
<220> FEATURE:
<221> NAME/KEY: misc_feature
<222> LOCATION: (914)
<223> OTHER INFORMATION: Wherein n is a or t or c or g.
<220> FEATURE:
<221> NAME/KEY: misc_feature
<222> LOCATION: (921)
<223> OTHER INFORMATION: Wherein n is a or t or c or g.
<220> FEATURE:
<221> NAME/KEY: misc_feature
<222> LOCATION: (960)..(962)
<223> OTHER INFORMATION: Wherein n is a or t or c or g.
<220> FEATURE:
<221> NAME/KEY: misc_feature
<222> LOCATION: (965)
<223> OTHER INFORMATION: Wherein n is a or t or c or g.
<220> FEATURE:
<221> NAME/KEY: misc_feature
<222> LOCATION: (967)..(970)
<223> OTHER INFORMATION: Wherein n is a or t or c or g.
<220> FEATURE:
<221> NAME/KEY: misc_feature
<222> LOCATION: (974)..(976)
<223> OTHER INFORMATION: Wherein n is a or t or c or g.
<220> FEATURE:
<221> NAME/KEY: misc_feature
<222> LOCATION: (978)
<223> OTHER INFORMATION: Wherein n is a or t or c or g.
<220> FEATURE:
<221> NAME/KEY: misc_feature
<222> LOCATION: (980)
<223> OTHER INFORMATION: Wherein n is a or t or c or g.

-continued

<220> FEATURE:
<221> NAME/KEY: misc_feature
<222> LOCATION: (982)
<223> OTHER INFORMATION: Wherein n is a or t or c or g.
<220> FEATURE:
<221> NAME/KEY: misc_feature
<222> LOCATION: (984)
<223> OTHER INFORMATION: Wherein n is a or t or c or g.
<220> FEATURE:
<221> NAME/KEY: misc_feature
<222> LOCATION: (988)
<223> OTHER INFORMATION: Wherein n is a or t or c or g.
<220> FEATURE:
<221> NAME/KEY: misc_feature
<222> LOCATION: (990)..(994)
<223> OTHER INFORMATION: Wherein n is a or t or c or g.
<220> FEATURE:
<221> NAME/KEY: misc_feature
<222> LOCATION: (997)
<223> OTHER INFORMATION: Wherein n is a or t or c or g.
<220> FEATURE:
<221> NAME/KEY: misc_feature
<222> LOCATION: (1000)
<223> OTHER INFORMATION: Wherein n is a or t or c or g.
<220> FEATURE:
<221> NAME/KEY: misc_feature
<222> LOCATION: (1004)..(1006)
<223> OTHER INFORMATION: Wherein n is a or t or c or g.
<220> FEATURE:
<221> NAME/KEY: misc_feature
<222> LOCATION: (1008)..(1009)
<223> OTHER INFORMATION: Wherein n is a or t or c or g.
<220> FEATURE:
<221> NAME/KEY: misc_feature
<222> LOCATION: (1011)..(1015)
<223> OTHER INFORMATION: Wherein n is a or t or c or g.
<220> FEATURE:
<221> NAME/KEY: misc_feature
<222> LOCATION: (1017)
<223> OTHER INFORMATION: Wherein n is a or t or c or g.

<400> SEQUENCE: 95
nnnncgnngn ananganntn cnncnanncg tgccnntgag nnanngantg gagtggtcag 60
angtnnnncc nntnnctcan nacganggnc cnaanccngt ngtnccnatn nnntacanng 120
aagagttnnn cgannntatg gattacttcc gtgcgattta cttctccgac gagcgntctc 180
ctcgcgcnct ncgactcacg gaagaagccc tccncttaaa ctccggcaac tacacngtgt 240
ggcatttcng gcgcttagta ctcgaggcgc ttaatnacga cttgtatgaa gaactcgagt 300
tcatcgaacg cattgctgag gataactcta agaactacca gntgtggcat catcgacgat 360
gggttgcaga gaaactgggt cctgatgttg caggnaanga acttgagttt acccgnaggg 420
tactntcact tgatgccaaa cattatcatg cttggtcaca taggcagtgg gcnctacaag 480
cattaggagg atgggaagat gagcttaatt actgccacga gctccttgaa gctgacgtct 540
ttaacaattc tgcntggaat cagaggtatt atgtcataac nagatctcct ttgttgggag 600
gcctagaagc catgagagaa tctgaagtaa gctacacaat caaagccatt ttagccaatc 660
ctgnaaacga gagctcntgg agatacctaa aagcncttta caaagacgac acagantcnt 720
ggattagtga tccaagtgtt tcctcagtct gtttgaangt tctntcncgc acngantgct 780
tccatggatt cgctctgagc accctttttgg atcttctatg cgatggnttg agaccaacca 840
acgagcatag agactcngtg aaagctctag ctaatgaaga accagagact aacttggcca 900
atttggtgtg tacnattctg ngtcgtgtag atccaataag agctaactat tgggcatggn 960
nnaanannnn gatnnnantn gnancaantn nnnnatntgn cgcnnnanna nnnnncnt 1018

<210> SEQ ID NO 96

-continued

<211> LENGTH: 1237
<212> TYPE: DNA
<213> ORGANISM: Artificial Sequence
<220> FEATURE:
<223> OTHER INFORMATION: Description of Artificial Sequence: Consensus
FTB
<220> FEATURE:
<221> NAME/KEY: misc_feature
<222> LOCATION: (1)..(34)
<223> OTHER INFORMATION: Wherein n is a or t or c or g.
<220> FEATURE:
<221> NAME/KEY: misc_feature
<222> LOCATION: (36)
<223> OTHER INFORMATION: Wherein n is a or t or c or g.
<220> FEATURE:
<221> NAME/KEY: misc_feature
<222> LOCATION: (40)
<223> OTHER INFORMATION: Wherein n is a or t or c or g.
<220> FEATURE:
<221> NAME/KEY: misc_feature
<222> LOCATION: (42)..(45)
<223> OTHER INFORMATION: Wherein n is a or t or c or g.
<220> FEATURE:
<221> NAME/KEY: misc_feature
<222> LOCATION: (48)
<223> OTHER INFORMATION: Wherein n is a or t or c or g.
<220> FEATURE:
<221> NAME/KEY: misc_feature
<222> LOCATION: (52)
<223> OTHER INFORMATION: Wherein n is a or t or c or g.
<220> FEATURE:
<221> NAME/KEY: misc_feature
<222> LOCATION: (54)
<223> OTHER INFORMATION: Wherein n is a or t or c or g.
<220> FEATURE:
<221> NAME/KEY: misc_feature
<222> LOCATION: (57)..(58)
<223> OTHER INFORMATION: Wherein n is a or t or c or g.
<220> FEATURE:
<221> NAME/KEY: misc_feature
<222> LOCATION: (60)..(61)
<223> OTHER INFORMATION: Wherein n is a or t or c or g.
<220> FEATURE:
<221> NAME/KEY: misc_feature
<222> LOCATION: (63)
<223> OTHER INFORMATION: Wherein n is a or t or c or g.
<220> FEATURE:
<221> NAME/KEY: misc_feature
<222> LOCATION: (67)
<223> OTHER INFORMATION: Wherein n is a or t or c or g.
<220> FEATURE:
<221> NAME/KEY: misc_feature
<222> LOCATION: (69)..(75)
<223> OTHER INFORMATION: Wherein n is a or t or c or g.
<220> FEATURE:
<221> NAME/KEY: misc_feature
<222> LOCATION: (78)..(79)
<223> OTHER INFORMATION: Wherein n is a or t or c or g.
<220> FEATURE:
<221> NAME/KEY: misc_feature
<222> LOCATION: (81)..(82)
<223> OTHER INFORMATION: Wherein n is a or t or c or g.
<220> FEATURE:
<221> NAME/KEY: misc_feature
<222> LOCATION: (84)
<223> OTHER INFORMATION: Wherein n is a or t or c or g.
<220> FEATURE:
<221> NAME/KEY: misc_feature
<222> LOCATION: (87)..(88)
<223> OTHER INFORMATION: Wherein n is a or t or c or g.
<220> FEATURE:
<221> NAME/KEY: misc_feature
<222> LOCATION: (90)..(91)
<223> OTHER INFORMATION: Wherein n is a or t or c or g.
<220> FEATURE:
<221> NAME/KEY: misc_feature
<222> LOCATION: (93)..(94)
<223> OTHER INFORMATION: Wherein n is a or t or c or g.
<220> FEATURE:

-continued

<221> NAME/KEY: misc_feature
<222> LOCATION: (96)..(99)
<223> OTHER INFORMATION: Wherein n is a or t or c or g.
<220> FEATURE:
<221> NAME/KEY: misc_feature
<222> LOCATION: (103)..(109)
<223> OTHER INFORMATION: Wherein n is a or t or c or g.
<220> FEATURE:
<221> NAME/KEY: misc_feature
<222> LOCATION: (111)
<223> OTHER INFORMATION: Wherein n is a or t or c or g.
<220> FEATURE:
<221> NAME/KEY: misc_feature
<222> LOCATION: (114)
<223> OTHER INFORMATION: Wherein n is a or t or c or g.
<220> FEATURE:
<221> NAME/KEY: misc_feature
<222> LOCATION: (117)
<223> OTHER INFORMATION: Wherein n is a or t or c or g.
<220> FEATURE:
<221> NAME/KEY: misc_feature
<222> LOCATION: (123)
<223> OTHER INFORMATION: Wherein n is a or t or c or g.
<220> FEATURE:
<221> NAME/KEY: misc_feature
<222> LOCATION: (126)
<223> OTHER INFORMATION: Wherein n is a or t or c or g.
<220> FEATURE:
<221> NAME/KEY: misc_feature
<222> LOCATION: (132)
<223> OTHER INFORMATION: Wherein n is a or t or c or g.
<220> FEATURE:
<221> NAME/KEY: misc_feature
<222> LOCATION: (135)
<223> OTHER INFORMATION: Wherein n is a or t or c or g.
<220> FEATURE:
<221> NAME/KEY: misc_feature
<222> LOCATION: (144)..(145)
<223> OTHER INFORMATION: Wherein n is a or t or c or g.
<220> FEATURE:
<221> NAME/KEY: misc_feature
<222> LOCATION: (165)
<223> OTHER INFORMATION: Wherein n is a or t or c or g.
<220> FEATURE:
<221> NAME/KEY: misc_feature
<222> LOCATION: (168)
<223> OTHER INFORMATION: Wherein n is a or t or c or g.
<220> FEATURE:
<221> NAME/KEY: misc_feature
<222> LOCATION: (171)..(172)
<223> OTHER INFORMATION: Wherein n is a or t or c or g.
<220> FEATURE:
<221> NAME/KEY: misc_feature
<222> LOCATION: (174)
<223> OTHER INFORMATION: Wherein n is a or t or c or g.
<220> FEATURE:
<221> NAME/KEY: misc_feature
<222> LOCATION: (177)
<223> OTHER INFORMATION: Wherein n is a or t or c or g.
<220> FEATURE:
<221> NAME/KEY: misc_feature
<222> LOCATION: (186)..(187)
<223> OTHER INFORMATION: Wherein n is a or t or c or g.
<220> FEATURE:
<221> NAME/KEY: misc_feature
<222> LOCATION: (189)
<223> OTHER INFORMATION: Wherein n is a or t or c or g.
<220> FEATURE:
<221> NAME/KEY: misc_feature
<222> LOCATION: (195)
<223> OTHER INFORMATION: Wherein n is a or t or c or g.
<220> FEATURE:
<221> NAME/KEY: misc_feature
<222> LOCATION: (201)
<223> OTHER INFORMATION: Wherein n is a or t or c or g.
<220> FEATURE:
<221> NAME/KEY: misc_feature
<222> LOCATION: (204)
<223> OTHER INFORMATION: Wherein n is a or t or c or g.

-continued

<220> FEATURE:
<221> NAME/KEY: misc_feature
<222> LOCATION: (207)
<223> OTHER INFORMATION: Wherein n is a or t or c or g.
<220> FEATURE:
<221> NAME/KEY: misc_feature
<222> LOCATION: (210)
<223> OTHER INFORMATION: Wherein n is a or t or c or g.
<220> FEATURE:
<221> NAME/KEY: misc_feature
<222> LOCATION: (215)..(216)
<223> OTHER INFORMATION: Wherein n is a or t or c or g.
<220> FEATURE:
<221> NAME/KEY: misc_feature
<222> LOCATION: (219)
<223> OTHER INFORMATION: Wherein n is a or t or c or g.
<220> FEATURE:
<221> NAME/KEY: misc_feature
<222> LOCATION: (227)
<223> OTHER INFORMATION: Wherein n is a or t or c or g.
<220> FEATURE:
<221> NAME/KEY: misc_feature
<222> LOCATION: (229)
<223> OTHER INFORMATION: Wherein n is a or t or c or g.
<220> FEATURE:
<221> NAME/KEY: misc_feature
<222> LOCATION: (231)
<223> OTHER INFORMATION: Wherein n is a or t or c or g.
<220> FEATURE:
<221> NAME/KEY: misc_feature
<222> LOCATION: (252)
<223> OTHER INFORMATION: Wherein n is a or t or c or g.
<220> FEATURE:
<221> NAME/KEY: misc_feature
<222> LOCATION: (261)..(262)
<223> OTHER INFORMATION: Wherein n is a or t or c or g.
<220> FEATURE:
<221> NAME/KEY: misc_feature
<222> LOCATION: (264)
<223> OTHER INFORMATION: Wherein n is a or t or c or g.
<220> FEATURE:
<221> NAME/KEY: misc_feature
<222> LOCATION: (267)
<223> OTHER INFORMATION: Wherein n is a or t or c or g.
<220> FEATURE:
<221> NAME/KEY: misc_feature
<222> LOCATION: (276)
<223> OTHER INFORMATION: Wherein n is a or t or c or g.
<220> FEATURE:
<221> NAME/KEY: misc_feature
<222> LOCATION: (279)
<223> OTHER INFORMATION: Wherein n is a or t or c or g.
<220> FEATURE:
<221> NAME/KEY: misc_feature
<222> LOCATION: (291)
<223> OTHER INFORMATION: Wherein n is a or t or c or g.
<220> FEATURE:
<221> NAME/KEY: misc_feature
<222> LOCATION: (294)
<223> OTHER INFORMATION: Wherein n is a or t or c or g.
<220> FEATURE:
<221> NAME/KEY: misc_feature
<222> LOCATION: (298)
<223> OTHER INFORMATION: Wherein n is a or t or c or g.
<220> FEATURE:
<221> NAME/KEY: misc_feature
<222> LOCATION: (315)
<223> OTHER INFORMATION: Wherein n is a or t or c or g.
<220> FEATURE:
<221> NAME/KEY: misc_feature
<222> LOCATION: (321)
<223> OTHER INFORMATION: Wherein n is a or t or c or g.
<220> FEATURE:
<221> NAME/KEY: misc_feature
<222> LOCATION: (328)
<223> OTHER INFORMATION: Wherein n is a or t or c or g.
<220> FEATURE:
<221> NAME/KEY: misc_feature
<222> LOCATION: (330)

-continued

<223> OTHER INFORMATION: Wherein n is a or t or c or g.
<220> FEATURE:
<221> NAME/KEY: misc_feature
<222> LOCATION: (333)
<223> OTHER INFORMATION: Wherein n is a or t or c or g.
<220> FEATURE:
<221> NAME/KEY: misc_feature
<222> LOCATION: (348)
<223> OTHER INFORMATION: Wherein n is a or t or c or g.
<220> FEATURE:
<221> NAME/KEY: misc_feature
<222> LOCATION: (352)
<223> OTHER INFORMATION: Wherein n is a or t or c or g.
<220> FEATURE:
<221> NAME/KEY: misc_feature
<222> LOCATION: (356)
<223> OTHER INFORMATION: Wherein n is a or t or c or g.
<220> FEATURE:
<221> NAME/KEY: misc_feature
<222> LOCATION: (358)
<223> OTHER INFORMATION: Wherein n is a or t or c or g.
<220> FEATURE:
<221> NAME/KEY: misc_feature
<222> LOCATION: (364)
<223> OTHER INFORMATION: Wherein n is a or t or c or g.
<220> FEATURE:
<221> NAME/KEY: misc_feature
<222> LOCATION: (366)..(367)
<223> OTHER INFORMATION: Wherein n is a or t or c or g.
<220> FEATURE:
<221> NAME/KEY: misc_feature
<222> LOCATION: (369)
<223> OTHER INFORMATION: Wherein n is a or t or c or g.
<220> FEATURE:
<221> NAME/KEY: misc_feature
<222> LOCATION: (382)
<223> OTHER INFORMATION: Wherein n is a or t or c or g.
<220> FEATURE:
<221> NAME/KEY: misc_feature
<222> LOCATION: (386)
<223> OTHER INFORMATION: Wherein n is a or t or c or g.
<220> FEATURE:
<221> NAME/KEY: misc_feature
<222> LOCATION: (390)
<223> OTHER INFORMATION: Wherein n is a or t or c or g.
<220> FEATURE:
<221> NAME/KEY: misc_feature
<222> LOCATION: (409)..(411)
<223> OTHER INFORMATION: Wherein n is a or t or c or g.
<220> FEATURE:
<221> NAME/KEY: misc_feature
<222> LOCATION: (414)
<223> OTHER INFORMATION: Wherein n is a or t or c or g.
<220> FEATURE:
<221> NAME/KEY: misc_feature
<222> LOCATION: (426)
<223> OTHER INFORMATION: Wherein n is a or t or c or g.
<220> FEATURE:
<221> NAME/KEY: misc_feature
<222> LOCATION: (429)
<223> OTHER INFORMATION: Wherein n is a or t or c or g.
<220> FEATURE:
<221> NAME/KEY: misc_feature
<222> LOCATION: (432)
<223> OTHER INFORMATION: Wherein n is a or t or c or g.
<220> FEATURE:
<221> NAME/KEY: misc_feature
<222> LOCATION: (444)
<223> OTHER INFORMATION: Wherein n is a or t or c or g.
<220> FEATURE:
<221> NAME/KEY: misc_feature
<222> LOCATION: (460)
<223> OTHER INFORMATION: Wherein n is a or t or c or g.
<220> FEATURE:
<221> NAME/KEY: misc_feature
<222> LOCATION: (462)..(463)
<223> OTHER INFORMATION: Wherein n is a or t or c or g.
<220> FEATURE:
<221> NAME/KEY: misc_feature -continued
<222> LOCATION: (468)
<223> OTHER INFORMATION: Wherein n is a or t or c or g.
<220> FEATURE:
<221> NAME/KEY: misc_feature
<222> LOCATION: (472)
<223> OTHER INFORMATION: Wherein n is a or t or c or g.
<220> FEATURE:
<221> NAME/KEY: misc_feature
<222> LOCATION: (486)
<223> OTHER INFORMATION: Wherein n is a or t or c or g.
<220> FEATURE:
<221> NAME/KEY: misc_feature
<222> LOCATION: (492)
<223> OTHER INFORMATION: Wherein n is a or t or c or g.
<220> FEATURE:
<221> NAME/KEY: misc_feature
<222> LOCATION: (495)..(496)
<223> OTHER INFORMATION: Wherein n is a or t or c or g.
<220> FEATURE:
<221> NAME/KEY: misc_feature
<222> LOCATION: (504)
<223> OTHER INFORMATION: Wherein n is a or t or c or g.
<220> FEATURE:
<221> NAME/KEY: misc_feature
<222> LOCATION: (510)..(511)
<223> OTHER INFORMATION: Wherein n is a or t or c or g.
<220> FEATURE:
<221> NAME/KEY: misc_feature
<222> LOCATION: (513)
<223> OTHER INFORMATION: Wherein n is a or t or c or g.
<220> FEATURE:
<221> NAME/KEY: misc_feature
<222> LOCATION: (516)
<223> OTHER INFORMATION: Wherein n is a or t or c or g.
<220> FEATURE:
<221> NAME/KEY: misc_feature
<222> LOCATION: (519)
<223> OTHER INFORMATION: Wherein n is a or t or c or g.
<220> FEATURE:
<221> NAME/KEY: misc_feature
<222> LOCATION: (542)..(543)
<223> OTHER INFORMATION: Wherein n is a or t or c or g.
<220> FEATURE:
<221> NAME/KEY: misc_feature
<222> LOCATION: (549)
<223> OTHER INFORMATION: Wherein n is a or t or c or g.
<220> FEATURE:
<221> NAME/KEY: misc_feature
<222> LOCATION: (555)
<223> OTHER INFORMATION: Wherein n is a or t or c or g.
<220> FEATURE:
<221> NAME/KEY: misc_feature
<222> LOCATION: (558)
<223> OTHER INFORMATION: Wherein n is a or t or c or g.
<220> FEATURE:
<221> NAME/KEY: misc_feature
<222> LOCATION: (576)
<223> OTHER INFORMATION: Wherein n is a or t or c or g.
<220> FEATURE:
<221> NAME/KEY: misc_feature
<222> LOCATION: (579)
<223> OTHER INFORMATION: Wherein n is a or t or c or g.
<220> FEATURE:
<221> NAME/KEY: misc_feature
<222> LOCATION: (581)
<223> OTHER INFORMATION: Wherein n is a or t or c or g.
<220> FEATURE:
<221> NAME/KEY: misc_feature
<222> LOCATION: (588)
<223> OTHER INFORMATION: Wherein n is a or t or c or g.
<220> FEATURE:
<221> NAME/KEY: misc_feature
<222> LOCATION: (595)
<223> OTHER INFORMATION: Wherein n is a or t or c or g.
<220> FEATURE:
<221> NAME/KEY: misc_feature
<222> LOCATION: (604)
<223> OTHER INFORMATION: Wherein n is a or t or c or g.
<220> FEATURE:

-continued

<221> NAME/KEY: misc_feature
<222> LOCATION: (606)
<223> OTHER INFORMATION: Wherein n is a or t or c or g.
<220> FEATURE:
<221> NAME/KEY: misc_feature
<222> LOCATION: (609)
<223> OTHER INFORMATION: Wherein n is a or t or c or g.
<220> FEATURE:
<221> NAME/KEY: misc_feature
<222> LOCATION: (618)
<223> OTHER INFORMATION: Wherein n is a or t or c or g.
<220> FEATURE:
<221> NAME/KEY: misc_feature
<222> LOCATION: (621)
<223> OTHER INFORMATION: Wherein n is a or t or c or g.
<220> FEATURE:
<221> NAME/KEY: misc_feature
<222> LOCATION: (623)..(624)
<223> OTHER INFORMATION: Wherein n is a or t or c or g.
<220> FEATURE:
<221> NAME/KEY: misc_feature
<222> LOCATION: (628)
<223> OTHER INFORMATION: Wherein n is a or t or c or g.
<220> FEATURE:
<221> NAME/KEY: misc_feature
<222> LOCATION: (634)..(635)
<223> OTHER INFORMATION: Wherein n is a or t or c or g.
<220> FEATURE:
<221> NAME/KEY: misc_feature
<222> LOCATION: (637)..(639)
<223> OTHER INFORMATION: Wherein n is a or t or c or g.
<220> FEATURE:
<221> NAME/KEY: misc_feature
<222> LOCATION: (645)..(646)
<223> OTHER INFORMATION: Wherein n is a or t or c or g.
<220> FEATURE:
<221> NAME/KEY: misc_feature
<222> LOCATION: (648)
<223> OTHER INFORMATION: Wherein n is a or t or c or g.
<220> FEATURE:
<221> NAME/KEY: misc_feature
<222> LOCATION: (654)
<223> OTHER INFORMATION: Wherein n is a or t or c or g.
<220> FEATURE:
<221> NAME/KEY: misc_feature
<222> LOCATION: (658)..(659)
<223> OTHER INFORMATION: Wherein n is a or t or c or g.
<220> FEATURE:
<221> NAME/KEY: misc_feature
<222> LOCATION: (672)
<223> OTHER INFORMATION: Wherein n is a or t or c or g.
<220> FEATURE:
<221> NAME/KEY: misc_feature
<222> LOCATION: (676)..(678)
<223> OTHER INFORMATION: Wherein n is a or t or c or g.
<220> FEATURE:
<221> NAME/KEY: misc_feature
<222> LOCATION: (684)
<223> OTHER INFORMATION: Wherein n is a or t or c or g.
<220> FEATURE:
<221> NAME/KEY: misc_feature
<222> LOCATION: (690)
<223> OTHER INFORMATION: Wherein n is a or t or c or g.
<220> FEATURE:
<221> NAME/KEY: misc_feature
<222> LOCATION: (693)
<223> OTHER INFORMATION: Wherein n is a or t or c or g.
<220> FEATURE:
<221> NAME/KEY: misc_feature
<222> LOCATION: (696)
<223> OTHER INFORMATION: Wherein n is a or t or c or g.
<220> FEATURE:
<221> NAME/KEY: misc_feature
<222> LOCATION: (699)
<223> OTHER INFORMATION: Wherein n is a or t or c or g.
<220> FEATURE:
<221> NAME/KEY: misc_feature
<222> LOCATION: (708)
<223> OTHER INFORMATION: Wherein n is a or t or c or g.

-continued

<220> FEATURE:
<221> NAME/KEY: misc_feature
<222> LOCATION: (721)
<223> OTHER INFORMATION: Wherein n is a or t or c or g.
<220> FEATURE:
<221> NAME/KEY: misc_feature
<222> LOCATION: (723)
<223> OTHER INFORMATION: Wherein n is a or t or c or g.
<220> FEATURE:
<221> NAME/KEY: misc_feature
<222> LOCATION: (734)
<223> OTHER INFORMATION: Wherein n is a or t or c or g.
<220> FEATURE:
<221> NAME/KEY: misc_feature
<222> LOCATION: (738)..(739)
<223> OTHER INFORMATION: Wherein n is a or t or c or g.
<220> FEATURE:
<221> NAME/KEY: misc_feature
<222> LOCATION: (741)..(743)
<223> OTHER INFORMATION: Wherein n is a or t or c or g.
<220> FEATURE:
<221> NAME/KEY: misc_feature
<222> LOCATION: (746)
<223> OTHER INFORMATION: Wherein n is a or t or c or g.
<220> FEATURE:
<221> NAME/KEY: misc_feature
<222> LOCATION: (751)
<223> OTHER INFORMATION: Wherein n is a or t or c or g.
<220> FEATURE:
<221> NAME/KEY: misc_feature
<222> LOCATION: (764)
<223> OTHER INFORMATION: Wherein n is a or t or c or g.
<220> FEATURE:
<221> NAME/KEY: misc_feature
<222> LOCATION: (768)
<223> OTHER INFORMATION: Wherein n is a or t or c or g.
<220> FEATURE:
<221> NAME/KEY: misc_feature
<222> LOCATION: (770)..(774)
<223> OTHER INFORMATION: Wherein n is a or t or c or g.
<220> FEATURE:
<221> NAME/KEY: misc_feature
<222> LOCATION: (779)
<223> OTHER INFORMATION: Wherein n is a or t or c or g.
<220> FEATURE:
<221> NAME/KEY: misc_feature
<222> LOCATION: (781)..(787)
<223> OTHER INFORMATION: Wherein n is a or t or c or g.
<220> FEATURE:
<221> NAME/KEY: misc_feature
<222> LOCATION: (789)
<223> OTHER INFORMATION: Wherein n is a or t or c or g.
<220> FEATURE:
<221> NAME/KEY: misc_feature
<222> LOCATION: (791)..(793)
<223> OTHER INFORMATION: Wherein n is a or t or c or g.
<220> FEATURE:
<221> NAME/KEY: misc_feature
<222> LOCATION: (799)..(811)
<223> OTHER INFORMATION: Wherein n is a or t or c or g.
<220> FEATURE:
<221> NAME/KEY: misc_feature
<222> LOCATION: (813)
<223> OTHER INFORMATION: Wherein n is a or t or c or g.
<220> FEATURE:
<221> NAME/KEY: misc_feature
<222> LOCATION: (815)..(816)
<223> OTHER INFORMATION: Wherein n is a or t or c or g.
<220> FEATURE:
<221> NAME/KEY: misc_feature
<222> LOCATION: (818)..(819)
<223> OTHER INFORMATION: Wherein n is a or t or c or g.
<220> FEATURE:
<221> NAME/KEY: misc_feature
<222> LOCATION: (821)
<223> OTHER INFORMATION: Wherein n is a or t or c or g.
<220> FEATURE:
<221> NAME/KEY: misc_feature
<222> LOCATION: (823)

-continued

<223> OTHER INFORMATION: Wherein n is a or t or c or g.
<220> FEATURE:
<221> NAME/KEY: misc_feature
<222> LOCATION: (825)..(826)
<223> OTHER INFORMATION: Wherein n is a or t or c or g.
<220> FEATURE:
<221> NAME/KEY: misc_feature
<222> LOCATION: (828)
<223> OTHER INFORMATION: Wherein n is a or t or c or g.
<220> FEATURE:
<221> NAME/KEY: misc_feature
<222> LOCATION: (831)..(834)
<223> OTHER INFORMATION: Wherein n is a or t or c or g.
<220> FEATURE:
<221> NAME/KEY: misc_feature
<222> LOCATION: (836)
<223> OTHER INFORMATION: Wherein n is a or t or c or g.
<220> FEATURE:
<221> NAME/KEY: misc_feature
<222> LOCATION: (838)
<223> OTHER INFORMATION: Wherein n is a or t or c or g.
<220> FEATURE:
<221> NAME/KEY: misc_feature
<222> LOCATION: (840)..(841)
<223> OTHER INFORMATION: Wherein n is a or t or c or g.
<220> FEATURE:
<221> NAME/KEY: misc_feature
<222> LOCATION: (845)
<223> OTHER INFORMATION: Wherein n is a or t or c or g.
<220> FEATURE:
<221> NAME/KEY: misc_feature
<222> LOCATION: (847)
<223> OTHER INFORMATION: Wherein n is a or t or c or g.
<220> FEATURE:
<221> NAME/KEY: misc_feature
<222> LOCATION: (850)
<223> OTHER INFORMATION: Wherein n is a or t or c or g.
<220> FEATURE:
<221> NAME/KEY: misc_feature
<222> LOCATION: (852)..(856)
<223> OTHER INFORMATION: Wherein n is a or t or c or g.
<220> FEATURE:
<221> NAME/KEY: misc_feature
<222> LOCATION: (861)..(863)
<223> OTHER INFORMATION: Wherein n is a or t or c or g.
<220> FEATURE:
<221> NAME/KEY: misc_feature
<222> LOCATION: (865)..(871)
<223> OTHER INFORMATION: Wherein n is a or t or c or g.
<220> FEATURE:
<221> NAME/KEY: misc_feature
<222> LOCATION: (873)..(875)
<223> OTHER INFORMATION: Wherein n is a or t or c or g.
<220> FEATURE:
<221> NAME/KEY: misc_feature
<222> LOCATION: (879)
<223> OTHER INFORMATION: Wherein n is a or t or c or g.
<220> FEATURE:
<221> NAME/KEY: misc_feature
<222> LOCATION: (882)..(883)
<223> OTHER INFORMATION: Wherein n is a or t or c or g.
<220> FEATURE:
<221> NAME/KEY: misc_feature
<222> LOCATION: (885)
<223> OTHER INFORMATION: Wherein n is a or t or c or g.
<220> FEATURE:
<221> NAME/KEY: misc_feature
<222> LOCATION: (889)
<223> OTHER INFORMATION: Wherein n is a or t or c or g.
<220> FEATURE:
<221> NAME/KEY: misc_feature
<222> LOCATION: (891)
<223> OTHER INFORMATION: Wherein n is a or t or c or g.
<220> FEATURE:
<221> NAME/KEY: misc_feature
<222> LOCATION: (893)
<223> OTHER INFORMATION: Wherein n is a or t or c or g.
<220> FEATURE:
<221> NAME/KEY: misc_feature -continued

```
<222> LOCATION: (895)
<223> OTHER INFORMATION: Wherein n is a or t or c or g.
<220> FEATURE:
<221> NAME/KEY: misc_feature
<222> LOCATION: (897)..(898)
<223> OTHER INFORMATION: Wherein n is a or t or c or g.
<220> FEATURE:
<221> NAME/KEY: misc_feature
<222> LOCATION: (902)..(906)
<223> OTHER INFORMATION: Wherein n is a or t or c or g.
<220> FEATURE:
<221> NAME/KEY: misc_feature
<222> LOCATION: (912)
<223> OTHER INFORMATION: Wherein n is a or t or c or g.
<220> FEATURE:
<221> NAME/KEY: misc_feature
<222> LOCATION: (914)
<223> OTHER INFORMATION: Wherein n is a or t or c or g.
<220> FEATURE:
<221> NAME/KEY: misc_feature
<222> LOCATION: (917)..(918)
<223> OTHER INFORMATION: Wherein n is a or t or c or g.
<220> FEATURE:
<221> NAME/KEY: misc_feature
<222> LOCATION: (920)
<223> OTHER INFORMATION: Wherein n is a or t or c or g.
<220> FEATURE:
<221> NAME/KEY: misc_feature
<222> LOCATION: (922)
<223> OTHER INFORMATION: Wherein n is a or t or c or g.
<220> FEATURE:
<221> NAME/KEY: misc_feature
<222> LOCATION: (925)..(926)
<223> OTHER INFORMATION: Wherein n is a or t or c or g.
<220> FEATURE:
<221> NAME/KEY: misc_feature
<222> LOCATION: (929)..(932)
<223> OTHER INFORMATION: Wherein n is a or t or c or g.
<220> FEATURE:
<221> NAME/KEY: misc_feature
<222> LOCATION: (936)..(937)
<223> OTHER INFORMATION: Wherein n is a or t or c or g.
<220> FEATURE:
<221> NAME/KEY: misc_feature
<222> LOCATION: (939)
<223> OTHER INFORMATION: Wherein n is a or t or c or g.
<220> FEATURE:
<221> NAME/KEY: misc_feature
<222> LOCATION: (942)..(944)
<223> OTHER INFORMATION: Wherein n is a or t or c or g.
<220> FEATURE:
<221> NAME/KEY: misc_feature
<222> LOCATION: (946)..(951)
<223> OTHER INFORMATION: Wherein n is a or t or c or g.
<220> FEATURE:
<221> NAME/KEY: misc_feature
<222> LOCATION: (955)..(957)
<223> OTHER INFORMATION: Wherein n is a or t or c or g.
<220> FEATURE:
<221> NAME/KEY: misc_feature
<222> LOCATION: (961)..(962)
<223> OTHER INFORMATION: Wherein n is a or t or c or g.
<220> FEATURE:
<221> NAME/KEY: misc_feature
<222> LOCATION: (967)..(968)
<223> OTHER INFORMATION: Wherein n is a or t or c or g.
<220> FEATURE:
<221> NAME/KEY: misc_feature
<222> LOCATION: (974)
<223> OTHER INFORMATION: Wherein n is a or t or c or g.
<220> FEATURE:
<221> NAME/KEY: misc_feature
<222> LOCATION: (980)
<223> OTHER INFORMATION: Wherein n is a or t or c or g.
<220> FEATURE:
<221> NAME/KEY: misc_feature
<222> LOCATION: (982)
<223> OTHER INFORMATION: Wherein n is a or t or c or g.
<220> FEATURE:
```

-continued

<221> NAME/KEY: misc_feature
<222> LOCATION: (984)
<223> OTHER INFORMATION: Wherein n is a or t or c or g.
<220> FEATURE:
<221> NAME/KEY: misc_feature
<222> LOCATION: (991)..(993)
<223> OTHER INFORMATION: Wherein n is a or t or c or g.
<220> FEATURE:
<221> NAME/KEY: misc_feature
<222> LOCATION: (998)
<223> OTHER INFORMATION: Wherein n is a or t or c or g.
<220> FEATURE:
<221> NAME/KEY: misc_feature
<222> LOCATION: (1000)
<223> OTHER INFORMATION: Wherein n is a or t or c or g.
<220> FEATURE:
<221> NAME/KEY: misc_feature
<222> LOCATION: (1006)
<223> OTHER INFORMATION: Wherein n is a or t or c or g.
<220> FEATURE:
<221> NAME/KEY: misc_feature
<222> LOCATION: (1009)
<223> OTHER INFORMATION: Wherein n is a or t or c or g.
<220> FEATURE:
<221> NAME/KEY: misc_feature
<222> LOCATION: (1018)
<223> OTHER INFORMATION: Wherein n is a or t or c or g.
<220> FEATURE:
<221> NAME/KEY: misc_feature
<222> LOCATION: (1020)..(1021)
<223> OTHER INFORMATION: Wherein n is a or t or c or g.
<220> FEATURE:
<221> NAME/KEY: misc_feature
<222> LOCATION: (1024)
<223> OTHER INFORMATION: Wherein n is a or t or c or g.
<220> FEATURE:
<221> NAME/KEY: misc_feature
<222> LOCATION: (1033)
<223> OTHER INFORMATION: Wherein n is a or t or c or g.
<220> FEATURE:
<221> NAME/KEY: misc_feature
<222> LOCATION: (1046)
<223> OTHER INFORMATION: Wherein n is a or t or c or g.
<220> FEATURE:
<221> NAME/KEY: misc_feature
<222> LOCATION: (1048)
<223> OTHER INFORMATION: Wherein n is a or t or c or g.
<220> FEATURE:
<221> NAME/KEY: misc_feature
<222> LOCATION: (1053)
<223> OTHER INFORMATION: Wherein n is a or t or c or g.
<220> FEATURE:
<221> NAME/KEY: misc_feature
<222> LOCATION: (1055)
<223> OTHER INFORMATION: Wherein n is a or t or c or g.
<220> FEATURE:
<221> NAME/KEY: misc_feature
<222> LOCATION: (1057)
<223> OTHER INFORMATION: Wherein n is a or t or c or g.
<220> FEATURE:
<221> NAME/KEY: misc_feature
<222> LOCATION: (1060)..(1062)
<223> OTHER INFORMATION: Wherein n is a or t or c or g.
<220> FEATURE:
<221> NAME/KEY: misc_feature
<222> LOCATION: (1066)
<223> OTHER INFORMATION: Wherein n is a or t or c or g.
<220> FEATURE:
<221> NAME/KEY: misc_feature
<222> LOCATION: (1084)
<223> OTHER INFORMATION: Wherein n is a or t or c or g.
<220> FEATURE:
<221> NAME/KEY: misc_feature
<222> LOCATION: (1087)
<223> OTHER INFORMATION: Wherein n is a or t or c or g.
<220> FEATURE:
<221> NAME/KEY: misc_feature
<222> LOCATION: (1090)
<223> OTHER INFORMATION: Wherein n is a or t or c or g.

-continued

<220> FEATURE:
<221> NAME/KEY: misc_feature
<222> LOCATION: (1093)
<223> OTHER INFORMATION: Wherein n is a or t or c or g.
<220> FEATURE:
<221> NAME/KEY: misc_feature
<222> LOCATION: (1096)
<223> OTHER INFORMATION: Wherein n is a or t or c or g.
<220> FEATURE:
<221> NAME/KEY: misc_feature
<222> LOCATION: (1100)..(1102)
<223> OTHER INFORMATION: Wherein n is a or t or c or g.
<220> FEATURE:
<221> NAME/KEY: misc_feature
<222> LOCATION: (1106)
<223> OTHER INFORMATION: Wherein n is a or t or c or g.
<220> FEATURE:
<221> NAME/KEY: misc_feature
<222> LOCATION: (1109)..(1110)
<223> OTHER INFORMATION: Wherein n is a or t or c or g.
<220> FEATURE:
<221> NAME/KEY: misc_feature
<222> LOCATION: (1116)
<223> OTHER INFORMATION: Wherein n is a or t or c or g.
<220> FEATURE:
<221> NAME/KEY: misc_feature
<222> LOCATION: (1120)
<223> OTHER INFORMATION: Wherein n is a or t or c or g.
<220> FEATURE:
<221> NAME/KEY: misc_feature
<222> LOCATION: (1124)..(1126)
<223> OTHER INFORMATION: Wherein n is a or t or c or g.
<220> FEATURE:
<221> NAME/KEY: misc_feature
<222> LOCATION: (1129)..(1130)
<223> OTHER INFORMATION: Wherein n is a or t or c or g.
<220> FEATURE:
<221> NAME/KEY: misc_feature
<222> LOCATION: (1135)
<223> OTHER INFORMATION: Wherein n is a or t or c or g.
<220> FEATURE:
<221> NAME/KEY: misc_feature
<222> LOCATION: (1138)
<223> OTHER INFORMATION: Wherein n is a or t or c or g.
<220> FEATURE:
<221> NAME/KEY: misc_feature
<222> LOCATION: (1141)..(1142)
<223> OTHER INFORMATION: Wherein n is a or t or c or g.
<220> FEATURE:
<221> NAME/KEY: misc_feature
<222> LOCATION: (1146)..(1148)
<223> OTHER INFORMATION: Wherein n is a or t or c or g.
<220> FEATURE:
<221> NAME/KEY: misc_feature
<222> LOCATION: (1150)..(1151)
<223> OTHER INFORMATION: Wherein n is a or t or c or g.
<220> FEATURE:
<221> NAME/KEY: misc_feature
<222> LOCATION: (1153)..(1154)
<223> OTHER INFORMATION: Wherein n is a or t or c or g.
<220> FEATURE:
<221> NAME/KEY: misc_feature
<222> LOCATION: (1156)
<223> OTHER INFORMATION: Wherein n is a or t or c or g.
<220> FEATURE:
<221> NAME/KEY: misc_feature
<222> LOCATION: (1159)..(1162)
<223> OTHER INFORMATION: Wherein n is a or t or c or g.
<220> FEATURE:
<221> NAME/KEY: misc_feature
<222> LOCATION: (1166)
<223> OTHER INFORMATION: Wherein n is a or t or c or g.
<220> FEATURE:
<221> NAME/KEY: misc_feature
<222> LOCATION: (1168)
<223> OTHER INFORMATION: Wherein n is a or t or c or g.
<220> FEATURE:
<221> NAME/KEY: misc_feature
<222> LOCATION: (1171)..(1174)

-continued

<223> OTHER INFORMATION: Wherein n is a or t or c or g.
<220> FEATURE:
<221> NAME/KEY: misc_feature
<222> LOCATION: (1177)
<223> OTHER INFORMATION: Wherein n is a or t or c or g.
<220> FEATURE:
<221> NAME/KEY: misc_feature
<222> LOCATION: (1180)
<223> OTHER INFORMATION: Wherein n is a or t or c or g.
<220> FEATURE:
<221> NAME/KEY: misc_feature
<222> LOCATION: (1183)..(1184)
<223> OTHER INFORMATION: Wherein n is a or t or c or g.
<220> FEATURE:
<221> NAME/KEY: misc_feature
<222> LOCATION: (1186)
<223> OTHER INFORMATION: Wherein n is a or t or c or g.
<220> FEATURE:
<221> NAME/KEY: misc_feature
<222> LOCATION: (1186)
<223> OTHER INFORMATION: Wherein n is a or t or c or g.
<220> FEATURE:
<221> NAME/KEY: misc_feature
<222> LOCATION: (1189)
<223> OTHER INFORMATION: Wherein n is a or t or c or g.
<220> FEATURE:
<221> NAME/KEY: misc_feature
<222> LOCATION: (1191)..(1227)
<223> OTHER INFORMATION: Wherein n is a or t or c or g.

<400> SEQUENCE: 96

```
nnnnnnnnnn nnnnnnnnnn nnnnnnnnnn nnnntngagn tnnnncgnga tnancanntn     60

nantatntnn nnnnnggnnt nngncanntn ngnncnnnnt ttnnnnnnnt ngangcnaat    120

cgnccntggc tntgntactg gatnnttcat tcaattgctt tgctnggnga nncngtngat    180

gatganntng aaaanaatgc natnganttn cttgnncgnt gccaggntnc ngatggtgga    240

tatggtggtg gncctggcca nntnccncat cttgcnacna cttatgctgc ngtnaatnca    300

cttgttactt taggngggtga naaagccntn tcntcaatta atagaganaa antgtntngt    360

tttntnngnc ggatgaagga tncaantggn ggtttcagga tgcatgatnn nggngaaatt    420

gatgtncgng cntgctacac tgcnatttcg gttgcaagcn tnntgaanat tntggatgat    480

gaactnaccc anggnntagg agantacatn ntnagntgnc aaacttatga aggtggcatt    540

gnnggggganc ctggntcnga agctcatggt gggtanacnt nctgtggntt ggctnctatg    600

attntnatna atgaggtnga ncnnttgnat ttgnntnnnt taatnnantg ggtngtannt    660

cgacaaggag tngaannngg attncaaggn agnacnaana aattggtnga tggttgctac    720

ncnttttggc aggnagcnnc nnntgntcta ntacaaagat tatnttcnan nnnngatang    780

nnnnnnnang nnncatcann nnnnnnnnnn ngngnnannt nangnncntg nnnnanangn    840

ncatnangan gnnnnncctg nnnannnnnn ngnnnatgnt gnntntgang ngnanannga    900

tnnnnnttca gngnatnntn anaannttnn nnatanntnt annnannnnn ncagnnnaat    960

nnaaccnntt tttnatagcn tngncttgca nnnatatntn ctcttntgnt ctcaggtncn   1020

nganggtgga ttnagagaca agccgngnaa acncngngan nnctancaca catgttactg   1080

cctnagnggn ctntcngtgn nncagnacnn ttggtnaaan gacnnngann ctccnccntt   1140

nnctcnnnan ntnntnggnn nntacncnaa nnnnctngan ccnntncanc nnnnnnnnnn   1200

nnnnnnnnnn nnnnnnnnnn nnnnnnnnnn nnnnnnn                            1237
```

<210> SEQ ID NO 97
<211> LENGTH: 1275
<212> TYPE: DNA
<213> ORGANISM: Arabidopsis thaliana -continued

<400> SEQUENCE: 97

```
atggcgattc ctttcatgga aaccgtcgtg ggttttatga tagtgatgta catttttgag     60
acgtatttgg atctgaggca actcactgct ctcaagcttc caactctccc gaaaaccttg    120
gttggtgtaa ttagccaaga gaagtttgag aaatcacgag catacagtct tgacaaaagc    180
tattttcact ttgttcatga gtttgtaact atacttatgg actctgcaat tttgttcttt    240
gggatcttgc cttggttttg gaagatgtct ggagctgttt taccgaggtt gggccttgat    300
ccggagaatg aaatactgca tactctttca ttcttggctg gtgttatgac atggtcacag    360
atcactgatt tgccattttc tttgtactca actttcgtga tcgagtctcg gcatgggttc    420
aacaaacaaa caatatggat gttcattagg gacatgatca aggaacattt cctctctgtc    480
atactaggcc cacccattgt tgctgcgata attttcatag tccagaaagg aggtccttat    540
cttgccatct atctgtgggc attcatgttt atcctgtctc tagtgatgat gactatatac    600
ccggtcttga tagcaccgct cttcaacaaa ttcactcctc ttccagatgg agacctccgg    660
gagaagattg agaaacttgc ttcttcccta aagtttcctt tgaagaagct gtttgttgtc    720
gatggatcta caaggtcaag ccatagcaat gcttacatgt atggtttctt taagaacaaa    780
aggattgttc tttatgatac gttgattcag cagtgcaaga atgaggatga aattgtggcg    840
gttattgcac acgagcttgg acattggaaa ctgaatcaca ctacatactc gttcattgca    900
gttcaaatcc ttgccttctt acaatttgga ggatacactc ttctcagaaa ctccactgat    960
ctcttcagga gtttcggatt tgatacacag cctgttctca ttggtttgat catatttcag   1020
cacactgtaa taccactgca acatctagta agctttggcc tgaacctcgt tagtcgagcg   1080
tttgagtttc aggctgatgc ttttgctgtg aagcttgact atgcaaaaga tcttcgtcct   1140
gctctagtga aactacagga agagaactta tcaacaatga acactgatcc attgtactca   1200
gcttatcact actcacatcc tcctcttgtt gaaaggcttc gagccactga tggagaagac   1260
aagaagacag attaa                                                    1275
```

<210> SEQ ID NO 98
<211> LENGTH: 424
<212> TYPE: PRT
<213> ORGANISM: Arabidopsis thaliana

<400> SEQUENCE: 98

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Val Gly Val Ile Ser Gln Glu Lys
        35                  40                  45

Phe Glu Lys Ser Arg Ala Tyr Ser Leu Asp Lys Ser Tyr Phe His Phe
    50                  55                  60

Val His Glu Phe Val Thr Ile Leu Met Asp Ser Ala Ile Leu Phe Phe
65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125
```

-continued

```
Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Leu Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
        355                 360                 365

Ala Val Lys Leu Asp Tyr Ala Lys Asp Leu Arg Pro Ala Leu Val Lys
    370                 375                 380

Leu Gln Glu Glu Asn Leu Ser Thr Met Asn Thr Asp Pro Leu Tyr Ser
385                 390                 395                 400

Ala Tyr His Tyr Ser His Pro Pro Leu Val Glu Arg Leu Arg Ala Thr
                405                 410                 415

Asp Gly Glu Asp Lys Lys Thr Asp
            420
```

```
<210> SEQ ID NO 99
<211> LENGTH: 5544
<212> TYPE: DNA
<213> ORGANISM: Artificial Sequence
<220> FEATURE:
<223> OTHER INFORMATION: Description of Artificial Sequence: Plasmid
      pBI121-AtCPP

<400> SEQUENCE: 99

gtttacccgc caatatatcc tgtcaaacac tgatagttta aactgaaggc gggaaacgac      60

aatctgatca tgagcggaga attaagggag tcacgttatg acccccgccg atgacgcggg     120

acaagccgtt ttacgtttgg aactgacaga accgcaacgt tgaaggagcc actcagccgc     180

gggtttctgg agtttaatga gctaagcaca tacgtcagaa accattattg cgcgttcaaa     240

agtcgcctaa ggtcactatc agctagcaaa tatttcttgt caaaaatgct ccactgacgt     300

tccataaatt cccctcggta tccaattaga gtctcatatt cactctcaat ccaaataatc     360
```

-continued

```
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
```

-continued

```
gacgattcaa ggcttgcttc acaaaccaag gcaagtaata gagattggag tctctaaaaa   2760

ggtagttccc actgaatcaa aggccatgga gtcaaagatt caaatagagg acctaacaga   2820

actcgccgta aagactggcg aacagttcat acagagtctc ttacgactca atgacaagaa   2880

gaaaatcttc gtcaacatgg tggagcacga cacacttgtc tactccaaaa atatcaaaga   2940

tacagtctca gaagaccaaa gggcaattga gacttttcaa caaagggtaa tatccggaaa   3000

cctcctcgga ttccattgcc cagctatctg tcactttatt gtgaagatag tggaaaagga   3060

aggtggctcc tacaaatgcc atcattgcga taaaggaaag gccatcgttg aagatgcctc   3120

tgccgacagt ggtcccaaag atggaccccc acccacgagg agcatcgtgg aaaaagaaga   3180

cgttccaacc acgtcttcaa agcaagtgga ttgatgtgat atctccactg acgtaaggga   3240

tgacgcacaa tcccactatc cttcgcaaga cccttcctct atataaggaa gttcatttca   3300

tttggagaga acacggggga ctctagagga tccatggcga ttcctttcat ggaaaccgtc   3360

gtgggtttta tgatagtgat gtacattttt gagacgtatt tggatctgag gcaactcact   3420

gctctcaagc ttccaactct cccgaaaacc ttggttggtg taattagcca agagaagttt   3480

gagaaatcac gagcatacag tcttgacaaa agctattttc actttgttca tgagtttgta   3540

actatactta tggactctgc aattttgttc tttgggatct tgccttggtt ttggaagatg   3600

tctggagctg ttttaccgag gttgggcctt gatccggaga atgaaatact gcatactctt   3660

tcattcttgg ctggtgttat gacatggtca cagatcactg atttgccatt ttctttgtac   3720

tcaactttcg tgatcgagtc tcggcatggg ttcaacaaac aaacaatatg gatgttcatt   3780

agggacatga tcaaaggaac attcctctct gtcatactag gcccacccat tgttgctgcg   3840

ataattttca tagtccagaa aggaggtcct tatcttgcca tctatctgtg ggcattcatg   3900

tttatcctgt ctctagtgat gatgactata tacccggtct tgatagcacc gctcttcaac   3960

aaattcactc ctcttccaga tggagacctc cgggagaaga ttgagaaact tgcttcttcc   4020

ctaaagtttc ctttgaagaa gctgtttgtt gtcgatggat ctacaaggtc aagccatagc   4080

aatgcttaca tgtatggttt ctttaagaac aaaaggattg ttctttatga tacgttgatt   4140

cagcagtgca agaatgagga tgaaattgtg gcggttattg cacacgagct tggacattgg   4200

aaactgaatc acactacata ctcgttcatt gcagttcaaa tccttgcctt cttacaattt   4260

ggaggataca ctcttctcag aaactccact gatctcttca ggagtttcgg atttgataca   4320

cagcctgttc tcattggttt gatcatattt cagcacactg taataccact gcaacatcta   4380

gtaagctttg gcctgaacct cgttagtcga gcgtttgagt ttcaggctga tgcttttgct   4440

gtgaagcttg actatgcaaa agatcttcgt cctgctctag tgaaactaca ggaagagaac   4500

ttatcaacaa tgaacactga tccattgtac tcagcttatc actactcaca tcctcctctt   4560

gttgaaaggc ttcgagccac tgatggagaa gacaagaaga cagattaacc cctcgaattt   4620

ccccgatcgt tcaaacattt ggcaataaag tttcttaaga ttgaatcctg ttgccggtct   4680

tgcgatgatt atcatataat ttctgttgaa ttacgttaag catgtaataa ttaacatgta   4740

atgcatgacg ttatttatga gatgggtttt tatgattaga gtcccgcaat tatacattta   4800

atacgcgata gaaaacaaaa tatagcgcgc aaactaggat aaattatcgc gcgcggtgtc   4860

atctatgtta ctagatcggg aattcactgg ccgtcgtttt acaacgtcgt gactgggaaa   4920

accctggcgt tacccaactt aatcgccttg cagcacatcc ccctttcgcc agctggcgta   4980

atagcgaaga ggcccgcacc gatcgccctt cccaacagtt gcgcagcctg aatggcgccc   5040

gctcctttcg ctttcttccc ttcctttctc gccacgttcg ccggctttcc ccgtcaagct   5100
```

-continued ctaaatcggg ggctcccttt agggttccga tttagtgctt tacggcacct cgaccccaaa 5160
aaacttgatt tgggtgatgg ttcacgtagt gggccatcgc cctgatagac ggtttttcgc 5220
cctttgacgt tggagtccac gttctttaat agtggactct tgttccaaac tggaacaaca 5280
ctcaacccta tctcgggcta ttcttttgat ttataaggga ttttgccgat ttcggaacca 5340
ccatcaaaca ggattttcgc ctgctggggc aaaccagcgt ggaccgcttg ctgcaactct 5400
ctcagggcca ggcggtgaag ggcaatcagc tgttgcccgt ctcactggtg aaaagaaaaa 5460
ccaccccagt acattaaaaa cgtccgcaat gtgttattaa gttgtctaag cgtcaatttg 5520
tttacaccac aatatatcct gcca 5544

<210> SEQ ID NO 100
<211> LENGTH: 6484
<212> TYPE: DNA
<213> ORGANISM: Artificial Sequence
<220> FEATURE:
<223> OTHER INFORMATION: Description of Artificial Sequence: Plasmid pBI121-HP-AtCpp

<400> SEQUENCE: 100
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560

-continued tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tcctcccaat gtccaagctc gtgtgcaata 3360
accgccacaa tttcatcctc attcttgcac tgctgaatca acgtatcata aagaacaatc 3420
cttttgttct taaagaaacc atacatgtaa gcattgctat ggcttgacct tgtagatcca 3480
tcgacaacaa acagcttctt caaaggaaac tttagggaag aagcaagttt ctcaatcttc 3540
tcccggaggt ctccatctgg aagaggagtg aatttgttga agagcggtgc tatcaagacc 3600
gggtatatag tcatcatcac tagagacagg ataaacatga atgcccacag atagatggca 3660
agataaggac ctcctttctg gactatgaaa attatcgcag caacaatggg tgggcctagt 3720
atgacagaga ggaatgttcc tttgatcatg tccctaatga acatccatat tgtttgtttg 3780
ttgaacccat gccgagactc gatcacgaaa gttgagtaca aagaaaatgg caaatcagtg 3840
atctgtgacc atgtcataac accagccaag aatgaaagag tatgcagtat ttcattctcc 3900

-continued ggatcaaggc ccaacctcgg taaaagagga tccccatcta cccgcttcgc gtcggcatcc 3960
ggtcagtggc agtgaagggc gaacagttcc tgattaacca caaaccgttc tactttactg 4020
gctttggtcg tcatgaagat gcggacttgc gtggcaaagg attcgataac gtgctgatgg 4080
tgcacgacca cgcattaatg gactggattg gggccaactc ctaccgtacc tcgcattacc 4140
cttacgctga agagatgctc gactgggcag atgaacatgg catcgtggtg attgatgaaa 4200
ctgctgctgt cggcttttcg ctctctttag gcattggttt cgaagcgggc aacaagccga 4260
aagaactgta cagcgaagag gcagtcaacg gggaaactca gcaagcgcac ttacaggcga 4320
ttaaagagct gatagcgcgt gacaaaaacc acccaagcgt ggtgatgtgg agtattgcca 4380
acgaaccgga tacccgtccg caaggtgcac gggaatattt cgcgccactg gcggaagcaa 4440
cgcgtaaact cgacccgacg cgtccgatca cctgcgtcaa tgtaatgttc tgcgacgctc 4500
acaccgatac catcagcgat ctctttgatg tgctgtgcct gaaccgttat tacggatggt 4560
atgtccaaag cggcgatttg gaaacggcag agaaggtact ggaaaaagaa cttctggcct 4620
ggcaggagaa actgtacacc gacatgtgga gtgaagagta tcagtgtgca tggctggata 4680
tgtatcaccg cgtctttgat cgcgtcagcg ccgtcgtcgg tgaacaggta tggaatttcg 4740
ccgattttgc gacctcgcaa ggcatattgc gcgttggcgg taacaagaaa gggatcttca 4800
ctcgcgaccg caaaccgaag tcggcggctt ttctgctgca aaaacgctgg actggcatga 4860
acttcggtga aaaaccgcag cagggaggca aacaatgaat caacaactct cctggcgcac 4920
catcgtcggc tacagcctcg ggaattgcta ccgagctctt ttaccgaggt tgggccttga 4980
tccggagaat gaaatactgc atactctttc attcttggct ggtgttatga catggtcaca 5040
gatcactgat ttgccatttt ctttgtactc aactttcgtg atcgagtctc ggcatgggtt 5100
caacaaacaa acaatatgga tgttcattag ggacatgatc aaaggaacat tcctctctgt 5160
catactaggc ccacccattg ttgctgcgat aattttcata gtccagaaag gaggtcctta 5220
tcttgccatc tatctgtggg cattcatgtt tatcctgtct ctagtgatga tgactatata 5280
cccggtcttg atagcaccgc tcttcaacaa attcactcct cttccagatg gagacctccg 5340
ggagaagatt gagaaacttg cttcttccct aaagtttcct ttgaagaagc tgtttgttgt 5400
cgatggatct acaaggtcaa gccatagcaa tgcttacatg tatggtttct ttaagaacaa 5460
aaggattgtt ctttatgata cgttgattca gcagtgcaag aatgaggatg aaattgtggc 5520
ggttattgca cacgagcttg gacattggga gctcgaattt ccccgatcgt tcaaacattt 5580
ggcaataaag tttcttaaga ttgaatcctg ttgccggtct tgcgatgatt atcatataat 5640
ttctgttgaa ttacgttaag catgtaataa ttaacatgta atgcatgacg ttatttatga 5700
gatgggtttt tatgattaga gtcccgcaat tatacattta atacgcgata gaaaacaaaa 5760
tatagcgcgc aaactaggat aaattatcgc gcgcggtgtc atctatgtta ctagatcggg 5820
aattcactgg ccgtcgtttt acaacgtcgt gactgggaaa accctggcgt tacccaactt 5880
aatcgccttg cagcacatcc ccctttcgcc agctggcgta atagcgaaga ggcccgcacc 5940
gatcgccctt cccaacagtt gcgcagcctg aatggcgccc gctcctttcg ctttcttccc 6000
ttcctttctc gccacgttcg ccggctttcc ccgtcaagct ctaaatcggg ggctcccttt 6060
agggttccga tttagtgctt tacggcacct cgaccccaaa aaacttgatt tgggtgatgg 6120
ttcacgtagt gggccatcgc cctgatagac ggtttttcgc cctttgacgt tggagtccac 6180
gttctttaat agtggactct tgttccaaac tggaacaaca ctcaacccta tctcgggcta 6240
ttcttttgat ttataaggga ttttgccgat ttcggaacca ccatcaaaca ggattttcgc 6300

-continued

```
ctgctggggc aaaccagcgt ggaccgcttg ctgcaactct ctcagggcca ggcggtgaag   6360

ggcaatcagc tgttgcccgt ctcactggtg aaaagaaaaa ccaccccagt acattaaaaa   6420

cgtccgcaat gtgttattaa gttgtctaag cgtcaatttg tttacaccac aatatatcct   6480

gcca                                                                6484


<210> SEQ ID NO 101
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 101

aaaggatcca tggcgattcc tttcatgg                                        28


<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 102

aaacccgggt taatctgtct tcttgtcttc tcca                                 34


<210> SEQ ID NO 103
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 103

ctggagctct tttaccgagg ttgggccttg atcc                                 34


<210> SEQ ID NO 104
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 104

attgagctcc caatgtccaa gctcgtgtgc aata                                 34


<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 105

gccgacagtg gtcccaaaga tgg                                             23


<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 106
```

-continued

```
aaacccggga tggcgattcc tttcatgg                                          28


<210> SEQ ID NO 107
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 107

aaaggatcct taatctgtct tcttgtcttc tcca                                   34


<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 108

gcaagaccgg caacagga                                                     18


<210> SEQ ID NO 109
<211> LENGTH: 1275
<212> TYPE: DNA
<213> ORGANISM: Brassica napus

<400> SEQUENCE: 109

atggcgattc ctttcatgga aaccgtcgtt ggttttatga tagtgatgta cgtttttgag     60

acgtatttgg atctgaggca acatactgct ctcaagcttc ccactctccc aaagactttg    120

gttggagtca ttagccaaga gaagtttgag aaatctcgag cttacagtct tgacaaaagc    180

cattttcact ttgttcatga gtttgttact atacttatgg actctgcgat tctgttcttt    240

gggatcttgc cttggttttg gaagatatct ggcggctttc taccaatggt gggactcgat    300

ccagagaatg aaatcctgca cactctttca ttcttggctg gtcttatgac atggtcacag    360

atcactgatt tgccattttc tttgtactca actttcgtga tcgagtctcg gcatgggttc    420

aacaaacaaa caatatggat gttcattagg gacatgatca aaggaatact cctctctgtc    480

atacctgccc ctcctatcgt tgccgcaatt attgttatag ttcagaaagg aggtccttac    540

ctcgccatct atctgtgggc attcatgttt atcctgtctc tagtgatgat gactatatac    600

cctgttttga ttgcacctct tttcaacaag ttcactcctc ttcctgatgg agacctccgg    660

gagaagattg agaaacttgc ttcttctcta aagtttcctc tgaagaagct gtttgttgtc    720

gatggatcta caaggtcaag ccatagtaat gcttacatgt atggtttctt caagaacaaa    780

aggattgttc tttatgacac attgattcag cagtgccaga atgagaatga aattgtggcg    840

gttattgcac acgagctggg acactggaag ctgaatcaca ctacatactc gttcattgct    900

gttcaaatcc ttgccttctt gcaatttgga ggatacactc ttgtcagaaa ctccactgat    960

ctcttcagga gttttggttt tgatacacaa ccagttctca ttggtttgat catatttcag   1020

cacactgtaa taccacttca acacctagta agctttgacc tcaaccttgt tagtcgagcg   1080

tttgagtttc aggctgatgc ttttgcagtg aatcttggtt atgcaaagga tctacgtcct   1140

gccctagtga agctacagga agagaactta tcagcgatga acacagaccc attgtactca   1200

gcttatcact actcacaccc tcctcttgta gagaggcttc gagccattga tggagaagac   1260

aagaagacag attaa                                                     1275
```

-continued

<210> SEQ ID NO 110
<211> LENGTH: 424
<212> TYPE: PRT
<213> ORGANISM: Brassica napus

<400> SEQUENCE: 110

```
Met Ala Ile Pro Phe Met Glu Thr Val Val Gly Phe Met Ile Val Met
  1               5                  10                  15

Tyr Val Phe Glu Thr Tyr Leu Asp Leu Arg Gln His Thr Ala Leu Lys
             20                  25                  30

Leu Pro Thr Leu Pro Lys Thr Leu Val Gly Val Ile Ser Gln Glu Lys
         35                  40                  45

Phe Glu Lys Ser Arg Ala Tyr Ser Leu Asp Lys Ser His Phe His Phe
     50                  55                  60

Val His Glu Phe Val Thr Ile Leu Met Asp Ser Ala Ile Leu Phe Phe
 65                  70                  75                  80

Gly Ile Leu Pro Trp Phe Trp Lys Ile Ser Gly Gly Phe Leu Pro Met
                 85                  90                  95

Val Gly Leu Asp Pro Glu Asn Glu Ile Leu His Thr Leu Ser Phe Leu
            100                 105                 110

Ala Gly Leu Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Ile Leu Leu Ser Val
145                 150                 155                 160

Ile Pro Ala Pro Pro Ile Val Ala Ala Ile Ile Val Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Gln Asn Glu Asn Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Asp Leu Asn Leu Val Ser Arg Ala Phe Glu Phe Gln Ala Asp Ala Phe
        355                 360                 365

Ala Val Asn Leu Gly Tyr Ala Lys Asp Leu Arg Pro Ala Leu Val Lys
    370                 375                 380
```

-continued

```
Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

<210> SEQ ID NO 111
<211> LENGTH: 1275
<212> TYPE: DNA
<213> ORGANISM: Artificial Sequence
<220> FEATURE:
<223> OTHER INFORMATION: Description of Artificial Sequence: Compliment to SEQ ID NO: 109

<400> SEQUENCE: 111

```
ttaatctgtc ttcttgtctt ctccatcaat ggctcgaagc ctctctacaa gaggagggtg     60

tgagtagtga taagctgagt acaatgggtc tgtgttcatc gctgataagt tctcttcctg    120

tagcttcact agggcaggac gtagatcctt tgcataacca agattcactg caaaagcatc    180

agcctgaaac tcaaacgctc gactaacaag gttgaggtca aagcttacta ggtgttgaag    240

tggtattaca gtgtgctgaa atatgatcaa accaatgaga actggttgtg tatcaaaacc    300

aaaactcctg aagagatcag tggagtttct gacaagagtg tatcctccaa attgcaagaa    360

ggcaaggatt tgaacagcaa tgaacgagta tgtagtgtga ttcagcttcc agtgtcccag    420

ctcgtgtgca ataaccgcca caatttcatt ctcattctgg cactgctgaa tcaatgtgtc    480

ataaagaaca atccttttgt tcttgaagaa accatacatg taagcattac tatggcttga    540

ccttgtagat ccatcgacaa caaacagctt cttcagagga aactttagag aagaagcaag    600

tttctcaatc ttctcccgga ggtctccatc aggaagagga gtgaacttgt tgaaaagagg    660

tgcaatcaaa acagggtata tagtcatcat cactagagac aggataaaca tgaatgccca    720

cagatagatg gcgaggtaag gacctccttt ctgaactata acaataattg cggcaacgat    780

aggaggggca ggtatgacag agaggagtat tcctttgatc atgtccctaa tgaacatcca    840

tattgtttgt ttgttgaacc catgccgaga ctcgatcacg aaagttgagt acaaagaaaa    900

tggcaaatca gtgatctgtg accatgtcat aagaccagcc aagaatgaaa gagtgtgcag    960

gatttcattc tctggatcga gtcccaccat tggtagaaag ccgccagata tcttccaaaa   1020

ccaaggcaag atcccaaaga acagaatcgc agagtccata agtatagtaa caaactcatg   1080

aacaaagtga aaatggcttt tgtcaagact gtaagctcga gatttctcaa acttctcttg   1140

gctaatgact ccaaccaaag tctttgggag agtgggaagc ttgagagcag tatgttgcct   1200

cagatccaaa tacgtctcaa aaacgtacat cactatcata aaaccaacga cggtttccat   1260

gaaaggaatc gccat                                                    1275
```

<210> SEQ ID NO 112
<211> LENGTH: 1275
<212> TYPE: DNA
<213> ORGANISM: Glycine max

<400> SEQUENCE: 112

```
atggcgtttc cctacatgga agccgttgtc ggatttatga tattaatgta catttttgaa     60

acttacttgg atgtgcgaca acatagggcc ctcaaacttc ctactcttcc aaagacttta    120

gagggtgtta tcagccaaga gaaatttgag aaatctagag cctatagtct tgataaaagc    180

cacttccatt ttgttcacga gtttgtgaca atagtgacag actctacaat tttgtacttt    240
```

-continued

```
ggggtattgc cctggttttg gaagaaatca ggagatttta tgacaatagc tggtttcaat    300

gctgagaatg aaatactgca taccottgcc ttcttagcag ggctgatgat ttggtcacag    360

ataacagatt tgccctttc tctgtactca acttttgtga ttgaggcccg tcatggtttt    420

aataagcaaa caccatggtt attctttagg gacatgctta aaggaatttt cctttctgta    480

ataattggtc cacctattgt ggctgcaatc attgtaatag tacagaaagg aggtccatac    540

ttggccatct atctttgggt ttttacgttt ggtctttcta ttgtgatgat gaccctttat    600

ccagtactaa tagctccact cttcaataag ttcactccac ttccagatgg tcaactcagg    660

gagaaaatcg agaaacttgc ttcctccctc aactatccgt taaagaaact atttgttgtc    720

gatggatcca caagatcaag tcacagcaat gcctatatgt atggattctt caagaacaag    780

aggattgtcc cttatgacac attaattcaa cagtgcaaag acgatgagga aattgttgct    840

gttattgccc atgagttggg acactggaag ctcaaccata ctgtgtacac atttgttgct    900

atgcagattc ttacacttct acaatttgga ggatatacac tagtgcgaaa ttcagctgat    960

ctgtatcgaa gctttgggtt tgatacgcag ccagtcctca ttgggctcat catatttcag   1020

catactgtaa tcccacttca gcaattggtc agctttggtc tgaacctagt cagccgatca   1080

tttgaatttc aggctgatgg ctttgccaag aagcttggat atgcatctgg attacgcggt   1140

ggtcttgtga aactacagga ggagaatctg tcagctatga atacagatcc ttggtactct   1200

gcttatcact attctcatcc tcccttgtt gaaagattgg ccgcgctgga cgaaccggat    1260

aagaaggaag actaa                                                    1275
```

<210> SEQ ID NO 113
<211> LENGTH: 424
<212> TYPE: PRT
<213> ORGANISM: Glycine max

<400> SEQUENCE: 113

```
Met Ala Phe Pro Tyr Met Glu Ala Val Val Gly Phe Met Ile Leu Met
  1               5                  10                  15

Tyr Ile Phe Glu Thr Tyr Leu Asp Val Arg Gln His Arg Ala Leu Lys
             20                  25                  30

Leu Pro Thr Leu Pro Lys Thr Leu Glu Gly Val Ile Ser Gln Glu Lys
         35                  40                  45

Phe Glu Lys Ser Arg Ala Tyr Ser Leu Asp Lys Ser His Phe His Phe
     50                  55                  60

Val His Glu Phe Val Thr Ile Val Thr Asp Ser Thr Ile Leu Tyr Phe
 65                  70                  75                  80

Gly Val Leu Pro Trp Phe Trp Lys Lys Ser Gly Asp Phe Met Thr Ile
                 85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Ile Val Ile Val Gln Lys
                165                 170                 175

Gly Gly Pro Tyr Leu Ala Ile Tyr Leu Trp Val Phe Thr Phe Gly Leu
```

-continued

```
            180                 185                 190

Ser Ile Val Met Met Thr Leu Tyr Pro Val Leu Ile Ala Pro Leu Phe
        195                 200                 205

Asn Lys Phe Thr Pro Leu Pro Asp Gly Gln Leu Arg Glu Lys Ile Glu
    210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Pro Tyr Asp Thr Leu Ile Gln Gln Cys
            260                 265                 270

Lys Asp Asp Glu Glu Ile Val Ala Val Ile Ala His Glu Leu Gly His
        275                 280                 285

Trp Lys Leu Asn His Thr Val Tyr Thr Phe Val Ala Met Gln Ile Leu
    290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
                325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
        355                 360                 365

Ala Lys Lys Leu Gly Tyr Ala Ser Gly Leu Arg Gly Gly Leu Val Lys
    370                 375                 380

Leu Gln Glu Glu Asn Leu Ser Ala Met Asn Thr Asp Pro Trp Tyr Ser
385                 390                 395                 400

Ala Tyr His Tyr Ser His Pro Pro Leu Val Glu Arg Leu Ala Ala Leu
                405                 410                 415

Asp Glu Pro Asp Lys Lys Glu Asp
            420
```

<210> SEQ ID NO 114
<211> LENGTH: 1275
<212> TYPE: DNA
<213> ORGANISM: Artificial Sequence
<220> FEATURE:
<223> OTHER INFORMATION: Description of Artificial Sequence: Compliment to SEQ ID NO: 112

<400> SEQUENCE: 114

```
ttagtcttcc ttcttatccg gttcgtccag cgcggccaat ctttcaacaa ggggaggatg     60

agaatagtga taagcagagt accaaggatc tgtattcata gctgacagat tctcctcctg    120

tagtttcaca agaccaccgc gtaatccaga tgcatatcca agcttcttgg caaagccatc    180

agcctgaaat tcaaatgatc ggctgactag gttcagacca aagctgacca attgctgaag    240

tgggattaca gtatgctgaa atatgatgag cccaatgagg actggctgcg tatcaaaccc    300

aaagcttcga tacagatcag ctgaatttcg cactagtgta tatcctccaa attgtagaag    360

tgtaagaatc tgcatagcaa caaatgtgta cacagtatgg ttgagcttcc agtgtcccaa    420

ctcatgggca ataacagcaa caatttcctc atcgtctttg cactgttgaa ttaatgtgtc    480

ataagggaca atcctcttgt tcttgaagaa tccatacata taggcattgc tgtgacttga    540

tcttgtggat ccatcgacaa caaatagttt ctttaacgga tagttgaggg aggaagcaag    600

tttctcgatt ttctccctga gttgaccatc tggaagtgga gtgaacttat tgaagagtgg    660
```

-continued

```
agctattagt actggataaa gggtcatcat cacaatagaa agaccaaacg taaaaaccca    720
aagatagatg gccaagtatg gacctccttt ctgtactatt acaatgattg cagccacaat    780
aggtggacca attattacag aaaggaaaat tcctttaagc atgtccctaa agaataacca    840
tggtgtttgc ttattaaaac catgacgggc ctcaatcaca aaagttgagt acagagaaaa    900
gggcaaatct gttatctgtg accaaatcat cagccctgct aagaaggcaa gggtatgcag    960
tatttcattc tcagcattga aaccagctat tgtcataaaa tctcctgatt tcttccaaaa   1020
ccagggcaat accccaaagt acaaaattgt agagtctgtc actattgtca caaactcgtg   1080
aacaaaatgg aagtggcttt tatcaagact ataggctcta gatttctcaa atttctcttg   1140
gctgataaca ccctctaaag tctttggaag agtaggaagt ttgagggccc tatgttgtcg   1200
cacatccaag taagtttcaa aaatgtacat taatatcata aatccgacaa cggcttccat   1260
gtagggaaac gccat                                                    1275
```

<210> SEQ ID NO 115
<211> LENGTH: 1275
<212> TYPE: DNA
<213> ORGANISM: Artificial Sequence
<220> FEATURE:
<223> OTHER INFORMATION: Description of Artificial Sequence: Compliment to SEQ ID NO: 97

<400> SEQUENCE: 115

```
ttaatctgtc ttcttgtctt ctccatcagt ggctcgaagc ctttcaacaa gaggaggatg     60
tgagtagtga taagctgagt acaatggatc agtgttcatt gttgataagt tctcttcctg    120
tagtttcact agagcaggac gaagatcttt tgcatagtca agcttcacag caaaagcatc    180
agcctgaaac tcaaacgctc gactaacgag gttcaggcca aagcttacta gatgttgcag    240
tggtattaca gtgtgctgaa atatgatcaa accaatgaga acaggctgtg tatcaaatcc    300
gaaactcctg aagagatcag tggagtttct gagaagagtg tatcctccaa attgtaagaa    360
ggcaaggatt tgaactgcaa tgaacgagta tgtagtgtga ttcagtttcc aatgtccaag    420
ctcgtgtgca ataaccgcca caatttcatc ctcattcttg cactgctgaa tcaacgtatc    480
ataaagaaca atcctttttgt tcttaaagaa accatacatg taagcattgc tatggcttga   540
ccttgtagat ccatcgacaa caaacagctt cttcaaagga aactttaggg aagaagcaag    600
tttctcaatc ttctcccgga ggtctccatc tggaagagga gtgaatttgt tgaagagcgg    660
tgctatcaag accgggtata tagtcatcat cactagagac aggataaaca tgaatgccca    720
cagatagatg gcaagataag gacctccttt ctggactatg aaaattatcg cagcaacaat    780
gggtgggcct agtatgacag agaggaatgt tcctttgatc atgtccctaa tgaacatcca    840
tattgtttgt ttgttgaacc catgccgaga ctcgatcacg aaagttgagt acaaagaaaa    900
tggcaaatca gtgatctgtg accatgtcat aacaccagcc aagaatgaaa gagtatgcag    960
tatttcattc tccggatcaa ggcccaacct cggtaaaaca gctccagaca tcttccaaaa   1020
ccaaggcaag atcccaaaga acaaaattgc agagtccata agtatagtta caaactcatg   1080
aacaaagtga aaatagcttt tgtcaagact gtatgctcgt gatttctcaa acttctcttg   1140
gctaattaca ccaaccaagg ttttcgggag agttggaagc ttgagagcag tgagttgcct   1200
cagatccaaa tacgtctcaa aaatgtacat cactatcata aaacccacga cggtttccat   1260
gaaaggaatc gccat                                                    1275
```

-continued

<210> SEQ ID NO 116
<211> LENGTH: 1275
<212> TYPE: DNA
<213> ORGANISM: Arabidopsis thaliana

<400> SEQUENCE: 116
atggcgattc ctttcatgga aaccgtcgtg ggttttatga tagtgatgta catttttgag 60
acgtatttgg atctgaggca actcactgct ctcaagcttc caactctccc gaaaaccttg 120
gttggtgtaa ttagccaaga gaagtttgag aaatcacgag catacagtct tgacaaaagc 180
tattttcact ttgttcatga gtttgtaact atacttatgg actctgcaat tttgttcttt 240
gggatcttgc cttggttttg gaagatgtct ggagctgttt taccgaggtt gggccttgat 300
ccagagaatg aaatactgca tactctttca ttcttggctg gtgttatgac atggtcacac 360
atcactgatt tgccattttc tttgtactca actttcgtga tcgagtctcg gcatgggttc 420
aacaaacaaa caatatggat gttcattagg gacatgatca aggaacatt cctctctgtc 480 atactaggcc cacccattgt tgccgcgata attttcatag tccagaaagg aggtccttat 540
cttgccatct atctgtgggc attcatgttt atcctgtctc tagtgatgat gactatatac 600
ccggtcttga tagcaccgct cttcaacaag ttcactcctc ttccagatgg agacctccgg 660
gagaagattg agaaacttgc ttcttctcta aagtttcctt tgaagaagct gtttgttgtc 720
gatggatcta caaggtcaag ccatagcaat gcttacatgt atggtttctt taagaacaaa 780
aggattgttc tttatgatac gttgattcag cagtgcaaga atgaggatga aattgtggcg 840
gttattgcac acgagcttgg acattggaaa ctgaatcaca ctacatactc gttcattgca 900
gttcaaatcc ttgccttctt acaatttgga ggatacactc ttgtcagaaa ctccactgat 960
ctcttcagga gtttcggatt tgatacacag cctgttctca ttggtttgat catatttcag 1020
cacactgtaa taccactgca acatccagta agctttggcc tcaaccttgt tagtcgagcg 1080
tttgagtttc aggctgatgc ttttgctgtg aagcttggct atgcaaaaga tcttcgtcct 1140
actctagtga aactacagga agagaactta tcagcaatga atactgatcc attgtactca 1200
gcttatcact actcacatcc tcctcttgtt gaaaggcttc gagccattga tggagaagac 1260
aagaagacag attaa 1275

<210> SEQ ID NO 117
<211> LENGTH: 424
<212> TYPE: PRT
<213> ORGANISM: Arabidopsis thaliana

<400> SEQUENCE: 117

Met Ala Ile Pro Phe Met Glu Thr Val Val Gly Phe Met Ile Val Met
1 5 10 15

Tyr Ile Phe Glu Thr Tyr Leu Asp Leu Arg Gln Leu Thr Ala Leu Lys
20 25 30

Leu Pro Thr Leu Pro Lys Thr Leu Val Gly Val Ile Ser Gln Glu Lys
35 40 45

Phe Glu Lys Ser Arg Ala Tyr Ser Leu Asp Lys Ser Tyr Phe His Phe
50 55 60

Val His Glu Phe Val Thr Ile Leu Met Asp Ser Ala Ile Leu Phe Phe
65 70 75 80

Gly Ile Leu Pro Trp Phe Trp Lys Met Ser Gly Ala Val Leu Pro Arg
85 90 95

Leu Gly Leu Asp Pro Glu Asn Glu Ile Leu His Thr Leu Ser Phe Leu
100 105 110

-continued

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Pro Val Ser Phe
            340                 345                 350

Gly Leu Asn Leu Val Ser Arg Ala Phe Glu Phe Gln Ala Asp Ala Phe
        355                 360                 365

Ala Val Lys Leu Gly Tyr Ala Lys Asp Leu Arg Pro Thr Leu Val Lys
    370                 375                 380

Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420

<210> SEQ ID NO 118
<211> LENGTH: 1275
<212> TYPE: DNA
<213> ORGANISM: Arabidopsis thaliana

<400> SEQUENCE: 118
atggcgattc ctttcatgga aaccgtcgtg ggttttatga tagtgatgta catttttgag      60
acgtatttgg atctgaggca actcactgct ctcaagcttc caactctccc gaaaaccttg     120
gttggtgtaa ttagccaaga gaagtttgag aaatcacgag catacagtct tgacaaaagc     180
tattttcact ttgttcatga gtttgtaact atacttatgg actctgcaat tttgttcttt     240
gggatcttgc cttggttttg gaagatgtct ggagcagttt taccgaggtt gggccttgat     300

-continued

```
ccagagaatg aaatactgca tactctttca ttcttggctg gtgttatgac atggtcacag    360

atcactgatt tgccattttc tttgtactca actttcgtga tcgagtctcg gcatgggttc    420

aacaaacaaa caatatggat gttcattagg gacatgatca aaggaacatt cctctctgtc    480

atactaggcc cacccattgt tgctgcgata attttcatag tccagaaagg aggtccttat    540

cttgccatct atctgtgggc attcatgttt atcctgtctc tagtgatgat gactatatac    600

ccggtcttga tagcaccgct cttcaacaag ttcactcctc ttccagatgg agacctccgg    660

gagaagattg agaaacttgc ttcttctcta aagtttcctt tgaagaagct gtttgttgtc    720

gatggatcta caaggtcaag ccatagcaat gcttacatgt atggtttctt taagaacaaa    780

aggattgttc tttatgatac gttgattcag cagtgcaaga atgaggatga aattgtggcg    840

gttattgcac acgagcttgg acattggaaa ctgaatcaca ctacatactc gttcattgca    900

gttcaaatcc ttgccttctt acaatttgga ggatacactc ttgtcagaaa ctccactgat    960

ctcttcagga gtttcggatt tgatacacag cctgttctca ttggtttgat catatttcag   1020

cacactgtaa taccactgca acatctagta agctttggcc tgaacctcgt tagtcgagcg   1080

tttgagtttc aggctgatgc ttttgctgtg aagcttggct atgcaaaaga tcttcgtcct   1140

gctctagtga aactacagga agagaactta tcagcaatga aaactgatct attgtactca   1200

gcttatcact actcacatcc tcctcttgtt gaaaggcttc gagccattga tggagaagac   1260

aagaagacag attaa                                                    1275
```

<210> SEQ ID NO 119
<211> LENGTH: 424
<212> TYPE: PRT
<213> ORGANISM: Arabidopsis thaliana

<400> SEQUENCE: 119

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Val Gly Val Ile Ser Gln Glu Lys
        35                  40                  45

Phe Glu Lys Ser Arg Ala Tyr Ser Leu Asp Lys Ser Tyr Phe His Phe
    50                  55                  60

Val His Glu Phe Val Thr Ile Leu Met Asp Ser Ala Ile Leu Phe Phe
65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
```

-continued

```
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
        355                 360                 365

Ala Val Lys Leu Gly Tyr Ala Lys Asp Leu Arg Pro Ala Leu Val Lys
    370                 375                 380

Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

<210> SEQ ID NO 120
<211> LENGTH: 1249
<212> TYPE: DNA
<213> ORGANISM: Zea mays

<400> SEQUENCE: 120

```
acgaggctga gtgctgagaa tgagataata cacacccttg ctttcttagc tggttccatg     60

gtttggtcgc agattacaga cttgccgttc tctctctatt caacttttgt tatagaggct    120

cgacatggtt ttaacaagca aactatatgg ctcttcatta gggatatgat caaaggaatt    180

ttactatcca tgatattggg gccaccaatc gtggctgcta tcatctacat agtacagatt    240

ggaggacctt acctggctat atatctctgg ggttttatgt ttgtattagc tctactgatg    300

atgacaatat accccattgt gatagctcct ctgttcaaca agttcactcc tcttcctgaa    360

ggagtcctca gggaaaaaat agagaagctg gcagcttccc tcaagtttcc tttgaaaaag    420

cttttcgtgg tagatgggtc taccagatca agccacagta atgcctacat gtatggtttt    480

ttcaagaaca agcgcatagt actctatgac acattgattc agcagtgtag caatgaggat    540

gagatagttt ctgttatagc acatgaactt ggacactgga aactcaatca tactgtctat    600

tcctttgtag ctgtccagct gcttatgttt cttcaatttg gaggatatac tctagtaagg    660

agctccaaag atctatttgg aagttttggc ttcaaggacc agccagtaat aattggattg    720

atcattttcc cgcacaccat aatacccatc caacaccttc tgagctttcg cctgaacctt    780

gtcagcagag catttgaatt tcaggctgat gcctttgcca agaaccttgg atatgcccct    840
```

-continued

```
cagctccgag cagcccttgt taaactacag gaggagaact tgtctgcgat gaacaccgat    900

ccttggtatt cggcatatca ctactcccac ccaccactcg tcgagaggct gcaagctttg    960

gaagattcag acgacaaaaa agaagattag tcgatccttg tatgaggttt acatatggat   1020

ttttccctgc cacatgcaca ccgattcagt gcttggatgg tgagggtttt gacataggag   1080

tgttgtcaaa gctttagagt gcatctttcg gtcaggtgca acagcctttc ggtcattgag   1140

acatataagc gaattagcta ttaaaaaaaa cagaactgtt gcatcaaaaa aaaaaaaaaa   1200

aaagaaacaa aaaaaaaaaa aaaaaaaaaa aagaaaaaaa aaaaaaaaa               1249
```

<210> SEQ ID NO 121
<211> LENGTH: 329
<212> TYPE: PRT
<213> ORGANISM: Zea mays

<400> SEQUENCE: 121

```
Thr Arg Leu Ser Ala Glu Asn Glu Ile Ile His Thr Leu Ala Phe Leu
1               5                   10                  15

Ala Gly Ser Met Val Trp Ser Gln Ile Thr Asp Leu Pro Phe Ser Leu
            20                  25                  30

Tyr Ser Thr Phe Val Ile Glu Ala Arg His Gly Phe Asn Lys Gln Thr
        35                  40                  45

Ile Trp Leu Phe Ile Arg Asp Met Ile Lys Gly Ile Leu Leu Ser Met
    50                  55                  60

Ile Leu Gly Pro Pro Ile Val Ala Ala Ile Ile Tyr Ile Val Gln Ile
65                  70                  75                  80

Gly Gly Pro Tyr Leu Ala Ile Tyr Leu Trp Gly Phe Met Phe Val Leu
                85                  90                  95

Ala Leu Leu Met Met Thr Ile Tyr Pro Ile Val Ile Ala Pro Leu Phe
            100                 105                 110

Asn Lys Phe Thr Pro Leu Pro Glu Gly Val Leu Arg Glu Lys Ile Glu
        115                 120                 125

Lys Leu Ala Ala Ser Leu Lys Phe Pro Leu Lys Lys Leu Phe Val Val
    130                 135                 140

Asp Gly Ser Thr Arg Ser Ser His Ser Asn Ala Tyr Met Tyr Gly Phe
145                 150                 155                 160

Phe Lys Asn Lys Arg Ile Val Leu Tyr Asp Thr Leu Ile Gln Gln Cys
                165                 170                 175

Ser Asn Glu Asp Glu Ile Val Ser Val Ile Ala His Glu Leu Gly His
            180                 185                 190

Trp Lys Leu Asn His Thr Val Tyr Ser Phe Val Ala Val Gln Leu Leu
        195                 200                 205

Met Phe Leu Gln Phe Gly Gly Tyr Thr Leu Val Arg Ser Ser Lys Asp
    210                 215                 220

Leu Phe Gly Ser Phe Gly Phe Lys Asp Gln Pro Val Ile Ile Gly Leu
225                 230                 235                 240

Ile Ile Phe Pro His Thr Ile Ile Pro Ile Gln His Leu Leu Ser Phe
                245                 250                 255

Arg Leu Asn Leu Val Ser Arg Ala Phe Glu Phe Gln Ala Asp Ala Phe
            260                 265                 270

Ala Lys Asn Leu Gly Tyr Ala Pro Gln Leu Arg Ala Ala Leu Val Lys
        275                 280                 285

Leu Gln Glu Glu Asn Leu Ser Ala Met Asn Thr Asp Pro Trp Tyr Ser
    290                 295                 300
```

-continued

Ala Tyr His Tyr Ser His Pro Pro Leu Val Glu Arg Leu Gln Ala Leu
305 310 315 320

Glu Asp Ser Asp Asp Lys Lys Glu Asp
325

<210> SEQ ID NO 122
<211> LENGTH: 1434
<212> TYPE: DNA
<213> ORGANISM: Glycine max

<400> SEQUENCE: 122
ctaatacgac tcactatagg gcaagcagtg gtaacaacgc agagtacgcg gggggagacg 60
catggttctg aactaattgt tataaataat acctaaaatt ttgagttgtc ctaaacattg 120
gggtttaaac aaatccaatc tctcaatata aaacccaatg atctcaccct cactccgttt 180
ctgatttctc actcttcgtt tctcgttcgg ttcatcagcg tgtgtctcag ccatggcgtt 240
tccctacatg gaagccgttg tcggatttat gatattaatg tacatttttg aaacttactt 300
ggatgtgcga caacataggg ccctcaaact tcctactctt ccaaagactt tagaaggtgt 360
tatcagccaa gagaaatttg agaaatctag agcctatagt cttgataaaa gccacttcca 420
ttttgttcac gagtttgtga caatagtgac agactctaca attttgtact ttggggtatt 480
gccctggttt tggaagaaat caggagattt tatgacaata gctggtttca atgctgagaa 540
tgaaatactg catacccttg ccttcttagc agggctgatg atttggtcac agataacaga 600
tttgcccttt tctctgtact caacttttgt gattgaggcc cgtcatggtt ttaataagca 660
aacaccatgg ttattcttta gggacatgct taaaggaatt ttcctttccg taataattgg 720
tccacctatt gtggctgcaa tcattgtaat agtacagaaa ggaggtccat acttggccat 780
ctatctttgg gtttttacgt ttggtctttc tattgtgatg atgacccttt atccagtact 840
aatagctcca ctcttcaata agttcactcc acttccagat ggtcaactca gggagaaaat 900
cgagaaactt gcttcctccc tcaactatcc gttaaagaaa ctatttgttg tcgatggatc 960
cacaagatca agtcacagca atgcctatat gtatggattc ttcaagaaca agaggattgt 1020
cctttatgac acattaattc aacagtgcaa agacgatgag gaaattgttg ctgttattgc 1080
ccatgagttg ggacactgga agctcaacca tactgtgtac acatttgttg ctatgcagat 1140
tcttacactt ctacaatttg gaggatatac actagtgcga aattcagctg atctgtatcg 1200
aagctttggg tttgatacgc agccagtcct cattgggctc atcatatttc agcatactgt 1260
aatcccactt cagcaattgg tcagctttgg tctgaaccta gtcagccgat catttgaatt 1320
tcaggctgat ggctttgcca agaagcttgg atatgcatct ggattacgcg gtggtcttgt 1380
gaaactacag gaggagaatc tgtcagctat gaatacagat ccttgctcgt gccg 1434

<210> SEQ ID NO 123
<211> LENGTH: 400
<212> TYPE: PRT
<213> ORGANISM: Glycine max

<400> SEQUENCE: 123

Met Ala Phe Pro Tyr Met Glu Ala Val Val Gly Phe Met Ile Leu Met
1 5 10 15

Tyr Ile Phe Glu Thr Tyr Leu Asp Val Arg Gln His Arg Ala Leu Lys
20 25 30

Leu Pro Thr Leu Pro Lys Thr Leu Glu Gly Val Ile Ser Gln Glu Lys
35 40 45

-continued

```
Phe Glu Lys Ser Arg Ala Tyr Ser Leu Asp Lys Ser His Phe His Phe
     50                  55                  60

Val His Glu Phe Val Thr Ile Val Thr Asp Ser Thr Ile Leu Tyr Phe
 65                  70                  75                  80

Gly Val Leu Pro Trp Phe Trp Lys Lys Ser Gly Asp Phe Met Thr Ile
                 85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Ile Val Ile Val Gln Lys
                165                 170                 175

Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
        195                 200                 205

Asn Lys Phe Thr Pro Leu Pro Asp Gly Gln Leu Arg Glu Lys Ile Glu
    210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asp Asp Glu Glu Ile Val Ala Val Ile Ala His Glu Leu Gly His
        275                 280                 285

Trp Lys Leu Asn His Thr Val Tyr Thr Phe Val Ala Met Gln Ile Leu
    290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
                325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
        355                 360                 365

Ala Lys Lys Leu Gly Tyr Ala Ser Gly Leu Arg Gly Gly Leu Val Lys
    370                 375                 380

Leu Gln Glu Glu Asn Leu Ser Ala Met Asn Thr Asp Pro Cys Ser Cys
385                 390                 395                 400
```

<210> SEQ ID NO 124
<211> LENGTH: 1275
<212> TYPE: DNA
<213> ORGANISM: Arabidopsis thaliana

<400> SEQUENCE: 124

```
atggcgattc ctttcatgga aaccgtcgtg ggttttatga tagtgatgta catttttgag      60

acgtatttgg atctgaggca actcactgct ctcaagcttc caactctccc gaaaaccttg     120
```

-continued

```
gttggtgtaa ttagccaaga gaagtttgag aaatcacgag catacagtct tgacaaaagc    180
tattttcact ttgttcatga gtttgtaact atacttatgg actctgcaat tttgttcttt    240
gggatcttgc cttggttttg gaagatgtct ggagctgttt taccgaggtt gggccttgat    300
ccagagaatg aaatactgca tactctttca ttcttggctg gtgttatgac atggtcacag    360
atcactgatt tgccattttc tttgtactca actttcgtga tcgagtctcg gcatgggttc    420
aacaaacaaa caatatggat gttcattagg gacatgatca aaggaacatt cctctctgtc    480
atactaggcc cacccattgt tgctgcgata attttcatag tccagaaagg aggtccttat    540
cttgccatct atctgtgggc attcatgttt atcctgtctc tagtgatgat gactatatac    600
ccggtcttga tagcaccgct cttcaacaag ttcactcctc ttccagatgg agacctccgg    660
gagaagattg agaaacttgc ttcttctcta aagtttcctt tgaagaagct gtttgttgtc    720
gatggatcta caaggtcaag ccatagcaat gcttacatgt atggtttctt taagaacaaa    780
aggattgttc tttatgatac gttgattcag cagtgcaaga atgaggatga aattgtggcg    840
gttattgcac acgagcttgg acattggaaa ctgaatcaca ctacatactc gttcattgca    900
gttcaaatcc ttgccttctt acaatttgga ggatacactc ttgtcagaaa ctccactgat    960
ctcttcagga gtttcggatt tgatacacag cctgttctca ttggtttgat catatttcag   1020
cacactgtaa taccactgca acatctagta agctttggcc tgaacctcgt tagtcgagcg   1080
tttgagtttc aggctgatgc ttttgccgtg aagcttggct atgcaaaaga tcttcgtcct   1140
gctctagtga aactacagga agagaactta tcagcaatga acactgatcc attgcactca   1200
gcttatcact actcacatcc tcctcttgtt gaaaggcttc gagccattga tggagaagac   1260
aagaagacag attaa                                                    1275
```

```
<210> SEQ ID NO 125
<211> LENGTH: 424
<212> TYPE: PRT
<213> ORGANISM: Arabidopsis thaliana

<400> SEQUENCE: 125

Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Val Gly Val Ile Ser Gln Glu Lys
         35                  40                  45

Phe Glu Lys Ser Arg Ala Tyr Ser Leu Asp Lys Ser Tyr Phe His Phe
     50                  55                  60

Val His Glu Phe Val Thr Ile Leu Met Asp Ser Ala Ile Leu Phe Phe
 65                  70                  75                  80

Gly Ile Leu Pro Trp Phe Trp Lys Met Ser Gly Ala Val Leu Pro Arg
                 85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
```

-continued

```
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
        355                 360                 365

Ala Val Lys Leu Gly Tyr Ala Lys Asp Leu Arg Pro Ala Leu Val Lys
    370                 375                 380

Leu Gln Glu Glu Asn Leu Ser Ala Met Asn Thr Asp Pro Leu His Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

<210> SEQ ID NO 126
<211> LENGTH: 1380
<212> TYPE: DNA
<213> ORGANISM: Arabidopsis thaliana

<400> SEQUENCE: 126

```
atggcgattc ctttcatgga aaccgtcgtg ggttttatga tagtgatgta catttttgag     60

acgtatttgg atctgaggca actcactgct ctcaagcttc caactctccc gaaaaccttg    120

gttggtgtaa ttagccaaga gaagtttgag aaatcacgag catacaggga tatcatcact    180

gagaacttta atatatgcag ctattttcac tttgttcatg agtttgtaac tatacttatg    240

gactctgcaa ttttgttctt tgggatcttg ccttggtttt ggaagatgtc tggagctgtt    300

ttaccgaggt tgggccttga tccagagaat gaaatactgc atactctttc attcttggct    360

ggtgttatga catggtcaca gatcactgat ttgccatttt ctttgtactc aactttcgtg    420

atcgagtctc ggcatgggtt caacaaacaa acaatatgga tgttcattag ggacatgatc    480

aaaggaacat tcctctctgt catactaggc ccacccattg ttgctgcgat aattttcata    540

gtccagaaag gaggtcctta tcttgccatc tatctgtggg cattcatgtt tatcctgtct    600

ctagtgatga tgactatata cccggtcttg atagcaccgc tcttcaacaa gttcactcct    660
```

-continued

```
cttccagatg gagacctccg ggagaagatt gagaaacttg cttcttctct aaagtttcct    720
ttgaagaagc tgtttgttgt cgatggatct acaaggtcaa gccatagcaa tgcttacatg    780
tatggtttct ttaagaacaa aaggattgtt ctttatgata cgttgattca gcagtgcaag    840
aatgaggatg aaattgtggc ggttattgca cacgagcttg gacattggaa actgaatcac    900
actacatact cgttcattgc agttcaaatc cttgccttct tacaatttgg aggatacact    960
cttgtcagaa actccactga tctcttcagg agtttcggat ttgatacaca gcctgttctc   1020
attggtttga tcatatttca gcacactgta ataccactgc aacatctagt aagctttggc   1080
ctgaacctcg ttagtcgagc gtttgagttt caggctgatg cttttgctgt gaagcttggc   1140
tatgcaaaag atcttcgtcc tgctctagtg aaactacagg tcagagaaga taacaacaga   1200
acacaaactg ttacctcaat ttgtgtcaca cacttaaatg gattttttgt tgggattttg   1260
caggaagaga acttatcagc aatgaacact gatccattgt actcagctta tcactactca   1320
catcctcctc ttgttgaaag gcttcgagcc attgatggag aagacaagaa gacagattaa   1380
```

<210> SEQ ID NO 127
<211> LENGTH: 459
<212> TYPE: PRT
<213> ORGANISM: Arabidopsis thaliana

<400> SEQUENCE: 127

```
Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Val Gly Val Ile Ser Gln Glu Lys
         35                  40                  45

Phe Glu Lys Ser Arg Ala Tyr Arg Asp Ile Ile Thr Glu Asn Phe Asn
     50                  55                  60

Ile Cys Ser Tyr Phe His Phe Val His Glu Phe Val Thr Ile Leu Met
 65                  70                  75                  80

Asp Ser Ala Ile Leu Phe Phe Gly Ile Leu Pro Trp Phe Trp Lys Met
                 85                  90                  95

Ser Gly Ala Val Leu Pro Arg Leu Gly Leu Asp Pro Glu Asn Glu Ile
            100                 105                 110

Leu His Thr Leu Ser Phe Leu Ala Gly Val Met Thr Trp Ser Gln Ile
        115                 120                 125

Thr Asp Leu Pro Phe Ser Leu Tyr Ser Thr Phe Val Ile Glu Ser Arg
    130                 135                 140

His Gly Phe Asn Lys Gln Thr Ile Trp Met Phe Ile Arg Asp Met Ile
145                 150                 155                 160

Lys Gly Thr Phe Leu Ser Val Ile Leu Gly Pro Pro Ile Val Ala Ala
                165                 170                 175

Ile Ile Phe Ile Val Gln Lys Gly Gly Pro Tyr Leu Ala Ile Tyr Leu
            180                 185                 190

Trp Ala Phe Met Phe Ile Leu Ser Leu Val Met Met Thr Ile Tyr Pro
        195                 200                 205

Val Leu Ile Ala Pro Leu Phe Asn Lys Phe Thr Pro Leu Pro Asp Gly
    210                 215                 220

Asp Leu Arg Glu Lys Ile Glu Lys Leu Ala Ser Ser Leu Lys Phe Pro
225                 230                 235                 240

Leu Lys Lys Leu Phe Val Val Asp Gly Ser Thr Arg Ser Ser His Ser
```

-continued

```
                245                 250                 255

Asn Ala Tyr Met Tyr Gly Phe Phe Lys Asn Lys Arg Ile Val Leu Tyr
            260                 265                 270

Asp Thr Leu Ile Gln Gln Cys Lys Asn Glu Asp Glu Ile Val Ala Val
        275                 280                 285

Ile Ala His Glu Leu Gly His Trp Lys Leu Asn His Thr Thr Tyr Ser
    290                 295                 300

Phe Ile Ala Val Gln Ile Leu Ala Phe Leu Gln Phe Gly Gly Tyr Thr
305                 310                 315                 320

Leu Val Arg Asn Ser Thr Asp Leu Phe Arg Ser Phe Gly Phe Asp Thr
                325                 330                 335

Gln Pro Val Leu Ile Gly Leu Ile Ile Phe Gln His Thr Val Ile Pro
            340                 345                 350

Leu Gln His Leu Val Ser Phe Gly Leu Asn Leu Val Ser Arg Ala Phe
        355                 360                 365

Glu Phe Gln Ala Asp Ala Phe Ala Val Lys Leu Gly Tyr Ala Lys Asp
    370                 375                 380

Leu Arg Pro Ala Leu Val Lys Leu Gln Val Arg Glu Asp Asn Asn Arg
385                 390                 395                 400

Thr Gln Thr Val Thr Ser Ile Cys Val Thr His Leu Asn Gly Phe Phe
                405                 410                 415

Val Gly Ile Leu Gln Glu Glu Asn Leu Ser Ala Met Asn Thr Asp Pro
            420                 425                 430

Leu Tyr Ser Ala Tyr His Tyr Ser His Pro Pro Leu Val Glu Arg Leu
        435                 440                 445

Arg Ala Ile Asp Gly Glu Asp Lys Lys Thr Asp
    450                 455
```

```
<210> SEQ ID NO 128
<211> LENGTH: 3098
<212> TYPE: DNA
<213> ORGANISM: Arabidopsis thaliana

<400> SEQUENCE: 128

atggcgattc ctttcatgga aaccgtcgtg ggtaagcttc aaaacctttt tctgagacat      60

tttactatcc tgtttcactc atcgtatttc gtttttgttt gggttttgct ttctgtgttg     120

tgtgtgttga gattccatga ctcgtttgtt tcatatacca tcgtctctgc ttctcgtttc     180

taaattttgt tcttttctaa tagtgcgtac cttgatctga ggttttatta ctcctactag     240

tttcttgtct tactcgtgcg tttgatttga tttgagctta tgtgatttca tcatctcttc     300

ctcggtttta gaatgtacgg agcttctctg ttaaccaaaa tctaggattt gggaagaaaa     360

gtcggagtct tttttttcct cattcccgat tggaaattga gaatcttgaa atttttcttt     420

gttcaagtca tacagcttga ggttttgggt tttcttgtca gggtattatt atgttcgtga     480

ctgcaactag agttttctgg agttttttga aatgggtttt gtgttgtgga accgtatgtg     540

aatgttgcat caaaactctt tcagtgctcc aatgtttcca tcagtagtca gcacaagaga     600

tctttttata tctggttgat caaaaaagta gatgatgtta ttgaattttc agtgatggag     660

tatctgttgt tgtggcattt agagtagatt cgtatttcat cttctgtttt attctttttc     720

ttacaggttt tatgatagtg atgtacattt ttgagacgta tttggatctg aggcaactca     780

ctgctctcaa gcttccaact ctcccgaaaa ccttggttgg tgtaattagc caagagaagt     840

ttgagaaatc acgagcatac agtcttgaca aaaggtttcg tcttgatcat atttatatca     900
```

-continued

```
ttttagtttt ttataattgc caggggatat catcactgag aactttaata tatgcagcta    960
ttttcacttt gttcatgagt ttgtaactat acttatggac tctgcaattt tgttctttgg   1020
gatcttgcct tggttttgga aggtacatat ctggtttcgg tatacagtat ctcattttga   1080
atatagagtt gttacattac aattgtaaag ttttcatttt taccttagat gtctggagct   1140
gttttaccga ggttgggcct tgatccagag aatgaaatac tgcatactct ttcattcttg   1200
gctggtgtta tgacatggtc acaggtgttc caaataaacc ccttcatata gtcctatacg   1260
tttagcatca aaatatctat tttcttaaga taataatatt tcttttatat tctgatgcag   1320
atcactgatt tgccattttc tttgtactca actttcgtga tcgagtctcg gcatgggttc   1380
aacaaagtat gtcgtatttc caacactacc ttgtgactta cgttttttta tcagagatgt   1440
ggattaaatt tgcttctaaa ttctgttgac agcaaacaat atggatgttc attagggaca   1500
tgatcaaagg aacattcctc tctgtcatac taggcccacc cattgttgct gcgataattt   1560
tcatagtcca ggtttgatga ttctggattc atcttatttc tgagtttttc acatggatga   1620
ctattctcca ttgagtgtga gcttcaaagt ttttagtttt cgtgttaaaa atttaaaatt   1680
tgcttctctg agcatgaagt ttctatcttt ttccagaaag gaggtcctta tcttgccatc   1740
tatctgtggg cattcatgtt tatcctgtct ctagtgatga tgactatata cccggtcttg   1800
atagcaccgc tcttcaacaa gttcactcct gtgtgtattt ctgtcatggc cattttacaa   1860
ttcactgctt gtttgcatat gttgttacca gacaatataa tctcccgctt ttttatggct   1920
atagcttcca gatggagacc tccgggagaa gattgagaaa cttgcttctt ctctaaagtt   1980
tcctttgaag aagctgtttg ttgtcgatgg atctacaagg tcaagccata gcaatgtgag   2040
aagcttgaga tctcttccta cctactttac tctagtttac cattagaagc ttacgtatct   2100
tgttacatca tacaggctta catgtatggt ttctttaaga acaaaaggat tgttctttat   2160
gatacgttga ttcagcaggt actgtgactc ttgatgcttc aaacgagcta tactcacatt   2220
tctgtttctg gttctgaaac ataacataat cttctattgt gcagtgcaag aatgaggatg   2280
aaattgtggc ggttattgca cacgagcttg gacattggaa actgaatcac actacatact   2340
cgttcattgc agttcaagtg aggctcaacc gacagttcaa aaacttactc acatctacat   2400
ttcacttaag aaatcatgtc ttatgaccct ctctcaatgt tttgcttgca gatccttgcc   2460
ttcttacaat ttggaggata cactcttgtc agaaactcca ctgatctctt caggagtttc   2520
ggatttgata cacagcctgt tctcattggt ttgatcatat ttcaggtttg ttatttttgc   2580
cttttgacac taatctaatg aatcaaggat ggattaagaa aaaaaaactc taaacctttg   2640
gttatatctc ctgtctgatt atcacagcac actgtaatac cactgcaaca tctagtaagc   2700
tttggcctga acctcgttag tcgagcgttt gagtttcagg taccatctta caatccctca   2760
agatccaacc atagtttctt tattgcaatg gcagcctcat ctactaatct gagttaacgt   2820
tcctttgca ggctgatgct tttgctgtga agcttggcta tgcaaaagat cttcgtcctg   2880
ctctagtgaa actacaggtc agagaagata acaacagaac acaaactgtt acctcaattt   2940
gtgtcacaca cttaaatgga ttttttgttg ggattttgca ggaagagaac ttatcagcaa   3000
tgaacactga tccattgtac tcagcttatc actactcaca tcctcctctt gttgaaaggc   3060
ttcgagccat tgatggagaa gacaagaaga cagattaa                           3098
```

<210> SEQ ID NO 129
<211> LENGTH: 316
<212> TYPE: PRT
<213> ORGANISM: Arabidopsis thaliana -continued

<400> SEQUENCE: 129

```
Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Ile Thr Asp Leu Pro Phe Ser Leu
         35                  40                  45

Tyr Ser Thr Phe Val Ile Glu Ser Arg His Gly Phe Asn Lys Gln Thr
     50                  55                  60

Ile Trp Met Phe Ile Arg Asp Met Ile Lys Gly Thr Phe Leu Ser Val
 65                  70                  75                  80

Ile Leu Gly Pro Pro Ile Val Ala Ala Ile Ile Phe Ile Val Gln Lys
                 85                  90                  95

Gly Gly Pro Tyr Leu Ala Ile Tyr Leu Trp Ala Phe Met Phe Ile Leu
            100                 105                 110

Ser Leu Val Met Met Thr Ile Tyr Pro Val Leu Ile Ala Pro Leu Phe
        115                 120                 125

Asn Lys Phe Thr Pro Leu Pro Asp Gly Asp Leu Arg Glu Lys Ile Glu
    130                 135                 140

Lys Leu Ala Ser Ser Leu Lys Phe Pro Leu Lys Lys Leu Phe Val Val
145                 150                 155                 160

Asp Gly Ser Thr Arg Ser Ser His Ser Asn Ala Tyr Met Tyr Gly Phe
                165                 170                 175

Phe Lys Asn Lys Arg Ile Val Leu Tyr Asp Thr Leu Ile Gln Gln Cys
            180                 185                 190

Lys Asn Glu Asp Glu Ile Val Ala Val Ile Ala His Glu Leu Gly His
        195                 200                 205

Trp Lys Leu Asn His Thr Thr Tyr Ser Phe Ile Ala Val Gln His Thr
    210                 215                 220

Val Ile Pro Leu Gln His Leu Val Ser Phe Gly Leu Asn Leu Val Ser
225                 230                 235                 240

Arg Ala Phe Glu Phe Gln Ala Asp Ala Phe Ala Val Lys Leu Gly Tyr
                245                 250                 255

Ala Lys Asp Leu Arg Pro Ala Leu Val Lys Leu Gln Val Arg Glu Asp
            260                 265                 270

Asn Asn Arg Thr Gln Thr Glu Glu Asn Leu Ser Ala Met Asn Thr Asp
        275                 280                 285

Pro Leu Tyr Ser Ala Tyr His Tyr Ser His Pro Pro Leu Val Glu Arg
    290                 295                 300

Leu Arg Ala Ile Asp Gly Glu Asp Lys Lys Thr Asp
305                 310                 315
```

<210> SEQ ID NO 130
<211> LENGTH: 5544
<212> TYPE: DNA
<213> ORGANISM: Artificial Sequence
<220> FEATURE:
<223> OTHER INFORMATION: Description of Artificial Sequence: Plasmid
pBI121-antisense-AtCPP

<400> SEQUENCE: 130

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180
```

-continued

```
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
```

-continued

```
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccttaatct gtcttcttgt cttctccatc   3360
agtggctcga agcctttcaa caagaggagg atgtgagtag tgataagctg agtacaatgg   3420
atcagtgttc attgttgata agttctcttc ctgtagtttc actagagcag gacgaagatc   3480
ttttgcatag tcaagcttca cagcaaaagc atcagcctga aactcaaacg ctcgactaac   3540
gaggttcagg ccaaagctta ctagatgttg cagtggtatt acagtgtgct gaaatatgat   3600
caaaccaatg agaacaggct gtgtatcaaa tccgaaactc ctgaagagat cagtggagtt   3660
tctgagaaga gtgtatcctc caaattgtaa gaaggcaagg atttgaactg caatgaacga   3720
gtatgtagtg tgattcagtt tccaatgtcc aagctcgtgt gcaataaccg ccacaatttc   3780
atcctcattc ttgcactgct gaatcaacgt atcataaaga acaatccttt tgttcttaaa   3840
gaaaccatac atgtaagcat tgctatggct tgaccttgta gatccatcga caacaaacag   3900
cttcttcaaa ggaaacttta gggaagaagc aagtttctca atcttctccc ggaggtctcc   3960
atctggaaga ggagtgaatt tgttgaagag cggtgctatc aagaccgggt atatagtcat   4020
catcactaga gacaggataa acatgaatgc ccacagatag atggcaagat aaggacctcc   4080
tttctggact atgaaaatta tcgcagcaac aatgggtggg cctagtatga cagagaggaa   4140
tgttcctttg atcatgtccc taatgaacat ccatattgtt tgtttgttga acccatgccg   4200
agactcgatc acgaaagttg agtacaaaga aaatggcaaa tcagtgatct gtgaccatgt   4260
cataacacca gccaagaatg aaagagtatg cagtatttca ttctccggat caaggcccaa   4320
cctcggtaaa acagctccag acatcttcca aaaccaaggc aagatcccaa agaacaaaat   4380
tgcagagtcc ataagtatag ttacaaactc atgaacaaag tgaaaatagc ttttgtcaag   4440
actgtatgct cgtgatttct caaacttctc ttggctaatt acaccaacca aggttttcgg   4500
gagagttgga agcttgagag cagtgagttg cctcagatcc aaatacgtct caaaaatgta   4560
catcactatc ataaaaccca cgacggtttc catgaaagga atcgccatcc cctcgaattt   4620
ccccgatcgt tcaaacattt ggcaataaag tttcttaaga ttgaatcctg ttgccggtct   4680
tgcgatgatt atcatataat ttctgttgaa ttacgttaag catgtaataa ttaacatgta   4740
atgcatgacg ttatttatga gatgggtttt tatgattaga gtcccgcaat tatacattta   4800
atacgcgata gaaaacaaaa tatagcgcgc aaactaggat aaattatcgc gcgcggtgtc   4860
atctatgtta ctagatcggg aattcactgg ccgtcgtttt acaacgtcgt gactgggaaa   4920
```

-continued

```
accctggcgt tacccaactt aatcgccttg cagcacatcc ccctttcgcc agctggcgta   4980

atagcgaaga ggcccgcacc gatcgccctt cccaacagtt gcgcagcctg aatggcgccc   5040

gctcctttcg ctttcttccc ttcctttctc gccacgttcg ccggctttcc ccgtcaagct   5100

ctaaatcggg ggctcccttt agggttccga tttagtgctt tacggcacct cgaccccaaa   5160

aaacttgatt tgggtgatgg ttcacgtagt gggccatcgc cctgatagac ggtttttcgc   5220

cctttgacgt tggagtccac gttctttaat agtggactct tgttccaaac tggaacaaca   5280

ctcaacccta tctcgggcta ttcttttgat ttataaggga ttttgccgat ttcggaacca   5340

ccatcaaaca ggattttcgc ctgctggggc aaaccagcgt ggaccgcttg ctgcaactct   5400

ctcagggcca ggcggtgaag ggcaatcagc tgttgcccgt ctcactggtg aaaagaaaaa   5460

ccaccccagt acattaaaaa cgtccgcaat gtgttattaa gttgtctaag cgtcaatttg   5520

tttacaccac aatatatcct gcca                                          5544
```

```
<210> SEQ ID NO 131
<211> LENGTH: 5668
<212> TYPE: DNA
<213> ORGANISM: Artificial Sequence
<220> FEATURE:
<223> OTHER INFORMATION: Description of Artificial Sequence: Plasmid
      pRD29A-AtCPP

<400> SEQUENCE: 131
```

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380
```

-continued

```
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccatg gcgattcctt tcatggaaac   3480
cgtcgtgggt tttatgatag tgatgtacat ttttgagacg tatttggatc tgaggcaact   3540
cactgctctc aagcttccaa ctctcccgaa aaccttggtt ggtgtaatta gccaagagaa   3600
gtttgagaaa tcacgagcat acagtcttga caaaagctat tttcactttg ttcatgagtt   3660
tgtaactata cttatggact ctgcaatttt gttctttggg atcttgcctt ggttttggaa   3720
```

-continued

```
gatgtctgga gctgttttac cgaggttggg ccttgatccg gagaatgaaa tactgcatac   3780
tctttcattc ttggctggtg ttatgacatg gtcacagatc actgatttgc cattttcttt   3840
gtactcaact ttcgtgatcg agtctcggca tgggttcaac aaacaaacaa tatggatgtt   3900
cattagggac atgatcaaag gaacattcct ctctgtcata ctaggcccac ccattgttgc   3960
tgcgataatt ttcatagtcc agaaaggagg tccttatctt gccatctatc tgtgggcatt   4020
catgtttatc ctgtctctag tgatgatgac tatataccg gtcttgatag caccgctctt    4080
caacaaattc actcctcttc cagatggaga cctccgggag aagattgaga aacttgcttc   4140
ttccctaaag tttcctttga agaagctgtt tgttgtcgat ggatctacaa ggtcaagcca   4200
tagcaatgct tacatgtatg gtttctttaa gaacaaaagg attgttcttt atgatacgtt   4260
gattcagcag tgcaagaatg aggatgaaat tgtggcggtt attgcacacg agcttggaca   4320
ttggaaactg aatcacacta catactcgtt cattgcagtt caaatccttg ccttcttaca   4380
atttggagga tacactcttc tcagaaactc cactgatctc ttcaggagtt tcggatttga   4440
tacacagcct gttctcattg gtttgatcat atttcagcac actgtaatac cactgcaaca   4500
tctagtaagc tttggcctga acctcgttag tcgagcgttt gagtttcagg ctgatgcttt   4560
tgctgtgaag cttgactatg caaaagatct tcgtcctgct ctagtgaaac tacaggaaga   4620
gaacttatca acaatgaaca ctgatccatt gtactcagct tatcactact cacatcctcc   4680
tcttgttgaa aggcttcgag ccactgatgg agaagacaag aagacagatt aacccctcga   4740
atttccccga tcgttcaaac atttggcaat aaagtttctt aagattgaat cctgttgccg   4800
gtcttgcgat gattatcata taatttctgt tgaattacgt taagcatgta ataattaaca   4860
tgtaatgcat gacgttattt atgagatggg tttttatgat tagagtcccg caattataca   4920
tttaatacgc gatagaaaac aaaatatagc gcgcaaacta ggataaatta tcgcgcgcgg   4980
tgtcatctat gttactagat cgggaattca ctggccgtcg ttttacaacg tcgtgactgg   5040
gaaaaccctg gcgttaccca acttaatcgc cttgcagcac atcccccttt cgccagctgg   5100
cgtaatagcg aagaggcccg caccgatcgc ccttcccaac agttgcgcag cctgaatggc   5160
gcccgctcct ttcgctttct tcccttcctt tctcgccacg ttcgccggct ttccccgtca   5220
agctctaaat cgggggctcc ctttagggtt ccgatttagt gctttacggc acctcgaccc   5280
caaaaaactt gatttgggtg atggttcacg tagtgggcca tcgccctgat agacggtttt   5340
tcgccctttg acgttggagt ccacgttctt taatagtgga ctcttgttcc aaactggaac   5400
aacactcaac cctatctcgg gctattcttt tgatttataa gggattttgc cgatttcgga   5460
accaccatca aacaggattt tcgcctgctg gggcaaacca gcgtggaccg cttgctgcaa   5520
ctctctcagg gccaggcggt gaagggcaat cagctgttgc ccgtctcact ggtgaaaaga   5580
aaaaccaccc cagtacatta aaaacgtccg caatgtgtta ttaagttgtc taagcgtcaa   5640
tttgtttaca ccacaatata tcctgcca                                      5668
```

<210> SEQ ID NO 132
<211> LENGTH: 6608
<212> TYPE: DNA
<213> ORGANISM: Artificial Sequence
<220> FEATURE:
<223> OTHER INFORMATION: Description of Artificial Sequence: Plasmid
pRD29A-HP-AtCPP

<400> SEQUENCE: 132

```
gtttacccgc caatatatcc tgtcaaacac tgatagttta aactgaaggc gggaaacgac     60
```

-continued

```
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
```

-continued

```
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctcc caatgtccaa gctcgtgtgc   3480
aataaccgcc acaatttcat cctcattctt gcactgctga atcaacgtat cataaagaac   3540
aatccttttg ttcttaaaga aaccatacat gtaagcattg ctatggcttg accttgtaga   3600
tccatcgaca acaaacagct tcttcaaagg aaactttagg gaagaagcaa gtttctcaat   3660
cttctcccgg aggtctccat ctggaagagg agtgaatttg ttgaagagcg gtgctatcaa   3720
gaccgggtat atagtcatca tcactagaga caggataaac atgaatgccc acagatagat   3780
ggcaagataa ggacctcctt tctggactat gaaaattatc gcagcaacaa tgggtgggcc   3840
tagtatgaca gagaggaatg ttcctttgat catgtcccta atgaacatcc atattgtttg   3900
tttgttgaac ccatgccgag actcgatcac gaaagttgag tacaaagaaa atggcaaatc   3960
agtgatctgt gaccatgtca taacaccagc caagaatgaa agagtatgca gtatttcatt   4020
ctccggatca aggcccaacc tcggtaaaag aggatcccca tctacccgct tcgcgtcggc   4080
atccggtcag tggcagtgaa gggcgaacag ttcctgatta accacaaacc gttctacttt   4140
actggctttg gtcgtcatga agatgcggac ttgcgtggca aaggattcga taacgtgctg   4200
atggtgcacg accacgcatt aatggactgg attggggcca actcctaccg tacctcgcat   4260
tacccttacg ctgaagagat gctcgactgg gcagatgaac atggcatcgt ggtgattgat   4320
gaaactgctg ctgtcggctt ttcgctctct ttaggcattg gtttcgaagc gggcaacaag   4380
ccgaaagaac tgtacagcga agaggcagtc aacggggaaa ctcagcaagc gcacttacag   4440
gcgattaaag agctgatagc gcgtgacaaa aaccacccaa gcgtggtgat gtggagtatt   4500
gccaacgaac cggatacccg tccgcaaggt gcacgggaat atttcgcgcc actggcggaa   4560
gcaacgcgta aactcgaccc gacgcgtccg atcacctgcg tcaatgtaat gttctgcgac   4620
gctcacaccg ataccatcag cgatctcttt gatgtgctgt gcctgaaccg ttattacgga   4680
tggtatgtcc aaagcggcga tttggaaacg gcagagaagg tactggaaaa agaacttctg   4740
gcctggcagg agaaactgta caccgacatg tggagtgaag agtatcagtg tgcatggctg   4800
```

-continued gatatgtatc accgcgtctt tgatcgcgtc agcgccgtcg tcggtgaaca ggtatggaat 4860
ttcgccgatt ttgcgacctc gcaaggcata ttgcgcgttg gcggtaacaa gaaagggatc 4920
ttcactcgcg accgcaaacc gaagtcggcg gcttttctgc tgcaaaaacg ctggactggc 4980
atgaacttcg gtgaaaaacc gcagcaggga ggcaaacaat gaatcaacaa ctctcctggc 5040
gcaccatcgt cggctacagc ctcgggaatt gctaccgagc tcttttaccg aggttgggcc 5100
ttgatccgga gaatgaaata ctgcatactc tttcattctt ggctggtgtt atgacatggt 5160
cacagatcac tgatttgcca ttttctttgt actcaacttt cgtgatcgag tctcggcatg 5220
ggttcaacaa acaaacaata tggatgttca ttagggacat gatcaaagga acattcctct 5280
ctgtcatact aggcccaccc attgttgctg cgataatttt catagtccag aaaggaggtc 5340
cttatcttgc catctatctg tgggcattca tgtttatcct gtctctagtg atgatgacta 5400
tatacccggt cttgatagca ccgctcttca acaaattcac tcctcttcca gatggagacc 5460
tccgggagaa gattgagaaa cttgcttctt ccctaaagtt tcctttgaag aagctgtttg 5520
ttgtcgatgg atctacaagg tcaagccata gcaatgctta catgtatggt ttctttaaga 5580
acaaaaggat tgttctttat gatacgttga ttcagcagtg caagaatgag gatgaaattg 5640
tggcggttat tgcacacgag cttggacatt gggagctcga atttccccga tcgttcaaac 5700
atttggcaat aaagtttctt aagattgaat cctgttgccg gtcttgcgat gattatcata 5760
taatttctgt tgaattacgt taagcatgta ataattaaca tgtaatgcat gacgttattt 5820
atgagatggg tttttatgat tagagtcccg caattataca tttaatacgc gatagaaaac 5880
aaaatatagc gcgcaaacta ggataaatta tcgcgcgcgg tgtcatctat gttactagat 5940
cgggaattca ctggccgtcg ttttacaacg tcgtgactgg gaaaaccctg gcgttaccca 6000
acttaatcgc cttgcagcac atcccccttt cgccagctgg cgtaatagcg aagaggcccg 6060
caccgatcgc ccttcccaac agttgcgcag cctgaatggc gcccgctcct ttcgctttct 6120
tcccttcctt tctcgccacg ttcgccggct ttccccgtca agctctaaat cgggggctcc 6180
ctttagggtt ccgatttagt gctttacggc acctcgaccc caaaaaactt gatttgggtg 6240
atggttcacg tagtgggcca tcgccctgat agacggtttt tcgccctttg acgttggagt 6300
ccacgttctt taatagtgga ctcttgttcc aaactggaac aacactcaac cctatctcgg 6360
gctattcttt tgatttataa gggattttgc cgatttcgga accaccatca aacaggattt 6420
tcgcctgctg gggcaaacca gcgtggaccg cttgctgcaa ctctctcagg gccaggcggt 6480
gaagggcaat cagctgttgc ccgtctcact ggtgaaaaga aaaaccaccc cagtacatta 6540
aaaacgtccg caatgtgtta ttaagttgtc taagcgtcaa tttgtttaca ccacaatata 6600
tcctgcca 6608

<210> SEQ ID NO 133
<211> LENGTH: 5668
<212> TYPE: DNA
<213> ORGANISM: Artificial Sequence
<220> FEATURE:
<223> OTHER INFORMATION: Description of Artificial Sequence: Plasmid
pRD29A-antisense-AtCPP

<400> SEQUENCE: 133
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180

-continued

```
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
```

-continued

```
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctta atctgtcttc ttgtcttctc   3480
catcagtggc tcgaagcctt tcaacaagag gaggatgtga gtagtgataa gctgagtaca   3540
atggatcagt gttcattgtt gataagttct cttcctgtag tttcactaga gcaggacgaa   3600
gatcttttgc atagtcaagc ttcacagcaa aagcatcagc ctgaaactca aacgctcgac   3660
taacgaggtt caggccaaag cttactagat gttgcagtgg tattacagtg tgctgaaata   3720
tgatcaaacc aatgagaaca ggctgtgtat caaatccgaa actcctgaag agatcagtgg   3780
agtttctgag aagagtgtat cctccaaatt gtaagaaggc aaggatttga actgcaatga   3840
acgagtatgt agtgtgattc agtttccaat gtccaagctc gtgtgcaata accgccacaa   3900
tttcatcctc attcttgcac tgctgaatca acgtatcata aagaacaatc cttttgttct   3960
taaagaaacc atacatgtaa gcattgctat ggcttgacct tgtagatcca tcgacaacaa   4020
acagcttctt caaaggaaac tttagggaag aagcaagttt ctcaatcttc tcccggaggt   4080
ctccatctgg aagaggagtg aatttgttga agagcggtgc tatcaagacc gggtatatag   4140
tcatcatcac tagagacagg ataaacatga atgcccacag atagatggca agataaggac   4200
ctcctttctg gactatgaaa attatcgcag caacaatggg tgggcctagt atgacagaga   4260
ggaatgttcc tttgatcatg tccctaatga acatccatat tgtttgtttg ttgaacccat   4320
gccgagactc gatcacgaaa gttgagtaca aagaaaatgg caaatcagtg atctgtgacc   4380
atgtcataac accagccaag aatgaaagag tatgcagtat ttcattctcc ggatcaaggc   4440
ccaacctcgg taaaacagct ccagacatct tccaaaacca aggcaagatc ccaaagaaca   4500
aaattgcaga gtccataagt atagttacaa actcatgaac aaagtgaaaa tagcttttgt   4560
caagactgta tgctcgtgat ttctcaaact tctcttggct aattacacca accaaggttt   4620
tcgggagagt tggaagcttg agagcagtga gttgcctcag atccaaatac gtctcaaaaa   4680
tgtacatcac tatcataaaa cccacgacgg tttccatgaa aggaatcgcc atcccctcga   4740
atttccccga tcgttcaaac atttggcaat aaagtttctt aagattgaat cctgttgccg   4800
gtcttgcgat gattatcata taatttctgt tgaattacgt taagcatgta ataattaaca   4860
tgtaatgcat gacgttattt atgagatggg tttttatgat tagagtcccg caattataca   4920
```

-continued

```
tttaatacgc gatagaaaac aaaatatagc gcgcaaacta ggataaatta tcgcgcgcgg   4980

tgtcatctat gttactagat cgggaattca ctggccgtcg ttttacaacg tcgtgactgg   5040

gaaaaccctg gcgttaccca acttaatcgc cttgcagcac atcccccttt cgccagctgg   5100

cgtaatagcg aagaggcccg caccgatcgc ccttcccaac agttgcgcag cctgaatggc   5160

gcccgctcct ttcgctttct tcccttcctt tctcgccacg ttcgccggct ttccccgtca   5220

agctctaaat cgggggctcc ctttagggtt ccgatttagt gctttacggc acctcgaccc   5280

caaaaaactt gatttgggtg atggttcacg tagtgggcca tcgccctgat agacggtttt   5340

tcgccctttg acgttggagt ccacgttctt taatagtgga ctcttgttcc aaactggaac   5400

aacactcaac cctatctcgg gctattcttt tgatttataa gggattttgc cgatttcgga   5460

accaccatca aacaggattt tcgcctgctg gggcaaacca gcgtggaccg cttgctgcaa   5520

ctctctcagg gccaggcggt gaagggcaat cagctgttgc ccgtctcact ggtgaaaaga   5580

aaaaccaccc cagtacatta aaaacgtccg caatgtgtta ttaagttgtc taagcgtcaa   5640

tttgtttaca ccacaatata tcctgcca                                      5668
```

<210> SEQ ID NO 134
<211> LENGTH: 5074
<212> TYPE: DNA
<213> ORGANISM: Artificial Sequence
<220> FEATURE:
<223> OTHER INFORMATION: Description of Artificial Sequence: Plasmid
MuA-AtCPP

<400> SEQUENCE: 134

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260
```

-continued atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc tgggaaattt ttcgccagtt 2520
ctaaatatcc ggaaacctct tgggatgcca ttgcccatct atctgtaatt tattgacgaa 2580
atagacgaaa aggaaggtgg ctcctataaa gcacatcatt gcgataacag aaaggccatt 2640
gttgaagata cctctgctga cattggtccc caagtggaag caccacccca tgaggagcac 2700
cgtggagtaa gaagacgttc gagccacgtc gaaaaagcaa gtgtgttgat gtagtatctc 2760
cattgacgta agggatgacg cacaatccaa ctatccatcg caagaccatt gctctatata 2820
agaaagttaa tatcatttcg agtggccacg ctgaggggga tccatggcga ttcctttcat 2880
ggaaaccgtc gtgggtttta tgatagtgat gtacattttt gagacgtatt tggatctgag 2940
gcaactcact gctctcaagc ttccaactct cccgaaaacc ttggttggtg taattagcca 3000
agagaagttt gagaaatcac gagcatacag tcttgacaaa agctattttc actttgttca 3060
tgagtttgta actatactta tggactctgc aattttgttc tttgggatct tgccttggtt 3120
ttggaagatg tctggagctg ttttaccgag gttgggcctt gatccggaga atgaaatact 3180
gcatactctt tcattcttgg ctggtgttat gacatggtca cagatcactg atttgccatt 3240
ttctttgtac tcaactttcg tgatcgagtc tcggcatggg ttcaacaaac aaacaatatg 3300
gatgttcatt agggacatga tcaaaggaac attcctctct gtcatactag gcccacccat 3360
tgttgctgcg ataattttca tagtccagaa aggaggtcct tatcttgcca tctatctgtg 3420
ggcattcatg tttatcctgt ctctagtgat gatgactata tacccggtct tgatagcacc 3480
gctcttcaac aaattcactc ctcttccaga tggagacctc cgggagaaga ttgagaaact 3540
tgcttcttcc ctaaagtttc ctttgaagaa gctgtttgtt gtcgatggat ctacaaggtc 3600
aagccatagc aatgcttaca tgtatggttt ctttaagaac aaaaggattg ttctttatga 3660

-continued

```
tacgttgatt cagcagtgca agaatgagga tgaaattgtg gcggttattg cacacgagct   3720
tggacattgg aaactgaatc acactacata ctcgttcatt gcagttcaaa tccttgcctt   3780
cttacaattt ggaggataca ctcttctcag aaactccact gatctcttca ggagtttcgg   3840
atttgataca cagcctgttc tcattggttt gatcatattt cagcacactg taataccact   3900
gcaacatcta gtaagctttg gcctgaacct cgttagtcga gcgtttgagt ttcaggctga   3960
tgcttttgct gtgaagcttg actatgcaaa agatcttcgt cctgctctag tgaaactaca   4020
ggaagagaac ttatcaacaa tgaacactga tccattgtac tcagcttatc actactcaca   4080
tcctcctctt gttgaaaggc ttcgagccac tgatggagaa gacaagaaga cagattaacc   4140
cctcgaattt ccccgatcgt tcaaacattt ggcaataaag tttcttaaga ttgaatcctg   4200
ttgccggtct tgcgatgatt atcatataat ttctgttgaa ttacgttaag catgtaataa   4260
ttaacatgta atgcatgacg ttatttatga gatgggtttt tatgattaga gtcccgcaat   4320
tatacattta atacgcgata gaaaacaaaa tatagcgcgc aaactaggat aaattatcgc   4380
gcgcggtgtc atctatgtta ctagatcggg aattcactgg ccgtcgtttt acaacgtcgt   4440
gactgggaaa accctggcgt tacccaactt aatcgccttg cagcacatcc ccctttcgcc   4500
agctggcgta atagcgaaga ggcccgcacc gatcgccctt cccaacagtt gcgcagcctg   4560
aatggcgccc gctcctttcg ctttcttccc ttcctttctc gccacgttcg ccggctttcc   4620
ccgtcaagct ctaaatcggg ggctcccttt agggttccga tttagtgctt tacggcacct   4680
cgaccccaaa aaacttgatt tgggtgatgg ttcacgtagt gggccatcgc cctgatagac   4740
ggtttttcgc cctttgacgt tggagtccac gttctttaat agtggactct tgttccaaac   4800
tggaacaaca ctcaacccta tctcgggcta ttcttttgat ttataaggga ttttgccgat   4860
ttcggaacca ccatcaaaca ggattttcgc ctgctggggc aaaccagcgt ggaccgcttg   4920
ctgcaactct ctcagggcca ggcggtgaag ggcaatcagc tgttgcccgt ctcactggtg   4980
aaaagaaaaa ccaccccagt acattaaaaa cgtccgcaat gtgttattaa gttgtctaag   5040
cgtcaatttg tttacaccac aatatatcct gcca                              5074
```

<210> SEQ ID NO 135
<211> LENGTH: 5076
<212> TYPE: DNA
<213> ORGANISM: Artificial Sequence
<220> FEATURE:
<223> OTHER INFORMATION: Description of Artificial Sequence: Plasmid MuA-GmCPP

<400> SEQUENCE: 135

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
```

-continued

```
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
atagacgaaa aggaaggtgg ctcctataaa gcacatcatt gcgataacag aaaggccatt   2640
gttgaagata cctctgctga cattggtccc caagtggaag caccacccca tgaggagcac   2700
cgtggagtaa gaagacgttc gagccacgtc gaaaaagcaa gtgtgttgat gtagtatctc   2760
cattgacgta agggatgacg cacaatccaa ctatccatcg caagaccatt gctctatata   2820
agaaagttaa tatcatttcg agtggccacg ctgagggga tcgggatggc gtttccctac   2880
atggaagccg ttgtcggatt tatgatatta atgtacattt ttgaaactta cttggatgtg   2940
```

-continued

```
cgacaacata gggccctcaa acttcctact cttccaaaga ctttagaggg tgttatcagc   3000
caagagaaat ttgagaaatc tagagcctat agtcttgata aaagccactt ccattttgtt   3060
cacgagtttg tgacaatagt gacagactct acaattttgt actttggggt attgccctgg   3120
ttttggaaga aatcaggaga ttttatgaca atagctggtt tcaatgctga gaatgaaata   3180
ctgcataccc ttgccttctt agcagggctg atgatttggt cacagataac agatttgccc   3240
ttttctctgt actcaacttt tgtgattgag gcccgtcatg gttttaataa gcaaacacca   3300
tggttattct ttagggacat gcttaaagga attttccttt ctgtaataat tggtccacct   3360
attgtggctg caatcattgt aatagtacag aaaggaggtc catacttggc catctatctt   3420
tgggttttta cgtttggtct ttctattgtg atgatgaccc tttatccagt actaatagct   3480
ccactcttca ataagttcac tccacttcca gatggtcaac tcagggagaa aatcgagaaa   3540
cttgcttcct ccctcaacta tccgttaaag aaactatttg ttgtcgatgg atccacaaga   3600
tcaagtcaca gcaatgccta tatgtatgga ttcttcaaga acaagaggat tgtcccttat   3660
gacacattaa ttcaacagtg caaagacgat gaggaaattg ttgctgttat tgcccatgag   3720
ttgggacact ggaagctcaa ccatactgtg tacacatttg ttgctatgca gattcttaca   3780
cttctacaat ttggaggata tacactagtg cgaaattcag ctgatctgta tcgaagcttt   3840
gggtttgata cgcagccagt cctcattggg ctcatcatat ttcagcatac tgtaatccca   3900
cttcagcaat tggtcagctt tggtctgaac ctagtcagcc gatcatttga atttcaggct   3960
gatggctttg ccaagaagct tggatatgca tctggattac gcggtggtct tgtgaaacta   4020
caggaggaga atctgtcagc tatgaataca gatccttggt actctgctta tcactattct   4080
catcctcccc ttgttgaaag attggccgcg ctggacgaac cggataagaa ggaagactaa   4140
gagctcgaat ttccccgatc gttcaaacat ttggcaataa agtttcttaa gattgaatcc   4200
tgttgccggt cttgcgatga ttatcatata atttctgttg aattacgtta agcatgtaat   4260
aattaacatg taatgcatga cgttatttat gagatgggtt tttatgatta gagtcccgca   4320
attatacatt taatacgcga tagaaaacaa aatatagcgc gcaaactagg ataaattatc   4380
gcgcgcggtg tcatctatgt tactagatcg ggaattcact ggccgtcgtt ttacaacgtc   4440
gtgactggga aaaccctggc gttacccaac ttaatcgcct tgcagcacat ccccctttcg   4500
ccagctggcg taatagcgaa gaggcccgca ccgatcgccc ttcccaacag ttgcgcagcc   4560
tgaatggcgc ccgctccttt cgctttcttc ccttcctttc tcgccacgtt cgccggcttt   4620
ccccgtcaag ctctaaatcg ggggctccct ttagggttcc gatttagtgc tttacggcac   4680
ctcgacccca aaaaacttga tttgggtgat ggttcacgta gtgggccatc gccctgatag   4740
acggtttttc gccctttgac gttggagtcc acgttcttta atagtggact cttgttccaa   4800
actggaacaa cactcaaccc tatctcgggc tattcttttg atttataagg gattttgccg   4860
atttcggaac caccatcaaa caggattttc gcctgctggg gcaaaccagc gtggaccgct   4920
tgctgcaact ctctcagggc caggcggtga agggcaatca gctgttgccc gtctcactgg   4980
tgaaaagaaa aaccaccccca gtacattaaa aacgtccgca atgtgttatt aagttgtcta   5040
agcgtcaatt tgtttacacc acaatatatc ctgcca                             5076
```

<210> SEQ ID NO 136
<211> LENGTH: 5549
<212> TYPE: DNA
<213> ORGANISM: Artificial Sequence
<220> FEATURE:
<223> OTHER INFORMATION: Description of Artificial Sequence: Plasmid -continued pBI121-GmCPP

<400> SEQUENCE: 136
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280

-continued

```
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccccgggat ggcgtttccc tacatggaag   3360
ccgttgtcgg atttatgata ttaatgtaca tttttgaaac ttacttggat gtgcgacaac   3420
atagggccct caaacttcct actcttccaa agactttaga gggtgttatc agccaagaga   3480
aatttgagaa atctagagcc tatagtcttg ataaaagcca cttccatttt gttcacgagt   3540
ttgtgacaat agtgacagac tctacaattt tgtactttgg ggtattgccc tggttttgga   3600
agaaatcagg agattttatg acaatagctg gtttcaatgc tgagaatgaa atactgcata   3660
cccttgcctt cttagcaggg ctgatgattt ggtcacagat aacagatttg cccttttctc   3720
tgtactcaac ttttgtgatt gaggcccgtc atggttttaa taagcaaaca ccatggttat   3780
tctttaggga catgcttaaa ggaattttcc tttctgtaat aattggtcca cctattgtgg   3840
ctgcaatcat tgtaatagta cagaaaggag gtccatactt ggccatctat ctttgggttt   3900
ttacgtttgg tctttctatt gtgatgatga ccctttatcc agtactaata gctccactct   3960
tcaataagtt cactccactt ccagatggtc aactcaggga gaaaatcgag aaacttgctt   4020
cctccctcaa ctatccgtta aagaaactat ttgttgtcga tggatccaca agatcaagtc   4080
acagcaatgc ctatatgtat ggattcttca agaacaagag gattgtccct tatgacacat   4140
taattcaaca gtgcaaagac gatgaggaaa ttgttgctgt tattgcccat gagttgggac   4200
actggaagct caaccatact gtgtacacat ttgttgctat gcagattctt acacttctac   4260
aatttggagg atatacacta gtgcgaaatt cagctgatct gtatcgaagc tttgggtttg   4320
atacgcagcc agtcctcatt gggctcatca tatttcagca tactgtaatc ccacttcagc   4380
aattggtcag ctttggtctg aacctagtca gccgatcatt tgaatttcag gctgatggct   4440
ttgccaagaa gcttggatat gcatctggat tacgcggtgg tcttgtgaaa ctacaggagg   4500
agaatctgtc agctatgaat acagatcctt ggtactctgc ttatcactat tctcatcctc   4560
cccttgttga aagattggcc gcgctggacg aaccggataa gaaggaagac taagagctcg   4620
```

-continued

```
aatttccccg atcgttcaaa catttggcaa taaagtttct taagattgaa tcctgttgcc   4680

ggtcttgcga tgattatcat ataatttctg ttgaattacg ttaagcatgt aataattaac   4740

atgtaatgca tgacgttatt tatgagatgg gtttttatga ttagagtccc gcaattatac   4800

atttaatacg cgatagaaaa caaaatatag cgcgcaaact aggataaatt atcgcgcgcg   4860

gtgtcatcta tgttactaga tcgggaattc actggccgtc gttttacaac gtcgtgactg   4920

ggaaaaccct ggcgttaccc aacttaatcg ccttgcagca catcccccttt tcgccagctg   4980

gcgtaatagc gaagaggccc gcaccgatcg cccttcccaa cagttgcgca gcctgaatgg   5040

cgcccgctcc tttcgctttc ttcccttcct ttctcgccac gttcgccggc tttccccgtc   5100

aagctctaaa tcgggggctc cctttagggt tccgatttag tgctttacgg cacctcgacc   5160

ccaaaaaact tgatttgggt gatggttcac gtagtgggcc atcgccctga tagacggttt   5220

ttcgcccttt gacgttggag tccacgttct ttaatagtgg actcttgttc caaactggaa   5280

caacactcaa ccctatctcg ggctattctt ttgatttata agggattttg ccgatttcgg   5340

aaccaccatc aaacaggatt ttcgcctgct ggggcaaacc agcgtggacc gcttgctgca   5400

actctctcag ggccaggcgg tgaagggcaa tcagctgttg cccgtctcac tggtgaaaag   5460

aaaaaccacc ccagtacatt aaaaacgtcc gcaatgtgtt attaagttgt ctaagcgtca   5520

atttgtttac accacaatat atcctgcca                                     5549
```

<210> SEQ ID NO 137
<211> LENGTH: 6352
<212> TYPE: DNA
<213> ORGANISM: Artificial Sequence
<220> FEATURE:
<223> OTHER INFORMATION: Description of Artificial Sequence: Plasmid pBI121-HP-GmCPP

<400> SEQUENCE: 137

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080
```

-continued

```
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagaccg gttcgtccag cgcggccaat ctttcaacaa   3360
ggggaggatg agaatagtga taagcagagt accaaggatc tgtattcata gctgacagat   3420
tctcctcctg tagtttcaca agaccaccgc gtaatccaga tgcatatcca agcttcttgg   3480
```

-continued

```
caaagccatc agcctgaaat tcaaatgatc ggctgactag gttcagacca aagctgacca   3540
attgctgaag tgggattaca gtatgctgaa atatgatgag cccaatgagg actggctgcg   3600
tatcaaaccc aaagcttcga tacagatcag ctgaatttcg cactagtgta tatcctccaa   3660
attgtagaag tgtaagaatc tgcatagcaa caaatgtgta cacagtatgg ttgagcttcc   3720
agtgtcccaa ctcatgggca ataacagcaa caatttcctc atcgtctttg cactgttgaa   3780
ttaatgtgtc ataagggaca atcctcttgt tcttgaagaa tccatacata taggcattgc   3840
tgtgacttga tcttgtggat ccccatctac ccgcttcgcg tcggcatccg gtcagtggca   3900
gtgaagggcg aacagttcct gattaaccac aaaccgttct actttactgg ctttggtcgt   3960
catgaagatg cggacttgcg tggcaaagga ttcgataacg tgctgatggt gcacgaccac   4020
gcattaatgg actggattgg ggccaactcc taccgtacct cgcattaccc ttacgctgaa   4080
gagatgctcg actgggcaga tgaacatggc atcgtggtga ttgatgaaac tgctgctgtc   4140
ggctttttcgc tctctttagg cattggtttc gaagcgggca acaagccgaa agaactgtac   4200
agcgaagagg cagtcaacgg ggaaactcag caagcgcact tacaggcgat taaagagctg   4260
atagcgcgtg acaaaaacca cccaagcgtg gtgatgtgga gtattgccaa cgaaccggat   4320
acccgtccgc aaggtgcacg ggaatatttc gcgccactgg cggaagcaac gcgtaaactc   4380
gacccgacgc gtccgatcac ctgcgtcaat gtaatgttct gcgacgctca caccgatacc   4440
atcagcgatc tctttgatgt gctgtgcctg aaccgttatt acggatggta tgtccaaagc   4500
ggcgatttgg aaacggcaga gaaggtactg gaaaaagaac ttctggcctg gcaggagaaa   4560
ctgtacaccg acatgtggag tgaagagtat cagtgtgcat ggctggatat gtatcaccgc   4620
gtctttgatc gcgtcagcgc cgtcgtcggt gaacaggtat ggaatttcgc cgattttgcg   4680
acctcgcaag gcatattgcg cgttggcggt aacaagaaag ggatcttcac tcgcgaccgc   4740
aaaccgaagt cggcggcttt tctgctgcaa aaacgctgga ctggcatgaa cttcggtgaa   4800
aaaccgcagc agggaggcaa acaatgaatc aacaactctc ctggcgcacc atcgtcggct   4860
acagcctcgg gaattgctac cgagctcaca agatcaagtc acagcaatgc ctatatgtat   4920
ggattcttca agaacaagag gattgtccct tatgacacat taattcaaca gtgcaaagac   4980
gatgaggaaa ttgttgctgt tattgcccat gagttgggac actggaagct caaccatact   5040
gtgtacacat ttgttgctat gcagattctt acacttctac aatttggagg atatacacta   5100
gtgcgaaatt cagctgatct gtatcgaagc tttgggtttg atacgcagcc agtcctcatt   5160
gggctcatca tatttcagca tactgtaatc ccacttcagc aattggtcag ctttggtctg   5220
aacctagtca gccgatcatt tgaatttcag gctgatggct ttgccaagaa gcttggatat   5280
gcatctggat tacgcggtgg tcttgtgaaa ctacaggagg agaatctgtc agctatgaat   5340
acagatcctt ggtactctgc ttatcactat tctcatcctc cccttgttga aagattggcc   5400
gcgctggacg aaccgggagc tcgaatttcc ccgatcgttc aaacatttgg caataaagtt   5460
tcttaagatt gaatcctgtt gccggtcttg cgatgattat catataattt ctgttgaatt   5520
acgttaagca tgtaataatt aacatgtaat gcatgacgtt atttatgaga tgggttttta   5580
tgattagagt cccgcaatta tacatttaat acgcgataga aaacaaaata tagcgcgcaa   5640
actaggataa attatcgcgc gcggtgtcat ctatgttact agatcgggaa ttcactggcc   5700
gtcgttttac aacgtcgtga ctgggaaaac cctggcgtta cccaacttaa tcgccttgca   5760
gcacatcccc ctttcgccag ctggcgtaat agcgaagagg cccgcaccga tcgcccttcc   5820
```

-continued

```
caacagttgc gcagcctgaa tggcgcccgc tcctttcgct ttcttccctt cctttctcgc   5880

cacgttcgcc ggctttcccc gtcaagctct aaatcggggg ctccctttag ggttccgatt   5940

tagtgcttta cggcacctcg accccaaaaa acttgatttg ggtgatggtt cacgtagtgg   6000

gccatcgccc tgatagacgg tttttcgccc tttgacgttg gagtccacgt tctttaatag   6060

tggactcttg ttccaaactg gaacaacact caaccctatc tcgggctatt cttttgattt   6120

ataagggatt ttgccgattt cggaaccacc atcaaacagg attttcgcct gctggggcaa   6180

accagcgtgg accgcttgct gcaactctct cagggccagg cggtgaaggg caatcagctg   6240

ttgcccgtct cactggtgaa aagaaaaacc accccagtac attaaaaacg tccgcaatgt   6300

gttattaagt tgtctaagcg tcaatttgtt tacaccacaa tatatcctgc ca           6352
```

```
<210> SEQ ID NO 138
<211> LENGTH: 5549
<212> TYPE: DNA
<213> ORGANISM: Artificial Sequence
<220> FEATURE:
<223> OTHER INFORMATION: Description of Artificial Sequence: Plasmid
      pBI121-antisense-GmCPP

<400> SEQUENCE: 138
```

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500
```

-continued

```
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccccgggtt agtcttcctt cttatccggt   3360
tcgtccagcg cggccaatct ttcaacaagg ggaggatgag aatagtgata agcagagtac   3420
caaggatctg tattcatagc tgacagattc tcctcctgta gtttcacaag accaccgcgt   3480
aatccagatg catatccaag cttcttggca aagccatcag cctgaaattc aaatgatcgg   3540
ctgactaggt tcagaccaaa gctgaccaat tgctgaagtg ggattacagt atgctgaaat   3600
atgatgagcc caatgaggac tggctgcgta tcaaacccaa agcttcgata cagatcagct   3660
gaatttcgca ctagtgtata tcctccaaat tgtagaagtg taagaatctg catagcaaca   3720
aatgtgtaca cagtatggtt gagcttccag tgtcccaact catgggcaat aacagcaaca   3780
atttcctcat cgtctttgca ctgttgaatt aatgtgtcat aagggacaat cctcttgttc   3840
ttgaagaatc catacatata ggcattgctg tgacttgatc ttgtggatcc atcgacaaca   3900
```

-continued

```
aatagtttct ttaacggata gttgagggag gaagcaagtt tctcgatttt ctccctgagt   3960

tgaccatctg gaagtggagt gaacttattg aagagtggag ctattagtac tggataaagg   4020

gtcatcatca caatagaaag accaaacgta aaaacccaaa gatagatggc caagtatgga   4080

cctcctttct gtactattac aatgattgca gccacaatag gtggaccaat tattacagaa   4140

aggaaaattc ctttaagcat gtccctaaag aataaccatg gtgtttgctt attaaaacca   4200

tgacgggcct caatcacaaa agttgagtac agagaaaagg gcaaatctgt tatctgtgac   4260

caaatcatca gccctgctaa gaaggcaagg gtatgcagta tttcattctc agcattgaaa   4320

ccagctattg tcataaaatc tcctgatttc ttccaaaacc agggcaatac cccaaagtac   4380

aaaattgtag agtctgtcac tattgtcaca aactcgtgaa caaaatggaa gtggctttta   4440

tcaagactat aggctctaga tttctcaaat ttctcttggc tgataacacc ctctaaagtc   4500

tttggaagag taggaagttt gagggcccta tgttgtcgca catccaagta agtttcaaaa   4560

atgtacatta atatcataaa tccgacaacg gcttccatgt agggaaacgc catgagctcg   4620

aatttccccg atcgttcaaa catttggcaa taaagtttct taagattgaa tcctgttgcc   4680

ggtcttgcga tgattatcat ataatttctg ttgaattacg ttaagcatgt aataattaac   4740

atgtaatgca tgacgttatt tatgagatgg gtttttatga ttagagtccc gcaattatac   4800

atttaatacg cgatagaaaa caaaatatag cgcgcaaact aggataaatt atcgcgcgcg   4860

gtgtcatcta tgttactaga tcgggaattc actggccgtc gttttacaac gtcgtgactg   4920

ggaaaaccct ggcgttaccc aacttaatcg ccttgcagca catcccccttt tcgccagctg   4980

gcgtaatagc gaagaggccc gcaccgatcg cccttcccaa cagttgcgca gcctgaatgg   5040

cgcccgctcc tttcgctttc ttcccttcct ttctcgccac gttcgccggc tttccccgtc   5100

aagctctaaa tcgggggctc cctttagggt tccgatttag tgctttacgg cacctcgacc   5160

ccaaaaaact tgatttgggt gatggttcac gtagtgggcc atcgccctga tagacggttt   5220

ttcgcccttt gacgttggag tccacgttct ttaatagtgg actcttgttc caaactggaa   5280

caacactcaa ccctatctcg ggctattctt ttgatttata agggattttg ccgatttcgg   5340

aaccaccatc aaacaggatt ttcgcctgct ggggcaaacc agcgtggacc gcttgctgca   5400

actctctcag ggccaggcgg tgaagggcaa tcagctgttg cccgtctcac tggtgaaaag   5460

aaaaaccacc ccagtacatt aaaaacgtcc gcaatgtgtt attaagttgt ctaagcgtca   5520

atttgtttac accacaatat atcctgcca                                     5549
```

<210> SEQ ID NO 139
<211> LENGTH: 5673
<212> TYPE: DNA
<213> ORGANISM: Artificial Sequence
<220> FEATURE:
<223> OTHER INFORMATION: Description of Artificial Sequence: Plasmid pRD29A-GmCPP

<400> SEQUENCE: 139

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360
```

-continued

```
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggcctcct gtcaatgctg gcggcggctc tggtggtggt    1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
```

-continued

```
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccccg ggatggcgtt tccctacatg   3480
gaagccgttg tcggatttat gatattaatg tacatttttg aaacttactt ggatgtgcga   3540
caacataggg ccctcaaact tcctactctt ccaaagactt tagagggtgt tatcagccaa   3600
gagaaatttg agaaatctag agcctatagt cttgataaaa gccacttcca ttttgttcac   3660
gagtttgtga caatagtgac agactctaca attttgtact ttggggtatt gccctggttt   3720
tggaagaaat caggagattt tatgacaata gctggtttca atgctgagaa tgaaatactg   3780
catacccttg ccttcttagc agggctgatg atttggtcac agataacaga tttgcccttt   3840
tctctgtact caacttttgt gattgaggcc cgtcatggtt ttaataagca aacaccatgg   3900
ttattcttta gggacatgct taaaggaatt ttcctttctg taataattgg tccacctatt   3960
gtggctgcaa tcattgtaat agtacagaaa ggaggtccat acttggccat ctatctttgg   4020
gtttttacgt ttggtctttc tattgtgatg atgacccttt atccagtact aatagctcca   4080
ctcttcaata agttcactcc acttccagat ggtcaactca gggagaaaat cgagaaactt   4140
gcttcctccc tcaactatcc gttaaagaaa ctatttgttg tcgatggatc cacaagatca   4200
agtcacagca atgcctatat gtatggattc ttcaagaaca agaggattgt cccttatgac   4260
acattaattc aacagtgcaa agacgatgag gaaattgttg ctgttattgc ccatgagttg   4320
ggacactgga agctcaacca tactgtgtac acatttgttg ctatgcagat tcttacactt   4380
ctacaatttg gaggatatac actagtgcga aattcagctg atctgtatcg aagctttggg   4440
tttgatacgc agccagtcct cattgggctc atcatatttc agcatactgt aatcccactt   4500
cagcaattgg tcagctttgg tctgaaccta gtcagccgat catttgaatt tcaggctgat   4560
ggctttgcca agaagcttgg atatgcatct ggattacgcg gtggtcttgt gaaactacag   4620
gaggagaatc tgtcagctat gaatacagat ccttggtact ctgcttatca ctattctcat   4680
cctccccttg ttgaaagatt ggccgcgctg gacgaaccgg ataagaagga agactaagag   4740
ctcgaatttc cccgatcgtt caaacatttg gcaataaagt ttcttaagat tgaatcctgt   4800
tgccggtctt gcgatgatta tcatataatt tctgttgaat tacgttaagc atgtaataat   4860
taacatgtaa tgcatgacgt tatttatgag atgggttttt atgattagag tcccgcaatt   4920
atacatttaa tacgcgatag aaaacaaaat atagcgcgca aactaggata aattatcgcg   4980
cgcggtgtca tctatgttac tagatcggga attcactggc cgtcgtttta caacgtcgtg   5040
actgggaaaa ccctggcgtt acccaactta atcgccttgc agcacatccc cctttcgcca   5100
```

gctggcgtaa tagcgaagag gcccgcaccg atcgcccttc ccaacagttg cgcagcctga 5160
atggcgcccg ctcctttcgc tttcttccct tcctttctcg ccacgttcgc cggctttccc 5220
cgtcaagctc taaatcgggg gctcccttta gggttccgat ttagtgcttt acggcacctc 5280
gaccccaaaa aacttgattt gggtgatggt tcacgtagtg ggccatcgcc ctgatagacg 5340
gtttttcgcc ctttgacgtt ggagtccacg ttctttaata gtggactctt gttccaaact 5400
ggaacaacac tcaaccctat ctcgggctat tcttttgatt tataagggat tttgccgatt 5460
tcggaaccac catcaaacag gattttcgcc tgctggggca aaccagcgtg gaccgcttgc 5520
tgcaactctc tcagggccag gcggtgaagg gcaatcagct gttgcccgtc tcactggtga 5580
aaagaaaaac caccccagta cattaaaaac gtccgcaatg tgttattaag ttgtctaagc 5640
gtcaatttgt ttacaccaca atatatcctg cca 5673

<210> SEQ ID NO 140
<211> LENGTH: 6476
<212> TYPE: DNA
<213> ORGANISM: Artificial Sequence
<220> FEATURE:
<223> OTHER INFORMATION: Description of Artificial Sequence: Plasmid pRD29A-HP-GmCPP

<400> SEQUENCE: 140
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440

-continued tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagggagcc 2520
atagatgcaa ttcaatcaaa ctgaaatttc tgcaagaatc tcaaacacgg agatctcaaa 2580
gtttgaaaga aaatttattt cttcgactca aaacaaactt acgaaattta ggtagaactt 2640
atatacatta tattgtaatt ttttgtaaca aaatgttttt attattatta tagaatttta 2700
ctggttaaat taaaaatgaa tagaaaaggt gaattaagag gagagaggag gtaaacattt 2760
tcttctattt tttcatattt tcaggataaa ttattgtaaa agtttacaag atttccattt 2820
gactagtgta aatgaggaat attctctagt aagatcatta tttcatctac ttcttttatc 2880
ttctaccagt agaggaataa acaatattta gctcctttgt aaatacaaat taattttcct 2940
tcttgacatc attcaatttt aattttacgt ataaaataaa agatcatacc tattagaacg 3000
attaaggaga aatacaattc gaatgagaag gatgtgccgt ttgttataat aaacagccac 3060
acgacgtaaa cgtaaaatga ccacatgatg ggccaataga catggaccga ctactaataa 3120
tagtaagtta cattttagga tggaataaat atcataccga catcagtttt gaaagaaaag 3180
ggaaaaaaag aaaaaataaa taaaagatat actaccgaca tgagttccaa aaagcaaaaa 3240
aaaagatcaa gccgacacag acacgcgtag agagcaaaat gactttgacg tcacaccacg 3300
aaaacagacg cttcatacgt gtccctttat ctctctcagt ctctctataa acttagtgag 3360
accctcctct gttttactca caaatatgca aactagaaaa caatcatcag gaataaaggg 3420
tttgattact tctattggaa aggactctag accggttcgt ccagcgcggc caatctttca 3480
acaaggggag gatgagaata gtgataagca gagtaccaag gatctgtatt catagctgac 3540
agattctcct cctgtagttt cacaagacca ccgcgtaatc cagatgcata tccaagcttc 3600
ttggcaaagc catcagcctg aaattcaaat gatcggctga ctaggttcag accaaagctg 3660
accaattgct gaagtgggat tacagtatgc tgaaatatga tgagcccaat gaggactggc 3720
tgcgtatcaa acccaaagct tcgatacaga tcagctgaat ttcgcactag tgtatatcct 3780

-continued

```
ccaaattgta gaagtgtaag aatctgcata gcaacaaatg tgtacacagt atggttgagc   3840
ttccagtgtc ccaactcatg ggcaataaca gcaacaattt cctcatcgtc tttgcactgt   3900
tgaattaatg tgtcataagg gacaatcctc ttgttcttga agaatccata catataggca   3960
ttgctgtgac ttgatcttgt ggatccccat ctacccgctt cgcgtcggca tccggtcagt   4020
ggcagtgaag ggcgaacagt tcctgattaa ccacaaaccg ttctacttta ctggctttgg   4080
tcgtcatgaa gatgcggact tgcgtggcaa aggattcgat aacgtgctga tggtgcacga   4140
ccacgcatta atggactgga ttggggccaa ctcctaccgt acctcgcatt acccttacgc   4200
tgaagagatg ctcgactggg cagatgaaca tggcatcgtg gtgattgatg aaactgctgc   4260
tgtcggcttt tcgctctctt taggcattgg tttcgaagcg ggcaacaagc cgaaagaact   4320
gtacagcgaa gaggcagtca acggggaaac tcagcaagcg cacttacagg cgattaaaga   4380
gctgatagcg cgtgacaaaa accacccaag cgtggtgatg tggagtattg ccaacgaacc   4440
ggatacccgt ccgcaaggtg cacgggaata tttcgcgcca ctggcggaag caacgcgtaa   4500
actcgacccg acgcgtccga tcacctgcgt caatgtaatg ttctgcgacg ctcacaccga   4560
taccatcagc gatctctttg atgtgctgtg cctgaaccgt tattacggat ggtatgtcca   4620
aagcggcgat ttggaaacgg cagagaaggt actggaaaaa gaacttctgg cctggcagga   4680
gaaactgtac accgacatgt ggagtgaaga gtatcagtgt gcatggctgg atatgtatca   4740
ccgcgtcttt gatcgcgtca gcgccgtcgt cggtgaacag gtatggaatt tcgccgattt   4800
tgcgacctcg caaggcatat tgcgcgttgg cggtaacaag aaagggatct tcactcgcga   4860
ccgcaaaccg aagtcggcgg cttttctgct gcaaaaacgc tggactggca tgaacttcgg   4920
tgaaaaaccg cagcagggag gcaaacaatg aatcaacaac tctcctggcg caccatcgtc   4980
ggctacagcc tcgggaattg ctaccgagct cacaagatca agtcacagca atgcctatat   5040
gtatggattc ttcaagaaca agaggattgt ccccttatgac acattaattc aacagtgcaa   5100
agacgatgag gaaattgttg ctgttattgc ccatgagttg ggacactgga agctcaacca   5160
tactgtgtac acatttgttg ctatgcagat tcttacactt ctacaatttg gaggatatac   5220
actagtgcga aattcagctg atctgtatcg aagctttggg tttgatacgc agccagtcct   5280
cattgggctc atcatatttc agcatactgt aatcccactt cagcaattgg tcagctttgg   5340
tctgaaccta gtcagccgat catttgaatt tcaggctgat ggctttgcca agaagcttgg   5400
atatgcatct ggattacgcg gtggtcttgt gaaactacag gaggagaatc tgtcagctat   5460
gaatacagat ccttggtact ctgcttatca ctattctcat cctcccccttg ttgaaagatt   5520
ggccgcgctg gacgaaccgg gagctcgaat ttccccgatc gttcaaacat ttggcaataa   5580
agtttcttaa gattgaatcc tgttgccggt cttgcgatga ttatcatata atttctgttg   5640
aattacgtta agcatgtaat aattaacatg taatgcatga cgttatttat gagatgggtt   5700
tttatgatta gagtcccgca attatacatt taatacgcga tagaaaacaa aatatagcgc   5760
gcaaactagg ataaattatc gcgcgcggtg tcatctatgt tactagatcg ggaattcact   5820
ggccgtcgtt ttacaacgtc gtgactggga aaaccctggc gttacccaac ttaatcgcct   5880
tgcagcacat ccccctttcg ccagctggcg taatagcgaa gaggcccgca ccgatcgccc   5940
ttcccaacag ttgcgcagcc tgaatggcgc ccgctccttt cgctttcttc ccttcctttc   6000
tcgccacgtt cgccggcttt ccccgtcaag ctctaaatcg ggggctccct ttagggttcc   6060
gatttagtgc tttacggcac ctcgacccca aaaaacttga tttgggtgat ggttcacgta   6120
gtgggccatc gccctgatag acggtttttc gccctttgac gttggagtcc acgttcttta   6180
```

-continued

```
atagtggact cttgttccaa actggaacaa cactcaaccc tatctcgggc tattcttttg   6240

atttataagg gattttgccg atttcggaac caccatcaaa caggattttc gcctgctggg   6300

gcaaaccagc gtggaccgct tgctgcaact ctctcagggc caggcggtga agggcaatca   6360

gctgttgccc gtctcactgg tgaaaagaaa aaccaccccca gtacattaaa aacgtccgca   6420

atgtgttatt aagttgtcta agcgtcaatt tgtttacacc acaatatatc ctgcca       6476
```

<210> SEQ ID NO 141
<211> LENGTH: 5673
<212> TYPE: DNA
<213> ORGANISM: Artificial Sequence
<220> FEATURE:
<223> OTHER INFORMATION: Description of Artificial Sequence: Plasmid pRD29A-antisense-GmCPP

<400> SEQUENCE: 141

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740
```

-continued

```
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccccg ggttagtctt ccttcttatc   3480
cggttcgtcc agcgcggcca atctttcaac aaggggagga tgagaatagt gataagcaga   3540
gtaccaagga tctgtattca tagctgacag attctcctcc tgtagtttca caagaccacc   3600
gcgtaatcca gatgcatatc caagcttctt ggcaaagcca tcagcctgaa attcaaatga   3660
tcggctgact aggttcagac caaagctgac caattgctga agtgggatta cagtatgctg   3720
aaatatgatg agcccaatga ggactggctg cgtatcaaac ccaaagcttc gatacagatc   3780
agctgaattt cgcactagtg tatatcctcc aaattgtaga agtgtaagaa tctgcatagc   3840
aacaaatgtg tacacagtat ggttgagctt ccagtgtccc aactcatggg caataacagc   3900
aacaatttcc tcatcgtctt tgcactgttg aattaatgtg tcataaggga caatcctctt   3960
gttcttgaag aatccataca tataggcatt gctgtgactt gatcttgtgg atccatcgac   4020
aacaaatagt ttctttaacg gatagttgag ggaggaagca agtttctcga ttttctccct   4080
```

-continued

```
gagttgacca tctggaagtg gagtgaactt attgaagagt ggagctatta gtactggata   4140

aagggtcatc atcacaatag aaagaccaaa cgtaaaaacc caaagataga tggccaagta   4200

tggacctcct ttctgtacta ttacaatgat tgcagccaca ataggtggac caattattac   4260

agaaaggaaa attcctttaa gcatgtccct aaagaataac catggtgttt gcttattaaa   4320

accatgacgg gcctcaatca caaaagttga gtacagagaa aagggcaaat ctgttatctg   4380

tgaccaaatc atcagccctg ctaagaaggc aagggtatgc agtatttcat tctcagcatt   4440

gaaaccagct attgtcataa aatctcctga tttcttccaa aaccagggca ataccccaaa   4500

gtacaaaatt gtagagtctg tcactattgt cacaaactcg tgaacaaaat ggaagtggct   4560

tttatcaaga ctataggctc tagatttctc aaatttctct tggctgataa caccctctaa   4620

agtctttgga agagtaggaa gtttgagggc cctatgttgt cgcacatcca agtaagtttc   4680

aaaaatgtac attaatatca taaatccgac aacggcttcc atgtagggaa acgccatgag   4740

ctcgaatttc cccgatcgtt caaacatttg gcaataaagt ttcttaagat tgaatcctgt   4800

tgccggtctt gcgatgatta tcatataatt tctgttgaat tacgttaagc atgtaataat   4860

taacatgtaa tgcatgacgt tatttatgag atgggttttt atgattagag tcccgcaatt   4920

atacatttaa tacgcgatag aaaacaaaat atagcgcgca aactaggata aattatcgcg   4980

cgcggtgtca tctatgttac tagatcggga attcactggc cgtcgtttta caacgtcgtg   5040

actgggaaaa ccctggcgtt acccaactta atcgccttgc agcacatccc cctttcgcca   5100

gctggcgtaa tagcgaagag gcccgcaccg atcgcccttc ccaacagttg cgcagcctga   5160

atggcgcccg ctcctttcgc tttcttccct tcctttctcg ccacgttcgc cggctttccc   5220

cgtcaagctc taaatcgggg gctcccttta gggttccgat ttagtgcttt acggcacctc   5280

gaccccaaaa aacttgattt gggtgatggt tcacgtagtg ggccatcgcc ctgatagacg   5340

gtttttcgcc ctttgacgtt ggagtccacg ttctttaata gtggactctt gttccaaact   5400

ggaacaacac tcaaccctat ctcgggctat tcttttgatt tataagggat tttgccgatt   5460

tcggaaccac catcaaacag gattttcgcc tgctggggca aaccagcgtg gaccgcttgc   5520

tgcaactctc tcagggccag gcggtgaagg gcaatcagct gttgcccgtc tcactggtga   5580

aaagaaaaac caccccagta cattaaaaac gtccgcaatg tgttattaag ttgtctaagc   5640

gtcaatttgt ttacaccaca atatatcctg cca                                5673
```

<210> SEQ ID NO 142
<211> LENGTH: 5544
<212> TYPE: DNA
<213> ORGANISM: Artificial Sequence
<220> FEATURE:
<223> OTHER INFORMATION: Description of Artificial Sequence: Plasmid pBI121-BnCPP

<400> SEQUENCE: 142

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420
```

-continued

```
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
```

-continued

```
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccatggcga ttcctttcat ggaaaccgtc   3360
gttggtttta tgatagtgat gtacgttttt gagacgtatt tggatctgag gcaacatact   3420
gctctcaagc ttcccactct cccaaagact ttggttggag tcattagcca agagaagttt   3480
gagaaatctc gagcttacag tcttgacaaa agccattttc actttgttca tgagtttgtt   3540
actatactta tggactctgc gattctgttc tttgggatct tgccttggtt ttggaagata   3600
tctggcggct ttctaccaat ggtgggactc gatccagaga atgaaatcct gcacactctt   3660
tcattcttgg ctggtcttat gacatggtca cagatcactg atttgccatt ttctttgtac   3720
tcaactttcg tgatcgagtc tcggcatggg ttcaacaaac aaacaatatg gatgttcatt   3780
agggacatga tcaaaggaat actcctctct gtcatacctg cccctcctat cgttgccgca   3840
attattgtta tagttcagaa aggaggtcct tacctcgcca tctatctgtg ggcattcatg   3900
tttatcctgt ctctagtgat gatgactata taccctgttt tgattgcacc tcttttcaac   3960
aagttcactc ctcttcctga tggagacctc cgggagaaga ttgagaaact tgcttcttct   4020
ctaaagtttc ctctgaagaa gctgtttgtt gtcgatggat ctacaaggtc aagccatagt   4080
aatgcttaca tgtatggttt cttcaagaac aaaaggattg ttctttatga cacattgatt   4140
cagcagtgcc agaatgagaa tgaaattgtg gcggttattg cacacgagct gggacactgg   4200
aagctgaatc acactacata ctcgttcatt gctgttcaaa tccttgcctt cttgcaattt   4260
ggaggataca ctcttgtcag aaactccact gatctcttca ggagttttgg ttttgataca   4320
caaccagttc tcattggttt gatcatattt cagcacactg taataccact tcaacaccta   4380
gtaagctttg acctcaacct tgttagtcga gcgtttgagt ttcaggctga tgcttttgca   4440
gtgaatcttg gttatgcaaa ggatctacgt cctgccctag tgaagctaca ggaagagaac   4500
ttatcagcga tgaacacaga cccattgtac tcagcttatc actactcaca ccctcctctt   4560
gtagagaggc ttcgagccat tgatggagaa gacaagaaga cagattaacc cctcgaattt   4620
ccccgatcgt tcaaacattt ggcaataaag tttcttaaga ttgaatcctg ttgccggtct   4680
tgcgatgatt atcatataat ttctgttgaa ttacgttaag catgtaataa ttaacatgta   4740
atgcatgacg ttatttatga gatgggtttt tatgattaga gtcccgcaat tatacattta   4800
atacgcgata gaaaacaaaa tatagcgcgc aaactaggat aaattatcgc gcgcggtgtc   4860
atctatgtta ctagatcggg aattcactgg ccgtcgtttt acaacgtcgt gactgggaaa   4920
accctggcgt tacccaactt aatcgccttg cagcacatcc ccctttcgcc agctggcgta   4980
atagcgaaga ggcccgcacc gatcgccctt cccaacagtt gcgcagcctg aatggcgccc   5040
gctcctttcg ctttcttccc ttcctttctc gccacgttcg ccggctttcc ccgtcaagct   5100
ctaaatcggg ggctcccttt agggttccga tttagtgctt tacggcacct cgaccccaaa   5160
```

-continued

```
aaacttgatt tgggtgatgg ttcacgtagt gggccatcgc cctgatagac ggtttttcgc   5220

cctttgacgt tggagtccac gttctttaat agtggactct tgttccaaac tggaacaaca   5280

ctcaacccta tctcgggcta ttcttttgat ttataaggga ttttgccgat ttcggaacca   5340

ccatcaaaca ggattttcgc ctgctggggc aaaccagcgt ggaccgcttg ctgcaactct   5400

ctcagggcca ggcggtgaag ggcaatcagc tgttgcccgt ctcactggtg aaaagaaaaa   5460

ccaccccagt acattaaaaa cgtccgcaat gtgttattaa gttgtctaag cgtcaatttg   5520

tttacaccac aatatatcct gcca                                          5544
```

```
<210> SEQ ID NO 143
<211> LENGTH: 6474
<212> TYPE: DNA
<213> ORGANISM: Artificial Sequence
<220> FEATURE:
<223> OTHER INFORMATION: Description of Artificial Sequence: Plasmid
      pBI121-HP-BnCPP

<400> SEQUENCE: 143

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620
```

-continued

```
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagacca gtgtcccagc tcgtgtgcaa taaccgccac   3360
aatttcattc tcattctggc actgctgaat caatgtgtca taaagaacaa tccttttgtt   3420
cttgaagaaa ccatacatgt aagcattact atggcttgac cttgtagatc catcgacaac   3480
aaacagcttc ttcagaggaa actttagaga agaagcaagt ttctcaatct tctcccggag   3540
gtctccatca ggaagaggag tgaacttgtt gaaaagaggt gcaatcaaaa cagggtatat   3600
agtcatcatc actagagaca ggataaacat gaatgcccac agatagatgg cgaggtaagg   3660
acctcctttc tgaactataa caataattgc ggcaacgata ggaggggcag gtatgacaga   3720
gaggagtatt cctttgatca tgtccctaat gaacatccat attgtttgtt tgttgaaccc   3780
atgccgagac tcgatcacga aagttgagta caaagaaaat ggcaaatcag tgatctgtga   3840
ccatgtcata agaccagcca agaatgaaag agtgtgcagg atttcattct ctggatcgag   3900
tcccaccatt ggtagaagga tccccatcta cccgcttcgc gtcggcatcc ggtcagtggc   3960
agtgaagggc gaacagttcc tgattaacca caaaccgttc tactttactg gctttggtcg   4020
```

-continued tcatgaagat gcggacttgc gtggcaaagg attcgataac gtgctgatgg tgcacgacca 4080
cgcattaatg gactggattg gggccaactc ctaccgtacc tcgcattacc cttacgctga 4140
agagatgctc gactgggcag atgaacatgg catcgtggtg attgatgaaa ctgctgctgt 4200
cggcttttcg ctctctttag gcattggttt cgaagcgggc aacaagccga aagaactgta 4260
cagcgaagag gcagtcaacg gggaaactca gcaagcgcac ttacaggcga ttaaagagct 4320
gatagcgcgt gacaaaaacc acccaagcgt ggtgatgtgg agtattgcca acgaaccgga 4380
tacccgtccg caaggtgcac gggaatattt cgcgccactg gcggaagcaa cgcgtaaact 4440
cgacccgacg cgtccgatca cctgcgtcaa tgtaatgttc tgcgacgctc acaccgatac 4500
catcagcgat ctctttgatg tgctgtgcct gaaccgttat tacggatggt atgtccaaag 4560
cggcgatttg gaaacggcag agaaggtact ggaaaaagaa cttctggcct ggcaggagaa 4620
actgtacacc gacatgtgga gtgaagagta tcagtgtgca tggctggata tgtatcaccg 4680
cgtctttgat cgcgtcagcg ccgtcgtcgg tgaacaggta tggaatttcg ccgattttgc 4740
gacctcgcaa ggcatattgc gcgttggcgg taacaagaaa gggatcttca ctcgcgaccg 4800
caaaccgaag tcggcggctt ttctgctgca aaaacgctgg actggcatga acttcggtga 4860
aaaaccgcag cagggaggca aacaatgaat caacaactct cctggcgcac catcgtcggc 4920
tacagcctcg ggaattgcta ccgagctctt ctaccaatgg tgggactcga tccagagaat 4980
gaaatcctgc acactctttc attcttggct ggtcttatga catggtcaca gatcactgat 5040
ttgccatttt ctttgtactc aactttcgtg atcgagtctc ggcatgggtt caacaaacaa 5100
acaatatgga tgttcattag ggacatgatc aaaggaatac tcctctctgt catacctgcc 5160
cctcctatcg ttgccgcaat tattgttata gttcagaaag gaggtcctta cctcgccatc 5220
tatctgtggg cattcatgtt tatcctgtct ctagtgatga tgactatata ccctgttttg 5280
attgcacctc ttttcaacaa gttcactcct cttcctgatg gagacctccg ggagaagatt 5340
gagaaacttg cttcttctct aaagtttcct ctgaagaagc tgtttgttgt cgatggatct 5400
acaaggtcaa gccatagtaa tgcttacatg tatggtttct tcaagaacaa aaggattgtt 5460
ctttatgaca cattgattca gcagtgccag aatgagaatg aaattgtggc ggttattgca 5520
cacgagctgg gacactggga gctcgaattt ccccgatcgt tcaaacattt ggcaataaag 5580
tttcttaaga ttgaatcctg ttgccggtct tgcgatgatt atcatataat ttctgttgaa 5640
ttacgttaag catgtaataa ttaacatgta atgcatgacg ttatttatga gatgggtttt 5700
tatgattaga gtcccgcaat tatacattta atacgcgata gaaaacaaaa tatagcgcgc 5760
aaactaggat aaattatcgc gcgcggtgtc atctatgtta ctagatcggg aattcactgg 5820
ccgtcgtttt acaacgtcgt gactgggaaa accctggcgt tacccaactt aatcgccttg 5880
cagcacatcc ccctttcgcc agctggcgta atagcgaaga ggcccgcacc gatcgccctt 5940
cccaacagtt gcgcagcctg aatggcgccc gctcctttcg ctttcttccc ttcctttctc 6000
gccacgttcg ccggctttcc ccgtcaagct ctaaatcggg ggctcccttt agggttccga 6060
tttagtgctt tacggcacct cgaccccaaa aaacttgatt tgggtgatgg ttcacgtagt 6120
gggccatcgc cctgatagac ggtttttcgc cctttgacgt tggagtccac gttctttaat 6180
agtggactct tgttccaaac tggaacaaca ctcaacccta tctcgggcta ttcttttgat 6240
ttataaggga ttttgccgat ttcggaacca ccatcaaaca ggattttcgc ctgctggggc 6300
aaaccagcgt ggaccgcttg ctgcaactct ctcagggcca ggcggtgaag ggcaatcagc 6360

-continued tgttgcccgt ctcactggtg aaaagaaaaa ccaccccagt acattaaaaa cgtccgcaat 6420
gtgttattaa gttgtctaag cgtcaatttg tttacaccac aatatatcct gcca 6474

<210> SEQ ID NO 144
<211> LENGTH: 5544
<212> TYPE: DNA
<213> ORGANISM: Artificial Sequence
<220> FEATURE:
<223> OTHER INFORMATION: Description of Artificial Sequence: Plasmid
      Plasmid pBI121-antisense-BnCPP

<400> SEQUENCE: 144
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920

-continued gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tccttaatct gtcttcttgt cttctccatc 3360
aatggctcga agcctctcta caagaggagg gtgtgagtag tgataagctg agtacaatgg 3420
gtctgtgttc atcgctgata agttctcttc ctgtagcttc actagggcag gacgtagatc 3480
ctttgcataa ccaagattca ctgcaaaagc atcagcctga aactcaaacg ctcgactaac 3540
aaggttgagg tcaaagctta ctaggtgttg aagtggtatt acagtgtgct gaaatatgat 3600
caaaccaatg agaactggtt gtgtatcaaa accaaaactc ctgaagagat cagtggagtt 3660
tctgacaaga gtgtatcctc caaattgcaa gaaggcaagg atttgaacag caatgaacga 3720
gtatgtagtg tgattcagct tccagtgtcc cagctcgtgt gcaataaccg cccacaatttc 3780 attctcattc tggcactgct gaatcaatgt gtcataaaga acaatccttt tgttcttgaa 3840
gaaaccatac atgtaagcat tactatggct tgaccttgta gatccatcga caacaaacag 3900
cttcttcaga ggaaacttta gagaagaagc aagtttctca atcttctccc ggaggtctcc 3960
atcaggaaga ggagtgaact tgttgaaaag aggtgcaatc aaaacagggt atatagtcat 4020
catcactaga gacaggataa acatgaatgc ccacagatag atggcgaggt aaggacctcc 4080
tttctgaact ataacaataa ttgcggcaac gataggaggg gcaggtatga cagagaggag 4140
tattcctttg atcatgtccc taatgaacat ccatattgtt tgtttgttga acccatgccg 4200
agactcgatc acgaaagttg agtacaaaga aaatggcaaa tcagtgatct gtgaccatgt 4260
cataagacca gccaagaatg aaagagtgtg caggatttca ttctctggat cgagtcccac 4320

-continued

```
cattggtaga aagccgccag atatcttcca aaaccaaggc aagatcccaa agaacagaat   4380

cgcagagtcc ataagtatag taacaaactc atgaacaaag tgaaaatggc ttttgtcaag   4440

actgtaagct cgagatttct caaacttctc ttggctaatg actccaacca aagtctttgg   4500

gagagtggga agcttgagag cagtatgttg cctcagatcc aaatacgtct caaaaacgta   4560

catcactatc ataaaaccaa cgacggtttc catgaaagga atcgccatcc cctcgaattt   4620

ccccgatcgt tcaaacattt ggcaataaag tttcttaaga ttgaatcctg ttgccggtct   4680

tgcgatgatt atcatataat ttctgttgaa ttacgttaag catgtaataa ttaacatgta   4740

atgcatgacg ttatttatga gatgggtttt tatgattaga gtcccgcaat tatacattta   4800

atacgcgata gaaaacaaaa tatagcgcgc aaactaggat aaattatcgc gcgcggtgtc   4860

atctatgtta ctagatcggg aattcactgg ccgtcgtttt acaacgtcgt gactgggaaa   4920

accctggcgt tacccaactt aatcgccttg cagcacatcc ccctttcgcc agctggcgta   4980

atagcgaaga ggcccgcacc gatcgccctt cccaacagtt gcgcagcctg aatggcgccc   5040

gctcctttcg ctttcttccc ttcctttctc gccacgttcg ccggctttcc ccgtcaagct   5100

ctaaatcggg ggctcccttt agggttccga tttagtgctt tacggcacct cgaccccaaa   5160

aaacttgatt tgggtgatgg ttcacgtagt gggccatcgc cctgatagac ggtttttcgc   5220

cctttgacgt tggagtccac gttctttaat agtggactct tgttccaaac tggaacaaca   5280

ctcaacccta tctcgggcta ttcttttgat ttataaggga ttttgccgat ttcggaacca   5340

ccatcaaaca ggattttcgc ctgctggggc aaaccagcgt ggaccgcttg ctgcaactct   5400

ctcagggcca ggcggtgaag ggcaatcagc tgttgcccgt ctcactggtg aaaagaaaaa   5460

ccaccccagt acattaaaaa cgtccgcaat gtgttattaa gttgtctaag cgtcaatttg   5520

tttacaccac aatatatcct gcca                                          5544
```

<210> SEQ ID NO 145
<211> LENGTH: 5668
<212> TYPE: DNA
<213> ORGANISM: Artificial Sequence
<220> FEATURE:
<223> OTHER INFORMATION: Description of Artificial Sequence: Plasmid pRD29A-BnCPP

<400> SEQUENCE: 145

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780
```

-continued

```
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
```

-continued

```
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccatg gcgattcctt tcatggaaac   3480
cgtcgttggt tttatgatag tgatgtacgt tttgagacg tatttggatc tgaggcaaca   3540
tactgctctc aagcttccca ctctcccaaa gactttggtt ggagtcatta gccaagagaa   3600
gtttgagaaa tctcgagctt acagtcttga caaaagccat tttcactttg ttcatgagtt   3660
tgttactata cttatggact ctgcgattct gttctttggg atcttgcctt ggttttggaa   3720
gatatctggc ggctttctac caatggtggg actcgatcca gagaatgaaa tcctgcacac   3780
tctttcattc ttggctggtc ttatgacatg gtcacagatc actgatttgc cattttcttt   3840
gtactcaact ttcgtgatcg agtctcggca tgggttcaac aaacaaacaa tatggatgtt   3900
cattagggac atgatcaaag gaatactcct ctctgtcata cctgcccctc ctatcgttgc   3960
cgcaattatt gttatagttc agaaaggagg tccttacctc gccatctatc tgtgggcatt   4020
catgtttatc ctgtctctag tgatgatgac tatataccct gttttgattg cacctctttt   4080
caacaagttc actcctcttc ctgatggaga cctccgggag aagattgaga aacttgcttc   4140
ttctctaaag tttcctctga agaagctgtt tgttgtcgat ggatctacaa ggtcaagcca   4200
tagtaatgct tacatgtatg gtttcttcaa gaacaaaagg attgttcttt atgacacatt   4260
gattcagcag tgccagaatg agaatgaaat tgtggcggtt attgcacacg agctgggaca   4320
ctggaagctg aatcacacta catactcgtt cattgctgtt caaatccttg ccttcttgca   4380
atttggagga tacactcttg tcagaaactc cactgatctc ttcaggagtt ttggttttga   4440
tacacaacca gttctcattg gtttgatcat atttcagcac actgtaatac cacttcaaca   4500
cctagtaagc tttgacctca accttgttag tcgagcgttt gagtttcagg ctgatgcttt   4560
tgcagtgaat cttggttatg caaaggatct acgtcctgcc ctagtgaagc tacaggaaga   4620
gaacttatca gcgatgaaca cagacccatt gtactcagct tatcactact cacaccctcc   4680
tcttgtagag aggcttcgag ccattgatgg agaagacaag aagacagatt aacccctcga   4740
atttccccga tcgttcaaac atttggcaat aaagtttctt aagattgaat cctgttgccg   4800
gtcttgcgat gattatcata taatttctgt tgaattacgt taagcatgta ataattaaca   4860
tgtaatgcat gacgttattt atgagatggg tttttatgat tagagtcccg caattataca   4920
tttaatacgc gatagaaaac aaaatatagc gcgcaaacta ggataaatta tcgcgcgcgg   4980
tgtcatctat gttactagat cgggaattca ctggccgtcg ttttacaacg tcgtgactgg   5040
gaaaaccctg gcgttaccca acttaatcgc cttgcagcac atccccctttt cgccagctgg   5100
cgtaatagcg aagaggcccg caccgatcgc ccttcccaac agttgcgcag cctgaatggc   5160
gcccgctcct ttcgctttct tcccttcctt tctcgccacg ttcgccggct ttccccgtca   5220
agctctaaat cgggggctcc ctttagggtt ccgatttagt gctttacggc acctcgaccc   5280
caaaaaactt gatttgggtg atggttcacg tagtgggcca tcgccctgat agacggtttt   5340
tcgccctttg acgttggagt ccacgttctt taatagtgga ctcttgttcc aaactggaac   5400
aacactcaac cctatctcgg gctattcttt tgatttataa gggattttgc cgatttcgga   5460
accaccatca aacaggattt tcgcctgctg gggcaaacca gcgtggaccg cttgctgcaa   5520
```

-continued ctctctcagg gccaggcggt gaagggcaat cagctgttgc ccgtctcact ggtgaaaaga 5580
aaaaccaccc cagtacatta aaaacgtccg caatgtgtta ttaagttgtc taagcgtcaa 5640
tttgtttaca ccacaatata tcctgcca 5668

<210> SEQ ID NO 146
<211> LENGTH: 6598
<212> TYPE: DNA
<213> ORGANISM: Artificial Sequence
<220> FEATURE:
<223> OTHER INFORMATION: Description of Artificial Sequence:Plasmid pRD29A-HP-BnCPP

<400> SEQUENCE: 146
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860

-continued

```
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag accagtgtcc cagctcgtgt gcaataaccg   3480
ccacaatttc attctcattc tggcactgct gaatcaatgt gtcataaaga acaatccttt   3540
tgttcttgaa gaaaccatac atgtaagcat tactatggct tgaccttgta gatccatcga   3600
caacaaacag cttcttcaga ggaaacttta gagaagaagc aagtttctca atcttctccc   3660
ggaggtctcc atcaggaaga ggagtgaact tgttgaaaag aggtgcaatc aaaacagggt   3720
atatagtcat catcactaga gacaggataa acatgaatgc ccacagatag atggcgaggt   3780
aaggacctcc tttctgaact ataacaataa ttgcggcaac gataggaggg gcaggtatga   3840
cagagaggag tattcctttg atcatgtccc taatgaacat ccatattgtt tgtttgttga   3900
acccatgccg agactcgatc acgaaagttg agtacaaaga aaatggcaaa tcagtgatct   3960
gtgaccatgt cataagacca gccaagaatg aaagagtgtg caggatttca ttctctggat   4020
cgagtcccac cattggtaga aggatcccca tctacccgct tcgcgtcggc atccggtcag   4080
tggcagtgaa gggcgaacag ttcctgatta accacaaacc gttctacttt actggctttg   4140
gtcgtcatga agatgcggac ttgcgtggca aaggattcga taacgtgctg atggtgcacg   4200
```

-continued

```
accacgcatt aatggactgg attggggcca actcctaccg tacctcgcat taccccttacg   4260
ctgaagagat gctcgactgg gcagatgaac atggcatcgt ggtgattgat gaaactgctg   4320
ctgtcggctt ttcgctctct ttaggcattg gtttcgaagc gggcaacaag ccgaaagaac   4380
tgtacagcga agaggcagtc aacggggaaa ctcagcaagc gcacttacag gcgattaaag   4440
agctgatagc gcgtgacaaa aaccacccaa gcgtggtgat gtggagtatt gccaacgaac   4500
cggatacccg tccgcaaggt gcacgggaat atttcgcgcc actggcggaa gcaacgcgta   4560
aactcgaccc gacgcgtccg atcacctgcg tcaatgtaat gttctgcgac gctcacaccg   4620
ataccatcag cgatctcttt gatgtgctgt gcctgaaccg ttattacgga tggtatgtcc   4680
aaagcggcga tttggaaacg gcagagaagg tactggaaaa agaacttctg gcctggcagg   4740
agaaactgta caccgacatg tggagtgaag agtatcagtg tgcatggctg gatatgtatc   4800
accgcgtctt tgatcgcgtc agcgccgtcg tcggtgaaca ggtatggaat ttcgccgatt   4860
ttgcgacctc gcaaggcata ttgcgcgttg gcggtaacaa gaaagggatc ttcactcgcg   4920
accgcaaacc gaagtcggcg gcttttctgc tgcaaaaacg ctggactggc atgaacttcg   4980
gtgaaaaacc gcagcaggga ggcaaacaat gaatcaacaa ctctcctggc gcaccatcgt   5040
cggctacagc ctcgggaatt gctaccgagc tcttctacca atggtgggac tcgatccaga   5100
gaatgaaatc ctgcacactc tttcattctt ggctggtctt atgacatggt cacagatcac   5160
tgatttgcca ttttctttgt actcaacttt cgtgatcgag tctcggcatg ggttcaacaa   5220
acaaacaata tggatgttca ttagggacat gatcaaagga atactcctct ctgtcatacc   5280
tgcccctcct atcgttgccg caattattgt tatagttcag aaaggaggtc cttacctcgc   5340
catctatctg tgggcattca tgtttatcct gtctctagtg atgatgacta tataccctgt   5400
tttgattgca cctcttttca acaagttcac tcctcttcct gatggagacc tccgggagaa   5460
gattgagaaa cttgcttctt ctctaaagtt tcctctgaag aagctgtttg ttgtcgatgg   5520
atctacaagg tcaagccata gtaatgctta catgtatggt ttcttcaaga acaaaaggat   5580
tgttctttat gacacattga ttcagcagtg ccagaatgag aatgaaattg tggcggttat   5640
tgcacacgag ctgggacact gggagctcga atttccccga tcgttcaaac atttggcaat   5700
aaagtttctt aagattgaat cctgttgccg gtcttgcgat gattatcata taatttctgt   5760
tgaattacgt taagcatgta ataattaaca tgtaatgcat gacgttattt atgagatggg   5820
tttttatgat tagagtcccg caattataca tttaatacgc gatagaaaac aaaatatagc   5880
gcgcaaacta ggataaatta tcgcgcgcgg tgtcatctat gttactagat cgggaattca   5940
ctggccgtcg ttttacaacg tcgtgactgg gaaaaccctg gcgttaccca acttaatcgc   6000
cttgcagcac atccccctttt cgccagctgg cgtaatagcg aagaggcccg caccgatcgc   6060
ccttcccaac agttgcgcag cctgaatggc gcccgctcct ttcgctttct tcccttcctt   6120
tctcgccacg ttcgccggct ttccccgtca agctctaaat cgggggctcc ctttagggtt   6180
ccgatttagt gctttacggc acctcgaccc caaaaaactt gatttgggtg atggttcacg   6240
tagtgggcca tcgccctgat agacggtttt tcgccctttg acgttggagt ccacgttctt   6300
taatagtgga ctcttgttcc aaactggaac aacactcaac cctatctcgg gctattcttt   6360
tgatttataa gggattttgc cgatttcgga accaccatca aacaggattt tcgcctgctg   6420
gggcaaacca gcgtggaccg cttgctgcaa ctctctcagg gccaggcggt gaagggcaat   6480
cagctgttgc ccgtctcact ggtgaaaaga aaaaccaccc cagtacatta aaaacgtccg   6540
caatgtgtta ttaagttgtc taagcgtcaa tttgtttaca ccacaatata tcctgcca     6598
```

-continued

<210> SEQ ID NO 147
<211> LENGTH: 5668
<212> TYPE: DNA
<213> ORGANISM: Artificial Sequence
<220> FEATURE:
<223> OTHER INFORMATION: Description of Artificial Sequence: Plasmid
pRD29A-antisense-BnCPP

<400> SEQUENCE: 147

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
```

-continued

```
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctta atctgtcttc ttgtcttctc   3480
catcaatggc tcgaagcctc tctacaagag gagggtgtga gtagtgataa gctgagtaca   3540
atgggtctgt gttcatcgct gataagttct cttcctgtag cttcactagg gcaggacgta   3600
gatcctttgc ataaccaaga ttcactgcaa aagcatcagc ctgaaactca aacgctcgac   3660
taacaaggtt gaggtcaaag cttactaggt gttgaagtgg tattacagtg tgctgaaata   3720
tgatcaaacc aatgagaact ggttgtgtat caaaaccaaa actcctgaag agatcagtgg   3780
agtttctgac aagagtgtat cctccaaatt gcaagaaggc aaggatttga acagcaatga   3840
acgagtatgt agtgtgattc agcttccagt gtcccagctc gtgtgcaata accgccacaa   3900
tttcattctc attctggcac tgctgaatca atgtgtcata aagaacaatc cttttgttct   3960
tgaagaaacc atacatgtaa gcattactat ggcttgacct tgtagatcca tcgacaacaa   4020
acagcttctt cagaggaaac tttagagaag aagcaagttt ctcaatcttc tcccggaggt   4080
ctccatcagg aagaggagtg aacttgttga aaagaggtgc aatcaaaaca gggtatatag   4140
tcatcatcac tagagacagg ataaacatga atgcccacag atagatggcg aggtaaggac   4200
ctcctttctg aactataaca ataattgcgg caacgatagg aggggcaggt atgacagaga   4260
ggagtattcc tttgatcatg tccctaatga acatccatat tgtttgtttg ttgaacccat   4320
gccgagactc gatcacgaaa gttgagtaca aagaaaatgg caaatcagtg atctgtgacc   4380
```

-continued

```
atgtcataag accagccaag aatgaaagag tgtgcaggat ttcattctct ggatcgagtc   4440

ccaccattgg tagaaagccg ccagatatct tccaaaacca aggcaagatc ccaaagaaca   4500

gaatcgcaga gtccataagt atagtaacaa actcatgaac aaagtgaaaa tggcttttgt   4560

caagactgta agctcgagat ttctcaaact tctcttggct aatgactcca accaaagtct   4620

ttgggagagt gggaagcttg agagcagtat gttgcctcag atccaaatac gtctcaaaaa   4680

cgtacatcac tatcataaaa ccaacgacgg tttccatgaa aggaatcgcc atcccctcga   4740

atttccccga tcgttcaaac atttggcaat aaagtttctt aagattgaat cctgttgccg   4800

gtcttgcgat gattatcata taatttctgt tgaattacgt taagcatgta ataattaaca   4860

tgtaatgcat gacgttattt atgagatggg tttttatgat tagagtcccg caattataca   4920

tttaatacgc gatagaaaac aaaatatagc gcgcaaacta ggataaatta tcgcgcgcgg   4980

tgtcatctat gttactagat cgggaattca ctggccgtcg ttttacaacg tcgtgactgg   5040

gaaaaccctg gcgttaccca acttaatcgc cttgcagcac atcccccttt cgccagctgg   5100

cgtaatagcg aagaggcccg caccgatcgc ccttcccaac agttgcgcag cctgaatggc   5160

gcccgctcct ttcgctttct tcccttcctt tctcgccacg ttcgccggct ttccccgtca   5220

agctctaaat cgggggctcc ctttagggtt ccgatttagt gctttacggc acctcgaccc   5280

caaaaaactt gatttgggtg atggttcacg tagtgggcca tcgccctgat agacggtttt   5340

tcgccctttg acgttggagt ccacgttctt taatagtgga ctcttgttcc aaactggaac   5400

aacactcaac cctatctcgg gctattcttt tgatttataa gggattttgc cgatttcgga   5460

accaccatca aacaggattt tcgcctgctg gggcaaacca gcgtggaccg cttgctgcaa   5520

ctctctcagg gccaggcggt gaagggcaat cagctgttgc ccgtctcact ggtgaaaaga   5580

aaaaccaccc cagtacatta aaaacgtccg caatgtgtta ttaagttgtc taagcgtcaa   5640

tttgtttaca ccacaatata tcctgcca                                      5668
```

```
<210> SEQ ID NO 148
<211> LENGTH: 5074
<212> TYPE: DNA
<213> ORGANISM: Artificial Sequence
<220> FEATURE:
<223> OTHER INFORMATION: Description of Artificial Sequence: Plasmid
      MuA-BnCPP

<400> SEQUENCE: 148
```

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720
```

-continued

```
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
atagacgaaa aggaaggtgg ctcctataaa gcacatcatt gcgataacag aaaggccatt   2640
gttgaagata cctctgctga cattggtccc caagtggaag caccacccca tgaggagcac   2700
cgtggagtaa gaagacgttc gagccacgtc gaaaaagcaa gtgtgttgat gtagtatctc   2760
cattgacgta agggatgacg cacaatccaa ctatccatcg caagaccatt gctctatata   2820
agaaagttaa tatcatttcg agtggccacg ctgaggggga tccatggcga ttcctttcat   2880
ggaaaccgtc gttggtttta tgatagtgat gtacgttttt gagacgtatt tggatctgag   2940
gcaacatact gctctcaagc ttcccactct cccaaagact ttggttggag tcattagcca   3000
agagaagttt gagaaatctc gagcttacag tcttgacaaa agccattttc actttgttca   3060
tgagtttgtt actatactta tggactctgc gattctgttc tttgggatct tgccttggtt   3120
```

-continued

```
ttggaagata tctggcggct ttctaccaat ggtgggactc gatccagaga atgaaatcct   3180

gcacactctt tcattcttgg ctggtcttat gacatggtca cagatcactg atttgccatt   3240

ttctttgtac tcaactttcg tgatcgagtc tcggcatggg ttcaacaaac aaacaatatg   3300

gatgttcatt agggacatga tcaaaggaat actcctctct gtcatacctg cccctcctat   3360

cgttgccgca attattgtta tagttcagaa aggaggtcct tacctcgcca tctatctgtg   3420

ggcattcatg tttatcctgt ctctagtgat gatgactata taccctgttt tgattgcacc   3480

tcttttcaac aagttcactc ctcttcctga tggagacctc cgggagaaga ttgagaaact   3540

tgcttcttct ctaaagtttc ctctgaagaa gctgtttgtt gtcgatggat ctacaaggtc   3600

aagccatagt aatgcttaca tgtatggttt cttcaagaac aaaaggattg ttctttatga   3660

cacattgatt cagcagtgcc agaatgagaa tgaaattgtg gcggttattg cacacgagct   3720

gggacactgg aagctgaatc acactacata ctcgttcatt gctgttcaaa tccttgcctt   3780

cttgcaattt ggaggataca ctcttgtcag aaactccact gatctcttca ggagttttgg   3840

ttttgataca caaccagttc tcattggttt gatcatattt cagcacactg taataccact   3900

tcaacaccta gtaagctttg acctcaacct tgttagtcga gcgtttgagt ttcaggctga   3960

tgcttttgca gtgaatcttg gttatgcaaa ggatctacgt cctgccctag tgaagctaca   4020

ggaagagaac ttatcagcga tgaacacaga cccattgtac tcagcttatc actactcaca   4080

ccctcctctt gtagagaggc ttcgagccat tgatggagaa gacaagaaga cagattaacc   4140

cctcgaattt ccccgatcgt tcaaacattt ggcaataaag tttcttaaga ttgaatcctg   4200

ttgccggtct tgcgatgatt atcatataat ttctgttgaa ttacgttaag catgtaataa   4260

ttaacatgta atgcatgacg ttatttatga gatgggtttt tatgattaga gtcccgcaat   4320

tatacattta atacgcgata gaaaacaaaa tatagcgcgc aaactaggat aaattatcgc   4380

gcgcggtgtc atctatgtta ctagatcggg aattcactgg ccgtcgtttt acaacgtcgt   4440

gactgggaaa accctggcgt tacccaactt aatcgccttg cagcacatcc ccctttcgcc   4500

agctggcgta atagcgaaga ggcccgcacc gatcgccctt cccaacagtt gcgcagcctg   4560

aatggcgccc gctcctttcg ctttcttccc ttcctttctc gccacgttcg ccggctttcc   4620

ccgtcaagct ctaaatcggg ggctcccttt agggttccga tttagtgctt tacggcacct   4680

cgaccccaaa aaacttgatt tgggtgatgg ttcacgtagt gggccatcgc cctgatagac   4740

ggtttttcgc cctttgacgt tggagtccac gttctttaat agtggactct tgttccaaac   4800

tggaacaaca ctcaacccta tctcgggcta ttcttttgat ttataaggga ttttgccgat   4860

ttcggaacca ccatcaaaca ggattttcgc ctgctggggc aaaccagcgt ggaccgcttg   4920

ctgcaactct ctcagggcca ggcggtgaag ggcaatcagc tgttgcccgt ctcactggtg   4980

aaaagaaaaa ccaccccagt acattaaaaa cgtccgcaat gtgttattaa gttgtctaag   5040

cgtcaatttg tttacaccac aatatatcct gcca                               5074
```

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 149

```
aaacccggga tggcgtttcc ctacatggaa gcc                                  33
```

-continued

<210> SEQ ID NO 150
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 150
aaagagctct tagtcttcct tcttatccgg ttcg 34

<210> SEQ ID NO 151
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 151
aaacccggga tggcgattcc tttcatgg 28

<210> SEQ ID NO 152
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 152
aaaggatcct taatctgtct tcttgtcttc tcc 33

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 153
aaagagctct tctaccaatg gtgggactcg 30

<210> SEQ ID NO 154
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 154
aaagagctcc cagtgtccca gctcgtgtg 29

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 155
aaaggatcct tctaccaatg gtgggactcg 30

<210> SEQ ID NO 156
<211> LENGTH: 29
<212> TYPE: DNA
<213> ORGANISM: Artificial Sequence
<220> FEATURE:
<223> OTHER INFORMATION: Description of Artificial Sequence: PCR Primer -continued

<400> SEQUENCE: 156
aaatctagac cagtgtccca gctcgtgtg 29

<210> SEQ ID NO 157
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 157
gatgagctca caagatcaag tcacagcaat gcct 34

<210> SEQ ID NO 158
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 158
aaagagctcc cggttcgtcc agcgcggcc 29

<210> SEQ ID NO 159
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 159
gatggatcca caagatcaag tcacagcaat gcct 34

<210> SEQ ID NO 160
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 160
ccttctagac cggttcgtcc agcgcggcc 29

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 161
tttaagcttg gagccataga tgcaattcaa 30

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 162
gcaagaccgg caacagga 18

<210> SEQ ID NO 163

-continued

<211> LENGTH: 603
<212> TYPE: DNA
<213> ORGANISM: Artificial Sequence
<220> FEATURE:
<223> OTHER INFORMATION: Description of Artificial Sequence: Consensus
sequence BASF

<400> SEQUENCE: 163

```
gttcgagaat gaatatcaac cttcttcttg cggatgtggt ccaatacgat tgcctttctt     60

tatcaacttt gtatgagccg catggttaaa acaaacatgg tttcttaggg aatgtaaagg    120

aattcttcta tatggccacc atgtgcgcat atatagtcag aggaggccta tgcattatct    180

tgggttagtt ttctttgatg atgacttacc ttatagcccc tttcaaaagt tcactccctt    240

ccgaggctcg ggaaaatgag aactgcctcc taattcctta aaactttgtg tgatggtcac    300

agtcaagcaa gaatgctaat gtatggtttt aagaacaaga tgtcttatga acttattcac    360

agtgaagaga gaatgtcgtt atgccagatg gacatggaac taacaactta ctttgctcat    420

cttttcaatt tggaggataa cctgtgatcg atcttgagtt ggttacagcc gttattggta    480

tcatttcgca actaatcctc acatagcttt gctaacctgt aggactttga tttcaggctg    540

atgtttgcga acttggtatg ctcgctgtaa actacaggag agaattcgca tgaaacgatc    600

tgc                                                                  603
```

<210> SEQ ID NO 164
<211> LENGTH: 525
<212> TYPE: PRT
<213> ORGANISM: Artificial Sequence
<220> FEATURE:
<223> OTHER INFORMATION: Description of Artificial Sequence: Consensus
sequence BASF
<220> FEATURE:
<221> NAME/KEY: VARIANT
<222> LOCATION: (1)..(101)
<223> OTHER INFORMATION: Wherein Xaa is any amino acid.
<220> FEATURE:
<221> NAME/KEY: VARIANT
<222> LOCATION: (106)
<223> OTHER INFORMATION: Wherein Xaa is any amino acid.
<220> FEATURE:
<221> NAME/KEY: VARIANT
<222> LOCATION: (110)
<223> OTHER INFORMATION: Wherein Xaa is any amino acid.
<220> FEATURE:
<221> NAME/KEY: VARIANT
<222> LOCATION: (115)
<223> OTHER INFORMATION: Wherein Xaa is any amino acid.
<220> FEATURE:
<221> NAME/KEY: VARIANT
<222> LOCATION: (120)
<223> OTHER INFORMATION: Wherein Xaa is any amino acid.
<220> FEATURE:
<221> NAME/KEY: VARIANT
<222> LOCATION: (136)
<223> OTHER INFORMATION: Wherein Xaa is any amino acid.
<220> FEATURE:
<221> NAME/KEY: VARIANT
<222> LOCATION: (145)
<223> OTHER INFORMATION: Wherein Xaa is any amino acid.
<220> FEATURE:
<221> NAME/KEY: VARIANT
<222> LOCATION: (147)
<223> OTHER INFORMATION: Wherein Xaa is any amino acid.
<220> FEATURE:
<221> NAME/KEY: VARIANT
<222> LOCATION: (149)
<223> OTHER INFORMATION: Wherein Xaa is any amino acid.
<220> FEATURE:
<221> NAME/KEY: VARIANT
<222> LOCATION: (153)
<223> OTHER INFORMATION: Wherein Xaa is any amino acid.

-continued

<220> FEATURE:
<221> NAME/KEY: VARIANT
<222> LOCATION: (156)..(157)
<223> OTHER INFORMATION: Wherein Xaa is any amino acid.
<220> FEATURE:
<221> NAME/KEY: VARIANT
<222> LOCATION: (160)
<223> OTHER INFORMATION: Wherein Xaa is any amino acid.
<220> FEATURE:
<221> NAME/KEY: VARIANT
<222> LOCATION: (162)
<223> OTHER INFORMATION: Wherein Xaa is any amino acid.
<220> FEATURE:
<221> NAME/KEY: VARIANT
<222> LOCATION: (172)
<223> OTHER INFORMATION: Wherein Xaa is any amino acid.
<220> FEATURE:
<221> NAME/KEY: VARIANT
<222> LOCATION: (176)
<223> OTHER INFORMATION: Wherein Xaa is any amino acid.
<220> FEATURE:
<221> NAME/KEY: VARIANT
<222> LOCATION: (187)
<223> OTHER INFORMATION: Wherein Xaa is any amino acid.
<220> FEATURE:
<221> NAME/KEY: VARIANT
<222> LOCATION: (189)
<223> OTHER INFORMATION: Wherein Xaa is any amino acid.
<220> FEATURE:
<221> NAME/KEY: VARIANT
<222> LOCATION: (191)
<223> OTHER INFORMATION: Wherein Xaa is any amino acid.
<220> FEATURE:
<221> NAME/KEY: VARIANT
<222> LOCATION: (193)..(195)
<223> OTHER INFORMATION: Wherein Xaa is any amino acid.
<220> FEATURE:
<221> NAME/KEY: VARIANT
<222> LOCATION: (195)
<223> OTHER INFORMATION: Wherein Xaa is any amino acid.
<220> FEATURE:
<221> NAME/KEY: VARIANT
<222> LOCATION: (199)
<223> OTHER INFORMATION: Wherein Xaa is any amino acid.
<220> FEATURE:
<221> NAME/KEY: VARIANT
<222> LOCATION: (202)
<223> OTHER INFORMATION: Wherein Xaa is any amino acid.
<220> FEATURE:
<221> NAME/KEY: VARIANT
<222> LOCATION: (203)
<223> OTHER INFORMATION: Wherein Xaa is any amino acid.
<220> FEATURE:
<221> NAME/KEY: VARIANT
<222> LOCATION: (216)
<223> OTHER INFORMATION: Wherein Xaa is any amino acid.
<220> FEATURE:
<221> NAME/KEY: VARIANT
<222> LOCATION: (218)
<223> OTHER INFORMATION: Wherein Xaa is any amino acid.
<220> FEATURE:
<221> NAME/KEY: VARIANT
<222> LOCATION: (228)
<223> OTHER INFORMATION: Wherein Xaa is any amino acid.
<220> FEATURE:
<221> NAME/KEY: VARIANT
<222> LOCATION: (231)..(232)
<223> OTHER INFORMATION: Wherein Xaa is any amino acid.
<220> FEATURE:
<221> NAME/KEY: VARIANT
<222> LOCATION: (273)..(276)
<223> OTHER INFORMATION: Wherein Xaa is any amino acid.
<220> FEATURE:
<221> NAME/KEY: VARIANT
<222> LOCATION: (280)
<223> OTHER INFORMATION: Wherein Xaa is any amino acid.
<220> FEATURE:
<221> NAME/KEY: VARIANT
<222> LOCATION: (295)

-continued

<223> OTHER INFORMATION: Wherein Xaa is any amino acid.
<220> FEATURE:
<221> NAME/KEY: VARIANT
<222> LOCATION: (297)
<223> OTHER INFORMATION: Wherein Xaa is any amino acid.
<220> FEATURE:
<221> NAME/KEY: VARIANT
<222> LOCATION: (299)
<223> OTHER INFORMATION: Wherein Xaa is any amino acid.
<220> FEATURE:
<221> NAME/KEY: VARIANT
<222> LOCATION: (301)
<223> OTHER INFORMATION: Wherein Xaa is any amino acid.
<220> FEATURE:
<221> NAME/KEY: VARIANT
<222> LOCATION: (303)
<223> OTHER INFORMATION: Wherein Xaa is any amino acid.
<220> FEATURE:
<221> NAME/KEY: VARIANT
<222> LOCATION: (305)..(306)
<223> OTHER INFORMATION: Wherein Xaa is any amino acid.
<220> FEATURE:
<221> NAME/KEY: VARIANT
<222> LOCATION: (317)
<223> OTHER INFORMATION: Wherein Xaa is any amino acid.
<220> FEATURE:
<221> NAME/KEY: VARIANT
<222> LOCATION: (319)
<223> OTHER INFORMATION: Wherein Xaa is any amino acid.
<220> FEATURE:
<221> NAME/KEY: VARIANT
<222> LOCATION: (322)..(323)
<223> OTHER INFORMATION: Wherein Xaa is any amino acid.
<220> FEATURE:
<221> NAME/KEY: VARIANT
<222> LOCATION: (328)..(329)
<223> OTHER INFORMATION: Wherein Xaa is any amino acid.
<220> FEATURE:
<221> NAME/KEY: VARIANT
<222> LOCATION: (333)
<223> OTHER INFORMATION: Wherein Xaa is any amino acid.
<220> FEATURE:
<221> NAME/KEY: VARIANT
<222> LOCATION: (340)
<223> OTHER INFORMATION: Wherein Xaa is any amino acid.
<220> FEATURE:
<221> NAME/KEY: VARIANT
<222> LOCATION: (343)
<223> OTHER INFORMATION: Wherein Xaa is any amino acid.
<220> FEATURE:
<221> NAME/KEY: VARIANT
<222> LOCATION: (346)
<223> OTHER INFORMATION: Wherein Xaa is any amino acid.
<220> FEATURE:
<221> NAME/KEY: VARIANT
<222> LOCATION: (348)..(350)
<223> OTHER INFORMATION: Wherein Xaa is any amino acid.
<220> FEATURE:
<221> NAME/KEY: VARIANT
<222> LOCATION: (353)
<223> OTHER INFORMATION: Wherein Xaa is any amino acid.
<220> FEATURE:
<221> NAME/KEY: VARIANT
<222> LOCATION: (360)
<223> OTHER INFORMATION: Wherein Xaa is any amino acid.
<220> FEATURE:
<221> NAME/KEY: VARIANT
<222> LOCATION: (367)
<223> OTHER INFORMATION: Wherein Xaa is any amino acid.
<220> FEATURE:
<221> NAME/KEY: VARIANT
<222> LOCATION: (370)..(371)
<223> OTHER INFORMATION: Wherein Xaa is any amino acid.
<220> FEATURE:
<221> NAME/KEY: VARIANT
<222> LOCATION: (376)..(377)
<223> OTHER INFORMATION: Wherein Xaa is any amino acid.
<220> FEATURE:
<221> NAME/KEY: VARIANT

```
<222> LOCATION: (380)..(381)
<223> OTHER INFORMATION: Wherein Xaa is any amino acid.
<220> FEATURE:
<221> NAME/KEY: VARIANT
<222> LOCATION: (394)
<223> OTHER INFORMATION: Wherein Xaa is any amino acid.
<220> FEATURE:
<221> NAME/KEY: VARIANT
<222> LOCATION: (398)..(525)
<223> OTHER INFORMATION: Wherein Xaa is any amino acid.

<400> SEQUENCE: 164

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Glu Asn Glu Ile Xaa His Thr Leu Xaa Phe Leu
            100                 105                 110

Ala Gly Xaa Met Xaa Trp Ser Xaa Ile Thr Asp Leu Pro Phe Ser Leu
        115                 120                 125

Tyr Ser Thr Phe Val Ile Glu Xaa Arg His Gly Phe Asn Lys Gln Thr
    130                 135                 140

Xaa Trp Xaa Phe Xaa Arg Asp Met Xaa Lys Gly Xaa Xaa Leu Ser Xaa
145                 150                 155                 160

Ile Xaa Gly Pro Pro Ile Val Ala Ala Ile Ile Xaa Ile Val Gln Xaa
                165                 170                 175

Gly Gly Pro Tyr Leu Ala Ile Tyr Leu Trp Xaa Phe Xaa Phe Xaa Leu
            180                 185                 190

Xaa Xaa Xaa Met Met Thr Xaa Tyr Pro Xaa Xaa Ile Ala Pro Leu Phe
        195                 200                 205

Asn Lys Phe Thr Pro Leu Pro Xaa Gly Xaa Leu Arg Glu Lys Ile Glu
    210                 215                 220

Lys Leu Ala Xaa Ser Leu Xaa Xaa Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Xaa Xaa Xaa Xaa Glu Ile Val Xaa Val Ile Ala His Glu Leu Gly His
        275                 280                 285

Trp Lys Leu Asn His Thr Xaa Tyr Xaa Phe Xaa Ala Xaa Gln Xaa Leu
    290                 295                 300

Xaa Xaa Leu Gln Phe Gly Gly Tyr Thr Leu Val Arg Xaa Ser Xaa Asp
305                 310                 315                 320

Leu Xaa Xaa Ser Phe Gly Phe Xaa Xaa Gln Pro Val Xaa Ile Gly Leu
                325                 330                 335

Ile Ile Phe Xaa His Thr Xaa Ile Pro Xaa Gln Xaa Xaa Xaa Ser Phe
            340                 345                 350
```

-continued

```
Xaa Leu Asn Leu Val Ser Arg Xaa Phe Glu Phe Gln Ala Asp Xaa Phe
        355                 360                 365

Ala Xaa Xaa Leu Gly Tyr Ala Xaa Xaa Leu Arg Xaa Xaa Leu Val Lys
    370                 375                 380

Leu Gln Glu Glu Asn Leu Ser Ala Met Xaa Thr Asp Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa
        515                 520                 525
```

<210> SEQ ID NO 165
<211> LENGTH: 1249
<212> TYPE: DNA
<213> ORGANISM: Artificial Sequence
<220> FEATURE:
<223> OTHER INFORMATION: Description of Artificial Sequence: Consensus
sequence Generic

<400> SEQUENCE: 165

```
atctctttat tggttttatg atagtgatgt acatttttga gacgtatttg gatctgaggc     60

aactcactgc tctcaagctt ccaactctcc cgaaaacctt ggttggtgta attagccaag    120

agaagtttga gaaatcacga gcatacagtt aaaagctatt ttcactttgt tcatgagttt    180

gtaactatac ttatggactc tgcaattttg ttctttggga tcttgccttg gttttggaag    240

atgtctggag ctgttttacc gaggttgggc cttgatccag agaatgaaat actgcatact    300

ctttcattct tggctggtgt tatgacatgg tcacagatca ctgatttgcc attttctttg    360

tactcaactt tcgtgatcga gtctcggcat gggttcaaca aacaaacaat atggatgttc    420

attagggaca tgatcaaagg aacattcctc tctgtcatac taggcccacc cattgttgct    480

gcgataattt tcatagtcca gaaaggaggt ccttatcttg ccatctatct gtgggcattc    540

atgtttatcc tgtctctagt gatgatgact atatacccgg tcttgatagc accgctcttc    600

aacaagttca ctcctcttcc agatggagac ctccgggaga agattgagaa acttgcttct    660

tctctaaagt ttcctttgaa gaagctgttt gttgtcgatg gatctacaag gtcaagccat    720

agcaatgctt acatgtatgg tttctttaag aacaaaagga ttgttcttta tgatacgttg    780

attcagcagt gcaagaatga ggatgaaatt gtggcggtta ttgcacacga gcttggacat    840

tggaaactga atcacactac atactcgttc attgcagttc aaatccttgc cttcttacaa    900

tttggaggat acactcttgt cagaaactcc actgatctct tcaggagttt cggatttgat    960

acacagcctg ttctcattgg tttgatcata tttcagcaca ctgtaatacc actgcaacat   1020

ctagtaagct ttggcctgaa cctcgttagt cgagcgtttg agtttcaggc tgatgctttt   1080
```

-continued

```
gcgtgaagct tggctatgca aaagatcttc gtcctgctct agtgaaacta caggaagaga   1140

acttatcagc aatgaacact gatccattga ctcagcttat cactactcac atcctcctct   1200

tgttgaaagg cttcgagcca ttgatggaga agacaagaag acagattaa               1249


<210> SEQ ID NO 166
<211> LENGTH: 459
<212> TYPE: PRT
<213> ORGANISM: Artificial Sequence
<220> FEATURE:
<223> OTHER INFORMATION: Description of Artificial Sequence: Consensus
      sequence generic
<220> FEATURE:
<221> NAME/KEY: VARIANT
<222> LOCATION: (41)..(97)
<223> OTHER INFORMATION: Wherein Xaa is any amino acid.
<220> FEATURE:
<221> NAME/KEY: VARIANT
<222> LOCATION: (98)..(320)
<223> OTHER INFORMATION: Wherein Xaa is any amino acid.
<220> FEATURE:
<221> NAME/KEY: VARIANT
<222> LOCATION: (322)
<223> OTHER INFORMATION: Wherein Xaa is any amino acid.
<220> FEATURE:
<221> NAME/KEY: VARIANT
<222> LOCATION: (324)..(343)
<223> OTHER INFORMATION: Wherein Xaa is any amino acid.
<220> FEATURE:
<221> NAME/KEY: VARIANT
<222> LOCATION: (345)..(346)
<223> OTHER INFORMATION: Wherein Xaa is any amino acid.
<220> FEATURE:
<221> NAME/KEY: VARIANT
<222> LOCATION: (349)
<223> OTHER INFORMATION: Wherein Xaa is any amino acid.
<220> FEATURE:
<221> NAME/KEY: VARIANT
<222> LOCATION: (351)..(355)
<223> OTHER INFORMATION: Wherein Xaa is any amino acid.
<220> FEATURE:
<221> NAME/KEY: VARIANT
<222> LOCATION: (359)..(366)
<223> OTHER INFORMATION: Wherein Xaa is any amino acid.
<220> FEATURE:
<221> NAME/KEY: VARIANT
<222> LOCATION: (369)..(384)
<223> OTHER INFORMATION: Wherein Xaa is any amino acid.
<220> FEATURE:
<221> NAME/KEY: VARIANT
<222> LOCATION: (386)..(417)
<223> OTHER INFORMATION: Wherein Xaa is any amino acid.
<220> FEATURE:
<221> NAME/KEY: VARIANT
<222> LOCATION: (419)..(424)
<223> OTHER INFORMATION: Wherein Xaa is any amino acid.

<400> SEQUENCE: 166

Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95
```

-continued

```
Xaa Gly Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Leu Xaa Arg Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Ile Xaa Xaa Gln His Xaa Val Xaa Xaa
            340                 345                 350

Xaa Xaa Xaa Leu Val Ser Xaa Xaa Xaa Xaa Xaa Xaa Xaa Xaa Ala Phe
        355                 360                 365

Xaa Xaa Xaa Xaa Xaa Xaa Xaa Xaa Xaa Xaa Xaa Xaa Xaa Xaa Xaa Xaa
    370                 375                 380

Leu Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Gly Xaa Xaa Xaa Xaa Xaa Xaa Leu Ser Ala Met Asn Thr Asp Pro
            420                 425                 430

Leu Tyr Ser Ala Tyr His Tyr Ser His Pro Pro Leu Val Glu Arg Leu
        435                 440                 445

Arg Ala Ile Asp Gly Glu Asp Lys Lys Thr Asp
    450                 455
```

<210> SEQ ID NO 167
<211> LENGTH: 945
<212> TYPE: DNA
<213> ORGANISM: Artificial Sequence
<220> FEATURE:
<223> OTHER INFORMATION: Description of Artificial Sequence: Consensus sequence PPI -continued

<400> SEQUENCE: 167

```
atggcgttcc tcatggaacc gtgtggttta tgatatatgt actttttgaa ctattggatt     60

ggcaacagcc tcaacttcca ctctccaaac ttggggtata gccaagagaa tttgagaaat    120

cgagctaagt cttgaaaaag cattcatttg ttcagagttt gtacatatag actctcattt    180

gtctttgggt ttgcctggtt ttggaagatc gggtttcagg tatcgagaat gaaatctgca    240

accttcttct tgcggtatga tggtcacaga tacgatttgc cttttcttgt actcaacttt    300

gtgatgagcc gcatggttaa aacaaacaat ggtttcttag ggacatgtaa aggaatcctt    360

ctgtatagcc ccatgtgcgc atatttatag tcagaaagga ggtcctatgc catctatctt    420

gggttagttt cttcttgtga tgatgactta ccgttatgcc cctttcaaaa ttcactccct    480

tccgatggac tcgggagaaa tgagaaactt gcttctccta attcctaaga acttttgttg    540

tcgatggatc acaagtcaag caagaatgct aatgtatggt tcttaagaac aaaggattgt    600

cttatgaact tattcacagt gcaagaagaa attgtgcgtt attgccagag tggacatgga    660

actaacaact taccttttgc tcaatcttct tcaatttgga ggataacctt gaaatcctga    720

tcttgagttg gtttgatacc accgtctcat tggtatcata tttcagcaac tgtaatccac    780

tcacatgtag ctttgctaac ctgtagcgac tttgatttca ggctgatgtt tgcgaacttg    840

tatgcagtcg tgctgtgaac tacaggagag aattcacatg aaacgacctg tactcgctta    900

tcactatcca cctcccttgt gaagtgcgag agaaagaaga gataa                    945
```

<210> SEQ ID NO 168
<211> LENGTH: 206
<212> TYPE: PRT
<213> ORGANISM: Artificial Sequence
<220> FEATURE:
<223> OTHER INFORMATION: Description of Artificial Sequence: Consensus
      sequence PPI

<400> SEQUENCE: 168

```
Met Ala Met Val Val Gly Met Met Tyr Thr Tyr Asp Arg His Ala Lys
  1               5                  10                  15

Thr Lys Thr Gly Val Ser Lys Lys Ser Arg Ala Tyr Ser Asp Lys Ser
             20                  25                  30

His His Val His Val Thr Asp Ser Gly Trp Trp Lys Ser Gly Gly Asn
         35                  40                  45

His Thr Ala Gly Met Trp Ser Thr Asp Ser Tyr Ser Thr Val Arg His
     50                  55                  60

Gly Asn Lys Thr Trp Arg Asp Met Lys Gly Ser Val Val Ala Ala Val
 65                  70                  75                  80

Val Lys Gly Gly Tyr Ala Tyr Trp Ser Val Met Met Thr Tyr Val Ala
                 85                  90                  95

Asn Lys Thr Asp Gly Arg Lys Lys Ala Ser Ser Lys Lys Val Val Asp
            100                 105                 110

Gly Ser Thr Arg Ser Ser His Ser Asn Ala Tyr Met Tyr Gly Lys Asn
        115                 120                 125

Lys Arg Val Tyr Asp Thr Cys Val Ala Val Ala His Gly His Trp Lys
    130                 135                 140

Asn His Thr Tyr Ala Gly Gly Tyr Thr Val Arg Asn Ser Asp Arg Ser
145                 150                 155                 160

Gly Asp Thr Val Gly His Thr Val Val Ser Asn Val Ser Arg Ala Asp
                165                 170                 175

Ala Gly Tyr Ala Arg Val Lys Asn Ser Ala Met Asn Thr Asp Tyr Ser
```

-continued 180 185 190

Ala Tyr His Tyr Ser His Val Arg Ala Asp Asp Lys Lys Asp
195 200 205

<210> SEQ ID NO 169
<211> LENGTH: 151
<212> TYPE: PRT
<213> ORGANISM: Artificial Sequence
<220> FEATURE:
<223> OTHER INFORMATION: Description of Artificial Sequence: Consensus Sequence PPI/generic

<400> SEQUENCE: 169

Met Ala Met Val Val Gly Met Met Tyr Thr Tyr Asp Arg Ala Lys Thr
1 5 10 15

Lys Thr Thr Asp Ser Tyr Ser Thr Val Arg His Gly Asn Lys Thr Trp
20 25 30

Arg Asp Met Lys Gly Ser Val Val Ala Ala Val Lys Gly Gly Tyr Ala
35 40 45

Tyr Trp Ser Val Met Met Thr Tyr Val Ala Asn Lys Thr Asp Gly Arg
50 55 60

Lys Lys Ala Ser Ser Lys Lys Val Val Asp Gly Ser Thr Arg Ser Ser
65 70 75 80

His Ser Asn Ala Tyr Met Tyr Gly Lys Asn Lys Arg Val Tyr Asp Thr
85 90 95

Cys Val Ala Val Ala His Gly His Trp Lys Asn His Thr Tyr Ala His
100 105 110

Thr Val Val Ser Asn Val Ser Arg Ala Asp Ala Gly Tyr Ala Arg Val
115 120 125

Lys Asn Ser Ala Met Asn Thr Asp Ser Ala Tyr His Tyr Ser His Val
130 135 140

Arg Ala Asp Asp Lys Lys Asp
145 150

<210> SEQ ID NO 170
<211> LENGTH: 2765
<212> TYPE: DNA
<213> ORGANISM: Artificial Sequence
<220> FEATURE:
<223> OTHER INFORMATION: Description of Artificial Sequence: Consensus Sequence PPI/generic

<400> SEQUENCE: 170
atggcgattc ctttcatgga aaccgtcgtg gttttatgat atatgtacat ttttgaacta 60
tttggattgg caacatgcct caacttccac tctccaaact tggtggtgta tagccaagag 120
aagtttgaga aatctgagct acagtcttga aaaagcattc atttgttcag agtttgtaca 180
tagttagact ctcaattttg tctttgggtt tgcctggttt tggaagattc gggttttgca 240
attggtcatc gagaatgaaa tctgcatacc ttcttcttgc ggtatgatgg tcacagatac 300
gatttgcctt ttcttgtact caactttgtg atgagtccgc atggttaaaa caaacacatg 360
gtttcttagg gacatgtaaa ggaatttcct tctgtatagc ccctattgtg ctgcaatatt 420
gtatagtcag aaaggaggtc ctatgccatc tatcttgggt ttagttttct tcttgtgatg 480
atgaccttac cgttatgccc ctcttcaaaa gttcactccc ttccagatgg actcgggaga 540
aatgagaaac ttgcttctcc taattcctta agaactattt gttgtcgatg gatcacaagt 600
caagcataga atgctaatgt atggttctta agaacaaagg attgtcttat gacacattat 660

-continued

```
tcacagtgca agaagaaatt gtgcgttatt gccagagtgg gacactggaa ctaacaactt    720
acacattatt gcttcaatct tctttacaat ttggaggata cacctagtga aatcctgatc    780
ttgagttggt ttgataccag ccgtctcatt ggtatcatat ttcagcatac tgtaatccac    840
ttcacatgta gctttgctaa cctgtagcga ctttgatttc aggctgatgc tttgcgaagc    900
ttggtatgca gtcggtgtct agtgaactac aggagagaat gtcagcatga aacagatcct    960
tgtactcgct tatcactatc cacctccctt gtgaaagatg ctgagagaaa gaagagataa   1020
tctaaattct ttccttttca tggaggtaac aaagtatgtc gtatttccaa cactaccttg   1080
tgacttacgt ttttttatca gagatgtgga ttaaatttgc ttctaaattc tgttgacagc   1140
aaacaatatg gatgttcatt agggacatga tcaaaggaac attcctctct gtcatactag   1200
gcccacccat tgttgctgcg ataattttca tagtccaggt ttgatgattc tggattcatc   1260
ttatttctga gtttttcaca tggatgacta ttctccattg agtgtgagct tcaaagtttt   1320
tagttttcgt gttaaaaatt taaaatttgc ttctctgagc atgaagtttc tatctttttc   1380
cagaaaggag gtccttatct tgccatctat ctgtgggcat tcatgtttat cctgtctcta   1440
gtgatgatga ctatataccc ggtcttgata gcaccgctct tcaacaagtt cactcctgtg   1500
tgtatttctg tcatggccat tttacaattc actgcttgtt tgcatatgtt gttaccagac   1560
aatataatct cccgcttttt tatggctata gcttccagat ggagacctcc gggagaagat   1620
tgagaaactt gcttcttctc taaagtttcc tttgaagaag ctgtttgttg tcgatggatc   1680
tacaaggtca agccatagca atgtgagaag cttgagatct cttcctacct actttactct   1740
agtttaccat tagaagctta cgtatcttgt tacatcatac aggcttacat gtatggtttc   1800
tttaagaaca aaaggattgt tctttatgat acgttgattc agcaggtact gtgactcttg   1860
atgcttcaaa cgagctatac tcacatttct gtttctggtt ctgaaacata acataatctt   1920
ctattgtgca gtgcaagaat gaggatgaaa ttgtggcggt tattgcacac gagcttggac   1980
attggaaact gaatcacact acatactcgt tcattgcagt tcaagtgagg ctcaaccgac   2040
agttcaaaaa cttactcaca tctacatttc acttaagaaa tcatgtctta tgaccctctc   2100
tcaatgtttt gcttgcagat ccttgccttc ttacaatttg gaggatacac tcttgtcaga   2160
aactccactg atctcttcag gagtttcgga tttgatacac agcctgttct cattggtttg   2220
atcatatttc aggtttgtta tttttgcctt ttgacactaa tctaatgaat caaggatgga   2280
ttaagaaaaa aaaactctaa acctttggtt atatctcctg tctgattatc acagcacact   2340
gtaataccac tgcaacatct agtaagcttt ggcctgaacc tcgttagtcg agcgtttgag   2400
tttcaggtac catcttacaa tccctcaaga tccaaccata gtttctttat tgcaatggca   2460
gcctcatcta ctaatctgag ttaacgttcc ttttgcaggc tgatgctttt gctgtgaagc   2520
ttggctatgc aaaagatctt cgtcctgctc tagtgaaact acaggtcaga gaagataaca   2580
acagaacaca aactgttacc tcaatttgtg tcacacactt aaatggattt tttgttggga   2640
ttttgcagga agagaactta tcagcaatga acactgatcc attgtactca gcttatcact   2700
actcacatcc tcctcttgtt gaaaggcttc gagccattga tggagaagac aagaagacag   2760
attaa                                                               2765
```

<210> SEQ ID NO 171
<211> LENGTH: 36
<212> TYPE: DNA
<213> ORGANISM: Artificial Sequence
<220> FEATURE:
<223> OTHER INFORMATION: Description of Artificial Sequence: REV Primer BamHI site

<400> SEQUENCE: 171
aaaggatcct catgctgctt taaagaagaa ctcgat 36

<210> SEQ ID NO 172
<211> LENGTH: 1461
<212> TYPE: DNA
<213> ORGANISM: Arabidopsis sp.

<400> SEQUENCE: 172
cccgggatgc cagtagtaac ccgcttgatt cgtttgaagt gtgtagggct cagacttgac 60
cggagtggac tcaatcggcg aatctgtcac ggaggacacg gggaatcaac gcggcggaga 120
gtgatggaag agctttcaag cctaaccgtg agtcagcgcg agcaatttct ggtggagaac 180
gatgtgttcg ggatctataa ttacttcgac gccagcgacg tttctactca aaaatacatg 240
atggagattc agcgagataa gcaattggat tatctgatga aaggcttaag gcagcttggt 300
ccgcagtttt cttccttaga tgctaatcga ccttggcttt gttactggat tcttcattca 360
atagctttgc ttggggagac tgtggatgat gaattagaaa gcaatgccat tgacttcctt 420
ggacgctgcc agggctctga aggtggatac ggtggtggtc ctggccaact tccacatctt 480
gcaactactt atgctgcagt gaatgcactt gttactttag gaggtgacaa agccctttct 540
tcaattaata gagaaaaaat gtcttgtttt ttaagacgga tgaaggatac aagtggaggt 600
ttcaggatgc atgatatggg agaaatggat gttcgtgcat gctacactgc aatttcggtt 660
gcaagcatcc taaatattat ggatgatgaa ctcacccagg gcctaggaga ttacatcttg 720
agttgccaaa cttatgaagg tggcattgga ggggaacctg gctccgaagc tcacggtggg 780
tatacctact gtggtttggc tgctatgatt ttaatcaatg aggtcgaccg tttgaatttg 840
gattcattaa tgaattgggc tgtacatcga caaggagtag aaatgggatt tcaaggtagg 900
acgaacaaat tggtcgatgg ttgctacaca ttttggcagg cagccccttg tgttctacta 960
caaagattat attcaaccaa tgatcatgac gttcatggat catcacatat atcagaaggg 1020
acaaatgaag aacatcatgc tcatgatgaa gatgaccttg aagacagtga tgatgatgat 1080
gattctgatg aggacaacga tgaagattca gtgaatggtc acagaatcca tcatacatcc 1140
acctacatta acaggagaat gcaactggtt tttgatagcc tcggcttgca gagatatgta 1200
ctcttgtgct ctaagatccc tgacggtgga ttcagagaca agccgaggaa accccgtgac 1260
ttctaccaca catgttactg cctgagcggc ttgtctgtgg ctcagcacgc ttggttaaaa 1320
gacgaggaca ctcctccttt gactcgcgac attatgggtg gctactcgaa tctccttgaa 1380
cctgttcaac ttcttcacaa cattgtcatg gatcagtata atgaagctat cgagttcttc 1440
tttaaagcag catgaggatc c 1461

<210> SEQ ID NO 173
<211> LENGTH: 5727
<212> TYPE: DNA
<213> ORGANISM: Artificial Sequence
<220> FEATURE:
<223> OTHER INFORMATION: Description of Artificial Sequence:
pBI121-AtFTB vector

<400> SEQUENCE: 173
gtttacccgc caatatatcc tgtcaaacac tgatagttta aactgaaggc gggaaacgac 60
aatctgatca tgagcggaga attaagggag tcacgttatg acccccgccg atgacgcggg 120

-continued

```
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
```

-continued

```
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcccccggga tgccagtagt aacccgcttg   3360
attcgtttga agtgtgtagg gctcagactt gaccggagtg gactcaatcg gcgaatctgt   3420
cacggaggac acggggaatc aacgcggcgg agagtgatgg aagagctttc aagcctaacc   3480
gtgagtcagc gcgagcaatt tctggtggag aacgatgtgt tcgggatcta taattacttc   3540
gacgccagcg acgtttctac tcaaaaatac atgatggaga ttcagcgaga taagcaattg   3600
gattatctga tgaaaggctt aaggcagctt ggtccgcagt tttcttcctt agatgctaat   3660
cgaccttggc tttgttactg gattcttcat tcaatagctt tgcttgggga gactgtggat   3720
gatgaattag aaagcaatgc cattgacttc cttggacgct gccagggctc tgaaggtgga   3780
tacggtggtg gtcctggcca acttccacat cttgcaacta cttatgctgc agtgaatgca   3840
cttgttactt taggaggtga caaagccctt tcttcaatta atagagaaaa aatgtcttgt   3900
tttttaagac ggatgaagga tacaagtgga ggtttcagga tgcatgatat gggagaaatg   3960
gatgttcgtg catgctacac tgcaatttcg gttgcaagca tcctaaatat tatggatgat   4020
gaactcaccc agggcctagg agattacatc ttgagttgcc aaacttatga aggtggcatt   4080
ggaggggaac ctggctccga agctcacggt gggtatacct actgtggttt ggctgctatg   4140
attttaatca atgaggtcga ccgtttgaat ttggattcat taatgaattg ggctgtacat   4200
cgacaaggag tagaaatggg atttcaaggt aggacgaaca aattggtcga tggttgctac   4260
acattttggc aggcagcccc ttgtgttcta ctacaaagat tatattcaac caatgatcat   4320
gacgttcatg gatcatcaca tatatcagaa gggacaaatg aagaacatca tgctcatgat   4380
gaagatgacc ttgaagacag tgatgatgat gatgattctg atgaggacaa cgatgaagat   4440
tcagtgaatg gtcacagaat ccatcataca tccacctaca ttaacaggag aatgcaactg   4500
gtttttgata gcctcggctt gcagagatat gtactcttgt gctctaagat ccctgacggt   4560
ggattcagag acaagccgag gaaaccccgt gacttctacc acacatgtta ctgcctgagc   4620
ggcttgtctg tggctcagca cgcttggtta aaagacgagg acactcctcc tttgactcgc   4680
gacattatgg gtggctactc gaatctcctt gaacctgttc aacttcttca caacattgtc   4740
atggatcagt ataatgaagc tatcgagttc ttctttaaag cagcatgagg atccctcgaa   4800
tttccccgat cgttcaaaca tttggcaata aagtttctta agattgaatc ctgttgccgg   4860
```

-continued

```
tcttgcgatg attatcatat aatttctgtt gaattacgtt aagcatgtaa taattaacat   4920

gtaatgcatg acgttattta tgagatgggt ttttatgatt agagtcccgc aattatacat   4980

ttaatacgcg atagaaaaca aaatatagcg cgcaaactag gataaattat cgcgcgcggt   5040

gtcatctatg ttactagatc gggaattcac tggccgtcgt tttacaacgt cgtgactggg   5100

aaaaccctgg cgttacccaa cttaatcgcc ttgcagcaca tccccctttc gccagctggc   5160

gtaatagcga agaggcccgc accgatcgcc cttcccaaca gttgcgcagc ctgaatggcg   5220

cccgctcctt tcgctttctt cccttccttt ctcgccacgt tcgccggctt tccccgtcaa   5280

gctctaaatc gggggctccc tttagggttc cgatttagtg ctttacggca cctcgacccc   5340

aaaaaacttg atttgggtga tggttcacgt agtgggccat cgccctgata gacggttttt   5400

cgccctttga cgttggagtc cacgttcttt aatagtggac tcttgttcca aactggaaca   5460

acactcaacc ctatctcggg ctattctttt gatttataag ggattttgcc gatttcggaa   5520

ccaccatcaa acaggatttt cgcctgctgg ggcaaaccag cgtggaccgc ttgctgcaac   5580

tctctcaggg ccaggcggtg aagggcaatc agctgttgcc cgtctcactg gtgaaaagaa   5640

aaaccacccc agtacattaa aaacgtccgc aatgtgttat taagttgtct aagcgtcaat   5700

ttgtttacac cacaatatat cctgcca                                       5727
```

```
<210> SEQ ID NO 174
<211> LENGTH: 34
<212> TYPE: DNA
<213> ORGANISM: Artificial Sequence
<220> FEATURE:
<223> OTHER INFORMATION: Description of Artificial Sequence:
      isoprenylcysteine carboxyl methyltransferase
      forward primer

<400> SEQUENCE: 174

aaaggatcca tgacagagat cttcagtgac acca                                 34
```

```
<210> SEQ ID NO 175
<211> LENGTH: 33
<212> TYPE: DNA
<213> ORGANISM: Artificial Sequence
<220> FEATURE:
<223> OTHER INFORMATION: Description of Artificial Sequence:
      isoprenylcysteine carboxyl methyltransferase
      reverse primer

<400> SEQUENCE: 175

aaagagctct cagttcacaa atggaacacc aga                                  33
```

```
<210> SEQ ID NO 176
<211> LENGTH: 594
<212> TYPE: DNA
<213> ORGANISM: Arabidopsis sp.

<400> SEQUENCE: 176

atgacagaga tcttcagtga caccagcatc agacagttat ctcaaatgct actatcacta     60

atcttcttcc acatatccga atacattcta gccatcacca ttcacggagc atcaaacgta    120

actcttagtt cgcttttaat caccaagcat tacgctttag caatgcttct gtcgcttctc    180

gaatacctaa cggagattat cctcttcccg gggctgaaac aacactggtg ggtcagcaac    240

tttggactca taatgatcat cgttggggaa atcatcagga aggcagcgat aataacagcg    300

ggaagatcgt tcactcacct cataaagatc aactacgaag agcatcacgg gcttgtgact    360

catggtgtgt atagactaat gaggcatcca agttactgcg gttttctcat ctggtcggtc    420
```

-continued

```
gggacacaag ttatgctctg taacccgtt tcagcagttg cgttcgcggt tgtcgtgtgg    480

cggtttttg ctcagagaat accgtacgag gagtattttc tgaatcagtt ttttggggta    540

cagtatctag agtatgcaga gagtgttgcc tctggtgttc catttgtgaa ctga         594
<210> SEQ ID NO 177

<211> LENGTH: 482
<212> TYPE: PRT
<213> ORGANISM: Arabidopsis sp.

<400> SEQUENCE: 177

Met Pro Val Val Thr Arg Leu Ile Arg Leu Lys Cys Val Gly Leu Arg
1               5                   10                  15

Leu Asp Arg Ser Gly Leu Asn Arg Arg Ile Cys His Gly Gly His Gly
            20                  25                  30

Glu Ser Thr Arg Arg Arg Val Met Glu Glu Leu Ser Ser Leu Thr Val
        35                  40                  45

Ser Gln Arg Glu Gln Phe Leu Val Glu Asn Asp Val Phe Gly Ile Tyr
    50                  55                  60

Asn Tyr Phe Asp Ala Ser Asp Val Ser Thr Gln Lys Tyr Met Met Glu
65                  70                  75                  80

Ile Gln Arg Asp Lys Gln Leu Asp Tyr Leu Met Lys Gly Leu Arg Gln
                85                  90                  95

Leu Gly Pro Gln Phe Ser Ser Leu Asp Ala Asn Arg Pro Trp Leu Cys
            100                 105                 110

Tyr Trp Ile Leu His Ser Ile Ala Leu Leu Gly Glu Thr Val Asp Asp
        115                 120                 125

Glu Leu Glu Ser Asn Ala Ile Asp Phe Leu Gly Arg Cys Gln Gly Ser
    130                 135                 140

Glu Gly Gly Tyr Gly Gly Gly Pro Gly Gln Leu Pro His Leu Ala Thr
145                 150                 155                 160

Thr Tyr Ala Ala Val Asn Ala Leu Val Thr Leu Gly Gly Asp Lys Ala
                165                 170                 175

Leu Ser Ser Ile Asn Arg Glu Lys Met Ser Cys Phe Leu Arg Arg Met
            180                 185                 190

Lys Asp Thr Ser Gly Gly Phe Arg Met His Asp Met Gly Glu Met Asp
        195                 200                 205

Val Arg Ala Cys Tyr Thr Ala Ile Ser Val Ala Ser Ile Leu Asn Ile
    210                 215                 220

Met Asp Asp Glu Leu Thr Gln Gly Leu Gly Asp Tyr Ile Leu Ser Cys
225                 230                 235                 240

Gln Thr Tyr Glu Gly Gly Ile Gly Gly Glu Pro Gly Ser Glu Ala His
                245                 250                 255

Gly Gly Tyr Thr Tyr Cys Gly Leu Ala Ala Met Ile Leu Ile Asn Glu
            260                 265                 270

Val Asp Arg Leu Asn Leu Asp Ser Leu Met Asn Trp Ala Val His Arg
        275                 280                 285

Gln Gly Val Glu Met Gly Phe Gln Gly Arg Thr Asn Lys Leu Val Asp
    290                 295                 300

Gly Cys Tyr Thr Phe Trp Gln Ala Ala Pro Cys Val Leu Leu Gln Arg
305                 310                 315                 320

Leu Tyr Ser Thr Asn Asp His Asp Val His Gly Ser Ser His Ile Ser
                325                 330                 335

Glu Gly Thr Asn Glu Glu His His Ala His Asp Glu Asp Asp Leu Glu
```

-continued

```
            340                 345                 350

Asp Ser Asp Asp Asp Asp Asp Ser Asp Glu Asp Asn Asp Glu Asp Ser
        355                 360                 365

Val Asn Gly His Arg Ile His His Thr Ser Thr Tyr Ile Asn Arg Arg
    370                 375                 380

Met Gln Leu Val Phe Asp Ser Leu Gly Leu Gln Arg Tyr Val Leu Leu
385                 390                 395                 400

Cys Ser Lys Ile Pro Asp Gly Gly Phe Arg Asp Lys Pro Arg Lys Pro
                405                 410                 415

Arg Asp Phe Tyr His Thr Cys Tyr Cys Leu Ser Gly Leu Ser Val Ala
            420                 425                 430

Gln His Ala Trp Leu Lys Asp Glu Asp Thr Pro Pro Leu Thr Arg Asp
        435                 440                 445

Ile Met Gly Gly Tyr Ser Asn Leu Leu Glu Pro Val Gln Leu Leu His
    450                 455                 460

Asn Ile Val Met Asp Gln Tyr Asn Glu Ala Ile Glu Phe Phe Phe Lys
465                 470                 475                 480

Ala Ala


<210> SEQ ID NO 178
<211> LENGTH: 1290
<212> TYPE: DNA
<213> ORGANISM: Arabidopsis sp.

<400> SEQUENCE: 178

atggagattc agcgagataa gcaattggat tatctgatga aaggcttaag gcagcttggt     60

ccgcagtttt cttccttaga tgctaatcga ccttggcttt gttactggat tcttcattca    120

atagctttgc ttggggagac tgtggatgat gaattagaaa gcaatgccat tgacttcctt    180

ggacgctgcc agggctctga aggtggatac ggtggtggtc ctggccaact tccacatctt    240

gcaactactt atgctgcagt gaatgcactt gttactttag gaggtgacaa agccctttct    300

tcaattaata gagaaaaaat gtcttgtttt ttaagacgga tgaaggatac aagtggaggt    360

ttcaggatgc atgatatggg agaaattgat gttcgtgcat gctacactgc aatttcggtt    420

gcaagcatcc taaatattat ggatgatgaa ctcacccagg gcctaggaga ttacatcttg    480

agttgccaaa cttatgaagg tggcattgga ggggaacctg gctccgaagc tcacggtggg    540

tatacctact gtggtttggc tgctatgatt ttaatcaatg aggtcgaccg tttgaatttg    600

gattcattaa tgaattgggc tgtacatcga caaggagtag aaatgggatt tcaaggtagg    660

acgaacaaat tggtcgatgg ttgctacaca ttttggcagg cagccccttg tgttctacta    720

caaagattat attcaaccaa tgatcatgac gttcatggat catcacatat atcagaaggg    780

acaaatgaag aacatcatgc tcatgatgaa gatgaccttg aagacagtga tgatgatgat    840

gattctgatg aggacaacga tgaagattca gtgaatggtc acagaatcca tcatacatcc    900

acctacatta acaggagaat gcaactggtt tttgatagcc tcggcttgca gagatatgta    960

ctcttgtgct ctaagatccc tgacggtgga ttcagagaca agccgaggaa accccgtgac   1020

ttctaccaca catgttactg cctgagcggc ttgtctgtgg ctcagcacgc ttggttaaaa   1080

gacgaggaca ctcctccttt gactcgcgac attatgggtg gctactcgaa tctccttgaa   1140

cctgttcaac ttcttcacaa cattgtcatg gatcagtata atgaagctat cgagttcttc   1200
```

-continued

| | |
|---|---|
| tttaaagcag catgacccgt tgttgctaat gtatgggaaa ccccaaacat aagagtttcc | 1260 |
| gtagtgttgt aacttgtaag atttcaaaag | 1290 |

STRESS TOLERANCE AND DELAYED SENESCENCE IN PLANTS

RELATED APPLICATION

This application is a Continuation-in-Part of U.S. Ser. No. 10/160,764, filed May 31, 2002 which claims the benefit of U.S. Ser. No. 60/294,766, filed May 31, 2001 and U.S. Ser. No. 60/348,909, filed Oct. 22, 2001 and a Continuation-in-Part of U.S. Ser. No. 10/210,760, filed Aug. 1, 2002 which claims the benefit of U.S. Ser. No. 60/309,396, filed Aug. 1, 2001 and U.S. Ser. No. 60/337,084, filed Dec. 4, 2001 and a Continuation-in-Part of U.S. Ser. No. 09/191,687, filed Nov. 13, 1998 now abandoned which claims priority to PCT Application No. PCT/US98/15664, filed Jul. 29, 1998, and U.S. Ser. No. 09/124,867, filed Jul. 30, 1998 both of which claim the benefit of U.S. Provisional Application No. 60/054,474, filed Aug. 1, 1997, the contents of all of these applications which are incorporated herein by reference in their entirety.

BACKGROUND OF THE INVENTION

Most higher plants encounter at least transient decreases in relative water content at some stage of their life cycle and, as a result, have evolved a number of desiccation protection mechanisms. If however, the change in water deficit is prolonged the effects on the plant's growth and development can be profound. Decreased water content due to drought, cold or salt stresses can irreparably damage plant cells which in turn limits plant growth and crop productivity in agriculture.

Plants respond to adverse conditions of drought, salinity and cold with a variety of morphological and physiological changes. Although our understanding of plant tolerance mechanisms to these stresses is fragmentary, the plant hormone abscisic acid (ABA) has been proposed to be an essential mediator between environmental stimulus and plant responses. ABA levels increase in response to water deficits and exogenously applied ABA mimics many of the responses normally induced by water stress. Once ABA is synthesized it causes the closure of the leaf stomata thereby decreasing water loss through transpiration.

The identification of genes that transduce ABA into a cellular response opens the possibility of exploiting these regulators to enhance desiccation tolerance in crop species. In principle, these ABA signaling genes can be coupled with the appropriate controlling elements to allow optimal plant growth and development. Thus, not only would these genes allow the genetic tailoring of crops to withstand transitory environmental insults, they should also broaden the environments where traditional crops can be grown.

In addition, little is known of the genetic mechanisms which control plant growth and development. Genes which further affect other metabolic processes such as senescence and growth habits of plants can be useful in a wide variety of crop and horticultural plants.

SUMMARY OF THE INVENTION

This invention relates to isolated nucleic acids which encode a farnesyl transferase comprising SEQ ID NO: 1 or SEQ ID NO: 172. Nucleic acids also encompassed by this invention are such hybridizing sequences which encode the functional equivalent or fragment thereof of SEQ ID NO: 1 or SEQ ID NO: 172. The present invention also relates to a method for enhancing the drought tolerance of plants using inhibitors of the products encoded by these nucleic acids. Further, this invention relates to the control of regulatory functions in photosynthetic organisms; for example, in the control of growth habit, flowering, seed production, seed germination, and senescence in such organisms.

This invention also relates to a method for enhancing the drought or stress tolerance of plants by means of alterations in isolated or recombinant nucleic acids encoding a farnesyl transferase (Ftase) protein or fragment thereof or its functional equivalent. Nucleic acids which hybridize to the Ftase-encoding gene (ERA 1) are also encompassed by this invention when such hybridizing sequences encode the functional equivalent of the Ftase protein. The present invention also relates to a method for enhancing the drought tolerance of plants through the genetic manipulation of ERA1 gene and its functional equivalents to improve stress tolerance in crop plants. Loss of ERA1 gene function confers enhanced tolerance to drought at the level of the mature plant. The nature of an era1 mutant with loss of Ftase activity, for example, demonstrates that inhibition of farnesylation enhances ABA responses in a plant.

Further, this invention relates to inhibition of senescence in photosynthetic organisms through inhibition of farnesyl transferase activity. The resulting photosynthetic organisms stay green and tissue viability is maintained for a longer period of time. Thus, methods to provide greener plants and a reduction in senescence are part of this invention.

In yet another embodiment, methods are provided to modify the growth habit and flower induction of plants. Loss of ERA1 gene function under particular environmental conditions results in a reduction in the number of lateral branches produced on a plant and an increase in the number of flowers per inflorescence.

The invention also provides method of producing a transgenic plant, which has an altered phenotype such as increased tolerance to stress (e.g., water deficit, increased biomass, increased yield), delayed senescence or increased ABA sensitivity by introducing into a plant cell a compound that inhibits farnesylation of a polypeptide comprising a CaaX motif. By inhibit Farnesylation is meant to include that the compound inhibits one or more steps in the three step process of farnesylation. In one aspect the compound inhibits farnesyltransferase, prenylprotease or prenylcysteine carboxyl methytransferase expression or activity. Alternatively, the compound is a anti-sense farnesyl transferase nucleic acid or a farnesyl transferase double stranded RNA-inhibition hair pin nucleic acid. In some aspects the nucleic acid is operably linked to a promoter such as a constitutive promoter, an ABA inducible promoter, tissue specific promoters or a guard cell-specific promoter.

Exemplary anti-antisense nucleic acids are 20 or more consecutive nucleic acids complementary to SEQ ID NO:1, 14, 40, 43, 80-85 or 172. Alternatively the anti-sense nucleic acids includes SEQ ID NO:36, 41, 44 or 54-64.

In various aspects the compound is a nucleic acid encoding a farnesyltransferase, prenylprotease or prenylcysteine carboxyl methytransferase polypeptide of fragment thereof. Alternatively, the compound is a nucleic acid encoding a mutated farnesyltransferase, prenylprotease or prenylcysteine carboxyl methytransferase polypeptide of fragment thereof. By mutated is meant that the polypeptide lacks at least on activity of the wild type polypeptide such as for example, subunit interaction, substrate binding or enzyme catalysis. A mutated polypeptide forms a dimer, such as a heterodimer. For example, a mutated farnesytransferase beta polypeptide forms a dimer with a farnesyltransferase alpha polypeptide. Preferably, the polypeptide is less than 400, 350, 314, 300 or 200 amino acids in length. For example, the compound includes SEQ ID NO:1, 14, 40, 43, 80-85 or 172.

In a further aspect the compound is a nucleic acid encoding a CaaX motif or a nucleic acid encoding a CaaX motif operably linked to a promoter.

Also included in the invention are the plants produced by the methods of the invention and the seed produced by the plants which produce a plant that has an altered phenotype.

This invention also relates to a regulatory sequence useful for genetic engineering of plant cells to provide a method of controlling the tissue pattern of expression of DNA sequences linked to this novel regulatory sequence.

BRIEF DESCRIPTION OF THE DRAWINGS

FIGS. 1A-1C show the nucleic acid sequence of the ERA1 gene (SEQ ID NO:1) in which the introns are underlined and the start codon (ATG) is at nucleotide positions 1-3.

FIG. 2 is the amino acid sequence of the ERA1 protein (SEQ ID NO:2).

FIGS. 3A-3B show the nucleic acid sequence of the ERA1 promoter (SEQ ID NO:3).

FIG. 4 is the amino acid sequence of the β subunit farnesylation domain from *Arabidopsis* (Arab.) (SEQ ID NO:2) aligned with the β subunit farnesylation domains from pea (SEQ ID NO:4), yeast (SEQ ID NO:5) and rat (SEQ ID NO:6). Residues that are identical to the *Arabidopsis*-sequence are indicated with a dot. A dash indicates a blank. The amino acid positions of the *Arabidopsis* gene are indicated on the right-hand side.

FIGS. 9A-9C are comparisons of transcript levels in aging leaves from control (wild-type) and era-2 mutant plants.

FIG. 17 is an illustration of the homology among FTA nucleic acid (A) and amino acid (B) sequences from various plant species based on ClustalW analysis (percent identity shown).

FIG. 18 is an illustration of the homology among FTB nucleic acid and amino acid sequences from various plant species based on ClustalW analysis (percent identity shown).

FIG. 26. is an illustration of (A) nucleic acid and (B) amino acid sequence identities as determined by ClustalW analysis.

FIG. 39. is a photograph showing Northern blot of ΔN90AtFTB arabidopsis plants.

Figure 5:
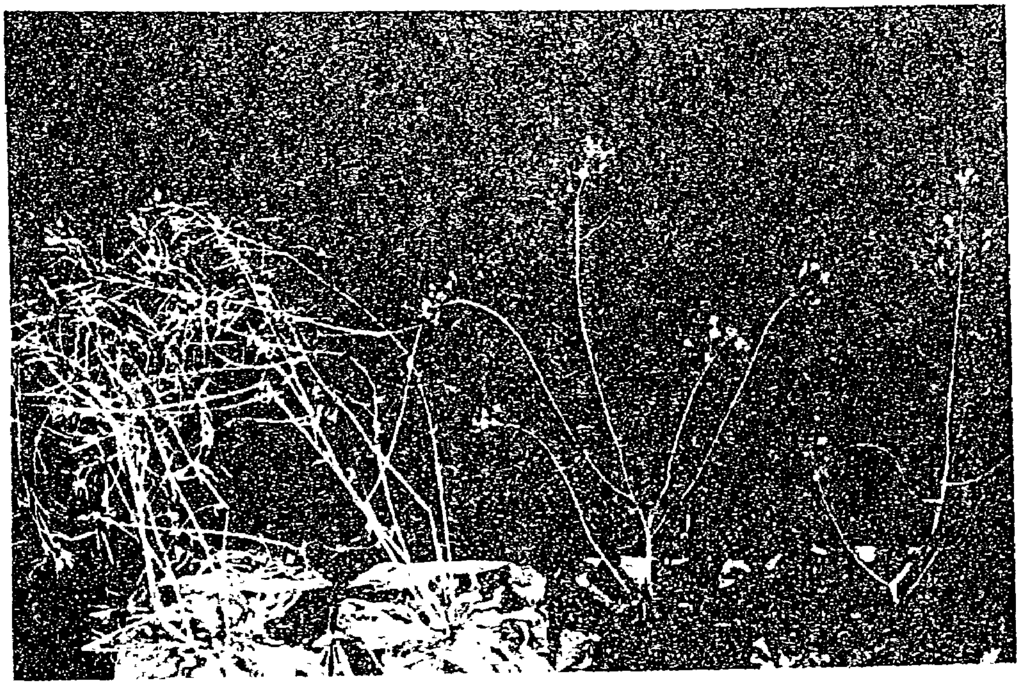
FIG. 5 is a photograph of an era1-transformed *Arabidopsis* plant (right) compared to the wild-type (control; i.e., naturally-occurring) plant (left) under extremely dry conditions.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

This invention relates to transgenic plants that display an altered phenotype, e.g., increased tolerance to stress, delayed senescence, increased ABA sensitivity, increased yield, increased productivity and increased biomass and methods of producing the plants by introducing to a plant cell a compound that inhibits farnesylation of a polypeptide comprising a CaaX motif Protein famesylation, the addition of a C-terminal, 15 carbon chain to protein and subsequent processing is a three step enzymatic reaction including famesylation, proteolytic cleavage and methylation. First, a farnesyltransferase adds the C-terminal 15 carbon chain to a conserved cysteine residue of the CaaX terminal motif, where "C" is a Cysteine "a" is an aliphatic amino acid and "X" is any amino acid. Second, the last three amino acid residues (aaX) are cleaved by a prenyl protease. Lastly, the modified cysteine is methylated by a methylase to create the final active product of the protein famesylation pathway. The Applicant's have shown that over-expression and down-regulation of the alpha or the beta famesyl transferase gene in plant cells (i.e., the first step in famesylation) results in plants with an altered phenotype such as but not limited to drought tolerance and delayed senescence. Applicants have also shown that over-expression and down-regulation of the prenyl protease gene (i.e., the second step in farnesylation) in plant cells also results in a plant displaying an altered phenotype including for example but not limited to drought tolerance and increased resistance to biotic and abiotic stress. These results taken together support the hypothesis that modification of the expression of any of the enzymes in the famesylation pathway (famesyltransferase, prenylprotease or prenycysteine carboxyl methytransferase in a plant cell will result in a plant displaying an altered phenotype.

The present invention also provides novel farnesyltransferase (i.e., alpha and beta), (Ftase) and CaaX prenyl protease (CPP) nucleic acid sequences isolated from for example *Arabidopsis thaliana* (At) *Brassica napus* (Bn) and *Glycine Max* (Gm). The invention also provides farnesyltransferase and CaaX prenyl protease antisense nucleic acids and constructs comprising these nucleic acids. The sequences are collectively referred to as "PPI nucleic acids", "PPI polynucleotides" or "PPI antisense nucleic acids" and the corresponding encoded polypeptide is referred to as a "PPI polypeptide" or "PPI protein". Unless indicated otherwise, "PPI" is meant to refer to any of the novel sequences disclosed herein. Table A below summarizes the nucleic acids and polypeptides according to the invention.

TABLE A

| PPI Sequence Description | SEQ ID NO: |
|---|---|
| era1 (FTB) | 1 |
| era1 (FTB) | 2 |
| ERa1 promoter | 3 |
| FTB pea | 4 |
| FTB yeast | 5 |
| FTB rat | 6 |
| AFC1 | 124 |
| AFC1 | 125 |
| AT4g01320 | 126 |
| AT4g01320 | 127 |
| AF007269 | 128 |
| AF007269 | 129 |
| pBI121-antisense-AtCPP | 130 |
| pRD29A-AtCPP | 131 |
| pRD29A-HP-AtCPP | 132 |
| pRD29A-antisense-AtCPP | 133 |
| MuA-AtCPP | 134 |
| MuA-GmCPP | 135 |
| pBI121-GmCPP | 136 |
| pBI121-HP-GmCPP | 137 |
| pBI121-antisense-GmCPP | 138 |
| pRD29A-GmCPP | 139 |
| pRD29A-HP-GmCPP | 140 |
| pRD29A-antisense-GmCPP | 141 |
| pBI121-BnCPP | 142 |
| pBI121-HP-BnCPP | 143 |
| pBI121-antisense-BnCPP | 144 |
| pRD29A-BnCPP | 145 |
| pRD29A-HP-BnCPP | 146 |
| pRD29A-antisense-BnCPP | 147 |
| MuA-BnCPP | 148 |
| GmCPP SmaFW | 149 |
| GmCPP SacRV | 150 |
| BnCPP-anti-SmaFW | 151 |
| BnCPP-anti-BamRV | 152 |
| BnCPP-HP-Sac-FW | 153 |
| BnCPP-HP-Sac-RV | 154 |
| BnCPP-HP-BamFW | 155 |
| BnCPP-HP-XbaRV | 156 |
| GmCPP-HP-Sac-FW | 157 |
| GmCPP-HP-Sac-RV | 158 |
| GmCPP-HP-BamFW | 159 |
| GmCPP-HP-XbaRV | 160 |
| pRD29AP | 161 |
| Nosterm-RV | 162 |
| Consensus-BASF | 163 |
| Consensus-BASF | 164 |
| Consensus-Generic | 165 |
| Consensus-Generic | 166 |
| Consensus- PPI | 167 |
| Consensus- PPI | 168 |
| Consensus- PPI/Generic | 169 |
| Consensus- PPI/Generic | 170 |
| Primer BamHI REV | 171 |
| Full Length AtFTB | 172 |
| BI121-AtFTB full length | 173 |
| primer | 174 |
| primer | 175 |
| isoprenylcysteine carboxyl methyltransferase | 176 |
| Full Length AtFTB | 177 |

This invention also relates to isolated nucleic acids and proteins encoded by these nucleic acids which modify the growth, reproduction and senescence of plants. In particular, the constructs of this invention include an isolated nucleic acid encoding a farnesyl transferase (Ftase) polypeptide comprising SEQ ID NO:1 or 172 or its functional equivalent or fragment thereof, and the Ftase polypeptides or proteins of fragments thereof encoded by these nucleic acids. In particular, this invention relates to a protein wherein the sequence is SEQ ID NO:2 or SEQ ID NO:177.

Further included in this invention are nucleic acid constructs which comprise a promoter (ERA1 promoter) operably-linked to isolated nucleic acid comprising SEQ ID NO:1 or 172 or its functional equivalent or a complement of either. When incorporated into a plant, the ERA1 promoter is regulated in the guard cells of the plant and can affect water loss through the stomates. This promoter consists of a nucleic acid comprising SEQ ID NO:3 (FIG. 3).

Transgenic plants, seeds, plant cell and tissues incorporating these constructs are also part of this invention. Accordingly, in one aspect of this invention, a method is provided for producing a gene product under the control of a promoter which operates primarily in guard cells through expression of a gene encoding the gene product in the cell of a plant comprising the steps of: transforming a plant cell with a DNA construct comprising a) a regulatory region comprising SEQ ID NO:3 or a functional portion thereof, DNA comprising a structural gene encoding a gene product, and a 3' untranslated region containing a polyadenylated region; regenerating a plant, photosynthetic organism or tissue culture from the cell; and placing the plant, photosynthetic organisms or tissue culture under conditions so that the promoter induces transcription of the structural gene and the gene product is expressed.

In the context of this disclosure, the terms “regulatory region” or “promoter” refer to a sequence of DNA, usually upstream (5') to the coding sequence of a structural gene, which controls the expression of the coding region by providing recognition and binding sites for RNA polymerase and/or other factors required for transcription to start at the correct site. The term “functional portion” or “functional fragment” refers to a truncated sequence of a promoter of this invention which maintains the capability of inducing transcription of an ERA structural gene under the conditions described for activity of an Ftase protein.

The constructs and methods described herein can be applied to all types of plants and other photosynthetic organisms, including, but not limited to: angiosperms (monocots and dicots), gymnosperms, spore-bearing or vegetatively-reproducing plants and the algae, including the cyanophyta (blue-green algae). Particularly preferred plants are those plants which provide commercially-valuable crops, such as corn, wheat, cotton, rice, canola, sugar cane, sugar beet, sunflowers, potatoes, tomatoes, broccoli, carrots, lettuce, apple, plum, orange, lemon, rose, and the like.

Further, the constructs and methods of this invention can be adapted to any plant part, protoplast, or tissue culture wherein the tissue is derived from a photosynthetic organism. The term “plant part” is meant to include a portion of a plant capable of producing a regenerated plant. Preferable plant parts include roots and shoots and meristematic portions thereof. Other plant parts encompassed by this invention are: leaves, flowers, seeds, epicotyls, hypocotyls, cotyledons, cotyledonary nodes, explants, pollen, ovules, meristematic or embryonic tissue, protoplasts, and the like. Transgenic plants can be regenerated from any of these plant parts, including tissue culture or protoplasts, and also from explants. Methods will vary according to the species of plant.

This invention relates to compositions and constructs comprising isolated nucleic acids (both DNA and RNA) encoding an Ftase and portions thereof of photosynthetic organisms. This invention further relates to compositions and constructs comprising isolated nucleic acids encoding an Ftase promoter. In particular, the ERA1 gene encoding the β subunit of Ftase from *Arabidopsis* and a regulatory sequence which regulates the transcription of the ERA1 gene have been isolated and sequenced. Nucleic acids which encode Ftases from photosynthetic organisms, and homologues or analogs of these nucleic acids, are encompassed by this invention.

The invention further relates to methods using isolated and/or recombinant nucleic acids (DNA or RNA) that are characterized by their ability to hybridize to (a) a nucleic acid encoding an Ftase protein or polypeptide, such as a nucleic acid having the sequences of SEQ ID NO:1 or 172 or (b) a portion of the foregoing (e.g., a portion comprising the minimum nucleotides required to encode a functional Ftase protein; or by the ability to encode a polypeptide having the amino acid sequence of an Ftase (e.g., SEQ ID NO:2 or SEQ ID NO:177, or to encode functional equivalents thereof; e.g., a polypeptide having at least 80% sequence similarity to SEQ ID NO:2 or SEQ ID NO:177, which when incorporated into a plant cell, facilitates the growth habit, seed germination, and metabolism in a photosynthetic organism in the same manner as SEQ ID NO:1 or 172). A functional equivalent of an Ftase therefore, would have at least an 80% similar amino acid sequence and similar characteristics to, or perform in substantially the same way as, the polypeptide encoded by SEQ ID NO:2 or SEQ ID NO:177. A nucleic acid which hybridizes to a nucleic acid encoding an Ftase polypeptide such as SEQ ID NO:2 or SEQ ID NO:177 can be double- or single-stranded. Hybridization to DNA such as DNA having the sequence SEQ ID NO:1 or 172, includes hybridization to the strand shown or its complementary strand.

In one embodiment, the percent amino acid sequence similarity between an Ftase polypeptide such as SEQ ID NO:2 or SEQ ID NO:177, and functional equivalents thereof is at least about 60% (≧60%). In a preferred embodiment, the percent amino acid sequence similarity between an Ftase polypeptide and its functional equivalents is at least about 75% (≧75%). More preferably, the percent amino acid sequence similarity between an Ftase polypeptide and its functional equivalents is at least about 80%, and still more preferably, at least about 90%, when consecutive amino acids are compared.

Isolated and/or recombinant nucleic acids meeting these criteria comprise nucleic acids having sequences identical to sequences of naturally occurring ERA1 genes and portions thereof, or variants of the naturally occurring genes. Such variants include mutants differing by the addition, deletion or substitution of one or more nucleotides, modified nucleic acids in which one or more nucleotides are modified (e.g., DNA or RNA analogs), and mutants comprising one or more modified nucleotides.

Such nucleic acids, including DNA or RNA, can be detected and isolated by hybridization under high stringency conditions or moderate stringency conditions, for example, which are chosen so as to not permit the hybridization of nucleic acids having non-complementary sequences. “Stringency conditions” for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1-2.10.16 (see particularly 2.10.8-11) and pages 6.3.1-6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures can (1) employ low ionic strength and high temperature for washing, such as 0.015 M NaCl/0.0015 M sodium citrate, pH 7.0 (0.1× SSC) with 0.1% sodium dodecyl sulfate (SDS) at 50° C.; (2) employ during hybridization 50% (vol/vol) formamide with 5× Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5× SSC at 42° C.; or (3) employ hybridization with 50% formamide, 5× SSC, 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C in 0.2× SSC and 0.1% SDS. Moderate stringency conditions would be similar except that hybridization would employ 25% formamide in place of 50% formamide.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson (1991) Methods in Enzymology, 200:546-556. Also, see especially page 2.10.11 in Current Protocols in Molecular Biology (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C decrease in the melting temperature $T_m$, for any chosen SSC concentration. Generally, doubling the concentration of SSC results in an increase in $T_m$ of ≈17C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding an Ftase polypeptide, such as the nucleic acids depicted as SEQ ID NO:1 or 172, (b) the complement of SEQ ID NO:1 or 172, (c) or a portion of (a) or (b) (e.g. under high or moderate stringency conditions), may further encode a protein or polypeptide having at least one functional characteristic of an Ftase polypeptide, such as regulation of lateral branching under diurnal light cycles, or regulation of the response to ABA, or regulation of senescence.

Enzymatic assays, complementation tests, or other suitable methods can also be used in procedures for the identification and/or isolation of nucleic acids which encode a polypeptide such as a polypeptide of the amino acid sequence SEQ ID NO:2 or SEQ ID NO:177 or a functional equivalent or fragment thereof of this polypeptide. The antigenic properties of proteins or polypeptides encoded by hybridizing nucleic acids can be determined by immunological methods employing antibodies that bind to an Ftase polypeptide such as immunoblot, immunoprecipitation and radioimmunoassay. PCR methodology, including RAGE (Rapid Amplification of Genomic DNA Ends), can also be used to screen for and detect the presence of nucleic acids which encode Ftase-like proteins and polypeptides, and to assist in cloning such nucleic acids from genomic DNA. PCR methods for these purposes can be found in Innis, M. A., et al. (1990) *PCR Protocols: A Guide to Methods and Applications*, Academic Press, Inc., San Diego, Calif., incorporated herein by reference.

The nucleic acids described herein are used in the methods of the present invention for production of proteins or polypeptides which are incorporated into cells, tissues, plant parts, plants and other photosynthetic organisms. In one embodiment, DNA containing all or part of the coding sequence for an Ftase polypeptide, or DNA which hybridizes to DNA having the sequence SEQ ID NO:2 or SEQ ID NO:177 is incorporated into a vector for expression of the encoded polypeptide in suitable host cells. The encoded polypeptide consisting of an Ftase subunit or its finctional equivalent is capable of farnesyl transferase activity. The term "vector" as used herein refers to a nucleic acid molecule capable of transporting another nucleic acid to which it has been linked.

Primers and probes consisting of 20 or more contiguous nucleotides of the above-described nucleic acids are also included as part of this invention. Thus, one nucleic acid of this invention comprises a specific sequence of about 20 to about 200 or more nucleotides which are identical or complementary to a specific sequence of nucleotides of the Ftase protein-encoding DNA or transcribed mRNA. These probes and primers can be used to identify and isolate Ftase-encoding nucleic acid from other photosynthetic organisms.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event.

Portions of the isolated nucleic acids which code for polypeptides having a certain fuinction can be identified and isolated by, for example, the method of Jasin, M., et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewmaker, et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO:1 or 172. For example, an antisense nucleic acid or oligonucleotide can be complementary to a target nucleic acid having the sequence shown as the strand of the open reading frame of SEQ ID NO:1 or 172, or nucleic acid encoding a functional equivalent or fragment thereof of Ftase, or to a portion of these nucleic acids sufficient to allow hybridization. A portion, for example, a sequence of 16 nucleotides could be sufficient to inhibit expression of the protein. Fragments comprising 25 or more consecutive nucleotides complementary to SEQ ID NO:1 or 172 could also be used. Or, an antisense nucleic acid or oligonucleotide complementary to 5' or 3' untranslated regions, or overlapping the translation initiation codon (5' untranslated and translated regions), of the ERA1 gene, or a gene encoding a functional equivalent or fragment thereof can also be effective. In another embodiment, the antisense nucleic acid is wholly or partially complementary to and can hybridize with a target nucleic acid which encodes an Ftase polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding an Ftase polypeptide or its functional equivalent. Frank-Kamenetskii, M. D. and Mirkin, S. M. (1995) *Ann. Rev. Biochem.* 64:65-95. Such oligonucleotides of the invention are constructed using the base-pairing rules of triple helix formation and the nucleotide sequence of the gene or mRNA for Ftase. These oligonucleotides can block Ftase-type activity in a number of ways, including prevention of transcription of the ERA1 gene or by binding to mRNA as it is transcribed by the gene.

Another aspect of the invention pertains to the use of post transcriptional gene silencing (PTGS) to repress gene expression. Double stranded RNA can initiate the sequence specific repression of gene expression in plants and animals. Double stranded RNA is processed to short duplex oligomers of 21-23 nucleotides in length. These small interfering RNA's suppress the expression of endogenous and heterologous genes in a sequence specific manner (Fire et al. Nature 391:806-811, Carthew, Curr. Opin. in Cell Biol., 13:244-248, Elbashir et al., Nature 411:494-498). A RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

Another aspect of the invention pertains to the use of post transcriptional gene silencing (PTGS) to repress gene expression. Double stranded RNA can initiate the sequence specific repression of gene expression in plants and animals. Double stranded RNA is processed to short duplex oligomers of 21-23 nucleotides in length. These small interfering RNA's suppress the expression of endogenous and heterologous genes in a sequence specific manner (Fire et al. Nature 391:806-811, Carthew, Curr. Opin. in Cell Biol., 13:244-248, Elbashir et al., Nature 411:494-498). A RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

Another aspect of the invention pertains to the use of the dominant-negative genetic approach. Briefly the presence of a dominant trait, i.e. the expression of a transgene, results in a reduction of enzyme activity or reduced production of the enzymatic end-product. It has been demonstrated that FT is a heterodimer formed by α- and β-subunits. FT activity relies on the proper dimedrzation between these subunits to form functional enzyme. Expression of a non-functional subunit will interact with the second subunit to produce a non-functional enzyme and hence reduced enzymatic activity. The non-functional aspect may be in respect to, but not limited to, subunit interaction, substrate binding or enzyme catalysis, for example. Alternatively the expressed trait may produce a substrate analogue which competes with native substrate, the end result being decreased farnesylation of biologically active substrate.

The invention also relates to proteins or polypeptides encoded by the novel nucleic acids described herein. The proteins and polypeptides of this invention can be isolated and/or recombinant. Proteins or polypeptides referred to herein as "isolated" are proteins or polypeptides purified to a state beyond that in which they exist in cells. In a preferred embodiment, they are at least 10% pure; i.e., substantially purified. "Isolated" proteins or polypeptides include proteins or polypeptides obtained by methods described infra, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of an Ftase; for example, catalytic activity affecting, e.g., normal lateral branching, florets/inflorescence, seed germination, or stomatal opening, and binding function, and/or antigenic function (e.g., binding of antibodies that also bind to naturally occurring Ftase). As such, these proteins are referred to as Ftases of plant origin, and include, for example, naturally occurring Ftase, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

The invention also relates to isolated and/or recombinant portions of an Ftase as described above, especially the β subunit of an Ftase protein. Portions of the enzyme can be made which have full or partial function on their own, or which when mixed together (though fully, partially, or nonfunctional alone), spontaneously assemble with one or more other polypeptides to reconstitute a functional protein having at least one functional characteristic of an Ftase of this invention.

A number of genes have been identified that are induced by ABA. This suggests that ABA-induced tolerance to adverse environmental conditions is a complex multigenic event. Thus, identification and transfer of single genes into crop plants which improves the viability of the plant under different environmental conditions due to increased responsiveness to ABA is novel and extremely useful.

To identify genes that could be more global controllers of ABA-regulated plant processes, genetic screens were applied in a number of plant species to isolate mutations that alter the response of the plant to the hormone.

Mutations that confer enhanced response to ABA (era) in *Arabidopsis* seeds were identified by their ability to prevent seed germination with low concentrations of ABA that normally permit wild-type (controls, i.e., naturally-occurring) seed germination. Of these, the era1mutant class, which includes one transferred DNA (T-DNA) line (era1-1, ecotype Wassilewskija) and two neutron-generated mutants (era1-2 and era1-3, ecotype Columbia), was of added interest because this class showed decreased germination efficiency under normal postimbibition. Mutations that enhance ABA responsiveness should, in principle, be more dormant. Dormancy in era1alleles was alleviated by a 4-day chilling period; the efficiency of era1 germination increased with the length of time the seeds are chilled. In many plant species, breaking dormancy to allow germination requires vernalization and exposure to moist, low-temperature environments for an extended period (Baskin and Baskin, 1971). The germination profile of era mutants could reflect an increased state of ABA-induced dormancy; consequently, these seeds require longer vernalization to germinate. Support for this contention came from construction of double mutants of era1 with both ABA biosynthetic (aba1-1) and insensitive mutants (abi1-1 and abi3-6). In all cases, the double mutants had reduced dormancy as compared with era 1, indicating that the increased dormancy observed in era1 seed was dependent on ABA synthesis or sensitivity.

Aside from broadening the spectrum of new ABA response mutants, supersensitivity screens were also used to identify negative regulators of ABA sensitivity. That is, inhibition of these gene functions enhances the ABA response. One of these genes (ERA1) has been cloned and demonstrated to encode the β-subunit of a heterodimeric protein farnesyl transferase (Ftase) (Cutler et al., 1996). The era1-1 mutation, which is due to a T-DNA insertion, allowed the isolation of plant genomic regions flanking the insertions. Using the flanking regions as probes, the wild-type cDNA and genomic clones were isolated. Sequence analysis of these described a gene encompassing 3.5 kb of genomic DNA. The gene contains 13 introns which are underlined in FIGS. 1A-1C and the T-DNA insertion site in era1-1 is in intron 8. Southern (DNA) analysis of wild-type DNA, era1-2, and era1-3 probed with Era1 cDNA revealed that both fast-neutron alleles contain deletions spanning the ERA1 locus. Fast-neutron mutagenesis induced small deletions in *Arabidopsis* (Shirley et al., 1992), and subsequent genomic analysis with a 14-kb probe that spans the ERA1 locus determined the size of the era1-2 deletion to be about 7.5 kb and the era1-3 deletion to be slightly larger. Thus all three era1alleles contained DNA disruptions at the same locus, confirming the identity of the ERA locus.

Conceptual translation of the longest open reading frame (404 amino acids) in the ERA1 gene produced a protein (FIGS. 2 and 4) with a high sequence similarity to yeast, pea, and mammalian protein farnesyl transferase β subunit genes (Goodman et al., 1988; Chen et al., 1991; Yang et al., 1993). Farnesyl transferases consist of α and β subunits that dimerize, forming an enzyme that catalyzes the attachment of farnesyl pyrophosphate (15 carbons) to proteins containing a COOH-terminal CaaX motif (Schafer and Rine, 1992), where C designates cysteine residue, aa is usually aliphatic amino acids, and X may designate a cysteine, serine, methionine, or glutamine residue. Both plant β subunit genes contain a region of about 50 amino acids near their COOH-terminus that is absent in yeast and animal β subunit genes.

In yeast and mammalian systems, Ftases modify several signal transduction proteins for membrane localization. This is achieved by the attachment of the lipophilic farnesyl sidechain to the protein target via the Ftase. The attachment of the farnesyl group causes a change in the overall hydrophobicity of the target allowing the protein to anchor itself into the membrane where it usually interacts with other signal transduction molecules. That the loss of farnesylation activity in the era1 mutant leads to an enhanced response of the seed to ABA suggests a target protein in *Arabidopsis* must be localized to the membrane to attenuate the ABA signal. Thus farnesylation in Arabidopsis, appears to be required for the normal function of a negative regulator of ABA sensitivity.

Figure 6:
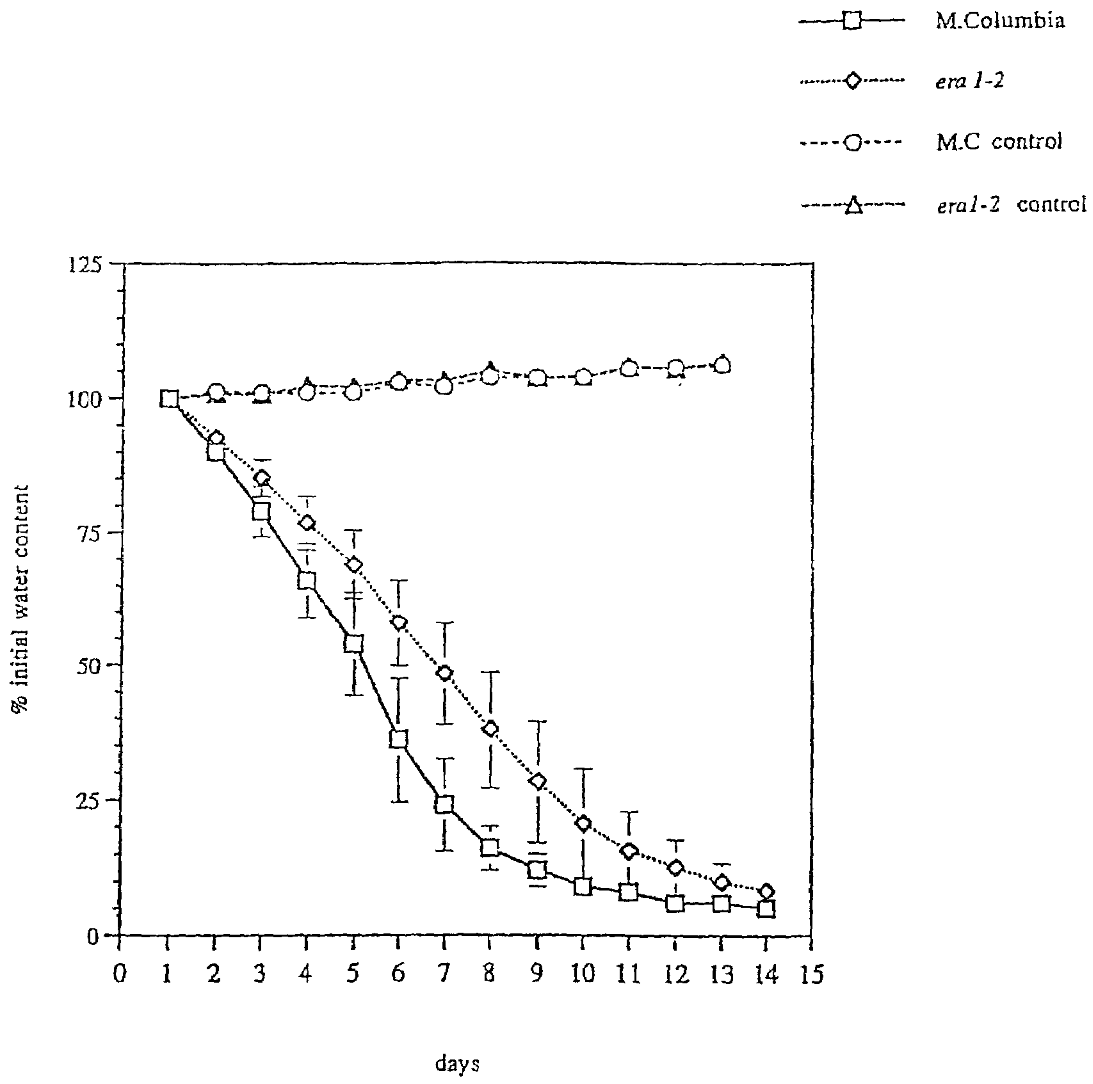
FIG. 6 is a graph comparing the water content of *Arabidopsis* plants with inactivated or mutant Ftase activity (*M. Columbia,* era 1-2) and controls (M.C. control, era 1-2 control).
Figure 7:
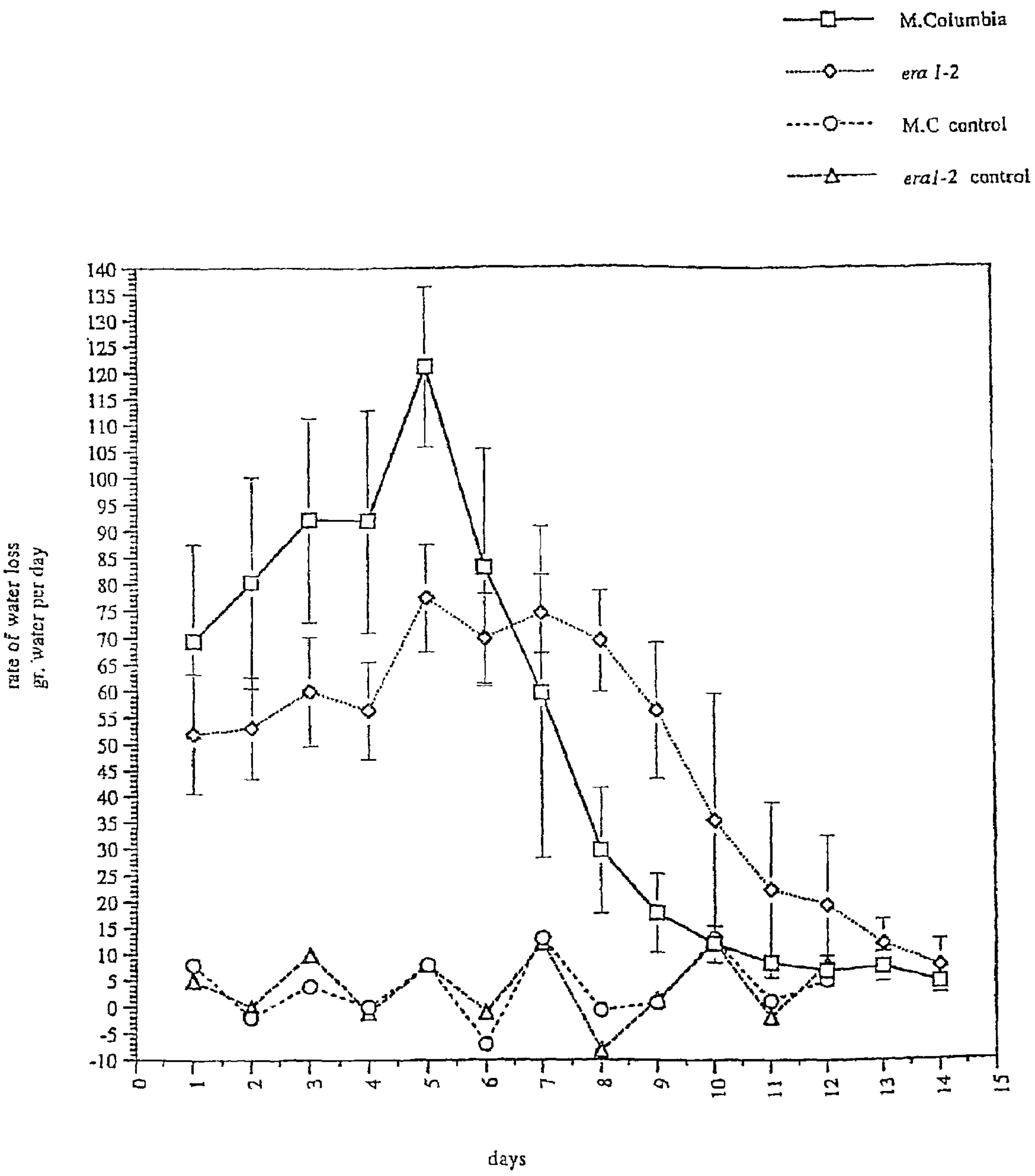
FIG. 7 is a graph comparing the rate of water loss for the *Arabidopsis* plants with inactivated or mutant Ftase activity (M. Columbia, era 1-2) and controls (M.C. control, era 1-2 control).
Figure 8A:
FIGS. 8A-8E are comparisons of aging leaves from control (wild-type) and era-2 mutant plants.
Figure 8B:
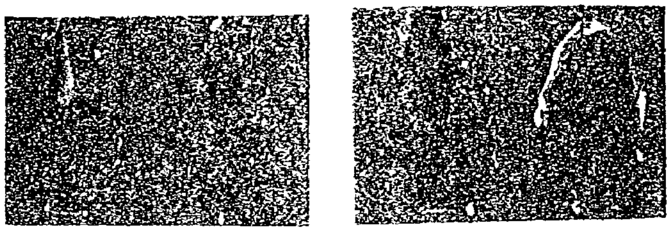
Figure 8C:
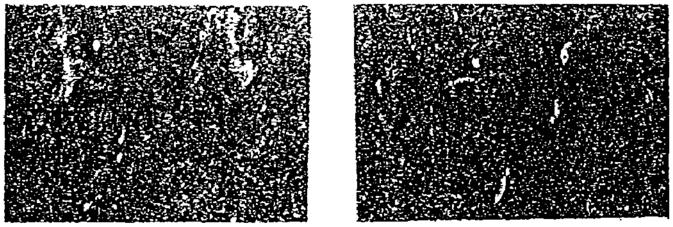
Figure 8D:
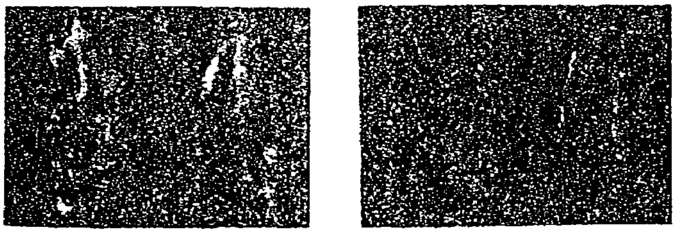
Figure 8E:
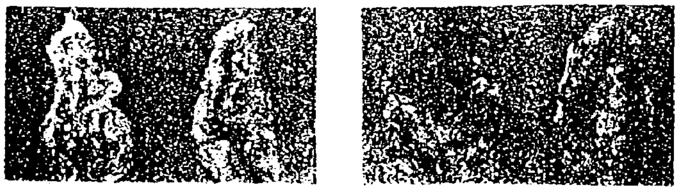

Subsequent work has shown that loss of ERA1 gene function in *Arabidopsis* confers an enhanced tolerance to enviromnental stresses at the level of the mature plant. For example, a comparison of wild-type plants and era1 mutant plants grown in soil under standard laboratory conditions (24 hr light, 150 μE m$^{-2}$sec$^{-1}$, 30% humidity) showed that the mutants did not require water as frequently as the wild-type plants in order to maintain viability (FIG. 5). When mutant and wild-type plants were grown until flowering occurred, watering was stopped and the plants were observed each subsequent day for signs of stress. Water loss was significantly reduced in the mutant plants compared to the wild-type plants (FIGS. 6 and 7).

To determine if the observed increased drought tolerance of era mutants was related to ERA1 gene function, transgenic plants containing a ERA1 promoter fusion to a reporter GUS gene (made by inserting a 5 Kb fragment of the ERA1 promoter into a promoterless GUS T-DNA plasmid), were constructed. Analysis of the transgenic plants showed that ERA1 is transcriptionally expressed in the epidermal tissue of *Arabidopsis* and that this expression is guard-cell specific. Expression of ERA1was also noted in the meristematic tissue of the plants and in root hairs. The guard cell expression of ERA1 is consistent with the drought tolerance of the mutant as these cells are the major regulators of water transpiration through the plant. It would be expected that ERA1-regulated stomatal conductance would require expression of the ERA1 gene in the guard cells. Hence loss of ERA1gene function results in guard cells which are more responsive to ABA which, in turn, leads to more drought responsive guard cell regulation. Therefore, modification of Ftase expression or activity in higher plants, especially crop plants, will have profound effects on stomatal conductance and transpiration rates in the plants.

The nature of the era1 mutation in *Arabidopsis* demonstrates that inhibition of farnesylation will enhance ABA responses in a plant and alteration of this enzyme activity in crop species. Inhibition of Ftase activity in crop plants can be achieved via a number of methods. For example, antisense technology of cognate ERA1 genes in a variety of crop species can be used to reduce Ftase activity, thus increasing drought tolerance. By specifically producing ERA1 antisense RNA in guard cells, the amount of Ftase synthesized can be reduced to a level which would mimic era mutant phenotypes. The ERA1 promoter is regulated in a number of different tissues ranging from shoot meristems to root hairs. By determining the elements of the ERA1 promoter which allow expression in specific tissues, it is possible to tailor the expression of antisense ERA1 to only one tissue or cell type, such as guard cells.

Another method to inhibit Ftase activity in plants is the production of specific peptide inhibitors of farnesylation in transgenic plants. In mammalian and yeast systems, the carboxyl terminal target sequence (CaaX, where C=cysteine, x=aliphatic, X=any amino acid) which allows the attachment of the farnesyl group to specific proteins has been clearly defined. Peptides which mimic these target sequences have been made and shown to inhibit farnesylation of the endogenous target proteins in these systems. Moreover, CAIM is farnesylated in vivo in, Arabidopsis. Thus, similar inhibitors can be applied to higher plants to competitively inhibit Ftase in vivo. Again, this can be done through expression of inhibitor peptides in transgenic plants by synthesizing the DNA sequence for a CaaX peptide and fusing it to a guard cell-specific promoter. In both methods, using the appropriate promoters, antisense Ftase or peptide inhibitors can be specifically targeted and controlled.

Also included in the invention are methods of producing a transgenic plant. The method includes introducing into one or more plant cells a compound that alters, e.g., inhibits farnesylation of a polypeptide having a carboxyl terminal CaaX motif in the plant to generate a transgenic plant cell and regenerating a transgenic plant from the transgenic cell. In some aspects the compound alters, e.g., increases or decreases CaaX prenyl protease expression or activity. Alternatively, the compound alters farnesyltransferase expression or activity. In other aspects the compound alters isoprenylcysteine carboxyl methytransferase expression or activity. The compound can be, e.g., (i) a CaaX prenyl protease, farnesyltransferase or isoprenylcysteine carboxyl methytransferase polypeptide; (ii) a nucleic acid encoding a CaaX prenyl protease, farnesyltransferase or isoprenylcysteine carboxyl methytransferase polypeptide; (iii) a nucleic acid that increases expression of a nucleic acid that encodes a CaaX prenyl protease, farnesyltransferase or isoprenylcysteine carboxyl methytransferase polypeptide; (iv) a nucleic acid that decreases the expression of a nucleic acid that encodes a CaaX prenyl protease, farnesyltransferase or isoprenylcysteine carboxyl methytransferase polypeptide; (v) a CaaX prenyl protease, farnesyltransferase or isoprenylcysteine carboxyl methytransferase antisense nucleic acid and derivatives, fragments, analogs and homologs thereof. A nucleic acid that increases expression of a nucleic acid that encodes a CaaX prenyl protease, farnesyltransferase or isoprenylcysteine carboxyl methytransferase polypeptide includes, e.g., promoters, enhancers. The nucleic acid can be either endogenous or exogenous. Preferably, the compound is a CaaX prenyl protease, famesyltransferase or isoprenylcysteine carboxyl methytransferase polypeptide or a nucleic acid encoding a CaaX prenyl protease, farnesyltransferase or isoprenylcysteine carboxyl methytransferase polypeptide.

Included in the invention are methods of producing a transgenic plant that has increased stress resistance, delayed senescence or increased sensitivity to ABA. The method includes introducing into one or more plant cells a compound that alters farnesyl transferase expression (i.e. farnesyl transferase alpha or beta) or activity in the plant. The compound can be, e.g., (i) a farnesyl transferase polypeptide inhibitor; (ii) a nucleic acid encoding a farnesyl transferase polypeptide inhibitor; (iii) a nucleic acid that decreases expression of a nucleic acid that encodes a farnesyl transferase polypeptide and, derivatives, fragments, analogs and homologs thereof; (iv) an antisense farnesyl transferase nucleic acid. A nucleic acid that decreases expression of a nucleic acid that encodes a famesyl transferase polypeptide includes, e.g., antisense nucleic acids or RNA inhibitory nucleic acids. The nucleic acid can be either endogenous or exogenous. Preferably the compound is a farnesyl transferase polypeptide or a nucleic acid encoding a farnesyl transferase polypeptide. More preferably the compound is a nucleic acid complementary to a nucleic acid encoding a farnesyl transferase polypeptide. For example an anti-sense nucleic acid molecule.

Alternatively the compound is a nucleic acid molecule comprising a nucleic acid sequence encoding a mutated farnesyl transferase, isoprenylcysteine carboxyl methytransferase or CaaX prenyl protease polypeptide. By mutated is meant that the polypeptide lacks one or more function of a wild-type polypeptide. For example, a mutated farnesyltransferase beta polypeptide is a polypeptide has less amino acids than a full length wild type polypeptide by still retains the ability to dimerize with an alpha subunit. For example a mutated farnesyltransferase beta polypeptide is less than 314 amino acids in length. Preferably, the mutated farnesyltransferase beta polypeptide comprises the amino acid sequence of SEQ ID NO: 1 or a thereof.

In another aspect the compound is a nucleic acid encoding a CaaX motif. Alternatively, the CaaX motif is operably liked to a promoter.

Also included in the invention is a plant where a mutation has been introduced in the gene encoding farnesyl transferase (i.e. alpha or beta) which results in a plant that has decreased farnesyl transferase activity and increased tolerance to stress as compared to a wild type plant. The mutation may be introduced by chemical or mechanical means.

In various aspects the transgenic plant has an altered phenotype as compared to a wild type plant (i.e., untransformed). By altered phenotype is meant that the plant has a one or more characteristic that is different from the wild type plant. For example, the transgenic plant has an increased resistance to stress. Increased stress resistance is meant that the transgenic plant can grow under stress conditions (e.g., high salt, decreased water, low temperatures, high temperatures) or under conditions that normally inhibit the growth of an untransformed Stresses include, for example, chilling stress, heat stress, heat shock, salt stress, water stress (i.e., drought), nutritional stress, disease, grazing pests, wound healing, pathogens such as for example fungi, bacteria, nematodes, viruses or parasitic weed and herbicides. Methodologies to determine plant growth or response to stress include for example, height measurements, weight or biomass measurements, leaf area or number, ability to flower, water use, transpiration rates and yield. Alternatively, the transformed plant has an increased (i.e., enhanced) ABA sensitivity. The enhanced ABA sensitivity is at the seedling growth stage. Alternatively, the enhanced ABA sensitivity is at the mature plant stage. Additional altered phenotypes include for example, enhanced vegetative growth (e.g., increased leaf number, thickness and overall biomass), delayed reproductive growth (e.g., flowering later); enhanced seedling vigor (e.g., increased root biomass and length), enhanced lateral root formation and therefore soil penetration more extensive vascular system resulting in an enhanced transport system.

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Gossypium, Picea, Caco,* and *Populus.*

This invention provides a method of producing drought-tolerant plants comprising: preparing a nucleic acid construct which comprises a promoter operably-linked to a nucleic acid comprising or encoding antisense to SEQ ID NO: 1, 14, 40, 43, 80-85 or 172, or nucleic acid comprising a functional equivalent or fragment thereof of the antisense; inserting the nucleic acid construct into a vector; transforming a plant, tissue culture, or plant cells with the vector; and growing the plant or regenerating a plant from the tissue culture or plant cells; wherein drought-tolerant plants are produced. This method can be used wherein the nucleic acid is selected from the group consisting of 25-200 or more consecutive nucleotides complementary to SEQ ID NO: 1, 14, 40, 43, 80-85 or 172, oligonucleotides consisting of 25 or more consecutive nucleotides of SEQ ID NO: 1, 14, 40, 43, 80-85 or 172 or its complement, or nucleic acid encoding a peptide inhibitor of farnesyl transferase In addition to stomatal regulation which is extremely sensitive to ABA, era plants also demonstrate delayed senescence under drought conditions, indicating that farnesylation negatively regulates a number of drought-induced responses in *Arabidopsis*. The era plants grown under normal laboratory conditions take longer to turn yellow. The mutant plants remained green and viable long after the wild-type had senesced and died. Detached leaves of an era mutant plant do not yellow as quickly as detached leaves of wild-type plants (FIG. 8). Similar-sized leaves which were developmentally identical were taken from wild-type and era plants and placed on agar-containing petri plates (See Example 7). Normally, a wild-type leaf begins to lose chlorophyll about five days later and eventually bleaches. The leaves of the mutant plants remained green for twice as long. Because the leaves were in constant contact with the agar they were not drought stressed, indicating the reduced senescence of the era1 mutant is not a drought-induced phenomenon.

Moreover, under a 10 hr day/16 hr night cycle, the plant life cycle can be doubled versus the wild-type plants (3 months). It appears therefore, that chlorophyll turnover and senescence signals are altered in the era1 mutant. For example, wild-type and mutant plants were grown in pots under well-watered conditions to stages of development where the wild-type plant leaves would begin to senesce (about the time of flower development). At this time, developmentally-similar leaves were assayed for senescence-induced marker genes by northern blot analysis (Example 8). Two genes, SAG12 and SAG13, in which transcription is normally induced during senescence in wild-type plants, were not induced in the era1 mutant (FIG. 9). Further, CAB transcription is maintained (FIG. 9). Taken together, these results indicate the senescence induction program in era1 mutants is delayed compared to wild-type plants, showing that loss of farnesylation activity causes a retardation of the induction of senescence in the plant even under conditions wherein water stress is not an environmental factor.

In addition to effects on senescence and water loss, the era1 mutants show a difference in branching and flowering habit when grown under diurnal light cycles. Under continuous (24 hours light/day) light, the branching pattern of mutants does not differ from that of wild-type plants. However, when given a dark period, the mutants do not produce as many lateral branches as wild-type plants. When measured, plants with loss of farnesylation activity produced only 2.4 branches per plant compared to 3.6 lateral branches per wild-type plant. This represents a 30% decrease in lateral branches per plant.

Flowering is affected by loss of Ftase activity as well. Plants lacking Ftase activity produce more flowers per plant (25-30 buds/inflorescence) than wild-type plants (10-15 buds/inflorescence). Thus, on average there are twice as many flower buds are present on the mutants than on the wild-type plants.

These pleiotrophic effects of the era1 loss of function mutants on whole plant development indicate that the ERA1 gene can be a coordinate regulator of a collection of plant developmental functions.

Until now, there was no known function for farnesylation in higher plants, including a role in ABA signal transduction. Ftases have been found in a number of higher plants such as tomato and pea, so it is clear that this enzyme has functions across species boundaries. Furthermore, overproduction of farnesyl transferase target peptides or the use of farnesylation inhibitors completely inactivates Ftase in mammalian and yeast systems. Thus, similar. inhibitors can be applied to higher plants to inactivate Ftase in vivo. In both cases with the appropriate promoters, antisense Ftase or peptide inhibitors can be specifically targeted and controlled.

The farnesylation deficient mutants are also supersensitive to exogenous auxin. That these mutants show reduced branching and minor alterations in meristem organization, can be explained by altered auxin regulation. Thus other hormone functions are affected in this mutant, which indicates that, in addition to ABA pathways, other hormone regulated pathways are controlled by Ftase activity. These results demonstrate that the ERA1 gene provides a molecular mechanism to coordinate regulation of different hormone signaling molecules.

In accordance with the present invention, the plants included within the scope of this invention are higher and lower plants of the plant kingdom. Mature plants, seedlings and seeds are included in the scope of the invention. A mature plant includes a plant at any stage in development beyond the seedling. A seedling is a very young, immature plant in the early stages of development. Plant parts, protoplasts and tissue culture are also provided by this invention.

Transgenic plants are included within the scope of the present invention which have the phenotype characterized by the era1 mutation. Seed of transgenic plants are provided by this invention and can be used to propagate more plants containing the constructs of this invention.

ERA1 function in a number of crop plants can be inhibited to enhance the plant's response to adverse environmental conditions that require ABA-mediated signaling. Control of farnesylation in higher plants regulates both embryonic and vegetative tissue response to this hormone (Cutler, et al., 1996). The increased sensitivity translates into a faster response of the tissue to stress conditions which in turn confers increased protection of the plant to the environmental stress. Because this only requires the control of a single gene, ERA1, it should be possible to control farnesylation in a variety of plants by controlling the synthesis or activity of this enzyme. Furthermore, the work described herein clearly indicates that altering the ABA signal transduction pathway by manipulating the genes that control the ABA response makes it possible to improve the plant's response to adverse water stress conditions.

To produce transgenic plants of this invention, a construct comprising the gene encoding Ftase, or nucleic acid encoding its functional equivalent, and a promoter are incorporated into a vector through methods known and used by those of skill in the art. The promoter can comprise all or part of SEQ ID NO:3. The construct can also include any other necessary regulators such as terminators or the like, operably linked to the coding sequence. It can also be beneficial to include a 5' leader sequence, such as the untranslated leader from the coat protein mRNA of alfalfa mosaic virus (Jobling, S. A. and Gehrke, L. (1987) *Nature* 325:622-625) or the maize chlorotic mottle virus (MCMV) leader (Lommel, S. A., et al. (1991)

Virology 81:382-385). Those of skill in the art will recognize the applicability of other leader sequences for various purposes. Exemplary constructs include SEQ ID NO: 54-64.

Targeting sequences are also useful and can be incorporated into the constructs of this invention. A targeting sequence is usually translated into a peptide which directs the polypeptide product of the coding nucleic acid sequence to a desired location within the cell, such as to the plastid, and becomes separated from the peptide after transit of the peptide is complete or concurrently with transit. Examples of targeting sequences useful in this invention include, but are not limited to, the yeast mitochondrial presequence (Schmitz, et al. (1989) *Plant Cell* 1:783-791), the targeting sequence from the pathogenesis-related gene (PR-1) of tobacco (Cornellisen, et al. (1986) *EMBO J.* 5:37-40), vacuole targeting signals (Chrispeels, M. J. and Raikhel, N. V. (1992) *Cell* 68:613-616), secretory pathway sequences such as those of the ER or Golgi (Chrispeels, M. J. (1991) *Ann. Rev. Plant Physiol. Plant Mol. Biol.* 42:21-53). Intraorganellar sequences may also be useful for internal sites, e.g., thylakoids in chloroplasts. Theg, S. M. and Scott, S. V. (1993) *Trends in Cell Biol.* 3:186-190.

In addition to 5' leader sequences, terminater sequences are usually incorporated into the construct. In plant constructs, a 3' untranslated region (3' UTR) is generally part of the expression plasmid and contains a polyA termination sequence. The termination region which is employed will generally be one of convenience, since termination regions appear to be relatively interchangeable. The octopine synthase and nopaline synthase termination regions, derived from the Ti-plasmid of *A. tumefaciens,* are suitable for such use in the constructs of this invention.

Any suitable technique can be used to introduce the nucleic acids and constructs of this invention to produce transgenic plants with an altered genome. For grasses such as maize, microprojectile bombardment (see for example, Sanford, J. C., et al., U.S. Pat. No. 5,100,792 (1992) can be used. In this embodiment, a nucleotide construct or a vector containing the construct is coated onto small particles which are then introduced into the targeted tissue (cells) via high velocity ballistic penetration. The vector can be any vector which permits the expression of the exogenous DNA in plant cells into which the vector is introduced. The transformed cells are then cultivated under conditions appropriate for the regeneration of plants, resulting in production of transgenic plants.

Transgenic plants carrying the construct are examined for the desired phenotype using a variety of methods including but not limited to an appropriate phenotypic marker, such as antibiotic resistance or herbicide resistance, or visual observation of the time of floral induction compared to naturally-occurring plants.

Other known methods of inserting nucleic acid constructs into plants include Agrobacterium-mediated transformation (see for example Smith, R. H., et al., U.S. Pat. No. 5,164,310 (1992)), electroporation (see for example, Calvin, N., U.S. Pat. No. 5,098,843 (1992)), introduction using laser beams (see for example, Kasuya, T., et al., U.S. Pat. No. 5,013,660 (1991)) or introduction using agents such as polyethylene glycol (see for example Golds, T. et al. (1993) *Biotechnology,* 11:95-97), and the like. In general, plant cells may be transformed with a variety of vectors, such as viral, episomal vectors, Ti plasmid vectors and the like, in accordance with well known procedures. The method of introduction of the nucleic acid into the plant cell is not critical to this invention.

The methods of this invention can be used with in planta or seed transformation techniques which do not require culture or regeneration. Examples of these techniques are described in Bechtold, N., et al. (1993) *CR Acad. Sci. Paris/Life Sciences* 316:118-93; Chang, S. S., et al. (1990) *Abstracts of the Fourth International Conference on Arabidopsis Research*, Vienna, p. 28; Feldmann, K. A. and Marks, D. M (1987) *Mol. Gen. Genet.* 208:1-9; Ledoux, L., et al. (1985) *Arabidopsis Inf. Serv.* 22:1-1 1; Feldmann, K. A. (1 992) In: *Methods in Arabidopsis Research* (Eds. Koncz, C., Chua, N-H, Schell, J.) pp. 274-289; Chee, et al., U.S. patent application Ser. No. 5,376,543.

The transcriptional initiation region may provide for constitutive expression or regulated expression. In addition to the ERA1 promoter, many promoters are available which are functional in plants.

Constitutive promoters for plant gene expression include, but are not limited to, the octopine synthase, nopaline synthase, or mannopine synthase promoters from *Agrobacterum*, the cauliflower mosaic virus (35S) promoter, the figwort mosaic virus (FMV) promoter, and the tobacco mosaic virus (TMV) promoter. Constitutive gene expression in plants can also be provided by the glutamine synthase promoter (Edwards, et al. (1990) *PNAS* 87:3459-3463), the maize sucrose synthetase 1 promoter (Yang, et al. (1990) *PNAS* 87:4144-4148), the promoter from the Rol-C gene of the TLDNA of Ri plasmid (Sagaya, et al. (1989) *Plant Cell Physiol.* 30:649-654), and the phloem-specific region of the pRVC-S-3A promoter (Aoyagi, et al. (1988) *Mol. Gen. Genet.* 213:179-185).

Heat-shock promoters, the ribulose-1,6-bisphosphate (RUBP) carboxylase small subunit (ssu) promoter, tissue specific promoters, and the like can be used for regulated expression of plant genes. Developmentally-regulated, stress-induced, wound-induced or pathogen-induced promoters are also useful.

The regulatory region may be responsive to a physical stimulus, such as light, as with the RUBP carboxylase ssu promoter, differentiation signals, or metabolites. The time and level of expression of the sense or antisense orientation can have a definite effect on the phenotype produced. Therefore, the promoters chosen, coupled with the orientation of the exogenous DNA, and site of integration of a vector in the genome, will determine the effect of the introduced gene.

Specific examples of regulated promoters also include, but are not limited to, the low temperature Kin1 and cor6.6 promoters (Wang, et al. (1995) *Plant Mol. Biol.* 28:605; Wang, et al. (1995) *Plant Mol. Biol.* 28:619-634), the ABA inducible promoter (Marcotte Jr., et al. (1989) *Plant Cell* 1:969-976), heat shock promoters, such as the inducible hsp70 heat shock promoter of *Drosphilia melanogaster* (Freeling, M., et al. (1985) *Ann. Rev. of Genetics* 19: 297-323), the cold inducible promoter from *B. napus* (White, T. C., et al. (1994) *Plant Physiol.* 106:917), the alcohol dehydrogenase promoter which is induced by ethanol (Nagao, R. T., et al., Miflin, B. J., Ed. *Oxford Surveys of Plant Molecular and Cell Biology*, Vol. 3, p 384-438, Oxford University Press, Oxford 1986), the phloem-specific sucrose synthase ASUS1 promoter from Arabidopsis (Martin, et al. (1993) *Plant J.* 4:367-377), the ACS1 promoter (Rodrigues-Pousada, et al. (1993) *Plant Cell* 5:897-911), the 22 kDa zein protein promoter from maize (Unger, et al. (1993) *Plant Cell* 5:831-841), the psl lectin promoter of pea (de Pater, et al. (1993) *Plant Cell* 5:877-886), the phas promoter from *Phaseolus vulgaris* (Frisch, et al. (1995) *Plant J.* 7:503-512), the lea promoter (Thomas, T. L. (1993) *Plant Cell* 5:1401-1410), the E8 gene promoter from tomato (Cordes, et al. (1989) *Plant Cell* 1:1025-1034), the PCNA promoter (Kosugi, et al. (1995) *Plant J.* 7:877-886), the NTP303 promoter (Weterings, et al. (1995) *Plant J.* 8:55-63), the OSEM promoter (Hattori, et al. (1995) *Plant J.* 7:913-925), the ADP GP promoter from potato (Muller-Rober, et al. (1994) *Plant Cell* 6:601-604), the Myb promoter from barley (Wissenbach, et al. (1993) *Plant J.* 4:411-422), and the plastocyanin promoter from *Arabidopsis* (Vorst, et al. (1993) *Plant J.* 4:933-945).

The vector can be introduced into cells by a method appropriate to the type of host cells (e.g., transformation, electroporation, transfection). For the purposes of this disclosure, the terms “transformed with”, “transformant”, “transformation”, “transfect with”, and “transfection” all refer to the introduction of a nucleic acid into a cell by one of the numerous methods known to persons skilled in the art. Transformation of prokaryotic cells, for example, is commonly achieved by treating the cells with calcium chloride so as to render them “competent” to take up exogenous DNA, and then mixing such DNA with the competent cells. Prokaryotic cells can also be infected with a recombinant bacteriophage vector.

Nucleic acids can be introduced into cells of higher organisms by viral infection, bacteria-mediated transfer (e.g., *Agrobacterium* T-DNA delivery system), electroporation, calcium phosphate co-precipitation, microinjection, lipofection, bombardment with nucleic-acid coated particles or other techniques, depending on the particular cell type. For grasses such as corn and sorghum, microprojectile bombardment as described, for example, in Sanford, J. C., et al., U.S. Pat. No. 5,100,792 (1992) can be used. Other useful protocols for the transformation of plant cells are provided in Gelvin et al., 1992. Suitable protocols for transforming and transfecting cells are also found in Sambrook et al., 1989. The nucleic acid constructs of this invention can also be incorporated into specific plant parts such as those described supra through the transformation and transfection techniques described herein.

To aid in identification of transformed plant cells, the constructs of this invention are further manipulated to include genes coding for plant selectable markers. Useful selectable markers include enzymes which provide for resistance to an antibiotic such as gentamycin, hygromycin, kanamycin, or the like. Similarly, enzymes providing for production of a compound identifiable by color change such as GUS (β-glucuronidase), or by luminescence, such as luciferase, are useful.

For example, antisense Ftase can be produced by integrating a complement of the ERA1 gene linked to DNA comprising SEQ ID NO:3 into the genome of a virus that enters the host cells. By infection of the host cells, the components of a system which permits the transcription of the antisense present in the host cells.

When cells or protoplasts containing the antisense gene driven by a promoter of the present invention are obtained, the cells or protoplasts are regenerated into whole plants. The transformed cells are then cultivated under conditions appropriate for the regeneration of plants, resulting in production of transgenic plants. Choice of methodology for the regeneration step is not critical, with suitable protocols being available for many varieties of plants, tissues and other photosynthetic organisms. See, e.g., Gelvin S. B. and Schilperoort R. A., eds. *Plant Molecular Biology Manual, Second Edition*, Suppl. 1 (1995) Kluwer Academic Publishers, Boston Mass., U.S.A.

Transgenic plants carrying the construct are examined for the desired phenotype using a variety of methods including but not limited to an appropriate phenotypic marker, such as antibiotic resistance or herbicide resistance as described supra, or visual observation of their growth compared to the growth of the naturally-occurring plants under the same conditions.

As used herein, the term transgenic plants includes plants that contain either DNA or RNA which does not naturally occur in the wild type (native) plant or known variants, or additional or inverted copies of the naturally-occurring DNA and which is introduced as described herein. Transgenic plants include those into which isolated nucleic acids have been introduced and their descendants, produced from seed, vegetative propagation, cell, tissue or protoplast culture, or the like wherein such alteration is maintained.

Such transgenic plants include, in one embodiment, transgenic plants which are angiosperms, both monocotyledons and dicotyledons. Transgenic plants include those into which DNA has been introduced and their progeny, produced from seed, vegetative propagation, cell, tissue or protoplast culture, or the like.

Seed can be obtained from the regenerated plant or from a cross between the regenerated plant and a suitable plant of the same species. Alternatively, the plant can be vegetatively propagated by culturing plant parts under conditions suitable for the regeneration of such plant parts.

In yet another aspect of this invention are provided plant tissue culture and protoplasts which contain DNA comprising antisense or an altered ERA1 nucleic acid operably linked to an ERA1 promoter, which alters the response of the tissue culture or protoplasts to varying environmental conditions.

The methods of this invention can also be used with in planta or seed transformation techniques which do not require culture or regeneration. Examples of these techniques are described in Bechtold, N., et al. (1993) *CR Acad. Sci. Paris/Life Sciences* 316:118-93; Chang, S. S., et al. (1990) *Abstracts of the Fourth International Conference on Arabidopsis Research*, Vienna, p. 28; Feldmann, K. A. and Marks, D. M (1987) *Mol. Gen. Genet.* 208:1-9; Ledoux, L., et al. (1985) *Arabidopsis Inf Serv.* 22:1-11; Feldmann, K.A. (1992) In: *Methods in Arabidopsis Research* (Eds. Koncz, C., Chua, N-H, Schell, J.) pp. 274-289; Chee, et al., U.S. patent application Ser. No. 5,376,543.

The isolated nucleic acid molecules of the invention can be used to express PPI protein (e.g., via a recombinant expression vector in a host cell), to detect PPI mRNA (e.g., in a biological sample) or a genetic lesion in a PPI gene, and to modulate PPI activity, as described further, below. In addition, the PPI proteins can be used to screen compounds that modulate the PPI protein activity or expression. In addition, the anti-PPI antibodies of the invention can be used to detect and isolate PPI proteins and modulate PPI activity.

The invention provides a method (also referred to herein as a "screening assay") for identifying modulators, i.e., candidate or test compounds or agents (e.g., peptides, peptidomimetics, small molecules or other drugs) that bind to PPI proteins or have a stimulatory or inhibitory effect on, e.g., PPI protein expression or PPI protein activity. The invention also includes compounds identified in the screening assays described herein.

In one embodiment, the invention provides assays for screening candidate or test compounds which bind to a PPI protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145. A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412-421), or on beads (Lam, 1991. *Nature* 354: 82-84), on chips (Fodor, 1993. *Nature* 364: 555-556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865-1869) or on phage (Scott and Smith, 1990. *Science* 249: 386-390; Devlin, 1990. *Science* 249: 404-406; Cwirla, et al., 1990. *Proc. Natl. Acad. Sci. U.S.A.* 87: 6378-6382; Felici, 1991. *J. Mol. Biol.* 222: 301-310; Ladner, U.S. Pat. No. 5,233,409.).

In one embodiment, an assay is a cell-based assay in which a cell which expresses a PPI protein, or a biologically-active portion thereof, is contacted with a test compound and the ability of the test compound to bind to a PPI protein determined. The cell, for example, can be of mammalian origin, plant cell or a yeast cell. Determining the ability of the test compound to bind to the PPI protein can be accomplished, for example, by coupling the test compound with a radioisotope or enzymatic label such that binding of the test compound to the PPI protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio-emission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a PPI protein, or a biologically-active portion thereof, with a known compound which binds PPI to form an assay mixture, contacting the assay mixture with a test compound, and determining the ability of the test compound to interact with a PPI protein, wherein determining the ability of the test compound to interact with a PPI protein comprises determining the ability of the test compound to preferentially bind to PPI protein or a biologically-active portion thereof as compared to the known compound.

In another embodiment, an assay is a cell-based assay comprising contacting a cell expressing a PPI protein, or a biologically-active portion thereof, with a test compound and determining the ability of the test compound to modulate (e.g., stimulate or inhibit) the activity of the PPI protein or biologically-active portion thereof. Determining the ability of the test compound to modulate the activity of PPI or a biologically-active portion thereof can be accomplished, for example, by determining the ability of the PPI protein to bind to or interact with a PPI target molecule. As used herein, a "target molecule" is a molecule with which a PPI protein binds or interacts in nature, for example, a molecule on the surface of a cell which expresses a PPI interacting protein, a molecule on the surface of a second cell, a molecule in the extracellular milieu, a molecule associated with the internal surface of a cell membrane or a cytoplasmic molecule. A PPI target molecule can be a non-PPI molecule or a PPI protein or polypeptide of the invention In one embodiment, a PPI target molecule is a component of a signal transduction pathway that facilitates transduction of an extracellular signal (e.g. a signal generated by binding of a compound to a membrane-bound molecule) through the cell membrane and into the cell. The target, for example, can be a second intercellular protein that has catalytic activity or a protein that facilitates the association of downstream signaling molecules with PPI.

Determining the ability of the PPI protein to bind to or interact with a PPI target molecule can be accomplished by one of the methods described above for determining direct binding. In one embodiment, determining the ability of the PPI protein to bind to or interact with a PPI target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a PPI-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a PPI protein or biologically-active portion thereof with a test compound and determining the ability of the test compound to bind to the PPI protein or biologically-active portion thereof. Binding of the test compound to the PPI protein can be determined either directly or indirectly as described above. In one such embodiment, the assay comprises contacting the PPI protein or biologically-active portion thereof with a known compound which binds PPI to form an assay mixture, contacting the assay mixture with a test compound, and determining the ability of the test compound to interact with a PPI protein, wherein determining the ability of the test compound to interact with a PPI protein comprises determining the ability of the test compound to preferentially bind to PPI or biologically-active portion thereof as compared to the known compound.

In still another embodiment, an assay is a cell-free assay comprising contacting PPI protein or biologically-active portion thereof with a test compound and determining the ability of the test compound to modulate (e.g. stimulate or inhibit) the activity of the PPI protein or biologically-active portion thereof. Determining the ability of the test compound to modulate the activity of PPI can be accomplished, for example, by determining the ability of the PPI protein to bind to a PPI target molecule by one of the methods described above for determining direct binding. In an alternative embodiment, determining the ability of the test compound to modulate the activity of PPI protein can be accomplished by determining the ability of the PPI protein further modulate a PPI target molecule. For example, the catalytic/enzymatic activity of the target molecule on an appropriate substrate can be determined as described above.

In yet another embodiment, the cell-free assay comprises contacting the PPI protein or biologically-active portion thereof with a known compound which binds PPI protein to form an assay mixture, contacting the assay mixture with a test compound, and determining the ability of the test compound to interact with a PPI protein, wherein determining the ability of the test compound to interact with a PPI protein comprises determining the ability of the PPI protein to preferentially bind to or modulate the activity of a PPI target molecule.

The cell-free assays of the invention are amenable to use of either the soluble form or the membrane-bound form of PPI protein. In the case of cell-free assays comprising the membrane-bound form of PPI protein, it may be desirable to utilize a solubilizing agent such that the membrane-bound form of PPI protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either PPI protein or its target molecule to facilitate separation of complexed from uncomplexed forms of one or both of the proteins, as well as to accommodate automation of the assay. Binding of a test compound to PPI protein, or interaction of PPI protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-PPI fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or PPI protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of PPI protein binding or activity determined using standard techniques.

Other techniques for immobilizing proteins on matrices can also be used in the screening assays of the invention. For example, either the PPI protein or its target molecule can be immobilized utilizing conjugation of biotin and streptavidin. Biotinylated PPI protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with PPI protein or target molecules, but which do not interfere with binding of the PPI protein to its target molecule, can be derivatized to the wells of the plate, and unbound target or PPI protein trapped in the wells by antibody conjugation. Methods for detecting such complexes, in addition to those described above for the GST-immobilized complexes, include immunodetection of complexes using antibodies reactive with the PPI protein or target molecule, as well as enzyme-linked assays that rely on detecting an enzymatic activity associated with the PPI protein or target molecule.

In another embodiment, modulators of PPI protein expression are identified in a method wherein a cell is contacted with a candidate compound and the expression of PPI mRNA or protein in the cell is determined. The level of expression of PPI mRNA or protein in the presence of the candidate compound is compared to the level of expression of PPI mRNA or protein in the absence of the candidate compound. The candidate compound can then be identified as a modulator of PPI mRNA or protein expression based. upon this comparison. For example, when expression of PPI mRNA or protein is greater (i.e., statistically significantly greater) in the presence of the candidate compound than in its absence, the candidate compound is identified as a stimulator of PPI mRNA or protein expression. Alternatively, when expression of PPI mRNA or protein is less (statistically significantly less) in the presence of the candidate compound than in its absence, the candidate compound is identified as an inhibitor of PPI mRNA or protein expression. The level of PPI mRNA or protein expression in the cells can be determined by methods described herein for detecting PPI mRNA or protein.

In yet another aspect of the invention, the PPI proteins can be used as "bait proteins" in a two-hybrid assay or three hybrid assay (see, e.g., U.S. Pat. No. 5,283,317; Zervos, et al., 1993. *Cell* 72: 223-232; Madura, et al., 1993. *J. Biol. Chem.* 268: 12046-12054; Bartel, et al., 1993. *Biotechniques* 14: 920-924; Iwabuchi, et al., 1993. *Oncogene* 8: 1693-1696; and Brent WO 94/10300), to identify other proteins that bind to or interact with PPI ("PPI-binding proteins" or "PPI-bp") and modulate PPI activity. Such PPI-binding proteins are also likely to be involved in the propagation of signals by the PPI proteins as, for example, upstream or downstream elements of the PPI pathway.

The two-hybrid system is based on the modular nature of most transcription factors, which consist of separable DNA-binding and activation domains. Briefly, the assay utilizes two different DNA constructs. In one construct, the gene that codes for PPI is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PPI-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with PPI.

In yet another aspect of the invention are methods which utilize the transgenic plants of the invention to identify PPI-interacting components via genetic screening protocols. These components can be for example, regulatory elements which modify PPI-gene expression, interacting proteins which directly modify PPI activity or interacting proteins which modify components of the same signal transduction pathway and thereby exert an effect on the expression or activity of PPI. Briefly, genetic screening protocols are applied to the transgenic plants of the invention and in so doing identify related genes which are not identified using a wild type background for the screen. For example an activation tagged library (Weigel, et al., 2000. *Plant Physiol.* 122: 1003-1013), can be produced using the transgenic plants of the invention as the genetic background. Plants are then screened for altered phenotypes from that displayed by the parent plants. Alternative methods of generating libraries from the transgenic plants of the invention can be used, for example, chemical or irradiation induced mutations, insertional inactivation or insertional activation methods.

The invention further pertains to novel agents identified by the aforementioned screening assays and uses thereof.

Recombinant Expression Vectors and Host Cells

Another aspect of the invention pertains to vectors, preferably expression vectors, containing a nucleic acid encoding a PPI protein, or derivatives, fragments, analogs or homologs thereof. As used herein, the term "vector" refers to a nucleic acid molecule capable of transporting another nucleic acid to which it has been linked. Exemplary expression vector constructs include for example the constructs of SEQ ID NO: 54-64. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). Examples of suitable promoters include for example constitutive promoters, ABA inducible promoters, tissue specific promoters or guard cell specific promoters. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PPI proteins, mutant forms of PPI proteins, fusion proteins, etc.).

The recombinant expression vectors of the invention can be designed for expression of PPI proteins in prokaryotic or eukaryotic cells. For example, PPI proteins can be expressed in bacterial cells such as *Escherichia coli*, insect cells (using baculovirus expression vectors) yeast cells, plant cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

In another embodiment, the PPI expression vector is a yeast expression vector. Examples of vectors for expression in yeast *Saccharomyces cerivisae* include pYepSec1 (Baldari, et al., 1987. *EMBOJ.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (Invitrogen Corp, San Diego, Calif.).

Alternatively, PPI can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In yet another embodiment, a nucleic acid of the invention is expressed in plants cells using a plant expression vector. Examples of plant expression vectors systems include tumor inducing (Ti) plasmid or portion thereof found in *Agrobacterum*, cauliflower mosaic virus (CAMV) DNA and vectors such as pB 1121.

For expression in plants, the recombinant expression cassette will contain in addition to the PPI nucleic acids, a plant promoter region, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable prometers include promoters from plant viruses such as the 35S promoter from cauliflower mosaic virus (CaMV). Odell, et al., Nature, 313: 810-812 (1985). and promoters from genes such as rice actin (McElroy, et al., Plant Cell, 163-171 (1990)); ubiquitin (Christensen, et al., Plant Mol. Biol., 12: 6 19-632 (1992); and Christensen, et al., Plant Mol. Biol., 18: 675-689 (1992)); pEMU (Last, et al., Theor. Appl. Genet., 81: 581-588 (1991)); MAS (Velten, et al., EMBO J., 3: 2723-2730 (1984)); maize H3 histone (Lepetit, et al., Mol. Gen. Genet., 231: 276-285 (1992); and Atanassvoa, et al., Plant Journal, 2(3): 291-300 (1992)), the 5'- or 3'-promoter derived from T-DNA of Agrobacterium tumefaciens, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as, Rsyn7, SCP and UCP promoters, ribulose-1,3-diphosphate carboxylase, fruit-specific promoters, heat shock promoters, seed-specific promoters and other transcription initiation regions from various plant genes, for example, include the various opine initiation regions, such as for example, octopine, mannopine, and nopaline.

Additional regulatory elements that may be connected to a PPI encoding nucleic acid sequence for expression in plant cells include terminaters, polyadenylation sequences, and nucleic acid sequences encoding signal peptides that permit localization within a plant cell or secretion of the protein from the cell. Such regulatory elements and methods for adding or exchanging these elements with the regulatory elements PPI gene are known, and include, but are not limited to, 3' termination and/or polyadenylation regions such as those of the *Agrobacterium tumefaciens* nopaline synthase (nos) gene (Bevan, et al., Nucl. Acids Res., 12: 369-385 (1983)); the potato proteinase inhibitor II (PINJI) gene (Keil, et al., Nuci. Acids Res., 14: 5641-5650 (1986) and hereby incorporated by reference); and An,, et al., Plant Cell, 1: 115-122 (1989)); and the CaMV 19S gene (Mogen, et al., Plant Cell, 2:1261-1272 (1990)).

Plant signal sequences, including, but not limited to, signal-peptide encoding DNA/RNA sequences which target proteins to the extracellular matrix of the plant cell (Dratewka-Kos, et al., J. Biol. Chem., 264: 4896-4900 (1989)) and the *Nicotiana plumbaginifolia* extension gene (DeLoose, et al., Gene, 99: 95-100 (1991)), or signal peptides which target proteins to the vacuole like the sweet potato sporamin gene (Matsuka, et al., Proc. Nat'l Acad. Sci. (USA), 88: 834 (1991)) and the barley lectin gene (Wilkins, et al., Plant Cell, 2: 301-313 (1990)), or signals which cause proteins to be secreted such as that of PRIb (Lind, et al., Plant Mol. Biol., 18: 47-53 (1992)), or those which target proteins to the plastids such as that of rapeseed enoyl-ACP reductase (Verwaert, et al., Plant Mol. Biol., 26: 189-202 (1994)) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the patatin class I promoter is transcriptionally activated only in the potato tuber and can be used to target gene expression in the tuber (Bevan, M., 1986, *Nucleic Acids Research* 14:4625-4636). Another potato-specific promoter is the granule-bound starch synthase (GBSS) promoter (Visser, R. G. R, et al., 1991, *Plant Molecular Biology* 17:691-699).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, P., 1986, *Trans. R. Soc. London* B314:343).

For in situ production of the antisense mRNA of GST, those regions of the GST gene which are transcribed into GST mRNA, including the untranslated regions thereof, are inserted into the expression vector under control of the promoter system in a reverse orientation. The resulting transcribed mRNA is then complementary to that normally produced by the plant.

The resulting expression system or cassette is ligated into or otherwise constructed to be included in a recombinant vector which is appropriate for plant transformation. The vector may also contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in a an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of types of cells may act as suitable host cells for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana, Nicotiana tabacum, Brassica napus, Zea mays, Oryza sativa, Gossypium hirsutum* and *Glycine max.*

Alternatively, it may be possible to produce a polypeptide in lower eukaryotes such as yeast or in prokaryotes such as bacteria. Potentially suitable yeast strains include *Saccharomyces cerevisiae, Schizosaccharomycespombe, Kluyveromyces* strains, *Candida,* or any yeast strain capable of expressing heterologous proteins. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain a functional polypeptide, if the polypeptide is of sufficient length and conformation to have activity. Such covalent attachments may be accomplished using known chemical or enzymatic methods.

A polypeptide may be prepared by culturing transformed host cells under culture conditions suitable to express the recombinant protein. The resulting expressed polypeptide or protein may then be purified from such culture (e.g., from culture medium or cell extracts) using known purification processes, such as gel filtration and ion exchange chromatography. The purification of the polypeptide or protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, a polypeptide or protein may also be expressed in a form which will facilitate purification. For example, it may be expressed as a fusion protein containing a six-residue histidine tag. The histidine-tagged protein will then bind to a Ni-affinity column. After elution of all other proteins, the histidine-tagged protein can be eluted to achieve rapid and efficient purification. One or more reverse-phase high performance liquid chromatography (RP-HPLC) steps employing hydrophobic RP-HPLC media, e.g., silica gel having pendant methyl or other aliphatic groups, can be employed to further purify a polypeptide. Some or all of the foregoing purification steps, in various combinations, can also be employed to provide a substantially homogeneous isolated recombinant polypeptide. The protein or polypeptide thus purified is substantially free of other plant proteins or polypeptides and is defined in accordance with the present invention as "isolated."

Transformed Plants Cells and Transgenic Plants

The invention includes protoplast, plants cells, plant tissue and plants (e.g., monocots and dicots transformed with a PPI nucleic acid (i.e., sense or antisense), a vector containing a PPI nucleic acid (i.e., sense or antisense)or an expression vector containing a PPI nucleic acid (i.e., sense or antisense). As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Gossypium, Picea, Caco, and Populus.

In some aspects of the invention, the transformed plant is resistant to biotic and abiotic stresses, e.g., chilling stress, salt stress, water stress (e.g., drought), disease, grazing pests and wound healing. Additionally, the invention also includes a transgenic plant that is resistant to pathogens such as for example fungi, bacteria, nematodes, viruses and parasitic weeds. Alternatively, the transgenic plant is resistant to herbicides or has delayed esenescence. The transgenic plant has an increase in yield, productivity, biomass or ABA sensitivity. By resistant is meant the plant grows under stress conditions (e.g., high salt, decreased water, low temperatures) or under conditions that normally inhibit, to some degree, the growth of an untransformed plant. Methodologies to determine plant growth or response to stress include for example, height measurements, weight measurements, leaf area, ability to flower, water use, transpiration rates and yield.

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols. See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88 and Andrew Bent in, Clough S J and Bent A F, 1998. Floral dipping: a simplified method for Agrobacterium-mediated transformation of *Arabidopsis thaliana*. The methods chosen vary with the host plant, and include chemical transfection methods such as calcium phosphate, polyethylene glycol (PEG) transformation, microorganism-mediated gene transfer such as *Agrobacterium* (Horsch, et al., Science, 227: 1229-31 (1985)), electroporation, protoplast transformation, micro-injection, flower dipping and biolistic bombardment.

Agrobacterium-Mediated Transformation

The most widely utilized method for introducing an expression vector into plants is based on the natural transformation system of *Agrobacterium. A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, Crit. Rev. Plant Sci., 10: 1-32 (1991). Descriptions of the *Agrobacterium* vector systems and methods for Agrobacterium-mediated gene transfer are provided in Gruber et al., supra; and Moloney, et al, Plant Cell Reports, 8: 238-242 (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for Agrobacterium-mediated transformation of *Arabidopsis thaliana*. Wild type plants are grown until the plant has both developing flowers and open flowers. The plant are inverted for 1 minute into a solution of *Agrobacterium* culture carrying the appropriate gene construct. Plants are then left horizontal in a tray and kept covered for two days to maintain humidity and then righted and bagged to continue growth and seed development. Mature seed is bulk harvested.

Direct Gene Transfer

A generally applicable method of plant transformation is microprojectile-mediated transformation, where DNA is carried on the surface of microprojectiles measuring about 1 to 4 mu.m. The expression vector is introduced into plant tissues with a biolistic device that accelerates the microprojectiles to speeds of 300 to 600 m/s which is sufficient to penetrate the plant cell walls and membranes. (Sanford, et al., Part. Sci. Technol., 5: 27-37 (1987); Sanford, Trends Biotech, 6: 299-302 (1988); Sanford, Physiol. Plant, 79: 206-209 (1990); Klein, et al., Biotechnology, 10: 286-291 (1992)).

Another method for physical delivery of DNA to plants is sonication of target cells as described in Zang, et al., BioTechnology, 9: 996-996 (1991). Alternatively, liposome or spheroplast fusions have been used to introduce expression vectors into plants. See, for example, Deshayes, et al., EMBO J., 4: 2731-2737 (1985); and Christou, et al., Proc. Nat'l. Acad. Sci. (USA), 84: 3962-3966 (1987). Direct uptake of DNA into protoplasts using CaCl.sub.2 precipitation, polyvinyl alcohol or poly-L-ornithine have also been reported. See, for example, Hain, et al., Mol. Gen. Genet., 199: 161 (1985); and Draper, et al., Plant Cell Physiol., 23: 451-458 (1982).

Electroporation of protoplasts and whole cells and tissues has also been described. See, for example, Donn, et al., (1990) In: Abstracts of the VIth Int;l. Congress on Plant Cell and Tissue Culture IAPTC, A2-38, page 53; D'Halluin et al., Plant Cell, 4: 1495-1505 (1992); and Spencer et al., Plant Mol. Biol., 24: 51-61 (1994).

Particle Wounding/*Agrobacterium* Delivery

Another useful basic transformation protocol involves a combination of wounding by particle bombardment, followed by use of *Agrobacterium* for DNA delivery, as described by Bidney, et al., Plant Mol. Biol., 18: 301-31 (1992). Useful plasmids for plant transformation include Bin 19. See Bevan, Nucleic Acids Research, 12: 8711-8721 (1984), and hereby incorporated by reference.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterum*. To start the co-cultivation for intact meristems, *Agrobacterium* is placed on the meristem. After about a 3-day co-cultivation period the meristems are transferred to culture medium with cefotaxime plus kanamycin for the NPTII selection.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterum*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime plus kanamycin for selection.

Transfer by Plant Breeding

Alternatively, once a single transformed plant has been obtained by the foregoing recombinant DNA method, conventional plant breeding methods can be used to transfer the gene and associated regulatory sequences via crossing and backcrossing. Such intermediate methods will comprise the further steps of: (1) sexually crossing the transgenic plant with a plant from a second taxon; (2) recovering reproductive material from the progeny of the cross; and (3) growing transgenic plants from the reproductive material. Where desirable or necessary, the agronomic characteristics of the second taxon can be substantially preserved by expanding this method to include the further steps of repetitively: (1) backcrossing the transgenic progeny with non-transgenic plants from the second taxon; and (2) selecting for expression of an associated marker gene among the progeny of the backcross, until the desired percentage of the characteristics of the second taxon are present in the progeny along with the gene or genes imparting marker gene trait.

By the term “taxon” herein is meant a unit of botanical classification. It thus includes, genus, species, cultivars, varieties, variants and other minor taxonomic groups which lack a consistent nomenclature.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the gene and its activity to its progeny. A more preferred transgenic plant is homozygous for the gene, and transmits that gene to all of its offspring on sexual mating. Seed from a transgenic plant may be grown in the field or greenhouse, and resultingsexually mature transgenic plants are self-pollinated to generate true breeding plants. The progeny from these plants become true breeding lines that are evaluated for increased expression of the transgene.

EMBODIMENTS

The constructs and methods of this invention have numerous applications of commercial value, especially in the prevention of desiccation of plant tissues under periods of water stress. Genetic manipulation of crop plants incorporating inhibitors of Ftase or inactivation of the gene encoding endogenous plant Ftase would allow such plants to withstand transitory environmental stress and can broaden the environments where these plants can be grown. Thus, improving tolerance of crop plants to cold, salt and drought stress, can improve the yield of the plants under such adverse conditions.

The technology described herein can also be used to alter harvesting time and harvest quality of plants. For example, overexpression of Ftase could lead to faster drying times of crops, such as corn and other grasses. Drying corn involves the use of large amounts of propane gas. Drying times of crops such as hay, which dry naturally in the fields, could be shortened, making it less likely that rain would deteriorate the crop.

In addition, inhibition of farnesylation in plants can also be used to control the senescence program of the plants so that leaves can be maintained in a green state longer and fruits can be kept immature. For example, if an antisense construct of ERA1 or CaaX box inhibitor protein construct was placed under the control of a senescence-induced promoter, the plant would induce an inhibitor of farnesylation as the senescence program was initiated, which would in turn inhibit senescence. The result would be a plant which remains green or fruits which remain immature. Thus, the plant could be kept producing a product, such as a vegetative part, flower or fruit much longer. Thus, horticulturalists could produce plants which stayed green and continued to grow even though a wild-type plant of the same variety would senesce under the same conditions. Cut flowers could be maintained longer. Or a fruit could be kept immature, an important product for the vegetable industry where produce lifetime to market is extremely important.

Further, the inhibition of Ftase in fruits and vegetables can reduce wilting. Thus, wilting of produce during transport and shipping could be reduced. Fruits and vegetables on the grocery shelf would also require less misting to keep them fresh and flavorful, and there would be less need to wax produce such as cucumber, apples and oranges to keep them from drying out.

Less watering would also mean that fungal and bacterial attacks on the crops, or fruits and vegetables would be reduced. For example, plant diseases in the field which result from splashing of plant pathogens from the soil to the plant leaves and fruits could be inhibited.

In the field of horticulture, many drought-resistant varieties could be produced for landscaping and for use as ornamental house plants. Especially valuable would be varieties of plants which are used for potting, as ornamentals inside or outside homes and offices, and which can survive infrequent water. This would be a considerable boon for gardeners, especially during the droughty summer months where forgotten plants dry out quickly in the sun. Further, plants grown under trees and in other shady areas often experience drought conditions and limited light. The technology provided herein can provide plant varieties which can better survive under these conditions.

In a further embodiment, horticulturalists could find many uses for plants wherein lateral branching and/or flower numbers can be regulated with light/dark cycles. Examples of plants in which longer, unbranched stems would confer marketable advantage include roses, carnations, lilies, and the like. The ability to increase the number of flowers or florets on the plant is also a highly valuable asset. These traits could also be useful for many agricultural crops in that yields can be increased in a manner which also made harvesting of the crop easier.

Another benefit of the constructs and methods provided herein is that the ERA1 promoter is active in the guard cells of leaves. A portion of the ERA1 gene promoter can be fused to antisense nucleic acid to the ERA1 gene so Ftase activity is diminished only in the guard cells.

A further embodiment is the use of the drought-resistant trait as a selectable marker of transformation in plants, plant cells and plant tissues. One method of detecting transformation in plants consists of: (a) incorporating a nucleic acid construct comprising a promoter operably-linked to nucleic acid comprising antisense to SEQ ID NO:1 or nucleic acid comprising a functional equivalent or fragment thereof of the antisense; (b) inserting the nucleic acid construct into a plant, plant cell or plant tissue; (c) growing the plant, or regenerating a plant from the plant cell or plant tissue until stomates are formed; and (d) placing the plant or regenerated plant under conditions wherein the plant is drought stressed, wherein survival of the plant under drought conditions compared to untransformed plants is indicative of transformation. Thus, this technology can be used as a selectable genetic marker, i.e., a visual marker especially when combined with plant selection and transformation schemes.

In addition, without resorting to stressing a transgenic plant, the branching and/or flowering habit of plants with loss of Ftase function differs substantially from that of wild-type plants and can be used as a marker for successful transformation. This method would be especially useful where in planta transformation techniques have been applied. Under diurnal light conditions, shoots of transgenic plants will demonstrate less lateral branching than that of untransformed shoots, thus indicating effective loss of Ftase activity without the use of selective antibiotic markers.

EXEMPLIFICATION

Example 1

Mutagenesis Conditions

*Arabidopsis* plants used in this study were grown under continuous light in soil- or agar-containing petri plates as described elsewhere (Haughn and Somerville 1986). Two distinct wild-types of *Arabidopsis* were used: Meyerowitz's Colombia (MCol) (Lelhe Seeds, Dripping Springs, Tex.) and Wassilewskija (Ws) (ABRC, Ohio State University). T-DNA mutagenized seeds were screened and mutants were isolated in the Wassilewskija background. These were obtained from the Ohio State *Arabidopsis* seed stock collection (ABRC stock numbers CS2606-2654). The T-DNA seed collection was comprised of 49 pools of 1200 fourth generation (T4) offspring derived from 100 mutagenized parents. A mutagenized parent was obtained by incubating wild-type (T1) seeds overnight in a saturating *Agrobacterium* culture containing a T-DNA plasmid carrying a gene conferring kanamycin resistance. The seeds were then washed in water and planted into pots. T2 generation seed were obtained from each plant and tested for kanamycin resistance. Kanamycin-resistant plants were advanced to the T3 generation. T4 generation plants were given to the stock center. Each pool was screened separately.

Fast neutron-irradiated seeds were screened and mutants were isolated in Meyerowitz's Columbia background. Mutagenized wild-type seeds (N1) were irradiated with 60 Gy of fast neutrons and grown to the next generation. The N2 seeds were obtained as pools of approximately 11,000 seeds generated from 1387 N1 parents. Ten of these pools were screened separately for ABA supersensitive mutations. In the initial screen, all seeds had been stored at 4° C. and were plated without imbibing. For all subsequent screens, seeds were imbibed at 4° C for one week on 0.3 μM ABA and scored for cotyledon emergence after 5-7 days at 22° C. in the light.

Example 2

Genetic Analysis

Mutant lines were backcrossed to wild type three times. T-DNA mutations were backcrossed to Ws and fast neutron mutants to MCol. Segregation of the era phenotype was followed by plating F2 seeds on both 0.3 μM ABA and imbibing four days at 4° C. Following imbibition, plates were transferred to room temperature in the light. Germination was measured as the presence or absence of expanded cotyledons in seedlings one week after imbibition. Double mutants were constructed by crossing lines homozygous for each mutation following segregation and identifying lines that carried one of the mutant phenotypes. The abi3 allele used in this study is abi3-6 (Nambara et al., 1994) and the abi1 allele is abi1-1 (Koornneef et al., 1982). The era1-2 allele was used as the era parent. Segregation analysis suggested era1 partially suppressed the insensitivity of abi1 to ABA, so F2 plants were first screened for insensitivity to 3 mM ABA, and F3 seed from these plants were scored for sensitivity to 0.3 μM ABA. Putative era1 abi1 double mutants were progeny-tested in the F4 generation and verified by DNA polymorphism analysis for both Era1 and Abi1.

For era1 abi3 double mutants, F2 seeds were screened for insensitivity to 3 μM ABA, and mature plants were scored for protruding carpels and immature green seeds (Nambara et al., 1994). Putative double mutant lines were also verified by DNA polymorphism analysis for both Eral and Abi3.

Example 3

DNA and RNA Analysis

The methods employed for DNA (Dellaporta et al., 1983) and RNA (Verwoerd et al., 1989) extractions were as described elsewhere. High stringency Southern blots were carried out at 65° C. according to standard protocols described elsewhere (Sambrook et al., 1989). All genomic and cDNA library screening was done on Gelman BioTrace NT membranes according to the manufacturer's specifications (Gelman Sciences). To clone insertion junctions between T-DNA and genomic DNA in the era1-1 mutant (isolated from T12W DNA) a library of T12W DNA was made in γ-ZAPII (Stratagene). Genomic Southern blots of T12W DNA digested with restriction endonuclease EcoR I and probed with right border (RB) T-DNA produced three bands (13.0 Kb, 7.0 Kb and 8.0 Kb). Subsequent analysis with additional restriction enzymes verified that the 7.0 and 8.0 Kb bands contained the insertion junctions between T-DNA and flanking plant DNA. These fragments were cloned by digesting genomic DNA with EcoR I, fractionating the digested DNA using a Prep Cell (Pharmacia), and identifying the fractions containing the 7.0 and 8.0 Kb by Southern blot analysis using the RB as a probe. Pooled fractions containing both the 7.0 and 8.0 Kb fragments were then ligated to the γ-ZAPII vector arms according to the manufacturer's instructions (Stratagene). A library containing approximately 40,000 individual recombinant bacteriophage was screened. Five positive plaques were identified and excised plasmid forms of the cloned inserts were isolated according to the manufacturer's instructions (Stratagene). Two plasmids which hybridized to the RB probe were designated pL4B and pL7 and selected for further characterization. A 2.3 kB EcoR I-BamH I restriction fragment from clone pL4B was subcloned into the plasmid pBluescript and designated pSC10. A 1.3 Kb Hind III-BamH I restriction fragment from clone pL7 was also subcloned into pBluescript and designated pSC11. Each of these plasmids contains approximately 1.2 Kb of T-DNA attached to the flanking plant genomic DNA. pSC10 was used as a probe to screen an *Arabidopsis* cDNA library called PRL2 λ-ZipLox (ABRC, Stock CD4-7). This screen identified five positive cDNAs, and the longest cDNA insert, clone pZL23, was used to screen an additional 200,000 recombinant PRL2 phage. Subsequently a longer cDNA insert, clone pZL51, which contained an insert of 1.35 Kb, was isolated. Both cDNA clones pZL23 and pZL51 were sequenced and used to screen 30,000 γ-ZAPII plaques made from wild-type *Columbia* genomic DNA partially digested with EcoR I. Construction of this library was as described above except the digested DNA was not size-fractionated. This screen identified four positive clones. The inserts were excised and excised plasmid forms of the cloned inserts were isolated according to the manufacturer's instructions. A 6 Kb region encompassing the entire pZL51 clone was completely sequenced. This genomic insert and a 14 Kb genomic insert isolated by screening a λ-FIX genomic library from Lansberg erecta via similar methods (ABRC Stock CD4-8) were used as probes to analyze deletion size in the fast neutron mutants era1-2 and era1-3.

Example 4

Protein Farnesyl Transferase Assay

Farnesyl transferase (Ftase) assays were performed using Ftase from cell-free extracts of wild-type and mutant plants and synthetic heptapeptides as substrate for the reaction. Peptides were purchased from Genemed Biotechnologies, Inc. The peptide sequences used were based on the data of Randall et al. (1993): GGCCAIM (-CAIM) and GGCCAIL (-CAIL). Solutions of peptides were prepared in 100% dimethyl sulfoxide (DMSO) containing 10 mM dithiotreitol (DTT) and diluted in 10 mM DTT without DMSO. The cell-free extracts contained soluble protein isolated from the buds of three week old plants, either wild-type or mutant strains. First 1 g of fresh buds was collected and homogenized in a buffer containing 50 mM Hepes (pH 7.5), 1 mM $MgCl_2$, 1 mM EGTA, 5 mM DTT, 2 μg/ml leupeptin, 2 μg/ml aprotinin, and 1 mM PMSF. Next, cellular debris and membranes were removed by centrifugation at 4° C. at 10,000×g for 10 minutes and 100,000×g for 30 minutes. Following the second centrifugation, the supernatant was decanted and total soluble protein was quantified by the method of Bradford (1976). Soluble protein extracts were incubated at 30° C. with a peptide substrate and radiolabeled $^3$H-farnesyl pyrophosphate (FPP) (Amersham) for 40 minutes. Each reaction mixture contained the following components in a final volume of 25 μl: 50 mM Hepes (pH 7.5), 5 mM $MgCl_2$, 5 mM DTT, 50 μM peptide, 0.5 μM [$^3$H]FPP, and 100 μg of soluble protein extract. One control reaction contained soluble protein extracts that had been boiled for 5 minutes to irreversibly denature all protein. Reactions were terminated by adding EDTA to a final concentration of 50 mM and then spotted onto Silica Gel 60 thin-layer chromatography (TLC) plates (Millipore). TLC plates were developed with n-propanol and water (7:3 v/v) for 4-5 hours. The plates were dried, sprayed with En$^3$Hance (New England Nuclear), and exposed to Kodak X-OMAT AR film at −70° C. for 4 days.

Example 5

ERA1-β-glucuronidase Gene Constructs and Transgenic Plants

ERA1-β-glucuronidase (ERA1-GUS) fusion constructs were made by inserting a 5 Kb EcoR I-Hind III genomic fragment of the ERA1 promoter into a promoterless GUS T-DNA plasmid pBI121 containing a gene conferring resistance to the antibiotic ampicillin. This construct was then transformed into *Agrobacterium* strain LB4404. The *Agrobacterium* was grown to a density of 0.8 O.D. units (measured at 595 nm). The cells were then washed extensively in water re-suspended in sterile 10% glycerol and purified plasmid DNA encoding the ERA1-GUS fusion construct was added. Finally, the mixture of cells and DNA was pulsed in an electroporator at 200 Ohms 25 p.F, 2.5 kvolts. Cells were then plated on Luria Broth agar plates containing 100 μg/ml ampicillin and grown for 2 days at 28° C. Ampicillin-resistant transformants were cultured and plasmid DNA isolated from the cultures by standard techniques was used in subsequent plant transformation experiments.

Transgenic plants were made by vacuum infiltrating plants with a saturated *Agrobacterium* culture grown to a density of 0.8 O.D. units as measured at 595 nm. Wild-type plants were grown under standard laboratory conditions (at 25° C., 150 μE $m^{-2}$ $sec^{-1}$, humidity, constant light) until they produced their first bolts at approximately 5 weeks. Next, plant stems were removed and the plants were submerged in a solution of *Agrobacterium* and placed under a 20 mBar vacuum for 5 minutes. After the vacuum was broken, the plants were transferred to soil and allowed to recover under standard laboratory conditions as described above. After two months, the plants produced new flowers and seed which was harvested and allowed to dry for 2 weeks. Seed from individual plants were planted onto Murashige and Skoog (MS) minimal medium plates containing 50 μg/ml kanamycin. Green kanamycin-resistant plantlets were identified and transferred to soil after 2 weeks and allowed to grow for seed. These seeds were germinated and the seedlings were tested for GUS activity using the fluorescent GUS substrate Imagene Green (Molecular Probes, Eugene, Oreg.). GUS activity was assayed by suspending seedlings in GUS buffer (50 mM Sodium phosphate, pH 7.0, 10 mM EDTA, 0.1% Triton X-100, 0.1% Sodium sarcosyl, 4 mM Imagene Green) for 2-4 hours in the dark at room temperature. Seedlings were viewed under a microscope at 25× magnification using blue light to generate a positive fluorescent signal. When this mixture is treated with blue light, GUS activity will produce yellow light in a background of red auto-fluorescence generated by red chlorophyll.

Example 6

Drought Experiments

Six wild-type and six era1-2 seedlings were grown for four weeks in constant light with constant watering (25° C., 150 μE $m^{-2}$ $sec^{-1}$, 70% humidity, constant light). The plant and pot were weighed and the pots were then covered with aluminum foil to retard soil evaporation. At this time, plants were no longer watered and each pot was weighed daily. At the end of the experiment plants were removed from the pots, which were allowed to dry for another two weeks, when they were weighed to determine the weight of the dry soil and pot. This weight was subtracted from each sample.

Example 7

Age-Related Changes in Detached Leaves

The chlorophyll content in adult rosette leaves in wild-type *Columbia* and era1-2 mutants were compared after detachment from plants. The plants were grown under constant light and temperature (150 μE/$m^2$·sec, 22° C.) to a similar developmental age of 3 weeks after germination. At this time, the fifth leaves of several plants which had emerged after germination were removed and placed on petri plates containing 0.8% agar with minimal salts. The plates were sealed and placed at 22° C. under constant light (50 μE/$m^2$·sec) for 12 days. Photographs were taken and color comparisons made at 0, 3, 6, 9, and 12 days.

Example 8

Determination of Transcript Levels for Selected Genes in Aging Leaves

Mutant (era1-2) and wild-type plants were grown under constant light and temperature (150 μE/$m^2$·sec, 22° C.) to a similar developmental age of 4 weeks after germination. At that time, the fifth rosette leaf which had emerged following germination was removed from all plants. These leaves were assayed for expression levels of three genes: *Arabidopsis* chlorophyll binding protein (CAB) and senescence-activated genes 12 and 13 (SAG12 and SAG13). mRNA transcript levels were assayed by Northern blot analysis at 0, 4, 8 days after the plants bolted. The CAB gene encodes the *Arabidopsis* chlorophyll binding protein which is involved in capturing light for photosynthesis. It is required for the green color of the leaf and is a good marker of chlorophyll turnover in the plant. CAB in wild-type plants shows transcript level reduction upon induction of senescence. No transcript level reduction was observed in aging leaves of era1-2 mutants. SAG12 and SAG13 are *Arabidopsis* genes cloned by differential expression during senescence (SAG stands for senescence activated gene). Transcription of both genes is induced during the onset of senescence in wild-type *Arabidopsis* plants. These genes were not induced under the same developmental conditions in the era1-2 mutants.

Example 9

Cloning of *Arabidopsis thaliana* FTA and Construction of Transformation Vector The *Arabidopsis thaliana* FTA sequence was obtained by RT-PCR from total RNA isolated from leaf tissue using primers corresponding to SEQ ID NO:17 and SEQ ID NO:18. The resulting fragment was digested with BamHI and SmaI and cloned into the plasmid pCR2.1 The Clonetech vector pBI121 was used as the backbone for the antisense construct. The GUS gene was removed by BamHI and Eco I CRI digestion and replaced with the FTA insert that was cut from pCR2.1-FTA using SmaI and BamHI and ligated into the vector SEQ ID NO:10.

TABLE 1

| | |
|---|---|
| 5'-AAAGGATCCTCAAATTGCTGCCACTGTAAT-3': | SEQ ID NO:17 |
| 5'-AAACCCGGGATGAATTTCGACGAGAACGTG-3': | SEQ ID NO:18 |

Example 10

Cloning of Non-Full Length *Brassica napus* FTA and FTB Nucleic Acid Sequences RNA was isolated from leaf and root tissue using the Qiagen RNeasy kit. RT-PCR was performed by known techniques using the primers shown in Table 2. The FTA sequence was obtained using the primer pair SEQ ID NO:25 and SEQ ID NO:26. The FTB sequence was obtained using the primer pair SEQ ID NO:27 and SEQ ID NO:28.

TABLE 2

| | |
|---|---|
| 5'-GGATCCATGGATTACTTCCGTGCGATTTACTTCTCC-3': | SEQ ID NO:25 |
| 5'-AAAAAGCTTCCATGCCCAATAGTTAGCTCTTATTGGATC-3': | SEQ ID NO:26 |
| 5'-AAAAGCTTTGGCTTTGTTACTGGATTCTTCATTCAAT-3': | SEQ ID NO:27 |
| 5'-AAATCTAGAAGCTTCATAATACCGATCCAAGACAATGTT-3': | SEQ ID NO:28 |

PCR products were separated from the RT-PCR reaction mixture using the Qiagen PCR column spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 11

Cloning of Non-Full Length FTA and FTB Nucleic Acid Sequences from *Glycine max* and *Zea maize*

RNA was isolated from leaf and root tissue using the Qiagen RNeasy kit. RT-PCR was performed by known techniques using the primers shown in Table 3. The *Glycine max* FTA sequence was obtained using the primer pair SEQ ID NO:29 and SEQ ID NO:30. The *Glycine max* FTB sequence was obtairied using the primer pair SEQ ID NO:31 and SEQ ID NO:32. The *Zea maize* FTB sequence was obtained using the primer pair SEQ ID NO:33 and SEQ ID NO:34

TABLE 3

| | |
|---|---|
| 5'-AAAGGATCCATGGAATCTGGGTCTAGCGA-3': | SEQ ID NO:29 |
| 5'-AAATCTAGAAGGAAGTCTGCTCTTGCGC-3': | SEQ ID NO:30 |
| 5'-AAATCTAGAGCCACCATTCCTCGCAACG-3': | SEQ ID NO:31 |

TABLE 3-continued

| | |
|---|---|
| 5'-AAAGAGCTCGTGGTGGAGAATCTGGGTGC-3': | SEQ ID NO:32 |
| 5'-GGCGGATCCCGACCTACCGAGG-3': | SEQ ID NO:33 |
| 5'-AAAGAGCTCGTGGATGGATTGGCTCCAGC-3': | SEQ ID NO:34 |

PCR products were separated from the RT-PCR reaction mixture using the Qiagen PCR colurn spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 12

Sequence Analysis

*Arabidopsis thaliana* FTA

A disclosed nucleic acid of 999 nucleotides (also referred to as FT1) is shown in Table 4A. The primers used in the PCR are depicted in bold.

TABLE 4A

| FT1 Nucleotide Sequence. | |
|---|---|
| **Aaacccgggatgaatttcgacgagaccgtg**ccactgagccaacgattggagtggtcagacgtggt | (SEQ ID NO:7) |
| cccattgactcaggacgatggtccgaatccagtggtgccaattgcctacaaggaagagttccgcg | |
| agactatggattacttccgtgcgatttacttttccgacgagcgatctcctcgcgcactacgactc | |
| acggaagaaaccctcctcttaaactccggcaactacacagtgtggcatttcaggcgcctagtact | |
| cgaggcccttaatcacgacttgtttgaagaactcgagttcatcgaacgcattgctgaggataact | |
| ctaagaactaccaactgtggcatcatcggcgatgggttgcagagaaactgggtcctgatgttgca | |
| gggagagaacttgaatttacccgtagagtactttcacttgatgccaaacattatcatgcttggtc | |
| acataggcagtggacactacgggcattaggaggatgggaagatgagctcgattactgtcacgagc | |
| tccttgaagctgacgtctttaacaattccgcctggaatcagaggtattatgtcatcacccaatct | |
| cctttgttgggaggcctagaagccatgagagaatctgaagtaagctacacaatcaaagccatttt | |
| aaccaatcctgcaaacgagagctcatggcgatacctaaaagcgctttacaaagacgacaaagaat | |
| cctggattagtgatccaagtgtttcctcagtctgtttgaatgttctatcccgcacagattgcttc | |
| catggattcgctctgagcaccctttggatcttctatgtgatggactgagaccaaccaacgagca | |
| taaagactcagtgagagctctagctaatgaagaaccagagactaacttggccaatttggtgtgta | |
| ctattcttggtcgtgtagatcctataagagctaactattgggcatggaggaagagcaagatt**aca** | |
| **gtggcagcaatttgaggatccttt** | |

A disclosed FT1 polypeptide (SEQ ID NO:11) encoded by SEQ ID NO:7 has 326 amino acid residues and is presented in Table 4B using the one-letter amino acid code.

TABLE 4B

| Encoded FT1 protein sequence. | |
|---|---|
| MNFDETVPLSQRLEWSDVVPLTQDDGPNPVVPIAYKEEFRETMDYFRAIYFSDERSPRALRLTE | (SEQ ID NO:11) |
| ETLLLNSGNYTVWHFRRLVLEALNHDLFEELEFIERIAEDNSKNYQLWHHRRWVAEKLGPDVAG | |
| RELEFTRRVLSLDAKHYHAWSHRQWTLRALGGWEDELDYCHELLEADVFNNSAWNQRYYVITQS | |
| PLLGGLEAMRESEVSYTIKAILTNPANESSWRYLKALYKDDKESWISDPSVSSVCLNVLSRTDC | |
| FHGFALSTLLDLLCDGLRPTNEHKDSVRALANEEPETNLANLVCTILGRVDPIRANYWAWRKSK | |
| ITVAAI | |

Due to the nature of the cloning strategy the sequence presented does not contain any 5' or 3' non-translated sequence. Using the sequences disclosed herein as hybridization probes, one is able to screen and isolate full length sequences from cDNA or genomic libraries or use the rapid amplification of cDNA ends (RACE) technology or other such PCR techniques. The percent identity of the *Arabidopsis thaliana* nucleotide sequence and its encoded amino acid sequence to that of published sequences is shown in FIG. 17.

The present invention also includes a nucleic acid sequence complementary to the *Arabidopsis thaliana* farnesyl transferase alpha subunit of SEQ ID NO:7. The disclosed complementary sequence is shown as SEQ ID NO:8. The nucleic acid sequence of SEQ ID NO:9 shows the nucleic acid sequence of SEQ ID NO:8 that has been prepared for ligation into an expression vector.

aaaggatcctcaaattgctgccactgtaatcttgctcttcctccatgcccaatagttagctctt SEQ ID NO:8
ataggatctacacgaccaagaatagtacacaccaaattggccaagttagtctctggttcttcat
tagctagagctctcactgagtctttatgctcgttggttggtctcagtccatcacatagaagatc
caaaagggtgctcagagcgaatccatggaagcaatctgtgcgggatagaacattcaaacagact
gaggaaacacttggatcactaatccaggattctttgtcgtctttgtaaagcgcttttaggtatc
gccatgagctctcgtttgcaggattggttaaaatggctttgattgtgtagcttacttcagattc
tctcatggcttctaggcctcccaacaaaggagattgggtgatgacataatacctctgattccag
gcggaattgttaaagacgtcagcttcaaggagctcgtgacagtaatcgagctcatcttcccatc
ctcctaatgcccgtagtgtccactgcctatgtgaccaagcatgataatgtttggcatcaagtga
aagtactctacgggtaaattcaagttctctccctgcaacatcaggacccagtttctctgcaacc
catcgccgatgatgccacagttggtagttcttagagttatcctcagcaatgcgttcgatgaact
cgagttcttcaaacaagtcgtgattaagggcctcgagtactaggcgcctgaaatgccacactgt
gtagttgccggagtttaagaggagggtttcttccgtgagtcgtagtgcgcgaggagatcgctcg
tcggaaaagtaaatcgcacggaagtaatccatagtctcgcggaactcttccttgtaggcaattg
gcaccactggattcggaccatcgtcctgagtcaatgggaccacgtctgaccactccaatcgttg
gctcagtggcacggtctcgtcgaaattcatcccgggttt gatcctcaaattgctgccactgtaatcttgctcttcctccatgcccaatagttagctcttatag SEQ ID NO:9
gatctacacgaccaagaatagtacacaccaaattggccaagttagtctctggttcttcattagc
tagagctctcactgagtctttatgctcgttggttggtctcagtccatcacatagaagatccaaa
agggtgctcagagcgaatccatggaagcaatctgtgcgggatagaacattcaaacagactgagg
aaacacttggatcactaatccaggattctttgtcgtctttgtaaagcgcttttaggtatcgcca
tgagctctcgtttgcaggattggttaaaatggctttgattgtgtagcttacttcagattctctc
atggcttctaggcctcccaacaaaggagattgggtgatgacataatacctctgattccaggcgg
aattgttaaagacgtcagcttcaaggagctcgtgacagtaatcgagctcatcttcccatcctcc -continued taatgcccgtagtgtccactgcctatgtgaccaagcatgataatgtttggcatcaagtgaaagt actctacgggtaaattcaagttctctccctgcaacatcaggacccagtttctctgcaacccatc gccgatgatgccacagttggtagttcttagagttatcctcagcaatgcgttcgatgaactcgag ttcttcaaacaagtcgtgattaagggcctcgagtactaggcgcctgaaatgccacactgtgtag ttgccggagtttaagaggagggtttcttccgtgagtcgtagtgcgcgaggagatcgctcgtcgg aaaagtaaatcgcacggaagtaatccatagtctcgcggaactcttccttgtaggcaattggcac cactggattcggaccatcgtcctgagtcaatgggaccacgtctgaccactccaatcgttggctc agtggcacggtctcgtcgaaattcatccc

*Brassica napus* FTA

A disclosed nucleic acid of 822 nucleotides (also referred to as FT2) is shown in Table 5A.

TABLE 5A

| FT2 Nucleotide Sequence. | |
|---|---|
| ATGGATTACTTCCGTGCGATTTACTTCTCCGACGAGCGTTCTGCTCGCGCGCTGCGACTCACGGA | (SEQ ID NO:12) |
| AGAAGCTCTCCGCTTAAACTCGGGCAACTACACCGTGTGGCACTTCGGGCGCTTAGTACTCGAGG | |
| AGCTTAATAACGACTTGTATGAAGAGCTCAAGTTCATCGAAAGCATTGCTGAGGATAACTCTAAG | |
| AACTACCAGTTGTGGCATCATCGACGATGGGTCGCAGAGAAACTGGGTCCTGATGTTGCAGGAAA | |
| GGAACTTGAGTTTACTCGGAGGGTACTATCACTTGATGCCAAGCATTATCATGCTTGGTCACATA | |
| GGCAGTGGGCGCTACAAGCATTAGGAGGATGGGAAAATGAGCTTAACTACTGCCACGAGCTCCTT | |
| GAAGCTGACGTCTTTAACAACTCTGCATGGAATCAGAGGTATTACGTTATAACTAGATCACCTTC | |
| GTTGGGAGGCCTAGAAGCCATGAGAGAATCTGAAGTAAGCTACACAGTCAAAGCCATTTTAGCAA | |
| ATCCCCGGAACGAGAGCTCTTGGAGGTACCTGAAAGCCCTTTACAAAGACGACACAGAGTCTTGG | |
| ATTAGTGATCCAAGTGTTTCCTCAGTCTGTTTGAAAGTTCTCTCACGCGCGGACTGCTTCCATGG | |
| ATTCGCTCTGAGCACCCTTTTGGATCTTCTGTGCGATGGGTTGAGACCAACCAACGAGCATAGAG | |
| ACTCGGTGAAAGCTCTAGCTAATGAAGAACCAGAGACTAACTTGGCCAATTTGGTGTGTACCATT | |
| CTGTGTCGTGTTGATCCAATAAGAGCTAACTATTGGGCATGG | |

A disclosed FT2 polypeptide (SEQ ID NO:13) encoded by SEQ ID NO:12 has 274 amino acid residues and is presented in Table 5B using the one-letter amino acid code.

TABLE 5B

| Encoded FT2 protein sequence. | |
|---|---|
| MDYFRAIYFSDERSAPALRLTEEALRLNSGNYTVWHFGRLVLEELNNDLYEELK | (SEQ ID NO:13) |
| FIESIAEDNSKNYQLWHHRRWVAEKLGPDVAGLEKEFTRRVLSLDAKHYHAWSH | |
| RQWALQALGGWENELNYCHELLEADVFNNSAWNQRYYVITRSPSLGGLEANRES | |
| EVSYTVKAILANPGNESSWRYLKALYKDDTESWISDPSVSSVCLKVLSRADCFH | |
| GFALSTLLDLLCDGLRPTNEHRDSVKALANEEPETNLANLVCTILCRVDPIRAN | |
| YWAWKL | |

Due to the nature of the cloning strategy the sequence presented is not full length. Compared to the *Arabidopsis thaliana* sequence there are 42 amino acids missing from the amino terminus and 10 amino acids from the carboxy terminus. The percent identity of the *Brassica napus* nucleotide sequence and its encoded amino acid sequence to that of published sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Brassica napus* farnesyl transferase alpha subunit of SEQ ID NO: 12. The disclosed complementary sequence is shown as SEQ ID NO:35.

```
CCATGCCCAATAGTTAGCTCTTATTGGATCAACACGACACAGAATGGTACACACCAAATTGGCC   SEQ ID NO:35
AAGTTAGTCTCTGGTTCTTCATTAGCTAGAGCTTTCACCGAGTCTCTATGCTCGTTGGTTGGTC
TCAACCCATCGCACAGPAGATCCAAAAGGGTGCTCAGAGCGAATCCATGGAAGCAGTCCGCGCG
TGAGAGAACTTTCAAACAGACTGAGGAAACACTTGGATCACTAATCCAAGACTCTGTGTCGTCT
TTGTAAAGGGCTTTCAGGTACCTCCAAGAGCTCTCGTTCCCGGGATTTGCTAAAATGGCTTTGA
CTGTGTAGCTTACTTCAGATTCTCTCATGGCTTCTAGGCCTCCCAACGAAGGTGATCTAGTTAT
AACGTAATACCTCTGATTCCATGCAGAGTTGTTAAAGACGTCAGCTTCAAGGAGCTCGTGGCAG
TAGTTAAGCTCATTTTCCCATCCTCCTAATGCTTGTAGCGCCCACTGCCTATGTGACCAAGCAT
GATAATGCTTGGCATCAAGTGATAGTACCCTCCGAGTAAACTCAAGTTCCTTTCCTGCAACATC
AGGACCCAGTTTCTCTGCGACCCATCGTCGATGATGCCACAACTGGTAGTTCTTAGAGTTATCC
TCAGCAATGCTTTCGATGAACTTGAGCTCTTCATACAAGTCGTTATTAAGCTCCTCGAGTACTA
AGCGCCCGAAGTGCCACACGGTGTAGTTGCCCGAGTTTAAGCGGAGAGCTTCTTCCGTGAGTCG
CAGCGCGCGAGCAGAACGCTCGTCGGAGAAGTAAATCGCACGGAAGTAATCCAT
```

*Brassica napus* FTB

A disclosed nucleic acid of 1110 nucleotides (also referred to as FT3) is shown in Table 6A.

TABLE 6A

| FT3 Nucleotide Sequence. |
|---|
| TGGCTTTGTTACTGGATTCTTCATTCAATTGCTTTGCTTGGGGAGTCTGTGGATGATGACTTAGA (SEQ ID NO:14) |
| AAACAATGCAATCGATTTTCTTGGACGTTGCCAGGGTTCTGATGGTGGATATGGTGGTGGTCCTG |
| GCCAACTTCCACATCTTGCAACAAGTTATGCTGCAGTGAATACACTTGTTACTTTAGGAGGTGAG |
| AAAGCCTTCTCTTCAATTAACAGAGAACAAATGGCTTGTTTCTTAAGACGAATGAAGGATACAAA |
| TGCAGGTTTCAGGATGCATAATATGGGAGAAATAGATGTGCGAGCGTGCTACACTGCGATTTTGA |
| TTGCAAGCATCCTGAACATTGTGGATGATGAACTCACCCGCGGCTTAGGAGATTACATTTTGAGT |
| TGCCAAACTTATGAAGGTGGCATTGGAGGGGAACCTGGCTCCGAAGCTCATGGTGGGTACACGTA |
| CTGTGGGTTGGCTACTATGATTTTAATCAATGAAGTCGACCGCTTGAATTTGGATTCGTTAATGA |
| ATTGGGTTGTACATCGACAAGGAGTAGAAATGGGATTCCAAGGTAGGACGAACAAATTGGTCGAC |
| GGTTGCTACACGTTTTGGCAGGCAGCCCCCTGTGTTCTACTACAGCGATTTTTTTCATCCCAGGA |
| TATGGCACCTCATGGATCATCATCACATATGTCACAAGGGACAGATGAAGATCACGAGGAACATG |
| GTCATGATGAAGATGATCCTGAAGACAGTGATGAAGATGATTCTGATGAGGATAGCGATGAAGAT |
| TCAGGGAATGGTCACCAAGTTCATCATACGTCTACCTACATTGACAGGAGAATTCAACCTGTTTT |
| TGATAGCCTCGGCTTGCAAAGATATGTGCTCTTGTGCTCTCAGGTTGCTGATGGTGGATTCAGAG |
| ACAAGCTGAGGAAACCCCGTGACTTCTACCACACATGTTACTGCCTAAGCGGTCTTTCCGTGGCT |
| CAACACGCTTGGTCAAAAGACGAGGACACTCCTCCTTTGACTCGTGACATTTTGCGTGGCTACGC |

TABLE 6A-continued

| FT3 Nucleotide Sequence. |
|---|
| AAACCACCTTGAACCTGTTCACCTCCTCCACAACATTGTCTTGGATCGGTATTATGAAGCTTCTA |
| GATTT |

A disclosed FT3 polypeptide (SEQ ID NO:15) encoded by SEQ ID NO:13 has 370 amino acid residues and is presented in Table 6B using the one-letter amino acid code.

TABLE 6B

| Encoded FT3 protein sequence. |
|---|
| WLCYWILHSIALLGESVDDDLENNAIDFLGRCQGSDGGYGGGPGQLPHLATSYA (SEQ ID NO:15) |
| AVNTLVTLGGEKAFSSINREQMACFLRRMKDTNGGFRMHNMGEIDVRACYTAIL |
| IASILNIVDDELTRGLGDYILSCQTYEGGIGGEPGSEAHGGYTYCGLATMILIN |
| EVDRLNLDSLMNWVVHRQGVEMGFQGRTNKLVDGCYTFWQAAPCVLLQRFFSSQ |
| DMAPHGSSSHMSQGTDEDHEEHGHDEDDPEDSDEDDSDEDSDEDSGNGHQVHHT |
| STYIDRRIQPVFDSLGLQRYVLLCSQVADGGFRDKLRKPRDFYHTCYCLSGLSV |
| AQHAWSKDEDTPPLTRDILGGYANHLEPVHLLHNILVDRYYEASRF |

Due to the nature of the cloning strategy the sequence presented is not fuill length. Compared to the *Arabidopsis thaliana* sequence there are 31 amino acids missing from the amino terminus and 5 amino acids from the carboxy terminus. The percent identity of the *Brassica napus* nucleotide sequence and its encoded amino acid sequence to that of published sequences is shown in FIG. 18.

Using the sequences disclosed herein as hybridization probes, one is able to screen and isolate fuill length sequences from cDNA or genomic libraries or use the rapid amplification of cDNA ends (RACE) technology or other such PCR techniques. Sequence comparisons have been performed and percent identities are shown in FIG. 17 and FIG. 18.

The present invention also includes a nucleic acid sequence complimentary to the *Brassica napsus* farnesyl transferase beta subunit of SEQ ID NO: 14. The disclosed complementary sequence is shown as SEQ ID NO:36.

AAATCTAGAAGCTTCATAATACCGATCCAAGACAATGTTGTGGAGGAGGTGAACAGGTTCAAGG SEQ ID NO:36

TGGTTTGCGTAGCCACCCAAAATGTCACGAGTCAAAGGAGGAGTGTCCTCGTCTTTTGACCAAG

CGTGTTGAGCCACGGAAAGACCGCTTAGGCAGTAACATGTGTGGTAGAAGTCACGGGGTTTCCT

CAGCTTGTCTCTGAATCCACCATCAGCAACCTGAGAGCACAAGAGCACATATCTTTGCAAGCCG

AGGCTATCAAAAACAGGTTGAATTCTCCTGTCAATGTAGGTAGACGTATGATGAACTTGGTGAC

CATTCCCTGAATCTTCATCGCTATCCTCATCAGAATCATCTTCATCACTGTCTTCAGGATCATC

TTCATCATGACCATGTTCCTCGTGATCTTCATCTGTCCCTTGTGACATATGTGATGATGATCCA

TGAGGTGCCATATCCTGGGATGAAAAAAATCGCTGTAGTAGAACACAGGGGGCTGCCTGCCAAA

ACGTGTAGCAACCGTCGACCAATTTGTTCGTCCTACCTTGGAATCCCATTTCTACTCCTTGTCG

ATGTACAACCCAATTCATTAACGAATCCAAATTCAAGCGGTCGACTTCATTGATTAAAATCATA

GTAGCCAACCCACAGTACGTGTACCCACCATGAGCTTCGGAGCCAGGTTCCCCTCCAATGCCAC

CTTCATAAGTTTGGCAACTCAAAATGTAATCTCCTAAGCCGCGGGTGAGTTCATCATCCACAAT

GTTCAGGATGCTTGCAATCAAAATCGCAGTGTAGCACGCTCGCACATCTATTTCTCCCATATTA

TGCATCCTGAAACCTCCATTTGTATCCTTCATTCGTCTTAAGAAACAAGCCATTTGTTCTCTGT

TAATTGAAGAGAAGGCTTTCTCACCTCCTAAAGTAACAAGTGTATTCACTGCAGCATAACTTGT

-continued

TGCAAGATGTGGAAGTTGGCCAGGACCACCACCATATCCACCATCAGAACCCTGGCAACGTCCA

AGAAAATCGATTGCATTGTTTTCTAAGTCATCATCCACAGACTCCCCAAGCAAAGCAATTGAAT

GAAGAATCCAGTAACAAAGCCA

*Glycine max* FTA

A disclosed nucleic acid of 1041 nucleotides (also referred to as FT4) is shown in Table 7A.

TABLE 7A

| FT4 Nucleotide Sequence. | |
|---|---|
| ATGGAATCTGGGTCTAGCGAAGGAGAAGAGGTGCAGCAACGCGTGCCGTTGAGGGAGACAGTGGA | (SEQ ID NO:37) |
| GTGGTCAGATGTTACTCCGGTTCCTCAAAACGACGGCCCTAACCCTGTCGTTCCGATCCAGTACA | |
| CTGAAGAGTTTTCCGAAGTTATGGATTACTTTCGCGCCGTTTACCTCACCGATGAACGCTCCCCT | |
| CGCGCCCTCGCTCTCACAGCCGAAGCCGTTCAATTCAACTCCGGCAACTACACTGTGTGGCATTT | |
| CCGACGGTTGTTACTTGAGTCGCTAAAAGTCGACTTGAACGATGAACTGGAGTTTGTGGAGCGTA | |
| TGGCCGCTGGAAATTCTAAAAATTATCAGATGTGnATGTTCTGTAGGCATCCTAGACGATGGGTT | |
| GCCGAGAAGTTAGGTCCTGAAGCTAGAAACAATGAGCTCGAGTTCACCAAAAAGATACTGTCCGT | |
| TGATGCCAAACATTATCATGCATGGTCTCATAGACAGTGGGCTCTTCAAACACTAGGAGGATGGG | |
| AAGATGAACTTAATTATTGCACAGAACTACTTAAAGAAGACATTTTTAACAATTCTGCTTGGAAT | |
| CAGAGATATTTTGTCATAACAAGGTCTCCTTTCTTGGGGGGCCTAAAAGCTATGAGAGAGTCTGA | |
| AGTGCTTTACACCATCGAAGCCATTATAGCCTACCCTGAAAATGAAAGCTCGTGGAGATATCTAC | |
| GAGGACTTTATAAAGGTGAAACTACTTCATGGGTAAATGATCCTCAAGTTTCTTCAGTATGCTTA | |
| AAGATTTTGAGAACTAAGAGCAACTACGTGTTTGCTCTTAGCACTATTTTAGATCTTATATGCTT | |
| TGGTTATCAACCAAATGAAGACATTAGAGATGCCATTGACGCCTTAAAGACCGCAGATATGGATA | |
| AACAAGATTTAGATGATGATGAGAAAGGGGAACAACAAAATTTAAATATAGCACGAAATATTTGT | |
| TCTATCCTAAAACAAGTTGATCCAATTAGAACCAACTATTGGATTTGGCGCAAGAGCAGACTTCCT | |

A disclosed FT4 polypeptide (SEQ ID NO:39) encoded by SEQ ID NO:37 has 347 amino acid residues and is presented in Table 7B using the one-letter amino acid code.

TABLE 7B

| Encoded FT4 protein sequence. | |
|---|---|
| MESGSSEGEEVQQRVPLRERVEWSDVTPVPQNDGPNPVVPIQYTEEFSEVMDYF | (SEQ ID NO:39) |
| RAVYLTDERSPRALALTAEAVQFNSGNYTVWHFRRLLLESLKVDLNDELEFVER | |
| MAAGNSKNYQMXMFCRHPRRWVAEKLGPEARNNELEFTKKILSVDAKHYHAWSH | |
| RQWALQTLGGWEDELNYCTELLKEDIFNNSAWNQRYFVITRSPFLGGLKAMRES | |
| EVLYTIEAIIAYPENESSWRYLRGLYKGETTSWVNDPQVSSVCLKILRTKSNYV | |
| FALSTILDLICFGYQPNEDIRDAIDALKTADMDKQDLDDDEKGEQQNLNIARNI | |
| CSILKQVDPIRTNYWIWRKSRLP | |

Due to the nature of the cloning strategy the sequence presented is not fuill length. The percent identity of the *Glycine max* nucleotide sequence and its encoded amino acid sequence to that of other sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Glycine max* alpha subunit of SEQ ID NO:37. The disclosed complementary sequence is shown as SEQ ID NO:38.

```
AGGAAGTCTGCTCTTGCGCCAAATCCAATAGTTGGTTCTAATTGGATCAACTTGTTTTAGGATA   SEQ ID NO:38
GAACAAATATTTCGTGCTATATTTAAATTTTGTTGTTCCCCTTTCTCATCATCATCTAAATCTT
GTTTATCCATATCTGCGGTCTTTAAGGCGTCAATGGCATCTCTAATGTCTTCATTTGGTTGATA
ACCAAAGCATATAAGATCTAAAATAGTGCTAAGAGCAAACACGTAGTTGCTCTTAGTTCTCAAA
ATCTTTAAGCATACTGAAGAAACTTGAGGATCATTTACCCATGAAGTAGTTTCACCTTTATAAA
GTCCTCGTAGATATCTCCACGAGCTTTCATTTTCAGGGTAGGCTATAATGGCTTCGATGGTGTA
AAGCACTTCAGACTCTCTCATAGCTTTTAGGCCCCCCAAGAAAGGAGACCTTGTTATGACAAAA
TATCTCTGATTCCAAGCAGAATTGTTAAAAATGTCTTCTTTAAGTAGTTCTGTGCAATAATTAA
GTTCATCTTCCCATCCTCCTAGTGTTTGAAGAGCCCACTGTCTATGAGACCATGCATGATAATG
TTTGGCATCAACGGACAGTATCTTTTTGGTGAACTCGAGCTCATTGTTTCTAGCTTCAGGACCT
AACTTCTCGGCAACCCATCGTCTAGGATGCCTACAGAACATNCACATCTGATAATTTTTAGAAT
TTCCAGCGGCCATACGCTCCACAAACTCCAGTTCATCGTTCAAGTCGACTTTTAGCGACTCAAG
TAACAACCGTCGGAAATGCCACACAGTGTAGTTGCCGGAGTTGAATTGAACGGCTTCGGCTGTG
AGAGCGAGGGCGCGAGGGGAGCGTTCATCGGTGAGGTAAACGGCGCGAAAGTAATCCATAACTT
CGGAAAACTCTTCAGTGTACTGGATCGGAACGACAGGGTTAGGGCCGTCGTTTTGAGGAACCGG
AGTAACATCTGACCACTCCACTCTCTCCCTCAACGGCACGCGTTGCTGCACCTCTTCTCCTTCG
CTAGACCCAGATTCCAT
```

*Glycine max* FTB

A disclosed nucleic acid of 1035 nucleotides (also referred to as FT5) is shown in Table 8A.

TABLE 8A

| FT5 Nucleotide Sequence. | |
|---|---|
| GCCACCATTCCTCGCAACGCCCAAACCCTCATGTTGGAGCTTCAACGCGATAATCACATGCAGTA | (SEQ ID NO:40) |
| TGTCTCCAAAGGCCTTCGCCATCTCAGTTCCGCATTTTCCGTTTTGGACGCTAATCGACCCTGGC | |
| TCTGCTACTGGATCTTCCACTCCATTGCTTTGTTGGGAGAATCCGTCGATGATGAACTCGAAGAT | |
| AACGCTATCGATTTTCTTAACCGTTGCCAGGATCCGAATGGTGGATATGCCGGGGGACCAGGCCA | |
| GATGCCTCATATTGCCACAACTTATGCTGCTGTTAATTCACTTATTACTTTGGGTGGTGAGAAAT | |
| CCCTGGCATCAATTAATAGAGATAAACTGTATGGGTTTCTGCGGCGGATGAAGCAACCAAATGGT | |
| GGATTCAGGATGCATGATGAAGGTGAAATTGATGTTCGAGCTTGCTACACTGCCATTTCTGTTGC | |
| AAGTGTTTTGAACATTTTGGATGATGAGCTGATCCAGAATGTTGGAGACTACATTATAAGCTGTC | |
| AAACATATGAGGGTGGCATTGCTGGTGAGCCTGGTTCTGAGGCTCATGGTGGGTACACCTTTTGT | |
| GGATTAGCTACAATGATTCTGATTGGTGAGGTTAATCACTTGGATCTGCCTCGATTAGTTGACTG | |
| GGTGGTATTCCGACAAGGTAAGGAATGTGGATTCCAGGGGAGAACAAATAAACTGGTGGATGGAT | |
| GCTATTCCTTTTGGCAGGGAGGTGCTGTTGCTCTATTGCAAAGATTATCTTCTATTATCAACAAA | |
| CAGATGGAAGAGACATCACAGATTTTTGCGGTATCTTATGTATCTGAAGCAAAAGAAAGTTTGGA | |
| TGGAACCTCTAGTCATGCAACATGCCGTGGTGAGCATGAAGGCACCAGTGAATCCAGTTCATCTG | |

TABLE 8A-continued

| FT5 Nucleotide Sequence. |
|---|
| ATTTTAAAAATATTGCCTATAAATTTATTAATGAGTGGAGAGCACAAGAACCACTTTTTCACAGT |
| ATTGCTTTACAGCAATATATTCTCTTATGTGCACAGGAGCAAGAGGGTGGACTGAGAGACAAACC |
| GGGTAAACGTAGAGATCATTATCACACATGTTACTGTTTAAGTGGACTCTCATTGTGCCAGTATA |
| GTTGGTCAAAGCACCCAGATTCTCCACCAC |

A disclosed FT5 polypeptide (SEQ ID NO:42) encoded by SEQ ID NO:40 has 378 amino acid residues and is presented in Table 8B using the one-letter amino acid code.

TABLE 8B

| Encoded FT5 protein sequence. |
|---|
| ATIPRNAQTLMLELQRDNHMQYVSKGLRHLSSAFSVLDANRPWLCYWIFHSIAL (SEQ ID NO:42) |
| LGESVDDELEDNATDFLNRCQDPNGGYAGGPGQMPHIATTYAAVNSLITLGGEK |
| SLASINRDKLYGFLRRMKQPNGGFRMHDEGEIDVRACYTAISVASVLNILDDEL |
| IQNVGDYITSCQTYEGGIAGEPGSEAHGGYTFCGLATMILIGEVNHLDLPRLVD |
| WVVFRQGKECGFQGRTNKLVDGCYSFWQGGAVALLQRLSSIINKQMEETSQIFA |
| VSYVSEAKESLDGTSSHATCRGEHEGTSESSSSDFKNIAYKFINEWPAQEPLFH |
| SIALQQYILLCAQEQEGGLRDKPGKRRDHYHTCYCLSGLSLCQYSWSKHPDSPP |

Due to the nature of the cloning strategy the sequence presented is not full length. The percent identity of the *Glycine max* nucleotide sequence and its encoded amino acid sequence to that of other sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Glycine max* beta subunit of SEQ ID NO:40. The disclosed complementary sequence is shown as SEQ ID NO:41.

GTGGTGGAGAATCTGGGTGCTTTGACCAACTATACTGGCACAATGAGAGTCCACTTAAACAGTA SEQ ID NO:41

ACATGTGTGATAATGATCTCTACGTTTACCCGGTTTGTCTCTCAGTCCACCCTCTTGCTCCTGT

GCACATAAGAGAATATATTGCTGTAAGCAATACTGTGTAAAAAGTGGTTCTTGTGCTCTCCACT

CATTAATAAATTTATAGGCAATATTTTTAAAATCAGATGAACTGGATTCACTGGTGCCTTCATG

CTCACCACGGCATGTTGCATGACTAGAGGTTCCATCCAAACTTTCTTTTGCTTCAGATACATAA

GATACCGCAAAAATCTGTGATGTCTCTTCCATCTGTTTGTTGATAATAGAAGATAATCTTTGCA

ATAGAGCAACAGCACCTCCCTGCCAAAAGGAATAGCATCCATCCACCAGTTTATTTGTTCTCCC

CTGGAATCCACATTCCTTACCTTGTCGGAATACCACCCAGTCAACTAATCGAGGCAGATCCAAG

TGATTAACCTCACCAATCAGAATCATTGTAGCTAATCCACAAAAGGTGTACCCACCATGAGCCT

CAGAACCAGGCTCACCAGCAATGCCACCCTCATATGTTTGACAGCTTATAATGTAGTCTCCAAC

ATTCTGGATCAGCTCATCATCCAAAATGTTCAAAACACTTGCAACAGAAATGGCAGTGTAGCAA

GCTCGAACATCAATTTCACCTTCATCATGCATCCTGAATCCACCATTTGGTTGCTTCATCCGCC

GCAGAAACCCATACAGTTTATCTCTATTAATTGATGCCAGGGATTTCTCACCACCCAAAGTAAT

AAGTGAATTAACAGCAGCATAAGTTGTGGCAATATGAGGCATCTGGCCTGGTCCCCCGGCATAT

-continued

CCACCATTCGGATCCTGGCAACGGTTAAGAAAATCGATAGCGTTATCTTCGAGTTCATCATCGA

CGGATTCTCCCAACAAAGCAATGGAGTGGAAGATCCAGTAGCAGAGCCAGGGTCGATTAGCGTC

CAAAACGGAAAATGCGGAACTGAGATGGCGAAGGCCTTTGGAGACATACTGCATGTGATTATCG

CGTTGAAGCTCCAACATGAGGGTTTGGGCGTTGCGAGGAATGGTGGC

*Zea maize* FTB

A disclosed nucleic acid of 1235 nucleotides (also referred to as FT6) is shown in Table 9A.

TABLE 9A

| FT6 Nucleotide Sequence. |
|---|
| GGCGGATCCCGACCTACCGAGGCTCACGGTGACGCAGGTGGAGCAGATGAAGGTGGAGGCCAGGG (SEQ ID NO:43) |
| TTGGCGACATCTACCGCTCCCTCTTCGGGGCCGCGCCCAACACGAAATCCATCATGCTAGAGCTG |
| TGGCGTGATCAGCATATCGAGTATCTGACGCCTGGGCTGAGGCATATGGGACCAGCCTTTCATGT |
| TCTAGATGCCAATCGCCCTTGGCTATGCTACTGGATGGTTCATCCACTTGCTTTGCTGGATGAAG |
| CACTTGATGATGATCTTGAGAATGATATCATAGACTTCTTAGCTCGATGTCAGGATAAAGATGGT |
| GGATATAGTGGTGGACCTGGACAGTTGCCTCACCTAGCTACGACTTATGCTGCTGTAAATACACT |
| TGTGACAATAGGGAGCGAAAGAGCATTGTCATCAATCAATAGGGGCAACCTGTACAATTTTATGC |
| TGCAGATGAAAGATGTATCAGGTGCTTTCAGAATGCATGATGGTGGCGAAATTGATGTCCGTGCT |
| TCCTACACCGCTATATCGGTTGCCAGCCTTGTGAATATTCTTGATTTTAAACTGGCAAAAGGTGT |
| AGGCGACTACATAGCAAGATGTCAAACTTATGAAGGTGGTATTGCTGGGGAGCCTTATGCTGAAG |
| CACATGGTGGGTATACATTCTGTGGATTGGCTGCTTTGATCCTGCTTAATGAGGCAGAGAAAGTT |
| GACTTGCCTAGTTTGATTGGCTGGGTGGCTTTTCGTCAAGGAGTGGAATGCGGATTTCAAGGACG |
| AACTAATAAATTGGTTGATGGTTGCTACTCCTTTTGGCAGGGAGCTGCCATTGCTTTCACACAAA |
| AGTTAATTACGATTGTTGATAAGCAATTGAGGTCCTCGTATTCCTGCAAAAGGCCATCAGGAGAG |
| GATGCCTGCAGCACCAGTTCATATGGGTGCACCGCGAATAAGTCTTCCTCTGCTGTGGACTATGC |
| GAAGTTTGGATTTGATTTTATACAACAGAGCAACCAAATTGGCCCACTCTTCCATAACATTGCCC |
| TGCAACAATACATCCTACTTTGTTCTCAGGTACTAGAGGGAGGCTTGAGGGATAAGCCTGGAAAG |
| AACAGAGATCACTATCATTCATGCTACTGCCTCAGTGGCCTCGCAGTTAGCCAGTACAGTGCCAT |
| GACTGATACTGGTTCGTGCCCATTACCTCAGCATGTGCTTGGACCGTACTCTAATTTGCTGGAGC |
| CAATCCATCC |

A disclosed FT6 polypeptide (SEQ ID NO:45) encoded by SEQ ID NO:43 has 414 amino acid residues and is presented in Table 9B using the one-letter amino acid code.

TABLE 9B

| Encoded FT6 protein sequence. |
|---|
| ADPDLPRLTVTQVEQMKVEARVGDIYRSLFGAAPNTKSIMLELWRDQHIEYLTP (SEQ ID NO:45) |
| GLRHMGPAFHVLDANRPWLCYWMVHPLALLDEALDDDLENDIIDFLARCQDKDG |
| GYSGGPGQLPHLATTYAAVNTLVTIGSERALSSINRGNLYNFMLQMKDVSGAFR |
| MHDGGEIDVRASYTAISVASLVNILDFKLAKGVGDYIARCQTYEGGIAGEPYAE |

TABLE 9B-continued

| Encoded FT6 protein sequence. |
|---|
| AHGGYTFCGLAALILLNEAEKVDLPSLIGWVAFRQGVECGFQGRTNKLVDGCYS |
| FWQGAAIAFTQKLITIVDKQLRSSYSCKRPSGEDACSTSSYGCTANKSSSAVDY |
| AKFGFDFIQQSNQIGPLFHNIALQQYILLCSQVLEGGLRDKPGKNRDHYHSCYC |
| LSGLAVSQYSAMTDTGSCPLPQHVLGPYSNLLEPIH |

Due to the nature of the cloning strategy the sequence presented is not full length. The percent identity of the *Glycine max* nucleotide sequence and its encoded amino acid sequence to that of other sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Zea maize* beta subunit of SEQ ID NO:43. The disclosed complementary sequence is shown as SEQ ID NO:44.

The FTA and FTB nucleic acids and amino acids disclosed above have homology to other members of the FT protein family (GenBank ID NOs: U63298, U83707, and U73203; WO 00/14207; Cutler et al., Science 273(5279): 1239-41, 1996; Ziegelhoffer et al., Proc Natl Acad Sci U S A. 97(13):7633-8, 2000). The homology between these and other sequences is shown graphically in the ClustalW analysis shown in Tables 10A-10D. In the ClustalW alignment, the black outlined amino acid residues indicate regions of conserved sequence (i.e., regions that may be required to preserve structural or fuinctional properties), whereas non-highlighted amino acid residues are less conserved and can potentially be altered to a much broader extent without altering protein structure or function.

```
GGATGGATTGGCTCCAGCAAATTAGAGTACGGTCCPAGCACATGCTGAGGTAATGGGCACGAAC   SEQ ID NO:44
CAGTATCAGTCATGGCACTGTACTGGCTAACTGCGAGGCCACTGAGGCAGTAGCATGAATGATA
GTGATCTCTGTTCTTTCCAGGCTTATCCCTCAAGCCTCCCTCTAGTACCTGAGAACAAAGTAGG
ATGTATTGTTGCAGGGCAATGTTATGGAAGAGTGGGCCAATTTGGTTGCTCTGTTGTATAAAAT
CAATCCAAACTTCGCATAAGTCCACAGCAGAGGAAGACTTATTCGCGGTGCACCCATATGAACT
GGTGCTGCAGGCATCCTCTCCTGATGGCCTTTTGCAGGAATACGAGGACCTCAATTGCTTATCA
ACAATCGTAATTAACTTTTGTGTGAAAGCAATGGCAGCTCCCTGCCAAAAGGAGTAGCAACCAT
CAACCAATTTATTAGTTCGTCCTTGAAATCCGCATTCCACTCCTTGACGAAAAGCCACCCAGCC
AATCAAACTAGGCAAGTCAACTTTCTCTGCCTCATTAAGCAGGATCAAGCAGCCAAATCCACAG
AATGTATACCCACCATGTGCTTCAGCATAAGGCTCCCCAGCAATACCACCTTCATAAGTTTGAC
ATCTTGCTATGTAGTCGCCTACACCTTTTGCCAGTTTAAAATCAAGAATATTCACAAGGCTGGC
AACCGATATAGCGGTGTAGGAAGCACGGACATCAATTTCGCCACCATCATGCATTCTGAAAGCA
CCTGATACATCTTTCATCTGCAGCATAAJAATTGTACAGGTTGCCCCTATTGATTGATGACATG
CTCTTTCGCTCCCTATTGTCACAAGTGTATTACAGCAGCATAAGGTCGTAGCTAGGTGAGGCAA
CTGTCCAGGTCCACCACTATATCCACCATCTTTATCCTGACATCGAGCTAAGAAGTCTATGATA
TCATTCTCAAGATCATCATCAAGTGCTTCATCCAGCAAAGCAAGTGGATGAACCATCCAGTAGC
ATAGCCAAGGGCGATTGGCATCTAGAACATGAAAGGCTGGTCCCATATGCCTCAGCCCAGGCGT
CAGATACTCGATATGCTGATCACGCCACAGCTCTAGCATGATGGATTTCGTGTTGGGCGCGGCC
CCGAAGAGGGAGCGGTAGATGTCGCCAACCCTGGCCTCCACCTTCATCTGCTCCACCTGCGTCA
CCGTGAGCCTCGGTAGGTCGGGATCCGCC
```

Table 10A. ClustalW Nucleic Acid Analysis of FT Alpha Subunits

1) BNA-12; FT2 (SEQ ID NO:12)
2) At-FT-A; FT1 (SEQ ID NO:7)
3) PPI-Soy-FTA; FT4 (SEQ ID NO:37)
4) Pea-FT-A (SEQ ID NO:65)
5) Tomato-FTA (SEQ ID NO:66)
6) Rice-FT-A (SEQ ID NO:67)
7) Zea mays-FT-A (SEQ ID NO:68)
8) Soy1-FT-A (SEQ ID NO:69)
9) Soy2-FT-A (SEQ ID NO:70)
10) Triticum-FT-A (SEQ ID NO:71)

```
                         10        20        30        40        50        60        70
                ....|....|....|....|....|....|....|....|....|....|....|....|....|....|
BnA-12          ----------------------------------------------------------------------
At-FT-A         ----------------------------------------------------------------------
PPI-Soy-FTA     ---------------------------------------------------------------AT--GGA
Pea-FT-A        CAACACCTACCTAGTGCTTCTAGTTCTGGTTCTAGGACTGAGAGTAAACAGAAGTGAAGAAGAATCCAGA
Tomato-FTA      ---TACCCCGAAGGCAATTCCAGTATTGAACTACCGCCGGCAGTTTTCCGATCGGATCCCGGAGCCGAGT
Rice-FT-A       -----------GCACGAGGTTCTAACGCCGCCGCCGCCGCCGCCGTCTCCGCA-GAATCTGATCGATGGC
Zea mays-FT-A   -----------------GCACGAGACAGCGCAATTACTTAAGCTATTTGTATTCGGATCTGATCCAACCC
Soy1-FT-A       --------------------------------------------GCACGAGGATTAACGAAGGAT--GGA
Soy2-FT-A       ------------------------GCACGAGCTTGCGTGTGGAGTGAAGAAGATTAACGAAGGAT--GGA
Triticum-FT-A   ----------------------------------------------------------------------

                         80        90       100       110       120       130       140
                ....|....|....|....|....|....|....|....|....|....|....|....|....|....|
BnA-12          ----------------------------------------------------------------------
At-FT-A         ---GAGTCGGGGAACATGAATTTCGACGAG---A-CCGTG----CCACTGAGCCAACGATTGGAGTGGTC
PPI-Soy-FTA     AT----CTGGGTCTAGCGAAGGAGAAGAGGTGCAGCAACGCGTGCCGTTGAGGGAGAGAGTGGAGTGGTC
Pea-FT-A        ACATGGCCGGGAATATCGAAGTTGAAGAAG---ACGATCGTGTGCCGCTAAGATTACGACCTGAGTGGTC
Tomato-FTA      ATCAAATGGACAGTTGTGAGGT--GACGAA---A-ACGCGAATTCCTTTCAAGGAAAGGCCCGACTGGGC
Rice-FT-A       GCCGTCGTCGACGTCGTCGGAGGGTGCCTC-CGACGAGTGGTTGCCACCCAGCCGGCGGCCGGAGCTGGC
Zea mays-FT-A   TGGTGGTCAGCTGGACTCATCGCCCATGGA-GCACACTAAGTCAGGCCCCAGCAGTTGGCCAGAACTGGC
Soy1-FT-A       AT----CTGGGTCTAGCGAAGGAGAAGAGGTGCAGCAACGCGTGCCGTTGAGGGAGAGAGTGGAGTGGTC
Soy2-FT-A       AT----CTGGGTCTAGCGAAGGAGAAGAGGTGCAGCAACGCGTGCCGTTGAGGGAGAGAGTGGAGTGGTC
```

```
Triticum-FT-A    ---------------------------------------------------------------------C

                          150       160       170       180       190       200       210
                 ....|....|....|....|....|....|....|....|....|....|....|....|....|....|
BnA-12           ----------------------------------------------------------------------
At-FT-A          AGACGTGGTCCCATTGACTCAGGACGATGGTCCGAATCCAGTGGTGCCAATTGCCTACAAGGAAGAGTTC
PPI-Soy-FTA      AGATGTTACTCCGGTTCCTCAAAACGACGGCCCTAACCCTGTCGTTCCGATCCAGTACACTGAAGAGTTT
Pea-FT-A         AGATGTTACTCCGATCCCACAAGACGATGGCCCTAGTCCCGTCGTGCCGATCAACTACTCCGAAGAGTTT
Tomato-FTA       CGATGTGAAGCCCGTTCCGCAAGACGACGGGCCCTGCCGGGTTGTTCCCATAGCCTACACAGAAGACTTC
Rice-FT-A        GGACGTGGTCCCCGTGACGCAGGACGACGGGCCCCACCCCGCTGGTGGCCATCGCCTACCGGGACGAGTTC
Zea mays-FT-A    CGACGTGGTGCCGGTGCCGCAGGACGATGGGCCTAGCCCGTGTGGTGTCCATCGCCTATCGAGATGACTTT
Soy1-FT-A        AGATGTTACTCCGGTTCCTCAAAACGACGGCCCTAACCCTGTCGTTCCGATCCAGTACACTGAAGAGTTT
Soy2-FT-A        AGATGTTACTCCGGTTCCTCAAAACGACGGCCCTAACCCTGTCGTTCCGATCCAGTACACTGAAGAGTTT
Triticum-FT-A    GGACGTGGCGCCGCTGCCGCAGGCCGACGGGCCCTGCCCCGTCGTCTCCATCGCTTACCGCGGCGACTTC

                          220       230       240       250       260       270       280
                 ....|....|....|....|....|....|....|....|....|....|....|....|....|....|
BnA-12           ---------ATGGATTACTTCCGTGCGATTTACTTCTCCGACGAGCCGTTCTGCTCGCGCGCTGCGACTCA
At-FT-A          CGCGAGACTATGGATTACTTCCGTGCGATTTACTTTTCCGACGAGCCGATCTCCTCGCGCACTACGACTCA
PPI-Soy-FTA      TCCGAAGTTATGGATTACTTTCGCGCCGTTTACCTCACCGATGAACGCTCCCCTCGCGCCCTCGCTCTCA
Pea-FT-A         TCAGAAGTTATGGATTACTTTCGTGCTGTTTACTTCGCCAAAGAACTTTCCTCTCGCGCTCTTGCTCTCA
Tomato-FTA       TCTGAAACCATGGACTACTTCCGGGCAATTTACGTAGCCGATGAGCGATCTACACGCGCCCTCCAGCTTA
Rice-FT-A        CGCGAGGTCATGGACTACTTCCGCGCCCTCTACTTCGCCGGCGAGCGCAGCGTCCGCGCCGCTCCACCTCA
Zea mays-FT-A    CGTGAGGTCATGGATTACTTCCGCGCCCTCTACCTCACCGGTGAGCGAAGCCCTCGCGCTCTCCGCCTCA
Soy1-FT-A        TCCGAAGTTATGGATTACTTTCGCGCCGTTTACCTCACCGATGAACGCTCCCCTCGCGCCCTCGCTCTCA
Soy2-FT-A        TCCGAAGTTATGGATTACTTTCGCGCCGTTTACCTCACCGATGAACGCTCCCCTCGCGCCCTCGCTCTCA
Triticum-FT-A    CGCGAGGTCATGGACTACTTCCGCGCCCTCTACGCCGCCGGCGAGCGCAGCCCCCGCGCCCTCCGCCTCA

                          290       300       310       320       330       340       350
                 ....|....|....|....|....|....|....|....|....|....|....|....|....|....|
BnA-12           CGGAAGAAGCTCTCCGCTTAAACTCGGGCAACTACACCGTGTGGCACTTCGGGCGCTTAGTACTCGAGGA
At-FT-A          CGGAAGAAACCCTCCTCTTAAACTCCGGCAACTACACAGTGTGGCATTTCAGGCGCCTAGTACTCGAGGC
PPI-Soy-FTA      CAGCCGAAGCCGTTCAATTCAACTCCGGCAACTACACTGTGTGGCATTTCCGACGGTTGTTACTTGAGTC
Pea-FT-A         CCGCCGAAGCTATCGGTTTAAACGCCGGAAACTACACTGTGTGGCATTTCCGGCGGTTATTACTTGAGTC
Tomato-FTA       CTGGTGAAGCTATTCAGCTAAACCCTGGAAATTACACTGTATGGCAATTTAGGCGTGTTGTGCTGGAGGC
Rice-FT-A        CCGCCGAGGTCATCGACCTTAATCCCGGCAACTACACGGTGTGGCATTTTAGGCGTCTTGTTCTAGAGGC
Zea mays-FT-A    CCGCCGAGGCCATCGAGCTCAAGCCCGGCAACTACACTGTCTGGCATTTCCGGCGCCTTATTCTGGAGTC
Soy1-FT-A        CAGCCGAAGCCGTTCAATTCAACTCCGGCAACTACACTGTGTGGCATTTCCGACGGTTGTTACTTGAGTC
Soy2-FT-A        CAGCCGAAGCCGTTCAATTCAACTCCGGCAACTACACTGTGTGGCATTTCCGACGGTTGTTACTTGAGTC
Triticum-FT-A    CCGCCGACGCCATCCACCTCAACCCCGGCAACTACACTGTATGGCATTTCAGGCGCGTTGTTCTAGAGGC

                          360       370       380       390       400       410       420
                 ....|....|....|....|....|....|....|....|....|....|....|....|....|....|
BnA-12           GCTTAATAACGACTTGTATGAAGAGCTCAAGTTCATCGAAAGCATTGCTGAGGATAACTCTAAGAACTAC
At-FT-A          CCTTAATCACGACTTGTTTGAAGAACTCGAGTTCATCGAACGCATTGCTGAGGATAACTCTAAGAACTAC
PPI-Soy-FTA      GCTAAAAGTCGACTTGAACGATGAACTGGAGTTTGTGGAGCGTATGGCCGCTGGAAATTCTAAAAATTAT
Pea-FT-A         ACTGAAAGTTGACCTACATGTTGAACGGGAATTCGTGGAGCGTGTTGCCAGTGGCAATTCAAAAAATTAT
Tomato-FTA       ATTGGGTGTTGATTTACGTGAAGAATTGAAGTTTGTTGATCGCATTGCTGGGGAGAATACCAAAAATTAT
Rice-FT-A        ACTGGATGCTGATCTGCGTGAGGAAATGGATTTTGTGGACCGAATTGTCGAATGTAACCCAAAAAATTAT
Zea mays-FT-A    ACTAGATTTTGATTTACTAGAGGAGATGAAATTTGTCGAAAAAATTGCTGAATGCAATCCAAAAAATTAC
Soy1-FT-A        GCTAAAAGTCGACTTGAACGATGAACTGGATTTTGTGGAGCGTATGGCCGCTGGAAATTCTAAAAATTAT
Soy2-FT-A        GCTAAAAGTCGACTTGAACGATGAACTGGAGTTTGTGGAGCGTATGGCCGCTGGAAATTCTAAAAATTAT
Triticum-FT-A    ACTGGATGCTGATTTATTGCTAGAAATGCATTTTGTGGACCAAATTGCTGAATCTAATCCAAAAAATTAC

                          430       440       450       460       470       480       490
                 ....|....|....|....|....|....|....|....|....|....|....|....|....|....|
BnA-12           CAGTTGTGG------------------------------------CATCATCGACGATGGGTCGCAGAGA
At-FT-A          CAACTGTGG------------------------------------CATCATCGGCGATGGGTTGCAGAGA
PPI-Soy-FTA      CAGATGTGN----ATGTTCTG----------TAG----------GCATCCTAGACGATGGGTTGCCGAGA
Pea-FT-A         CAGATTTGG------------------------------------CATCATAGACGATGGGTTGCTGAGA
Tomato-FTA       CAAATATGG------------------------------------CATCATAGACGGTGGCTTGCTGAGA
Rice-FT-A        CAAATCTGG------------------------------------CATCACAAGAGATGGCTTGCGGAGA
Zea mays-FT-A    CAAATCTGG------------------------------------CACCATAAGAGATGGCTTGCTGAGA
Soy1-FT-A        CAGATGTGG------------------------------------CATCATAGACGATGGGTTGCCGAGA
Soy2-FT-A        CAGATGTGGTGTGATGCTCTGCTCTGCTCTTTCTTCCATACTTTGCATCATAGACGATGGGTTGCCGAGA
Triticum-FT-A    CAAGTCTGG------------------------------------CATCACAAGAGATGGCTTGCTGAGA

                          500       510       520       530       540       550       560
                 ....|....|....|....|....|....|....|....|....|....|....|....|....|....|
BnA-12           AACTGGGTCCTGATGTTGCAGGAAAGGAACTTGAGTTTACTCGGAGGGTACTATCACTTGATGCCAAGCA
At-FT-A          AACTGGGTCCTGATGTTGCAGGGAGAGAACTTGAATTTACCCGTAGAGTACTTTCACTTGATGCCAAACA
```

```
PPI-Soy-FTA       AGTTAGGTCCTGAAGCTAGAAACAATGAGCTCGAGTTCACCAAAAAGATACTGTCCGTTGATGCCAAACA
Pea-FT-A          AATTAGGACCTGAAGCTAGAAACAGTGAACTTGAGTTCACCAAAAAGATTCTGTCTGTTGACGCCAAACA
Tomato-FTA        AGCTGGCAGCTGATGCTGTGACAAATGAGCTAGAATTCACCAAGAAAATATTTTCTCAGGATGCAAAAAA
Rice-FT-A         AATTAGGACCAGATATTGCAAATAAAGAGCACGAATTTACAAGGAAGATACTTTCTATGGATGCTAAAAA
Zea mays-FT-A     AATTAGGACCTGGTATTGCAAACAAAGAGCATGAATTCACAATGAAGATACTTGCTATTGATGCAAAAAA
Soy1-FT-A         AGTTAGGTCCTGAAGCTAGAAACAATGAGCTCGAGTTCACCAAAAAGATACTGTCCGTTGATGCCAAACA
Soy2-FT-A         AGTTAGGTCCTGAAGCTAGAAACAATGAGCTCGAGTTCACCAAAAAGATACTGTCCGTTGATGCCAAACA
Triticum-FT-A     AAATAGGACCAGATGCTGCAAATAGTGAACATGACTTCACAAGGAAGATACTTGCTATGGATGCTAAAAA

                          570       580       590       600       610       620       630
                  ....|....|....|....|....|....|....|....|....|....|....|....|....|....|
BnA-12            TTATCATGCTTGGTCACATAGGCAGTGGGCGCTACAAGCATTAGGAGGATGGGAAAATGAGCTTAACTAC
At-FT-A           TTATCATGCTTGGTCACATAGGCAGTGGACACTACGGGCATTAGGAGGATGGGAAGATGAGCTCGATTAC
PPI-Soy-FTA       TTATCATGCATGGTCTCATAGACAGTGGGCTCTTCAAACACTAGGAGGATGGGAAGATGAACTTAATTAT
Pea-FT-A          CTATCATGCATGGTCTCATAGGCAGTGGGTTCTTCAAAATCTAGGAGGATGGAAGATGAACTCAGTTAT
Tomato-FTA        TTATCATGCTTGGTCCCATCGGCAGTGGGTCCTTCAAGCACTTGGAGGATGGGAAGATGAGCTTGCTTAT
Rice-FT-A         TTACCATGCTTGGTCTCATAGGCAGTGGGTTCTTCAAGCACTGGGTGGATGGGAGACTGAAGTACAGTAT
Zea mays-FT-A     TTATCATGCTTGGTCTCATAGGCAGTGGGTTCTTCAAGCGTTGGGGGGATGGGAGACTGAATTAGAATAC
Soy1-FT-A         TTATCATGCATGGTCTCATAGACAGTGGGCTCTTCAAACACTAGGAGGATGGGAAGATGAACTTAATTAT
Soy2-FT-A         TTATCATGCATGGTCTCATAGACAGTGGGCTCTTCAAACACTAGGAGGATGGGAAGATGAACTTAATTAT
Triticum-FT-A     CTACCATGCTTGGTCCCATAGGCAGTGGGTTCTTCAAGCATTGGGTGGATGGGAGAGTGAACTGCAGTAC

                          640       650       660       670       680       690       700
                  ....|....|....|....|....|....|....|....|....|....|....|....|....|....|
BnA-12            TGCCACGAGCTCCTTGAAGCTGACGTCTTTAACAACTCTGCATGGAATCAGAGGTATTACGTTATAACTA
At-FT-A           TGTCACGAGCTCCTTGAAGCTGACGTCTTTAACAATTCCGCCTGGAATCAGAGGTATTATGTCATCACCC
PPI-Soy-FTA       TGCACAGAACTACTTAAAGAAGACATTTTTAACAATTCTGCTTGGAATCAGAGATATTTTGTCATAACAA
Pea-FT-A          TGTAGTGAACTGCTTGCAGAAGACATATTTAACAATTCTGCTTGGAATCAGAGATACTTCGTCATAACAA
Tomato-FTA        TGTCAACAACTCCTTGAAGATGATATTTACAACAATTCTGCTTGGAATCAGAGATACTTTGTCGTAACAC
Rice-FT-A         TGCAACCAGCTGCTTGAGGAAGACGTCTTCAATAATTCAGCTTGGAATCAGAGATACCTTGTAATAACAA
Zea mays-FT-A     TGTGACCACTTACTTAAGGAAGACGTCTTCAATAATTCAGCTTGGAATCAGAGATACTTTGTTATAACAA
Soy1-FT-A         TGCACAGAACTACTTAAAGAAGACATTTTTAACAATTCTGCTTGGAATCAGAGATATTTTGTCATAACAA
Soy2-FT-A         TGCACAGAACTACTTAAAGAAGACATTTTTAACAATTCTGCTTGGAATCAGAGATATTTTGTCATAACAA
Triticum-FT-A     TGCAACCAGCTTCTTGAGGAAGATGTCTTCAATAACTCAGCTTGGAATCAGAGATACCTTGTGGTAACAC

                          710       720       730       740       750       760       770
                  ....|....|....|....|....|....|....|....|....|....|....|....|....|....|
BnA-12            GATCACCTTCGTTGGGAGGCCTAGAAGCCATGAGAGAATCTGAAGTAAGCTACACAGTCAAAGCCATTTT
At-FT-A           AATCTCCTTTGTTGGGAGGCCTAGAAGCCATGAGAGAATCTGAAGTAAGCTACACAATCAAAGCCATTTT
PPI-Soy-FTA       GGTCTCCTTTCTTGGGGGGCCTAAAAGCTATGAGAGAGTCTGAAGTGCTTTACACCATCGAAGCCATTAT
Pea-FT-A          GGTCTCCCGTCTTGGGAGGGCTAAAAGCCATGAGAGAGTCTGAAGTGCTTTTCACCGTTGAAGCCATTAT
Tomato-FTA        GATCACCTCTACTAGGGGGCCTAGTGGCAATGAGGGAATTGGAAGTGAATTACACAGTTCAAGCCATCAG
Rice-FT-A         GTTCACCACTTCTTGGAGGCCTTGCAGCAATGCGTGACTCGGAAGTGGATTACACAGTTGGGGCTATTCT
Zea mays-FT-A     GATCACCATTTCTTGGTGGCCTTGCGGCAATGCGTGATTCAGAAGTAGACTACACAATTGAAGCTATTCT
Soy1-FT-A         GGTCTCCTTTCTTGGGGGGCCTAAAAGCTATGAGAGAGTCTGAAGTGCTTTACACCATTGAAGCCATTAT
Soy2-FT-A         GGTCTCCTTTCTTGGGGGGCCTAAAAGCTATGAGAGAGTCTGAAGTGCTTTACACCATTGAAGCCATTAT
Triticum-FT-A     GATCACCAATTCTTGGGGGCCTTGCGGCAATGCGCGACTCAGAAGTAGATTACACAGTTGAGGCCATTAT

                          780       790       800       810       820       830       840
                  ....|....|....|....|....|....|....|....|....|....|....|....|....|....|
BnA-12            AGCAAATCCCGGGAACGAGAGCTCTTGGAGGTACCTGAAAGCCCTTTACAAAGACGACACAGAGTCTTGG
At-FT-A           AACCAATCCTGCAAACGAGAGCTCATGGCGATACCTAAAAGCGCTTTACAAAGACGACAAAGAATCCTGG
PPI-Soy-FTA       AGCCTACCCTGAAAATGAAAGCTCGTGGAGATATCTACGAGGACTTTATAAAGGTGAAACTACTTCATGG
Pea-FT-A          TTCTTACCCAGAAAATGAAAGCTCATGGAGATATCTTCGAGGACTTTTCAAAGATGAATCCACGTTATAT
Tomato-FTA        AGCTAGTCCAGAGAATGAAAGTCCTTGGAGGTATCTTCGTGGTCTTTACAAGAATGATACACAATCTCTA
Rice-FT-A         GGCTAACCCTCAGAATGAAAGCCCCTGGAGATACCTCAAAGGCCTGTACAAGGGTGAAAATAACTTGCTG
Zea mays-FT-A     AGCAAACGCTCAGAATGAAAGCCCCTGGAGGTACCTCAAGGGTCTATACAAGGGTGAGAATAACCTGCTA
Soy1-FT-A         AGCCTACCCTGAAAATGAAAGCTCGTGGAGATATCTACGAGGACTTTATAAAGGTGAAACTACTTCATGG
Soy2-FT-A         AGCCTACCCTGAAAATGAAAGCTCGTGGAGATATCTACGAGGACTTTATAAAGGTGAAACTACTTCATGG
Triticum-FT-A     GGTGAACCCTCAGAATGAAAGCCCCTGGAGATACCTCAGAGGTTTATATAAGGATGATAACAATTTGCTG

                          850       860       870       880       890       900       910
                  ....|....|....|....|....|....|....|....|....|....|....|....|....|....|
BnA-12            ATTAGTGATCCAAGTGTTTCCTCAGTCTGTTTGAAAGTTCTCTCACGCGCGGACTGCTTCCATGGATTCG
At-FT-A           ATTAGTGATCCAAGTGTTTCCTCAGTCTGTTTGAATGTTCTATCCCGCACAGATTGCTTCCATGGATTCG
PPI-Soy-FTA       GTAAATGATCCTCAAGTTTCTTCAGTATGCTTAAAGATTTTGAGAACTAAGAGCAAC---TACGTGTTTG
Pea-FT-A          GTAAATGATGCCCAAGTATCTTCATTATGTTTAAAGATTTTGAAAACTAAGAGCAAC---TATTTGTTTG
Tomato-FTA        GTTCAGGATTCTCAAGTAGCATCAGTACTTTGGGACGTCTTAACCTCCCAAAATAGT---CATGTGCACG
Rice-FT-A         ATGGCTGATGAGCGCATCTCTGATGTTTGTCTCAAGGTCCTGAAACATGATTCGACC---TGCGTATTTG
Zea mays-FT-A     GTAGAGGACGAGCGCATCTCTGCTGTTTGTTTCAAGGTCCTGAAGAATGATTGGACT---TGTGTATTTG
Soy1-FT-A         GTAAATGATCCTCAAGTTTCTTCAGTATGCTTAAAGATTTTGAGAACTAAGAGCAAC---TACGTGTTTG
```

```
Soy2-FT-A       GTAAATGATCCTCAAGTTTCTTCAGTATGCTTAAAGATTTTGAGAACTAAGAGCAAC---TACGTGTTTG
Triticum-FT-A   GTGGCTGATAATCGCATTTCTGATGCTTGCCTCAAGGTCCTGAATAAGGATTGGACA---TGCGTATTTG

                         920       930       940       950       960       970       980
                ....|....|....|....|....|....|....|....|....|....|....|....|....|....|
BnA-12          CTCTGAGCACCCTTTTGGATCTTCTGTGCGATGGCT-TGAGACCAACCAACGAGCATAGAGACTCGGTGA
At-FT-A         CTCTGAGCACCCTTTTGGATCTTCTATGTGATGGAC-TGAGACCAACCAACGAGCATAAAGACTCAGTGA
PPI-Soy-FTA     CTCTTAGCACTATTTTAGATCTTATATGCTTTGGTTAT-CAACCAAATGAAGACATTAGAGATGCCATTG
Pea-FT-A        CTCTAAGTACTCTGCTGGATCT-ATCTGCCTCGGTTATTCAACCAAATGAAGATTTCAGAGATGCCATTG
Tomato-FTA      CTCTGAGGTTCTTGTTGGATCTTCTTTGTCATGATT-TGGAACCGAGCCAAGAATTGAAAAGTGCTGTAG
Rice-FT-A       CTTTGAGCTTGCTGCTCGATCTTCTTCAAATTGGTT-TACAACCTTCAGATGAACTCAAAGGAACTATCG
Zea mays-FT-A   CTTTGAGCTTTGCTGCTCGATCTTCTCTGCACTGGTT-TGCAGCCTTCAGATGAACTTAGGTCCACTCTTG
Soy1-FT-A       CTCTTAGCACTATTTTAGATCTTATATGCTTTGGTTAT-CAACCAAATGAAGACATTAGAGATGCCATTG
Soy2-FT-A       CTCTTAGCACTATTTTAGATCTTATATGCTTTGGTTAT-CAACCAAATGAAGACATTAGAGATGCCATTG
Triticum-FT-A   CTTTGAGCTTCCTGCTTGATCTTCTTCGCATGGGTT-TGCAGCCTTCGAATGAACTTAAAGGAACCATCG

                         990      1000      1010      1020      1030      1040      1050
                ....|....|....|....|....|....|....|....|....|....|....|....|....|....|
BnA-12          AAGCTCTAG---CT------AATGAAGA---------------------------------A-CCAGAGAC
At-FT-A         GAGCTCTAG---CT------AATGAAGA---------------------------------A-CCAGAGAC
PPI-Soy-FTA     ACGCCTTAAAGACCGCAGATATGGATAAACAAGATTTAGATGATGATGAGAAAGGGGAACAAACAAAATTT
Pea-FT-A        AGGCTTTAA-GACTTCAGATTTTGATAAA--------------------------------A-CAAGATTC
Tomato-FTA      ATGTTCTTA---CTCCC--CAGTCATGCTC-------------------------------A-CCAGATTC
Rice-FT-A       AAGCAATAAAGAACTCTGATCCTGAAGCAGATGA--------------------AG---CA-GTAGATGC
Zea mays-FT-A   AAACAATAAGGAGCTCCCATCCTGAAACCGC----------------------------------GGATGA
Soy1-FT-A       ACGCCTTAAAGACCGCAGATATGGATAAACAAGATTTAGATGATGATGAGAAAGGGGAACAAACAAAATTT
Soy2-FT-A       ACGCCTTAAAGACCGCAGATATGGATAAACAAGATTTAGATGATGATGAGAAAGGGGAACAAACAAAATTT
Triticum-FT-A   AAGCAATGGAGAACTCTGATCCTGAAACGGG----------------------------------ACATGC

                        1060      1070      1080      1090      1100      1110      1120
                ....|....|....|....|....|....|....|....|....|....|....|....|....|....|
BnA-12          TAACTTGGCCAATTTGGTGTGTACCATTCTGTGTCGTGTTGATCCAATAAGAGCTAACTATTGGCATGG
At-FT-A         TAACTTGGCCAATTTGGTGTGTACTATTCTTGGTCGTGTAGATCCTATAAGAGCTAACTATTGGCATGG
PPI-Soy-FTA     AAATATAGCACGAAATATTTGTTCTATCCTAAAACAAGTTGATCCAATTAGAACCAACTATTGGATTTGG
Pea-FT-A        AGATATAGCACAATAACTATTTGTTCTATTTTAGAACAAGTTGATCCAATTAGAGTCAACTATTGGGTCTGG
Tomato-FTA      AGCACTGACAAAGAAAATTTGTTCCATCTTGGAACATGCTGATCCAATGAGAGTAAACTATTGGGTCTGG
Rice-FT-A       TGATCTTGCGACTGCAATCTGCTCAATATTGCAGAGATGTGATCCCCTGCGGATAAATTATTGGAATTGG
Zea mays-FT-A   TGATCCTGCAGCCGCTGTTTGCTGTATCCTGCAGAAATGTGATCCCCTGCGGGTAAATTATTGGTCTTGG
Soy1-FT-A       AAATATAGCACGAAATATTTGTTCTATCCTAAAACAAGTTGATCCAATTAGAACCAACTATTGGATTTGG
Soy2-FT-A       AAATATAGCACGAAATATTTGTTCTATCCTAAAACAAGTTGATCCAATTAGAACCAACTATTGGATTTGG
Triticum-FT-A   TGATATTGCAGTAGCTGTCTGCTCAATCCTGCAGAAATGTGATCCCCTGCGGATAAACTACTGGTCATGG

                        1130      1140      1150      1160      1170      1180      1190
                ....|....|....|....|....|....|....|....|....|....|....|....|....|....|
BnA-12          ----------------------------------------------------------------------
At-FT-A         AGGAAGAGCAAGATTACA----GTGGC-AGCAATTTGAATATGTGACGCCCCAAAATCACACTTGAAAAA
PPI-Soy-FTA     CGCAAGAGCAGACTTC--------CT--------------------------------------------
Pea-FT-A        CGGAAGAGTAGACTTC--------CTCA-GGCAGCGTAAAGGACAAACTTATGTCATATGTGTAATTTTTA
Tomato-FTA      CGCAAGAGCATGGTTCGG----GTTCA-ATTACTTCAGAGTCAGAATGCAGAGAGGTTG-GCTAATTTGA
Rice-FT-A       TACAGGACCACTATTTCT----TCTCA-AAC--CTGAAG----CATGCAGTGGCCTCCATGA------GG
Zea mays-FT-A   TTCAAGGACACTCTTTCTCAGATCTCATGACTTCACATGGGTTCACCCCTTGTCCGCGCTGGTCCGGGGCT
Soy1-FT-A       CGCAAGAGCAGACTTC--------CTCT-ATCAGCTTAGTAACCAAAGTAATTAAA---GGGCAACTCTGT
Soy2-FT-A       CGCAAGAGCAGACTTC--------CTCT-ATCAGCTTAGTAACCAAAGTAATTAAA---GGGCAACTCTGT
Triticum-FT-A   TACCAGACCACTCTTTCT----TCTTA-GACATCTCAAAA-TTCAGCTGAAGACAGTTTTAG------CA

                        1200      1210      1220      1230      1240      1250      1260
                ....|....|....|....|....|....|....|....|....|....|....|....|....|....|
BnA-12          ----------------------------------------------------------------------
At-FT-A         GACTTGATTAT--TAGT-TTTTACGT----------AATTAACTGCTTATTTATGAATCACATG-TTCAT
PPI-Soy-FTA     ----------------------------------------------------------------------
Pea-FT-A        GTCTATTGGAATTTGACGTCATGGAT----------AACAGGGTGGTTGTTTTTGTTATGATAT-GTTTT
Tomato-FTA      GTGTTCAAGAA--TGAC-TTGTGAGA----------ATATTGTACTGTGTTTACGAAATACATA-CTTGC
Rice-FT-A       TCATAATGGAGATATCTTCTAT---------------------------CTTCGTGTGA---------TTCTG
Zea mays-FT-A   CTGTGAGATAGACATGTTTTAGATAGTTTCATTGGACACCCAAACAGAGCGGACAGAGTGTATGGCTGCT
Soy1-FT-A       GTTATGTGTAACCTAGT-TTATTGA-----------AACTGGATTTTTATTT--ATTATTATTT-TTTAT
Soy2-FT-A       GTTATGTGTAACCTAGT-TTATTGA-----------AACTGGATGTTTATTT--ATTATTATTT-TTTAT
Triticum-FT-A   GCATGATGTAAACTCAATCGAAGGGGTT--------------GACGCAGTGTATGAAAAACCT--TTCCT

                        1270      1280      1290      1300      1310      1320      1330
                ....|....|....|....|....|....|....|....|....|....|....|....|....|....|
BnA-12          ----------------------------------------------------------------------
```

At-FT-A GT-TAACATGTATCAAAACAATCTTGATTTCTCAAAAAAAAAAAAAAAAAAAAAAAAAAAAAA-------
PPI-Soy-FTA ----------------------------------------------------------------------
Pea-FT-A CC-AGATGTATTTCTATATTTAACAGCAAAGTTGATTTAACATTGGTGTTAACAAACCAATGATCTCCAA
Tomato-FTA ATCTAAGGTGATCCTTCGGGCACATGTGCTGGGAAGTGACTGAATATCACGAAGAACTAAAAAAACTGTG
Rice-FT-A GGCGTTGAGGTGCCT---AGCTACATTTGTTATGAACTTTCCTTGGGCATAACTGATCACTGATATTAC-
Zea mays-FT-A ACCTTCTCCGTGACTGAAAGCAGTGCTTGTAACGA--TTTTGTTTAGTAAAATTTGTGAGTGTTACTGCT
Soy1-FT-A GT-TGTCATGTATCTGTTTGT----GCAAATTT------ATCTTTTTGTCATGCCATTACTGGCATTTGA
Soy2-FT-A GT-TGTCATGTATCTGTTTGT----GCAAATTT------ATCTTTTTGTCATGCCATTACTGGCATTTGA
Triticum-FT-A GTGATCTTGGTGCGG---AGCAA--TTTGTACTGA--TTTTACTGGGAAAAATCAATCAATGACAGCATG 1340 1350 1360 1370 1380 1390 1400
....|....|....|....|....|....|....|....|....|....|....|....|....|....|
BnA-12 ----------------------------------------------------------------------
At-FT-A ----------------------------------------------------------------------
PPI-Soy-FTA ----------------------------------------------------------------------
Pea-FT-A AAAATCAATGTTTTATTTCTCTTCATTTGTCTGATTTTGTGGCATAACATTCTTGATGAT-TTTGTGGTA
Tomato-FTA ATTGGCAACATTGTACTACTCCAAATAGGTCACTTTCGATGACTTTTTGTACTGCCTTGA-GTTTTGGCT
Rice-FT-A TCCAATATTGTGTTCTAAA---------------------------------------------------
Zea mays-FT-A CCAAACAACACCTTATGCAACCATATTTGAATAT----TTCACATGTAAGCT---TGA--------A-TC
Soy1-FT-A GTG--TAAGGATTGAAAGCCATGCA-------GAATAAGAAATTTAAGTTTTT-------TTTCCGTTG
Soy2-FT-A GTG--TAAGGATTGAAAGCCATGCA-------GAATAAGAAATTTAAGTTTTT-------TTTCCGTTG
Triticum-FT-A CCCAACAATGTCTTGTGTGAATATGTTACTGCCTGATATTCACATGTTAGCAGAATGAGAATAACCAATC 1410 1420 1430 1440 1450 1460 1470
....|....|....|....|....|....|....|....|....|....|....|....|....|....|
BnA-12 ----------------------------------------------------------------------
At-FT-A ----------------------------------------------------------------------
PPI-Soy-FTA ----------------------------------------------------------------------
Pea-FT-A AAAAAAAAAAAAAAAAAAAA--------------------------------------------------
Tomato-FTA CTGCTATGTTTTGTAAGTTTTGGATATGGATGCATAGCTTATTGATACTTTTGGTGACTTAAAATACTCT
Rice-FT-A ----------------------------------------------------------------------
Zea mays-FT-A CAGGTGTGTTTGTTAATGTATTACACTT--G-CCATGGGAGCCTAAATGAGACCCATAATCACTTCCACT
Soy1-FT-A AAAA------------------------------------------------------------------
Soy2-FT-A AAAAAAAAAAAAAAAAAAAA--------------------------------------------------
Triticum-FT-A AAACTCCAACGAGCAGATTGTTACAGTAACGGCCACTGGTGGTGTGAAAATCCTGAAATCTGCTTCAGTC 1480 1490 1500 1510 1520 1530 1540
....|....|....|....|....|....|....|....|....|....|....|....|....|....|
BnA-12 ----------------------------------------------------------------------
At-FT-A ----------------------------------------------------------------------
PPI-Soy-FTA ----------------------------------------------------------------------
Pea-FT-A ----------------------------------------------------------------------
Tomato-FTA GGAAGGCAGGTAGCATGTGTATAATTCACTGTTACTTCCCATGTCGAGTTAGATGCTTGAAAATTTTAGT
Rice-FT-A ----------------------------------------------------------------------
Zea mays-FT-A AGAGTCGGAAGACCGT-GTCGAGCAGTTCACTCATATGGTCACTTAAAGCAAAAAAAAAAAAAAAAAAA-
Soy1-FT-A ----------------------------------------------------------------------
Soy2-FT-A ----------------------------------------------------------------------
Triticum-FT-A ACTTTGCCTTGTTTACAGTTGAGTCTGTTGTTGTGATCTGTACCTAATGCATGTACACAATCATCAAATT 1550 1560 1570 1580 1590 1600 1610
....|....|....|....|....|....|....|....|....|....|....|....|....|....|
BnA-12 ----------------------------------------------------------------------
At-FT-A ----------------------------------------------------------------------
PPI-Soy-FTA ----------------------------------------------------------------------
Pea-FT-A ----------------------------------------------------------------------
Tomato-FTA AGGTGTTCTTTTATGAAGCACACATTAATGTGGAAAAAAAAAAAAAAAAAAAAAAAAAAAAAAAAAAAAA
Rice-FT-A ----------------------------------------------------------------------
Zea mays-FT-A ----------------------------------------------------------------------
Soy1-FT-A ----------------------------------------------------------------------
Soy2-FT-A ----------------------------------------------------------------------
Triticum-FT-A ATTAGTTTTTGTACCAATGAGTATTCGATGAAAAAAAAAAAAAAAA------------------------

.
BnA-12 -
At-FT-A -
PPI-Soy-FTA -
Pea-FT-A -
Tomato-FTA A
Rice-FT-A -
Zea mays-FT-A -

```
Soy1-FT-A      -
Soy2-FT-A      -
Triticum-FT-A  -
```

Table 10B. ClustalW Amino Acid Analysis of FT Alpha Subunits

1) BNA-12; FT2 (SEQ ID NO:13)
2) At-FT-A; FT1 (SEQ ID NO:11)
3) PPI-Soy-FTA; FT4 (SEQ ID NO:39)
4) Pea-FT-A (SEQ ID NO:72)
5) Tomato-FTA (SEQ ID NO:73)
6) Rice-FT-A (SEQ ID NO:74)
7) Zea mays-FT-A (SEQ ID NO:75)
8) Soy1-FT-A (SEQ ID NO:76)
9) Soy2-FT-A (SEQ ID NO:77)
10) Triticum-FT-A (SEQ ID NO:78)

```
                        10        20        30        40        50        60        70
                ....|....|....|....|....|....|....|....|....|....|....|....|....|....|
BnA-12          ---------------------------------------------------MDYFRAIYFSDERSARALR
At-FT-A         ---------MNFDETVPLSQRLEWSDVVPLTQDDGPNPVVPIAYKEEFRETMDYFRAIYFSDERSPRALR
PPI-Soy-FTA     -MESGSSEGEEVQQRVPLRERVEWSDVTPVPQNDGPNPVVPIQYTEEFSEVMDYFRAVYLTDERSPRALA
Pea-FT-A        --MAGNIEVEE-DDRVPLRLRPEWSDVTPIPQDDGPSPVVPINYSEEFSEVMDYFRAVYFAKELSSRALA
Tomato-FT-A     -----MDSCEVTKTRIPFKERPDWADVKPVPQDDGPCPVVPIAYTEDFSETMDYFRAIYVADERSTRALQ
RiceFT-A        MAPSSTSSEGASDEWLPPSRRPELADVVPVTQDDGPHPVVAIAYRDEFREVMDYFRALYFAGERSVRALH
Zea mays-FT-A   ----------MEHTLSGPSSWPELADVVPVPQDDGPSPVVSIAYRDDFRGVMDYFRALYLTGERSPRALR
Soy1-FT-A       -MESGSSEGEEVQQRVPLRERVEWSDVTPVPQNDGPNPVVPIQYTEEFSEVMDYFRAVYLTDERSPRALA
Soy2-FT-A       -MESGSSEGEEVQQRVPLRERVEWSDVTPVPQNDGPNPVVPIQYTEEFSEVMDYFRAVYLTDERSPRALA
Triticum-FT-A   ------------------------DVAPLPQADGPCPVVSIAYRGDFREVMDYFRALYAAGERSPRALR

                        80        90       100       110       120       130       140
                ....|....|....|....|....|....|....|....|....|....|....|....|....|....|
BnA-12          LTEEALRLNSGNYTVWHFGRLVLEELNNDLYEELKFIESIAEDNSKNYQLW------------HHRRWVA
At-FT-A         LTEETILLNSGNYTVWHFRRLVLEALNHDLFEELEFIERIAEDNSKNYQLW------------HHRRWVA
PPI-Soy-FTA     LTAEAVQFNSGNYTVWHFRRLLLESLKVDLNDELEFVERMAAGNSKNYQMX--------MFCRHPRRWVA
Pea-FT-A        LTAEAIGLNAGNYTVWHFRRLLLESLKVDLHVEREFVERVASGNSKNYQIW------------HHRRWVA
Tomato-FT-A     LTGEAIQLNPGNYTVWQFRRVVLEALGVDLREELKFVDRIAGENTKNYQIW------------HHRRWLA
RiceFT-A        LTAEVIDLNPGNYTVWHFRRLVLEALDADLREEMDFVDRIVECNPKNYQIW------------HHKRWLA
Zea mays-FT-A   LTAEAIELNPGNYTVWHFRRLILESLDFDLLEEMKFVELIAECNPKNYQIW------------HHLRWLA
Soy1-FT-A       LTAEAVQFNSGNYTVWHFRRLLLESLKVDLNDELDFVERMAAGNSKNYQMW------------HHRRWVA
Soy2-FT-A       LTAEAVQFNSGNYTVWHFRRLLLESLKVDLNDELEFVERMAAGNSKNYQMWCDALLCSFFHTLHHRRWVA
Triticum-FT-A   LTADAIHLNPGNYTVWHFRRVVLGALDADLLLEMHFVDQIAESNPLNYQVW------------HHKRWLA

                       150       160       170       180       190       200       210
                ....|....|....|....|....|....|....|....|....|....|....|....|....|....|
BnA-12          EKLGPDVAGLEKEFTRRVLSLDAKHYHAWSHRQWALQALGGWENELNYCHELLEADVFNNSAWNQRYYVI
At-FT-A         EKLGPDVAGRELEFTRRVLSLDAKHYHAWSHRQWTLRALGGWEDELDYCHELLEADVFNNSAWNQRYYVI
PPI-Soy-FTA     EKLGPEARNNELEFTKKILSVDAKHYHAWSHRQWALQTLGGWEDELNYCTELLKEDIFNNSAWNQRYFVI
Pea-FT-A        EKLGPEARNSELEFTKKILSVDAKHYHAWSHRQWVLQNLGGWEDELSYCSELLAEDIFNNSAWNQRYFVI
Tomato-FT-A     EKLGADAVTNELEFTKKIFSQDAKNYHAWSHRQWVLQALGGWEDELAYCQQLLEDDIYNNSAWNQRYFVV
RiceFT-A        EKLGPDIANKEHEFTRKILSMDAKNYHAWSHRQWVLQALGGWETELQYCNQLLEEDVFNNSAWNQRYLVI
Zea mays-FT-A   EKLGPGIANKEHEFTMKILAIDALNYHAWSHRQWVLQALGGWETELEYCDHLLKEDVFNNSAWNQRYFVI
Soy1-FT-A       EKLGPEARNNELEFTKKILSVDAKHYHAWSHRQWALQTLGGWEDELNYCTELLKEDIFNNSAWNQRYFVI
Soy2-FT-A       EKLGPEARNNELEFTKKILSVDAKHYHAWSHRQWALQTLGGWEDELNYCTELLKEDIFNNSAWNQRYFVI
Triticum-FT-A   EKIGPDAANSEHDFTRKILAMDAKNYHAWSHRQWVLQALGGWESELQYCNQLLEEDVFNNSAWNQRYLVV

                       220       230       240       250       260       270       280
                ....|....|....|....|....|....|....|....|....|....|....|....|....|....|
BnA-12          TRSPSLGGLEAMRESEVSYTVKAILANPGNESSWRYLKALYKDDTESWISDPSVSSVCLKVLSRADCFHG
At-FT-A         TQSPLLGGLEAMRESEVSYTIKAILTNPANESSWRYLKALYKDDKESWISDPSVSSVCLNVLSRTDCFHG
PPI-Soy-FTA     TRSPFLGGLKAMRESEVLYTIEAIIAYPENESSWRYLRGLYKGETTSWVNDPQVSSVCLKIL-RTKSNYV
Pea-FT-A        TRSPVLGGLKAMRESEVLFTVEAIISYPENESSWRYLRGLFKDESTLYVNDAQVSSLCLKIL-KTKSNYL
Tomato-FT-A     TRSPLLGGLVAMRELEVNYTVQAIRASPENESPWRYLRGLYKNDTQSLVQDSQVASVLWDVL-TSQNSHV
RiceFT-A        TSSPLLGGLAAMRDSEVDYTVGAILANPQNESPWRYLKGLYKGENNLLMADERISDVCLKVL-KHDSTCV
```

```
PPI-Corn-FTB  -------------------------------------------GGCGGATCCCGACCTACCGAGGCTCAC
DuP-Corn-FTB  -------------------------------------------GGCGGATCCCGACCTACCGAGGCTCAC
Pea FT-B      --------------------------------------------CGGACCCCCCCGTCCACAATCGTGAT
Tomato        GTCGCTGACGAAATTTACAGTCAAGAGTAGTAACCGGTTGTAGTGAAAAAATGGAGTCGAGGAAAGTGAC
Tobacco       -------------------------------------------------------GGCACGAGCGGC-AC

                      150       160       170       180       190       200       210
              ....|....|....|....|....|....|....|....|....|....|....|....|....|....|
PPI-BnFTb     ----------------------------------------------------------------------
era1          ----------------------------------------------------------------------
Wiggum        CGTGAGTCAGCGCGAGCAATTTCTGGTGGAGAACGATGTGTTCGGGATCTATAATTACTTCGACGCCAGC
PPI-Soy-FTB   ------------------------------------------------------------GCCACCATTC
DuP-Soy-FTB   ------------------------------------------------------------GCCACCATTC
PPI-Corn-FTB  GGTGACGCAGGTGGAGCAGATGAAGGTGGAGGCCAGGGTTGGCGACATCTACCGCTCCCTCTTCGGGGCC
DuP-Corn-FTB  GGTGACGCAGGTGGAGCAGATGAAGGTGGAGGCCAGGGTTGGCGACATCTACCGCTCCCTCTTCGGGGCC
Pea FT-B      GATGACGTCTCCGCGAGCATTTCAACAACCAGTTACTCAAACCACCGCGGAGTAACACATGGAAGCTTCA
Tomato        GAAGACGCTGGAAGATCAATGGGTGGTGGAGCGTCGAGTCCGAGAGATATACGATTATTTCTACAGCATT
Tobacco       GAGGACACTGGAAGATCAATGGATGGTGGAGCGTCAAGTTCGGGAGATATACAATTTTTTCTACAGCATT

                      220       230       240       250       260       270       280
              ....|....|....|....|....|....|....|....|....|....|....|....|....|....|
PPI-BnFTb     ----------------------------------------------------------------------
era1          ------------------------ATGGAGATTCAGCGAGATAAGCAATT-GGATTATC-----TGATGA
Wiggum        GACGTTTCTACTCAAAAATACATGATGGAGATTCAGCGAGATAAGCAATT-GGATTATC-----TGATGA
PPI-Soy-FTB   CTCGCAACGCCCAAACCCTCAT-GTTGGAGCTTCAACGCGATAATCACAT-GCAGTAT-----GTCTCCA
DuP-Soy-FTB   CTCGCAACGCCCAAACCCTCAT-GTTGGAGCTTCAACGCGATAATCACAT-GCAGTAT-----GTCTCCA
PPI-Corn-FTB  GCGCCCAACACGAAATCCATCATGCTAGAGCTGTGGCGTGATCAGCATAT-CGAGTATC-----TGACGC
DuP-Corn-FTB  GCGCCCAACACGAAATCCATCATGCTAGAGCTGTGGCGTGATCAGCATAT-CGAGTATC-----TGACGC
Pea FT-B      ACCGCGGCGGAGACACCAACTCCGACGGTGAGTCAGAGAGATCAATGGATAGTAGAATCACAGGTCTTTC
Tomato        TCCCCCAACTCTCCGTCCGACCTCATAGAGATCGAACGTGACAAACACTT-CGGTTATC-----TAAGCC
Tobacco       CCNCCCAATTC---------CCACTTAGAGACTTCAACAGAAAAGCACTT-CGATTATC-----TCACTC

                      290       300       310       320       330       340       350
              ....|....|....|....|....|....|....|....|....|....|....|....|....|....|
PPI-BnFTb     --------------------------------------------------------TGGCTTTGTTACTG
era1          AAGGCTTAAGGCAGCTT---GGTCCGCAGTTTTCTTCCTTAGATGCTAATCGACCTTGGCTTTGTTACTG
Wiggum        AAGGCTTAAGGCAGCTT---GGTCCGCAGTTTTCTTCCTTAGATGCTAATCGACCTTGGCTTTGTTACTG
PPI-Soy-FTB   AAGGCCTTCGCCATCTC---AGTTCCGCATTTTCCGTTTTGGACGCTAATCGACCCTGGCTCTGCTACTG
DuP-Soy-FTB   AAGGCCTTCGCCATCTC---AGTTCCGCATTTTCCGTTTTGGACGCTAATCGACCCTGGCTCTGCTACTG
PPI-Corn-FTB  CTGGGCTGAGGCATATG---GGACCAGCCTTTCATGTTCTAGATGCCAATCGCCCTTGGCTATGCTACTG
DuP-Corn-FTB  CTGGGCTGAGGCATATG---GGACCAGCCTTTCATGTTCTAGATGCCAATCGCCCTTGGCTATGCTACTG
Pea FT-B      ATATTTATCAACTCTTCGCCAATATTCCTCCTAACGCCCAATCTATCATTCGACCTTGGCTGTGTTACTG
Tomato        AAGGTCTCAGAAAACTT---GGTCCGTCGTTTTCCGTTTTGGATGCCAGTCGACCATGGCTTTGCTACTG
Tobacco       GAGGTCTCAGAAAACTT---GGTCCGTCGTTCTCCGTCTTGGATGCTAATCGACCATGGCTTTGCTACTG

                      360       370       380       390       400       410       420
              ....|....|....|....|....|....|....|....|....|....|....|....|....|....|
PPI-BnFTb     GATTCTTCATTCAATTGCTTTGCTTGGGGAGTCTGTGGATGATGACTTAGAAAACAATGCAATCGATTTT
era1          GATTCTTCATTCAATAGCTTTGCTTGGGGAGACTGTGGATGATGAATTAGAAAGCAATGCCATTGACTTC
Wiggum        GATTCTTCATTCAATAGCTTTGCTTGGGGAGACTGTGGATGATGAATTAGAAAGCAATGCCATTGACTTC
PPI-Soy-FTB   GATCTTCCACTCCATTGCTTTGTTGGGAGAATCCGTCGATGATGAACTCGAAGATAACGCTATCGATTTT
DuP-Soy-FTB   GATCTTCCACTCCATTGCTTTGTCGGGAGAATCCGTCGATGATGAACTCGAAGATAACGCTATCGATTTT
PPI-Corn-FTB  GATGGTTCATCCACTTGCTTTGCTGGATGAAGCACTTGATGATGATCTTGAGAATGATATCATAGACTTC
DuP-Corn-FTB  GATGGTTCATCCACTTGCTTTGCTGGATGAAGCACTTGATGATGATCTTGAGAATGATATCATAGACTTC
Pea FT-B      GATTATTCATTCAATTGCTTTGTTGGGAGAATCTATTGATGATGATCTCGAAGATAACACTGTCGATTTT
Tomato        GACACTTCATTCAATCGCTTTGTTGGGAGAATCTATTGGTGGCAAACTGGAAAATGATGCAATTGACTTT
Tobacco       GATACTTCATTCAATCGCTTTGTTGGGAGAATCTATTGATGCCCAACTGGAAAATGATGCAATTGACTTT

                      430       440       450       460       470       480       490
              ....|....|....|....|....|....|....|....|....|....|....|....|....|....|
PPI-BnFTb     CTTGGACGTTGCCAGGGTTCTGATGGTGGATATGGTGGTGGTCCTGGCCAACTTCCACATCTTGCAACAA
era1          CTTGGACGCTGCCAGGGCTCTGAAGGTGGATACGGTGGTGGTCCTGGCCAACTTCCACATCTTGCAACTA
Wiggum        CTTGGACGCTGCCAGGGCTCTGAAGGTGGATACGGTGGTGGTCCTGGCCAACTTCCACATCTTGCAACTA
PPI-Soy-FTB   CTTAACCGTTGCCAGGATCCGAATGGTGGATATGCCGGGGGACCAGGCCAGATGCCTCATATTGCCACAA
DuP-Soy-FTB   CTTAACCGTTGCCAGGATCCGAATGGTGGATATGCCGGGGGACCAGGCCAGATGCCTCATATTGCCACAA
PPI-Corn-FTB  TTAGCTCGATGTCAGGATAAAGATGGTGGATATAGTGGTGGACCTGGACAGTTGCCTCACCTAGCTACGA
DuP-Corn-FTB  TTAGCTCGATGTCAGGATAAAGATGGTGGATATAGTGGTGGACCTGGACAGTTGCCTCACCTAGCTACGA
Pea FT-B      CTTAACCGTTGCCAGGATCCAAATGGTGGATATGCTGGGGGACCTGGTCAGATGCCTCATCTTGCCACAA
Tomato        CTGACCCGTTGCCAGGATAAAGATGGTGGCTATGGAGGTGGACCTGGTCAGATGCCTCATCTTGCAACTA
Tobacco       CTGAGCCGTTGCCAGGATGAAGATGGTGGCTATGGTGGTGGACCTGGTCAGATGCCTCATCTTGCAACTA
```

```
                       500       510       520       530       540       550       560
              ....|....|....|....|....|....|....|....|....|....|....|....|....|....|
PPI-BnFTb     GTTATGCTGCAGTGAATACACTTGTTACTTTAGGAGGTGAGAAAGCCTTCTCTTCAATTAACAGAGAACA
era1          CTTATGCTGCAGTGAATGCACTTGTTACTTTAGGAGGTGACAAAGCCCTTTCTTCAATTAATAGAGAAAA
Wiggum        CTTATGCTGCAGTGAATGCACTTGTTACTTTAGGAGGTGACAAAGCCCTTTCTTCAATTAATAGAGAAAA
PPI-Soy-FTB   CTTATGCTGCTGTTAATTCACTTATTACTTTGGGTGGTGAGAAATCCCTGGCATCAATTAATAGAGATAA
DuP-Soy-FTB   CTTATGCTGCTGTTAATTCACTTATTACTTTGGGTGGTGAGAAATCCCTGGCATCAATTAATAGAGATAA
PPI-Corn-FTB  CTTATGCTGCTGTAAATACACTTGTGACAATAGGGAGCGAAAGAGCATTGTCATCAATCAATAGGGGCAA
DuP-Corn-FTB  CTTATGCTGCTGTAAATACACTTGTGACAATAGGGAGCCAAAGAGCATTGTCATCAATCAATAGGGGCAA
Pea FT-B      CTTATGCTGCAGTCAATACTCTTATTACTCTGGGTGGTGAGAAATCTTTGGCATCTATTAATAGAAATAA
Tomato        CTTATGCTGCAGTCAATTCACTAATAACTTTGGGCAAACCTGAAGCTCTGTCATCAATTAATAGAGAAAA
Tobacco       CTTATGCTGCAGTCAATTCACTCATAACTTTGGGCAGCCCTAAAGCTCTGTCATCAATCAATAGAGAAAA

                       570       580       590       600       610       620       630
              ....|....|....|....|....|....|....|....|....|....|....|....|....|....|
PPI-BnFTb     AATGGCTTGTTTCTTAAGACGAATGAAGGATACAAATGGAGGTTTCAGGATGCATAATATGGGAGAAATA
era1          AATGTCTTGTTTTTTAAGACGGATGAAGGATACAAGTGGAGGTTTCAGGATGCATGATATGGGAGAAATT
Wiggum        AATGTCTTGTTTTTTAAGACGGATGAAGGATACAAGTGGAGGTTTCAGGATGCATGATATGGGAGAAATG
PPI-Soy-FTB   ACTGTATGGGTTTCTGCGGCGGATGAAGCAACCAAATGGTGGATTCAGGATGCATGATGAAGGTGAAATT
DuP-Soy-FTB   ACTGTATGGGTTTCTGCGGCGGATGAAGCAACCAAATGGTGGATTCAGGATGCATGATGAAGGTGAAATT
PPI-Corn-FTB  CCTGTACAATTTTATGCTGCAGATGAAAGATGTATCAGGTGCTTTCAGAATGCATGATGGTGGCGAAATT
DuP-Corn-FTB  CCTGTACAATTTTATGCTGCAGATGAAAGATGTATCAGGTGCTTTCAGAATGCATGATGGTGGCGAAATT
Pea FT-B      GTTGTACGGGTTTATGCGGCGGATGAAACAGCCAAACGGCGGATTCAGGATGCATGACGAGGGAGAAATT
Tomato        GTTGTACACATTTTTGCTGCGAATGAAAGACGCAAGTGGTGGATTCAGGATGCACGATGGTGGAGAAGTA
Tobacco       ATTGTATACATTTTGGCTGCAAATGAAAGACACAAGTGGTGGCTTCAGGATGCATGATGGTGGAGAAGTA

                       640       650       660       670       680       690       700
              ....|....|....|....|....|....|....|....|....|....|....|....|....|....|
PPI-BnFTb     GATGTGCGAGCGTGCTACACTGCGATTTTGATTGCAAGCATCCTGAACATTGTGGATGATGAACTCACCC
era1          GATGTTCGTGCATGCTACACTGCAATTTCGGTTGCAAGCATCCTAAATATTATGGATGATGAACTCACCC
Wiggum        GATGTTCGTGCATGCTACACTGCAATTTCGGTTGCAAGCATCCTAAATATTATGGATGATGAACTCACCC
PPI-Soy-FTB   GATGTTCGAGCTTGCTACACTGCCATTTCTGTTGCAAGTGTTTTGAACATTTTGGATGATGAGCTGATCC
DuP-Soy-FTB   GATGTTCGAGCTTGCTACACTGCCATTTCTGTTGCAAGTGTTTTGAACATTTTGGATGATGAGCTGATCC
PPI-Corn-FTB  GATGTCCGTGCTTCCTACACCGCTATATCGGTTGCCAGCCTTGTGAATATTCTTGATTTTAAACTGGCAA
DuP-Corn-FTB  GATGTCCGTGCTTCCTACACCGCTATATCGGTTGCCAGCCTTGTGAATATTCTTGATTTTAAACTGGCAA
Pea FT-B      GACGTTCGAGCTTGCTACACTGCCATCTCTGTGGCAAGTGTTCTGAACATTTTGGATGATGAGCTGATCA
Tomato        GATGTTCGTGCCTGTTATACTGCCATTTCTGTTGCAAATATATTAAACATTGTGGATGACGAGCTGATTC
Tobacco       GATGTTCGTGCCTGTTATACTGCCATTTCTGTTGCAAGTATATTGCAAATTGTGGATGATGAACTGATTA

                       710       720       730       740       750       760       770
              ....|....|....|....|....|....|....|....|....|....|....|....|....|....|
PPI-BnFTb     GCGGCTTAGGAGATTACATTTTGAGTTGCCAAACTTATGAAGGTGGCATTGGAGGGGAACCTGGCTCCGA
era1          AGGGCCTAGGAGATTACATCTTGAGTTGCCAAACTTATGAAGGTGGCATTGGAGGGGAACCTGGCTCCGA
Wiggum        AGGGCCTAGGAGATTACATCTTGAGTTGCCAAACTTATGAAGGTGGCATTGGAGGGGAACCTGGCTCCGA
PPI-Soy-FTB   AGAATGTTGGAGACTACATTATAAGCTGTCAAACATATGAGGGTGGCATTGCTGGTGAGCCTGGTTCTGA
DuP-Soy-FTB   AGAATGTTGGAGACTACATTATAAGCTGTCAAACATATGAGGGTGGCATTGCTGGTGAGCCTGGTTCTGA
PPI-Corn-FTB  AAGGTGTAGGCGACTACATAGCAAGATGTCAAACTTATGAAGGTGGTATTGCTGGGGAGCCTTATGCTGA
DuP-Corn-FTB  AAGGTGTAGGCGACTACATAGCAAGATGTCAAACTTATGAAGGTGGTATTGCTGGGGAGCCTTATGCTGA
Pea FT-B      AGAATGTTGGAGACTTCATTTTAAGCTGTCAAACATATGAGGGAGGCCTTGCTGGTGAGCCTGGGTCTGA
Tomato        ATGGTGTTGGAAATTACATCCTAAGTTGTCAGACTTATGAAGGTGGAATTGCTGGCGAACCAGGTTCTGA
Tobacco       ATGATGTTGGGAATTACATCCTAAGTTGTCAGACTTATGAAGGTGGAATTGCTGGCGAACCAGGTTCTGA

                       780       790       800       810       820       830       840
              ....|....|....|....|....|....|....|....|....|....|....|....|....|....|
PPI-BnFTb     AGCTCATGGTGGGTACACGTACTGTGGGTTGGCTACTATGATTTTAATCAATGAAGTCGACCGCTTGAAT
era1          AGCTCACGGTGGGTATACCTACTGTGGTTTGGCTGCTATGATTTTAATCAATGAGGTCGACCGTTTGAAT
Wiggum        AGCTCACGGTGGGTATACCTACTGTGGTTTGGCTGCTATGATTTTAATCAATGAGGTCGACCGTTTGAAT
PPI-Soy-FTB   GGCTCATGGTGGGTACACCTTTTGTGGATTAGCTACAATGATTCTGATTGGTGAGGTTAATCACTTGGAT
DuP-Soy-FTB   GGCTCATGGTGGGTACACCTTTTGTGGATTAGCTACAATGATTCTGATTGGTGAGGTTAATCACTTGGAT
PPI-Corn-FTB  AGCACATGGTGGGTATACATTCTGTGGATTGGCTGCTTTGATCCTGCTTAATGAGGCAGAGAAAGTTGAC
DuP-Corn-FTB  AGCACATGGTGGGTATACATTCTGTGGATTGGCTGCTTTGATCCTGCTTAATGAGGCAGAGAAAGTTGAC
Pea FT-B      GGCTCATGGCGGGTATACCTTTTGTGGGTTAGCTGCAATGATTCTGATTGGTGAGGTTAATCGCTTGGAT
Tomato        AGCTCATGGTGGGTATACTTTCTGTGGGTTGGCTGCAATGATTCTGATCAACGAAGTAGATCGATTGGAC
Tobacco       AGCTCATGGTGGGTATACCTTCTGTGGGTTGGCTGCAATGATTCTGATTAACGAAGCGAATCGATTGGAC

                       850       860       870       880       890       900       910
              ....|....|....|....|....|....|....|....|....|....|....|....|....|....|
PPI-BnFTb     TTGGATTCGTTAATGAATTGGGTTGTACATCGACAAGGAGTAGAAATGGGATTCCAAGGTAGGACGAACA
era1          TTGGATTCATTAATGAATTGGGCTGTACATCGACAAGGAGTAGAAATGGGATTCCAAGGTAGGACGAACA
Wiggum        TTGGATTCATTAATGAATTGGGCTGTACATCGACAAGGAGTAGAAATGGGATTTCAAGGTAGGACGAACA
PPI-Soy-FTB   CTGCCTCGATTAGTTGACTGGGTGGTATTCCGACAAGGTAAGGAATGTGGATTCCAGGGGAGAACAAATA
```

```
DuP-Soy-FTB   CTGCCTCGATTAGTTGACTGGGTGGTATTCCGACAAGGTAAGGAATGTGGATTCCAGGGGAGAACAAATA
PPI-Corn-FTB  TTGCCTAGTTTGATTGGCTGGGTGGCTTTTCGTCAAGGAGTGGAATGCGGATTTCAAGGACGAACTAATA
DuP-Corn-FTB  TTGCCTAGTTTGATTGGCTGGGTGGCTTTTCGTCAAGGAGTGGAATGCGGATTTCAAGGACGAACTAATA
Pea FT-B      CTGCCTCGTTTACTTGATTGGGTTGTGTTTCGGCAAGGTAAAGAGTGTGGATTTCAGGGGAGAACGAATA
Tomato        TTGCCAGGTTTAATTGATTGGGTGGTATTTAGACAAGGGGTCGAAGGTGGATTTCAAGGCAGGACAAATA
Tobacco       TTGCCAAGATTAATTGATTGGGTGGTATTTAGACAAGGAGTCGAAGGTGGATTTCAAGGCAGGACAAATA

                  920       930       940       950       960       970       980
              ....|....|....|....|....|....|....|....|....|....|....|....|....|
PPI-BnFTb     AATTGGTCGACGGTTGCTACACGTTTTGGCAGGCAGCCCCCTGTGTTCTACTACAGCGATTTTTTTCATC
eral          AATTGGTCGATGGTTGCTACACATTTTGGCAGGCAGCCCCTTGTGTTCTACTACAAAGATTATATTCAAC
Wiggum        AATTGGTCGATGGTTGCTACACATTTTGGCAGGCAGCCCCTTGTGTTCTACTACAAAGATTATATTCAAC
PPI-Soy-FTB   AACTGGTGGATGGATGCTATTCCTTTTGGCAGGGAGGTGCTGTTGCTCTATTGCAAAGATTATCTTCTAT
DuP-Soy-FTB   AACTGGTGGATGGATGCTATTCCTTTTGGCAGGGAGGTGCTGTTGCTCTATTGCAAAGATTATCTTCTAT
PPI-Corn-FTB  AATTGGTTGATGGTTGCTACTCCTTTTGGCAGGGAGCTGCCATTGCTTTCACACAAAGTTAATTACGAT
DuP-Corn-FTB  AATTGGTTGATGGTTGCTACTCCTTTTGGCAGGGAGCTGCCATTGCTTTCACACAAAGTTAATTACGAT
Pea FT-B      AATTGGTAGATGGATGCTACTCGTTTTGGCAGGGAGGTGCTGTTGCCCTATTGCAAAGATTACATTCTAT
Tomato        AATTAGTCGATGGCTGCTATTCCTTTTGGCAGGGCGCGGTAGTGTTTCTTATACAAAGACTAAATTTGAT
Tobacco       AATTAGTCGATGGCTGCTATTCCTTTTGGCAGGCCGCGGTAGCTTTTCTTATACAAAGATTAAAATCGAC

                  990       1000      1010      1020      1030      1040      1050
              ....|....|....|....|....|....|....|....|....|....|....|....|....|
PPI-BnFTb     CCAGGAT-ATGGCACC------TCATGGATCATCATCA------------CATATGTCACAAGGACAGAT
eral          CAATGATCATGACGT-------TCATGGATCATCA---------------CATATATCAGAAGGACAAAT
Wiggum        CAATGATCATGACGT-------TCATGGATCATCA---------------CATATATCAGAAGGACAAAT
PPI-Soy-FTB   TATCAACAAACAGATG------GAAGAGA-CATCA---------------CAGATTTTTGCGGTATCTTAT
DuP-Soy-FTB   TATCAACAAACAGATG------GAAGAGA-CATCA---------------CAGATTTTTGCGGTATCTTAT
PPI-Corn-FTB  TGTTGATAAGCAATTGAGGTCCTCGTA-----T---------------------TCCTGCAAAA----GG
DuP-Corn-FTB  TGTTGATAAGCAATTGAAGTCCTCGTA-----T---------------------TCCTGCAAAA----GG
Pea FT-B      TATCGACGAACAAATG------GCAGAGG-CATCA---------------CAGTTTGTTACAGTATCTGAT
Tomato        AGTCCATGAACAACTAGGGCTGTCAAATGACCTCAGTACAGAAAGTGCTGATGATTCTTCAGAGTCAGAG
Tobacco       AGTCCATGAACAACTAGGGCTGTCAAATGAACTCAGTACAGAAAGTGCTGATGATTCTTCGGAGTCAGAG

                  1060      1070      1080      1090      1100      1110      1120
              ....|....|....|....|....|....|....|....|....|....|....|....|....|
PPI-BnFTb     GAAGATCACGAGGA-ACATGGTCATGATGAAGATGATCCTGAAGACAGTGATGAAGATGA---TTCTGAT
eral          GAAGAACAT-------CATGCTCATGATGAAGATGACCTTGAAGACAGTGATGATGATGATGATTCTGAT
Wiggum        GAAGAACAT-------CATGCTCATGATGAAGATGACCTTGAAGACAGTGATGATGATGATGATTCTGAT
PPI-Soy-FTB   GTATCTGAAG------CAAAAGAAAGTTTGGATGGAACCTCTAGTCA-TGCAACATGCCGTGGTGAGCAT
DuP-Soy-FTB   GTATCTGAAG------CAAAAGAAAGTTTGGATGGAACCTCTAGTCA-TGCAACATGCCGTGGTGAGCAT
PPI-Corn-FTB  CCATCAGGAGAG----GATGCCTGCAG----CACCAGTTCATAT----GGGTGCACC--------G-CGA
DuP-Corn-FTB  CCATCAGGAGAG----GATGCCTGCAG----CACCAGTTCATAT----GGGTGCACC--------G-CGA
Pea FT-B      GCACCTGAAG------AAAAGGAATGTTTGGACGGAACCTCAAGTCA-TGCAACTTCCCATATTAGGCAT
Tomato        TTATCTGATGAAGAAGAGCATTTGGAAGGGATATCCTCTCATGTTCA-GGATACTTTCCCTCTTGGACAA
Tobacco       TTATCTGATGAA---GAGCATTTGCAAGGGACATCATCTCATGTTCA-GAAGACTTGCCCTCTTGGACAA

                  1130      1140      1150      1160      1170      1180      1190
              ....|....|....|....|....|....|....|....|....|....|....|....|....|
PPI-BnFTb     GAGGAT---------AGCGATGAA---GATTCAGGGAATGGTCACCAAGTTCATCATACGTCTAC-CTAC
eral          GAGGAC---------AACGATGAA---GATTCAGTGAATGGTCACAGAATCCATCATACATCCAC-CTAC
Wiggum        GAGGAC---------AACGATGAA---GATTCAGTGAATGGTCACAGAATCCATCATACATCCAC-CTAC
PPI-Soy-FTB   GAAGGC---------ACCAGTGAATCCAGTTCATCTGATTTTAAAAATATTGCCTATAAATTTAT-TAAT
DuP-Soy-FTB   GAAGGC---------ACCAGTGAATCCAGTTCATCTGATTTTAAAAATATTGCCTATAAATTTAT-TAAT
PPI-Corn-FTB  ATAAGT----------------CTTCCTCTGCTGTGGACTATGCGAAGTTTGGATTTGATTTTATACAAC
DuP-Corn-FTB  AAAAGT----------------CTTCCTCTGCTGTGGACTATGCGAAGTTTGGATTTGATTTTATACAAC
Pea FT-B      GAAGGC---------ATGAATGAATCCTGCTCATCTGACGTTAAAAATATTGGTTATAACTTTAT-TAGT
Tomato        GCAGGTGCTTGTCAAGAAAATGCTTCTCATAGCCCAAAAATAGCAGATACTGGATATGAGTTTAT-CAAC
Tobacco       GAAGGA------CAGGAAAATGCTTCAGATCCCACAAAGATAGCAGATACTGGTTATGATTTTGT-CAAT

                  1200      1210      1220      1230      1240      1250      1260
              ....|....|....|....|....|....|....|....|....|....|....|....|....|
PPI-BnFTb     ATTGACAGGAGAATTCAACCTGTTTTTGATAGCCTCGGCTTGCAAAGATATGTGCTCTTGTGCTCTCAGG
eral          ATTAACAGGAGAATGCAACTGGTTTTTGATAGCCTCGGCTTGCAGAGATATGTACTCTTGTGCTCTAAGA
Wiggum        ATTAACAGGAGAATGCAACTGGTTTTTGATAGCCTCGGCTTGCAGAGATATGTACTCTTGTGCTCTAAGA
PPI-Soy-FTB   GAGTGGAGAGCACAAGAACCACTTTTTCACAGTATTGCTTTACAGCAATATATTCTCTTATGTGCACAGG
DuP-Soy-FTB   GAGTGGAGAGCACAAGAACCACTTTTTCACAGTATTGCTTTACAGCAATATATTCTCTTATGTGCACAGG
PPI-Corn-FTB  AGAGCAACCAA-ATTGGCCCACTCTTCCATAACATTGCCCTGCAACAATACATCCTACTTTGTTCTCAGG
DuP-Corn-FTB  AGAGCAACCAA-ATTGGCCCACTCTTCCATAACATTGCCCTGCAACAATACATCCTACTTTGTTCTCAGG
Pea FT-B      GAGTGGAGACAAAGTGAACCACTTTTTCACAGCATTGCCTTACAGCAATATATTCTTTTATGTTCACAGG
Tomato        CGACCCATAGCTATGAGGCCTCTCTTTGACAGCATGTATCTGCAGCAATATGTTCTTCTTTGCTCTCAGA
Tobacco       CGNACGATAGCTATGCGACCTGTGTTTGACAGCTTTTATCTGCAGCAATACGTTCTTCTCTGCTCCCAGA
```

```
                     1270      1280      1290      1300      1310      1320      1330
                 ....|....|....|....|....|....|....|....|....|....|....|....|....|....|
PPI-BnFTb        TTGCTGATGGTGGATTCAGAGACAAGCTGAGGAAACCCCGTGACTTCTACCACACATGTTACTGCCTAAG
eral             TCCCTGACGGTGGATTCAGAGACAAGCCGAGGAAACCCCGTGACTTCTACCACACATGTTACTGCCTGAG
Wiggum           TCCCTGACGGTGGATTCAGAGACAAGCCGAGGAAACCCCGTGACTTCTACCACACATGTTACTGCCTGAG
PPI-Soy-FTB      AGCAAGAGGGTGGACTGAGAGACAAACCGGGTAAACGTAGAGATCATTATCACACATGTTACTGTTTAAG
DuP-Soy-FTB      AGCAAGAGGGTGGACTGAGAGACAAACCGGGTAAACGTAGAGATCATTATCACACATGTTACTGTTTAAG
PPI-Corn-FTB     TACTAGAGGGAGGCTTGAGGGATAAGCCTGGAAAGAACAGAGATCACTATCATTCATGCTACTGCCTCAG
DuP-Corn-FTB     TACTAGAGGGAGGCTTGAGGGATAAGCCTGGAAAGAACAGAGATCACTACCATTCATGCTACTGCCTCAG
Pea FT-B         AGCAAGATGGTGGGCTCAGGGACAAACCGGGTAAAGGCAGGGATCATTATCATTCATGTTACTGTTTAAG
Tomato           TTGAAGTTGGTGGTTTCAGAGACAAACCTGGGAAGGGTAGAGACTACTACCATACCTGTTACTGTTTAAG
Tobacco          T---AGATGGAGGTTTCAGAGACAAACCTGGGAAGGGTAGAGACCACTACCATACTTGCTACTGTTTAAG

                     1340      1350      1360      1370      1380      1390      1400
                 ....|....|....|....|....|....|....|....|....|....|....|....|....|
PPI-BnFTb        CGGTCTTTCCGTGGCTCAACACGCTTGGTCAAAAGACGAGGACACTCCTCCTTTGACTCGTGACATTTTG
eral             CGGCTTGTCTGTGGCTCAGCACGCTTGGTTAAAAGACGAGGACACTCCTCCTTTGACTCGCGACATTATG
Wiggum           CGGCTTGTCTGTGGCTCAGCACGCTTGGTTAAAAGACGAGGACACTCCTCCTTTGACTCGCGACATTATG
PPI-Soy-FTB      TGGACTCTCATTGTGCCAGTATAGTTGGTCAAAGCACCCAGATTCTCCACCAC-----------------
DuP-Soy-FTB      TGGACTCTCATTGTGCCAGTATAGTTGGTCAAAGCACCCAGATTCTCCACCAC-----------------
PPI-Corn-FTB     TGGCCTCGCAGTTAGCCAGTACAGTGCCATGACTGATACTGGTTCGTGCCCATTACCTCAGCATGTGCTT
DuP-Corn-FTB     TGGCCTCGCAGTTAGCCAGTACAGTGCCATGACTGATACTGGTTCGTGCCCATTACCTCAGCATGTGCTT
Pea FT-B         TGGGTTGTCACTGTGCCAGTATAGTTGGTCGAAGCGCCCAGATTCTCCACCGCTGCCTAAGGTAGTAATG
Tomato           TGGTCTTTCAATTGCTCAGTATAGCTGGACCGACGAAGCTGATTCTACACCATTACCCAGGGATGTATTT
Tobacco          TGGTCTTTCAATTGCTCAATATAGCTGGACCAACGAAGCTGATGCGCCACCATTACCCAGGGATGTATTT

                     1410      1420      1430      1440      1450      1460      1470
                 ....|....|....|....|....|....|....|....|....|....|....|....|....|
PPI-BnFTb        GGTGGCTACGCA-AA--CCACCTTGAACCTGTTCACCTCCTCCACAACATTGTCTTGGATCGGTATTATG
eral             GGTGGCTACTCG-AA--TCTCCTTGAACCTGTTCAACTTCTTCACAACATTGTCATGGATCAGTATAATG
Wiggum           GGTGGCTACTCG-AA--TCTCCTTGAACCTGTTCAACTTCTTCACAACATTGTCATGGATCAGTATAATG
PPI-Soy-FTB      ----------------------------------------------------------------------
DuP-Soy-FTB      ----------------------------------------------------------------------
PPI-Corn-FTB     GGACCGTACTCT-AA--TTTGCTGGAGCCAATCCATCC--------------------------------
DuP-Corn-FTB     GGACCGTACTCT-AA--TTTGCTGGAGCCAATCCATCC--------------------------------
Pea FT-B         GGCCCATACTCC-AA--TCTCTTAGAACCCATCCATCCTCTCTTTAATGTTGTTTTGGATCGATATCGTG
Tomato           GGTCCTTATTCCAAATGTCTGTTGGAACAGGTTCACCCACTCTTCAACGTAGTGTTGGATCGGTATTATG
Tobacco          GGTCCTTATTCTCAAAATCTTTTGGAACAGATTCACCCACTTTACAACGTAGTGTTGGATCGGTATTATG

                     1480      1490      1500      1510      1520      1530      1540
                 ....|....|....|....|....|....|....|....|....|....|....|....|....|
PPI-BnFTb        AAGCTTCTAGATTT--------------------------------------------------------
eral             AAGCTATCGAGTTCTTCTTTAAAGCAGCATGACCCGTTGTTGCTAATGTATGGGAAACCCCAAACATAAG
Wiggum           AAGCTATCGAGTTCTTCTTTAAAGCAGCATGACCCGTTGTTGCTAATGTATGGGAAACTCCAAACATAAG
PPI-Soy-FTB      ----------------------------------------------------------------------
DuP-Soy-FTB      ----------------------------------------------------------------------
PPI-Corn-FTB     ----------------------------------------------------------------------
DuP-Corn-FTB     ----------------------------------------------------------------------
Pea FT-B         AAGCTCATGAATTCTTTTCTCAGTTGTGACGGATGACAAGGTTTTAGCTACCAATAGCTC-GATCATTAG
Tomato           AAGCTCGCGAATACT-CTCAGGCTTGTGAGACTGTTTCAC-CACTTTCATTAGCACCAAC--TTTTTCAG
Tobacco          AAGCTCGTAGCTTCTTCTCATGCTTGTGATAATATTTTACGCGATAGCTGTAGCTGGAAT--GTTACC--

                     1550      1560      1570      1580      1590      1600      1610
                 ....|....|....|....|....|....|....|....|....|....|....|....|....|
PPI-BnFTb        ----------------------------------------------------------------------
eral             AGTTTCCGTAGTGTTGTAACTTGTAAGATTTCAAAAG---------------------------------
Wiggum           AGTTTTCGTAGTGTTGTAACTTGTAAGATTTCAAAAGAAGTTTCACTAATTTAACCTTAAAACCTGTTAC
PPI-Soy-FTB      ----------------------------------------------------------------------
DuP-Soy-FTB      ----------------------------------------------------------------------
PPI-Corn-FTB     ----------------------------------------------------------------------
DuP-Corn-FTB     ----------------------------------------------------------------------
Pea FT-B         AATGTAAAATGTAAACTAAAATATGAAATATGAAATACCAAAAAGATATTATTGGATGAAATTCACGTGG
Tomato           AAACTTAGTTGCAATCCAGAAGTTAAAAGTGTCATTGGGTTCAAAAGAGTTGTGATCGTTTATGTACATA
Tobacco          ---TCTAGTTG---TTCAGAATCAGAGACTAATCTATTATTTGAGGGATTGGATTCAAAAAAAAAAAAA

                     1620      1630      1640      1650      1660      1670      1680
                 ....|....|....|....|....|....|....|....|....|....|....|....|....|
PPI-BnFTb        ----------------------------------------------------------------------
eral             ----------------------------------------------------------------------
Wiggum           TTTTTATTACGTATATACCATTTATCATATCTTTGGTTTACGACTTAAAGAATTTGATGATTGTTGAAA
```

```
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        ATCTAATACAACTGCGTGGTTTTCATTCCTGATTTGATTTTGATTTACATGAGTTAAAACGTTAAACCCT
Tomato          TCCTTGCATTTGTATACGTGATACAAGTTGAGAGAATAACGGGTACTTTCTGAACTTGCTGAACTAGCAC
Tobacco         AAAAAAA---------------------------------------------------------------

                      1690      1700      1710      1720      1730      1740      1750
                ....|....|....|....|....|....|....|....|....|....|....|....|....|....|
PPI-BnFTb       ----------------------------------------------------------------------
era1            ----------------------------------------------------------------------
Wiggum          ----------------------------------------------------------------------
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        TCTTATTCATACATTTGTTAAGAGCTTAAGGCTTAATGGTTAAGCCAATGATATAAATATTTATGCAGAA
Tomato          GTAAATTCGTCTCTGGTTTAGTGAGGTCTGTAAACATCAATGTGAAATTGCGAGATATGCATGTAATAGT
Tobacco         ----------------------------------------------------------------------

                      1760      1770      1780      1790      1800      1810      1820
                ....|....|....|....|....|....|....|....|....|....|....|....|....|....|
PPI-BnFTb       ----------------------------------------------------------------------
era1            ----------------------------------------------------------------------
Wiggum          ----------------------------------------------------------------------
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        AGCTGTTGCTTATCACCAACGGTAATATTAATAAGCAAACAAGTATTCTGTGAT----------------
Tomato          GGCTAAGATTTACAAATCTGGATACCGGTTATTAGTGATCAGAAATTTCATTCAATTTCCCAAACGGTCA
Tobacco         ----------------------------------------------------------------------

                      1830      1840      1850      1860      1870      1880      1890
                ....|....|....|....|....|....|....|....|....|....|....|....|....|....|
PPI-BnFTb       ----------------------------------------------------------------------
era1            ----------------------------------------------------------------------
Wiggum          ----------------------------------------------------------------------
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        ----------------------------------------------------------------------
Tomato          CCTAAGTTTAGGATATTGCTTTAAAATATTATTTATTTTTCATTTAAGAATCAAAAAAAAAAAAAAAAAA
Tobacco         ----------------------------------------------------------------------

                ....|....
PPI-BnFTb       ---------
era1            ---------
Wiggum          ---------
PPI-Soy-FTB     ---------
DuP-Soy-FTB     ---------
PPI-Corn-FTB    ---------
DuP-Corn-FTB    ---------
Pea FT-B        ---------
Tomato          AAAAAAAAA
Tobacco         ---------
```

Table 10D. ClustalW Amino Acid Analysis of FT Beta Subunits

1) PPI-BnFTB; FT3 (SEQ ID NO:15)
2) era1 (SEQ ID NO:2)
3) Wiggum (SEQ ID NO:87)
4) PPI-Soy-FTB; FT5 (SEQ ID NO:42)

5) DuP-Soy-FTB (SEQ ID NO:88)
6) PPI-Corn-FTB; FT6 (SEQ ID NO:45)
7) DuP-Corn-FTB (SEQ ID NO:89)
8) Pea-FT-B (SEQ ID NO:90)
9) Tomato (SEQ ID NO:91)
10) Tobacco (SEQ ID NO:92)

```
                       10        20        30        40        50        60        70
               ....|....|....|....|....|....|....|....|....|....|....|....|....|....|
PPI-BnFTB      ----------------------------------------------------------------------
era1           ----------------------------------------------------------------------
Wiggum         MPVVTRLIRLKCVGLRLDRSGLNRRICHGGHGESTRRRVMEELSSLTVSQREQFLVENDVFGIYNYFDAS
PPI-Soy-FTB    -------------------------------------------------------------------ATI
DuP-Soy-FTB    -------------------------------------------------------------------ATI
PPI-Corn-FTB   --------------------------------------ADPDLPRLTVTQVEQMKVEARVGDIYRSLFGA
DuP-Corn-FTB   --------------------------------------ADPDLPRLTVTQVEQMKVEARVGDIYRSLFGA
Pea FT-B       -------------------------------------------------------------------MEA
Tomato         ----------------------------------------MESRKVTKTLEDQWVVERRVREIYDYFYSI
Tobacco        ------------------------------------------GTSGTRTLEDQWMVERQVREIYNFFYSI

                       80        90       100       110       120       130       140
               ....|....|....|....|....|....|....|....|....|....|....|....|....|....|
PPI-BnFTB      --------------------------------------------WLCYWILHSIALLGESVDDDLENNAI
era1           --------MEIQRDKQLDYLMKGLRQLGPQFSSLDAN-----RPWLCYWILHSIALLGETVDDELESNAI
Wiggum         DVSTQKYMMEIQRDKQLDYLMKGLRQLGPQFSSLDAN-----RPWLCYWILHSIALLGETVDDELESNAI
PPI-Soy-FTB    PRNAQTLMLELQRDNHMQYVSKGLRHLSSAFSVLDAN-----RPWLCYWIFHSIALLGESVDDELEDNAI
DuP-Soy-FTB    PRNAQTLMLELQRDNHMQYVSKGLRHLSSAFSVLDAN-----RPWLCYWIFHSIALSGESVDDELEDNAI
PPI-Corn-FTB   APNTKSIMLELWRDQHIEYLTPGLRHMGPAFHVLDAN-----RPWLCYWMVHPLALLDEALDDDLENDII
DuP-Corn-FTB   APNTKGIMLELWRDQHIEYLTPGLRHMGPAFHVLDAN-----RPWLCYWMVHPLALLDEALDDDLENDII
Pea FT-B       STAAETPTPTVSQRDQWIVESQ-VFHIYQLFANIPPNAQSIIRPWLCYWIIHSIALLGESIDDDLEDNTV
Tomato         SPNSPSDLIEIERDKHFGYLSQGLRKLGPSFSVLDAS-----RPWLCYWTLHSIALLGESIGGKLENDAI
Tobacco        PPNS---HLETSTEKHFDYLTRGLRKLGPSFSVLDAN-----RPWLCYWILHSIALLGESIDAQLENDAI

                      150       160       170       180       190       200       210
               ....|....|....|....|....|....|....|....|....|....|....|....|....|....|
PPI-BnFTB      DFLGRCQGSDGGYGGGPGQLPHLATSYAAVNTLVTLGGEKAFSSINREQMACFLRRMKDTNGGFRMHNMG
era1           DFLGRCQGSEGGYGGGPGQLPHLATTYAAVNALVTLGGDKALSSINREKMSCFLRRMKDTSGGFRMHDMG
Wiggum         DFLGRCQGSEGGYGGGPGQLPHLATTYAAVNALVTLGGDKALSSINREKMSCFLRRMKDTSGGFRMHDMG
PPI-Soy-FTB    DFLNRCQDPNGGYAGGPGQMPHIATTYAAVNSLITLGGEKSLASINRDKLYGFLRRMKQPNGGFRMHDEG
DuP-Soy-FTB    DFLNRCQDPNGGYAGGPGQMPHIATTYAAVNSLITLGGEKSLASINRDKLYGFLRRMKQPNGGFRMHDFG
PPI-Corn-FTB   DFLARCQDKDGGYSGGPGQLPHLATTYAAVNTLVTIGSERALSSINRGNLYNFMLQMKDVSGAFRMHDGG
DuP-Corn-FTB   DFLARCQDKDGGYSGGPGQLPHLATTYAAVNTLVTIGSQRALSSINRGNLYNFMLQMKDVSGAFRMHDGG
Pea FT-B       DFLNRCQDPNGGYAGGPGQMPHLATTYAAVNTLITLGGEKSLASINRNKLYGFMRRMKQPNGGFRMHDEG
Tomato         DFLTRCQDKDGGYGGGPGQMPHLATTYAAVNSLITLGKPEALSSINREKLYTFLLRMKDASGGFRMHDGG
Tobacco        DFLSRCQDEDGGYGGGPGQMPHLATTYAAVNSLITLGSPKALSSINREKLYTFWLQMKDTSGGFRMHDGG

                      220       230       240       250       260       270       280
               ....|....|....|....|....|....|....|....|....|....|....|....|....|....|
PPI-BnFTB      EIDVRACYTAILIASILNIVDDELTRGLGDYILSCQTYEGGIGGEPGSEAHGGYTYCGLATMILINEVDR
era1           EIDVRACYTAISVASILNIMDDELTQGLGDYILSCQTYEGGIGGEPGSEAHGGYTYCGLAAMILINEVDR
Wiggum         EMDVRACYTAISVASILNIMDDELTQGLGDYILSCQTYEGGIGGEPGSEAHGGYTYCGLAAMILINEVDR
PPI-Soy-FTB    EIDVRACYTAISVASVLNILDDELIQNVGDYIISCQTYEGGIAGEPGSEAHGGYTFCGLATMILIGEVNH
DuP-Soy-FTB    EIDVRACYTAISVASVLNILDDELIQNVGDYIISCQTYEGGIAGEPGSEAHGGYTFCGLATMILIGEVNH
PPI-Corn-FTB   EIDVRASYTAISVASLVNILDFKLAKGVGDYIARCQTYEGGIAGEPYAEAHGGYTFCGLAALILLNEAEK
DuP-Corn-FTB   EIDVRASYTAISVASLVNILDFKLAKGVGDYIARCQTYEGGIAGEPYAEAHGGYTFCGLAALILLNEAEK
Pea FT-B       EIDVRACYTAISVASVLNILDDELIKNVGDFILSCQTYEGGLAGEPGSEAHGGYTFCGLAAMILIGEVNR
Tomato         EVDVRACYTAISVANILNIVDDELIHGVGNYILSCQTYEGGIAGEPGSEAHGGYTFCGLAAMILINEVDR
Tobacco        EVDVRACYTAISVASILQIVDDELINDVGNYILSCQTYEGGIAGEPGSEAHGGYTFCGLAAMILINEANR

                      290       300       310       320       330       340       350
               ....|....|....|....|....|....|....|....|....|....|....|....|....|....|
PPI-BnFTB      LNLDSLMNWVVHRQGVEMGFQGRTNKLVDGCYTFWQAAPCVLLQRFFSSQDMAPHGSSSHMSQGTDEDHE
era1           LNLDSLMNWAVHRQGVEMGFQGRTNKLVDGCYTFWQAAPCVLLQRLYSTNDHDVHG-SSHISEGTNEEH-
Wiggum         LNLDSLMNWAVHRQGVEMGFQGRTNKLVDGCYTFWQAAPCVLLQRLYSTNDHDVHG-SSHISEGTNEEH-
PPI-Soy-FTB    LDLPRLVDWVVFRQGKECGFQGRTNKLVDGCYSFWQGGAVALLQRLSSIINKQMEETSQIFAVSYVSEA-
DuP-Soy-FTB    LDLPRLVDWVVFRQGKECGFQGRTNKLVDGCYSFWQGGAVALLQRLSSIINKQMEETSQIFAVSYVSEA-
PPI-Corn-FTB   VDLPSLIGWVAFRQGVECGFQGRTNKLVDGCYSFWQGAAIAFTQKLITIVDKQLRSSYSCKRPSGEDACS
DuP-Corn-FTB   VDLPSLIGWVAFRQGVECGFQGRTNKLVDGCYSFWQGAAIAFTQKLITIVDKQLKSSYSCKRPSGEDACS
Pea FT-B       LDLPRLLDWVVFRQGKECGFQGRTNKLVDGCYSFWQGGAVALLQRLHSIIDEQMAEASQFVTVSDAPEE-
```

```
Tomato        LDLPGLIDWVVFRQGVEGGFQGRTNKLVDGCYSFWQGAVMFLIQRLNLEVHEQLGLSNDLSTESADDSSE
Tobacco       LDLPRLIDWVVFRQGVEGGFQGRTNKLVDGCYSFWQAAVAFLIQRLKSTVHEQLGLSNELSTESADDSSE

                        360       370       380       390       400       410       420
              ....|....|....|....|....|....|....|....|....|....|....|....|....|....|
PPI-BnFTB     EHGHDED-DPE--DSDEDD-S--DEDS--DEDSGNGHQVHHT-STYIDR--RIQPVFDSLGLQRYVLLCS
era1          -HAHDED-DLE--DSDDDDDS--DEDN--DEDSVNGHRIHHT-STYINR--RMQLVFDSLGLQRYVLLCS
Wiggum        -HAHDED-DLE--DSDDDDDS--DEDN--DEDSVNGHRIHHT-STYINR--RMQLVFDSLGLQRYVLLCS
PPI-Soy-FTB   -----KE-SLDGTSSHATCRG--EHEG---TSESSSSDFKNIAYKFINEWRAQEPLFHSIALQQYILLCA
DuP-Soy-FTB   -----KE-SLDGTSSHATCRG--EHEG---TSESSSSDFKNIAYKFINEWRAQEPLFHSIALQQYILLCA
PPI-Corn-FTB  ------------TSSYGCTAN----------KSSSAVDYAKFGFDFIQQSNQIGPLFHNIALQQYILLCS
DuP-Corn-FTB  ------------TSSYGCTAK----------KSSSAVDYAKFGFDFIQQSNQIGPLFHNIALQQYILLCS
Pea FT-B      -----KE-CLDGTSSHATSHI--RHEG---MNESCSSDVKNIGYNFISEWRQSEPLFHSIALQQYILLCS
Tomato        SELSDEEEHLEGISSHVQDTFPLGQAGACQENASHSPKLADTGYEFINRPIAMRPLFDSMYLQQYVLLCS
Tobacco       SELSDEE-HLQGTSSHVQKTCPLGQEG--QENASDPTKLADTGYDFVNRTIAMRPVFDSFYLQQYVLLCS

                        430       440       450       460       470       480       490
              ....|....|....|....|....|....|....|....|....|....|....|....|....|....|
PPI-BnFTB     QVADGGFRDKLRKPRDFYHTCYCLSGLSVAQHAWSKDEDTPPLTRDILGGYAN-HLEPVHLLHNILVDRY
era1          KIPDGGFRDKPRKPRDFYHTCYCLSGLSVAQHAWLKDEDTPPLTRDIMGGYSN-LLEPVQLLHNIVMDQY
Wiggum        KIPDGGFRDKPRKPRDFYHTCYCLSGLSVAQHAWLKDEDTPPLTRDIMGGYSN-LLEPVQLLHNIVMDQY
PPI-Soy-FTB   QEQEGGLRDKPGKRRDHYHTCYCLSGLSLCQYSWSKHPDSPP----------------------------
DuP-Soy-FTB   QEQEGGLRDKPGKRRDHYHTCYCLSGLSLCQYSWSKHPDSPP----------------------------
PPI-Corn-FTB  QVLEGGLRDKPGKNRDHYHSCYCLSGLAVSQYSAMTDTGSCPLPQHVLGPYSN-LLEPIH----------
DuP-Corn-FTB  QVLEGGLRDKPGKNRDHYHSCYCLSGLAVSQYSAMTDTGSCPLPQHVLGPYSN-LLEPIH----------
Pea FT-B      QEQDGGLRDKPGKRRDHYHSCYCLSGLSLCQYSWSKRPDSPPLPKVVMGPYSSNLLEPIHPLFNVVLDRY
Tomato        QIEVGGFRDKPGKGRDYYHTCYCLSGLSIAQYSWTDEADSTPLPRDVFGPYSKCLLEQVHPLFNVVLDRY
Tobacco       QID-GGFRDKPGKGRDHYHTCYCLSGLSIAQYSWINEADAPPLPRDVFGPYSQNLLEQIHPLYNVVLDRY

                        500       510
              ....|....|....|....|....|
PPI-BnFTB     YEASRF-------------------
era1          NEAIEFFFKAA--------------
Wiggum        NEAIEFFFKAA--------------
PPI-Soy-FTB   -------------------------
DuP-Soy-FTB   -------------------------
PPI-Corn-FTB  -------------------------
DuP-Corn-FTB  -------------------------
Pea FT-B      REAHEFFSQL---------------
Tomato        YEAREYSQACETVSPLSLAPTFSET
Tobacco       YEARSFFSCL---------------
```

Table 10E ClustalW Amino Acid Analysis of FT Alpha

```
                       10        20        30        40        50        60        70
               ....|....|....|....|....|....|....|....|....|....|....|....|....|....|
BnA-12         --------------------------------------------------MDYFRAIYFSDERSARALRL
At-FT-A        --------MNFDETVPLSQRLEWSDVVPLTQDDGPNPVVPIAYKEEFRETMDYFRAIYFSDERSPRALRL
PPI-Soy-FTA    MESGSSEGEEVQQRVPLRERVEWSDVTPVPQNDGPNPVVPIQYTEEFSEVMDYFRAVYLTDERSPRALAL
Consensus      --------      VPL  R EWSDV P  Q DGPNPVVPI Y EEF E MDYFRAIYFSDERSPRALRL
```

Also included in invention is the farnesyl transferase alpha consensus sequence of SEQ ID NO:93 and the farnesyl transferase beta consensus sequence of SEQ ID NO:94 To generate the consensus sequence, the farnesyl tranferase alpha and farnesyl transferase beta sequences of the invention where aligned using program BioEdit. The homology between the farnesyl tranferase alpha (FTA) polypeptide sequences of the invention is shown graphically in the ClustalW analysis shown in Table 10E. The homology between the farnesyl transferase beta (FTB) polypeptide sequences of the invention is shown graphically in the ClustalW analysis shown in Table 10F.

```
                        80        90       100       110       120       130       140
               ....|....|....|....|....|....|....|....|....|....|....|....|....|....|
BnA-12         TEEALRLNSGNYTVWHFGRLVLEELNNDLYEELKFIESIAEDNSKNYQL----WHHRRWVAEKLGPDVAG
At-FT-A        TEETLLLNSGNYTVWHFRRLVLEALNHDLFEELEFIERIAEDNSKNYQL----WHHRRWVAEKLGPDVAG
PPI-Soy-FTA    TAEAVQFNSGNYTVWHFRRLLLESLKVDLNDELEFVERMAAGNSKNYQMXMFCRHPRRWVAEKLGPEARN
Consensus      TEEAL LNSGNYTVWHFRRLVLE LN DL EELEFIERIAEDNSKNYQL----WHHRRWVAEKLGPDVAG

                       150       160       170       180       190       200       210
               ....|....|....|....|....|....|....|....|....|....|....|....|....|....|
BnA-12         LEKEFTRRVLSLDAKHYHAWSHRQWALQALGGWENELNYCHELLEADVFNNSAWNQRYYVITRSPSLGGL
At-FT-A        RELEFTRRVLSLDAKHYHAWSHRQWTLRALGGWEDELDYCHELLEADVFNNSAWNQRYYVITQSPLLGGL
PPI-Soy-FTA    NELEFTKKILSVDAKHYHAWSHRQWALQTLGGWEDELNYCTELLKEDIFNNSAWNQRYFVITRSPFLGGL
Consensus       ELEFTRRVLSLDAKHYHAWSHRQWALQALGGWEDELNYCHELLEADVFNNSAWNQRYYVITRSP LGGL

                       220       230       240       250       260       270       280
               ....|....|....|....|....|....|....|....|....|....|....|....|....|....|
BnA-12         EAMRESEVSYTVKAILANPGNESSWRYLKALYKDDTESWISDPSVSSVCLKVLSRADCFHGFALSTLLDL
At-FT-A        EAMRESEVSYTIKAILTNPANESSWRYLKALYKDDKESWISDPSVSSVCLNVLSRTDCFHGFALSTLLDL
PPI-Soy-FTA    KAMRESEVLYTIEAIIAYPENESSWRYLRGLYKGETTSWVNDPQVSSVCLKIL-RTKSNYVFALSTILDL
Consensus      EAMRESEVSYTIKAILANP NESSWRYLKALYKDDTESWISDPSVSSVCLKVLSRTDCFHGFALSTLLDL

                       290       300       310       320       330       340       350
               ....|....|....|....|....|....|....|....|....|....|....|....|....|....|
BnA-12         LCDGLRPTNEHRDSVKALAN--------------EEPETNLANLVCTILCRVDPIRANYWAWKL------
At-FT-A        LCDGLRPTNEHKDSVRALAN--------------EEPETNLANLVCTILGRVDPIRANYWAWRKSKITVA
PPI-Soy-FTA    ICFGYQPNEDIRDAIDALKTADMDKQDLDDDEKGEQQNLNIARNICSILKQVDPIRTNYWIWRKSRLP--
Consensus      LCDGLRPTNEHRDSV ALAN--------------EEPETNLANLVCTIL RVDPIRANYWAWRKS    --

               ..
BnA-12         -- (SEQ ID NO:13)
At-FT-A        AI (SEQ ID NO:8)
PPI-Soy-FTA    -- (SEQ ID NO:39)
Consensus      -- (SEQ ID NO:93)
```

Table 10F ClustalW Amino Acid Analysis of FT Beta

```
                        10        20        30        40        50        60        70
               ....|....|....|....|....|....|....|....|....|....|....|....|....|....|
PPI-BnFTB      ----------------------------------------------------------------------
PPI-Soy-FTB    --------ATIPR----------------------NAQTLMLELQRDNHMQYVSKGLRHLSSAFSVLDANR
PPI-Corn-FTB   ADPDLPRLTVTQVEQMKVEARVGDIYRSLFGAAPNTKSIMLELWRDQHIEYLTPGLRHMGPAFHVLDANR
Consensus      -------- T  ----------------------N    MLEL RD H  Y  GLRH   AF VLDANR

                        80        90       100       110       120       130       140
               ....|....|....|....|....|....|....|....|....|....|....|....|....|....|
PPI-BnFTB      -WLCYWILHSIALLGESVDDDLENNAIDFLGRCQGSDGGYGGGPGQLPHLATSYAAVNTLVTLGGEKAFS
PPI-Soy-FTB    PWLCYWIFHSIALLGESVDDELEDNAIDFLNRCQDPNGGYAGGPGQMPHIATTYAAVNSLITLGGEKSLA
PPI-Corn-FTB   PWLCYWMVHPLALLDEALDDDLENDIIDFLARCQDKDGGYSGGPGQLPHLATTYAAVNTLVTIGSERALS
Consensus      PWLCYWI HSIALLGESVDDDLENNAIDFL RCQD DGGY GGPGQLPHLATTYAAVNTLVTLGGEKALS

                       150       160       170       180       190       200       210
               ....|....|....|....|....|....|....|....|....|....|....|....|....|....|
PPI-BnFTB      SINREQMACFLRRMKDTNGGFRMHNMGEIDVRACYTAILIASILNIVDDELTRGLGDYILSCQTYEGGIG
PPI-Soy-FTB    SINRDKLYGFLRRMKQPNGGFRMHDEGEIDVRACYTAISVASVLNILDDELIQNVGDYIISCQTYEGGIA
PPI-Corn-FTB   SINRGNLYNFNLQMKDVSGAFRMHDGGEIDVRASYTAISVASLVNILDFKLAKGVGDYIARCQTYEGGIA
Consensus      SINR  LY FLRRMKD NGGFRMHD GEIDVRACYTAISVAS LNILDDEL  GVGDYI SCQTYEGGIA

                       220       230       240       250       260       270       280
               ....|....|....|....|....|....|....|....|....|....|....|....|....|....|
PPI-BnFTB      GEPGSEAHGGYTYCGLATMILINEVDRLNLDSLMNWVVHRQGVEMGFQGRTNKLVDGCYTFWQAAPCVLL
PPI-Soy-FTB    GEPGSEAHGGYTFCGLATMILIGEVNHLDLPRLVDWVVFRQGKECGFQGRTNKLVDGCYSFWQGGAVALL
PPI-Corn-FTB   GEPYAEAHGGYTFCGLAALILLNEAEKVDLPSLIGWVAFRQGVECGFQGRTNKLVDGCYSFWQGAAIAFT
Consensus      GEPGSEAHGGYTFCGLATMILINEV  LDLPSL  WVVFRQGVECGFQGRTNKLVDGCYSFWQGAA ALL

                       290       300       310       320       330       340       350
               ....|....|....|....|....|....|....|....|....|....|....|....|....|....|
PPI-BnFTB      QRFFSSQDMAPHGSSS--HMSQGTDEDHEEHGHDEDDPEDSDEDDSDEDSDEDSGNGHQVHHTSTYIDRR
PPI-Soy-FTB    QRLSSIINKQMEETSQIFAVSYVSEAKESLDGTSSHATCRGEHEGTSESSSSDFKN---LAYKFINEWRA
PPI-Corn-FTB   QKLITIVDKQLRSS-----YSCKRPSGEDACSTSSYG-CTANKS----SSAVDYAK---FGEDFIQQSNQ
```

```
Consensus       QRL SI DKQ  SS --  S      E   GTSS   C          ESS  D  N---    FI   R

                          360       370       380       390       400       410       420
                ....|....|....|....|....|....|....|....|....|....|....|....|....|....|
PPI-BnFTB       ICPVFDSLGLQRYVLLCSQVADGGFRDKLRKPRDFYHTCYCLSGLSVAQHAWSKDEDTPPLTRDILGGYA
PPI-Soy-FTB     QEPLFHSIALQQYILLCAQEQEGGLRDKPGKRRDHYHTCYCLSGLSLCQYSWSKHPDSPP----------
PPI-Corn-FTB    IGPLFHNIALQQYILLCSQVLEGGLRDKPGKNRDHYHSCYCLSGLAVSQYSAMTDTGSCPLPQHVLGPYS
Consensus       I PLFHSIALQQYILLCSQV EGGLRDKPGK RDHYHTCYCLSGLSV QYSWSKD DSPPL    LG Y

                          430       440
                ....|....|....|....|...
PPI-BnFTB       NHLEPVHLLHNILVDRYYEASRF (SEQ ID NO:15)
PPI-Soy-FTB     ----------------------- (SEQ ID NO:42)
PPI-Corn-FTB    NLLEPIH---------------- (SEQ ID NO:45)
Consensus       N LEP H---------------- (SEQ ID NO:94)
```

Table 10G ClustalW Nucleic Acid Analysis of FT Alpha

```
                       10        20        30        40        50        60
               ....|....|....|....|....|....|....|....|....|....|....|....|
BnA-12         ------------------------------------------------------------ 1
At-FT-A        -------------GAGTCGGGGAACATGAATTTCGACGAGACCGTGCCACTGAGCCAACG 47
PPI-Soy-FTA    ATGGAATCTGGGTCTAGCGAAGGAGAAGAGGTGCAGCAACGC-GTGCCGTTGAGGGAGAG 59
Consensus      -------------    CG  G A A GA  T C  C A  C-GTGCC  TGAG  A  G 23

                       70        80        90       100       110       120
               ....|....|....|....|....|....|....|....|....|....|....|....|
BnA-12         ------------------------------------------------------------ 1
At-FT-A        ATTGGAGTGGTCAGACGTGGTCCCATTGACTCAGGACGATGGTCCGAATCCAGTGGTGCC 107
PPI-Soy-FTA    AGTGGAGTGGTCAGATGTTACTCCGGTTCCTCAAAACGACGGCCCTAACCCTGTCGTTCC 119
Consensus      A TGGAGTGGTCAGA GT    CC  T  CTCA  ACGA GG CC AA CC GT GT CC 64

                      130       140       150       160       170       180
               ....|....|....|....|....|....|....|....|....|....|....|....|
BnA-12         -------------------------------ATGGATTACTTCCGTGCGATTTACTTCTC 29
At-FT-A        AATTGCCTACAAGGAAGAGTTCCGCGAGACTATGGATTACTTCCGTGCGATTTACTTTTC 167
PPI-Soy-FTA    GATCCAGTACACTGAAGAGTTTTCCGAAGTTATGGATTACTTTCGCGCCGTTTACCTCAC 179
Consensus       AT    TACA  GAAGAGTT   CGA   TATGGATTACTTCCGTGCGATTTACTTCTC 111

                      190       200       210       220       230       240
               ....|....|....|....|....|....|....|....|....|....|....|....|
BnA-12         CGACGAGCGTTCTGCTCGCGCGCTGCGACTCACGGAAGAAGCTCTCCGCTTAAACTCGGG 89
At-FT-A        CGACGAGCGATCTCCTCGCGCACTACGACTCACGGAAGAAACCCTCCTCTTAAACTCCGG 227
PPI-Soy-FTA    CGATGAACGCTCCCCTCGCGCCCTCGCTCTCACAGCCGAAGCCGTTCAATTCAACTCCGG 239
Consensus      CGACGAGCG TCTCCTCGCGC CT CGACTCACGGAAGAAGCCCTCC CTTAAACTCCGG 167

                      250       260       270       280       290       300
               ....|....|....|....|....|....|....|....|....|....|....|....|
BnA-12         CAACTACACCGTGTGGCACTTCGGGCGCTTAGTACTCGAGGAGCTTAATAACGACTTGTA 149
At-FT-A        CAACTACACAGTGTGGCATTTCAGGCGCCTAGTACTCGAGGCCCTTAATCACGACTTGTT 287
PPI-Soy-FTA    CAACTACACTGTGTGGCATTTCCGACGGTTGTTACTTGAGTCGCTAAAAGTCGACTTGAA 299
Consensus      CAACTACAC GTGTGGCATTTC GGCGCTTAGTACTCGAGGCGCTTAAT ACGACTTGTA 224
```

Also included in the invention is the farnesyl transferase alpha consensus sequence of SEQ ID NO:95 and the farnesyl transferase beta consensus sequence of SEQ ID NO:96. To generate the consensus sequence, the farnesyl transferase alpha and farnesyl transferase beta sequences of the invention were aligned using the program BioEdit. The homology between the farnesyl transferase alpha (FTA) nucleic acid sequences of the invention is shown graphically in the ClustalW analysis shown in Table 10G. The homology between the farnesyl transferase beta sequences of the invention were aligned using the program BioEdit. The homology between the farnesyl transferase alpha (FTA) nucleic acid sequences of the invention is shown graphically in the ClustalW anaylsisanalysis shown in Table 10G. The homology between the farnesyl transferase beta (FTB) nucleic acid sequences of the invention is shown graphically in the ClustalW analysis shown in Table 10H.

```
                     310       320       330       340       350       360
BnA-12       TGAAGAGCTCAAGTTCATCGAAAGCATTGCTGAGGATAACTCTAAGAACTACCAGTTGTG 209
At-FT-A      TGAAGAACTCGAGTTCATCGAACGCATTGCTGAGGATAACTCTAAGAACTACCAACTGTG 347
PPI-Soy-FTA  CGATGAACTGGAGTTTGTGGAGCGTATGGCCGCTGGAAATTCTAAAAATTATCAGATGTG 359
Consensus    TGAAGAACTCGAGTTCATCGAACGCATTGCTGAGGATAACTCTAAGAACTACCAG TGTG 283

                     370       380       390       400       410       420
BnA-12       G------------CATCATCGACGATGGGTCGCAGAGAAACTGGGTCCTGATGTTGCAGG 257
At-FT-A      G------------CATCATCGGCGATGGGTTGCAGAGAAACTGGGTCCTGATGTTGCAGG 395
PPI-Soy-FTA  NATGTTCTGTAGGCATCCTAGACGATGGGTTGCCGAGAAGTTAGGTCCTGAAGCTAGAAA 419
Consensus    G------------CATCATCGACGATGGGTTGCAGAGAAACTGGGTCCTGATGTTGCAGG 331

                     430       440       450       460       470       480
BnA-12       AAAGGAACTTGAGTTTACTCGGAGGGTACTATCACTTGATGCCAAGCATTATCATGCTTG 317
At-FT-A      GAGAGAACTTGAATTTACCCGTAGAGTACTTTCACTTGATGCCAAACATTATCATGCTTG 455
PPI-Soy-FTA  CAATGAGCTCGAGTTCACCAAAAAGATACTGTCCGTTGATGCCAAACATTATCATGCATG 479
Consensus     AA GAACTTGAGTTTACCCG AGGGTACT TCACTTGATGCCAAACATTATCATGCTTG 387

                     490       500       510       520       530       540
BnA-12       GTCACATAGGCAGTGGGCGCTACAAGCATTAGGAGGATGGGAAAATGAGCTTAACTACTG 377
At-FT-A      GTCACATAGGCAGTGGACACTACGGGCATTAGGAGGATGGGAAGATGAGCTCGATTACTG 515
PPI-Soy-FTA  GTCTCATAGACAGTGGGCTCTTCAAACACTAGGAGGATGGGAAGATGAACTTAATTATTG 539
Consensus    GTCACATAGGCAGTGGGC CTACAAGCATTAGGAGGATGGGAAGATGAGCTTAATTACTG 446

                     550       560       570       580       590       600
BnA-12       CCACGAGCTCCTTGAAGCTGACGTCTTTAACAACTCTGCATGGAATCAGAGGTATTACGT 437
At-FT-A      TCACGAGCTCCTTGAAGCTGACGTCTTTAACAATTCCGCCTGGAATCAGAGGTATTATGT 575
PPI-Soy-FTA  CACAGAACTACTTAAAGAAGACATTTTTAACAATTCTGCTTGGAATCAGAGATATTTTGT 599
Consensus    CCACGAGCTCCTTGAAGCTGACGTCTTTAACAATTCTGC TGGAATCAGAGGTATTATGT 505

                     610       620       630       640       650       660
BnA-12       TATAACTAGATCACCTTCGTTGGGAGGCCTAGAAGCCATGAGAGAATCTGAAGTAAGCTA 497
At-FT-A      CATCACCCAATCTCCTTTGTTGGGAGGCCTAGAAGCCATGAGAGAATCTGAAGTAAGCTA 635
PPI-Soy-FTA  CATAACAAGGTCTCCTTTCTTGGGGGGCCTAAAAGCTATGAGAGAGTCTGAAGTGCTTTA 659
Consensus    CATAAC AGATCTCCTTTGTTGGGAGGCCTAGAAGCCATGAGAGAATCTGAAGTAAGCTA 564

                     670       680       690       700       710       720
BnA-12       CACAGTCAAAGCCATTTTAGCAAATCCCGGGAACGAGAGCTCTTGGAGGTACCTGAAAGG 557
At-FT-A      CACAATCAAAGCCATTTTAACCAATCCTGCAAACGAGAGCTCATGGCGATACCTAAAAGC 695
PPI-Soy-FTA  CACCATCGAAGCCATTATAGCCTACCCTGAAAATGAAAGCTCGTGGAGATATCTACGAGG 719
Consensus    CACAATCAAAGCCATTTTAGCCAATCCTG AAACGAGAGCTC TGGAGATACCTAAAAGC 622

                     730       740       750       760       770       780
BnA-12       CCTTTACAAAGACGACACAGAGTCTTGGATTAGTGATCCAAGTGTTTCCTCAGTCTGTTT 617
At-FT-A      GCTTTACAAAGACGACAAAGAATCCTGGATTAGTGATCCAAGTGTTTCCTCAGTCTGTTT 755
PPI-Soy-FTA  ACTTTATAAAGGTGAAACTACTTCATGGGTAAATGATCCTCAAGTTTCTTCAGTATGCTT 779
Consensus     CTTTACAAAGACGACACAGA TC TGGATTAGTGATCCAAGTGTTTCCTCAGTCTGTTT 679

                     790       800       810       820       830       840
BnA-12       GAAAGTTCTCTCACGCGCGGACTGCTTCCATGGATTCGCTCTGAGCACCCTTTTGGATCT 677
At-FT-A      GAATGTTCTATCCCGCACAGATTGCTTCCATGGATTCGCTCTGAGCACCCTTTTGGATCT 815
PPI-Soy-FTA  AAAGATTTTGA---GAACTAAGAGCAACTACGTGTTTGCTCTTAGCACTATTTTAGATCT 836
Consensus    GAA GTTCT TC CGCAC GA TGCTTCCATGGATTCGCTCTGAGCACCCTTTTGGATCT 734

                     850       860       870       880       890       900
BnA-12       TCTGTGCGATGGGTTGAGACCAACCAACGAGCATAGAGACTCGGTGAAAGCTCTAGCTAA 737
At-FT-A      TCTATGTGATGGACTGAGACCAACCAACGAGCATAAAGACTCAGTGAGAGCTCTAGCTAA 875
PPI-Soy-FTA  TATATGCTTTGGTTATCAACCAAATGAAGACATTAGAGATGCCATTGACGCCTTAAAGAC 896
Consensus    TCTATGCGATGG TTGAGACCAACCAACGAGCATAGAGACTC GTGAAAGCTCTAGCTAA 792
```

```
                    910       920       930       940       950       960
                ....|....|....|....|....|....|....|....|....|....|....|....|
BnA-12          TGAAGAACCAGAGACTAACTTGGCCAATTTGGTGTGTACCATTCTGTGTCGTGTTGATCC 797
At-FT-A         TGAAGAACCAGAGACTAACTTGGCCAATTTGGTGTGTACTATTCTTGGTCGTGTAGATCC 935
PPI-Soy-FTA     CGCAGA--TATGGATAAACAAGATTTAGATGATGATGAGAAAGGGGAACAACAAAATTTA 954
Consensus       TGAAGAACCAGAGACTAACTTGGCCAATTTGGTGTGTAC ATTCTG GTCGTGTAGATCC 850

                    970       980       990      1000      1010      1020
                ....|....|....|....|....|....|....|....|....|....|....|....|
BnA-12          AATA-AGAGCTAACTATTGGGC--ATGG-------------------------------- 822
At-FT-A         TATA-AGAGCTAACTATTGGGC--ATGGAGGAAGAGCAAGATTACAGTGGCAGCAATTTG 992
PPI-Soy-FTA     AATATAGCACGAAATATTTGTTCTATCCTAAAACAAGTTGATCCAATTAGAACCAACTAT 1014
Consensus       AATA-AGAGCTAACTATTGGGC--ATGG    AA A     GAT   A T G A CAA T   889

                   1030      1040      1050      1060      1070      1080
                ....|....|....|....|....|....|....|....|....|....|....|....|
BnA-12          ------------------------------------------------------------ 822
At-FT-A         AATATGTGACGCCCCAAAATCACACTTGAAAAAGACTTGATTATTAGTTTTACGTAATT 1052
PPI-Soy-FTA     TGGATTTGGCGCAAGAGCAGACTTCCT--------------------------------- 1041
Consensus          AT TG CGC   A  A      C T--------------------------------- 900

                   1090      1100      1110      1120      1130      1140
                ....|....|....|....|....|....|....|....|....|....|....|....|
BnA-12          ------------------------------------------------------------ 822
At-FT-A         AACTGCTTATTTATGAATCACATGTTCATGTTAACATGTATCAAAACAATCTTGATTTCT 1112
PPI-Soy-FTA     ------------------------------------------------------------ 1041
Consensus       ------------------------------------------------------------ 900

                   1150      1160      1170
                ....|....|....|....|....|....|.
BnA-12          ------------------------------- 822  (SEQ ID NO:12)
At-FT-A         CAAAAAAAAAAAAAAAAAAAAAAAAAAAAAA 1143 (SEQ ID NO:7)
PPI-Soy-FTA     ------------------------------- 1041 (SEQ ID NO:37)
Consensus       ------------------------------- 900  (SEQ ID NO:95)
```

Table 10H ClustalW Nucleic Acid Analysis of FT Beta

```
                     10        20        30        40        50        60
                ....|....|....|....|....|....|....|....|....|....|....|....|
PPI-BnFTb       ------------------------------------------------------------ 1
eral            ------------------------------------------------------------ 1
PPI-Soy-FTB     ------------------------------------------------------------ 1
PPI-Corn-FTB    GGCGGATCCCGACCTACCGAGGCTCACGGTGACGCAGGTGGAGCAGATGAAGGTGGAGGC 60
Consensus       ------------------------------------------------------------ 1

                     70        80        90       100       110       120
                ....|....|....|....|....|....|....|....|....|....|....|....|
PPI-BnFTb       ------------------------------------------------------------ 1
eral            ------------------------------------------------------------ 1
PPI-Soy-FTB     ----------------------------GCCACCATTCCTCGCAACGCCCAAACCCTCAT 32
PPI-Corn-FTB    CAGGGTTGGCGACATCTACCGCTCCCTCTTCGGGGCCGCGCCCAACACGAAATCCATCAT 120
Consensus       ----------------------------                                 1

                    130       140       150       160       170       180
                ....|....|....|....|....|....|....|....|....|....|....|....|
PPI-BnFTb       ------------------------------------------------------------ 1
eral            -ATGGAGATTCAGCGAGATAAGCAATTGGATTATCTGATGAAAGGCTTAAGGCAGCTTGG 59
PPI-Soy-FTB     GTTGGAGCTTCAACGCGATAATCACATGCAGTATGTCTCCAAAGGCCTTCGCCATCTCAG 92
PPI-Corn-FTB    GCTAGAGCTGTGGCGTGATCAGCATATCGAGTATCTGACGCCTGGGCTGAGGCATATGGG 180
Consensus         T GAG T     CG GAT A CA  T  A TAT T        GG  T  G CA  T  G 27

                    190       200       210       220       230       240
                ....|....|....|....|....|....|....|....|....|....|....|....|
PPI-BnFTb       ----------------------------------TGGCTTTGTTACTGGATTCTTCATTC 26
eral            TCCGCAGTTTTCTTCCTTAGATGCTAATCGACCTTGGCTTTGTTACTGGATTCTTCATTC 119
PPI-Soy-FTB     TTCCGCATTTTCCGTTTTGGACGCTAATCGACCCTGGCTCTGCTACTGGATCTTCCACTC 152
PPI-Corn-FTB    ACCAGCCTTTCATGTTCTAGATGCCAATCGCCCTTGGCTATGCTACTGGATGGTTCATCC 240
Consensus         C    TTT         T GA GC AATCG CC TGGCT TG TACTGGAT  TTCATTC 65

                    250       260       270       280       290       300
                ....|....|....|....|....|....|....|....|....|....|....|....|
```

```
PPI-BnFTb     AATTGCTTTGCTTGGGGAGTCTGTGGATGATGACTTAGAAAACAATGCAATCGATTTTCT  86
eral          AATAGCTTTGCTTGGGGAGACTGTGGATGATGAATTAGAAAGCAATGCCATTGACTTCCT  179
PPI-Soy-FTB   CATTGCTTTGTTGGGAGAATCCGTCGATGATGAACTCGAAGATAACGCTATCGATTTTCT  212
PPI-Corn-FTB  ACTTGCTTTGCTGGATGAAGCACTTGATGATGATCTTGAGAATGATATCATAGACTTCTT  300
Consensus     AATTGCTTTGCT GG GA  C GT GATGATGA  T GAAAA AATGC AT GA TT CT  111

                        310       320       330       340       350       360
PPI-BnFTb     TGGACGTTGCCAGGGTTCTGATGGTGGATATGGTGGTGGTCCTGGCCAACTTCCACATCT  146
eral          TGGACGCTGCCAGGGCTCTGAAGGTGGATACGGTGGTGGTCCTGGCCAACTTCCACATCT  239
PPI-Soy-FTB   TAACCGTTGCCAGGATCCGAATGGTGGATATGCCGGGGGACCAGGCCAGATGCCTCATAT  272
PPI-Corn-FTB  AGCTCGATGTCAGGATAAAGATGGTGGATATAGTGGTGGACCTGGACAGTTGCCTCACCT  360
Consensus     TG  CG TGCCAGG T C GATGGTGGATATGGTGGTGG CCTGGCCA  T CC CATCT  160

                        370       380       390       400       410       420
PPI-BnFTb     TGCAACAAGTTATGCTGCAGTGAATACACTTGTTACTTTAGGAGGTGAGAAAGCCTTCTC  206
eral          TGCAACTACTTATGCTGCAGTGAATGCACTTGTTACTTTAGGAGGTGACAAAGCCCTTTC  299
PPI-Soy-FTB   TGCCACAACTTATGCTGCTGTTAATTCACTTATTACTTTGGGTGGTGAGAAATCCCTGGC  332
PPI-Corn-FTB  AGCTACGACTTATGCTGCTGTAAATACACTTGTGACAATAGGAGGCGAAAGAGCATTGTC  420
Consensus     TGC AC ACTTATGCTGC GT AAT CACTTGTTACTTTAGG GGTGA AAAGCC T TC  211

                        430       440       450       460       470       480
PPI-BnFTb     TTCAATTAACAGAGAACAAATGGCTTGTTTCTTAAGACGAATGAAGGATACAAATGGAGG  266
eral          TTCAATTAATAGAGAAAAAATGTCTTGTTTTTTAAGACGGATGAAGGATACAAGTGGAGG  359
PPI-Soy-FTB   ATCAATTAATAGAGATAAACTGTATGGGTTTCTGCGGCGGATGAAGCAACCAAATGGTGG  392
PPI-Corn-FTB  ATCAATCAATAGGGGCAACCTGTACAATTTTATGCTGCAGATGAAAGATGTATCAGGTGC  480
Consensus      TCAATTAATAGAGA AAA TGT T GTTTT T  G CGGATGAAGGAT CAA TGG GG  259

                        490       500       510       520       530       540
PPI-BnFTb     TTTCAGGATGCATAATATGGGAGAAATAGATGTGCGAGCGTGCTACACTGCGATTTTGAT  326
eral          TTTCAGGATGCATGATATGGGAGAAATTGATGTTCGTGCATGCTACACTGCAATTTCGGT  419
PPI-Soy-FTB   ATTCAGGATGCATGATGAAGGTGAAATTGATGTTCGAGCTTGCTACACTGCCATTTCTGT  452
PPI-Corn-FTB  TTTCAGAATGCATGATGGTGGCGAAATTGATGTCCGTGCTTCCTACACCGCTATATCGGT  540
Consensus     TTTCAGGATGCATGAT    GG GAAATTGATGT CG GC TGCTACACTGC ATTTCGGT  311

                        550       560       570       580       590       600
PPI-BnFTb     TGCAAGCATCCTGAACATTGTGGATGATGAACTCACCCGCGGCTTAGGAGATTACATTTT  386
eral          TGCAAGCATCCTAAATATTATGGATGATGAACTCACCCAGGGCCTAGGAGATTACATCTT  479
PPI-Soy-FTB   TGCAAGTGTTTTGAACATTTTGGATGATGAGCTGATCCAGAATGTTGGAGACTACATTAT  512
PPI-Corn-FTB  TGCCAGCCTTGTGAATATTCTTGATTTTAAACTGGCAAAAGGTGTAGGCGACTACATAGC  600
Consensus     TGCAAGC T  TGAA ATT TGGATGATGAACT ACCCA GG  TAGGAGA TACAT  T  359

                        610       620       630       640       650       660
PPI-BnFTb     GAGTTGCCAAACTTATGAAGGTGGCATTGGAGGGGAACCTGGCTCCGAAGCTCATGGTGG  446
eral          GAGTTGCCAAACTTATGAACGTGGCATTGGAGGGGAACCTGGCTCCGAAGCTCACGGTGG  539
PPI-Soy-FTB   AAGCTGTCAAACATATGAGGGTGGCATTGCTGGTGAGCCTGGTTCTGAGGCTCATGGTGG  572
PPI-Corn-FTB  AAGATGTCAAACTTATGAAGGTGGTATTGCTGGGGAGCCTTATGCTGAAGCACATGGTGG  660
Consensus      AG TG CAAACTTATGAAGGTGGCATTG  GGGGA CCTGG TC GAAGCTCATGGTGG  411

                        670       680       690       700       710       720
PPI-BnFTb     GTACACGTACTGTGGGTTGGCTACTATGATTTTAATCAATGAACTCGACCGCTTGAATTT  506
eral          GTATACCTACTGTGGTTTGGCTGCTATGATTTTAATCAATGAGGTCGACCGTTTGAATTT  599
PPI-Soy-FTB   GTACACCTTTTGTGGATTAGCTACAATGATTCTGATTGGTGAGGTTAATCACTTGGATCT  632
PPI-Corn-FTB  GTATACATTCTGTGGATTGGCTGCTTTGATCCTGCTTAATGAGGCAGAGAAAGTTGACTT  720
Consensus     GTA AC T CTGTGG TTGGCT CTATGATT T AT AATGAGGT GA C  TTG ATTT  458

                        730       740       750       760       770       780
PPI-BnFTb     GGATTCGTTAATGAATTGGGTTGTACATCGACAAGGAGTAGAAATGGGATTCCAAGGTAG  566
eral          GGATTCATTAATGAATTGGGCTGTACATCGACAAGGAGTAGAAATGGGATTTCAAGGTAG  659
PPI-Soy-FTB   GCCTCGATTAGTTGACTGGGTGGTATTCCGACAAGGTAAGGAATGTGGATTCCAGGGGAG  692
PPI-Corn-FTB  GCCTAGTTTGATTGGCTGGGTGGCTTTTCGTCAAGGAGTGGAATGCGGATTTCAAGGCACG 780
Consensus     G T  TTAAT A TGGGT GTA TCGACAAGGAGT GAA  GGATT CAAGG AG  501

                        790       800       810       820       830       840
```

```
              ....|....|....|....|....|....|....|....|....|....|....|....|
PPI-BnFTb     GACGAACAAATTGGTCGACGGTTGCTACACGTTTTGGCAGGCAGCCCCCTGTGTTCTACT 626
eral          GACGAACAAATTGGTCGATGGTTGCTACACATTTTGGCAGGCAGCCCCTTGTGTTCTACT 719
PPI-Soy-FTB   AACAAATAAACTGGTGGATGGATGCTATTCCTTTTGGCAGGGAGGTGCTGTTGCTCTATT 752
PPI-Corn-FTB  AACTAATAAATTGGTTGATGGTTGCTACTCCTTTTGGCAGGGAGCTGCCATTGCTTTCAC 840
Consensus      AC AA AAATTGGT GATGGTTGCTAC C TTTTGGCAGG AGC   C   TG TCTA T 547

                   850       860       870       880       890       900
              ....|....|....|....|....|....|....|....|....|....|....|....|
PPI-BnFTb     ACAGCGATTTTTTTCATCCCAGGAT-ATGGCACCTCATGGATCATCATCACATATGTCAC 685
eral          ACAAAGATTATATTCAACCAATGATCATGACGT-TCATGGATCATCA---CATATATCAG 775
PPI-Soy-FTB   GCAAAGATTATCTTCTATTATCAAC-AAACAGATGGAAGAGACATCA-C-----AGATTT 805
PPI-Corn-FTB  ACAAAAGTTAATTACGATTGTTGAT-AAGCAA---------------------------- 871
Consensus     ACAAAGATTAT TTC A       GAT-A G        A G   CATCA- -          574

                   910       920       930       940       950       960
              ....|....|....|....|....|....|....|....|....|....|....|....|
PPI-BnFTb     AAGGCACAGATGAAGATGACGAGGAACATGGTCATGATGAAGATGATCCTGAAGACAGTG 745
eral          AAGGCACAAATGAAGAACAT------CATGCTCATGATGAAGATGACCTTGAAGACAGTG 829
PPI-Soy-FTB   TTGCGGTATCTTATGTATCTGAAGCAAAAGAAAGTTGGATGGAACCTCTAGTCATGCAA 865
PPI-Corn-FTB  TTGAGGT-CCTCGTATTGCTG---CAAAAGGCCATCAGGAGAGGATGCCTG--CA-GCAC 924
Consensus       G G  A  T A G  C TG    A A G  CAT A GA G     CCTG   A      598

                   970       980       990      1000      1010      1020
              ....|....|....|....|....|....|....|....|....|....|....|....|
PPI-BnFTb     ATGAAGATGAT---TCTGATGAGGATAGCGATGAAGATTCAGGGAATGGTCACCAAGTTC 802
eral          ATGATGATGATGATTCTGATGAGGACAACGATGAAGATTCAGTGAATGGTCACAGAATCC 889
PPI-Soy-FTB   CATGCCGTGGTGAGCATGAAGGCACCAGTGAATCCAGTTCATCTGATTTAAAAATATTG 925
PPI-Corn-FTB  CAGTTCATA-TGGGTGCACCGCGAATAAGTCTTCCTCTGCTGTGGACTATGCGAAGTTTG 983
Consensus       G   ATG TG   T TGA G G A A GAT     TTCAG G AT  T A AA  TT   629

                  1030      1040      1050      1060      1070      1080
              ....|....|....|....|....|....|....|....|....|....|....|....|
PPI-BnFTb     ATCATACGTCTACCTACATTGACAGGAGAATTCAACCTGTTTTTGATAGCCTCGGCTTGC 862
eral          ATCATACATCCACCTACATTAACAGGAGAATGCAACTGGTTTTTGATAGCCTCGGCTTGG 949
PPI-Soy-FTB   CCTATAAATTTATTAATGAGTGGAGAGCACAAGAACCACTTTTTCACAGTATTGCTTTAC 985
PPI-Corn-FTB  GATTTGATTTTATACAACAGAGCAACCAAATTGGCCCACTCTTCCATAACATTGCCCTGC 1043
Consensus        ATA  T TA   A    CAG   AAT  AACC   TTTTT ATAGC T G CTTGC 663

                  1090      1100      1110      1120      1130      1140
              ....|....|....|....|....|....|....|....|....|....|....|....|
PPI-BnFTb     AAAGATATGTGCTCTTGTGCTCTCAGGTTGCTGATGGTGGATTCAGAGACAAGCTGAGGA 922
eral          AGAGATATGTACTCTTGTGCTCTAAGATCCCTGACGGTGGATTCAGAGACAAGCCGAGGA 1009
PPI-Soy-FTB   AGCAATATATTCTCTTATGTGCACAGGAGCAAGAGGGTGGACTGAGAGACAAACCGGGTA 1045
PPI-Corn-FTB  AACAATACATCCTACTTTGTTCTCAGGTACTAGAGGGAGGCTTGAGGGATAAGCCTGGAA 1103
Consensus     A    ATAT T CTCTT TG TCTCAGGT C  GA GGTGGATT AGAGACAAGCCG G A 709

                  1150      1160      1170      1180      1190      1200
              ....|....|....|....|....|....|....|....|....|....|....|....|
PPI-BnFTb     AACCCCGTGACTTCTACCACACATGTTACTGCCTAAGCGGTCTTTCCGTGGCTCAACACG 982
eral          AACCCCGTGACTTCTACCACACATGTTACTGCCTGAGCGGCTTGTCTGTGGCTCAGCACG 1069
PPI-Soy-FTB   AACGTAGAGATCATTATCACACATGTTACTGTTTAAGTGGACTCTCATTGTGCCAGTATA 1105
PPI-Corn-FTB  AGAACAGAGATCACTATCATTCATGCTACTGCCTCAGTGGCCTCGCAGTTAGCCAGTACA 1163
Consensus     AAC C G GA   CTA CACACATGTTACTGCCT AG GG CT TC GTG  CAG AC  752

                  1210      1220      1230      1240      1250      1260
              ....|....|....|....|....|....|....|....|....|....|....|....|
PPI-BnFTb     CTTGGTCAAAAGACGAGGACACTCCTCCTTTGACTCGTGACATTTGGGTGGCTACGCAA 1042
eral          CTTGGTTAAAAGACGAGGACACTCCTCCTTTGACTCGCGACATTATGGGTGGCTACTCGA 1129
PPI-Soy-FTB   GTTGGTCAAAGCACCCAGATTCTCCACCAC------------------------------ 1135
PPI-Corn-FTB  GTGCCATGACTGATACTGGTTCGTGCCCATTACCTCAGCATGTGCTTGGACCGTACTCTA 1223
Consensus      TTGGT AAA GAC   GA  CTCC CC TT   CTC   A  T   T GG   TAC C A 786

                  1270      1280      1290      1300      1310      1320
              ....|....|....|....|....|....|....|....|....|....|....|....|
PPI-BnFTb     ACCACCTTGAACCTGTTCACCTCCTCCACAACATTGTCTTGGATCGGTATTATGAAGCTT 1102
eral          ATCTCCTTGAACCTGTTCAACTTCTTCACAACATTGTCATGGATCAGTATAATGAAGCTA 1189
PPI-Soy-FTB   ------------------------------------------------------------ 1135
PPI-Corn-FTB  ATTTGCTGGAGCCAATCCATGC-------------------------------------- 1245
Consensus     A    CT GA CC  T CA C                                        797
```

Also included in the invention is the CPP consensus sequences. The consensus sequences were generated by alignment of the CPP polypeptide and nucleic acid ssequences as well as sequences homogous using the program BioEdit.

The "x" in the consensus sequence represents any amino acid or nucleotide. Preferably "x" a conservative amino acid or nucleotide substitution. More preferably, "x" is the most amino acid or nucleotide most prevalent at a given postion. For example, the amino acid at postion 145 of SEQ ID NO: 168 is a proline as it occurs 66% of the time.

3) BASF-Corn (SEQ ID NO:120)
4) BASF-Soy (SEQ ID NO:122)
5) Consensus (SEQ ID NO:163)

```
                   10        20        30        40        50        60
           ....|....|....|....|....|....|....|....|....|....|....|....|
BASF_AT1   ------------------------------------------------------------ 1
BASF_AT2   ------------------------------------------------------------ 1
BASF-Corn  ------------------------------------------------------------ 1
BASF-Soy   CTAATACGACTCACTATAGGGCAAGCAGTGGTAACAACGCAGAGTACGCGGGGGGAGACG 60
Consensus  XXXXXXXXXXXXXXXXXXXXXXXXXXXXXXXXXXXXXXXXXXXXXXXXXXXXXXXXXXXX 60

                   70        80        90       100       110       120
           ....|....|....|....|....|....|....|....|....|....|....|....|
BASF_AT1   ------------------------------------------------------------ 1
BASF_AT2   ------------------------------------------------------------ 1
BASF-Corn  ------------------------------------------------------------ 1
BASF-Soy   CATGGTTCTGAACTAATTGTTATAAATAATACCTAAAATTTTGAGTTGTCCTAAACATTG 120
Consensus  XXXXXXXXXXXXXXXXXXXXXXXXXXXXXXXXXXXXXXXXXXXXXXXXXXXXXXXXXXXX 120

                  130       140       150       160       170       180
           ....|....|....|....|....|....|....|....|....|....|....|....|
BASF_AT1   ------------------------------------------------------------ 1
BASF_AT2   ------------------------------------------------------------ 1
BASF-Corn  ------------------------------------------------------------ 1
BASF-Soy   GGGTTTAAACAAATCCAATCTCTCAATATAAAACCCAATGATCTCACCCTCACTCCGTTT 180
Consensus  XXXXXXXXXXXXXXXXXXXXXXXXXXXXXXXXXXXXXXXXXXXXXXXXXXXXXXXXXXXX 180

                  190       200       210       220       230       240
           ....|....|....|....|....|....|....|....|....|....|....|....|
BASF_AT1   ----------------------------------------------------ATGGCGAT 8
BASF_AT2   ----------------------------------------------------ATGGCGAT 8
BASF-Corn  ------------------------------------------------------------ 1
BASF-Soy   CTGATTTCTCACTCTTCGTTTCTCGTTCGGTTCATCAGCGTGTGTCTCAGCCATGGCGTT 240
Consensus  XXXXXXXXXXXXXXXXXXXXXXXXXXXXXXXXXXXXXXXXXXXXXXXXXXXXXXXXXXXX 240

                  250       260       270       280       290       300
           ....|....|....|....|....|....|....|....|....|....|....|....|
BASF_AT1   TCCTTTCATGGAAACCGTCGTGGGTTTTATGATAGTGATGTACATTTTTGAGACGTATTT 68
BASF_AT2   TCCTTTCATGGAAACCGTCGTGGGTTTTATGATAGTGATGTACATTTTTGAGACGTATTT 68
BASF-Corn  ------------------------------------------------------------ 1
BASF-Soy   TCCCTACATGGAAGCCGTTGTCGGATTTATGATATTAATGTACATTTTTGAAACTTACTT 300
Consensus  XXXXXXXXXXXXXXXXXXXXXXXXXXXXXXXXXXXXXXXXXXXXXXXXXXXXXXXXXXXX 300

                  310       320       330       340       350       360
           ....|....|....|....|....|....|....|....|....|....|....|....|
BASF_AT1   GGATCTGAGGCAACTCACTGCTCTCAAGCTTCCAACTCTCCCGAAAACCTTGGTTGGTGT 128
BASF_AT2   GGATCTGAGGCAACTCACTGCTCTCAAGCTTCCAACTCTCCCGAAAACCTTGGTTGGTGT 128
BASF-Corn  ------------------------------------------------------------ 1
BASF-Soy   GGATGTGCGACAACATAGGGCCCTCAAACTTCCTACTCTTCCAAAGACTTTAGAAGGTGT 360
Consensus  XXXXXXXXXXXXXXXXXXXXXXXXXXXXXXXXXXXXXXXXXXXXXXXXXXXXXXXXXXXX 360

                  370       380       390       400       410       420
           ....|....|....|....|....|....|....|....|....|....|....|....|
BASF_AT1   AATTAGCCAAGAGAAGTTTGAGAAATCACGAGCATACAGTCTTGACAAAAGCTATTTTCA 188
BASF_AT2   AATTAGCCAAGAGAAGTTTGAGAAATCACGAGCATACAGTCTTGACAAAAGCTATTTTCA 188
BASF-Corn  ------------------------------------------------------------ 1
BASF-Soy   TATCAGCCAAGAGAAATTTGAGAAATCTAGAGCCTATAGTCTTGATAAAAGCCACTTCCA 420
Consensus  XXXXXXXXXXXXXXXXXXXXXXXXXXXXXXXXXXXXXXXXXXXXXXXXXXXXXXXXXXXX 420

                  430       440       450       460       470       480
           ....|....|....|....|....|....|....|....|....|....|....|....|
BASF_AT1   CTTTGTTCATGAGTTTGTAACTATACTTATGGACTCTGCAATTTTGTTCTTTGGGATCTT 248
BASF_AT2   CTTTGTTCATGAGTTTGTAACTATACTTATGGACTCTGCAATTTTGTTCTTTGGGATCTT 248
BASF-Corn  ------------------------------------------------------------ 1
BASF-Soy   TTTTGTTCACGAGTTTGTGACAATAGTGACAGACTCTACAATTTTGTACTTTGGGGTATT 480
Consensus  XXXXXXXXXXXXXXXXXXXXXXXXXXXXXXXXXXXXXXXXXXXXXXXXXXXXXXXXXXXX 480

                  490       500       510       520       530       540
           ....|....|....|....|....|....|....|....|....|....|....|....|
```

Example 13

Vector Constructs for Transformation

The FTA or FTB sequences have been used to produce constructions suitable for transformation into plants and under the control of appropriate regulatory sequences. The gene sequences were in either the sense orientation for over-expression of the antisense orientation for down-regulation. Portions of these sequences have been used to construct a double-stranded-RNA-inhibition (dsRNAi) construct. A sequence of preferably not less than 21 nt was cloned as an inverse repeat separated by a linker that when expressed results in down-regulation of the target gene. Double antisense (DA) vectors have been created in which a direct repeat of an antisense sequence is separated by a spacer sequence such as GUS. Promoters have been used for constitutive expression such as the 35S CaMV promoter, the MuA *Zea maize* promoter or inducible by specific environmental or cellular cues such as the ABA levels or drought conditions which induce expression of the RD29A promoter. Alternatively, tissue or organelle specific promoters such as the HIC or CUT1 promoter can be used. Such constructs have been transformed into *Arabidopsis thaliana, Brassica, Zea maize, Glycine max*. Other species can be transformed as desired. Each species to be transformed may make use of specific regulatory sequences as appropriate for those particular species. Transformed plants have been selected and their phenotypic properties analyzed. The transgenic plants were assessed for characteristics such as increased tolerance to drought, altered biomass accumulation, yield, nutritional requirements such as minerals or micro-nutrients, biotic stress such as fungal, bacterial, or other such pathogen infection or attack or any other such physical or biochemical characteristic.

Example 14

Plant Transformation

*Arabidopsis thaliana* transgenic plants were made by flower dipping method into an *Agrobacterium* culture. Wild type plants were grown under standard conditions until they began flowering., The plant was inverted for 2 min into a solution of *Agrobacterium* culture. Plants were then bagged for two days to maintain humidity and then uncovered to continue growth and seed development. Mature seed was bulk harvested.

Transformed T1 plants were selected by germination and growth on MS plates containing 50 μg/ml kanamycin. Green, kanamycin resistant seedlings were identified after 2 weeks growth and transplanted to soil. Plants were bagged to ensure self fertilization and the T2 seed of each plant harvested separately. During growth of T1 plants leaf samples were harvested, DNA extracted and Southern analysis performed.

T2 seeds were analyzed for $Kan^R$ segregation. From those lines that showed a 3:1 resistant phenotype surviving T2 plants were grown, bagged during seed set, and T3 seed harvested from each line. T3 seed was again used for KanR segregation analysis and those lines showing 100% $Kan^R$ phenotype were selected as homozygous lines. Further analysis was done using T3 seed.

Transgenic *Brassica napus* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 μl Tween20) and left for approximately 15 minutes. Solution I was removed and replaced with 30 ml of solution II (0.25% mecuric chloride, 100 μl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained for 5 days at 24° C., with 16,8 hr light dark cycles. Explants were transferred to Medium II (Medium I, 300 mg/L timentin,) for a further 7 days and then to Medium III (Medium II, 20 mg/L kanamycin). Any root or shoot tissue which had developed at this time was dissected away. Transfer explants to fresh plates of Medium III after 14-21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10× IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil.

Transgenic *Glycine max, Zea maize* and cotton can be produced using *Agrobacterum*-based methods which are known to one of skill in the art. Alternatively one can use a particle or non-particle biolistic bombardment transformation method. An example of non-particle biolistic transformation is given in U.S. patent application Ser. No. 20010026941. Viable plants are propogated and homozygous lines are generated. Plants are tested for the presence of drought tolerance, physiological and biochemical phenotypes as described elsewhere.

The following table identifies the constructs and the species which they have been transformed.

TABLE 11

| SEQ ID NO: | SEQ | Species Transformed | |
|---|---|---|---|
| SEQ ID NO:10 | pBI121-35S-anti-AtFTA | *Arabidopsis thaliana* | |
| SEQ ID NO:46 | pBI121-35S-AtFTA | *Arabidopsis thaliana* | *Brassica napus* |
| SEQ ID | pBI121-rd29A-anti-AtFTA | *Arabidopsis* | *Brassica* |

TABLE 11-continued

| SEQ ID NO: | SEQ | Species Transformed | | | |
|---|---|---|---|---|---|
| NO:47 | | *thaliana* | *napus* | | |
| SEQ ID NO:48 | pBI121-35S-DA-AtFTA | *Arabidopsis thaliana* | *Brassica napus* | | |
| SEQ ID NO:49 | pBI121-RD29A-DA-AtFTA | *Arabidopsis thaliana* | *Brassica napus* | | |
| SEQ ID NO:50 | MuA-anti-GmFTA | | | | *Glycine max* |
| SEQ ID NO:51 | RD29A-anti-GmFTA | | | | *Glycine max* |
| SEQ ID NO:52 | MuA-HP-GmFTA-Nos-Term | | | | *Glycine max* |
| SEQ ID NO:53 | RD29AP-HP-GmFTA-Nos-Term | | | | *Glycine max* |
| SEQ ID NO:54 | pBI121-35S-Anti-AtFTB | *Arabidopsis thaliana* | *Brassica napus* | | |
| SEQ ID NO:55 | pBI121-RD29AP-Anti-AtFTB | *Arabidopsis thaliana* | *Brassica napus* | | |
| SEQ ID NO:56 | pBI121-35S-HP-AtFTB | *Arabidopsis thaliana* | *Brassica napus* | | |
| SEQ ID NO:57 | pBI121-RD29AP-HP-AtFTB | *Arabidopsis thaliana* | *Brassica napus* | | |
| SEQ ID NO:58 | pBI121-35S-AtFTB | *Arabidopsis thaliana* | | | |
| SEQ ID NO:59 | MuA-anti-GmFTB-Nos-Term | | | | *Glycine max* |
| SEQ ID NO:60 | RD29AP-anti-GmFTB-Nos-Term | | | | *Glycine max* |
| SEQ ID NO:61 | MuA-HP-GmFTB-Nos-Term | | | | *Glycine max* |
| SEQ ID NO:62 | RD29AP-HP-GmFTB-Nos-Term | | | | *Glycine max* |
| SEQ ID NO:63 | MuA-anti-*Zea maize*FTB-Nos-Term | | | *Zea maize* | |
| SEQ ID NO:64 | MuA-HP-*Zea maize*FTB-Nos-Term | | | *Zea maize* | |

Non-limiting examples of vector constructs suitable for plant transformation are given in SEQ ID NO:10, 46-64.

*gtttacccgccaatatatcctgtc*aaacactgatagtttaaactgaaggcgggaaacgacaatctgatcatgagcgg SEQ ID NO:10 agaattaagggagtcacgttatgacccccgccgatgacgcgggacaagccgttttacgtttggaactgacagaaccg caacgttgaaggagccactcagccgcgggtttctggagtttaatgagctaagcacatacgtcagaaaccattattgc gcgttcaaaagtcgcctaaggtcactatcagctagcaaatatttcttgtcaaaaatgctccactgacgttccataaa ttcccctcggtatccaattagagtctcatattcactctcaatccaaataatctgcaccggatctggatcgtttcgca tgattgaacaagatggattgcacgcagttctccggccgcttgggtggagaggctattcggctatgactgggcacaa cagacaatcggctgctctgatgccgccgtgttccggctgtcagcgcaggggcgcccggttctttttgtcaagaccga cctgtccggtgccctgaatgaactgcaggacgaggcagcgcggctatcgtggctggccacgacgggcgttccttgcg cagctgtgctcgacgttgtcactgaagcgggaagggactggctgctattgggcgaagtgccggggcaggatctcctg tcatctcaccttgctcctgccgagaaagtatccatcatggctgatgcaatgcggcggctgcataCgcttgatccggc tacctgcccattcgaccaccaagcgaaacatcgcatcgagcgagcacgtactcggatggaagccggtCttgtcgatc aggatgatctggacgaagagcatcaggggctcgcgccagccgaactgttcgccaggctcaaggcgcgcatgcccgac ggcgatgatctcgtcgtgacccatggcgatgcctgcttgccgaatatcatggtggaaaatggccgcttttctggatt catcgactgtggccggctgggtgtggcggaccgctatcaggacatagcgttggctacccgtgatattgctgaagagc ttggcgggcgaatgggctgaccgcttcctcgtgctttacggtatcgccgctccgattcgcagcgcatcgccttctat cgccttcttgacgagttcttctgagcgggactctggggttcgaaatgaccgaccaagcgacgcccaacctgccatca

-continued cgagatttcgattccaccgccgccttctatgaaaggttgggcttcggaatcgttttccgggacgccggctggatgat cctccagcgcggggatctcatgctggagttcttcgcccacgggatctctgcggaacaggcggtcgaaggtgccgata tcattacgacagcaacggccgacaagcacaacgccacgatcctgagcgacaatatgatcgggcccggcgtccacatc aacggcgtcggcggcgactgcccaggcaagaccgagatgcaccgcgatatcttgctgcgttcggatattttcgtgga gttcccgccacagacccggatgatccccgatcgttcaaacatttggcaataaagtttcttaagattgaatcctgttg ccggtcttgcgatgattatcatataatttctgttgaattacgttaagcatgtaataattaacatgtaatgcatgacg ttatttatgagatgggtttttatgattagagtcccgcaattatacatttaatacgcgatagaaaacaaaatatagcg cgcaaactaggataaattatcgcgcgcggtgtcatctatgttactagatcgggcctcctgtcaatgctggcggcggc tctggtggtggttctggtggcggctctgagggtggtggctctgagggtggcggttctgagggtggcggctctgaggg aggcggttccggtggtggctctggttccggtgattttgattatgaaaagatggcaaacgctaataagggggctatga ccgaaaatgccgatgaaaacgcgctacagtctgacgctaaaggcaaacttgattctgtcgctactgattacggtgct gctatcgatggtttcattggtgacgtttccggccttgctaatggtaatggtgctatggtgattttgctggctctaa ttcccaaatggctcaagtcggtgacggtgataattcacctttaatgaataatttccgtcaatatttaccttccctcc ctcaatcggttgaatgtcgcccttttgtctttggcccaatacgcaaaccgcctctccccgcgcgttggccgattcat taatgcagctggcacgacaggtttcccgactggaaagcgggcagtgagcgcaacgcaattaatgtgagttagctcac tcattaggcaccccaggctttacactttatgcttccgctcgtatgttgtgtggaattgtgagcggataacaatttc acacaggaaacagctatgaccatgattacgccaagcttgcatgcctgcagcccacagatggttagagaggcttacgc agcaggtctcatcaagacgatctacccgagcaataatctccaggaaatcaaataccttcccaagaaggttaaagatg cagtcaaaagattcaggactaactgcatcaagaacacagagaaagatatatttctcaagatcagaagtactattcca gtatggacgattcaaggcttgcttcacaaaccaaggcaagtaatagagattggagtctctaaaaaggtagtccccac tgaatcaaaggccatggagtcaaagattcaaatagaggacctaacagaactcgccgtaaagactggcgaacagttca tacagagtctcttacgactcaatgacaagaagaaaatcttcgtcaacatggtggagcacgacacacttgtctactcc aaaaatatcaaagatacagtctcagaagaccaaagggcaattgagacttttcaacaaagggtaatatccggaaaccc cctcggattccattgcccagctatctgtcactttattgtgaagatagtggaaaaggaaggtggctcctacaaatgcc atcattgcgataaaggaaaggccatcgttgaagatgcctctgccgacagtggtcccaaagatggacccccacccacg aggagcatcgtggaaaaagaagacgttccaaccacgtcttcaaagcaagtggattgatgtgatatctccactgacgt aagggatgacgcacaatcccactatccttcgcaagacccttcctctatataaggaagttcatttcatttggagagaa cacgggggactctagaggatcctcaaattgctgccactgtaatcttgctcttcctccatgcdcaatagttagctctt ataggatctacacgaccaagaatagtacacaccaaattggccaagttagtctctggttcttcattagctagagctct cactgagtctttatgctcgttggttggtctcagtccatcacatagaagatccaaaagggtgctcagagcgaatccat ggaagcaatctgtgcgggatagaacattcaaacagactgaggaaacacttggatcactaatccaggattctttgtcg tctttgtaaagcgcttttaggtatcgccatgagctctcgtttgcaggattggttaaaatggcttcgattgtgtagct tacttcagattctctcatggcttctaggcctcccaacaaaggagattgggtgatgacataatacctctgattccagg cggaattgttaaagacgtcagcttcaaggagctcgtgacagtaatcgagctcatcttcccatcctcctaatgcccgt agtgtccactgcctatgtgaccaagcatgataatgtttggcatcaagtgaaagtactctacgggtaaattcaagttc tctccctgcaacatcaggacccagtttctctgcaacccatcgccgatgatgccacagttggtagttcttagagttat cctcagcaatgcgttcgatgaactcgagttcttcaaacaagtcgtgattaagggcctcgagtactaggcgcctgaaa tgccacactgtgtagttgccggagtttaagaggagggtttcttccgtgagtcgtagtgcgcgaggagatcgctcgtc ggaaaagtaaatcgcacggaagtaatccatagtctcgcggaactcttccttgtaggcaattggcaccactggattcg gaccatcgtcctgagtcaatgggaccacgtctgaccactccaatcgttggctcagtggcacggtctcgtcgaaattc -continued atccccctcgaatttccccgatcgttcaaacatttggcaataaagtttcttaagattgaatcctgttgccggtcttgc gatgattatcatataatttctgttgaattacgttaagcatgtaataattaacatgtaatgcatgacgttatttatgc gatgggtttttatgattagagtcccgcaattatacatttaatacgcgatagaaaacaaaatatagcgcgcaaactag gataaattatcgcgcgcggtgtcatctatgttactagatcgggaattcactggccgtcgttttacaacgtcgtgact gggaaaaccctggcgttacccaacttaatcgccttgcagcacatccccctttcgccagctggcgtaatagcgaagag gcccgcaccgatcgcccttcccaacagttgcgcagcctgaatggcgcccgctcctttcgctttcttcccttcctttc tcgccacgttcgccggctttccccgtcaagctctaaatcgggggctccctttagggttccgatttagtgctttacgg cacctcgaccccaaaaaacttgatttgggtgatggttcacgtagtgggccatcgccctgatagacggtttttcgccc tttgacgttggagtccacgttctttaatagtggactcttgttccaaactggaacaacactcaaccctatctcgggct attcttttgatttataagggattttgccgatttcggaaccaccatcaaacaggattttcgcctgctggggcaaacca gcgtggaccgcttgctgcaactctctcagggccaggcggtgaagggcaatcagctgttgcccgtctcactggtgaaa agaaaaaccaccccagtacattaaaaacgtccgcaatgtgttattaagttgtctaagcgtcaattt*gtttacaccac*

*aatatatcctgcca*

SEQ ID NO:10 is the nucleic acid sequence of pBI121-antisense-FTA vector construct used to transform *Arabidopsis* plants. Italicized sequences are the right and left border repeats (1-24, 5226-5230). Underlined sequence is the 35S promoter (2515-3318). Bold sequence is the anti-sense Farnesyl transferase alpha sequence (3334-4317).

*gtttacccgccaatatatcctgtc*aaacactgatagtttaaactgaaggcgggaaacgacaatc SEQ ID NO:46 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc -continued ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggggactctagag gatccatgaatttcgacgagaccgtgccactgagccaacgattggagtggtcagacgtggtccc attgactcaggacgatggtccgaatccagtggtgccaattgcctacaaggaagagttccgcgag actatggattacttccgtgcgatttacttttccgacgagcgatctcctcgcgcactacgactca cggaagaaaccctcctcttaaactccggcaactacacagtgtggcatttcaggcgcctagtact cgaggcccttaatcacgacttgtttgaagaactcgagttcatcgaacgcattgctgaggataac tctaagaactaccaactgtggcatcatcggcgatgggttgcagagaaactgggtcctgatgttg cagggagagaacttgaatttacccgtagagtactttcacttgatgccaaacattatcatgcttg gtcacataggcagtggacactacgggcattaggaggatgggaagatgagctcgattactgtcac gagctccttgaagctgacgtctttaacaattccgcctggaatcagaggtattatgtcatcaccc aatctcctttgttgggaggcctagaagccatgagagaatctgaagtaagctacacaatcaaagc cattttaaccaatcctgcaaacgagagctcatggcgatacctaaaagctctttacaaagacgac

-continued aaagaatcctggattagtgatccaagtgtttcctcagtctgtttgaatgttctatcccgcacag attgcttccatggattcgctctgagcaccctttttggatcttctatgtgatggactgagaccaac caacgagcataaagactcagtgagagctctagctaatgaagaaccagagactaacttggccaat ttggtgtgtactattcttggtcgtgtagatcctgtaagagctaactattgggcatggaggaaga gcaagattacagtggcagcaatttgactcgaatttccccgatcgttcaaacatttggcaataaa gtttcttaagattgaatcctgttgccggtcttgcgatgattatcatataatttctgttgaatta cgttaagcatgtaataattaacatgtaatgcatgacgttatttatgagatgggtttttatgatt agagtcccgcaattatacatttaatacgcgatagaaaacaaaatatagcgcgcaaactaggata aattatcgcgcgcggtgtcatctatgttactagatcgggaattcactggccgtcgttttacaac gtcgtgactgggaaaaccctggcgttacccaacttaatcgccttgcagcacatccccctttcgc cagctggcgtaatagcgaagaggcccgcaccgatcgcccttcccaacagttgcgcagcctgaat ggcgcccgctcctttcgctttcttcccttcctttctcgccacgttcgccggctttccccgtcaa gctctaaatcgggggctccctttagggttccgatttagtgctttacggcacctcgaccccaaaa aacttgatttgggtgatggttcacgtagtgggccatcgccctgatagacggtttttcgcccttt gacgttggagtccacgttctttaatagtggactcttgttccaaactggaacaacactcaaccct atctcgggctattcttttgatttataagggattttgccgatttcggaaccaccatcaaacagga ttttcgcctgctggggcaaaccagcgtggaccgcttgctgcaactctctcagggccaggcggtg aagggcaatcagctgttgcccgtctcactggtgaaaagaaaaaccaccccagtacattaaaaac gtccgcaatgtgttattaagttgtctaagcgtcaattt*gtttacaccacaatatatcctgcca*

(Underlined Seq: 35S promoter; Bold: AtFTA)

*gtttacccgccaatatatcctgtc*aaacactgatagtttaaactgaaggcgggaaacgacaatc SEQ ID NO:47 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggagacgatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc -continued gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacactgtgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgacgcgaacgcaa
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaagatttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtctgggttt
atctctctcagtctctctataaacttagtgagaccctcctctgttttactcacaaatatgcaaa
ctagaaaacaatcatcaggaataaagggtttgattacttctattggaaacagtctagaggatcc
tcaaattgctgccactgtaatcttgctcttcctccatgcccaatagttagctcttataggatct
acacgaccaagaatagtacacaccaaattggccaagttagtctctggttcttcattagctagag
ctctcactgagtctttatgctcgttggttggtctcagtccatcacatagaagatccaaaagggt
gctcagagcgaatccatggaagcaatctgtgcgggatagaacattcaaacagactgaggaaaca
cttggatcactaatccaggattctttgtcgtctttgtaaagcgcttttaggtatcgccatgagc
tctcgtttgcaggattggttaaaatggctttgattgtgtagcttacttcagattctctcatggc

-continued ttctaggcctcccaacaaaggagattgggtgatgacataatacctctgattccaggcggaattg ttaaagacgtcagcttcaaggagctcgtgacagtaatcgagctcatcttcccatcctcctaatg cccgtagtgtccactgcctatgtgaccaagcatgataatgtttggcatcaagtgaaagtactct acgggtaaattcaagttctctccctgcaacatcaggacccagtttctctgcaacccatcgccga tgatgccacagttggtagttcttagagttatcctcagcaatgcgttcgatgaactcgagttctt caaacaagtcgtgattaagggcctcgagtactaggcgcctgaaatgccacactgtgtagttgcc ggagtttaagaggagggtttcttccgtgagtcgtagtgcgcgaggagatcgctcgtcggaaaag taaatcgcacggaagtaatccatagtctcgcggaactcttccttgtaggcaattggcaccactg gattcggaccatcgtcctgagtcaatgggaccacgtctgaccactccaatcgttggctcagtgg cacggtctcgtcgaaattcatcccctcgaatttccccgatcgttcaaacatttggcaataaagt ttcttaagattgaatcctgttgccggtcttgcgatgattatcatataatttctgttgaattacg ttaagcatgtaataattaacatgtaatgcatgacgttatttatgagatgggtttttatgattag agtcccgcaattatacatttaatacgcgatagaaaacaaaatatagcgcgcaaactaggataaa ttatcgcgcgcggtgtcatctatgttactagatcgggaattcactggccgtcgttttacaacgt cgtgactgggaaaaccctggcgttacccaacttaatcgccttgcagcacatccccctttcgcca gctggcgtaatagcgaagaggcccgcaccgatcgcccttcccaacagttgcgcagcctgaatgg cgcccgctcctttcgctttcttcccttcctttctcgccacgttcgccggctttccccgtcaagc tctaaatcgggggctccctttagggttccgatttagtgctttacggcacctcgaccccaaaaaa cttgatttgggtgatggttcacgtagtgggccatcgccctgatagacggtttttcgccctttga cgttggagtccacgttctttaatagtggactcttgttccaaactggaacaacactcaaccctat ctcgggctattcttttgatttataagggattttgccgatttcggaaccaccatcaaacaggatt ttcgcctgctggggcaaaccagcgtggaccgcttgctgcaactctctcagggccaggcggtgaa gggcaatcagctgttgcccgtctcactggtgaaaagaaaaaccaccccagtacattaaaaacgt ccgcaatgtgttattaagttgtctaagcgtcaattt*gtttacaccacaatatatcctgcca*

(Underlined Seq: RD29A promoter; Bold: Anti-sense-AtFTA)

*gtttacccgccaatatatcctgtc*aaacactgatagtttaaactgaaggcgggaaacgacaatc SEQ ID NO:48 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc -continued ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggactctagag gatcctcGCTCTTCCTCCATGCCCAATAGTTAGCTCTTACAGGATCTACACGACCAAGAATAGT

ACACACCAAATTGGCCAAGTTAGTCTCTGGTTCTTCATTAGCTAGAGCTCTCACTGAGTCTTTA

TGCTCGTTGGTTGGTCTCAGTCCATCACATAGAAGATCCAAAAGGGTGCTCAGAGCGAATCCAT

-continued

GGAAGCAATCTGTGCGGGATAGAACATTCAAACAGACTGAGGAAACACTTGGATCACTAATCCA

GGATTCTTTGTCGTCTTTGTAAAGAGCTTTTAGGTATCGCCATGAGCTCTCGTTTGCAGGATTG

GTTAAAATGGCTTTGATTGTGTAGCTTACTTCAGATTCTCTCATGGCTTCTAGGCCTCCCAACA

AAGGAGATTGGGTGATGACATAATACCTCTGATTCCAGGCGGAATTGTTAAAGACGTCAGCTTC

AAGGAGCTCGTGACAGTAATCGAGCTCATCTTCCCATCCTCCTAATGCCCGgaggatccccATC

TACCCGCTTCGCGTCGGCATCCGGTCAGTGGCAGTGAAGGGCGAACAGTTCCTGATTAACCACA

AACCGTTCTACTTTACTGGCTTTGGTCGTCATGAAGATGCGGACTTGCGTGGCAAAGGATTCGA

TAACGTGCTGATGGTGCACGACCACGCATTAATGGACTGGATTGGGGCCAACTCCTACCGTACC

TCGCATTACCCTTACGCTGAAGAGATGCTCGACTGGGCAGATGAACATGGCATCGTGGTGATTG

ATGAAACTGCTGCTGTCGGCTTTTCGCTCTCTTTAGGCATTGGTTTCGAAGCGGGCAACAAGCC

GAAAGAACTGTACAGCGAAGAGGCAGTCAACGGGGAAACTCAGCAAGCGCACTTACAGGCGATT

AAAGAGCTGATAGCGCGTGACAAAAACCACCCAAGCGTGGTGATGTGGAGTATTGCCAACGAAC

CGGATACCCGTCCGCAAGGTGCACGGGAATATTTCGCGCCACTGGCGGAAGCAACGCGTAAACT

CGACCCGACGCGTCCGATCACCTGCGTCAATGTAATGTTCTGCGACGCTCACACCGATACCATC

AGCGATCTCTTTGATGTGCTGTGCCTGAACCGTTATTACGGATGGTATGTCCAAAGCGGCGATT

TGGAAACGGCAGAGAAGGTACTGGAAAAAGAACTTCTGGCCTGGCAGGAGAAACTGTACACCGA

CATGTGGAGTGAAGAGTATCAGTGTGCATGGCTGGATATGTATCACCGCGTCTTTGATCGCGTC

AGCGCCGTCGTCGGTGAACAGGTATGGAATTTCGCCGATTTTGCGACCTCGCAAGGCATATTGC

GCGTTGGCGGTAACAAGAAAGGGATCTTCACTCGCGACCGCAAACCGAAGTCGGCGGCTTTTCT

GCTGCAAAAACGCTGGACTGGCATGAACTTCGGTGAAAAACCGCAGCAGGGAGGCAAACAATGA

ATCAACAACTCTCCTGGCGCACCATCGTCGGCTACAGCCTCGGGAATTGCTACCGAGCTCGCTC

TTCCTCCATGCCCAATAGTTAGCTCTTACAGGATCTACACGACCAAGAATAGTACACACCAAAT

TGGCCAAGTTAGTCTCTGGTTCTTCATTAGCTAGAGCTCTCACTGAGTCTTTATGCTCGTTGGT

TGGTCTCAGTCCATCACATAGAAGATCCAAAAGGGTGCTCAGAGCGAATCCATGGAAGCAATCT

GTGCGGGATAGAACATTCAAACAGACTGAGGAAACACTTGGATCACTAATCCAGGATTCTTTGT

CGTCTTTGTAAAGAGCTTTTAGGTATCGCCATGAGCTCTCGTTTGCAGGATTGGTTAAAATGGC

TTTGATTGTGTAGCTTACTTCAGATTCTCTCATGGCTTCTAGGCCTCCCAACAAAGGAGATTGG

GTGATGACATAATACCTCTGATTCCAGGCGGAATTGTTAAAGACGTCAGCTTCAAGGAGCTCGT

GACAGTAATCGAGCTCATCTTCCCATCCTCCTAATGCCCGctcgaatttccccgatcgttcaaa catttggcaataaagtttcttaagattgaatcctgttgccggtcttgcgatgattatcatataa tttctgttgaattacgttaagcatgtaataattaacatgtaatgcatgacgttatttatgagat gggtttttatgattagagtcccgcaattatacatttaatacgcgatagaaaacaaaatatagcg cgcaaactaggataaattatcgcgcgcggtgtcatctatgttactagatcgggaattcactggc cgtcgttttacaacgtcgtgactgggaaaaccctggcgttacccaacttaatcgccttgcagca catccccctttcgccagctggcgtaatagcgaagaggcccgcaccgatcgcccttcccaacagt tgcgcagcctgaatggcgcccgctcctttcgctttcttcccttcctttctcgccacgttcgccg gctttccccgtcaagctctaaatcgggggctccctttagggttccgatttagtgctttacggca cctcgaccccaaaaaacttgatttgggtgatggttcacgtagtgggccatcgccctgatagacg gtttttcgccctttgacgttggagtccacgttctttaatagtggactcttgttccaaactggaa caacactcaaccctatctcgggctattcttttgatttataagggattttgccgatttcggaacc -continued accatcaaacaggattttcgcctgctggggcaaaccagcgtggaccgcttgctgcaactctctc agggccaggcggtgaagggcaatcagctgttgcccgtctcactggtgaaaagaaaaaccacccc agtacattaaaaacgtccgcaatgtgttattaagttgtctaagcgtcaatttg*tttacaccaca*

*atatatcctgcca*

(Underlined Seq: 35S promoter; Bold: AtFTA anti-sense sequence separated by GUS Seq.)

*gtttacccgccaatatatcctgtc*aaacactgatagtttaaactgaaggcgggaaacgacaatc SEQ ID NO:49 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcaqcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc -continued ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc ctcGCTCTTCCTCCATGCCCAATAGTTAGCTCTTACAGGATCTACACGACCAAGAATAGTACAC

ACCAAATTGGCCAAGTTAGTCTCTGGTTCTTCATTAGCTAGAGCTCTCACTGAGTCTTTATGCT

CGTTGGTTGGTCTCAGTCCATCACATAGAAGATCCAAAAGGGTGCTCAGAGCGAATCCATGGAA

GCAATCTGTGCGGGATAGAACATTCAAACAGACTGAGGAAACACTTGGATCACTAATCCAGGAT

TCTTTGTCGTCTTTGTAAAGAGCTTTTAGGTATCGCCATGAGCTCTCGTTTGCAGGATTGGTTA

AAATGGCTTTGATTGTGTAGCTTACTTCAGATTCTCTCATGGCTTCTAGGCCTCCCAACAAAGG

AGATTGGGTGATGACATAATACCTCTGATTCCAGGCGGAATTGTTAAAGACGTCAGCTTCAAGG

AGCTCGTGACAGTAATCGAGCTCATCTTCCCATCCTCCTAATGCCCGgaggatccccATCTACC

CGCTTCGCGTCGGCATCCGGTCAGTGGCAGTGAAGGGCGAACAGTTCCTGATTAACCACAAACC

GTTCTACTTTACTGGCTTTGGTCGTCATGAAGATGCGGACTTGCGTGGCAAAGGATTCGATAAC

GTGCTGATGGTGCACGACCACGCATTAATGGACTGGATTGGGGCCAACTCCTACCGTACCTCGC

ATTACCCTTACGCTGAAGAGATGCTCGACTGGGCAGATGAACATGGCATCGTGGTGATTGATGA

AACTGCTGCTGTCGGCTTTTCGCTCTCTTTAGGCATTGGTTTCGAAGCGGGCAACAAGCCGAAA

GAACTGTACAGCGAAGAGGCAGTCAACGGGGAAACTCAGCAAGCGCACTTACAGGCGATTAAAG

AGCTGATAGCGCGTGACAAAAACCACCCAAGCGTGGTGATGTGGAGTATTGCCAACGAACCGGA

TACCCGTCCGCAAGGTGCACGGGAATATTTCGCGCCACTGGCGGAAGCAACGCGTAAACTCGAC

CCGACGCGTCCGATCACCTGCGTCAATGTAATGTTCTGCGACGCTCACACCGATACCATCAGCG

ATCTCTTTGATGTGCTGTGCCTGAACCGTTATTACGGATGGTATGTCCAAAGCGGCGATTTGGA

AACGGCAGAGAAGGTACTGGAAAAAGAACTTCTGGCCTGGCAGGAGAAACTGTACACCGACATG

TGGAGTGAAGAGTATCAGTGTGCATGGCTGGATATGTATCACCGCGTCTTTGATCGCGTCAGCG

CCGTCGTCGGTGAACAGGTATGGAATTTCGCCGATTTTGCGACCTCGCAAGGCATATTGCGCGT

-continued

TGGCGGTAACAAGAAAGGGATCTTCACTCGCGACCGCAAACCGAAGTCGGCGGCTTTTCTGCTG

CAAAAACGCTGGACTGGCATGAACTTCGGTGAAAAACCGCAGCAGGGAGGCAAACAATGAATCA

ACAACTCTCCTGGCGCACCATCGTCGGCTACAGCCTCGGGAATTGCTACCGAGCTCGCTCTTCC

TCCATGCCCAATAGTTAGCTCTTACAGGATCTACACGACCAAGAATAGTACACACCAAATTGGC

CAAGTTAGTCTCTGGTTCTTCATTAGCTAGAGCTCTCACTGAGTCTTTATGCTCGTTGGTTGGT

CTCAGTCCATCACATAGAAGATCCAAAAGGGTGCTCAGAGCGAATCCATGGAAGCAATCTGTGC

GGGATAGAACATTCAAACAGACTGAGGAAACACTTGGATCACTAATCCAGGATTCTTTGTCGTC

TTTGTAAAGAGCTTTTAGGTATCGCCATGAGCTCTCGTTTGCAGGATTGGTTAAAATGGCTTTG

ATTGTGTAGCTTACTTCAGATTCTCTCATGGCTTCTAGGCCTCCCAACAAAGGAGATTGGGTGA

TGACATAATACCTCTGATTCCAGGCGGAATTGTTAAAGACGTCAGCTTCAAGGAGCTCGTGACA

GTAATCGAGCTCATCTTCCCATCCTCCTAATGCCCGctcgaatttccccgatcgttcaaacatt tggcaataaagtttcttaagattgaatcctgttgccggtcttgcgatgattatcatataatttc tgttgaattacgttaagcatgtaataattaacatgtaatgcatgacgttatttatgagatgggt ttttatgattagagtcccgcaattatacatttaatacgcgatagaaaacaaaatatagcgcgca aactaggataaattatcgcgcgcggtgtcatctatgttactagatcgggaattcactggccgtc gttttacaacgtcgtgactgggaaaaccctggcgttacccaacttaatcgccttgcagcacatc ccccctttcgccagctggcgtaatagcgaagaggcccgcaccgatcgcccttcccaacagttgcg cagcctgaatggcgcccgctcctttcgctttcttcccttcctttctcgccacgttcgccggctt tcaccgtcaagctctaaatcgggggctccctttagggttccgatttagtgctttacggcacctc gaccccaaaaaacttgatttgggtgatggttcacgtagtgggccatcgccctgatagacggttt ttcgccctttgacgttggagtccacgttctttaatagtggactcttgttccaaactggaacaac actcaaccctatctcgggctattcttttgatttataagggattttgccgatttcggaaccacca tcaaacaggattttcgcctgctggggcaaaccagcgtggaccgcttgctgcaactctctcaggg ccaggcggtgaagggcaatcagctgttgcccgtctcactggtgaaaagaaaaaccaccccagta cattaaaaacgtccgcaatgtgttattaagttgtctaagcgtcaattt*gtttacaccacaatat*

*atcctgcca*

(Underlined Seq: RD29A promoter; Bold: AtFTA anti-sense sequence, separated by GUS Seq.)

GAATTCAAATTTTTCGCCAGTTCTAAATATCCGGAAACCTCTTGGGATGCCATTGCCCATCTAT SEQ ID NO:50

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCAGGAAGTCTGCTCTTGCGCCAAAT

CCAATAGTTGGTTCTAATTGGATCAACTTGTTTTAGGATAGAACAAATATTTCGTGCTATATTT

AAATTTTGTTGTTCCCCTTTCTCATCATCATCTAAATCTTGTTTATCCATATCTGCGGTCTTTA

AGGCGTCAATGGCATCTCTAATGTCTTCATTTGGTTGATAACCAAAGCATATAAGATCTAAAAT

AGTGCTAAGAGCAAACACGTAGTTGCTCTTAGTTCTCAAAATCTTTAAGCATACTGAAGAAACT

TGAGGATCATTTACCCATGAAGTAGTTTCACCTTTATAAAGTCCTCGTAGATATCTCCACGAGC

TTTCATTTTCAGGGTAGGCTATAATGGCTTCGATGGTGTAAAGCACTTCAGACTCTCTCATAGC

TTTTAGGCCCCCCAAGAAAGGAGACCTTGTTATGACAAAATATCTCTGATTCCAAGCAGAATTG

-continued

TTAAAAATGTCTTCTTTAAGTAGTTCTGTGCAATAATTAAGTTCATCTTCCCATCCTCCTAGTG

TTTGAAGAGCCCACTGTCTATGAGACCATGCATGATAATGTTTGGCATCAACGGACAGTATCTT

TTTGGTGAACTCGAGCTgagctcgaatttccccgatcgttcaaacatttggcaataaagtttct taagattgaatcctgttgccggtcttgcgatgattatcatataatttctgttgaattacgttaa gcatgtaataattaacatgtaatgcatgacgttatttatgagatgggtttttatgattagagtc ccgcaattatacatttaatacgcgatagaaaacaaaatatagcgcgcaaactaggataaattat cgcgcgcggtgtcatctatgttactagatcgggaattc
(Underlined MuA Promoter; Bold: *Glycine max* anti-FTA; lower case: NOS terminater Seq.)

GGAGCCATAGATGCAATTCAATCAAACTGAAATTTCTGCAAGAATCTCAAACACGGAGATCTCA SEQ ID NO:51

AAGTTTGAAAGAAAATTTATTTCTTCGACTCAAAACAAACTTACGAAATTTAGGTAGAACTTAT

ATACATTATATTGTAATTTTTTGTAACAAAATGTTTTTATTATTATTATAGAATTTTACTGGTT

AAATTAAAAATGAATAGAAAAGGTGAATTAAGAGGAGAGAGGAGGTAAACATTTTCTTCTATTT

TTTCATATTTTCAGGATAAATTATTGTAAAAGTTTACAAGATTTCCATTTGACTAGTGTAAATG

AGGAATATTCTCTAGTAAGATCATTATTTCATCTACTTCTTTTATCTTCTACCAGTAGAGGAAT

AAACAATATTTAGCTCCTTTGTAAATACAAATTAATTTTCCTTCTTGACATCATTCAATTTTAA

TTTTACGTATAAAATAAAAGATCATACCTATTAGAACGATTAAGGAGAAATACAATTCGAATGA

GAAGGATGTGCCGTTTGTTATAATAAACAGCCACACGACGTAAACGTAAAATGACCACATGATG

GGCCAATAGACATGGACCGACTACTAATAATAGTAAGTTACATTTTAGGATGGAATAAATATCA

TACCGACATCAGTTTTGAAAGAAAAGGGAAAAAAAGAAAAAATAAATAAAAGATATACTACCGA

CATGAGTTCCAAAAAGCAAAAAAAAAGATCAAGCCGACACAGACACGCGTAGAGAGCAAAATGA

CTTTGACGTCACACCACGAAAACAGACGCTTCATACGTGTCCCTTTATCTCTCTCAGTCTCTCT

ATAAACTTAGTGAGACCCTCCTCTGTTTTACTCACAAATATGCAAACTAGAAAACAATCATCAG

GAATAAAGGGTTTGATTACTTCTATTGGAAAGAGGAAGTCTGCTCTTGCGCCAAATCCAATAGT

TGGTTCTAATTGGATCAACTTGTTTTAGGATAGAACAAATATTTCGTGCTATATTTAAATTTTG

TTGTTCCCCTTTCTCATCATCATCTAAATCTTGTTTATCCATATCTGCGGTCTTTAAGGCGTCA

ATGGCATCTCTAATGTCTTCATTTGGTTGATAACCAAAGCATATAAGATCTAAAATAGTGCTAA

GAGCAAACACGTAGTTGCTCTTAGTTCTCAAAATCTTTAAGCATACTGAAGAAACTTGAGGATC

ATTTACCCATGAAGTAGTTTCACCTTTATAAAGTCCTCGTAGATATCTCCACGAGCTTTCATTT

TCAGGGTAGGCTATAATGGCTTCGATGGTGTAAAGCACTTCAGACTCTCTCATAGCTTTTAGGC

CCCCCAAGAAAGGAGACCTTGTTATGACAAAATATCTCTGATTCCAAGCAGAATTGTTAAAAAT

GTCTTCTTTAAGTAGTTCTGTGCAATAATTAAGTTCATCTTCCCATCCTCCTAGTGTTTGAAGA

GCCCACTGTCTATGAGACCATGCATGATAATGTTTGGCATCAACGGACAGTATCTTTTTGGTGA

ACTCGAGCTgagctcgaatttccccgatcgttcaaacatttggcaataaagtttcttaagattg aatcctgttgccggtcttgcgatgattatcatataatttctgttgaattacgttaagcatgtaa taattaacatgtaatgcatgacgttatttatgagatgggtttttatgattagagtcccgcaatt atacatttaatacgcgatagaaaacaaaatatagcgcgcaaactaggataaattatcgcgcgcg gtgtcatctatgttactagatcgggaattc
(Underlined RD29A Promoter; Bold: *Glycine max* anti-Glycine max FTA; lower case: NOS terminater Seq.)

GAATTCAAATTTTTCGCCAGTTCTAAATATCCGGAAACCTCTTGGGATGCCATTGCCCATCTAT SEQ ID NO:52

CTGTAATTTATTGACGAAATAGACGAAAAGGAAGGTGGCTCCTATAAAGCACATCATTGCGATA

-continued

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCAGGAAGTCTGCTCTTGCGCCAAAT

CCAATAGTTGGTTCTAATTGGATCAACTTGTTTTAGGATAGAACAAATATTTCGTGCTATATTT

AAATTTTGTTGTTCCCCTTTCTCATCATCATCTAAATCTTGTTTATCCATATCTGCGGTCTTTA

AGGCGTCAATGGCATCTCTAATGTCTTCATTTGGTTGATAACCAAAGCATATAAAGATCTAAAT

AGTGCTAAGAGCAAACACGTAGTTGCTCTTAGTTCTCAAAATCTTTAAGCATACTGAAGAAACT

TGAGGATCATTTACCCATGAAGTAGTTTCACCTTTATAAAGTCCTCGTAGATATCTCCACGAGC

TTTCATTTTCAGGGTAGGCTATAATGGCTTCGATGGTGTAAAGCACTTCAGACTCTCTCATAGC

TTTTAGGCCCCCCAAGAAAGGAGACCTTGTTATGACAAAATATCTCTGATTCCAAGCAGAATTG

TTAAAAATGTCTTCTTTAAGTAGTTCTGTGCAATAATTAAGTTCATCTTCCCATCCTCCTAGTG

TTTGAAGAGCCCACTGTCTATGAGACCATGCATGATAATGTTTGGCATCAACGGACAGTATCTT

TTTGGTGAACTCGAGCT*TAAAGGTGAAACTACTTCATGGGTAAATGATCCTCAAGTTTCTTCAG*

*TATGCTTAAAGATTTTGAGAACTAAGAGCAACTACGTGTTTGCTCTTAGCACTATTTTAGATCT*

*TATATGCTTTGGTTATCAACCAATGAAGACATTAGAGAGAGCCATTGACGCCTTAAAGACCGCA*

*GATATGGATAAACAAGATTTAGATGAGGATTGAGAAGGGGAACAAACAAATTTAAATATAGCAC*

*GAAATATTTGTTCTATCCTAAAACAAGTTGATCCAATTAGAACCAACTATTGGATTTGGCGCAA*

*GAGCAGACTTCCT*gagctcgaatttccccgatcgttcaaacatttggcaataaagtttcttaag attgaatcctgttgccggtcttgcgatgattatcatataatttctgttgaattacgttaagcat gtaataattaacatgtaatgcatgacgttatttatgagatgggtttttatgattagagtcccgc aattatacatttaatacgcgatagaaaacaaaatatagcgcgcaaactaggataaattatcgcg cgcggtgtcatctatgttactagatcgggaattc (Underlined: *Glycine max* FTA Anti-Sense section; Bold: MuA Promoter; Italics: *Glycine max* FTA Sense section; lower case: NOS tenninater Seq.)

ggagccatagatgcaattcaatcaaactgaaatttctgcaagaatctcaaacacggagatctca SEQ ID NO:53 aagtttgaaagaaaatttatttcttcgactcaaaacaaacttacgaaatttaggtagaacttat atacattatattgtaatttttttgtaacaaaatgtttttattattattatagaattttactggtt aaattaaaaatgaatagaaaaggtgaattaagaggagagaggaggtaaacattttcttctattt tttcatattttcaggataaattattgtaaaagtttacaagatttccatttgactagtgtaaatg aggaatattctctagtaagatcattatttcatctacttcttttatcttctaccagtagaggaat aaacaatatttagctcctttgtaaatacaaattaattttccttcttgacatcattcaattttaa ttttacgtataaaataaaagatcatacctattagaacgattaaggagaaatacaattcgaatga gaaggatgtgccgtttgttataataaacagccacacgacgtaaacgtaaaatgaccacatgatg ggccaatagacatggaccgactactaataatagtaagttacattttaggatggaataaatatca taccgacatcagttttgaaagaaaagggaaaaaaagaaaaaataaataaaagatatactaccga catgagttccaaaaagcaaaaaaaaagatcaagccgacacagacacgcgtagagagcaaaatga ctttgacgtcacaccacgaaaacagacgcttcatacgtgtccctttatctctctcagtctctct ataaacttagtgagaccctcctctgttttactcacaaatatgcaaactagaaaacaatcatcag gaataaagggtttgattacttctattggaaagAGGAAGTCTGCTCTTGCGCCAAATCCAATAGT

TGGTTCTAATTGGATCAACTTGTTTTAGGATAGAACAAATATTTCGTGCTATATTTAAATTTTG

-continued

TTGTTCCCCTTTCTCATCATCATCTAAATCTTGTTTATCCATATCTGCGGTCTTTAAGGCGTCA

ATGGCATCTCTAATGTCTTCATTTGGTTGATAACCAAAGCATATAAGATCTAAAATAGTGCTAA

GAGCAAACACGTAGTTGCTCTTAGTTCTCAAAATCTTTAAGCATACTGAAGAAACTTGAGGATC

ATTTACCCATGAAGTAGTTTCACCTTTATAAAGTCCTCGTAGATATCTCCACGAGCTTTCATTT

TCAGGGTAGGCTATAATGGCTTCGATGGTGTAAAGCACTTCAGACTCTCTCATAGCTTTTAGGC

CCCCCAAGAAAGGAGACCTTGTTATGACAAAATATCTCTGATTCCAAGCAGAATTGTTAAAAAT

GTCTTCTTTAAGTAGTTCTGTGCAATAATTAAGTTCATCTTCCCATCCTCCTAGTGTTTGAAGA

GCCCACTGTCTATGAGACCATGCATGATAATGTTTGGCATCAACGGACAGTATCTTTTTGGTGA

ACTCGAGCTTAAAGGTGAAACTACTTCATGGGTAAATGATCCTCAAGTTTCTTCAGTATGCTTA

AAGATTTTGAGAACTAAGAGCAACTACGTGTTTGCTCTTAGCACTATTTTAGATCTTATATGCT

TTGGTTATCAACCAAATGAAGACATTAGAGATGCCATTGACGCCTTAAAGACCGCAGATATGGA

TAAACAAGATTTAGATGATGATGAGAAAGGGGAACATCAAAATTTAAATATAGCACGAAATATT

TGTTCTATCCTAAAACAAGTTGATCCAATTAGAACCAACTATTGGATTTGGCGCAAGAGCAGAC

TTCCTgagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattc
(Bold lower case: RD29A Promoter; Underline, Upper case: Antisense GmFTA; Upper case: Sense GmFTA; lower case: NOS terminater)

*gtttacccgccaatatatcctgtc*aaacactgatagtttaaactgaaggcgggaaacgacaatc SEQ ID NO:54 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga -continued atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacaqctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccgtccggaattcccgggtcgacccacgcgtccgggagattcagcgagataagcaattgga ttatctgatgaaaggcttaaggcagcttggtccgcagttttcttccttagatgctaatcgacct tggctttgttactggattcttcattcaatagctttgcttggggagactgtggatgatgaattag aaagcaatgccattgacttccttggacgctgccagggctctgaaggtggatacggtggtggtcc tggccaacttccacatcttgcaactacttatgctgcagtgaatgcacttgttactttaggaggt gacaaagccctttcttcaattaatagagaaaaaatgtcttgtttttttaagacggatgaaggata caagtggaggtttcaggatgcatgatatgggagaaatggatgttcgtgcatgctacactgcaat ttcggttgcaagcatcctaaatattatggatgatgaactcacccagggcctaggagattacatc

-continued ttgagttgccaaacttatgaaggtggcattggaggggaacctggctccgaagctcacggtgggt atacctactgtggtttggctgctatgattttaatcaatgaggtcgaccgtttgaatttggattc attaatgaattgggctgtacatcgacaaggagtagaaatgggatttcaaggtaggacgaacaaa ttggtcgatggttgctacacattttggcaggcagccccttgtgttctactacaaagattatatt caaccaatgatcatgacgttcatggatcatcacatatatcagaagggacaaatgaagaacatca tgctcatgatgaagatgaccttgaagacagtgatgatgatgatgattctgatgaggacaacgat gaagattcagtgaatggtcacagaatccatcatacatccacctacattaacaggagaatgcaac tggtttttgatagcctcggcttgcagagatatgtactcttgtgctctaagatccctgacggtgg attcagagacaagccgaggaaaccccgtgacttctaccacacatgttactgcctgagcggcttg tctgtggctcagcacgcttggttaaaagacgaggacactcctcctttgactcgcgacattatgg gtggctactcgaatctccttgaacctgttcaacttcttcacaacattgtcatggatcagtataa tgaagctatcgagttcttctttaaagcagcatgactcgaatttccccgatcgttcaaacatttg gcaataaagtttcttaagattgaatcctgttgccggtcttgcgatgattatcatataatttctg ttgaattacgttaagcatgtaataattaacatgtaatgcatgacgttatttatgagatgggttt ttatgattagagtcccgcaattatacatttaatacgcgatagaaaacaaaatatagcgcgcaaa ctaggataaattatcgcgcgcggtgtcatctatgttactagatcgggaattcactggccgtcgt tttacaacgtcgtgactgggaaaaccctggcgttacccaacttaatcgccttgcagcacatccc cctttcgccagctggcgtaatagcgaagaggcccgcaccgatcgcccttcccaacagttgcgca gcctgaatggcgcccgctcctttcgctttcttcccttcctttctcgccacgttcgccggctttc cccgtcaagctctaaatcgggggctccctttagggttccgatttagtgctttacggcacctcga ccccaaaaaacttgatttgggtgatggttcacgtagtgggccatcgccctgatagacggttttt cgccctttgacgttggagtccacgttctttaatagtggactcttgttccaaactggaacaacac tcaaccctatctcgggctattcttttgatttataagggattttgccgatttcggaaccaccatc aaacaggattttcgcctgctggggcaaaccagcgtggaccgcttgctgcaactctctcagggcc aggcggtgaagggcaatcagctgttgcccgtctcactggtgaaaagaaaaaccaccccagtaca ttaaaaacgtccgcaatgtgttattaagttgtctaagcgtcaattt*gtttacaccacaatatat*

*cctgcca*
(Underline: 35S promoter; Bold: anti-AtFTB)

*gtttacccgccaatatatcctgtc*aaacactgatagtttaaactgaaggcgggaaacgacaatc SEQ ID NO:55 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttcttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag -continued ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa -continued ctagaaaacaatcatcaggaataaagggtttgattacttctattggaaaggactctagaggatc cgtccggaattcccgggtcgacccacgcgtccgggagattcagcgagataagcaattggattat ctgatgaaaggcttaaggcagcttggtccgcagttttcttccttagatgctaatcgaccttggc tttgttactggattcttcattcaatagctttgcttggggagactgtggatgatgaattagaaag caatgccattgacttccttggacgctgccagggctctgaaggtggatacggtggtggtcctggc caacttccacatcttgcaactacttatgctgcagtgaatgcacttgttactttaggaggtgaca aagccctttcttcaattaatagagaaaaaatgtcttgtttttaagacggatgaaggatacaag tggaggtttcaggatgcatgatatgggagaaatggatgttcgtgcatgctacactgcaatttcg gttgcaagcatcctaaatattatggatgatgaactcacccagggcctaggagattacatcttga gttgccaaacttatgaaggtggcattggaggggaacctggctccgaagctcacggtgggtatac ctactgtggtttggctgctatgattttaatcaatgaggtcgaccgtttgaatttggattcatta atgaattgggctgtacatcgacaaggagtagaaatgggatttcaaggtaggacgaacaaattgg tcgatggttgctacacattttggcaggcagccccttgtgttctactacaaagattatattcaac caatgatcatgacgttcatggatcatcacatatatcagaagggacaaatgaagaacatcatgct catgatgaagatgaccttgaagacagtgatgatgatgatgattctgatgaggacaacgatgaag attcagtgaatggtcacagaatccatcatacatccacctacattaacaggagaatgcaactggt ttttgatagcctcggcttgcagagatatgtactcttgtgctctaagatccctgacggtggattc agagacaagccgaggaaaccccgtgacttctaccacacatgttactgcctgagcggcttgtctg tggctcagcacgcttggttaaaagacgaggacactcctcctttgactcgcgacattatgggtgg ctactcgaatctccttgaacctgttcaacttcttcacaacattgtcatggatcagtataatgaa gctatcgagttcttctttaaagcagcatgactcgaatttccccgatcgttcaaacatttggcaa taaagtttcttaagattgaatcctgttgccggtcttgcgatgattatcatataatttctgttga attacgttaagcatgtaataattaacatgtaatgcatgacgttatttatgagatgggtttttat gattagagtcccgcaattatacatttaatacgcgatagaaaacaaaatatagcgcgcaaactag gataaattatcgcgcgcggtgtcatctatgttactagatcgggaattcactggccgtcgtttta caacgtcgtgactgggaaaaccctggcgttacccaacttaatcgccttgcagcacatccccctt tcgccagctggcgtaatagcgaagaggcccgcaccgatcgcccttcccaacagttgcgcagcct gaatggcgcccgctcctttcgctttcttcccttcctttctcgccacgttcgccggctttccccg tcaagctctaaatcgggggctccctttagggttccgatttagtgctttacggcacctcgacccc aaaaaacttgatttgggtgatggttcacgtagtgggccatcgccctgatagacggtttttcgcc ctttgacgttggagtccacgttctttaatagtggactcttgttccaaactggaacaacactcaa ccctatctcgggctattcttttgatttataagggattttgccgatttcggaaccaccatcaaac aggattttcgcctgctggggcaaaccagcgtggaccgcttgctgcaactctctcagggccaggc ggtgaagggcaatcagctgttgcccgtctcactggtgaaaagaaaaaccaccccagtacattaa aaacgtccgcaatgtgttattaagttgtctaagcgtcaatttt*gtttacaccacaatatatcctg*

*cca*

(Underline: RD29A Promoter; Bold: anti-AtFTB)

*gtttacccgccaatatatcctgtc*aaacactgatagtttaaactgaaggcgggaaacgacaatc SEQ ID NO:56 tgatcatgagcggagaattaagggagtcacgttatgacccccgccgatgacgcgggacaagccg ttttacgtttggaactgacagaaccgcaacgttgaaggagccactcagccgcgggtttctggag -continued tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcqcaggg gcgcccggttctttttgtcaagaccgacctgtcdggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatgqcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc -continued tctaaaaaggtagttcccactgaatcaaaggccatggagtcaaagattcaaatagaggacctaa
cagaactcgccgtaaagactggcgaacagttcatacagagtctcttacgactcaatgacaagaa
gaaaatcttcgtcaacatggtggagcacgacacacttgtctactccaaaaatatcaaagataca
gtctcagaagaccaaagggcaattgagacttttcaacaaagggtaatatccggaaacctcctcg
gattccattgcccagctatctgtcactttattgtgaagatagtggaaaaggaaggtggctccta
caaatgccatcattgcgataaaggaaaggccatcgttgaagatgcctctgccgacagtggtccc
aaagatggacccccacccacgaggagcatcgtggaaaaagaagacgttccaaccacgtcttcaa
agcaagtggattgatgtgatatctccactgacgtaagggatgacgcacaatcccactatccttc
gcaagacccttcctctatataaggaagttcatttcatttggagagaacacggggactctagag
gatcctcCTCCTAGGCCCTGGGTGAGTTCATCATCCATAATATTTAGGATGCTTGCAACCGAAA
TTGCAGTGTAGCATGCACGAACATCCATTTCTCCCATATCATGCATCCTGAAACCTCCACTTGT
ATCCTTCATCCGTCTTAAAAAACAAGACATTTTTTCTCTATTAATTGAAGAAAGGGCTTTGTCA
CCTCCTAAAGTAACAAGTGCATTCACTGCAGCATAAGTAGTTGCAAGATGTGGAAGTTGGCCAG
GACCACCACCGTATCCACCTTCAGAGCCCTGGCAGCGTCCAAGGAAGTCAATGGCATTGCTTTC
TAATTCATCATCCACAGTCTCCCCAAGCAAAGCTATTGAATGAAGAATCCAGTAACAAAGCCAA
GGTCGATTAGCATCTAAGGAAGAAAACTGCGGACCAAGCTGCCTTAAGCCTTTCATCAGATAAT
CCAATTGCTTATCTCGCTGAATCTCCCGGACGCGTGGGTCGACCCGGGAATTCCGGACgaggat
ccccATCTACCCGCTTCGCGTCGGCATCCGGTCAGTGGCAGTGAAGGGCGAACAGTTCCTGATT
AACCACAAACCGTTCTACTTTACTGGCTTTGGTCGTCATGAAGATGCGGACTTGCGTGGCAAAG
GATTCGATAACGTGCTGATGGTGCACGACCACGCATTAATGGACTGGATTGGGGCCAACTCCTA
CCGTACCTCGCATTACCCTTACGCTGAAGAGATGCTCGACTGGGCAGATGAACATGGCATCGTG
GTGATTGATGAAACTGCTGCTGTACGCTTTTCGCTCTCTTTAGGCATTGGTTTCGAAGCGGGCA
ACAAGCCGAAAGAACTGTACAGCGAAGAGGCAGTCAACGGGGAAACTCAGCAAGCGCACTTACA
GGCGATTAAAGAGCTGATAGCGCGTGACAAAAACCACCCAAGCGTGGTGATGTGGAGTATTGCC
AACGAACCGGATACCCGTCCGCAAGGTGCACGGGAATATTTCGCGCCACTGGCGGAAGCAACGC
GTAAACTCGACCCGACGCGTCCGATCACCTGCGTCAATGTAATGTTCTGCGACGCTCACACCGA
TACCATCAGCGATCTCTTTGATGTGCTGTGCCTGAACCGTTATTACGGATGGTATGTCCAAAGC
GGCGATTTGGAAACGGCAGAGAAGGTACTGGAAAAAGAACTTCTGGCCTGGCAGGAGAAACTGT
ACACCGACATGTGGAGTGAAGAGTATCAGTGTGCATGGCTGGATATGTATCACCGCGTCTTTGA
TCGCGTCAGCGCCGTCGTCGGTGAACAGGTATGGAATTTCGCCGATTTTGCGACCTCGCAAGGC
ATATTGCGCGTTGGCGGTAACAAGAAAGGGATCTTCACTCGCGACCGCAAACCGAAGTCGGCGG
CTTTTCTGCTGCAAAAACGCTGGACTGGCATGAACTTCGGTGAAAAACCGCAGCAGGGAGGCAA
ACAATGAATCAACAACTCTCCTGGCGCACCATCGTCGGCTACAGCCTCGGGAATTGCTACCGAG
CTCgtccggaattcccgggtcgacccacgcgtccgggagattcagcgagataagcaattggatt
atctgatgaaaggcttaaggcagcttggtccgcagttttcttccttagatgctaatcgaccttg
gctttgttactggattcttcattcaatagctttgcttggggagactgtggatgatgaattagaa
agcaatgccattgacttccttggacgctgccagggctctgaaggtggatacggtggtggtcctg
gccaacttccacatcttgcaactacttatgctgcagtgaatgcacttgttactttaggaggtga
caaagccctttcttcaattaatagagaaaaaatgtcttgtttttttaagacggatgaaggataca
agtggaggtttcaggatgcatgatatgggagaaatggatgttcgtgcatgctacactgcaattt

-continued cggttgcaagcatcctaaatattatggatgatgaactcacccagggcctaggagctcgaatttc cccgatcgttcaaacatttggcaataaagtttcttaagattgaatcctgttgccggtcttgcga tgattatcatataatttctgttgaattacgttaagcatgtaataattaacatgtaatgcatgac gttatttatgagatgggtttttatgattagagtcccgcaattatacatttaatacgcgatagaa aacaaaatatagcgcgcaaactaggataaattatcgcgcgcggtgtcatctatgttactagatc gggaattcactggccgtcgttttacaacgtcgtgactgggaaaaccctggcgttacccaactta atcgccttgcagcacatccccctttcgccagctggcgtaatagcgaagaggcccgcaccgatcg cccttcccaacagttgcgcagcctgaatggcgcccgctcctttcgctttcttcccttcctttct cgccacgttcgccggctttccccgtcaagctctaaatcgggggctccctttagggttccgattt agtgctttacggcacctcgaccccaaaaaacttgatttgggtgatggttcacgtagtgggccat cgccctgatagacggtttttcgccctttgacgttggagtccacgttctttaatagtggactctt gttccaaactggaacaacactcaaccctatctcgggctattcttttgatttataagggattttg ccgatttcggaaccaccatcaaacaggattttcgcctgctggggcaaaccagcgtggaccgctt gctgcaactctctcagggccaggcggtgaagggcaatcagctgttgcccgtctcactggtgaaa agaaaaaccaccccagtacattaaaaacgtccgcaatgtgttattaagttgtctaagcgtcaat tt*gtttacaccacaatatatcctgcca*
(Underline: 35S promoter; Bold uppercase: antisense AtFTB; Lower case Bold: sense AtFTB)

*gtttacccgccaatatatcctgtc*caaacactgatagtttaaactgaaggcgggaaacgacaatc SEQ ID NO:57 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc -continued ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc ctcCTCCTAGGCCCTGGGTGAGTTCATCATCCATAATATTTAGGATGCTTGCAACCGAAATTGC

AGTGTAGCATGCACGAACATCCATTTCTCCCATATCATGCATCCTGAAACCTCCACTTGTATCC

TTCATCCGTCTTAAAAAACAAGACATTTTTTCTCTATTAATTGAAGAAAGGGCTTTGTCACCTC

CTAAAGTAACAAGTGCATTCACTGCAGCATAAGTAGTTGCAAGATGTGGAAGTTGGCCAGGACC

ACCACCGTATCCACCTTCAGAGCCCTGGCAGCGTCCAAGGAAGTCAATGGCATTGCTTTCTAAT

TCATCATCCACAGTCTCCCCAAGCAAAGCTATTGAATGAAGAATCCAGTAACAAAGCCAAGGTC

GATTAGCATCTAAGGAAGAAAACTGCGGACCAAGCTGCCTTAAGCCTTTCATCAGATAATCCAA

TTGCTTATCTCGCTGAATCTCCCGGACGCGTGGGTCGACCCGGGAATTCCGGACgaggatcccc

ATCTACCCGCTTCGCGTCGGCATCCGGTCAGTGGCAGTGAAGGGCGAACAGTTCCTGATTAACC

-continued

ACAACCGTTCTACTTTACTGGCTTTGGTCGTCATGAAAGATGCGGACTTGCGTGGCAAAGGATT

CGATAACGTGCTGATGGTGCACGACCACGCATTAATGGACTGGATTGGGGCCAACTCCTACCGT

ACCTCGCATTACCCTTACGCTGAAGAGATGCTCGACTGGGCAGATGAACATGGCATCGTGGTGA

TTGATGAAACTGCTGCTGTCGGCTTTTCGCTCTCTTTAGGCATTGGTTTCGAAGCGGGCAACAA

GCCGAAAGAACTGTACAGCGAAGAGGCAGTCAACGGGGAAACTCAGCAAGCGCACTTACAGGCG

ATTAAAGAGCTGATAGCGCGTGACAAAAACCACCCAAGCGTGGTGATGTGGAGTATTGCCAACG

AACCGGATACCCGTCCGCAAGGTGCACGGGAATATTTCGCGCCACTGGCGGAAGCAACGCGTAA

ACTCGACCCGACGCGTCCGATCACCTGCGTCAATGTAATGTTCTGCGACGCTCACACCGATACC

ATCAGCGATCTCTTTGATGTGCTGTGCCTGAACCGTTATTACGGATGGTATGTCCAAAGCGGCG

ATTTGGAAACGGCAGAGAAGGTACTGGAAGAAAAACTTCTGGCCTGGCAGGAGAAACTGTACAC

CGACATGTGGAGTGAAGAGTATCAGTGTGCATGGCTGGATATGTATCACCGCGTCTTTGATCGC

GTCAGCGCCGTCGTCGGTGAACAGGTATGGAATTTCGCCGATTTTGCGACCTCGCAAGGCATAT

TGCGCGTTGGCGGTAACAAGAGGGAAATCTTCACTCGCGACCGCAAACCGAAGTCGGCGGCTTT

TCTGCTGCAAAAACGCTGGACTGGCATGAACTTCGGTGAAAAACCGCAGCAGGGAGGCAAACAA

TGAATCAACAACTCTCCTGGCGCACCATCGTCGGCTACAGCCTCGGGAATTGCTACCGAGCTCg tccggaattcccgggtcgacccacgcgtccgggagattcagcgagataagcaattggattatct gatgaaaggcttaaggcagcttggtccgcagttttcttccttagatgctaatcgaccttggctt tgttactggattcttcattcaatagctttgcttggggagactgtggatgatgaattagaaagca atgccattgacttccttggacgctgccagggctctgaaggtggatacggtggtggtcctggcca acttccacatcttgcaactacttatgctgcagtgaatgcacttgttactttaggaggtgacaaa gccctttcttcaattaatagagaaaaaatgtcttgtttttttaagacggatgaaggatacaagtg gaggtttcaggatgcatgatatgggagaaatggatgttcgtgcatgctacactgcaatttcggt tgcaagcatcctaaatattatggatgatgaactcacccagggcctaggagctcgaatttccccg atcgttcaaacatttggcaataaagtttcttaagattgaatcctgttgccggtcttgcgatgat tatcatataatttctgttgaattacgttaagcatgtaataattaacatgtaatgcatgacgtta tttatgagatgggtttttatgattagagtcccgcaattatacatttaatacgcgatagaaaaca aaatatagcgcgcaaactaggataaattatcgcgcgcggtgtcatctatgttactagatcggga attcactggccgtcgttttacaacgtcgtgactgggaaaaccctggcgttacccaacttaatcg ccttgcagccatcccccttcgccaagctggcgtaatagcgaagaggcccgcaccgatcgccct tcccaacagttgcagcagccgaatggcgcccgctcctttcgctttcttcccttcctttctcgcc acgttcgccggctttccccgtcaagctctaaatcgggggctccctttagggttccgatttagtg ctttacggcacctcgaccccaaaaaacttgatttgggtgatggttcacgtagtgggccatcgcc ctgatagacggtttttcgccctttgacgttggagtccacgttctttaatagtggactcttgttc caaactggaacaacactcaaccctatctcgggctattcttttgatttataagggattttgccga tttcggaaccaccatcaaacaggattttcgcctgctggggcaaaccagcgtggaccgcttgctg caactctctcagggccaggcggtgaagggcaatcagctgttgcccgtctcactggtgaaaagaa aaaccaccccagtacattaaaaacgtccgcaatgtgttattaagttgtctaagcgtcaatttg*gt*

*ttacaccacaatatatcctgcca*

(Underline: RD29A promoter; Bold uppercase: antisense AtFTB;
Lower case Bold: sense AtFTB)

*gtttacccgccaatatatcctgtc*aaacactgatagtttaaactgaaggcgggaaacgacaatc SEQ ID NO:58

-continued tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatgtgctgctacggtgattttgctggctctaatcccaaatggctcaagtcg gtgttgaatgtcgccctttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac -continued tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggactctagag gatccatgccagtagtaacccgcttgattcgtttgaagtgtgtagggctcagacttgaccggag tggactcaatcggcgaatctgtcacggaggacacggggaatcaacgcggcggagagtgatggaa gagctttcaagcctaaccgtgagtcagcgcgagcaatttctggtggagaacgatgtgttcggga tctataattacttcgacgccagcgacgtttctactcaaaaatacatgatggagattcagcgaga taagcaattggattatctgatgaaaggcttaaggcagcttggtccgcagttttcttccttagat gctaatcgaccttggctttgttactggattcttcattcaatagctttgcttggggagactgtgg atgatgaattagaaagcaatgccattgacttccttggacgctgccagggctctgaaggtggata cggtggtggtcctggccaacttccacatcttgcaactacttatgctgcagtgaatgcacttgtt actttaggaggtgacaaagccctttcttcaattaatagagaaaaaatgtcttgtttttttaagac ggatgaaggatacaagtggaggtttcaggatgcatgatatgggagaaatggatgttcgtgcatg ctacactgcaatttcggttgcaagcatcctaaatattatggatgatgaactcacccagggccta ggagattacatcttgagttgccaaacttatgaaggtggcattggaggggaacctggctccgaag ctcacggtgggtatacctactgtggtttggctgctatgattttaatcaatgaggtcgaccgttt gaatttggattcattaatgaattgggctgtacatcgacaaggagtagaaatgggatttcaaggt aggacgaacaaattggtcgatggttgctacacattttggcaggcagccccttgtgttctactac aaagattatattcaaccaatgatcatgacgttcatggatcatcacatatatcagaagggacaaa tgaagaacatcatgctcatgatgaagatgaccttgaagacagtgatgatgatgatgattctgat gaggacaacgatgaagattcagtgaatggtcacagaatccatcatacatccacctacattaaca ggagaatgcaactggtttttgatagcctcggcttgcagagatatgtactcttgtgctctaagat ccctgacggtggattcagagacaagccgaggaaaccccgtgacttctaccacacatgttactgc ctgagcggcttgtctgtggctcagcacgcttggttaaaagacgaggacactcctcctttgactc gcgacattatgggtggctactcgaatctccttgaacctgttcaacttcttcacaacattgtcat ggatcagtataatgaagctatcgagttcttctttaaagcagcatgactcgaatttccccgatcg ttcaaacatttggcaataaagtttcttaagattgaatcctgttgccggtcttgcgatgattatc atataatttctgttgaattacgttaagcatgtaataattaacatgtaatgcatgacgttattta tgagatgggtttttatatgattagagtcccgcaattatacatttaatacgcgatagaaaacaaaat atagcgcgcaaactaggataaattatcgcgcgcggtgtcatctatgttactagatcgggaattc actggccgtcgttttacaacgtcgtgactgggaaaaccctggcgttacccaacttaatcgcctt gcagcacatccccctttcgccagctggcgtaatagcgaagaggcccgcaccgatcgcccttccc aacagttgcgcagcctgaatggcgcccgctcctttcgctttcttcccttcctttctcgccacgt -continued tcgccggctttccccgtcaagctctaaatcgggggctccctttagggttccgatttagtgcttt acggcacctcgaccccaaaaaacttgatttgggtgatggttcacgtagtgggccatcgccctga tagacggtttttcgccctttgacgttggagtccacgttctttaatagtggactcttgttccaaa ctggaacaacactcaaccctatctcgggctattcttttgatttataagggattttgccgatttc ggaaccaccatcaaacaggattttcgcctgctggggcaaaccagcgtggaccgcttgctgcaac tctctcagggccaggcggtgaagggcaatcagctgttgcccgtctcactggtgaaaagaaaaac caccccagtacattaaaaacgtccgcaatgtgttattaagttgtctaagcgtcaattt*gtttac*

*accacaatatatcctgcca*

(Underlined: 35S promoter; Bold: Sense AtFTB)

GAATTCAAATTTTTCGCCAGTTCTAAATATCCGGAAACCTCTTGGGATGCCATTGCCCATCTAT SEQ ID NO:59

CTGTAATTTATTGACGAAATAGCGAAAAGGAAGGTGGCCTCCTATAAAGCACATCATTGCGATA

ACAGAAAGGCCATTGTTGAGATACCTCTGCTGACATTGGTCCCCAAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCGTGGTGGAGAATCTGGGTGCTTTG

ACCAACTATACTGGCACAATGAGAGTCACTTAAACAGTAACATGTGTGATTAATGATCTCTACG

TTTACCCGGTTTGTCTCTCAGTCCACCCTCTTGCTCCTGTGCACATAAGAGAATATATTGCTGT

AAGCAATACTGTGAAAAAGTGGTTCTTGTGCTCTCCACTCATTAATAAATTTATAGGCAAATAT

TTTTAAAATCAGATGAACTGGATTCACTGGTGCCTTCATGCTCACCACGGCATGTTGCATGACT

AGAGGTTCCATCCAACTTTCTTTTGCTTCAGATACATAAGATAACCGCAAAAATCTGTGATGTC

TCTTCCATCTGTTTGTTGATAATAGAAGATAATCTTTGCAATAGAGCAACAGCACCTCCCTGCC

AAAAGGAATAGCATCCATCCACCAGTTTATTTGTTCTCCCCTGGAATCCACATTCCTTACCTTG

TCGGAATACCACCCAGTCAACTAATCGAGGCAGATCCAAGTGATTAACCTCACCAATCAGAATC

ATTGTAGCTAATCCACAAAAGGTGTACCCACCATGAGCCTCAGAACCAGGCTCACCAGCAATGC

CACCCTCATATGTTTGACAGCTTATAATGTAGTCTCCAACATTCTGGATCAGCTCATCATCCAA

AATGTTCAAAACACTTGCAACAGAAATGGCAGTGTAGCAAGCTCGAACATCAATTTCACCTTCA

TCATGCATCCTGAATCCACCATTTGGTTGCTTCATCCGCCGCAGAAACCCATACAGTTTATCTC

TATTAATTGATGCCAGGGATTTCTCACCACCCAAAGTAATAAGTGAATTAACAGCAGCATAAGT

TGTGGCAATATGAGGCATCTGGCCTGGTCCCCCGGCATATCCACCATTCGGATCCTGGCAACGG

TTAAGAAAATCGATAGCGTTATCTTCGAGTTCATCATCGACGGATTCTCCCAACAAAGCAATGG

AGTGGAAAGATCCAGTAGCAGAGCCAGGGTCGATTAGCTCCAAAACGGAAAATGCGGAACTGAG

ATGGCGAAGGCCTTTGGAGACATACTGCATGTGATTATCGCGTTGAAGCTCCAACATGAGGGTT

TGGGCGTTGCGAGGAATGGTGGCgagctcgaatttccccgatcgttcaaacatttggcaataaa gtttcttaagattgaatcctgttgccggtcttgcgatgattatcatataatttctgttgaatta cgttaagcatgtaataattaacatgtaatgcatgacgttatttatgagatgggtttttatgatt agagtcccgcaattatacatttaatacgcgatagaaaacaaaatatagcgcgcaaactaggata aattatcgcgcgcggtgtcatctatgttactagatcgggaattc (Upper Case: MuA Promoter; Underlined: Antisense GmFTB; Lower ease: NOS terminater)

GGAGCCATAGATGCAATTCAATCAAACTGAATTTCTGCAAGAATCTCAAAACACGGAGATCTCA SEQ ID NO:60

AAGTTTGAAAGAAAATTTATTTCTTCGACTCAAAACAAACTTACGAAATTTAGGTAGAACTTAT

ATACATTATATTGTATTTTTTTGTTAACAAATGTTTTTATTATTATTATAGAATTTTACTGGTT

-continued

AAATTAAAAATGAATAGAAAAGGTGAATTAAGAGGAGAGAGGAGGTAAACATTTTCTTCTATTT

TTTCATATTTTCAGGATAAATTATTGTAAAAGTTTACAAGATTTCCATTTGACTAGTGTAAATG

AGGAATATTCTCTAGTAAGATCATTATTTCATCTACTTCTTTTATCTTCTACCAGTAGAGGAAT

AAACAATATTTAGCTCCTTTGTAAATACAAATTAATTTTCCTTCTTGACATCATTCAATTTTAA

TTTTACGTATAAAATAAAAGATCATACCTATTAGAACGATTAAGGAGAAATACAATTCGAATGA

GAAGGATGTGCCGTTTGTTATAATAACAGCCACCACGACGTAAACGTAAAATGACCACATGATG

GGCCAATAGACATGGACCGACTACTAATAATAGTAAGTTACATTTTAGGATGGAATAAATATCA

TACCGACATCAGTTTTGAAAGAAAAGGGAAAAAAAGAAAAAATAAATAAAAGATATACTACCGA

CATGAGTTCCAAAAAGCAAAAAAAAAGATCAAGCCGACACAGACACGCGTAGAGAGCAAAATGA

CTTTGACGTCACACCACGAAAACAGACGCTTCATACGTGTCCCTTTATCTCTCTCAGTCTCTCT

ATAACTTAGTGAGACCCTCCTCTGTTTTACTCACAAATATGCAACTAGAAAACAAAATCATCAG

GAATAAAGGGTTTGATTACTTCTATTGGAAAGGTGGTGGAGAATCTGGGTGCTTTGACCAACTA

TACTGGCACAATGAGAGTCCACTTAAACAGTAACATGTGTGATAATGATCTCTACGTTTACCCG

GTTTGTCTCTCAGTCCACCCTCTTGCTCCTGTGCACATAAGAGAATATATTGCTGTAAAGCAAT

ACTGTGAAAAAGTGGTTCTTGTGCTCTCCACTCATTAATAAATTTATAGGCAATATTTTTAAAA

TCAGATGAACTGGATTCACTGGTGCCTTCATGCTCACCACGGCATGTTGCATGACTAGAGGTTC

CATCCAAACTTTCTTTTGCTTACAGATACATAAGATACCGCAAAATCTGTGATGTCTCTTCCAT

CTGTTTGTTGATAATAGAAGATAATCTTTGCAATAGAGCAACAGCACCTCCCTGCCAAAAGGAA

TAGCATCCATCCACCAGTTTATTTGTTCTCCCCTGGAATCCACATTCCTTACCTTGTCGGAATA

CCACCCAGTCAACTAATCGAGGCAGATCCAAGTGATTAACCTCACCAATCAGAATCATTGTAGC

TAATCCACAAAAGGTGTACCCACCATGAGCCTCAGAACCAGGCTCACCAGCAATGCCACCCTCA

TATGTTTGACAGCTTATAATGTAGTCTCCAACATTCTGGATCAGCTCATCATCCAAAATGTTCA

AAACACTTGCAACAGAAATGGCAGTGTAGCAAGCTCGAACATCAATTTCACCTTCATCATGCAT

CCTGAATCCACCATTTGGTTGCTTCATCCGCCGCAGAAACCCATACAGTTTATCTCTATTAATT

GATGCCAGGGATTTCTCACCACCCAAAGTAATAAGTGAATTAACAGCAGCATAAGTTGTGGCAA

TATGAGGCATCTGGCCTGGTCCCCCGGCATATCCACCATTCGGATCCTGGCAACGGTTAAGAAA

ATCGATAGCGTTATCTTCGAGTTCATCATCGACGGATTCTCCCAACAAAGCAATGGAGTGGAAG

ATCCAGTAGCAGAGCCAGGGTCGATTAGCGTCCAAAAACGGAAATGCGGAACTGAGATGGCGAA

GGCCTTTGGAGACATACTGCATGTGATTATCGCGTTGAAGCTCCAACATGAGGGTTTGGGCGTT

GCGAGGAATGGTGGCgagctcgaatttccccgatcgttcaaacatttggcaataaagtttctta agattgaatcctgttgccggtcttgcgatgattatcatataatttctgttgaattacgttaagc atgtaataattaacatgtaatgcatgacgttatttatgagatgggtttttatgattagagtccc gcaattatacatttaatacgcgatagaaaacaaaatatagcgcgcaaactaggataaattatcg cgcgcggtgtcatctatgttactagatcgggaattc
(Upper Case: RD29A Promoter; Underlined: Antisense GmFTB; Lower case: NOS) terminater

GAATTCAAATTTTTCGCCAGTTCTAAATATCCGGAAACCTCTTGGGATGCCATTGCCCATCTAT SEQ ID NO:61

CTGTAATTTATTGACGAATAGACGAAAAGGAAGGTGGCCTCCTATAAAGCACATCATTGCGATA

ACAGAAGGCCATTGTTGAAGATACCTCTGCTGACAATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGATGACGCACAATCCAACTATCCATCGCAAAGACCATTGCTCTATA

-continued

TAAGAAAGTTAATATCATTTCGAGTGGCCACGCTGAGCTCGTGGTGGAAGATCTGGGTGCTTTG

ACCAACTATACTGGCACAATGAGAGTCCACTTAAACAGTAACATGTGTGATAATGATCTCTACG

TTTACCCGGTTTGTCTCTCAGTCCACCCTCTTGCTCTGTGCACATAAAGAGAATATATTGCTGT

AAAGCAATACTGTGAAAAAGTGGTTCTTGTGCTCTCCACTCATTPATAAATTTATAGGCAATAT

TTTTAAAATCAGATGAACTGGATTCACTGGTGCCTTCATGCTCACCACGGCATGTTGCATGACT

AGAGGTTCCATCCAAACTTTCTTTTGCTTCAGATACATAAGATACCGCAAAAATCTGTGATGTC

TCTTCCATCTGTTTGTTGATAATAGAAGATAATCTTTGCAATAGAGCAACAGCACCTCCCTGCC

AAAAGGAATAGCATCCATCCACCAGTTTATTTGTTCTCCCCTGGAATCCACATTCCTTACCTTG

TCGGAATACCACCCAGTCAACTAATCGAGGCAGATCCAAGTGATTAACCTCACCAATCAGAATC

ATTGTAGCTAATCCACAIAGGTGTACCCACCATGAGCCTCAGAACCAGGCTCACCAAGCAATGC

CACCCTCATATGTTTGACAGCTTATAATGTAGTCTCCAACATTCTGGATCAGCTCATCATCCAA

AATGTTCAAAACACTTGCAACAGAAATGGCAGTGTAGCAAGCTCGAACATCAATTTCACCTTCA

TCATGCATCCTGAATCCACCATTTGGTTGCTTCATCCGCCGCAGAAACCCATACAGTTTATCTC

TATTAATTGATGCCAGGGATTTCTCACCACCCAAAGTAATAAGTGAATTAACAGCAGCATAAGT

TGTGGCAATATGAGGCATCTGGCCTGGTCCCCCGGCATATCCACCATTCGGATCCTGGCAACGG

TTAAGAAAATCGATAGCGTTATCTTCGAGTTCATCATCGACGGATTCTCCCAACAAAGCAATGG

AGTGGAAGATCCAGTAGCAGGGCCAGGGTCGATTAGCGTCCAAAACGGAAAATGCGGAACTGAG

ATGGCGAAGGCCTTTGGAGACATACTGCATGTGATTATCGCGTTGAAGCTCCAACATGAGGGTT

TGGGCGTTGCGAGGAATGGTGGCGGTGAGGTTAATCACTTGGATCTGCCTCGATTAGTTGACTG

GGTGGTATTCCGACAAGGTAGGAATGTGGAATCCAGGGGGAGAACAAATAAACTGGTGGATGGA

TGCTATTCCTTTTGGCAGGGAGGTGCTGTTGCTCTATTGCAAAGATTATCTTCTATTATCAACA

AACAGATGGAAGAGACATCACAGATTTTTGCGGTATCTTATGTATCTGAAGCAAAAGAAAGTTT

GGATGGAACCTCTAGTCATGCAACATGCCGTGGTGAGCATGAAGGCACCAGTGAATCCAGTTCA

TCTGATTTTAAAAATATTGCCTATAAATTTATTAATGAGTGGAGAGCACAAGAACCACTTTTTC

ACAGTATTGCTTTACAGCAATATATTCTCTTATGTGCACAGGAGCAAGAGGGTGGACTGAGAGA

CAAACCGGGTAAACGTAGAGATCATTATCACACATGTTACTGTTTAAGTGGACTCTCATTGTGC

CAGTATAGTTGGTCAAAGCACCCAGATTCTCCACCACgagctcgaatttccccgatcgttcaaa catttggcaataaagtttcttaagattgaatcctgttgccggtcttgcgatgattatcatataa tttctgttgaattacgttaagcatgtaataattaacatgtaatgcatgacgttatttatgagat gggtttttatgattagagtcccgcaattatacatttaatacgcgatagaaaacaaaatatagcg cgcaaactaggataaattatcgcgcgcggtgtcatctatgttactagatcgggaattc
(Upper Case: MuA Promoter; Underlined: Antisense GmFTB; Bold: Sense GmFTB; Lower case: NOS terminater)

GGAGCCATAGATGCAATTCAATCAAACTGAAATTTCTGCAAGAATCTCAAACACGGAGATCTCA SEQ ID NO:62

AAGTTTGAAAGAAAATTTATTTCTTCGACTCAAAACAAACTTACGAAATTTAGGTAGAACTTAT

ATACATTATATTGTAATTTTTTGTAACAAAATGTTTTTATTATTATTATAGAATTTTACTGGTT

AAATTAAAAATGAATAGAAAAGGTGAATTAAGAGGAGAGAGGAGGTAAACATTTTCTTCTATTT

TTTCATATTTTCAGGATAAATTATTGTAAAAGTTTACAGATTTCCATTTGACTAGTGTTAAATG

AGGAATATTCTCTAGTAAGATCATTATTTCATCTACTTCTTTTATCTTCTACCAGTAGAGGAAT

AAACAATATTTAGCTCCTTTGTAAATACAAATTAATTTTCCTTCTTGACATCATTCAATTTTAA

TTTTACGTATAAAATAAAAGATCATACCTATTAGAACGATTAAGGAGAAATACAATTCGAATGA

-continued

GAAGGATGTGCCGTTTGTTATAATAAACAGCCACACGACGTAAACGTAAAATGACCACATGATG
GGCCAAATAGACATGGACCGACTACTAATATAGTAAGTTACATTTTAGGATGGAATAAATATCA
TACCGACATCAGTTTTGAAAGAAAAGGGAAAAAAAGAAAAAATAAATAAAAGATATACTACCGA
CATGAGTTCCAAAAAGCAAAAAAAAAGATCAAGCCGACACAGACACGCGTAGAGAGCAAAATGA
CTTTGACGTCACACCACGAAAACAGACGCTTCATACGTGTCCCTTTATCTCTCTCAGTCTCTCT
ATAAACTTAGTGAGACCCTCCTCTGTTTTACTCACAAATATGCAAACTAGAAAACAATCATCAG
GAATAAAGGGTTTGATTACTTCTATTGGAAAGGTGGTGGAGAATCTGGGTGCTTTGACCAACTA
TACTGGCACAATGAGAGTCCACTTAAACAGTAACATGTGTGATAATGATCTCTAGCTTTACCCG
GTTTGTCTCTCAGTCCACCCTCTTGCTCCTGTGCACATAAGAAGTTATATTGCTCTAAAGCAAT
ACTGTGAAAAAGTGGTTCTTGTGCTCTCCACTCATTAATAAATTTATAGGCAATATTTTTAAAA
TCAGATGAACTGGATTCACTGGTGCCTTCATGCTCACCACGGCATGTTGCATGACTAGAGGTTC
CATCCAAACTTTCTTTTGCTTCAGATACATAAGATACCGCAAAAATCTGTGATGTCTCTTCCAT
CTGTTTGTTGATAATAGAAGATAATCTTTGCAATAGAGCAACAGCACCTCCCTGCCAAAAGGAA
TAGCATCCATCCACCAGTTTATTTGTTCTCCCCTGGAATCCACATTCCTTACCTTGTCGGAATA
CCACCCAGTCAACTAATCGAGGCAGATCCAAGTGATTAACCTCACCAATCAGAATCATTGTAGC
TAATCCACAAAAGGTGTACCCACCATGAGCCTCAGAACCAGGCTCACCAGCAATGCCACCCTCA
TATGTTTGACAGCTTATAATGTAGTCTCCAACATTCTGGATCAGCTCATCATCCAAAATGTTCA
AAACACTTGCAACAGAAATGGCAGTGTAGCAAGCTCGAACATCAATTTCACCTTCATCATGCAT
CCTGAATCCACCATTTGGTTGCTTCATCCGCCGCAGAAACCCATACAGTTTATCTCTATTAATT
GATGCCAGGGATTTCTCACCACCCAAAGTAATAAGTGAATTAACAGCAGCATAAGTTGTGGCAA
TATGAGGCATCTGGCCTGGTCCCCCGGCATATCCACCATTCGGATCCTGGCAACGGTTAAGAAA
ATCGATAGCGTTATCTTCGAGTTCATCATCGACGGATTCTCCCAACAAAGCAATGGAGTGGAAG
ATCCAGTAGCAGAGCCAGGGTCGATTAGCGTCCAAAACGGAAAATGCGGAACTGAGATGGCGAA
GGCCTTTGGAGACATACTGCATGTGATTATCGCGTTGAAGCTCCAACATGAGGGTTTGGGCGTT
GCGAGGAATGGTGGCGGTGAGGTTAATCACTTGGATCTGCCTCGATTAGTTGACTGGGTGGTAT
TCCGACAAGGTAAGGAATGTGGATTCCAGGGGAGAACAAATAAACTGGTGGATGGATGCTATTC
CTTTTGGCAGGGAGGTGCTGTTGCTCTAATTGCAAGATTATCTTCTATTATCAACAAACAGATG
GAAGAGACATCACAGATTTTTGCGGTATCTTATGTAATCTGAAGCAAAGAAAGTTTGGATGGAA
CCTCTAGTCATGCAACATGCCGTGGTGAGCATGAAGGCACCAGTGAATCCAGTTCATCTGATTT
TAAAAATATTGCCTATAAATTTATTAATGAGTGGAGAGCACAAGAACCACTTTTTCACAGTATT
GCTTTACAGCAATATATTCTCTTATGTGCACAGGAGCAAGAGGGTGGACTGAGAGACAAACCGG
GTAAACGTAGAGATCATTATCACACATGTTACTGTTTAAGTGGACTCTCATTGTGCCAGTATAG
TTGGTCAAAGCACCCAGATTCTCCACCACgagctcgaatttccccgatcgttcaaacatttggc
aataaagtttcttaagattgaatcctgttgccggtcttgcgatgattatcatataatttctgtt
gaattacgttaagcatgtaataattaacatgtaatgcatgacgttatttatgagatgggttttt
atgattagagtcccgcaattatacatttaatacgcgatagaaaacaaaatatagcgcgcaaact
aggataaattatcgcgcgcggtgtcatctatgttactagatcgggaattc
(Upper Case: RD29A Promoter; Underlined: Antisense GmFTB; Bold: Sense GmFTB; Lower case: NOS terminater)

GAATTCAAATTTTTCGCCAGTTCTAAATATCCGGAAACCTCTTGGGATGCCATTGCCCATCTAT SEQ ID NO:63
CTGTAATTTATTGACGAAATAGACGAAAAGGAAGGTGGCTCCTATAAAGCACATCATTGCGATA

-continued

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCCAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCGGATGGATTGGCTCCAGCAAATTA

GAGTACGGTCCAAGCACATGCTGAGGTAATGGGCACGAACCAGTATCAGTCATGGCACTGTACT

GGCTAACTGCGAGGCCACTGAGGCAGTAGCATGAATGATAGTGATCTCTGTTCTTTCCAGGCTT

ATCCCTCAAGCCTCCCTCTAGTACCTGAGAACAAAGTAGGATGTATTGTTGCAGGGCAATGTTA

TGGAAGAGTGGGCCAATTTGGTTGCTCTGTTGTATAAAATCAAATCCAAACTTCGCATAGTCCA

CAGCAGAGGAAGACTTATTCGCGGTGCACCCATATGAACTGGTGCTGCAGGCATCCTCTCCTGA

TGGCCTTTTGCAGGAATACGAGGACCTCAATTGCTTATCAACAATCGTAATTAACTTTTGTGTG

AAAGCAATGGCAGCTCCCTGCCAAAAGGAGTAGCAACCATCAACCAATTTATTAGTTCGTCCTT

GAAATCCGCATTCCACTCCTTGACGAAAAGCCACCCAGCCTAATCAACTAGGCAAGTCAACTTT

CTCTGCCTCATTAAGCAGGATCCAAAGCAGCCAATCCACAGAATGTATACCACCATGTGCTTCA

GCATAAGGCTCCCCAGCAATACCACCTTCATAAGTTTGACATCTTGCTATGTAGTCGCCTACAC

CTTTTGCCAGTTTAAATCAAGAATATTCACAAGGCTGGCAAACCGATATAGCGGTGTAGGAAGC

ACGGACATCAATTTCGCCACCATCATGCATTCTGAAAGCACCTGATACATCTTTCATCTGCAGC

ATAAAATTGTACAGGTTGCCCCTATTGATTGATGACAATGCTCTTTCGCTCCCTATTGTCACAA

GTGTATTTACAGCAGCATAAGTCGTAGCTAGGTGAGGCAACTGTCCAGGTCCACCACTATATCC

ACCATCTTTATCCTGACATCGAGCTAAGAGTCTATGAATATCATTCTCAAGATCATCATCAAGT

GCTTCATCCAGCAAAGCAAGTGGATGAACCATCCAGTAGCATAGCCAAGGGCGATTGGCATCTA

GAACATGAAAGGCTGGTCCCATATGCCTCAGCCCAGGCGTCAGATACTCGATATGCTGATCACG

CCACAGCTCTAGCATGATGGATTTCGTGTTGGGCGCGGCCCCGAAGAGGGAGCGGTAGATGTCG

CCAACCCTGGCCTCCACCTTCATCTGCTCCACCTGCGTCACCGTGAGCCTCGGTAGGTCGGGAT

CCGCCgagctcgaatttccccgatcgttcaaacatttggcaataaagtttcttaagattgaatc ctgttgccggtcttgcgatgattatcatataatttctgttgaattacgttaagcatgtaataat taacatgtatgcaatgacgttatttatgagatgggtttttatgattagagtcccgcaattatac atttaatacgcgatagaaaacaaaatatagcgcgcaaactaggataaattatcgcgcgcggtgt catctatgttactagatcgggaattc (Upper Case: MuA Promoter; Underlined: Antisense *Zea maize*-FTB; Lower case: NOS terminater)

GAATTCAAATTTTTCGCCAGTTCTAAATATCCGGAAACCTCTTGGGATGCCATTGCCCATCTAT SEQ ID NO:64

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCGGATGGATTGGCTCCAGCAAATTA

GAGTACGGTCCAAGCACATGCTGAGGTAATGGGCACGAACCAGTATCAGTCATGGCACTGTACT

GGCTAACTGCGAGGCCACTGAGGCAGTAGCATGAATGATAGTGATCTCTGTTCTTTCCAGGCTT

ATCCCTCAAGCCTCCCTCTAGTACCTGAGAACAAAGTAGGATGTATTGTTGCAGGGCAATGTTA

-continued

TGGAAGAGTGGGCCAATTTGGTTGCTCTGTTGTATAAAATCAAATCCAAACTTCGCATAGTCCA

CAGCAGAGGAAGACTTATTCGCGGTGCACCCATATGAACTGGTGCTGCAGGCATCCTCTCCTGA

TGGCCTTTTGCAGGAATACGAGGACCTCAATTGCTTATCAACAATCGTAATTAACTTTTGTGTG

AAAGCAATGGCAGCTCCCTGCCAAAAGGAGTAGCAACCATCAACCAATTTATTAGTTCGTCCTT

GAAATCCGCATTCCACTCCTTGACGAAAAGCCACCCAGCCAATCAAACTAGGCAAGTCAACTTT

CTCTGCCTCATTAAGCAGGATCAAAGCAGCCAATCCACAGAATGTATACCCACCATGTGCTTCA

GCATAAGGCTCCCCAGCAATACCACCTTCATAAGTTTGACATCTTGCTATGTAGTCGCCTACAC

CTTTTGCCAGTTTAAAATCAAGAATATTCACAAGGCTGGCAACCGATATAGCGGTGTAGGAAGC

ACGGACATCAATTTCGCCACCATCATGCATTCTGAAAGCACCTGATACATCTTTCATCTGCAGC

ATAAAATTGTACAGGTTGCCCCTATTGATTGATGACAATGCTCTTTCGCTCCCTATTGTCACAA

GTGTATTTACAGCAGCATAAGTCGTAGCTAGGTGAGGCAACTGTCCAGGTCCACCACTATATCC

ACCATCTTTATCCTGACATCGAGCTAAGAAGTCTATGATATCATTCTCAAGATCATCATCAAGT

GCTTCATCCAGCAAAGCAAGTGGATGAACCATCCAGTAGCATAGCCAAGGGCGATTGGCATCTA

GAACATGAAAGGCTGGTCCCATATGCCTCAGCCCAGGCGTCAGATACTCGATATGCTGATCACG

CCACAGCTCTAGCATGATGGATTTCGTGTTGGGCGCGGCCCCGAAGAGGGAGCGGTAGATGTCG

CCAACCCTGGCCTCCACCTTCATCTGCTCCACCTGCGTCACCGTGAGCCTCGGTAGGTCGGGAT

CCGCCggatccGCTGGGGAGCCTTATGCTGAAGCACATGGTGGGTATACATTCTGTGGATTGGC

TGCTTTGATCCTGCTTAATGAGGCAGAGAAAGTTGACTTGCCTAGTTTGATTGGCTGGGTGGCT

TTTCGTCAAGGAGTGGAATGCGGATTTCAAGGACGAACTAATAAATTGGTTGATGGTTGCTACT

CCTTTTGGCAGGGAGCTGCCATTGCTTTCACACAAAAGTTAATTACGATTGTTGATAAGCAATT

GAGGTCCTCGTATTCCTGCAAAAGGCCATCAGGAGAGGATGCCTGCAGCACCAGTTCATATGGG

TGCACCGCGAATAAGTCTTCCTCTGCTGTGGACTATGCGAAGTTTGGATTTGATTTTATACAAC

AGAGCAACCAAATTGGCCCACTCTTCCATAACATTGCCCTGCAACAATACATCCTACTTTGTTc

TCAGGTACTAGAGGGAGGCTTGAGGGATAAGCCTGGAAAGAACAGAGATCACTATCATTCATGC

TACTGCCTCAGTGGCCTCGCAGTTAGCCAGTACAGTGCCATGACTGATACTGGTTCGTGCCCAT

TACCTCAGCATGTGCTTGGACCGTACTCTAATTTGCTGGAGCCAATCCATCCaagcttgaattt ccccgatcgttcaaacatttggcaataaagtttcttaagattgaatcctgttgccggtcttgcg atgattatcatataatttctgttgaattacgttaagcatgtaataattaacatgtaatgcatga cgttatttatgagatgggtttttatgattagagtcccgcaattatacatttaatacgcgataga aaacaaaatatagcgcgcaaactaggataaattatcgcgcgcggtgtcatctatgttactagat cggaagctt
(Upper Case: MuA Promoter; Underlined: Antisense *Zea maize*-FTB;
Bold:
Sense *Zea maize*-FTB; Lower case: NOS terminater)

(Upper Case: MuA Promoter; Underlined: Antisense *Zea maize*—FTB; Bold: Sense *Zea maize*—FTB; Lower case: NOS terminater)

Example 15

PCR Analysis of Putative Transgenic Plants

To verify that the putative transgenic plants carried the gene of interest PCR analysis was performed. Genomic DNA was isolated and PCR run according to standard protocols and conditions which are known to one of skill in the art. A typical reaction was performed in a volume of 25 μl and primer pairs used were dependent on the gene and promoter combination of the particular construct (Table 12).

Figure 24:
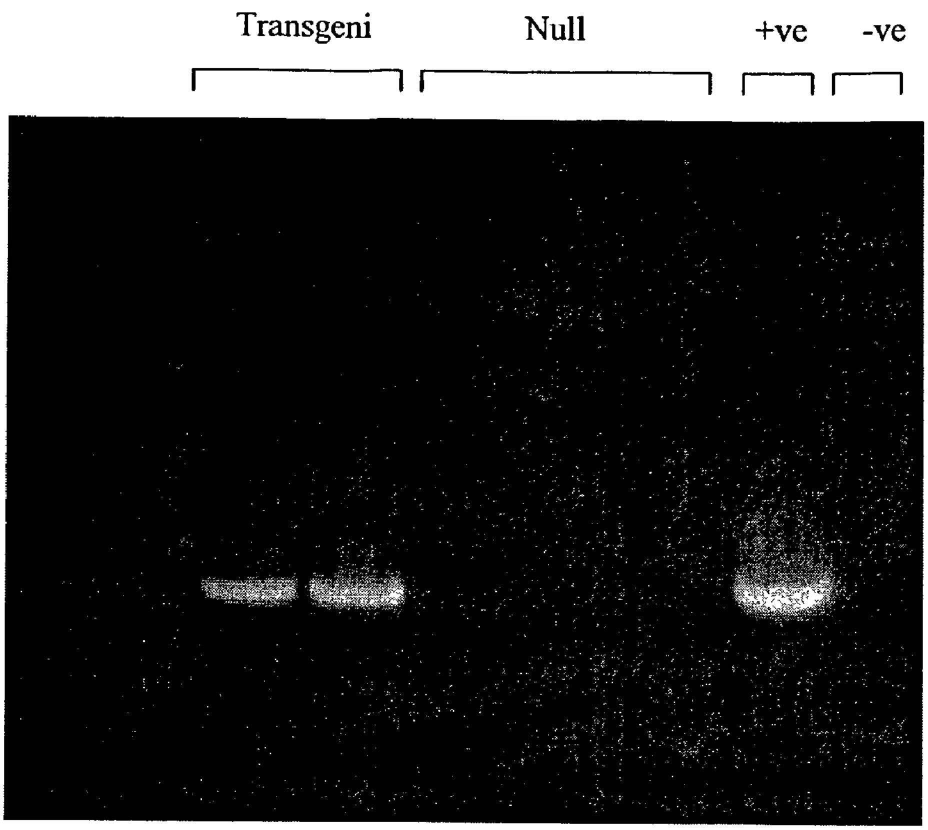
FIG. 24 is a representative illustration of gel electrophoresis analysis of PCR products in an assay to detect transgenic lines of *Brassica napus.*

Putative transgenic *Brassica napus* plants were screened using the primer combinations detailed in the table below. A representative gel showing PCR analysis results is shown in FIG. 24 which represents transgenic plants carrying the pRD29A-anti-FTA construct. Transformants were confirmed in an analogous manner for each species and construct transformation done.

TABLE 12

| Construct Name | Primer Name | Primer Sequence (5'-3') |
|---|---|---|
| 35S-antiFTA | SEQ ID NO:16 | GCCGACAGTGGTCCCAAAGATGG |
| | SEQ ID NO:17 | AAAGGATCCTCAAATTGCTGCCACTGTAAT |
| rd29A-antiFTA | SEQ ID NO:18 | AAACCCGGGATGAATTTCGACGAGAACGTG |
| | SEQ ID NO:19 | GCAAGACCGGCAACAGGA |
| rd29B-antiFTA | SEQ ID NO:20 | TTTAAGCTTGACAGAAACAGTCAGCGAGAC |
| | SEQ ID NO:17 | AAACCCGGGATGAATTTCGACGAGAACGTG |
| 35S-DA-FTA | SEQ ID NO:21 | GCTCTTCCTCCATGCCCA |
| | SEQ ID NO:19 | GCAAGACCGGCAACAGGA |
| rd29A-DA-FTA | SEQ ID NO:22 | TTTAAGCTTGGAGCCATAGATGCAATTCAA |
| | SEQ ID NO:23 | CGGGCATTAGGAGGATGGGAA |
| 35S-HP-FTB | SEQ ID NO:16 | GCCGACAGTGGTCCCAAAGATGG |
| | SEQ ID NO:24 | GTCCGGAATTCCCGGGTC |
| rd29A-HP-FTB | SEQ ID NO:22 | TTTAAGCTTGGAGCCATAGATGCAATTCAA |
| | SEQ ID NO:24 | GTCCGGAATTCCCGGGTC |

Example 16

Southern Analysis

Figure 11:
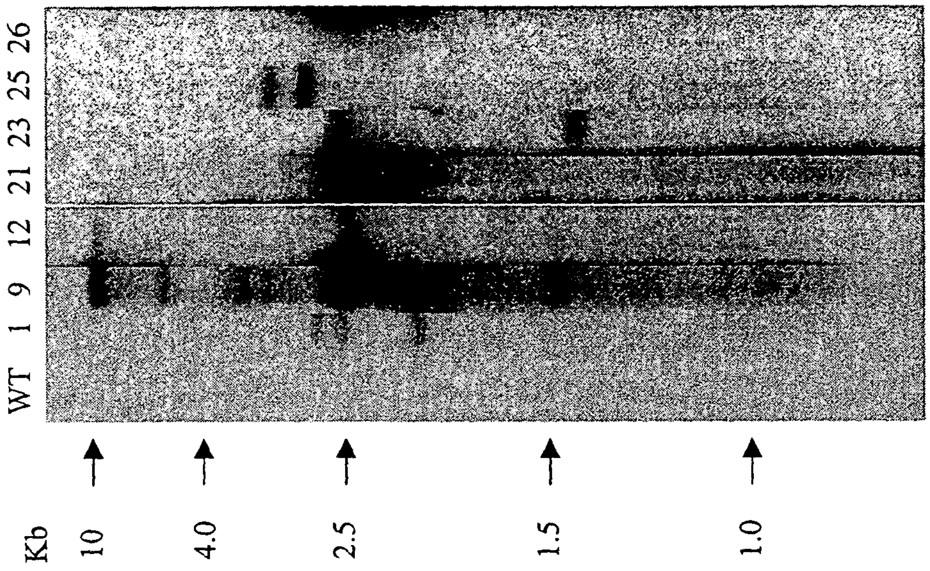
FIG. 11 is an illustration of genomic Southern hybridization analysis of anti-FTA transgenic *Arabidopsis thaliana.*

Genomic Southern analysis of anti-FTA transgenic *Arabidopsis thaliana*. The numbers indicate the line numbers. Five micrograms of genomic DNA of T1 plants was digested with HindIII (a unique site in the T-DNA plasmid) and separated in a 0.8% agarose gel. The NPTII coding region was used as the probe for radio-labeling. FIG. 11 shows a typical result from Southern analysis indicating the presence of the transgene.

Example 17

Northern Blots of Antisense FTA Lines

Figure 12:
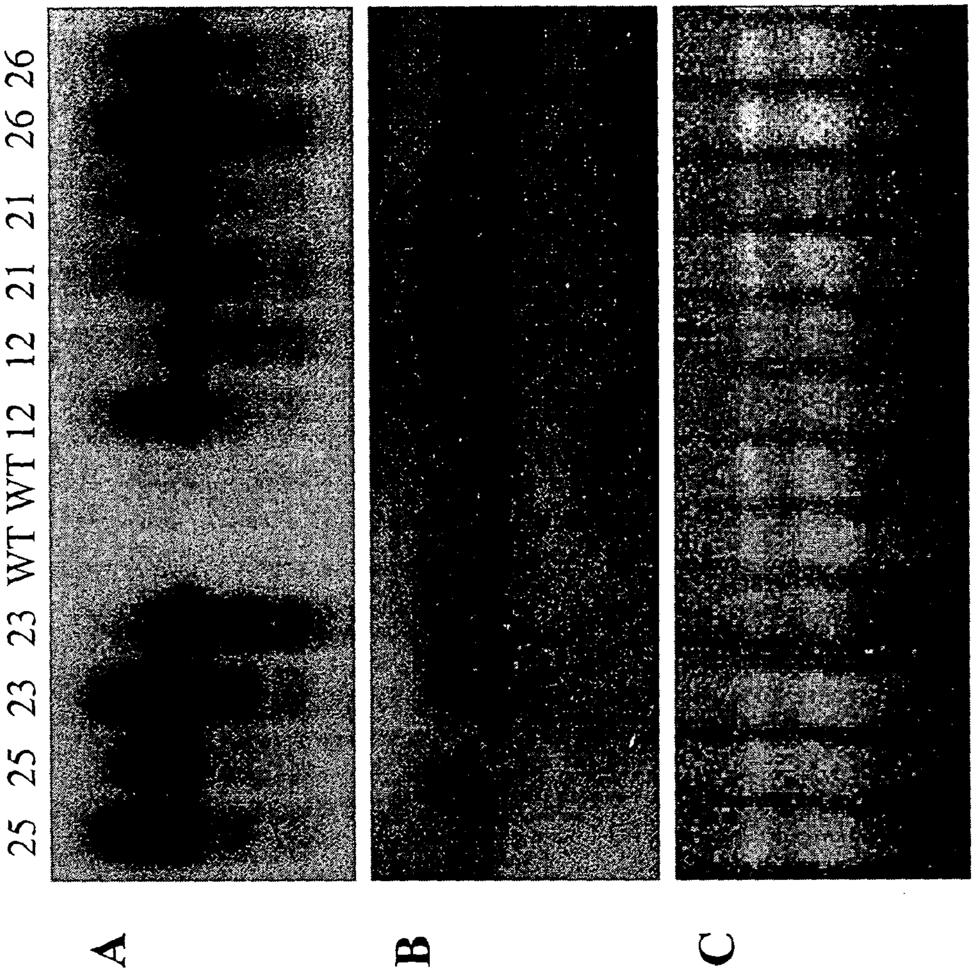
FIG. 12 is an illustration of Northern analysis of five 35S-anti-FTA *Arabidopsis thaliana* lines (T3 plants).

RNA was isolated from developing leaf tissue of five 35S-anti-FTA *Arabidopsis thaliana* lines (T3 plants). The blot was first probed with $P^{32}$ labeled, single-stranded sense transcript of FTA (FIG. 3 panel A) which detects antisense transcript, then stripped and re-probed with the single-stranded anti-sense transcript of FTA (FIG. 12 panel B) that detects the sense transcript. FIG. 3 panel C shows the ethidium bromide stained gel for the blot. Approximately 5 μg of total RNA was loaded into each lane. FIG. 3 indicates the accumulation of the transgene anti-sense transcript and a reduction in the sense transcript in transgenic plants.

Example 18

Western Blot Antisense FTA Lines with Anti-FT-c Antibodies

Figure 13:
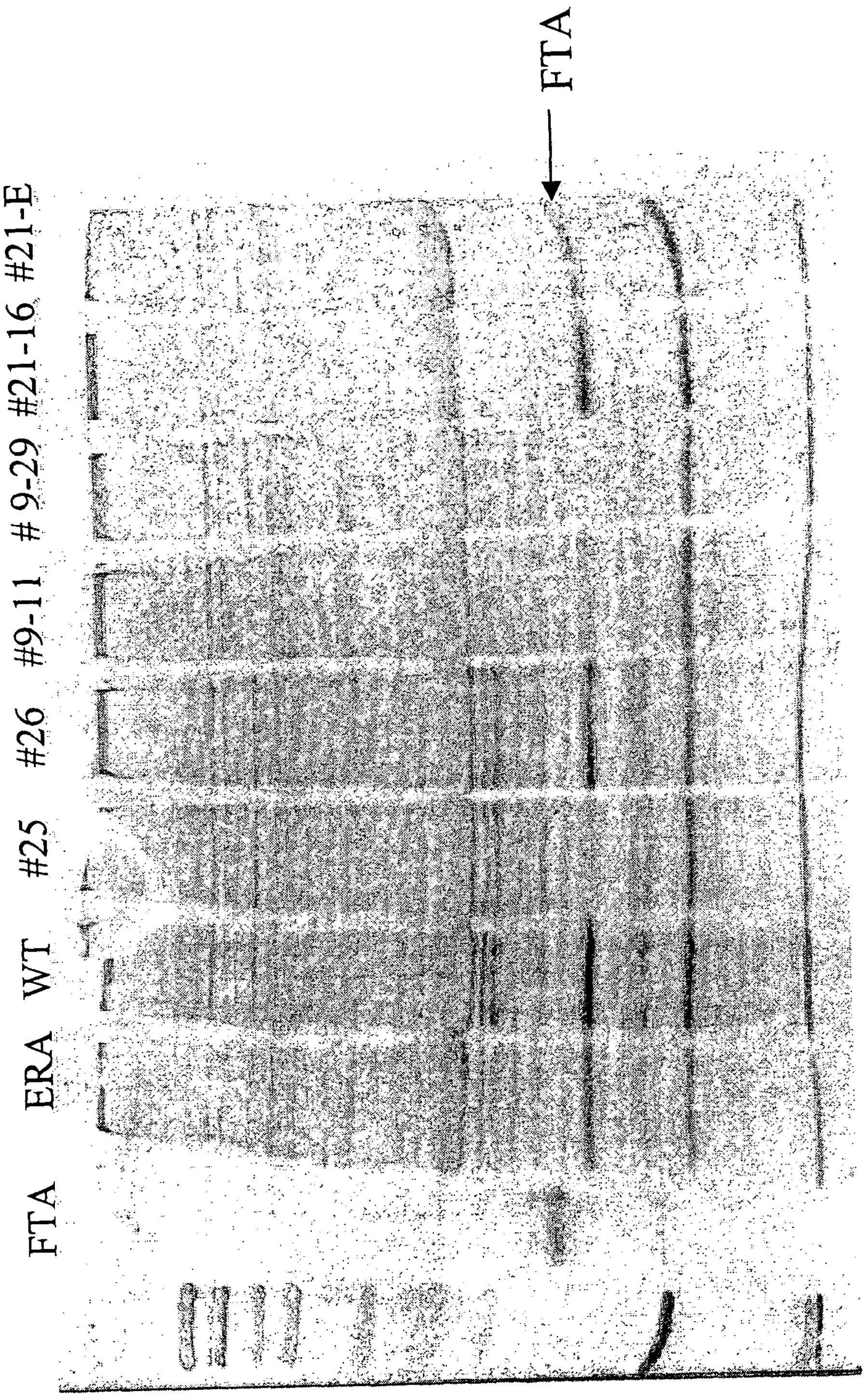
FIG. 13 shows a Western expression analysis using anti-FTA antibodies to detect the FTA polypeptides.

The antibodies produced according to the methods of Example 27 were used to analyze protein extracts from transgenic plants on western blots. Lane 1 of FIG. 13 is a molecular weight standard, lane 2 purified FTA protein, lanes 3-10 are protein extracts from the ERA1 mutant, wild type, and 4 lines of transgenic *Arabidopsis thaliana*. FIG. 13 illustrates the reduction of detectable FTA protein in transgenic lines.

Example 19

ABA Sensitivity of Transgenic Seedlings

Figure 14:
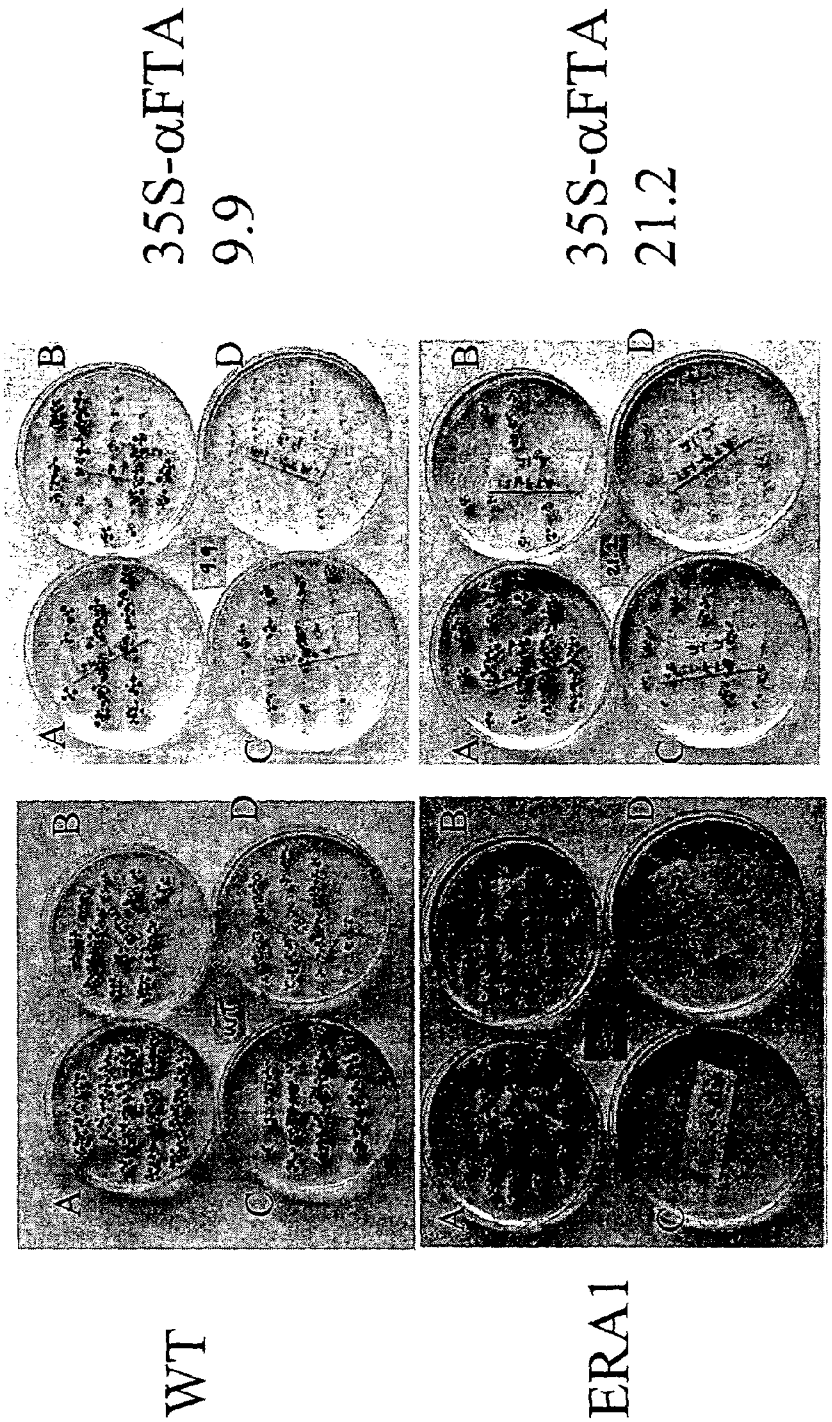
FIG. 14 is a set of photographs showing ABA effects on seedling growth and development. FTA antisense transgenic seedlings exhibit enhanced ABA sensitivity.

Seeds of wild type Columbia, era1-2 and T3 homozygous seeds of two antisense, drought tolerant lines of 35S-antisense-FTA were plated on minimum medium (½ MS) supplemented with no ABA (A), 0.3 μM (B), 0.5 μM (C) or 1.0 μM ABA (D). Plates were chilled for 3 days in 4° C. in the dark, and incubated for 11 days at 22° C. with 24 hour continuous light. era1 and transgenic lines were more inhibited in germination than wild type plants. Results are shown in FIG. 14.

Figure 15:
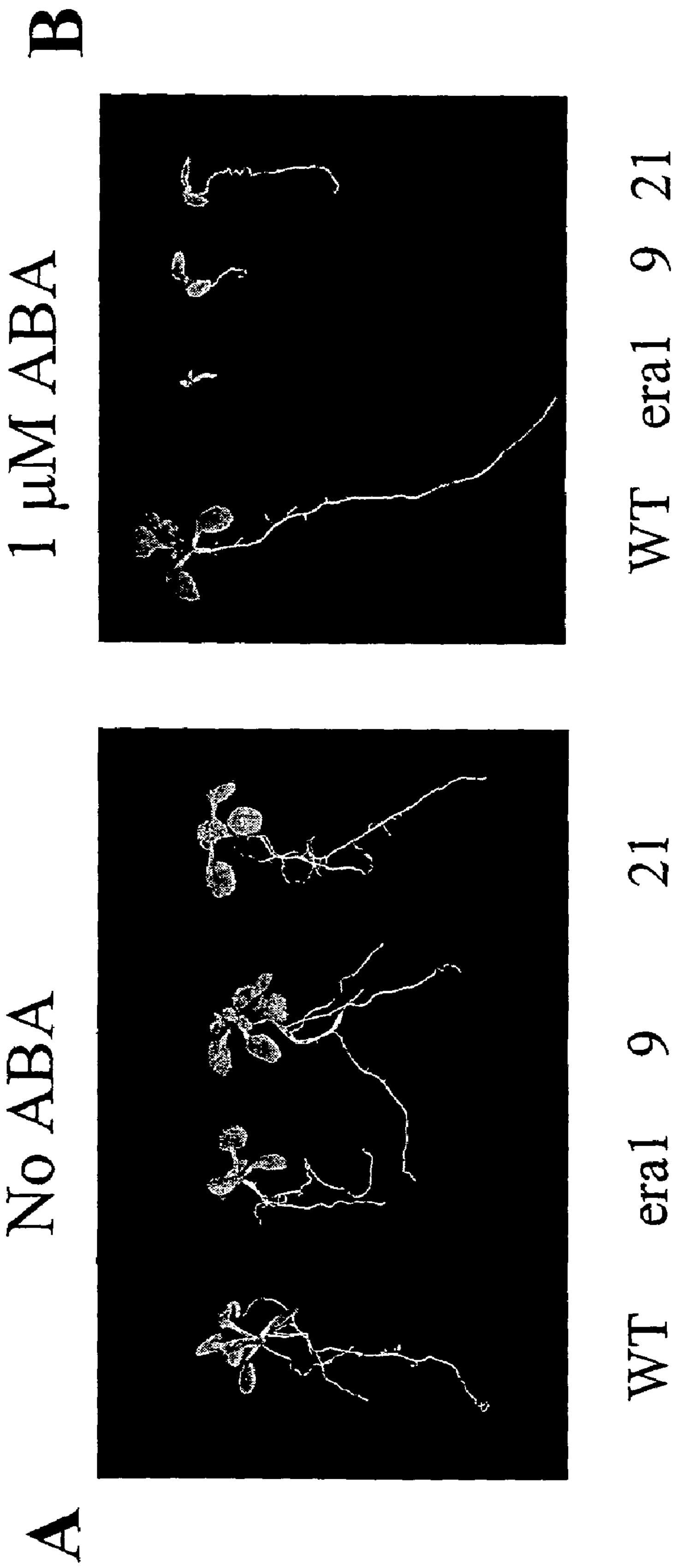
FIG. 15 shows the effect of ABA on seedling growth and development.

Twelve day old seedling phenotypes of wild type Columbia, era1-2 and two drought tolerant 35S-antisense-FTA lines (9.9 & 21.2) in minimum medium without (A) or with (B) 1 μM ABA. FIG. 15 shows-the reduced root growth and development of era1 and transgenic lines relative to wild type plants. The 35S-antisense-FTA lines show reduced root growth, similar to the era1 mutant, in response to ABA.

A transgenic *Brassica napus* line carrying the 35S-antisense-FTA construct was assessed for ABA sensitivity. At about 10 μm an effect was observed showing reduced seedling development and vigor at the cotyledon and first leaf stage, thereby indicating an increased sensitivity to ABA ABA sensitivity is assessed in all transgenic plants engineered to have reduced or increased FTA or FTB expression or activity by the methods above. The ABA concentration used varies depending upon the species under examination.

Example 20

Drought Experiment

To assess the response of plants under water stress or drought one can expose plants to various situations. For example, the plant can be removed from soil or media and placed on paper towel for a period of time, such as 4 hours, then returned to a plate to continue growth and development. Survival and vigor can be assessed.

Figure 16:
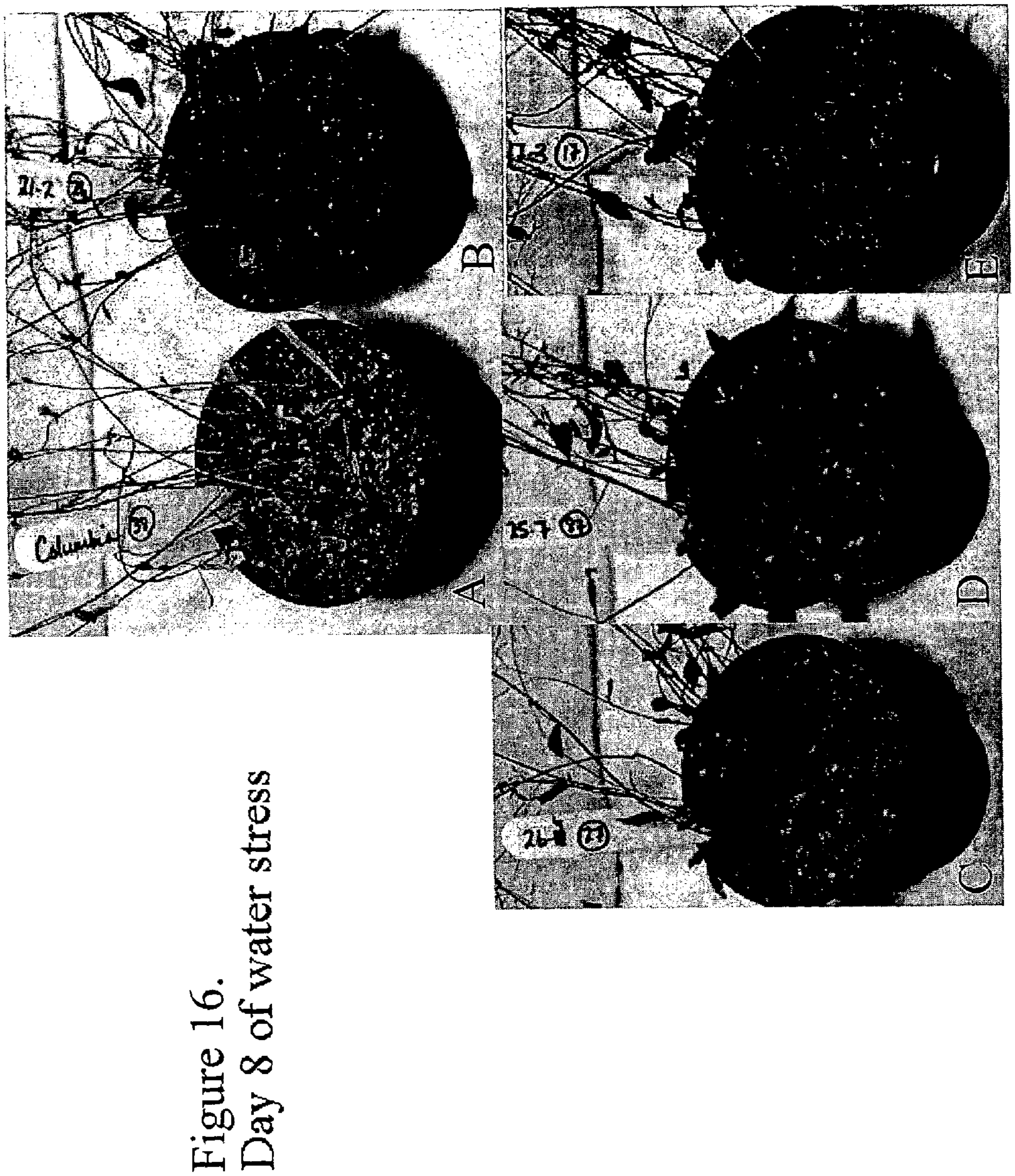
FIG. 16 shows photographs of wild type *Columbia* (A) and four antisense FTA transgenic lines (B, C, D, E) of *Arabidopsis thaliana* after 8 days without watering.
Figure 19:
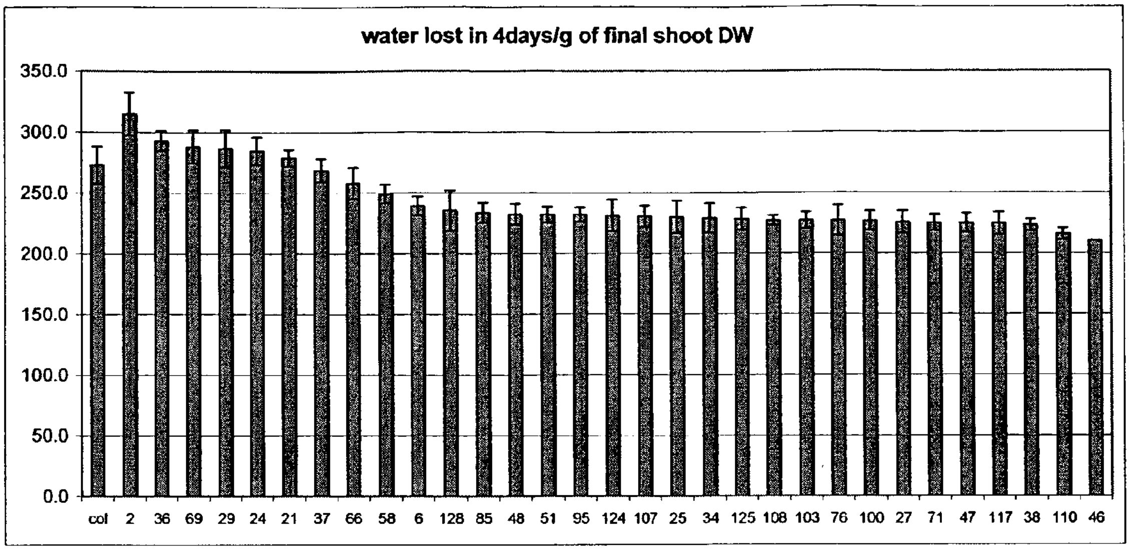
FIG. 19 is an illustration of transgenic performance during water stress.

Alternatively one can impose a water stress in such a way as to more closely resemble a field situation by withholding water for a period of time, such as up to 6 days. Plants were grown five plants per four inch pot, in a replicated water-stress experiment. All pots were filled with equal amounts of homogeneous premixed and wetted soil. Growth conditions were 16 hour daylight (150-200 $\mu mol/m^2/s$) at 22° C. and 70% relative humidity. On the day that the first flower opened drought treatment was initiated first by equalizing the soil water content in each pot on a weight basis and then cessation of watering. At the end of the water stress treatment plants were typically either harvested for biomass data or re-watered to complete the life cycle and determination of biomass and yield data. Physiological parameters have been assessed under stressed and optimal conditions, for example, shoot and root biomass accumulation, soil water content, water loss alone or as a function of parameters such as biomass, seed yield, and leaf number and leaf area. FIG. 16 shows photographs of wild type *Columbia* (A) and four 35S-antisense-FTA transgenic *Arabidopsis thaliana* lines (B,C,D,E) after 8 days of water stress treatment. The control plant is visibly stressed and less healthy. This experiment has been conducted on transgenic lines containing vectors described by SEQ ID NO: 10, 46-64.

Drought or water stress tolerance is assessed in all transgenic plants engineered to have reduced or increased FTA or FTB expression or activity by the described methods.

Example 21

Figure 10:
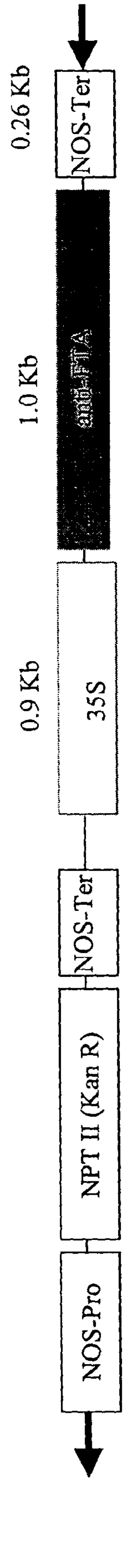
FIG. 10 is an illustration depicting the pBI121 antisense FTA vector construct.

Analysis of Water Loss in *Arabidopsis thaliana* pRD29A-DA-FTA Lines During Drought Stress Plants were grown 5 plants per 4 inch pot and 6 pots per line. When the plants had grown to the first flower stage drought treatment was initiated as described in Example 20. Pots were weighed daily and at the end of the 7 day drought treatment all plants were harvested for shoot fresh weight and dry weight determinations. FIG. 10 shows the water loss on a per shoot dry weight basis at 4 days of water stress treatment. Of the 31 lines examined in this experiment 25 showed lower water loss relative to the *Columbia* wild type, 22 of which were statistically significant. All lines had been assessed for ABA sensitivity as described in Example 14, increased ABA sensitivity ($ABA^S$) also correlated with a decreased water loss during drought treatment. Those lines determined to have wild type ABA sensitivity ($ABA^{WT}$) were the same 6 lines (lines 2, 36, 69, 29, 24, 21) that did not show a reduced water loss compared to wild type.

The above experiment was repeated using two $ABA^S$ lines, one $ABA^{WT}$ line and a Columbia control. Plants were harvested after 2, 4 and 6 days of water stress treatment for shoot dry weight determinations. $ABA^S$ transgenics had greater leaf and shoot biomass, greater soil water contents and lower water loss per shoot dry weight when compared to the $ABA^{WT}$ or Columbia controls. Results were consistent at all three harvest stages.

The data shown in this example was obtained using transgenic plants carrying the pRD29A-DA-FTA construct. The experiment has also been conducted on lines carrying variations of this construct such as 35S-DA-FTA, pRD29A-antisense-FTA or 35S-antisense-FTA, with similar water stress tolerant trends observed. Soil water loss is assessed in all transgenic plants engineered to have reduced or increased FTA or FTB expression or activity by the described methods.

Example 22

Figure 20:
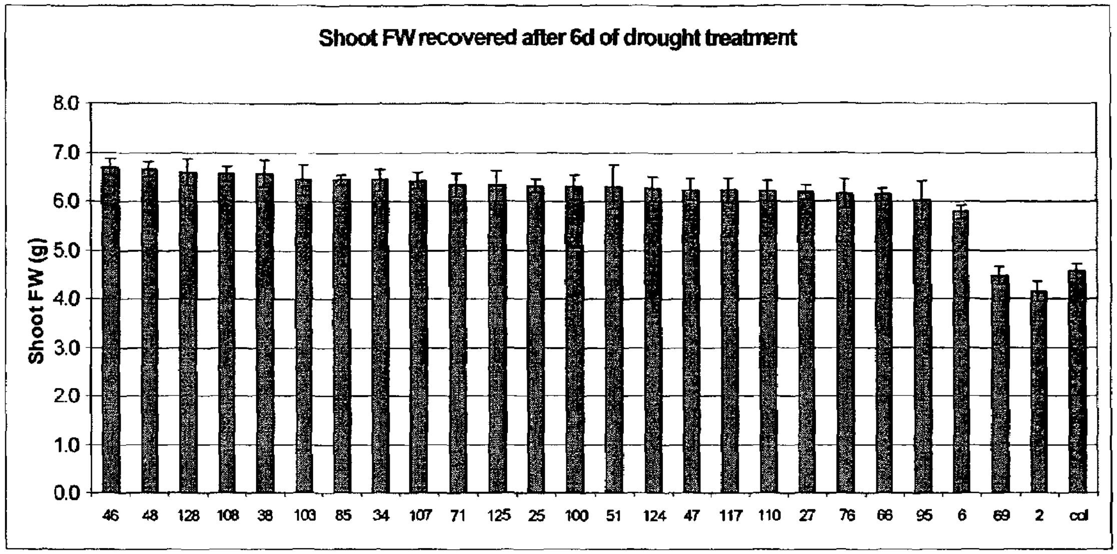
FIG. 20 is an illustration of shoot fresh weight, or biomass accumulation, after 6 days of water stress treatment and 6 days recovery time.

Analysis of Shoot Fresh Weight in *Arabidopsis thaliana* pRD29A-DA-FTA Lines During Drought Stress Plants were grown 5 plants per 4 inch pot and 8 pots per line. When the plants had grown to the first flower stage drought treatment was initiated as described in Example 20. Plants were re-watered after 6 days drought treatment and allowed to recover for an additional 6 days. Plants were harvested and shoot fresh weights determined. FIG. 20 shows the shoot fresh weights. This experiment consisted of 25 transgenic lines, 2 of which are $ABA^{WT}$ (line 2 and 69) and a *Columbia* wild type control. All 23 $ABA^S$ transgenic lines had statistically significant greater shoot fresh weights, on average 44% greater.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 23

Analysis of Seed Yield in *Arabidopsis thaliana* pRD29A-DA-FTA Lines During Drought Stress and Under Optimal Conditions Plants were grown 1 plant per 4 inch pot. When the plants had grown to the first flower stage drought treatment was initiated as described in Example 20. Plants were re-watered after 6 days drought treatment and allowed to grow to maturity. The optimal group was not exposed to the drought treatment.

Figure 21:
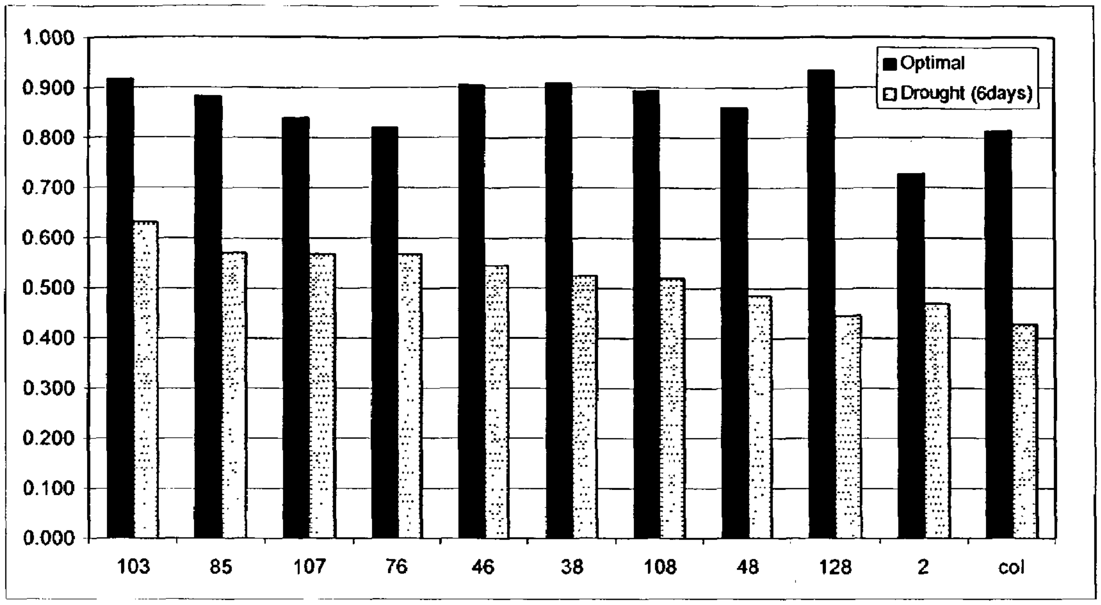
FIG. 21 is an illustration of seed yield (grams) obtained under optimal conditions or following a 6 day water stress treatment.

Yield analysis indicates that although drought treatment results in decreased yields, the transgenics do not suffer as severely as controls and maintain a productivity advantage (FIG. 21) as shown previously in Experiment 22. Comparison of the yields produced by the $ABA^S$ transgenics versus the control plants show that a 15% greater yield was obtained under optimal conditions and a 20% increase under drought conditions. In the drought treatment group 8 of 9 transgenic lines showed greater yield than controls. Expression of yield of each line obtained under drought treatment as a percentage of its performance under optimum conditions indicates that 8 of 9 $ABA^S$ lines outperformed the control line while 4 of 9 out performed the $ABA^{WT}$ controls.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 24

Figure 22:
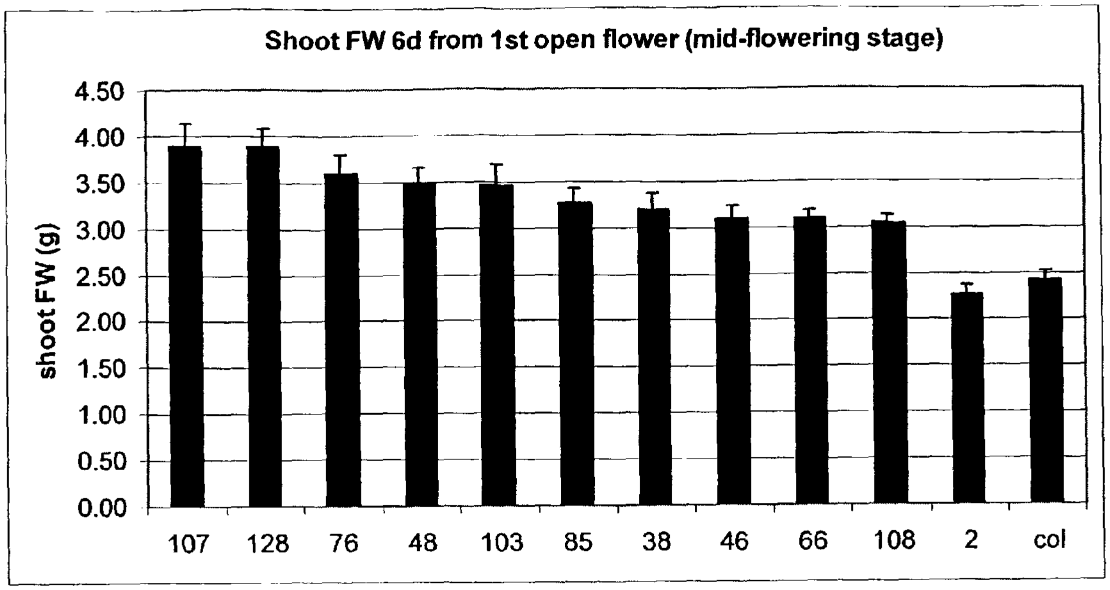
FIG. 22 is an illustration of vegetative growth under optimal conditions, shown is shoot fresh weight 6 days after the first flower opened.

Analysis of Vegetative Growth in *Arabidopsis thaliana* pRD29A-DA-FTA Lines Under Optimum Growth Conditions Plants were grown 1 plant per 3 inch pot and 8 pots per line. Plants were harvested at three stages and fresh weights determined. Vegetative stage was defined as 14 day old seedlings, bolting stage as the appearance of first flower (19-21 day seedlings) and mid-flowering as 6 days from first flower. At each of the above stages respectively 7, 8 and 10 of the 10 $ABA^S$ transgenic lines tested showed statistically greater shoot fresh weight biomass than the control plants (FIG. 22). One *Columbia* line and an $ABA^{WT}$ (line 2) line were used as the control group. Additionally, there was a statistically significant trend for the transgenic lines to have an increased number of rosette leaves.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 25

Figure 23:
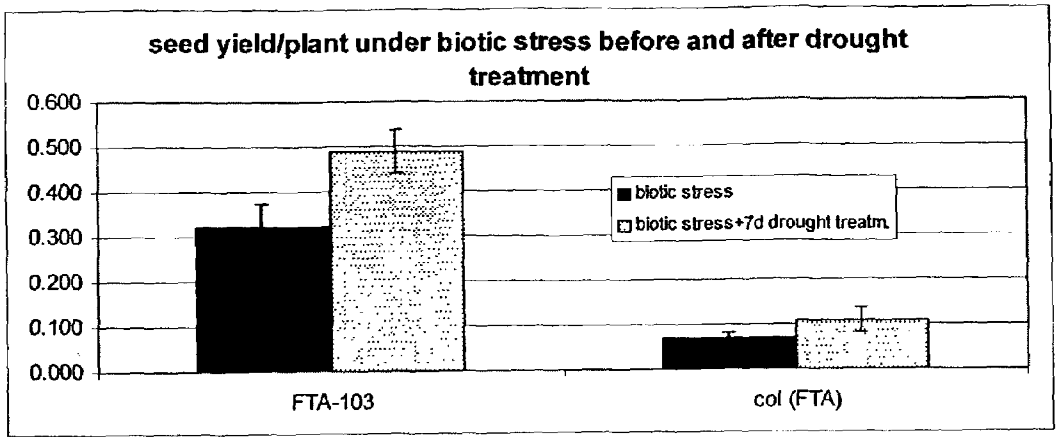
FIG. 23 is an illustration of the effect of a biotic stress coupled with drought stress treatment on seed yield.

Analysis of *Arabidopsis thaliana* pRD29A-DA-FTA Lines Under Drought Treatment and Biotic Stress Plants were grown 1 plant per 4 inch pot and 8 pots. When the plants had grown to the first flower stage drought treatment was initiated as described in Example 20. Plants were re-watered after 7 days drought treatment and allowed to grow to maturity. One Columbian control line (col) and one transgenic line were evaluated. Analysis of seed yield indicated less than normal yields, approximately 12% of expected optimal yield. It was determined that the soil used contained a fingal contaminant that was responsible for the reduced yields as the biotic stress could be negated by sterilization of the soil prior to use. This biotic stress was less severe in the transgenic line compared to the control which had a yield 22% of the transgenic line. In the drought treatment groups of plants the biotic stress was reduced however, transgenics outperformed controls by nearly 4.5 fold (FIG. 23).

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 26

Analysis of *Arabidopsis thaliana* pRD29A-DA-FTA Lines for Stomatal Number

The number of stomata on both the upper and lower surface of the leaf was assessed on two transgenic lines and a wild type *Columbia* control. Nail polish imprints were made of both upper and lower leaf surfaces of the fifth leaf, plants were at the early flowering stage. No differences in stoma density were observed.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 27

Production of Polyclonal Antibodies Against FT-A and FT-B

The isolated *Arabidopsis* thaliana FT sequences were cloned into the *E. coil* expression vector derived from pET11D. To generate the Histidine tagged FT-B construct the *Arabidopsis thaliana* FT-B clone and pET vector were digested with BamHI and ligated together. Restriction digests were performed to verify the orientation of the insert. To produce the FT-A construct the *Arabidopsis thaliana* FT-A clone and pET vector were digested with BamHI and EcoRI and subsequently ligated together. The resultant plasmids directed the expression of fusion proteins containing 6 consecutive histidine residues at the N-termini of AtFTA and AtFTB. The fusion proteins were expressed in the bacterial host BL21(DE3) and purified using Hi-Trap chelating chromatography as described by the manufacturer (Pharmacia). The soluble fraction of the crude bacterial extract containing the His-FT fusion proteins were loaded to a Hi-Trap column (1.5 cm×2.0 cm), and the proteins eluted with a 200 ml linear gradient of 0.0 to 0.3 M imidazole in column buffer (25 mM Tris-HCl, pH 7.5, 1 mM DTT). Fractions containing purified His-FT proteins were pooled, desalted and concentrated with a Centriprep-30 concentrator (Amicon). All purification steps were carried out at 4° C. To generate an antibody, the purified fusion protein was further separated by SDS/PAGE and the Coomassie stained band corresponding to the fusion protein was excised. Protein was eluted from the gel slice by electroelution and then emulsified in Ribi adjuvant (Ribi Immunochem) to a final volume of 1 ml. His-AtFTA or His-AtFTB (250 μg) were injected into a 3 kg New Zealand rabbit on day 1 and booster injections given on day 21 and day 35 with 200 μg of the protein. High-titer antisera were obtained one week after the final injection. These antibodies were used in the western analysis of example 18, FIG. 13.

Example 28

Screening for Related Genes

The transgenic plants of the invention can be used to identify genes which interact with the genes of the present invention. One can make use of the transgenic plants of the invention to screen for related genes, for example, suppressors, enhancers or modulators of gene expression or activity can be identified through genetic screening protocols. By way of example, a mutant library can be generated using the transgenic plants of the invention as the genetic background. Various methods are available and would be known to one of skill in the art. For example, chemical mutagens such as EMS can be used to induce point mutations in the genome, fast neutron irradiation of seeds can result in deletion mutations, T-DNA libraries can be produced that inactivate genes through insertional effects or activation tagging methods can be used to produce libraries with up-regulated genes. Analysis of these types of libraries can identify genes which rescue or modulate the phenotypes observed in the transgenic plants of the present invention.

Example 29

RT-PCR Amplification and Cloning of CaaX Prenyl Proteases

Total RNA was isolated from leaf tissue of *Arabidopsis thaliana, Brassica napus* and *Glycine max*, using the Qiagen RNeasy kit and used as template to amplify the CPP genes by RT-PCR. Reaction conditions were as follows; 1× reaction buffer (10 mM Tris-HCl pH 8.8, 1.5 mM $MgCl_2$, 50 mM KCl), dNTP's at 200 μM, 1 pM AtCPP BamFW and AtCPP SmaRV primers, 2.5U. Pfu DNA polymerase, and template plus water to a final volume of 100 μL. Reactions were run at 1 minute 94° C., 1 minute 60° C., 1 minute 72° C., for 30 cycles. Primers used to PCR amplify *Arabidopsis* and Brassica sequences were those identified by SEQ ID NO:101 and SEQ ID NO:102. Primers used to PCR amplify the Glycine sequence were those identified by SEQ ID NO:149 and SEQ ID NO:150. PCR products were separated from the RT-PCR reaction mixture using the Qiagen PCR column spin kit and ligated into the prepared cloning vector, pBluescript KS+. The vector had been prepared by digestion with EcoRV and treated with Taq polymerase in the presence of dTTP to produce a 3' overhand suitable for ligation with the PCR products. The ligation products were transformed into *E. coli* DH5α cells, positive colonies selected and the resulting inserts sequenced. The above methodology is applicable to obtain homologous sequences and may require alternative primers.

TABLE 13

| | | |
|---|---|---|
| AtCPP BamFW: | 5'-AAAGGATCCATGGCGATTCCTTTCATGG-3' | (SEQ ID NO:101 |
| AtCPP SmaRV: | 5'-AAACCCGGGTTAATCTGTCTTCTTGTCTTCTCCA-3' | (SEQ ID NO:102) |
| GmCPP SmaFW: | 5'-AAACCCGGGATGGCGTTTCCCTACATGGAAGCC-3' | (SEQ ID NO:149) |
| GmCPP SacRV: | 5'-AAAGAGCTCTTAGTCTTCCTTCTTATCCGGTTCG-3' | (SEQ ID NO:150) |

Example 30

Vector Construction

Figure 25:
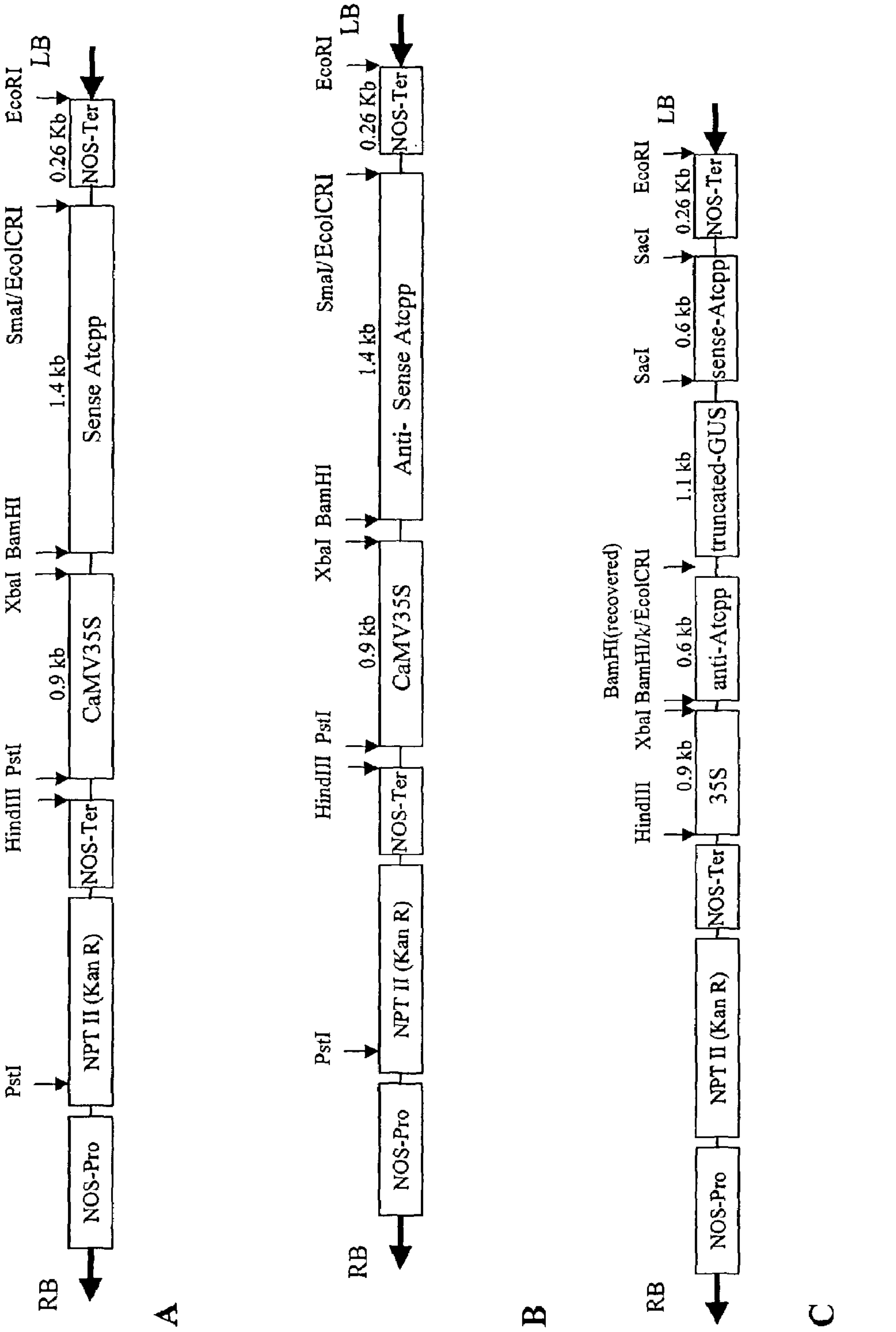
FIG. 25 is a -schematic representation of the vector constructs; A) pBI121-AtCPP, B) pBI121-antisense-AtCPP, C) pBI121-HP-AtCPP.

Construction of the pBI121-AtCPP construct (SEQ ID NO: 99) was prepared as follows. The pBI121 vector was digested with BamHI and SmaI. The AtCPP, 1.4 kb DNA fragment from RT-PCR (SEQ ID NO: 97) was digested with BamHI and SmaI and ligated into the pBI121 vector. The GUS sequence was then removed by digestion with SmaI and EcolCRI and the vector ligated after purification of the vector from the GUS insert to produce the pBI121-AtCPP vector (FIG. 25A). This construct was used to further generate constructs expressing the CPP gene from Brassica and Glycine. To produce the pBI121-BnCPP construct (SEQ ID NO:142) X primer pairs identified by SEQ ID NO:101 and SEQ ID NO:102 are used to PCR amplify the appropriate fragment which is ligated into the prepared parent vector. To produce the pBI121-GmCPP construct (SEQ ID NO:136) primer pairs identified by SEQ ID NO:149 and SEQ ID NO:150 are used to PCR amplify the appropriate fragment which is ligated into the prepared parent vector.

Construction of the pBI121-antisense-AtCPP construct (SEQ ID NO:130). The antisense fragment was produced using PCR amplification with SEQ ID NO:97 as template and primers identified as SEQ ID NO:106 and SEQ ID NO:107, listed in Table 14. This fragment was digested with BamHI and SmaI and used to replace the sense fragment of the pBI121-AtCPP construct (SEQ ID NO:99), to yield SEQ ID NO:130 (FIG. 25B) . This construct, SEQ ID NO:130, was used to further generate constructs expressing the antisense CPP gene from Brassica and Glycine. To produce the pBI121-antisense-BnCPP construct (SEQ ID NO:144) primer pairs identified by SEQ ID NO:151 and SEQ ID NO:152 are used to PCR amplify the appropriate fragment which is ligated into the prepared parent vector. To produce the pBI121-antisense-GmCPP construct (SEQ ID NO:138) primer pairs identified by SEQ ID NO:153 and SEQ ID NO:154 are used to PCR amplify the appropriate fragment which is ligated into the prepared parent vector. Construction of the pBI121-HP-AtCPP construct (SEQ ID NO:100). The cloning strategy involved truncating the GUS gene of pBI121 and flanking the GUS sequence with a AtCPP fragment in the antisense orientation upstream of the GUS and in the sense orientation on the downstream side of GUS. The pBI121 vector was digested with SmaI and Sad, the GUS sequence and the vector fragments were purified from one another. The isolated GUS fragment was digested using EcoRV and the 1079 bp. blunt ended EcoRV/SacI fragment isolated. This was ligated back into the digested parent vector at the SmaI/Sad sites. This intermediate vector was used in the subsequent production of the hair-pin vectors. The AtCPP fragment to be used as the gene specific hair-pin sequence was isolated by PCR. Primers identified as SEQ ID NO:103 and SEQ ID NO:104, listed in Table 14, were used to generate a 596 bp fragment. Cloning of the sense orientation fragment was achieved by digesting the PCR AtCPP fragment with Sad and ligation into the Sad site at the 3' end of GUS. To insert the same fragment upstream of GUS, the BamHI site was opened and the ends blunted with Klenow. The PCR amplified AtCPP fragment was digested with EcolCRI, which is an isoschizomer of Sad but leaves blunt ends, and ligated into the blunted BamHI site of the vector to yield the final construct (FIG. 25C). The intermediate construct used to produce SEQ ID NO: 100 above contained only the truncated GUS gene and no CPP sequences this intermediate vector was used to further generate constructs expressing hair-pin CPP gene constructs from *Brassica* and *Glycine*. To produce the pBI121-HP-BnCPP construct (SEQ ID NO:143) primer pairs identified by SEQ ID NO:153 and SEQ ID NO:154 are used to PCR amplify the sense fragment and primer pairs identified by SEQ ID NO:155 and SEQ ID NO:156 are used to PCR amplify the antisense fragment. These fragments are cloned into the prepared intermediate vector described above. To produce the pBI121-HP-GmCPP construct (SEQ ID NO:137) primer pairs identified by SEQ ID NO:157 and SEQ ID NO:158 are used to PCR amplify the sense fragment and primer pairs identified by SEQ ID NO:159 and SEQ ID NO: 160 are used to PCR amplify the antisense fragment. These fragments are cloned into the prepared intermediate vector described above.

The above vector constructs were modified to place the genes under the control of alternative promoters, such as, but not limited to, the RD29A or MuA . This was accomplished by excising the 35S promoter sequence and replacing it with an appropriate promoter sequence. In this way SEQ ID NO's:134 and 135 were generated and SEQ ID NO's:133, 136-148 can be constructed.

TABLE 14

| | | |
|---|---|---|
| AtCPP-HP-SacFW | 5'-CTGGAGCTCTTTTACCGAGGTTGGGCCTTGATCC-3' | (SEQ ID NO:103) |
| AtCPP-HP-SacRV | 5'-ATTGAGCTCCCAATGTCCAAGCTCGTGTGCAATA-3' | (SEQ ID NO:104) |
| AtCPP-anti-SmaFW | 5'-AAACCCGGGATGGCGATTCCTTTCATGG-3' | (SEQ ID NO:106) |
| AtCPP-anti-BamRV | 5'-AAAGGATCCTTAATCTGTCTTCTTGTCTTCTCCA-3' | (SEQ ID NO:107) |
| BnCPP-anti-SmaFW | 5'-AAACCCGGGATGGCGATTCCTTTCATGG-3' | (SEQ ID NO:151) |

TABLE 14-continued

| | | |
|---|---|---|
| BnCPP-anti-BamRV | 5'-AAAGGATCCTTAATCTGTCTTCTTGTCTTCTCC-3' | (SEQ ID NO:152) |
| BnCPP-HP-Sac-FW | 5'-AAAGAGCTCTTCTACCAATGGTGGGACTCG-3' | (SEQ ID NO:153) |
| BnCPP-HP-Sac-RV | 5'-AAAGAGCTCCCAGTGTCCCAGCTCGTGTG-3' | (SEQ ID NO:154) |
| BnCPP-HP-BamFW | 5'-AAAGGATCCTTCTACCAATGGTGGGACTCG-3' | (SEQ ID NO:155) |
| BnCPP-HP-XbaRV | 5'-AAATCTAGACCAGTGTCCCAGCTCGTGTG-3' | (SEQ ID NO:156) |
| GmCPP-HP-Sac-FW | 5'-GATGAGCTCACAAGATCAAGTCACAGCAATGCCT-3' | (SEQ ID NO:157) |
| GmCPP-HP-Sac-RV | 5'-AAAGAGCTCCCGGTTCGTCCAGCGCGGCC-3' | (SEQ ID NO:158) |
| GmCPP-HP-BamFW | 5'-GATGGATCCACAAGATCAAGTCACAGCAATGCCT-3' | (SEQ ID NO:159) |
| GmCPP-HP-XbaRV | 5'-CCTTCTAGACCGGTTCGTCCAGCGCGGCC-3' | (SEQ ID NO:160) |

Example 31

Sequence Analysis

*Arabidopsis thaliana* CPP (AtCPP)

A disclosed nucleic acid of 1275 nucleotides (SEQ ID NO:97) and also referred to as AtCPP, is shown in Table 15.

TABLE 15A

AtCPP Nucleotide Sequence.

ATGGCGATTCCTTTCATGGAAACCGTCGTGGGTTTTATGATAGTGATGTACATTTTTGAG  (SEQ ID NO:97)
ACGTATTTGGATCTGAGGCAACTCACTGCTCTCAAGCTTCCAACTCTCCCGAAAACCTTG
GTTGGTGTAATTAGCCAAGAGAAGTTTGAGAAATCACGAGCATACAGTCTTGACAAAAGC
TATTTTCACTTTGTTCATGAGTTTGTAACTATACTTATGGACTCTGCAATTTTGTTCTTT
GGGATCTTGCCTTGGTTTTGGAAGATGTCTGGAGCTGTTTTACCGAGGTTGGGCCTTGAT
CCGGAGAATGAAATACTGCATACTCTTTCATTCTTGGCTGGTGTTATGACATGGTCACAG
ATCACTGATTTGCCATTTTCTTTGTACTCAACTTTCGTGATCGAGTCTCGGCATGGGTTC
AACAAACAAACAATATGGATGTTCATTAGGGACATGATCAAAGGAACATTCCTCTCTGTC
ATACTAGGCCCACCCATTGTTGCTGCGATAATTTTCATAGTCCAGAAAGGAGGTCCTTAT
CTTGCCATCTATCTGTGGGCATTCATGTTTATCCTGTCTCTAGTGATGATGACTATATAC
CCGGTCTTGATAGCACCGCTCTTCAACAAATTCACTCCTCTTCCAGATGGAGACCTCCGG
GAGAAGATTGAGAAACTTGCTTCTTCCCTAAAGTTTCCTTTGAAGAAGCTGTTTGTTGTC
GATGGATCTACAAGGTCAAGCCATAGCAATGCTTACATGTATGGTTTCTTTAAGAACAAA
AGGATTGTTCTTTATGATACGTTGATTCAGCAGTGCAAGAATGAGGATGAAATTGTGGCG
GTTATTGCACACGAGCTTGGACATTGGAAACTGAATCACACTACATACTCGTTCATTGCA
GTTCAAATCCTTCCCTTCTTACAATTTGGAGGATACACTCTTCTCAGAAACTCCACTGAT
CTCTTCAGGAGTTTCGGATTTGATACACAGCCTGTTCTCATTGGTTTGATCATATTTCAG
CACACTGTAATACCACTGCAACATCTAGTAAGCTTTGGCCTGAACCTCGTTAGTCGAGCG
TTTGAGTTTCAGGCTGATGCTTTTGCTGTGAAGCTTGACTATGCAAAAGATCTTCGTCCT
GCTCTAGTGAAACTACAGGAAGAGAACTTATCAACAATGAACACTGATCCATTGTACTCA
GCTTATCACTACTCACATCCTCCTCTTGTTGAAAGGCTTCGAGCCACTGATGGAGAAGAC
AAGAAGACAGATTAA

A disclosed CPP polypeptide (SEQ ID NO:98) encoded by SEQ ID NO:97 has 424 amino acid residues and is presented in Table 15B using the one-letter amino acid code.

TABLE 15B

| Encoded CPP protein sequence. | |
|---|---|
| MAIPFMETVVGFMIVMYIFETYLDLRQLTALKLPTLPKTLVGVISQEKFEKSRAYSLDKS | (SEQ ID NO:98) |
| YFHFVHEFVTILMDSAILFFGILPWFWKMSGAVLPRLGLDPENEILHTLSFLAGVMTWSQ | |
| ITDLPFSLYSTFVIESRHGFNKQTIWMFIRDMIKGTFLSVILGPPIVAAIIFIVQKGGPY | |
| LAIYLWAFMFILSLVMMTIYPVLIAPLFNKFTPLPDGDLREKIEKLASSLKFPLKKLFVV | |
| DGSTRSSHSNAYMYGFFKNKRIVLYDTLIQQCKNEDEIVAVIAHELGHWKLNHTTYSFIA | |
| VQILAFLQFGGYTLLRNSTDLFRSFGFDTQPVLIGLIIFQHTVIPLQHLVSFGLNLVSRA | |
| FEFQADAFAVKLDYAKDLRPALVKLQEENLSTMNTDPLYSAYHYSHPPLVERLRATDGED | |
| KKTD | |

The present invention also includes a nucleic acid sequence complimentary to the *Arabidopsis thaliana* CaaX prenyl protease of SEQ ID NO:97. The disclosed complimentary sequence is shown as SEQ ID NO:115.

| | |
|---|---|
| TTAATCTGTCTTCTTGTCTTCTCCATCAGTGGCTCGAAGCCTTTCAACAAGAGGAGGATGTGAG | SEQ ID NO:115 |
| TAGTGATAAGCTGAGTACAATGGATCAGTGTTCATTGTTGATAAGTTCTCTTCCTGTAGTTTCA | |
| CTAGAGCAGGACGAAGATCTTTTGCATAGTCAAGCTTCACAGCAAAAGCATCAGCCTGAAACTC | |
| AAACGCTCGACTAACGAGGTTCAGGCCAAAGCTTACTAGATGTTGCAGTGGTATTACAGTGTGC | |
| TGAAATATGATCAAACCAATGAGAACAGGCTGTGTATCAAATCCGAAACTCCTGAAGAGATCAG | |
| TGGAGTTTCTGAGAAGAGTGTATCCTCCAAATTGTAAGAAGGCAAGGATTTGAACTGCAATGAA | |
| CGAGTATGTAGTGTGATTCAGTTTCCAATGTCCAAGCTCGTGTGCAATAACCGCCACAATTTCA | |
| TCCTCATTCTTGCACTGCTGAATCAACGTATCATAAAGAACAATCCTTTTGTTCTTAAAGAAAC | |
| CATACATGTAAGCATTGCTATGGCTTGACCTTGTAGATCCATCGACAACAAACAGCTTCTTCAA | |
| AGGAAACTTTAGGGAAGAAGCAAGTTTCTCAATCTTCTCCCGGAGGTCTCCATCTGGAAGAGGA | |
| GTGAATTTGTTGAAGAGCGGTGCTATCAAGACCGGGTATATAGTCATCATCACTAGAGACAGGA | |
| TAAACATGAATGCCCACAGATAGATGGCAAGATAAGGACCTCCTTTCTGGACTATGAAAATTAT | |
| CGCAGCAACAATGGGTGGGCCTAGTATGACAGAGAGGAATGTTCCTTTGATCATGTCCCTAATG | |
| AACATCCATATTGTTTGTTTGTTGAACCCATGCCGAGACTCGATCACGAAAGTTGAGTACAAAG | |
| AAAATGGCAAATCAGTGATCTGTGACCATGTCATAACACCAGCCAAGAATGAAAGAGTATGCAG | |
| TATTTCATTCTCCGGATCAAGGCCCAACCTCGGTAAAACAGCTCCAGACATCTTCCAAAACCAA | |
| GGCAAGATCCCAAAGAACAAAATTGCAGAGTCCATAAGTATAGTTACAAACTCATGAACAAAGT | |
| GAAAATAGCTTTTGTCAAGACTGTATGCTCGTGATTTCTCAAACTTCTCTTGGCTAATTACACC | |
| AACCAAGGTTTTCGGGAGAGTTGGAAGCTTGAGAGCAGTGAGTTGCCTCAGATCCAAATACGTC | |
| TCAAAAATGTACATCACTATCATAAAACCCACGACGGTTTCCATGAAAGGAATCGCCAT | |

Due to the nature of the cloning strategy the sequence presented is not full length but is missing the 5' and 3' non-translated regions. The percent identities of the *Arabidopsis thaliana* nucleotide sequence and its encoded amino acid sequence to that of other CPP sequences as determined by ClustalW analysis are shown in FIG. 26.

Using the sequences disclosed herein as hybridization probes, one is able to screen and isolate full length sequences from cDNA or genomic libraries or use the rapid amplification of cDNA ends (RACE) technology or other such PCR techniques.

*Brassica napus* CPP (BnCPP)

A disclosed nucleic acid of 1275 nucleotides (SEQ ID NO:109) and also referred to as BnCPP, is shown in Table 16.

TABLE 16A

| BnCPP Nucleotide Sequence. |
|---|
| ATGGCGATTCCTTTCATGGAAACCGTCGTTGGTTTTATGATAGTGATGTA (SEQ ID NO:109) |
| CGTTTTTGAGACGTATTTGGATCTGAGGCAACATACTGCTCTCAAGCTTC |
| CCACTCTCCCAAAGACTTTGGTTGGAGTCATTAGCCAAGAGAAGTTTGAG |
| AAATCTCGAGCTTACAGTCTTGACAAAAGCCATTTTCACTTTGTTCATGA |
| GTTTGTTACTATACTTATGGACTCTGCGATTCTGTTCTTTGGGATCTTGC |
| CTTGGTTTTGGAAGATATCTGGCGGCTTTCTACCAATGGTGGGACTCGAT |
| CCAGAGAATGAAATCCTGCACACTCTTTCATTCTTGGCTGGTCTTATGAC |
| ATGGTCACAGATCACTGATTTGCCATTTTCTTTGTACTCAACTTTCGTGA |
| TCGAGTCTCGGCATGGGTTCAACAAACAAACAATATGGATGTTCATTAGG |
| GACATGATCAAAGGAATACTCCTCTCTGTCATACCTGCCCCTCCTATCGT |
| TGCCGCAATTATTGTTATAGTTCAGAAAGGAGGTCCTTACCTCGCCATCT |
| ATCTGTGGGCATTCATGTTTATCCTGTCTCTAGTGATGATGACTATATAC |
| CCTGTTTTGATTGCACCTCTTTTCAACAAGTTCACTCCTCTTCCTGATGG |
| AGACCTCCGGGAGAAGATTGAGAAACTTGCTTCTTCTCTAAAGTTTCCTC |
| TGAAGAAGCTGTTTGTTGTCGATGGATCTACAAGGTCAAGCCATAGTAAT |
| GCTTACATGTATGGTTTCTTCAAGAACAAAAGGATTGTTCTTTATGACAC |
| ATTGATTCAGCAGTGCCAGAATGAGAATGAAATTGTGGCGGTTATTGCAC |
| ACGAGCTGGGACACTGGAAGCTGAATCACACTACATACTCGTTCATTGCT |
| GTTCAAATCCTTGCCTTCTTGCAATTTGGAGGATACACTCTTGTCAGAAA |
| CTCCACTGATCTCTTCAGGAGTTTTGGTTTTGATACACAACCAGTTCTCA |
| TTGGTTTGATCATATTTCAGCACACTGTAATACCACTTCAACACCTAGTA |
| AGCTTTGACCTCAACCTTGTTAGTCGAGCGTTTGAGTTTCAGGCTGATGC |
| TTTTGCAGTGAATCTTGGTTATGCAAAGGATCTACGTCCTGCCCTAGTGA |
| AGCTACAGGAAGAGAACTTATCAGCGATGAACACAGACCCATTGTACTCA |
| GCTTATCACTACTCACACCCTCCTCTTGTAGAGAGGCTTCGAGCCATTGA |
| TGGAGAAGACAAGAAGACAGATTAA |

A disclosed CPP polypeptide (SEQ ID NO:110) encoded by SEQ ID NO:109 has 424 amino acid residues and is presented in Table 16B using the one-letter amino acid code.

TABLE 16B

| Encoded CPP protein sequence. |
|---|
| MAIPFMETVVGFMIVMYVFETYLDLRQHTALKLPTLPKTLVGVISQEKFE (SEQ ID NO:110) |
| KSRAYSLDKSHFHFVHEFVTILMDSAILFFGILPWFWKISGGFLPMVGLD |

TABLE 16B-continued

| Encoded CPP protein sequence. |
|---|
| PENETLHTLSFLAGLMTWSQITDLPFSLYSTFVIESRHGFNKQTIWMFIR |
| DMIKGILLSVIPAPPIVAAIIVIVQKGGPYLIAYLWAFMFILSLVMMTIY |
| PVLIAPLFNKFTPLPDGDLREKIEKLASSLKFPLKKLFVVDGSTRSSHSN |
| AYMYGFFKNKRIVLYDTLIQQCQNENEIVAVIAHELGHWKLNHTTYSFIA |
| VQILAFLQFGGYTLVRNSTDLFRSFGFDTQPVLIGLIIFQHTVIPLQHLV |
| SFDLNLVSRAFEFQADAFAVNLGYAKDLRPALVKLQEENLSAMNTDPLYS |
| AYHYSHPPLVERLRAIDGEDKKTD |

The present invention also includes a nucleic acid sequence complimentary to the *Brassica napus* CaaX prenyl protease of SEQ ID NO:109. The disclosed complimentary sequence is shown as SEQ ID NO:111.

```
TTAATCTGTCTTCTTGTCTTCTCCATCAATGGCTCGAAGCCTCTCTACAAGAGGAGGGTGTGAG   SEQ ID NO:111
TAGTGATAAGCTGAGTACAATGGGTCTGTGTTCATCGCTGATAAGTTCTCTTCCTGTAGCTTCA
CTAGGGCAGGACGTAGATCCTTTGCATAACCAAGATTCACTGCAAAAGCATCAGCCTGAAACTC
AAACGCTCGACTAACAAGGTTGAGGTCAAAGCTTACTAGGTGTTGAAGTGGTATTACAGTGTGC
TGAAATATGATCAAACCAATGAGAACTGGTTGTGTATCAAAACCAAAACTCCTGAAGAGATCAG
TGGAGTTTCTGACAAGAGTGTATCCTCCAAATTGCAAGAAGGCAAGGATTTGAACAGCAATGAA
CGAGTATGTAGTGTGATTCAGCTTCCAGTGTCCCAGCTCGTGTGCAATAACCGCCACAATTTCA
TTCTCATTCTGGCACTGCTGAATCAATGTGTCATAAAGAACAATCCTTTTGTTCTTGAAGAAAC
CATACATGTAAGCATTACTATGGCTTGACCTTGTAGATCCATCGACAACAAACAGCTTCTTCAG
AGGAAACTTTAGAGAAGAAGCAAGTTTCTCAATCTTCTCCCGGAGGTCTCCATCAGGAAGAGGA
GTGAACTTGTTGAAAAGAGGTGCAATCAAAACAGGGTATATAGTCATCATCACTAGAGACAGGA
TAAACATGAATGCCCACAGATAGATGGCGAGGTAAGGACCTCCTTTCTGAACTATAACAATAAT
TGCGGCAACGATAGGAGGGGCAGGTATGACAGAGAGGAGTATTCCTTTGATCATGTCCCTAATG
AACATCCATATTGTTTGTTTGTTGAACCCATGCCGAGACTCGATCACGAAAGTTGAGTACAAAG
AAAATGGCAAATCAGTGATCTGTGACCATGTCATAAGACCAGCCAAGAATGAAAGAGTGTGCAG
GATTTCATTCTCTGGATCGAGTCCCACCATTGGTAGAAAGCCGCCAGATATCTTCCAAAACCAA
GGCAAGATCCCAAAGAACAGAATCGCAGAGTCCATAAGTATAGTAACAAACTCATGAACAAAGT
GAAAATGGCTTTTGTCAAGACTGTAAGCTCGAGATTTCTCAAACTTCTCTTGGCTAATGACTCC
AACCAAAGTCTTTGGGAGAGTGGGAAGCTTGAGAGCAGTATGTTGCCTCAGATCCAAATACGTC
TCAAAAACGTACATCACTATCATAAAACCAACGACGGTTTCCATGAAAGGAATCGCCAT
```

Due to the nature of the cloning strategy the sequence presented is not full length but is missing the 5' and 3' non-translated regions. The percent identities of the *Brassica napus* nucleotide sequence and its encoded amino acid sequence to that of other CPP sequences as determined by ClustalW analysis are shown in FIG. 26.

Using the sequences disclosed herein as hybridization probes, one is able to screen and isolate full length sequences from cDNA or genomic libraries or use the rapid amplification of cDNA ends (RACE) technology or other such PCR techniques.

*Glycine max* CPP (GmCPP)

A disclosed nucleic acid of 1275 nucleotides (SEQ ID NO:112) and also referred to as GmCPP, is shown in Table 17.

TABLE 17A

| GmCPP Nucleotide Sequence. |
| --- |
| ATGGCGTTTCCCTACATGGAAGCCGTTGTCGGATTTATGATATTAATGTA (SEQ ID NO:112) |
| CATTTTTGAAACTTACTTGGATGTGCGACAACATAGGGCCCTCAAACTTC |
| CTACTCTTCCAAAGACTTTAGAGGGTGTTATCAGCCAAGAGAAATTTGAG |
| AAATCTAGAGCCTATAGTCTTGATAAAAGCCACTTCCATTTTGTTCACGA |
| GTTTGTGACAATAGTGACAGACTCTACAATTTTGTACTTTGGGGTATTGC |
| CCTGGTTTTGGAAGAAATCAGGAGATTTTATGACAATAGCTGGTTTCAAT |
| GCTGAGAATGAAATACTGCATACCCTTGCCTTCTTAGCAGGGCTGATGAT |
| TTGGTCACAGATAACAGATTTGCCCTTTTCTCTGTACTCAACTTTTGTGA |
| TTGAGGCCCGTCATGGTTTTAATAAGCAAACACCATGGTTATTCTTTAGG |
| GACATGCTTAAAGGAATTTTCCTTTCTGTAATAATTGGTCCACCTATTGT |
| GGCTGCAATCATTGTAATAGTACAGAAAGGAGGTCCATACTTGGCCATCT |
| ATCTTTGGGTTTTTACGTTTGGTCTTTCTATTGTGATGATGACCCTTTAT |
| CCAGTACTAATAGCTCCACTCTTCAATAAGTTCACTCCACTTCCAGATGG |
| TCAACTCAGGGAGAAAATCGAGAAACTTGCTTCCTCCCTCAACTATCCGT |
| TAAAGAAACTATTTGTTGTCGATGGATCCACAAGATCAAGTCACAGCAAT |
| GCCTATATGTATGGATTCTTCAAGAACAAGAGGATTGTCCCTTATGACAC |
| ATTAATTCAACAGTGCAAAGACGATGAGGAAATTGTTGCTGTTATTGCCC |
| ATGAGTTGGGACACTGGAAGCTCAACCATACTGTGTACACATTTGTTGCT |
| ATGCAGATTCTTACACTTCTACAATTTGGAGGATATACACTAGTGCGAAA |
| TTCAGCTGATCTGTATCGAAGCTTTGGGTTTGATACGCAGCCAGTCCTCA |
| TTGGGCTCATCATATTTCAGCATACTGTAATCCCACTTCAGCAATTGGTC |
| AGCTTTGGTCTGAACCTAGTCAGCCGATCATTTGAATTTCAGGCTGATGG |
| CTTTGCCAAGAAGCTTGGATATGCATCTGGATTACGCGGTGGTCTTGTGA |
| AACTACAGGAGGAGAATCTGTCAGCTATGAATACAGATCCTTGGTACTCT |
| GCTTATCACTATTCTCATCCTCCCCTTGTTGAAAGATTGGCCGCGCTGGA |
| CGAACCGGATAAGAAGGAAGACTAA |

A disclosed CPP polypeptide (SEQ ID NO:113) encoded by SEQ ID NO:112 has 424 amino acid residues and is presented in Table 17B using the one-letter amino acid code.

TABLE 17B

| Encoded CPP protein sequence. |
| --- |
| MAFPYMEAVVGFMILMYIFETYLDVRQHRALKLPTLPKTLEGVISQEKFE (SEQ ID NO:113) |
| KSRAYSLDKSHFHFVHEFVTIVTDSTILYFGVLPWFWKKSGDFMTIAGFN |
| AENEILHTLAFLAGLMIWSQITDLPFSLYSTFVIEARHGFNKQTPWLFFR |
| DMLKGIFLSVIIGPPIVAAIIVIVQKGGPYLAIYLWVFTFGLSIVMMTLY |
| PVLIAPLFNKFTPLPDGQLREKIEKLASSLNYPLKKLFVVDGSTRSSHSN |
| AYMYGFFKNKRIVPYDTLIQQCKDDEEIVAVIAHELGHWKLNHTVYTFVA |
| MQILTLLQFGGYTLVRNSADLYRSFGFDTQPVLIGLIIFQHTVIPLQQLV |

TABLE 17B-continued

| Encoded CPP protein sequence. |
|---|
| SFGLNLVSRSFEFQADGFAKKLGYASGLRGGLVKLQEENLSAMNTDPWYS |
| AYHYSHPPLVERLAALDEPDKKED |

The present invention also includes a nucleic acid sequence complimentary to the *Glycine max* CaaX prenyl protease of SEQ ID NO:112. The disclosed complimentary sequence is shown as SEQ ID NO:114.

```
TTAGTCTTCCTTCTTATCCGGTTCGTCCAGCGCGGCCAATCTTTCAACAAGGGGAGGATGAGAA   SEQ ID NO:114
TAGTGATAAGCAGAGTACCAAGGATCTGTATTCATAGCTGACAGATTCTCCTCCTGTAGTTTCA
CAAGACCACCGCGTAATCCAGATGCATATCCAAGCTTCTTGGCAAAGCCATCAGCCTGAAATTC
AAATGATCGGCTGACTAGGTTCAGACCAAAGCTGACCAATTGCTGAAGTGGGATTACAGTATGC
TGAAATATGATGAGCCCAATGAGGACTGGCTGCGTATCAAACCCAAAGCTTCGATACAGATCAG
CTGAATTTCGCACTAGTGTATATCCTCCAAATTGTAGAAGTGTAAGAATCTGCATAGCAACAAA
TGTGTACACAGTATGGTTGAGCTTCCAGTGTCCCAACTCATGGGCAATAACAGCAACAATTTCC
TCATCGTCTTTGCACTGTTGAATTAATGTGTCATAAGGGACAATCCTCTTGTTCTTGAAGAATC
CATACATATAGGCATTGCTGTGACTTGATCTTGTGGATCCATCGACAACAAATAGTTTCTTTAA
CGGATAGTTGAGGGAGGAAGCAAGTTTCTCGATTTTCTCCCTGAGTTGACCATCTGGAAGTGGA
GTGAACTTATTGAAGAGTGGAGCTATTAGTACTGGATAAAGGGTCATCATCACAATAGAAAGAC
CAAACGTAAAAACCCAAAGATAGATGGCCAAGTATGGACCTCCTTTCTGTACTATTACAATGAT
TGCAGCCACAATAGGTGGACCAATTATTACAGAAAGGAAAATTCCTTTAAGCATGTCCCTAAAG
AATAACCATGGTGTTTGCTTATTAAAACCATGACGGGCCTCAATCACAAAAGTTGAGTACAGAG
AAAAGGGCAAATCTGTTATCTGTGACCAAATCATCAGCCCTGCTAAGAAGGCAAGGGTATGCAG
TATTTCATTCTCAGCATTGAAACCAGCTATTGTCATAAAATCTCCTGATTTCTTCCAAAACCAG
GGCAATACCCCAAAGTACAAAATTGTAGAGTCTGTCACTATTGTCACAAACTCGTGAACAAAAT
GGAAGTGGCTTTTATCAAGACTATAGGCTCTAGATTTCTCAAATTTCTCTTGGCTGATAACACC
CTCTAAAGTCTTTGGAAGAGTAGGAAGTTTGAGGGCCCTATGTTGTCGCACATCCAAGTAAGTT
TCAAAAATGTACATTAATATCATAAATCCGACAACGGCTTCCATGTAGGGAAACGCCAT
```

Due to the nature of the cloning strategy the sequence presented is not full length but is missing the 5' and 3' non-translated regions. The percent identities of the *Glycine max* nucleotide sequence and its encoded amino acid sequence to that of other CPP sequences as determined by ClustalW analysis are shown in FIG. 26.

Using the sequences disclosed herein as hybridization probes, one is able to screen and isolate full length sequences from cDNA or genomic libraries or use the rapid amplification of cDNA ends (RACE) technology or other such PCR techniques.

The CPP nucleic acids and amino acids disclosed above have homology to other disclosed CPP sequences (GenBank ID NOs: AL161491 (AT4g01320), AF007269 and AF353722; WO 02/16625 A2 ). The homology between these and other sequences is shown in the ClustalW alignment analysis shown in Tables 18A-18B.

Table 18A. ClustalW Nucleic Acid Analysis of CaaX Prenyl Protease

TABLE 18A

| ClustalW Nucleic Acid Analysis of CaaX Penyl Protease |
|---|
| 1: PPI-AtCPP SEQ ID NO:97 |
| 2: PPI-BnCPP SEQ ID NO:109 |

TABLE 18A-continued

ClustalW Nucleic Acid Analysis of CaaX Penyl Protease

```
 3: PPI-GmCPP SEQ ID NO:112

 4: BASF_AT1  SEQ ID NO:116

 5: BASF_AT2  SEQ ID NO:118

 6: BASF-Corn SEQ ID NO:120

 7: BASF-Gm   SEQ ID NO:122

 8: AFC1      SEQ ID NO:124

 9: AT4g01320 SEQ ID NO:126

10: AF007269  SEQ ID NO:128
```

CLUSTAL W (1.81) multiple sequence alignment

```
PPI-CmCPP     ------------------------------------------------------------
BASF-Gm       ------------------------------------------------------------
AT4g01320     ------------------------------------------------------------
AF007269      ATGGCGATTCCTTTCATGGAAACCGTCGTGGGTAAGCTTCAAAACCTTTTTCTGAGACAT
PPI-ALCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------
PPI-GmCPP     ------------------------------------------------------------
BASF-Gm       ------------------------------------------------------------
AT4g01320     ------------------------------------------------------------
AF007269      TTTACTATCCTGTTTCACTCATCGTATTTCGTTTTTGTTTGGGTTTTGCTTTCTGTGTTG
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------
PPI-GmCPP     ------------------------------------------------------------
BASF-Gm       ------------------------------------------------------------
AT4g01320     ------------------------------------------------------------
AF007269      TGTCTGTTGAGATTCCATGACTCGTTTGTTTCATATACCATCGTCTCTGCTTCTCGTTTC
PPI-AtCPP     ------------------------------------------------------------
BASF_AT2      ------------------------------------------------------------
atc1          ------------------------------------------------------------
BASF_AT1      ------------------------------------------------------------
PPI-BnCPP     ------------------------------------------------------------
BASF-Corn     ------------------------------------------------------------
```

TABLE 18A-continued

ClustalW Nucleic Acid Analysis of CaaX Penyl Protease

```
PPI-GmCPP    ------------------------------------------------------------
BASF-Gm      ------------------------------------------------------------
AT4g01320    ------------------------------------------------------------
AF007269     TAAATTTTGTTCTTTTCTAATAGTGCGTACCTTGATCTGAGGTTTTATTACTCCTACTAG
PPI-ALCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASE-Corn    ------------------------------------------------------------
PPI-GmCPP    ------------------------------------------------------------
BASE-Gm      ------------------------------------------------------------
AT4g01320    ------------------------------------------------------------
AF007269     ------------------------------------------------------------
PPI-AtCPP    ------------------------------------------------------------
BASE_AT2     ------------------------------------------------------------
afc1         ------------------------------------------------------------
BASE_AT1     ------------------------------------------------------------
PPI-BnCPP    ------------------------------------------------------------
BASE-Corn    ------------------------------------------------------------
PPI-GmCPP    ------------------------------------------------------------
BASF-Gm      ------------------------------------------------------------
AT4g01320    ------------------------------------------------------------
AF007269     CTCGGTTTTAGAATGTACGGAGCTTCTCTGTTAACCAAAATCTAGGATTTGGGAAGAAAA
PPI-AtCPP    ------------------------------------------------------------
BASE_AT2     ------------------------------------------------------------
afc1         ------------------------------------------------------------
BASE_AT1     ------------------------------------------------------------
PPI-BnCPP    ------------------------------------------------------------
BASE-Corn    ------------------------------------------------------------
PPI-GmCPP    ------------------------------------------------------------
BASF-Gm      ------------------------------------------------------------
AT4g01320    ------------------------------------------------------------
AF007269     GTCGGAGTCTTTTTTTTCCTCATTCCCGATTGGAAATTGAGAATCTTGAAATTTTTCTTT
PPI-AtCPP    ------------------------------------------------------------
BASE_AT2     ------------------------------------------------------------
afc1         ------------------------------------------------------------
BASE_AT1     ------------------------------------------------------------
PPI-BnCPP    ------------------------------------------------------------
```

TABLE 18A-continued

| ClustalW Nucleic Acid Analysis of CaaX Penyl Protease | |
|---|---|
| BASE-Corn | ------------------------------------------------------------ |
| PPI-GmCPP | ------------------------------------------------------------ |
| BASE-Gm | --------------------------------------CTAATACGACTCACTATAGGGC |
| AT4g01320 | ------------------------------------------------------------ |
| AF007269 | GTTCAAGTCATACAGCTTGAGGTTTTGGGTTTTCTTGTCAGGGTATTATTATGTTCGTGA |
| PPI-AtCPP | ------------------------------------------------------------ |
| BASE_AT2 | ------------------------------------------------------------ |
| afc1 | ------------------------------------------------------------ |
| BASE_AT1 | ------------------------------------------------------------ |
| PPI-BnCPP | ------------------------------------------------------------ |
| BASE-Corn | ------------------------------------------------------------ |
| PPI-GmCPP | ------------------------------------------------------------ |
| BASE-Gm | AAGCAGTGGTAACAACGCAGAGTACGCGGGGGGAGACGCATGGTTCTGAACTAATTGTTA |
| AT4g01320 | ------------------------------------------------------------ |
| AF007269 | CTGCAACTAGAGTTTTCTGGAGTTTTTTGAAATGGGTTTTGTGTTGTGGAACCGTATGTG |
| PPI-AtCPP | ------------------------------------------------------------ |
| BASE_AT2 | ------------------------------------------------------------ |
| afc1 | ------------------------------------------------------------ |
| BASE_AT1 | ------------------------------------------------------------ |
| PPI-BnCPP | ------------------------------------------------------------ |
| BASE-Corn | ------------------------------------------------------------ |
| PPI-GmCPP | ------------------------------------------------------------ |
| BASF-Gm | TAAATAATACCTAAAATTTTGAGTTGTCCTAAACATTGGGGTTTAAACAAATCCAATCTC |
| AT4g01320 | ------------------------------------------------------------ |
| AF007269 | AATGTTGCATCAAAACTCTTTCAGTGCTCCAATGTTTCCATCAGTAGTCAGCACAAGAGA |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | ------------------------------------------------------------ |
| PPI-GmCPP | ------------------------------------------------------------ |
| ASF-Gm | TCAATATAAAACCCAATGATCTCACC--CTCACTCCGTTTCTGATTTCTCACTCTTCGTT |
| AT4g01320 | ------------------------------------------------------------ |
| AF007269 | TCTTTTTATATCTGGTTGATCAAAAAAGTAGATGATGTTATTGAATTTTCAGTGATGGAG |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |

TABLE 18A-continued

ClustalW Nucleic Acid Analysis of CaaX Penyl Protease

```
PPI-BnCPP     ------------------------------------------------------------
BASF-Corn     ------------------------------------------------------------
PPI-GmCPP     ---------------------------------ATGGCGTTTCCC--TACATGGAAGCCG
BASF-Gm       TCTCGTTCGGTTCATGAGCGTGTGTCTCAGC-CATGGCGTTTCCC--TACATGGAAGCCG
AT4g01320     ---------------------------------ATGGCGATTCCT--TTCATGGAAACCG
AF007269      TATCTGTTGTTGTGGCATTTAGAGTAGATTCGTATTTGATCTTCTGTTTTATTCTTTTTC
PPI-AtCPP     ---------------------------------ATGGCGATTCCT--TTCATGGAAACCG
BASF_AT2      ---------------------------------ATGGCGATTCCT--TTCATGGAAACCG
afc1          ---------------------------------ATGGCGATTCCT--TTCATGGAAACCG
BASF_AT1      ---------------------------------ATGGCGATTCCT--TTCATGGAAACCG
PPI-BnCPP     ---------------------------------ATGGCGATTCCT--TTCATGGAAACCG
BASF-Corn     ------------------------------------------------------------
PPI-GmCPP     TTGTCGGATTTATGATATTAATGTACATTTTTGAAACTTACTTGGATGTGCGACAACATA
BASF-Gm       TTGTCGGATTTATGATATTAATGTACATTTTTGAAACTTACTTGGATGTGCGACAACATA
AT4g01320     TCCTGGGTTTTATGATAGTGATGTACATTTTTGAGACGTATTTGGATCTGAGGCAACTCA
AF007269      TTACAGGTTTTATGATAGTGATGTACATTTTTGAGACGTATTTGGATCTGAGGCAACTCA
PPI-AtCPP     TCGTGGGTTTTATGATAGTGATGTACATTTTTGAGACGTATTTGGATCTGAGGCAACTCA
BASF_AT2      TCGTGGGTTTTATGATAGTGATGTACATTTTTGAGACGTATTTGGATCTGAGGCAACTCA
afc1          TCGTGGGTTTTATGATAGTGATGTACATTTTTGAGACGTATTTGGATCTGAGCCAACTCA
BASF_AT1      TCGTGGGTTTTATGATAGTGATGTACATTTTTGAGACGTATTTGCATCTGAGGCAACTCA
PPI-BnCPP     TCGTTGGTTTTATGATAGTGATGTACCTTTTTGAGACGTATTTGGATCTGAGGCAACATA
BASF-Corn     ------------------------------------------------------------
PPI-GmCPP     GGGCCCTCAAACTTCCTACTCTTCCAAAGACTTTAGAGGGTGTTATCAGCCAAGAGAAAT
BASF-Gm       GGGCCCTCAAACTTCCTACTCTTCCAAAGACTTTAGAAGGTGTTATCAGCCAAGAGAAAT
AT4g01320     CTGCTCTCAAGCTTCCAACTCTCCCGAAAACCTTGGTTGGTGTAATTAGCCAAGAGAAGT
AF007269      CTGCTCTCAAGCTTCCAACTCTCCCGAAAACCTTGGTTGGTGTAATTAGCCAAGAGAAGT
PPI-AtCPP     CTGCTCTCAAGCTTCCAACTCTCCCGAAAACCTTGGTTGGTGTAATTAGCCAAGAGAAGT
BASF_AT2      CTGCTCTCAAGCTTCCAACTCTCCCGAAAACCTTGGTTGGTGTAATTAGCCAAGAGAAGT
afc1          CTGCTCTCAAGCTTCCAACTCTCCCGAAAACCTTGGTTGGTGTAATTAGCCAAGAGAAGT
BASF_AT1      CTGCTCTCAAGCTTCCAACTCTCCCGAAAACCTTGGTTGGTGTAATTAGCCAAGAGAAGT
PPI-BnCPP     CTCCTCTCAAGCTTCCCACTCTCCCAAAGACTTTGGTTGGAGTCATTAGCCAAGAGAAGT
BASF-Corn     ------------------------------------------------------------
PPI-GmCPP     TTGAGAAATCTAGAGCCTATAG--------------------------------------
BASF-Gm       TTGAGAAATCTAGAGCCTATAG--------------------------------------
AT4g01320     TTGAGAAATCACGAGCATACAG--------------------------------------
AF007269      TTGAGAAATCACGAGCATACAGTCTTGACAAAAGGTTTCGTCTTGATCATATTTATATCA
PPI-AtCPP     TTGAGAAATCACGAGCATACAG--------------------------------------
BASF_AT2      TTGAGAAATCACGAGCATACAG--------------------------------------
afc1          TTGAGAAATCACGAGCATACAG--------------------------------------
```

TABLE 18A-continued

| ClustalW Nucleic Acid Analysis of CaaX Penyl Protease | |
|---|---|
| BASF_AT1 | TTGAGAAATCACGAGCATACAG-------------------------------------- |
| PPI-BnCPP | TTGAGAAATCTCGAGCTTACAG-------------------------------------- |
| BASF-Corn | ------------------------------------------------------------ |
| PPI-GmCPP | ------------------------------------------TCTTGATAAA---AGCCA |
| BASF-Gm | ------------------------------------------TCTTGATAAA---AGCCA |
| AT4g01320 | ------------------------GGATATCATCACTGAGAACTTTAATATATGCAGCTA |
| AF007269 | TTTTAGTTTTTTATAATTGCCAGGGGATATCATCACTGAGAACTTTAATATATGCAGCTA |
| PPI-AtCPP | ------------------------------------------TCTTGACAAA---AGCTA |
| BASF_AT2 | ------------------------------------------TCTTGACAAA---AGCTA |
| afc1 | ------------------------------------------TCTTGACAAA---AGCTA |
| BASF_AT1 | ------------------------------------------TCTTGACAAA---AGCTA |
| PPI-BnCPP | ------------------------------------------TCTTGACAAA---AGCCA |
| BASF-Corn | ------------------------------------------------------------ |
| PPI-GmCPP | CTTCCATTTTGTTCACGAGTTTGTGACAATAGTGACAGACTCTACAATTTTGTACTTTGG |
| BASF-Gm | CTTCCATTTTGTTCACGAGTTTGTGACAATAGTGACAGACTCTACAATTTTGTACTTTGG |
| AT4g01320 | TTTTCACTTTGTTCATGAGTTTGTAACTATACTTATGGACTCTGCAATTTTGTTCTTTGG |
| AF007269 | TTTTCACTTTGTTCATGAGTTTGTAACTATACTTATGGACTCTGCAATTTTGTTCTTTGG |
| PPI-AtCPP | TTTTCACTTTGTTCATGAGTTTGTAACTATACTTATGGACTCTGCAATTTTGTTCTTTGG |
| BASF_AT2 | TTTTCACTTTGTTCATGAGTTTGTAACTATACTTATGGACTCTGCAATTTTGTTCTTTGG |
| afc1 | TTTTCACTTTGTTCATGAGTTTGTAACTATACTTATGGACTCTGCAATTTTGTTCTTTGG |
| BASF_AT1 | TTTTCACTTTGTTCATGAGTTTGTAACTATACTTATGGACTCTGCAATTTTGTTCTTTGG |
| PPI-BnCPP | TTTTCACTTTGTTCATGAGTTTGTTACTATACTTATGGACTCTGCGATTCTGTTCTTTGG |
| BASF-Corn | ------------------------------------------------------------ |
| PPI-GmCPP | GGTATTGCCCTGGTTTTGGAAG-------------------------------------- |
| BASF-Gm | GGTATTGCCCTGGTTTTGGAAG-------------------------------------- |
| AT4g01320 | GATCTTGCCTTGGTTTTGGAAG-------------------------------------- |
| AF007269 | GATCTTGCCTTGGTTTTGGAAGGTACATATCTGGTTTCGGTATACACTATCTCATTTTGA |
| PPI-AtCPP | GATCTTGCCTTGGTTTTGGAAG-------------------------------------- |
| BASF_AT2 | GATCTTGCCTTGGTTTTGGAAG-------------------------------------- |
| afc1 | GATCTTGCCTTGGTTTTGGAAG-------------------------------------- |
| BASF_AT1 | GATCTTGCCTTGGTTTTGGAAG-------------------------------------- |
| PPI-BnCPP | GATCTTGCCTTGGTTTTGGAAG-------------------------------------- |
| BASF-Corn | ------------------------------------------------------------ |
| PPI-GmCPP | ------------------------------------------------AAATCAGGAGAT |
| BASF-Gm | ------------------------------------------------AAATCAGGAGAT |
| AT4g01320 | ------------------------------------------------ATGTCTGGAGCT |
| AF007269 | ATATAGAGTTGTTACATTACAATTGTAAAGTTTTCATTTTTACCTTAGATGTCTGGAGCT |
| PPI-AtCPP | ------------------------------------------------ATGTCTGGAGCT |
| BASF_AT2 | ------------------------------------------------ATGTCTGGAGCA |

TABLE 18A-continued

ClustalW Nucleic Acid Analysis of CaaX Penyl Protease

```
afc1         ------------------------------------------------ATGTCTGGAGCT

BASF_AT1     ------------------------------------------------ATGTCTGGAGCT

PPI-BnCPP    ------------------------------------------------ATATCTGGCGGC

BASF-Corn    ------------------------------------------------------------

PPI-GmCPP    TTTATGACAATAGCTGGTTTCAATGCTGAGAATGAAATACTGCATACCCTTGCCTTCTTA

BASF-Gm      TTTATGACAATAGCTGGTTTCAATGCTGAGAATGAAATACTGCATACCCTTGCCTTCTTA

AT4g01320    GTTTTACCGAGGTTGGGCCTTGATCCAGAGAATGAAATACTGCATACTCTTTCATTCTTG

AF007269     GTTTTACCGAGGTTGGGCCTTGATCCAGAGAATGAAATACTGCATACTCTTTCATTCTTG

PPI-AtCPP    GTTTTACCGAGGTTGGGCCTTGATCCGGAGAATGAAATACTGCATACTCTTTCATTCTTG

BASF_AT2     GTTTTACCGAGGTTGGGCCTTGATCCAGAGAATGAAATACTGCATACTCTTTCATTCTTG

afc1         GTTTTACCGAGGTTGGGCCTTGATCCAGAGAATGAAATACTGCATACTCTTTCATTCTTG

BASF_AT1     GTTTTACCGAGGTTGGGCCTTGATCCAGAGAATGAAATACTGCATACTCTTTCATTCTTG

PPI-BnCPP    TTTCTACCAATGGTGGGACTCGATCCAGAGAATGAAATCCTGCACACTCTTTCATTCTTG

BASF-Corn    ------------ACGAGGCTGAGTGCTGAGAATGAGATAATACACACCCTTGCTTTCTTA
                             *  *   * * ******** **  * ** ** *** * *****

PPI-GmCPP    GCAGGGCTGATGATTTGGTCACAG------------------------------------

BASF-Gm      GCAGGGCTGATGATTTGGTCACAG------------------------------------

AT4g01320    GCTGGTGTTATGACATGGTCACAG------------------------------------

AF007269     GCTGGTGTTATGACATGGTCACAGGTGTTCCAAATAAACCCCTTCATATAGTCCTATACG

PPI-AtCPP    GCTGGTGTTATGACATGGTCACAG------------------------------------

BASF_AT2     GCTGGTGTTATGACATGGTCACAG------------------------------------

afc1         GCTGGTGTTATGACATGGTCACAG------------------------------------

BASF_AT1     GCTGGTGTTATGACATGGTCACAC------------------------------------

PPI-BnCPP    GCTGGTCTTATGACATGGTCACAG------------------------------------

BASF-Corn    GCTGGTTCCATGGTTTGGTCGCAG------------------------------------
             ** **    ***   ***** **

PPI-GmCPP    ------------------------------------------------------------

BASF-Gm      ------------------------------------------------------------

AT4g01320    ------------------------------------------------------------

AF007269     TTTACCATCAAAATATCTATTTTCTTAAGATAATAATATTTCTTTTATATTCTGATGCAG

PPI-AtCPP    ------------------------------------------------------------

BASF_AT2     ------------------------------------------------------------

afc1         ------------------------------------------------------------

BASF_AT1     ------------------------------------------------------------

PPI-BnCPP    ------------------------------------------------------------

BASF-Corn    ------------------------------------------------------------

PPI-GmCPP    ATAACAGATTTGCCCTTTTCTCTGTACTCAACTTTTGTGATTGAGGCCCGTCATGGTTTT

BASF-Gm      ATAACAGATTTGCCCTTTTCTCTGTACTCAACTTTTGTGATTGAGGCCCGTCATGGTTTT

AT4g01320    ATCACTGATTTGCCATTTTCTTTGTACTCAACTTTCGTGATCGAGTCTCGGCATGGGTTC

AF007269     ATCACTGATTTGCCATTTTCTTTGTACTCAACTTTCGTGATCGAGTCTCGGCATGGGTTC
```

TABLE 18A-continued

ClustalW Nucleic Acid Analysis of CaaX Penyl Protease

```
PPI-AtCPP      ATCACTGATTTGCCATTTTCTTTGTACTCAACTTTCGTGATCGAGTCTCGGCATGGGTTC

BASF_AT2       ATCACTGATTTGCCATTTTCTTTGTACTCAACTTTCGTGATCGAGTCTCGGCATGGGTTC

afc1           ATCACTGATTTGCCATTTTCTTTGTACTCAACTTTCGTGATCGAGTCTCGGCATGGGTTC

BASF_AT1       ATCACTGATTTGCCATTTTCTTTGTACTCAACTTTCGTGATCGAGTCTCGGCATGGGTTC

PPI-BnCPP      ATCACTGATTTGCCATTTTCTTTGTACTCAACTTTCGTGATCGAGTCTCGGCATGGGTTC

BASF-Corn      ATTACAGACTTGCCGTTCTCTCTCTATTCAACTTTTGTTATAGAGGCTCGACATGGTTTT
               **  ** ** ***** ** *** *  ** ******** ** ** *** * ** ***** **

PPI-GmCPP      AATAAG------------------------------------------------------

BASF-Gm        AATAAG------------------------------------------------------

AT4g01320      AACAAA------------------------------------------------------

AF007269       AACAAAGTATGTCGTATTTCCAACACTACCTTGTGACTTACGTTTTTTTATCAGAGATGT

PPI-AtCPP      AACAAA------------------------------------------------------

BASF_AT2       AACAAA------------------------------------------------------

afc1           AACAAA------------------------------------------------------

BASF_AT1       AACAAA------------------------------------------------------

PPI-BnCPP      AACAAA------------------------------------------------------

BASF-Corn      AACAAG------------------------------------------------------
               ** **

PPI-GmCPP      --------------------------------CAAACACCATGGTTATTCTTTAGGGACA

BASF-Gm        --------------------------------CAAACACCATGGTTATTCTTTAGGGACA

AT4g01320      --------------------------------CAAACAATATGGATGTTCATTAGGGACA

AF007269       GGATTAAATTTGCTTCTAAATTCTGTTGACAGCAAACAATATGGATGTTCATTAGGGACA

PPI-AtCPP      --------------------------------CAAACAATATGGATGTTCATTAGGGACA

BASF_AT2       --------------------------------CAAACAATATGGATGTTCATTAGGGACA

afc1           --------------------------------CAAACAATATGGATGTTCATTAGGGACA

BASF_AT1       --------------------------------CAAACAATATGGATGTTCATTAGGGACA

PPI-BnCPP      --------------------------------CAAACAATATGGATGTTCATTAGGGACA

BASF-Corn      --------------------------------CAAACTATATGGCTCTTCATTAGGGATA
                                                *****  **** * *** ******* *

PPI-GmCPP      TGCTTAAAGGAATTTTCCTTTCTGTAATAATTGGTCCACCTATTGTGGCTGCAATCATTG

BASF-Gm        TGCTTAAAGGAATTTTCCTTTCCGTAATAATTGGTCCACCTATTGTGGCTGCAATCATTG

AT4g01320      TGATCAAAGGAACATTCCTCTCTGTCATACTAGGCCCACCCATTGTTGCTGCGATAATTT

AF007269       TGATCAAAGGAACATTCCTCTCTGTCATACTAGGCCCACCCATTGTTGCTGCGATAATTT

PPI-AtCPP      TGATCAAAGGAACATTCCTCTCTGTCATACTAGGCCCACCCATTGTTGCTGCGATAATTT

BASF_AT2       TGATCAAAGGAACATTCCTCTCTGTCATACTAGGCCCACCCATTGTTGCTGCGATAATTT

afc1           TGATCAAAGGAACATTCCTCTCTGTCATACTAGGCCCACCCATTGTTGCTGCGATAATTT

BASF_AT1       TGATCAAAGGAACATTCCTCTCTGTCATACTAGGCCCACCCATTGTTGCCGCGATAATTT

PPI-BnCPP      TGATCAAAGGAATACTCCTCTCTGTCATACCTGCCCCTCCTATCGTTGCCGCAATTATTG

BASF-Corn      TGATCAAAGGAATTTTACTATCCATGATATTGGGGCCACCAATCGTGGCTGCTATCATCT
               ** * *******   * ** ** * ***    *  ** **  ** ** ** ** ** **

PPI-GmCPP      TAATAGTACAG-------------------------------------------------
```

TABLE 18A-continued

ClustalW Nucleic Acid Analysis of CaaX Penyl Protease

```
BASF-Gm       TAATAGTACAG-------------------------------------------------
AT4g01320     TCATAGTCCAG-------------------------------------------------
AF007269      TCATAGTCCAGGTTTGATGATTCTGGATTCATCTTATTTCTGAGTTTTTCACATGGATGA
PPI-AtCPP     TCATAGTCCAG-------------------------------------------------
BASF_AT2      TCATAGTCCAG-------------------------------------------------
afc1          TCATAGTCCAG-------------------------------------------------
BASF_AT1      TCATAGTCCAG-------------------------------------------------
PPI-BnCPP     TTATAGTTCAG-------------------------------------------------
BASF-Corn     ACATAGTACAG-------------------------------------------------
                ***** ***
PPI-GmCPP     ------------------------------------------------------------
BASF-Gm       ------------------------------------------------------------
AT4g01320     ------------------------------------------------------------
AF007269      CTATTCTCCATTGAGTGTGAGCTTCAAAGTTTTTAGTTTTCGTGTTAAAAATTTAAAATT
PPI-AtCPP     ------------------------------------------------------------
BASF_AT2      ------------------------------------------------------------
atc1          ------------------------------------------------------------
BASF_AT1      ------------------------------------------------------------
PPI-BnCPP     ------------------------------------------------------------
BASF-Corn     ------------------------------------------------------------
PPI-GmCPP     ------------------------------------AAAGGAGGTCCATACTTGGCCATC
BASF-Gm       ------------------------------------AAACCAGCTCCATACTTGGCCATC
AT4g01320     ------------------------------------AAAGGAGGTCCTTATCTTGCCATC
AF007269      TGCTTCTCTGAGCATGAAGTTTCTATCTTTTTCCAGAAAGGAGGTCCTTATCTTGCCATC
PPI-AtCPP     ------------------------------------AAAGGAGGTCCTTATCTTGCCATC
BASF_AT2      ------------------------------------AAAGGAGGTCCTTATCTTGCCATC
afc1          ------------------------------------AAAGGAGGTCCTTATCTTGCCATC
BASF_AT1      ------------------------------------AAAGGAGGTCCTTATCTTGCCATC
PPI-BnCPP     ------------------------------------AAAGGAGGTCCTTACCTCGCCATC
BASF-Corn     ------------------------------------ATTGGAGGACCTTACCTGGCTATA
                                                  *  ***** ** **  * ** **
PPI-GmCPP     TATCTTTGGGTTTTTACGTTTGGTCTTTCTATTGTGATGATGACCCTTTATCCAGTACTA
BASF-Gm       TATCTTTGGGTTTTTACGTTTGGTCTTTCTATTGTGATGATGACCCTTTATCCAGTACTA
AT4g01320     TATCTGTGGGCATTCATGTTTATCCTGTCTCTAGTGATGATGACTATATACCCGGTCTTG
AF007269      TATCTGTGGGCATTCATGTTTATCCTGTCTCTAGTGATGATGACTATATACCCGGTCTTG
PPI-AtCPP     TATCTGTGGGCATTCATGTTTATCCTGTCTCTAGTGATGATGACTATATACCCGGTCTTG
BASF_AT2      TATCTGTGGGCATTCATGTTTATCCTGTCTCTAGTGATGATGACTATATACCCGGTCTTG
afc1          TATCTGTGGGCATTCATGTTTATCCTGTCTCTAGTGATGATGACTATATACCCGGTCTTG
BASF_AT1      TATCTGTGCGCATTCATGTTTATCCTGTCTCTAGTGATGATGACTATATACCCGGTCTTG
PPI-BnCPP     TATCTGTGGGCATTCATGTTTATCCTGTCTCTAGTGATGATGACTATATACCCTGTTTTG
```

TABLE 18A-continued

ClustalW Nucleic Acid Analysis of CaaX Penyl Protease

| | |
|---|---|
| BASF-Corn | TATCTCTGGGGTTTTATGTTTGTATTAGCTCTACTGATGATGACAATATACCCCATTGTG |
| | ***** **** ** * ****   * ** * *********  * ** ** * * |
| PPI-GmCPP | ATAGCTCCACTCTTCAATAAGTTCACTCCA------------------------------ |
| BASF-Gm | ATAGCTCCACTCTTCAATAAGTTCACTCCA------------------------------ |
| AT4g01320 | ATAGCACCGCTCTTCAACAAGTTCACTCCT------------------------------ |
| AF007269 | ATAGCACCGCTCTTCAACAACTTCACTCCTGTGTGTATTTCTGTCATGGCCATTTTACAA |
| PPI-AtCPP | ATAGCACCGCTCTTCAACAAATTCACTCCT------------------------------ |
| BASF_AT2 | ATAGCACCGCTCTTCAACAAGTTCACTCCT------------------------------ |
| afc1 | ATAGCACCGCTCTTCAACAAGTTCACTCCT------------------------------ |
| BASF_AT1 | ATAGCACCGCTCTTCAACAAGTTCACTCCT------------------------------ |
| PPI-BnCPP | ATTGCACCTCTTTTCAACAAGTTCACTCCT------------------------------ |
| BASF-Corn | ATAGCTCCTCTGTTCAACAAGTTCACTCCT------------------------------ |
| | ** ** ** ** ***** ** ******** |
| PPI-GmCPP | ------------------------------------------------------------ |
| BASF-Gm | ------------------------------------------------------------ |
| AT4g01320 | ------------------------------------------------------------ |
| AF007269 | TTCACTGCTTGTTTGCATATGTTGTTACCAGACAATATAATCTCCCGCTTTTTTATGGCT |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | ------------------------------------------------------------ |
| PPI-GmCPP | ----CTTCCAGATGGTCAACTCAGGGAGAAAATCGAGAAACTTGCTTCCTCCCTCAACTA |
| BASF-Gm | ----CTTCCAGATGGTCAACTCAGGGAGAAAATCGAGAAACTTGCTTCCTCCCTCAACTA |
| AT4g01320 | ----CTTCCAGATGGAGACCTCCGGGAGAAGATTGAGAAACTTGCTTCTTCTCTAAAGTT |
| AF007269 | ATAGCTTCCAGATGGAGACCTCCGGGAGAAGATTGAGAAACTTGCTTCTTCTCTAAAGTT |
| PPI-AtCPP | ----CTTCCAGATGGAGACCTCCGGGAGAAGATTGACAAACTTGCTTCTTCCCTAAAGTT |
| BASF_AT2 | ----CTTCCAGATGGAGACCTCCGGGAGAAGATTGAGAAACTTGCTTCTTCTCTAAAGTT |
| afc1 | ----CTTCCAGATGGAGACCTCCGGGAGAAGATTGAGAAACTTGCTTCTTCTCTAAAGTT |
| BASF_AT1 | ----CTTCCAGATGGAGACCTCCGGGAGAAGATTGAGAAACTTGCTTCTTCTCTAAAGTT |
| PPI -BnCPP | ----CTTCCTGATGGAGACCTCCGGGAGAAGATTGAGAAACTTGCTTCTTCTCTAAAGTT |
| BASF-Corn | ----CTTCCTGAAGGAGTCCTCAGGGAAAAAATAGAGAAGCTGGCAGCTTCCCTCAAGTT |
| | ***** ** **    *** **** ** ** ***** ** **  * ** ** ** * |
| PPI-GmCPP | TCCGTTAAAGAAACTATTTGTTGTCGATGGATCCACAAGATCAAGTCACAGCAATG---- |
| BASF-Gm | TCCGTTAAAGAAACTATTTGTTGTCGATGGATCCACAAGATCAAGTCACAGCAATG---- |
| AT4g01320 | TCCTTTGAAGAAGCTGTTTGTTGTCGATGGATCTACAAGGTCAAGCCATAGCAATG---- |
| AF007269 | TCCTTTCAACAAGCTGTTTGTTGTCGATGGATCTACAAGGTCAAGCCATAGCAATGTGAG |
| PPI-AtCPP | TCCTTTGAAGAAGCTGTTTGTTGTCGATGGATCTACAAGGTCAAGCCATAGCAATG---- |
| BASF_AT2 | TCCTTTGAAGAAGCTGTTTGTTGTCGATGGATCTACAAGGTCAAGCCATAGCAATG---- |
| afc1 | TCCTTTGAAGAAGCTGTTTGTTGTCGATGGATCTACAAGGTCAAGCCATAGCAATG---- |

TABLE 18A-continued

ClustalW Nucleic Acid Analysis of CaaX Penyl Protease

```
BASF_AT1        TCCTTTGAAGAAGCTGTTTGTTGTCGATGGATCTACAAGGTCAAGCCATAGCAATG----

PPI-BnCPP       TCCTCTGAAGAAGCTGTTTGTTGTCGATGGATCTACAAGGTCAAGCCATAGTAATC----

BASF-Corn       TCCTTTGAAAAAGCTTTTCGTGGTAGATGGGTCTACCAGATCAAGCCACAGTAATG----
                ***  * ** ** ** ** ** ** ***** ** ** ** ***** ** ** ****

PPI-GmCPP       ------------------------------------------------------------

BASF-Gm         ------------------------------------------------------------

AT4g01320       ------------------------------------------------------------

AF007269        AAGCTTGAGATCTCTTCCTACCTACTTTACTCTAGTTTACCATTAGAAGCTTACGTATCT

PPI-AtCPP       ------------------------------------------------------------

BASF_AT2        ------------------------------------------------------------

afc1            ------------------------------------------------------------

BASF_AT1        ------------------------------------------------------------

PPI-BnCPP       ------------------------------------------------------------

BASF-Corn       ------------------------------------------------------------

PPI-GmCPP       ----------------CCTATATGTATGGATTCTTCAAGAACAAGAGGATTGTCCCTTAT

BASF-Gm         ----------------CCTATATGTATGGATTCTTCAAGAACAAGAGGATTGTCCTTTAT

AT4g01320       ----------------CTTACATGTATGGTTTCTTTAAGAACAAAAGGATTGTTCTTTAT

AF007269        TGTTACATCATACAGGCTTACATGTATGGTTTCTTTAAGAACAAAAGGATTGTTCTTTAT

PPI-AtCPP       ----------------CTTACATGTATGGTTTCTTTAAGAACAAAAGGATTGTTCTTTAT

BASF_AT2        ----------------CTTACATGTATGGTTTCTTTAAGAACAAAAGGATTGTTCTTTAT

afc1            ----------------CTTACATGTATGGTTTCTTTAAGAACAAAAGGATTGTTCTTTAT

BASF_AT1        ----------------CTTACATGTATGGTTTCTTTAAGAACAAAAGGATTGTTCTTTAT

PPI-BnCPP       ----------------CTTACATGTATGGTTTCTTCAAGAACAAAAGGATTGTTCTTTAT

BASF-Corn       ----------------CCTACATGTATGGTTTTTTCAAGAACAAGCGCATAGTACTCTAT
                                * ** ******** ** ** ********  * ** ** *  ***

PPI-GmCPP       GACACATTAATTCAACAG------------------------------------------

BASF-Gm         GACACATTAATTCAACAG------------------------------------------

AT4g01320       GATACGTTGATTCAGCAG------------------------------------------

AF007269        GATACGTTGATTCAGCAGGTACTGTGACTCTTGATGCTTCAAACGAGCTATACTCACATT

PPI-AtCPP       GATACGTTGATTCAGCAG------------------------------------------

BASF_AT2        GATACGTTGATTCAGCAG------------------------------------------

afc1            GATACGTTGATTCAGCAG------------------------------------------

BASF_AT1        GATACGTTGATTCAGCAG------------------------------------------

PPI-BnCPP       GACACATTGATTCAGCAG------------------------------------------

BASF-Corn       GACACATTGATTCAGCAG------------------------------------------
                ** ** ** ***** ***

PPI-GmCPP       --------------------------------------------TGCAAAGACGATGAGG

BASF-Gm         --------------------------------------------TGCAAAGACGATGAGG

AT4g01320       --------------------------------------------TGCAAGAATGAGGATG

AF007269        TCTGTTTCTGGTTCTGAAACATAACATAATCTTCTATTGTGCAGTGCAAGAATGAGGATG
```

TABLE 18A-continued

ClustalW Nucleic Acid Analysis of CaaX Penyl Protease

```
PPI-AtCPP     --------------------------------------------TGCAAGAATGAGGATG

BASF_AT2      --------------------------------------------TGCAAGAATGAGGATG

afc1          --------------------------------------------TGCAAGAATGAGGATG

BASF_AT1      --------------------------------------------TGCAAGAATGAGGATG

PPI-BnCPP     --------------------------------------------TGCCAGAATGAGAATG

BASF-Corn     --------------------------------------------TGTAGCAATGAGGATG
                                                        **     * **  * *

PPI-GmCPP     AAATTGTTGCTGTTATTGCCCATGAGTTGGGACACTGGAAGCTCAACCATACTGTGTACA

BASF-Gm       AAATTGTTGCTGTTATTGCCCATGAGTTGGGACACTGGAAGCTCAACCATACTGTGTACA

AT4g01320     AAATTGTGGCGGTTATTGCACACGAGCTTGGACATTGGAAACTGAATCACACTACATACT

AF007269      AAATTGTGGCGGTTATTGCACACGAGCTTGGACATTGGAAACTGAATCACACTACATACT

PPI-AtCPP     AAATTGTGGCGGTTATTGCACACGAGCTTGGACATTGGAAACTGAATCACACTACATACT

BASF_AT2      AAATTGTGGCGGTTATTGCACACGAGCTTGGACATTGGAAACTGAATCACACTACATACT

afc1          AAATTGTGGCGGTTATTGCACACGAGCTTGGACATTGGAAACTGAATCACACTACATACT

BASF_AT1      AAATTGTGGCGGTTATTGCACACGAGCTTGGACATTGGAAACTGAATCACACTACATACT

PPI-BnCPP     AAATTGTGGCGGTTATTGCACACCAGCTGGGACACTGGAAGCTGAATCACACTACATACT

BASF-Corn     AGATAGTTTCTGTTATAGCACATGAACTTGGACACTGGAAACTCAATCATACTGTCTATT
              * ** **  * ***** ** ** **  * ***** ***** ** ** ** ***  **

PPI-GmCPP     CATTTGTTGCTATGCAG-------------------------------------------

BASF-Gm       CATTTGTTGCTATGCAG-------------------------------------------

AT4g01320     CGTTCATTGCAGTTCAA-------------------------------------------

AF007269      CGTTCATTGCAGTTCAAGTGAGGCTCAACCGACAGTTCAAAAACTTACTCACATCTACAT

PPI-AtCPP     CGTTCATTGCAGTTCAA-------------------------------------------

BASF_AT2      CGTTCATTGCAGTTCAA-------------------------------------------

afc1          CGTTCATTGCAGTTCAA-------------------------------------------

BASF_AT1      CGTTCATTGCAGTTCAA-------------------------------------------

PPI-BnCPP     CGTTCATTGCTGTTCAA-------------------------------------------

BASF-Corn     CCTTTGTAGCTGTCCAG-------------------------------------------
              * **  * **  * **

PPI-GmCPP     ---------------------------------------------------ATTCTTACA

BASF-Gm       ---------------------------------------------------ATTCTTACA

AT4g01320     ---------------------------------------------------ATCCTTGCC

AF007269      TTCACTTAAGAAATCATGTCTTATGACCCTCTCTCAATGTTTTGCTTGCAGATCCTTGCC

PPI-AtCPP     ---------------------------------------------------ATCCTTGCC

BASF_AT2      ---------------------------------------------------ATCCTTGCC

afc1          ---------------------------------------------------ATCCTTGCC

BASF_AT1      ---------------------------------------------------ATCCTTGCC

PPI-BnCPP     ---------------------------------------------------ATCCTTGCC

BASF-Corn     ---------------------------------------------------CTGCTTATG
                                                                  * ***

PPI-GmCPP     CTTCTACAATTTGGAGGATATACACTAGTGCGAAATTCAGCTGATCTGTATCGAAGCTTT
```

TABLE 18A-continued

| ClustalW Nucleic Acid Analysis of CaaX Penyl Protease | |
|---|---|
| BASF-Gm | CTTCTACAATTTGGAGGATATACACTAGTGCGAAATTCAGCTGATCTGTATCGAAGCTTT |
| AT4g01320 | TTCTTACAATTTGGAGGATACACTCTTGTCAGAAACTCCACTGATCTCTTCAGGAGTTTC |
| AF007269 | TTCTTACAATTTGGAGGATACACTCTTGTCAGAAACTCCACTGATCTCTTCAGGAGTTTC |
| PPI-AtCPP | TTCTTACAATTTGGAGGATACACTCTTCTCAGAAACTCCACTGATCTCTTCAGGAGTTTC |
| BASF_AT2 | TTCTTACAATTTGGAGGATACACTCTTGTCAGAAACTCCACTGATCTCTTCAGGAGTTTC |
| afc1 | TTCTTACAATTTGGAGGATACACTCTTGTCAGAAACTCCACTGATCTCTTCAGGAGTTTC |
| BASF_AT1 | TTCTTACAATTTGGAGGATACACTCTTGTCAGAAACTCCACTGATCTCTTCAGGAGTTTC |
| PPI-BnCPP | TTCTTGCAATTTGGAGGATACACTCTTGTCAGAAACTCCACTGATCTCTTCAGGAGTTTT |
| BASF-Corn | TTTCTTCAATTTGGAGGATATACTCTAGTAAGGAGCTCCAAAGATCTATTTGGAAGTTTT |
| | * * ************** ** ** * * * ** ***** * * ** ** |
| PPI-GmCPP | GGGTTTGATACGCAGCCAGTCCTCATTGGGCTCATCATATTTCAG--------------- |
| BASF-Gm | GGGTTTGATACGCAGCCAGTCCTCATTGGGCTCATCATATTTCAG--------------- |
| AT4g01320 | GGATTTGATACACAGCCTGTTCTCATTGGTTTGATCATATTTCAG--------------- |
| AF007269 | GGATTTGATACACAGCCTGTTCTCATTGGTTTGATCATATTTCAGGTTTGTTATTTTTGC |
| PPI-AtCPP | GGATTTGATACACAGCCTGTTCTCATTGGTTTGATCATATTTCAG--------------- |
| BASF_AT2 | GGATTTGATACACAGCCTGTTCTCATTGGTTTGATCATATTTCAG--------------- |
| afc1 | GGATTTGATACACAGCCTGTTCTCATTGGTTTGATCATATTTCAG--------------- |
| BASF_AT1 | GGATTTGATACACAGCCTGTTCTCATTGGTTTGATCATATTTCAG--------------- |
| PPI-BnCPP | GGTTTTGATACACAACCAGTTCTCATTGGTTTGATCATATTTCAG--------------- |
| BASF-Corn | GGCTTCAAGGACCAGCCAGTAATAATTGGATTGATCATTTTCCCG--------------- |
| | ** ** * ** ** ** * ***** * ***** ** * * |
| PPI-GmCPP | ------------------------------------------------------------ |
| BASF-Gm | ------------------------------------------------------------ |
| AT4g01320 | ------------------------------------------------------------ |
| AF007269 | CTTTTGACACTAATCTAATGAATCAAGGATGGATTAAGAAAAAAAAAACTCTAAACCTTG |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | ------------------------------------------------------------ |
| PPI-GmCPP | ---------------------------CATACTGTAATCCCACTTCAGCAATTGGTCAGC |
| BASF-Gm | ---------------------------CATACTGTAATCCCACTTCAGCAATTGGTCAGC |
| AT4g01320 | ---------------------------CACACTGTAATACCACTGCAACATCTAGTCAGC |
| AF007269 | GTTATATCTCCTGTCTGATTATCACAGCACACTGTAATACCACTGCAACATCTAGTAAGC |
| PPI-AtCPP | ---------------------------CACACTGTAATACCACTGCAACATCTAGTAAGC |
| BASF_AT2 | ---------------------------CACACTGTAATACCACTGCAACATCTAGTAAGC |
| afc1 | ---------------------------CACACTGTAATACCACTGCAACATCTAGTAAGC |
| BASF_AT1 | ---------------------------CACACTGTAATACCACTGCAACATCTAGTAAGC |
| PPI-BnCPP | ---------------------------CACACTGTAATACCACTTCAACACCTAGTAAGC |

TABLE 18A-continued

ClustalW Nucleic Acid Analysis of CaaX Penyl Protease

```
BASF-Corn     ---------------------------CACACCATAATACCCATTCAACACCTAGTAAGC
                                         ** **  **** **  * ** **    * ***

PPI-GmCPP     TTTGGTCTGAACCTAGTCAGCCGATCATTTGAATTTCAGG--------------------

BASF-Gm       TTTGGTCTGAACCTAGTCAGCCGATCATTTGAATTTCAGG--------------------

AT4g01320     TTTGGCCTGAACCTCGTTAGTCGAGCGTTTGAGTTTCAGG--------------------

AF007269      TTTGGCCTGAACCTCGTTAGTCGAGCGTTTGAGTTTCAGGTACCATCTTACAATCCCTCA

PPI-AtCPP     TTTGGCCTGAACCTCGTTAGTCGAGCGTTTGAGTTTCAGG--------------------

BASF_AT2      TTTCGCCTGAACCTCGTTAGTCCAGCGTTTGAGTTTCAGG--------------------

afc1          TTTGGCCTGAACCTCGTTAGTCGAGCGTTTGAGTTTCAGG--------------------

BASF_AT1      TTTGGCCTCAACCTTGTTAGTCGAGCGTTTGAGTTTCAGG--------------------

PPI-BnCPP     TTTGACCTCAACCTTGTTAGTCGAGCGTTTGAGTTTCAGG--------------------

BASF-Corn     TTTCGCCTGAACCTTGTCAGCAGAGCATTTGAATTTCAGG--------------------
              ***   ** ***** ** **   ** * ***** *******

PPI-GmCPP     ------------------------------------------------------------

BASF-Gm       ------------------------------------------------------------

AT4g01320     ------------------------------------------------------------

AF007269      AGATCCAACCATAGTTTCTTTATTGCAATGGCAGCCTCATCTACTAATCTGAGTTAACGT

PPI-AtCPP     ------------------------------------------------------------

BASF_AT2      ------------------------------------------------------------

afc1          ------------------------------------------------------------

BASF_AT1      ------------------------------------------------------------

PPI-BnCPP     ------------------------------------------------------------

BASF-Corn     ------------------------------------------------------------

PPI-GmCPP     ------------CTGATGGCTTTGCCAAGAAGCTTGGATATGCATCTGGATTACGCGGTG

BASF-Gm       ------------CTGATGGCTTTGCCAAGAAGCTTGGATATGCATCTGGATTACCCGGTG

AT4g01320     ------------CTGATGGCTTTGCCAAGAAGCTTGGATATGCATCTGGATTACCCGGTG

AF007269      TCCTTTTGCAGGCTGATGCTTTTGCTGTGAAGCTTGGCTATGCAAAAGATCTTCGTCCTG

PPI-AtCPP     ------------CTGATGCTTTTGCTGTGAAGCTTGACTATGCAAAAGATCTTCGTCCTG

BASF_AT2      ------------CTGATGCTTTTGCTGTGAAGCTTGGCTATGCAAAAGATCTTCGTCCTG

afc1          ------------CTGATGCTTTTGCCGTGAAGCTTGGCTATGCAAAAGATCTTCGTCCTG

BASF_AT1      ------------CTGATGCTTTTGCTGTGAAGCTTGGCTATGCAAAAGATCTTCGTCCTA

PPI-BnCPP     ------------CTGATGCTTTTGCAGTGAATCTTGGTTATGCAAAGGATCTACGTCCTG

BASF-Corn     ------------CTGATGCCTTTGCCAAGAACCTTGGATATGCCCCTCAGCTCCGAGCAG
                          ******  *****   *** ****  *****        * **

PPI-GmCPP     GTCTTGTGAAACTACAGG------------------------------------------

BASF-Gm       GTCTTGTGAAACTACAGG------------------------------------------

AT4g01320     CTCTAGTGAAACTACAGGTCAGAGAAGATAACAACAGAACACAAACTGTTACCTCAATTT

AF007269      CTCTAGTGAAACTACAGGTCAGAGAAGATAACAACAGAACACAAACTGTTACCTCAATTT

PPI-AtCPP     CTCTAGTGAAACTACAGG------------------------------------------

BASF_AT2      CTCTAGTGAAACTACAGG------------------------------------------

afc1          CTCTAGTGAAACTACAGG------------------------------------------
```

TABLE 18A-continued

ClustalW Nucleic Acid Analysis of CaaX Penyl Protease

```
BASF_AT1     CTCTAGTGAAACTACAGG------------------------------------------
PPI-BnCPP    CCCTAGTGAAGCTACAGG------------------------------------------
BASF-Corn    CCCTTGTTAAACTACAGG------------------------------------------
               ** ** *********

PPI-GmCPP    ------------------------------------------AGGAGAATCTGTCAGCTA
BASF-Gm      ------------------------------------------AGGAGAATCTGTCAGCTA
AT4g01320    GTGTCACACACTTAAATGGATTTTTTGTTGGGATTTTGCAGGAAGAGAACTTATCAGCAA
AF007269     GTGTCACACACTTAAATGGATTTTTTGTTGGGATTTTGCAGGAAGAGAACTTATCAGCAA
PPI-AtCPP    ------------------------------------------AAGAGAACTTATCAACAA
BASF_AT2     ------------------------------------------AAGAGAACTTATCAGCAA
afc1         ------------------------------------------AAGAGAACTTATCAGCAA
BASF_AT1     ------------------------------------------AAGAGAACTTATCAGCAA
PPI-BnCPP    ------------------------------------------AAGAGAACTTATCAGCGA
BASF-Corn    ------------------------------------------AGGAGAACTTGTCTGCGA
                                                       * *****  * **  * *

PPI-GmCPP    TGAATACAGATCCTTGGTACTCTGCTTATCACTATTCTCATCCTCCCCTTGTTGAAAGAT
BASF-Gm      TGAATACAGATCCTTGCT--CGTGCCG---------------------------------
AT4g01320    TGAACACTGATCCATTGTACTCAGCTTATCACTACTCACATCCTCCTCTTGTTGAAAGGC
AF007269     TGAACACTGATCCATTGTACTCAGCTTATCACTACTCACATCCTCCTCTTGTTGAAAGGC
PPI-AtCPP    TGAACACTGATCCATTGTACTCAGCTTATCACTACTCACATCCTCCTCTTGTTGAAAGGC
BASF_AT2     TGAAAACTGATCTATTGTACTCAGCTTATCACTACTCACATCCTCCTCTTGTTGAAAGGC
afc1         TGAACACTGATCCATTGTACTCAGCTTATCACTACTCACATCCTCCTCTTGTTGAAAGGC
BASF_AT1     TGAACACTGATCCATTGTACTCAGCTTATCACTACTCACATCCTCCTCTTGTTGAAAGGC
PPI-BnCPP    TGAACACTGATCCATTGTACTCAGCTTATCACTACTCACATCCTCCTCTTGTTGAAAGGC
BASF-Corn    TGAACACTGATCCATTGTACTCAGCTTATCACTACTCACATCCTCCTCTTGTTGAAAGGC
             **** ** ** *  *        **

PPI-GmCPP    TGGCCGCGCTGGACGA---ACCGGATAAGAAGGAAGACTAA-------------------
BASF-Gm      ------------------------------------------------------------
AT4g01320    TTCGAGCCATTGATGG---AGAAGACAAGAAGACAGATTAA-------------------
AF007269     TTCGAGCCATTGATGG---AGAAGACAAGAAGACAGATTAA-------------------
PPI-AtCPP    TTCGAGCCACTGATGG---AGAAGACAAGAAGACACATTAA-------------------
BASF_AT2     TTCGAGCCATTGATGG---AGAAGACAAGAAGACAGATTAA-------------------
afc1         TTCCAGCCATTGATGG---AGAAGACAAGAAGACAGATTAA-------------------
BASE_AT1     TTCGAGCCATTGATGG---AGAAGACAAGAAGACAGATTAA-------------------
PPI-BnCPP    TTCGAGCCATTGATGG---AGAAGACAAGAAGACAGATTAA-------------------
BASF-Corn    TGCAAGCTTTGGAAGATTCAGACGACAAAAAAGAAGATTAGTCGATCCTTGTATGAGGTT
PPI-GmCPP    ------------------------------------------------------------
BASF-Gm      ------------------------------------------------------------
AT4g01320    ------------------------------------------------------------
AF007269     ------------------------------------------------------------
```

TABLE 18A-continued

| ClustalW Nucleic Acid Analysis of CaaX Penyl Protease | |
|---|---|
| PPI-AtCPP | ------------------------------------------------------------ |
| BASE_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | TACATATGGATTTTTCCCTGCCACATGCACACCGATTCAGTGCTTGGATGGTGAGGGTTT |
| PPI-GmCPP | ------------------------------------------------------------ |
| BASF-Gm | ------------------------------------------------------------ |
| AT4g01320 | ------------------------------------------------------------ |
| AF007269 | ------------------------------------------------------------ |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | TGACATAGGAGTGTTGTCAAAGCTTTAGAGTGCATCTTTCGGTCAGGTGCAACAGCCTTT |
| PPI-GmCPP | ------------------------------------------------------------ |
| BASF-Gm | ------------------------------------------------------------ |
| AT4g01320 | ------------------------------------------------------------ |
| AF007269 | ------------------------------------------------------------ |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | CGGTCATTGAGACATATAAGCGAATTAGCTATTAAAAAAAACAGAACTGTTGCATCAAAA |
| PPI-GmCPP | ------------------------------------------------------------ |
| BASF-Gm | ------------------------------------------------------------ |
| AT4g01320 | ------------------------------------------------------------ |
| AF007269 | ------------------------------------------------------------ |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | AAAAAAAAAAAAAAAAAAAAAAAAAAAAAAAAAAAAAAAAAAAAAAAAAAAAAAAAAAAA |
| PPI-GmCPP | ---------------------------------------------------- |
| BASF-Gm | ---------------------------------------------------- |
| AT4g01320 | ---------------------------------------------------- |

TABLE 18A-continued

| ClustalW Nucleic Acid Analysis of CaaX Penyl Protease | |
|---|---|
| AF007269 | -------------------------------------------------- |
| PPI-AtCPP | -------------------------------------------------- |
| BASF_AT2 | -------------------------------------------------- |
| afc1 | -------------------------------------------------- |
| BASF_AT1 | -------------------------------------------------- |
| PPI-BnCPP | -------------------------------------------------- |
| BASF-Corn | AAAAAGTGCTCTGCGTTGTTACCACTGCTTGCCCTATAGTGATCGTATCAGA |

TABLE 18B

| ClustalW Amino Acid Analysis of CaaX Prenyl Protease | |
|---|---|
| 1: PPI-AtCPP | SEQ ID NO:98 |
| 2: PPI-BnCPP | SEQ ID NO:110 |
| 3: PPI-GmCPP | SEQ ID NO:113 |
| 4: BASF_AT1 | SEQ ID NO:117 |
| 5: BASF_AT2 | SEQ ID NO:119 |
| 6: BASF-Corn | SEQ ID NO:121 |
| 7: BASF-Gm | SEQ ID NO:123 |
| 8: AFC1 | SEQ ID NO:125 |
| 9: AT4g01320 | SEQ ID NO:127 |
| 10: AF007269 | SEQ ID NO:129 |
| PPI-GmCP | MAFPYMEAVVGFMILMYIFETYLDVRQHRALKLPTLPKTLEG-------VISQEKFEKSR |
| BASF-Gm | MAFPYMEAVVGFMILMYIFETYLDVRQHRALKLPTLPKTLEG-------VISQEKFEKSR |
| AF007269 | MAIPFMETVVGFMIVMYIFETYLDLRQLTALKLPTLPKTLI------------------- |
| AT4g-AtCPP | MAIPFMETVVGFMIVMYIFETYLDLRQLTALKLPTLPKTLVGVISQEKFEKSRAYRDIIT |
| BASF_AT2 | MAIPFMETVVGFMIVMYIFETYLDLRQLTALKLPTLPKTLVG-------VISQEKFEKSR |
| AFC1 | MAIPFMETVVGFMIVMYIFETYLDLRQLTALKLPTLPKTLVG-------VISQEKFEKSR |
| BASF_AT1 | MAIPFMETVVGFMIVMYIFETYLDLRQLTALKLPTLPKTLVG-------VISQEKFEKSR |
| PPI-AtCPP | MAIPFMETVVGFMIVMYIFETYLDLRQLTALKLPTLPKTLVG-------VISQEKFEKSR |
| PPI-BnCPP | MAIPFMETVVGFMIVMYVFETYLDLRQHTALKLPTLPKTLVG-------VISQEKFEKSR |
| BASF-Corn | ------------------------------------------------------------ |
| PPI-GmCPP | AYSLDKSHFHFVHEFVTIVTDSTILYFGVLPWFWKKSGDFMTIAGFNAENEILHTLAFLA |
| BASF-Gm | AYSLDKSHFHFVHEFVTIVTDSTILYFGVLPWFWKKSGDFMTIAGFNAENEILHTLAFLA |
| AF007269 | ------------------------------------------------------------ |
| AT4g-AtCPP | ENFNICSYFHFVHEFVTILMDSAILFFGILPWFWKMSGAVLPRLGLDPENEILHTLSFLA |
| BASF_AT2 | AYSLDKSYFHFVHEFVTILMDSAILFFGILPWFWKMSGAVLPRLGLDPENEILHTLSFLA |
| AFC1 | AYSLDKSYFHFVHEFVTILMDSAILFFGILPWFWKMSGAVLPRLGLDPENEILHTLSFLA |
| BASF_AT1 | AYSLDKSYFHFVHEFVTILMDSAILFFGILPWFWKMSGAVLPRLGLDPENEILHTLSFLA |
| PPI-AtCPP | AYSLDKSYFHFVHEFVTILMDSAILFFGILPWFWKMSGAVLPRLGLDPENEILHTLSFLA |
| PPI-BnCPP | AYSLDKSYFHFVHEFVTILMDSAILFFGILPWFWKMSGAVLPRLGLDPENEILHTLSFLA |

TABLE 18B-continued

ClustalW Amino Acid Analysis of CaaX Prenyl Protease

```
BASF-Corn     --------------------------------------------TRLSAENEIIHTLAFLA

PPI-GmCPP     GLMIWSQITDLPFSLYSTFVIEARHGFNKQTPWLFFRDMLKGIFLSVIIGPPIVAAIIVI

BASF-Gm       GLMIWSQITDLPFSLYSTFVIEARHGFNKQTPWLFFRDMLKGIFLSVIIGPPIVAAIIVI

AF007269      --------TDLPFSLYSTFVIESRHGFNKQTIWMFIRDMIKGTFLSVILGPPIVAAIIFI

AT4G-AtCPP    GLMTWSQITDLPFSLYSTFVIESRHGFNKQTIWMFIRDMIKGTFLSVILGPPIVAAIIFI

BASF_AT2      GVMTWSQITDLPFSLYSTFVIESRHGFNKQTIWMFIRDMIKGTFLSVILGPPIVAAIIFI

AFC1          GVMTWSQITDLPFSLYSTFVIESRNGFNKQTIWMFIRDMIKGTFLSVILGPPIVAAIIFI

BASF_AT1      GVMTWSQITDLPFSLYSTFVIESRHGFNKQTIWMFIRDMIKGTFLSVILGPPIVAAIIFI

PPI-AtCPP     GVMTWSQITDLPFSLYSTFVIESRHGFNKQTIWMFIRDMIKGTFLSVILGPPIVAAIIFI

PPI-BnCPP     GLMTWSQITDLPFSLYSTFVIESRHGFNKQTIWMFIRDMIKGILLSVIPAPPIVPAIIVI

BASF-Corn     GSMVWSQITDLPFSLYSTFVIEARHGFNKQTIWLFIRDMIKGILLSMILGPPIVPAIIVI
                      **************:******** *:*:***:**:**:* :******** *

PPI -GmCPP    VQKGGPYLAIYLWVFTFGLSIVMMTLYPVLIAPLFNKFTPLPDGQLREKIEKLASSLNYP

BASF-Gm       VQKGGPYLAIYLWVFTFGLSIVMMTLYPVLIAPLFNKFTPLPDGQLREKIEKIASSLNYP

AF007269      VQKGGPYLAIYLWVFTFGLSIVMMTLYPVLIAPLFNKFTPLPDGQLREKIEKIASSLNYP

AT4g-AtCPP    VQKGGPYLAIYLWAFMFILSLVMMTIYPVLIAPLFNKFTPLPDGDLREKIEKIASSLKFP

BASF_AT2      VQKGCPYLAIYLWAFMFILSLVMMTIYPVLIAPLFNKFTPLPDGDLREKIEKIASSLKFP

AFC1          VQKGGPYLAIYLWAFMFILSLVMMTIYPVLIAPLFNKFTPLPDGDLREKIEKIASSLKFP

BASF_AT1      VQKGGPYLAIYLWAFMFILSLVMMTIYPVLIAPLFNKFTPLPDGDLREKIEKIASSLKFP

PPI-AtCPP     VQKGGPYLAIYLWAFMFILSLVMMTIYPVLIAPLFNKFTPLPDGDLREKIEKIASSLKFP

PPI-BnCPP     VQKGGPYLAIYLWAFMFILSLVMMTIYPVLIAPLFNKFTPLPDGDLREKIEKIASSLKFP

BASF-Corn     VQIGGPYLAIYLWGFMFVLALLMMTIYPIVIAPLFNKFTPLPEGVLREKIEKIASSLKFP
              ** ********** * * *:::***:**::************:* *********:**::*

PPI-GmCPP     LKKLFVVDGSTRSSHSNAYMYGFFKNKRIVPYDTLIQQCKDDEEIVAVIAHELGHWKLNH

BASF-Gm       LKKLFVVDGSTRSSHSNAYMYGFFKNKRIVPYDTLIQQCKDDEEIVAVIAHELGHWKLNH

AF007269      LKKLFVVDGSTRSSHSNAYMYGFFKNKRIVPYDTLIQQCKDDEEIVAVIAHELGHWKLNH

AT4g-AtCPP    LKKLFVVDGSTRSSHSNAYMYGFFKNKRIVPYDTLIQQCKDDEEIVAVIAHELGHWKLNH

BASF_AT2      LKKLFVVDGSTRSSHSNAYMYGFFKNKRIVPYDTLIQQCKDDEEIVAVIAHELGHWKLNH

AFC1          LKKLFVVDGSTRSSHSNAYMYGFFKNKRIVPYDTLIQQCKDDEEIVAVIAHELGHWKLNH

BASF_AT1      LKKLFVVDGSTRSSHSNAYMYGFFKNKRIVPYDTLIQQCKDDEEIVAVIAHELGHWKLNH

PPI-AtCPP     LKKLFVVDGSTRSSHSNAYMYGFFKNKRIVPYDTLIQQCKDDEEIVAVIAHELGHWKLNH

PPI-BnCPP     LKKLFVVDGSTRSSHSNAYMYGFFKNKRIVPYDTLIQQCKDDEEIVAVIAHELGHWKLNH

BASF-Corn     LKKLFVVDGSTRSSHSNAYMYGFFKNKRIVPYDTLIQQCKDDEEIVAVIAHELGHWKLNH
              ************************************* *********.:::***:

PPI-GmCPP     TVYTFVAMQILTLLQFGGYTLVRNSADLYRSFGFDTQPVLIGLIIFQHTVIPLQQLVSFG

BASF-Gm       TVYTFVAMQILTLLQFGGYTLVRNSADLYRSFGFDTQPVLIGLIIFQHTVIPLQQLVSFG

AF007269      TTYSFIAV--------------------------------------QHTVIPLQHLVSFG

AT4g-AtCPP    TTYSFIAVQILAFLQFGGYTLVRNSTDLFRSFGFDTQPVLIGLIIFQHTVIPLQHLVSFG

BASF_AT2      TTYSFIAVQILAFLQFGGYTLVRNSTDLFRSFGFDTQPVLIGLIIFQHTVIPLQHLVSFG

AFC1          TTYSFIAVQILAFLQFGGYTLVRNSTDLFRSFGFDTQPVLIGLIIFQHTVIPLQHLVSFG
```

TABLE 18B-continued

| ClustalW Amino Acid Analysis of CaaX Prenyl Protease | |
|---|---|
| BASF_AT1 | TTYSFIAVQILAFLQFGGYTLVRNSTDLFRSFGFDTQPVLIGLIIFQHTVIPLQHPVSFG |
| PPI-AtCPP | TTYSFIAVQILAFLQFGGYTLLRNSTDLFRSFGFDTQPVLIGLIIFQHTVIPLQHLVSFG |
| PPI-BnCPP | TTYSFIAVQILAFLQFGGYTLVRNSTDLFRSFGFDTQPVLIGLIIFQHTVIPLQHLVSFD |
| BASF-Corn | TVYSFVAVQLLMFLQFGGYTLVRSSKDLFGSFGFKDQPVIIGLIIFPHTIIPIQHLLSFR |
| | *.*:*:*: **:**:*: :** |
| PPI-GmCPP | LNLVSRSFEFQADGFAKKLGYASGLRG--------------------------------- |
| BASF-Gm | LNLVSRSFEFQADGFAKKLGYASGLRG--------------------------------- |
| AF007269 | LNLVSRAFEFQADAFAVKLGYAKDLR-------PALV----KLQVREDNNRTQ------- |
| AT4g-AtCPP | LNLVSRAFEFQADAFAVKLGYAKDLR-------PALV----KLQVREDNNRTQTVTSICV |
| BASF_AT2 | LNLVSRAFEFQADAFAVKLGYAKDLR-------PALV----KLQE--------------- |
| AFC1 | LNLVSRAFEFQADAFAVKLGYAKDLR-------PALVKLQE------------------- |
| BASF_AT1 | LNLVSRAFEFQADAFAVKLGYAKDLRPTLVKLQ--------------------------- |
| PPI-AtCPP | LNLVSRAFEFQADAFAVKLGYAKDLRPTLVKLQ--------------------------- |
| PPI-BnCPP | LNLVSRAFEFQADAFAVNLGYAKDLRP--------------------------------- |
| BASF-Corn | LNLVSRAFEFQADAFAKNLGYAPQLR---------------------------------- |
| | ******:******.** :*.** ** |
| PPI-GmCPP | ------GLVKLQEENLSAMNTDPWYSAYHYSHPPLVERLAALDEPDKKED- |
| BASF-Gm | ------GLVKLQEENLSAMNTDPCSC------------------------ |
| AF007269 | -----------TEENLSAMMTDPLYSAYHYSHPPLVERLPAIDGEDKKTD- |
| AT4g-AtCPP | THLNGFFVGILQEENLSANNTDPLYSAYHYSHPPLVERLPAIDGEDKKTD- |
| BASF_AT2 | -------------ENLSANNTDPLYSAYHYSHPPLVERLRAIDGEDKKTD- |
| AFC1 | -------------ENLSANNTDPLHSAYMYSHPPLVERLRAIDGEDKKTD- |
| BASF_AT1 | ------------EENLSANNTDPLYSAYHYSHPPLVERLRAIDGEDKKTD- |
| PPI-AtCPP | ------------EENLSTMNTDPLYSAYUYSHPPLVERLPATDGEDKKTD- |
| PPI-BnCPP | ------ALVKLQEENLSAMNTDPLYSAYHYSHPPLVERLRAIDGEDKKTD- |
| BASF-Corn | -----AALVKLQEENLSAMNTDPWYSAYHYSHPPLVERLQALEDSDDKKED |
| | ****:***** . |

Example 32

Plant Transformation

*Arabidopsis* transgenic plants were made by the method of dipping flowering plants into an *Agrobacterium* culture, based on the method of Andrew Bent in, Clough S J and Bent A F, 1998. Floral dipping: a simplified method for *Agrobacterum*-mediated transformation of *Arabidopsis thaliana*. Wild type plants were grown under standard conditions until the plant has both developing flowers and open flowers. The plant was inverted for 2 minutes into a solution of *Agrobacterium* culture carrying the appropriate gene construct. Plants were then left horizontal in a tray and kept covered for two days to maintain humidity and then righted and bagged to continue growth and seed development. Mature seed was bulk harvested.

Transformed T1 plants were selected by germination and growth on MS plates containing 50 μg/ml kanamycin. Green, kanamycin resistant (KanR) seedlings were identified after 2 weeks growth and transplanted to soil. Plants were bagged to ensure self fertilization and the T2 seed of each plant harvested separately. During growth of T1 plants leaf samples were harvested, DNA extracted and Southern blot and PCR analysis performed.

T2 seeds were analysed for $Kan^R$ segregation. From those lines that showed a 3:1 resistant phenotype, surviving T2 plants were grown, bagged during seed set, and T3 seed harvested from each line. T3 seed was again used for $Kan^R$ segregation analysis and those lines showing 100% $Kan^R$ phenotype were selected as homozygous lines. Further molecular and physiological analysis was done using T3 seedlings.

Transgenic *Brassica napus, Glycine max* and *Zea maize* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 μP Tween20) and left for approximately 15 minutes. Solution I was removed and replaced with 30 ml of solution II (0.25% mecuric chloride, 100 µl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained, for 5 days at 24° C., with 16, 8 hr light dark cycles.

Explants were transferred to Medium II (Medium I, 300 mg/L timentin,) for a further 7 days and then to Medium III (Medium II, 20 mg/L kanamycin). Any root or shoot tissue which had developed at this time was dissected away. Transfer explants to fresh plates of Medium III after 14-21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10× IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil. The above method, with or without modifications, is suitable for the transformation of numerous plant species including *Glycine max, Zea maize* and cotton.

Transgenic *Glycine max, Zea maize* and cotton can be produced using *Agrobacterum*-based methods which are known to one of skill in the art. Alternatively one can use a particle or non-particle biolistic bombardment transformation method. An example of non-particle biolistic transformation is given in U.S. patent application Ser. No. 20010026941. This method has been used to produce transgenic *Glycine max* and *Zea maize* plants. Viable plants are propagated and homozygous lines are generated. Plants are tested for the presence of drought tolerance, physiological and biochemical phenotypes as described elsewhere.

The following table identifies the constructs and the species which they have been transformed.

TABLE 19

Transformation List

| SEQ ID NO: | Construct | Species Transformed |
|---|---|---|
| 99 | pBII121-AtCPP | *A. thaliana, B. napus* |
| 100 | pBII121-HP-AtCPP | *A. thaliana* |
| 131 | pRD29A-AtCPP | *A. thaliana, B. napus* |
| 132 | pRD29A-HP-AtCPP | *A. thaliana* |
| 134 | MuA-AtCPP | *Glycine max, Zea mays* |

Non-limiting examples of vector constructs suitable for plant transformation are given in SEQ ID NO: 99, 5, 35-53.

*gtttacccgccaatatatcctgt*caaacactgatagtttaaactgaaggcgggaaacgacaatc SEQ ID NO:99 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacqagatttcgattccaccgccgccttctatgaaaggttgggcttcgga atcgttttccgggacgccggctggatgatcctccagcgcggggatctcatgctggagttcttcg -continued cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggactctagag gatccatggcgattcctttcatggaaaccgtcgtgggttttatgatagtgatgtacatttttga gacgtatttggatctgaggcaactcactgctctcaagcttccaactctcccgaaaaccttggtt ggtgtaattagccaagagaagtttgagaaatcacgagcatacagtcttgacaaaagctattttc actttgttcatgagtttgtaactatacttatggactctgcaattttgttctttgggatcttgcc ttggttttggaagatgtctggagctgttttaccgaggttgggccttgatccggagaatgaaata ctgcatactctttcattcttggctggtgttatgacatggtcacagatcactgatttgccatttt ctttgtactcaactttcgtgatcgagtctcggcatgggttcaacaaacaaacaatatggatgtt cattagggacatgatcaaaggaacattcctctctgtcatactaggcccacccattgttgctgcg ataattttcatagtccagaaaggaggtccttatcttgccatctatctgtgggcattcatgttta

-continued tcctgtctctagtgatgatgactatatacccggtcttgatagcaccgctcttcaacaaattcac tcctcttccagatggagacctccgggagaagattgagaaacttgcttcttccctaaagtttcct ttgaagaagctgtttgttgtcgatggatctacaaggtcaagccatagcaatgcttacatgtatg gtttctttaagaacaaaaggattgttctttatgatacgttgattcagcagtgcaagaatgagga tgaaattgtggcggttattgcacacgagcttggacattggaaactgaatcacactacatactcg ttcattgcagttcaaatccttgccttcttacaatttggaggatacactcttctcagaaactcca ctgatctcttcaggagtttcggatttgatacacagcctgttctcattggtttgatcatatttca gcacactgtaataccactgcaacatctagtaagctttggcctgaacctcgttagtcgagcgttt gagtttcaggctgatgcttttgctgtgaagcttgactatgcaaaagatcttcgtcctgctctag tgaaactacaggaagagaacttatcaacaatgaacactgatccattgtactcagcttatcacta ctcacatcctcctcttgttgaaaggcttcgagccactgatggagaagacaagaagacagattaa ccccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:99 is the nucleic acid sequence of pBI121-AtCPP. Italicized sequences are the right and left border repeats. Underlined sequence is the 35S promoter and bolded sequence is the AtCPP sense sequence.

*gtttacccgccaatatatcctgtc*aaacactgatagtttaaactgaaggcgggaaacgacaatc SEQ ID NO:100 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca -continued gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc -continued aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggg actctagag gatcctcccaatgtccaagctcgtgtgcaataaccgccacaatttcatcctcattcttgcactg ctgaatcaacgtatcataaagaacaatccttttgttcttaaagaaaccatacatgtaagcattg ctatggcttgaccttgtagatccatcgacaacaaacagcttcttcaaaggaaactttagggaag aagcaagtttctcaatcttctcccggaggtctccatctggaagaggagtgaatttgttgaagag cggtgctatcaagaccgggtatatagtcatcatcactagagacaggataaacatgaatgcccac agatagatggcaagataaggacctcctttctggactatgaaaattatcgcagcaacaatgggtg ggcctagtatgacagagaggaatgttcctttgatcatgtccctaatgaacatccatattgtttg tttgttgaacccatgccgagactcgatcacgaaagttgagtacaaagaaaatggcaaatcagtg atctgtgaccatgtcataacaccagccaagaatgaaagagtatgcagtatttcattctccggat caaggcccaacctcggtaaaagaggatccccATCTACCCGCTTCGCGTCGGCATCCGGTCAGTG

GCAGTGAAGGGCGAACAGTTCCTGATTAACCACAAACCGTTCTACTTTACTGGCTTTGGTCGTC

ATGAAGATGCGGACTTGCGTGGCAAAGGATTCGATAACGTGCTGATGGTGCACGACCACGCATT

AATGGACTGGATTGGGGCCAACTCCTACCGTACCTCGCATTACCCTTACGCTGAAGAGATGCTC

GACTGGGCAGATGAACATGGCATCGTGGTGATTGATGAAACTGCTGCTGTCGGCTTTTCGCTCT

CTTTAGGCATTGGTTTCGAAGCGGGCAACAAGCCGAAAGAACTGTACAGCGAAGAGGCAGTCAA

CGGGGAAACTCAGCAAGCGCACTTACAGGCGATTAAGAGCTGATAGCGCGTGACAAAAAACCAC

CCAAGCGTGGTGATGTGGAGTATTGCCAACGAACCGGATACCCGTCCGCAAGGTGCACGGGAAT

ATTTCGCGCCACTGGCGGAAGCAACGCGTAAACTCGACCCGACGCGTCCGATCACCTGCGTCAA

TGTAATGTTCTGCGACGCTCACACCGATACCATCAGCGATCTCTTTGATGTGCTGTGCCTGAAC

CGTTATTACGGATGGTATGTCCAAAGCGGCGATTTGGAAACGGCAGAGAAGGTACTGGAAAAAG

AACTTCTGGCCTGGCAGGAGAAACTGTACACCGACATGTGGAGTGAAGAGTATCAGTGTGCATG

GCTGGATATGTATCACCGCGTCTTTGATCGCGTCAGCGCCGTCGTCGGTGAACAGGTATGGAAT

TTCGCCGATTTTGCGACCTCGCAAGGCATATTGCGCGTTGGCGGTAACAAGAAAGGGATCTTCA

CTCGCGACCGCAAACCGAAGTCGGCGGCTTTTCTGCTGCAAAAACGCTGGACTGGCATGAACTT

CGGTGAAAAACCGCAGCAGGGAGGCAAACAATGAATCAACAACTCTCCTGGCGCACCATCGTCG

GCTACAGCCTCGGGAATTGCTACCGAGCTCttttaccgaggttgggccttgatccggagaatga aatactgcatactctttcattcttggctggtgttatgacatggtcacagatcactgatttgcca ttttctttgtactcaactttcgtgatcgagtctcggcatgggttcaacaaacaaacaatatgga tgttcattagggacatgatcaaaggaacattcctctctgtcatactaggcccacccattgttgc tgcgataattttcatagtccagaaaggaggtccttatcttgccatctatctgtgggcattcatg tttatcctgtctctagtgatgatgactatatacccggtcttgatagcaccgctcttcaacaaat tcactcctcttccagatggagacctccgggagaagattgagaaacttgcttcttccctaaagtt tcctttgaagaagctgtttgttgtcgatggatctacaaggtcaagccatagcaatgcttacatg tatggtttctttaagaacaaaaggattgttctttatgatacgttgattcagcagtgcaagaatg aggatgaaattgtggcggttattgcacacgagcttggacattgggagctcgaatttccccgatc gttcaaacatttggcaataaagtttcttaagattgaatcctgttgccggtcttgcgatgattat catataatttctgttgaattacgttaagcatgtaataattaacatgtaatgcatgacgttattt -continued atgagatgggtttttatgattagagtcccgcaattatacatttaatacgcgatagaaaacaaaa tatagcgcgcaaactaggataaattatcgcgcgcggtgtcatctatgttactagatcgggaatt cactggccgtcgttttacaacgtcgtgactgggaaaaccctggcgttacccaacttattcgcct tgcagcacatccccctttcgccagctggcgtaatagcgaagaggcccgcaccgatcgcccttcc caacagttgcgcagcctgaatggcgcccgctcctttcgctttcttcccttcctttctcgccacg ttcgccggctttccccgtcaagctctaaatcgggggctccctttagggttccgatttagtgctt tacggcacctcgaccccaaaaaacttgatttgggtgatggttcacgtagtgggccatcgccctg atagacggtttttcgccctttgacgttggagtccacgttctttaatagtggactcttgttccaa actggaacaacactcaaccctatctcgggctattcttttgatttataagggattttgccgattt cggaaccaccatcaaacaggattttcgcctgctggggcaaaccagcgtggaccgcttgctgcaa ctctctcagggccaggcggtgaagggcaatcagctgttgcccgtctcactggtgaaaagaaaaa ccaccccagtacattaaaaacgtccgcaatgtgttattaagttgtctaagcgtcaattt*gttta*

*caccacaatatatcctgcca*

SEQ ID NO:100 is the nucleic acid sequence of pBI121-HP-AtCPP. Italicized sequences are the right and left border repeats. Underlined sequence is the 35S promoter and bolded sequence is the AtCPP anti-sense sequence. Sequence in upper case is the truncated GUS fragment. Sequence in bold and underlined is the AtCPP sense sequence.

*gtttacccgccaatatatcctgtc*aaacactgatagtttaaactgaaggcgggaaacgacaatc SEQ ID NO:130 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg -continued cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagcccacagatggttagagaggcttacgcagcaggtctcatcaagacg
atctacccgagcaataatctccaggaaatcaaataccttcccaagaaggttaaagatgcagtca
aaagattcaggactaactgcatcaagaacacagagaaagatatatttctcaagatcagaagtac
tattccagtatggacgattcaaggcttgcttcacaaaccaaggcaagtaatagagattggagtc
tctaaaaaggtagttcccactgaatcaaaggccatggagtcaaagattcaaatagaggacctaa
cagaactcgccgtaaagactggcgaacagttcatacagagtctcttacgactcaatgacaagaa
gaaaatcttcgtcaacatggtggagcacgacacacttgtctactccaaaaatatcaaagataca
gtctcagaagaccaaagggcaattgagacttttcaacaaagggtaatatccggaaacctcctcg
gattccattgcccagctatctgtcactttattgtgaagatagtggaaaaggaaggtggctccta
caaatgccatcattgcgataaaggaaaggccatcgttgaagatgcctctgccgacagtggtccc
aaagatggacccccacccacgaggagcatcgtggaaaaagaagacgttccaaccacgtcttcaa
agcaagtggattgatgtgatatctccactgacgtaagggatgacgcacaatcccactatccttc
gcaagacccttcctctatataaggaagttcatttcatttggagagaacacggggggactctagag
gatccTTAATCTGTCTTCTTGTCTTCTCCATCAGTGGCTCGAAGCCTTTCAACAAGAGGAGGAT
GTGAGTAGTGATAAGCTGAGTACAATGGATCAGTGTTCATTGTTGATAAGTTCTCTTCCTGTAG
TTTCACTAGAGCAGGACGAAGATCTTTTGCATAGTCAAGCTTCACAGCAAAAGCATCAGCCTGA
AACTCAAACGCTCGACTAACGAGGTTCAGGCCAAAGCTTACTAGATGTTGCAGTGGTATTACAG
TGTGCTGAAATATGATCAAACCAATGAGAACAGGCTGTGTATCAAATCCGAAACTCCTGAAGAG
ATCAGTGGAGTTTCTGAGAAGAGTGTATCCTCCAAATTGTAAGAAGGCAAGGATTTGAACTGCA
ATGAACGAGTATGTAGTGTGATTCAGTTTCCAATGTCCAAGCTCGTGTGCAATAACCGCCACAA
TTTCATCCTCATTCTTGCACTGCTGAATCAACGTATCATAAAGAACAATCCTTTTGTTCTTAAA
GAAACCATACATGTAAGCATTGCTATGGCTTGACCTTGTAGATCCATCGACAACAAACAGCTTC -continued

TTCAAAGGAAACTTTAGGGAAGAAGCAAGTTTCTCAATCTTCTCCCGGAGGTCTCCATCTGGAA

GAGGAGTGAATTTGTTGAAGAGCGGTGCTATCAAGACCGGGTATATAGTCATCATCACTAGAGA

CAGGATAAACATGAATGCCCACAGATAGATGGCAAGATAAGGACCTCCTTTCTGGACTATGAAA

ATTATCGCAGCAACAATGGGTGGGCCTAGTATGACAGAGAGGAATGTTCCTTTGATCATGTCCC

TAATGAACATCCATATTGTTTGTTTGTTGAACCCATGCCGAGACTCGATCACGAAAGTTGAGTA

CAAAGAAAATGGCAAATCAGTGATCTGTGACCATGTCATAACACCAGCCAAGAATGAAAGAGTA

TGCAGTATTTCATTCTCCGGATCAAGGCCCAACCTCGGTAAAACAGCTCCAGACATCTTCCAAA

ACCAAGGCAAGATCCCAAAGAACAAAATTGCAGAGTCCATAAGTATAGTTACAAACTCATGAAC

AAAGTGAAAATAGCTTTTGTCAAGACTGTATGCTCGTGATTTCTCAAACTTCTCTTGGCTAATT

ACACCAACCAAGGTTTTCGGGAGAGTTGGAAGCTTGAGAGCAGTGAGTTGCCTCAGATCCAAAT

ACGTCTCAAAAATGTACATCACTATCATAAAACCCACGACGGTTTCCATGAAAGGAATCGCCAT cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:130 is the nucleic acid sequence of pBI121-antisense-AtCPP. Italicized sequences are the right and left border repeats. Underlined sequence is the 35S promoter. Sequence in upper case is the AtCPP anti-sense sequence.

SEQ ID NO:131

*gtttacccgccaatatatcctgt*caaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca -continued gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacatttttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt -continued aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc catggcgattcctttcatggaaaccgtcgtgggttttatgatagtgatgtacatttttgagacg tatttggatctgaggcaactcactgctctcaagcttccaactctcccgaaaaccttggttggtg taattagccaagagaagtttgagaaatcacgagcatacagtcttgacaaaagctattttcactt tgttcatgagtttgtaactatacttatggactctgcaattttgttctttgggatcttgccttgg ttttggaagatgtctggagctgttttaccgaggttgggccttgatccggagaatgaaatactgc atactctttcattcttggctggtgttatgacatggtcacagatcactgatttgccattttcttt gtactcaactttcgtgatcgagtctcggcatgggttcaacaaacaaacaatatggatgttcatt agggacatgatcaaaggaacattcctctctgtcatactaggcccacccattgttgctgcgataa ttttcatagtccagaaaggaggtccttatcttgccatctatctgtgggcattcatgtttatcct gtctctagtgatgatgactatatacccggtcttgatagcaccgctcttcaacaaattcactcct cttccagatggagacctccgggagaagattgagaaacttgcttcttccctaaagtttcctttga agaagctgtttgttgtcgatggatctacaaggtcaagccatagcaatgcttacatgtatggttt ctttaagaacaaaaggattgttctttatgatacgttgattcagcagtgcaagaatgaggatgaa attgtggcggttattgcacacgagcttggacattggaaactgaatcacactacatactcgttca ttgcagttcaaatccttgccttcttacaatttggaggatacactcttctcagaaactccactga tctcttcaggagtttcggatttgatacacagcctgttctcattggtttgatcatatttcagcac actgtaataccactgcaacatctagtaagctttggcctgaacctcgttagtcgagcgtttgagt ttcaggctgatgcttttgctgtgaagcttgactatgcaaaagatcttcgtcctgctctagtgaa actacaggaagagaacttatcaacaatgaacactgatccattgtactcagcttatcactactca catcctcctcttgttgaaaggcttcgagccactgatggagaagacaagaagacagattaacccc tcgaatttccccgatcgttcaaacatttggcaataaagtttcttaagattgaatcctgttgccg gtcttgcgatgattatcatataatttctgttgaattacgttaagcatgtaataattaacatgta atgcatgacgttatttatgagatgggtttttatgattagagtcccgcaattatacatttaatac gcgatagaaaacaaaatatagcgcgcaaactaggataaattatcgcgcgcggtgtcatctatgt tactagatcgggaattcactggccgtcgttttacaacgtcgtgactgggaaaaccctggcgtta cccaacttaatcgccttgcagcacatccccctttcgccagctggcgtaatagcgaagaggcccg caccgatcgcccttcccaacagttgcgcagcctgaatggcgcccgctcctttcgctttcttccc ttcctttctcgccacgttcgccggctttccccgtcaagctctaaatcgggggctccctttaggg ttccgatttagtgctttacggcacctcgaccccaaaaaacttgatttgggtgatggttcacgta gtgggccatcgccctgatagacggtttttcgccctttgacgttggagtccacgttctttaatag tggactcttgttccaaactggaacaacactcaaccctatctcgggctattcttttgatttataa gggattttgccgatttcggaaccaccatcaaacaggattttcgcctgctggggcaaaccagcgt ggaccgcttgctgcaactctctcagggccaggcggtgaagggcaatcagctgttgcccgtctca ctggtgaaaagaaaaaccaccccagtacattaaaaacgtccgcaatgtgttattaagttgtcta agcgtcaattt*gtttacaccacaatatatcctgcca*

SEQ ID NO:131 is the nucleic acid sequence of RD29A-AtCPP. Italicized sequences are the right and left border repeats. Underlined sequence is the RD29A promoter. Sequence in bold is the AtCPP sense sequence.

*gtttacccgccaatatatcctgtc*aaacactgatagtttaaactgaaggcgggaaacgacaatc SEQ ID NO:132 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa -continued ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc ctcccaatgtccaagctcgtgtgcaataaccgccacaatttcatcctcattcttgcactgctga atcaacgtatcataaagaacaatccttttgttcttaaagaaaccatacatgtaagcattgctat ggcttgaccttgtagatccatcgacaacaaacagcttcttcaaaggaaactttagggaagaagc aagtttctcaatcttctcccggaggtctccatctggaagaggagtgaatttgttgaagagcggt gctatcaagaccgggtatatagtcatcatcactagagacaggataaacatgaatgcccacagat agatggcaagataaggacctcctttctggactatgaaaattatcgcagcaacaatgggtgggcc tagtatgacagagaggaatgttcctttgatcatgtccctaatgaacatccatattgtttgtttg ttgaacccatgccgagactcgatcacgaaagttgagtacaaagaaaatggcaaatcagtgatct gtgaccatgtcataacaccagccaagaatgaaagagtatgcagtatttcattctccggatcaag gcccaacctcggtaaaagaggatccccATCTACCCGCTTCGCGTCGGCATCCGGTCAGTGGCAG

TGAAGGGCGAACAGTTCCTGATTAACCACAAACCGTTCTACTTTACTGGCTTTGGTCGTCATGA

AGATGCGGACTTGCGTGGCAAAGGATTCGATAACGTGCTGATGGTGCACGACCACGCATTAATG

GACTGGATTGGGGCCAACTCCTACCGTACCTCGCATTACCCTTACGCTGAAGAGATGCTCGACT

GGGCAGATGAACATGGCATCGTGGTGATTGATGAAACTGCTGCTGTCGGCTTTTCGCTCTCTTT

AGGCATTGGTTTCGAAGCGGGCAACAAGCCGAAAGAACTGTACAGCGAAGAGGCAGTCAACGGG

GAAACTCAGCAAGCGCACTTACAGGCGATTAAAGAGCTGATAGCGCGTGACAAAAACCACCCAA

GCGTGGTGATGTGGAGTATTGCCAACGAACCGGATACCCGTCCGCAAGGTGCACGGGAATATTT

CGCGCCACTGGCGGAAGCAACGCGTAAACTCGACCCGACGCGTCCGATCACCTGCGTCAATGTA

ATGTTCTGCGACGCTCACACCGATACCATCAGCGATCTCTTTGATGTGCTGTGCCTGAACCGTT

ATTACGGATGGTATGTCCAAAGCGGCGATTTGGAAACGGCAGAGAAGGTACTGGAAAAAGAACT

TCTGGCCTGGCAGGAGAAACTGTACACCGACATGTGGAGTGAAGAGTATCAGTGTGCATGGCTG

GATATGTATCACCGCGTCTTTGATCGCGTCAGCGCCGTCGTCGGTGAACAGGTATGGAATTTCG

CCGATTTTGCGACCTCGCAAGGCATATTGCGCGTTGGCGGTAACAAGAAAGGATCTTCACTCG

-continued

CGACCGCAAACCGAAGTCGGCGGCTTTTCTGCTGCAAAAACGCTGGACTGGCATGAACTTCGGT

GAAAAACCGCAGCAGGGAGGCAAACAATGAATCAACAACTCTCCTGGCGCACCATCGTCGGCTA

CAGCCTCGGGAATTGCTACCGAGCTCttttaccgaggttgggccttgatccggagaatgaaata ctgcatactctttcattcttggctggtgttatgacatggtcacagatcactgatttgccatttt ctttgtactcaactttcgtgatcgagtctcggcatgggttcaacaaacaaacaatatggatgtt cattagggacatgatcaaaggaacattcctctctgtcatactaggcccacccattgttgctgcg ataattttcatagtccagaaaggaggtccttatcttgccatctatctgtgggcattcatgttta tcctgtctctagtgatgatgactatatacccggtcttgatagcaccgctcttcaacaaattcac tcctcttccagatggagacctccgggagaagattgagaaacttgcttcttccctaaagtttcct ttgaagaagctgtttgttgtcgatggatctacaaggtcaagccatagcaatgcttacatgtatg gtttctttaagaacaaaaggattgttctttatgatacgttgattcagcagtgcaagaatgagga tgaaattgtggcggttattgcacacgagcttggacattgggagctcgaatttccccgatcgttc aaacatttggcaataaagtttcttaagattgaatcctgttgccggtcttgcgatgattatcata taatttctgttgaattacgttaagcatgtaataattaacatgtaatgcatgacgttatttatga gatgggtttttatgattagagtcccgcaattatacatttaatacgcgatagaaaacaaaatata gcgcgcaaactaggataaattatcgcgcgcggtgtcatctatgttactagatcgggaattcact ggccgtcgttttacaacgtcgtgactgggaaaaccctggcgttacccaacttaatcgccttgca gcacatccccctttcgccagctggcgtaatagcgaagaggcccgcaccgatcgcccttcccaac agttgcgcagcctgaatggcgcccgctcctttcgctttcttcccttcctttctcgccacgttcg ccggctttccccgtcaagctctaaatcgggggctccctttagggttccgatttagtgctttacg gcacctcgaccccaaaaaacttgatttgggtgatggttcacgtagtgggccatcgccctgatag acggtttttcgccctttgacgttggagtccacgttctttaatagtggactcttgttccaaactg gaacaacactcaaccctatctcgggctattcttttgatttataagggattttgccgatttcgga accaccatcaaacaggattttcgcctgctggggcaaaccagcgtggaccgcttgctgcaactct ctcagggccaggcggtgaagggcaatcagctgttgcccgtctcactggtgaaaagaaaaaccac cccagtacattaaaaacgtccgcaatgtgttattaagttgtctaagcgtcaattt*gtttacacc*

*acaatatatcctgcca*

SEQ ID NO:132 is the nucleic acid sequence of RD29A-HP-AtCPP. Italicized sequences are the right and left border repeats. Underlined sequence is the RD29A promoter. Sequence in bold is the AtCPP anti-sense sequence. Upper case sequence represents the truncated GUS fragment. Bold and underlined sequence represents the *A. thaliana* CaaX prenyl protease sense fragment.

*gtttacccgccaatatatcctgtc*aaacactgatagtttaaactgaaggcgggaaacgacaatc SEQ ID NO:133 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct -continued atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacatttttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga -continued gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaggatc
cTTAATCTGTCTTCTTGTCTTCTCCATCAGTGGCTCGAAGCCTTTCAACAAGAGGAGGATGTGA
GTAGTGATAAGCTGAGTACAATGGATCAGTGTTCATTGTTGATAAGTTCTCTTCCTGTAGTTTC
ACTAGAGCAGGACGAAGATCTTTTGCATAGTCAAGCTTCACAGCAAAAGCATCAGCCTGAAACT
CAAACGCTCGACTAACGAGGTTCAGGCCAAAGCTTACTAGATGTTGCAGTGGTATTACAGTGTG
CTGAAATATGATCAAACCAATGAGAACAGGCTGTGTATCAAATCCGAAACTCCTGAAGAGATCA
GTGGAGTTTCTGAGAAGAGTGTATCCTCCAAATTGTAAGAAGGCAAGGATTTGAACTGCAATGA
ACGAGTATGTAGTGTGATTCAGTTTCCAATGTCCAAGCTCGTGTGCAATAACCGCCACAATTTC
ATCCTCATTCTTGCACTGCTGAATCAACGTATCATAAAGAACAATCCTTTTGTTCTTAAAGAAA
CCATACATGTAAGCATTGCTATGGCTTGACCTTGTAGATCCATCGACAACAAACAGCTTCTTCA
AAGGAAACTTTAGGGAAGAAGCAAGTTTCTCAATCTTCTCCCGGAGGTCTCCATCTGGAAGAGG
AGTGAATTTGTTGAAGAGCGGTGCTATCAAGACCGGGTATATAGTCATCATCACTAGAGACAGG
ATAAACATGAATGCCCACAGATAGATGGCAAGATAAGGACCTCCTTTCTGGACTATGAAAATTA
TCGCAGCAACAATGGGTGGGCCTAGTATGACAGAGAGGAATGTTCCTTTGATCATGTCCCTAAT
GAACATCCATATTGTTTGTTTGTTGAACCCATGCCGAGACTCGATCACGAAAGTTGAGTACAAA
GAAAATGGCAAATCAGTGATCTGTGACCATGTCATAACACCAGCCAAGAATGAAAGAGTATGCA
GTATTTCATTCTCCGGATCAAGGCCCAACCTCGGTAAAACAGCTCCAGACATCTTCCAAAACCA
AGGCAAGATCCCAAAGAACAAAATTGCAGAGTCCATAAGTATAGTTACAAACTCATGAACAAAG
TGAAAATAGCTTTTGTCAAGACTGTATGCTCGTGATTTCTCAAACTTCTCTTGGCTAATTACAC
CAACCAAGGTTTTCGGGAGAGTTGGAAGCTTGAGAGCAGTGAGTTGCCTCAGATCCAAATACGT
CTCAAAAATGTACATCACTATCATAAAACCCACGACGGTTTCCATGAAAGGAATCGCCATcccc
tcgaatttccccgatcgttcaaacatttggcaataaagtttcttaagattgaatcctgttgccg
gtcttgcgatgattatcatataatttctgttgaattacgttaagcatgtaataattaacatgta
atgcatgacgttatttatgagatgggtttttatgattagagtcccgcaattatacatttaatac
gcgatagaaaacaaaatatagcgcgcaaactaggataaattatcgcgcgcggtgtcatctatgt
tactagatcgggaattcactggccgtcgttttacaacgtcgtgactgggaaaaccctggcgtta
cccaacttaatcgccttgcagcacatccccctttcgccagctggcgtaatagcgaagaggcccg
caccgatcgcccttcccaacagttgcgcagcctgaatggcgcccgctcctttcgctttcttccc
ttcctttctcgccacgttcgccggctttccccgtcaagctctaaatcgggggctccctttaggg
ttccgatttagtgctttacggcacctcgaccccaaaaaacttgatttgggtgatggttcacgta
gtgggccatcgccctgatagacggtttttcgccctttgacgttggagtccacgttctttaatag
tggactcttgttccaaactggaacaacactcaaccctatctcgggctattcttttgatttataa
gggattttgccgatttcggaaccaccatcaaacaggattttcgcctgctggggcaaaccagcgt
ggaccgcttgctgcaactctctcagggccaggcggtgaagggcaatcagctgttgcccgtctca -continued ctggtgaaaagaaaaaccaccccagtacattaaaaacgtccgcaatgtgttattaagttgtcta agcgtcaattt*gtttacaccacaatatatcctgcca*

SEQ ID NO:133 is the nucleic acid sequence of RD29A-antisense-AtCPP. Italicized sequences are the right and left border repeats. Underlined sequence is the RD29A promoter. Sequence in upper case sequence is the AtCPP anti-sense sequence.

*gtttacccgccaatatatcctgtc*aaacactgatagtttaaactgaaggcgggaaacgacaatc SEQ ID NO:134 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa -continued actttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagctGGGAAATTTTTCGCCAGTTCTAAATATCCGGAAACCTCTTGGATGCCATTGCCCATCT

ATCTGTAATTTATTGACGAAATAGACGAAAAGGAAGGTGGCTCCTATAAAGCACATCATTGCGA

TAACAGAAAGGCCATTGTTGAAGATACCTCTGCTGACATTGGTCCCCAAGTGGAAGCACCACCC

CATGAGGAGCACCGTGGAGTAAGAAGACGTTCGAGCCACGTCGAAAAAGCAAGTGTGTTGATGT

AGTATCTCCATTGACGTAAGGGATGACGCACAATCCAACTATCCATCGCAAGACCATTGCTCTA

TATAAGAAAGTTAATATCATTTCGAGTGGCCACGCTGAGGGGGATCCatggcgattcctttcat ggaaaccgtcgtgggttttatgatagtgatgtacatttttgagacgtatttggatctgaggcaa ctcactgctctcaagcttccaactctcccgaaaaccttggttggtgtaattagccaagagaagt ttgagaaatcacgagcatacagtcttgacaaaagctattttcactttgttcatgagtttgtaac tatacttatggactctgcaattttgttctttgggatcttgccttggttttggaagatgtctgga gctgttttaccgaggttgggccttgatccggagaatgaaatactgcatactctttcattcttgg ctggtgttatgacatggtcacagatcactgatttgccattttctttgtactcaactttcgtgat cgagtctcggcatgggttcaacaaacaaacaatatggatgttcattagggacatgatcaaagga acattcctctctgtcatactaggcccacccattgttgctgcgataattttcatagtccagaaag gaggtccttatcttgccatctatctgtgggcattcatgtttatcctgtctctagtgatgatgac tatatacccggtcttgatagcaccgctcttcaacaaattcactcctcttccagatggagacctc cgggagaagattgagaaacttgcttcttccctaaagtttcctttgaagaagctgtttgttgtcg atggatctacaaggtcaagccatagcaatgcttacatgtatggtttctttaagaacaaaaggat tgttctttatgatacgttgattcagcagtgcaagaatgaggatgaaattgtggcggttattgca cacgagcttggacattggaaactgaatcacactacatactcgttcattgcagttcaaatccttg ccttcttacaatttggaggatacactcttctcagaaactccactgatctcttcaggagtttcgg atttgatacacagcctgttctcattggtttgatcatatttcagcacactgtaataccactgcaa catctagtaagctttggcctgaacctcgttagtcgagcgtttgagtttcaggctgatgcttttg ctgtgaagcttgactatgcaaaagatcttcgtcctgctctagtgaaactacaggaagagaactt atcaacaatgaacactgatccattgtactcagcttatcactactcacatcctcctcttgttgaa aggcttcgagccactgatggagaagacaagaagacagattaacccctcgaatttccccgatcgt tcaaacatttggcaataaagtttcttaagattgaatcctgttgccggtcttgcgatgattatca tataatttctgttgaattacgttaagcatgtaataattaacatgtaatgcatgacgttatttat gagatgggtttttatgattagagtcccgcaattatacatttaatacgcgatagaaaacaaaata tagcgcgcaaactaggataaattatcgcgcgcggtgtcatctatgttactagatcgggaattca ctggccgtcgttttacaacgtcgtgactgggaaaaccctggcgttacccaacttaatcgccttg cagcacatccccctttcgccagctggcgtaatagcgaagaggcccgcaccgatcgcccttccca acagttgcgcagcctgaatggcgcccgctcctttcgctttcttcccttcctttctcgccacgtt -continued cgccggctttccccgtcaagctctaaatcgggggctccctttagggttccgatttagtgcttta cggcacctcgaccccaaaaaacttgatttgggtgatggttcacgtagtgggccatcgccctgat agacggtttttcgccctttgacgttggagtccacgttctttaatagtggactcttgttccaaac tggaacaacactcaaccctatctcgggctattcttttgatttataagggattttgccgatttcg gaaccaccatcaaacaggattttcgcctgctggggcaaaccagcgtggaccgcttgctgcaact ctctcagggccaggcggtgaagggcaatcagctgttgcccgtctcactggtgaaaagaaaaacc accccagtacattaaaaacgtccgcaatgtgttattaagttgtctaagcgtcaatttt*gtttaca*

*ccacaatatatcctgcca*

SEQ ID NO:134 is the nucleic acid sequence of MuA-AtCPP. Italicized sequences are the right and left border repeats. Sequence in upper case is the MuA promoter. The *A. thaliana* CaaX prenyl protease sense sequence is in bold.

*gtttacccgccaatatatcctgtc*aaacactgatagtttaaactgaaggcgggaaacgacaatc SEQ ID NO:135 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc -continued gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagctGGGAAATTTTTCGCCAGTTCTAAATATCCGGAAACCTCTTGGGATGCCATTGCCCATCT

ATCTGTAATTTATTGACGAAATAGACGAAAAGGAAGGTGGCTCCTATAAAGCACATCATTGCGA

TAACAGAAAGGCCATTGTTGAAGATACCTCTGCTGACATTGGTCCCCAAGTGGAAGCACCACCC

CATGAGGAGCACCGTGGAGTAAGAAGACGTTCGAGCCACGTCGAAAAAGCAAGTGTGTTGATGT

AGTATCTCCATTGACGTAAGGGATGACGCACAATCCAACTATCCATCGCAAGACCATTGCTCTA

TATAAGAAAGTTAATATCATTTCGAGTGGCCACGCTGAGGGGGATCGGGATGGCGTTTCCCTAC

ATGGAAGCCGTTGTCGGATTTATGATATTAATGTACATTTTTGAAACTTACTTGGATGTGCGAC

AACATAGGGCCCTCAAACTTCCTACTCTTCCAAAGACTTTAGAGGGTGTTATCAGCCAAGAGAA

ATTTGAGAAATCTAGAGCCTATAGTCTTGATAAAAGCCACTTCCATTTTGTTCACGAGTTTGTG

ACAATAGTGACAGACTCTACAATTTTGTACTTTGGGGTATTGCCCTGGTTTTGGAAGAAATCAG

GAGATTTTATGACAATAGCTGGTTTCAATGCTGAGAATGAAATACTGCATACCCTTGCCTTCTT

AGCAGGGCTGATGATTTGGTCACAGATAACAGATTTGCCCTTTTCTCTGTACTCAACTTTTGTG

ATTGAGGCCCGTCATGGTTTTAATAAGCAAACACCATGGTTATTCTTTAGGGACATGCTTAAAG

GAATTTTCCTTTCTGTAATAATTGGTCCACCTATTGTGGCTGCAATCATTGTAATAGTACAGAA

AGGAGGTCCATACTTGGCCATCTATCTTTGGGTTTTTACGTTTGGTCTTTCTATTGTGATGATG

ACCCTTTATCCAGTACTAATAGCTCCACTCTTCAATAAGTTCACTCCACTTCCAGATGGTCAAC

TCAGGGAGAAAATCGAGAAACTTGCTTCCTCCCTCAACTATCCGTTAAAGAAACTATTTGTTGT

CGATGGATCCACAAGATCAAGTCACAGCAATGCCTATATGTATGGATTCTTCAAGAACAAGAGG

ATTGTCCCTTATGACACATTAATTCAACAGTGCAAAGACGATGAGGAAATTGTTGCTGTTATTG

CCCATGAGTTGGGACACTGGAAGCTCAACCATACTGTGTACACATTTGTTGCTATGCAGATTCT

TACACTTCTACAATTTGGAGGATATACACTAGTGCGAAATTCAGCTGATCTGTATCGAAGCTTT

GGGTTTGATACGCAGCCAGTCCTCATTGGGCTCATCATATTTCAGCATACTGTAATCCCACTTC

AGCAATTGGTCAGCTTTGGTCTGAACCTAGTCAGCCGATCATTTGAATTTCAGGCTGATGGCTT

TGCCAAGAAGCTTGGATATGCATCTGGATTACGCGGTGGTCTTGTGAAACTACAGGAGGAGAAT

CTGTCAGCTATGAATACAGATCCTTGGTACTCTGCTTATCACTATTCTCATCCTCCCCTTGTTG

AAAGATTGGCCGCGCTGGACGAACCGGATAAGAAGGAAGACTAAgagctcgaatttccccgatc gttcaaacatttggcaataaagtttcttaagattgaatcctgttgccggtcttgcgatgattat catataatttctgttgaattacgttaagcatgtaataattaacatgtaatgcatgacgttattt atgagatgggtttttatgattagagtcccgcaattatacatttaatacgcgatagaaaacaaaa -continued tatagcgcgcaaactaggataaattatcgcgcgcggtgtcatctatgttactagatcgggaatt
cactggccgtcgttttacaacgtcgtgactgggaaaaccctggcgttacccaacttaatcgcct
tgcagcacatcccccctttcgccagctggcgtaatagcgaagaggcccgcaccgatcgcccttcc
caacagttgcgcagcctgaatggcgcccgctcctttcgctttcttcccttcctttctcgccacg
ttcgccggctttccccgtcaagctctaaatcgggggctccctttagggttccgatttagtgctt
tacggcacctcgaccccaaaaaacttgatttgggtgatggttcacgtagtgggccatcgccctg
atagacggtttttcgccctttgacgttggagtccacgttctttaatagtggactcttgttccaa
actggaacaacactcaaccctatctcgggctattcttttgatttataagggattttgccgattt
cggaaccaccatcaaacaggattttcgcctgctggggcaaaccagcgtggaccgcttgctgcaa
ctctctcagggccaggcggtgaagggcaatcagctgttgcccgtctcactggtgaaaagaaaaa
ccaccccagtacattaaaaacgtccgcaatgtgttattaagttgtctaagcgtcaattt*gttta*
*caccacaatatatcctgcca*

SEQ ID NO:135 is the nucleic acid sequence of MuA-GmCPP. Italicized sequences are the right and left border repeats. Sequence in upper case is the MuA promoter. The *G. max* CaaX prenyl protease sense sequence is in upper case and bold.

*gtttacccgccaatatatcctgtc*aaacactgatagtttaaactgaaggcgggaaacgacaatc SEQ ID NO:136
tgatcatgagcggagaattaagggagtcacgttatgacccccgccgatgacgcgggacaagccg
ttttacgtttggaactgacagaaccgcaacgttgaaggagccactcagccgcgggtttctggag
tttaatgagctaagcacatacgtcagaaaccattattgcgcgttcaaaagtcgcctaaggtcac
tatcagctagcaaatatttcttgtcaaaaatgctccactgacgttccataaattcccctcggta
tccaattagagtctcatattcactctcaatccaaataatctgcaccggatctggatcgtttcgc
atgattgaacaagatggattgcacgcaggttctccggccgcttgggtggagaggctattcggct
atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga -continued caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccccgggatggcgtttccctacatggaagccgttgtcggatttatgatattaatgtacatt tttgaaacttacttggatgtgcgacaacatagggccctcaaacttcctactcttccaaagactt tagagggtgttatcagccaagagaaatttgagaaatctagagcctatagtcttgataaaagcca cttccattttgttcacgagtttgtgacaatagtgacagactctacaattttgtactttggggta ttgccctggttttggaagaaatcaggagattttatgacaatagctggtttcaatgctgagaatg aaatactgcatacccttgccttcttagcagggctgatgatttggtcacagataacagatttgcc cttttctctgtactcaacttttgtgattgaggcccgtcatggttttaataagcaaacaccatgg ttattctttagggacatgcttaaaggaattttcctttctgtaataattggtccacctattgtgg ctgcaatcattgtaatagtacagaaaggaggtccatacttggccatctatctttgggttttttac gtttggtctttctattgtgatgatgaccctttatccagtactaatagctccactcttcaataag

-continued ttcactccacttccagatggtcaactcagggagaaaatcgagaaacttgcttcctccctcaact atccgttaaagaaactatttgttgtcgatggatccacaagatcaagtcacagcaatgcctatat gtatggattcttcaagaacaagaggattgtcccttatgacacattaattcaacagtgcaaagac gatgaggaaattgttgctgttattgcccatgagttgggacactggaagctcaaccatactgtgt acacatttgttgctatgcagattcttacacttctacaatttggaggatatacactagtgcgaaa ttcagctgatctgtatcgaagctttgggtttgatacgcagccagtcctcattgggctcatcata tttcagcatactgtaatcccacttcagcaattggtcagctttggtctgaacctagtcagccgat catttgaatttcaggctgatggctttgccaagaagcttggatatgcatctggattacgcggtgg tcttgtgaaactacaggaggagaatctgtcagctatgaatacagatccttggtactctgcttat cactattctcatcctccccttgttgaaagattggccgcgctggacgaaccggataagaaggaag actaagagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattcactggccgtcgttttacaacgtcgtgactgggaaaacc ctggcgttacccaacttaatcgccttgcagcacatccccctttcgccagctggcgtaatagcga agaggcccgcaccgatcgcccttcccaacagttgcgcagcctgaatggcgcccgctcctttcgc tttcttcccttcctttctcgccacgttcgccggctttccccgtcaagctctaaatcgggggctc cctttagggttccgatttagtgctttacggcacctcgaccccaaaaaacttgatttgggtgatg gttcacgtagtgggccatcgccctgatagacggtttttcgccctttgacgttggagtccacgtt ctttaatagtggactcttgttccaaactggaacaacactcaaccctatctcgggctattctttt gatttataagggattttgccgatttcggaaccaccatcaaacaggattttcgcctgctggggca aaccagcgtggaccgcttgctgcaactctctcagggccaggcggtgaagggcaatcagctgttg cccgtctcactggtgaaaagaaaaaccaccccagtacattaaaaacgtccgcaatgtgttatta agttgtctaagcgtcaattt*gtttacaccacaatatatcctgcca*

SEQ ID NO:135 is the nucleic acid sequence of pBI121-GmCPP. Italicized sequences are the right and left border repeats. Underlined sequence is the 35S promoter. The *G. max* CaaX prenyl protease sense sequence is in bold.

*gtttacccgccaatatatcctgtc*aaacactgatagtttaaactgaaggcgggaaacgacaatc SEQ ID NO:137 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct -continued tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc -continued gcaagacccttcctctatataaggaagttcatttcatttggagagaacacgggggactctagac
cggttcgtccagcgcggccaatctttcaacaaggggaggatgagaatagtgataagcagagtac
caaggatctgtattcatagctgacagattctcctcctgtagtttcacaagaccaccgcgtaatc
cagatgcatatccaagcttcttggcaaagccatcagcctgaaattcaaatgatcggctgactag
gttcagaccaaagctgaccaattgctgaagtgggattacagtatgctgaaatatgatgagccca
atgaggactggctgcgtatcaaacccaaagcttcgatacagatcagctgaatttcgcactagtg
tatatcctccaaattgtagaagtgtaagaatctgcatagcaacaaatgtgtacacagtatggtt
gagcttccagtgtcccaactcatgggcaataacagcaacaatttcctcatcgtctttgcactgt
tgaattaatgtgtcataagggacaatcctcttgttcttgaagaatccatacatataggcattgc
tgtgacttgatcttgtggatccccATCTACCCGCTTCGCGTCGGCATCCGGTCAGTGGCAGTGA
AGGGCGAACAGTTCCTGATTAACCACAAACCGTTCTACTTTACTGGCTTTGGTCGTCATGAAGA
TGCGGACTTGCGTGGCAAAGGATTCGATAACGTGCTGATGGTGCACGACCACGCATTAATGGAC
TGGATTGGGGCCAACTCCTACCGTACCTCGCATTACCCTTACGCTGAAGAGATGCTCGACTGGG
CAGATGAACATGGCATCGTGGTGATTGATGAAACTGCTGCTGTCGGCTTTTCGCTCTCTTTAGG
CATTGGTTTCGAAGCGGGCAACAAGCCGAAAGAACTGTACAGCGAAGAGGCAGTCAACGGGGAA
ACTCAGCAAGCGCACTTACAGGCGATTAAAGAGCTGATAGCGCGTGACAAAAACCACCCAAGCG
TGGTGATGTGGAGTATTGCCAACGAACCGGATACCCGTCCGCAAGGTGCACGGGAATATTTCGC
GCCACTGGCGGAAGCAACGCGTAAACTCGACCCGACGCGTCCGATCACCTGCGTCAATGTAATG
TTCTGCGACGCTCACACCGATACCATCAGCGATCTCTTTGATGTGCTGTGCCTGAACCGTTATT
ACGGATGGTATGTCCAAAGCGGCGATTTGGAAACGGCAGAGAAGGTACTGGAAAAAGAACTTCT
GGCCTGGCAGGAGAAACTGTACACCGACATGTGGAGTGAAGAGTATCAGTGTGCATGGCTGGAT
ATGTATCACCGCGTCTTTGATCGCGTCAGCGCCGTCGTCGGTGAACAGGTATGGAATTTCGCCG
ATTTTGCGACCTCGCAAGGCATATTGCGCGTTGGCGGTAACAAGAAAGGGATCTTCACTCGCGA
CCGCAAACCGAAGTCGGCGGCTTTTCTGCTGCAAAAACGCTGGACTGGCATGAACTTCGGTGAA
AAACCGCAGCAGGGAGGCAAACAATGAatcaacaactctcctggcgcaccatcgtcggctacag
cctcgggaattgctaccgagctcacaagatcaagtcacagcaatgcctatatgtatggattctt
caagaacaagaggattgtcccttatgacacattaattcaacagtgcaaagacgatgaggaaatt
gttgctgttattgcccatgagttgggacactggaagctcaaccatactgtgtacacatttgttg
ctatgcagattcttacacttctacaatttggaggatatacactagtgcgaaattcagctgatct
gtatcgaagctttgggtttgatacgcagccagtcctcattgggctcatcatatttcagcatact
gtaatcccacttcagcaattggtcagctttggtctgaacctagtcagccgatcatttgaatttc
aggctgatggctttgccaagaagcttggatatgcatctggattacgcggtggtcttgtgaaact
acaggaggagaatctgtcagctatgaatacagatccttggtactctgcttatcactattctcat
cctccccttgttgaaagattggccgcgctggacgaaccgggagctcgaatttccccgatcgttc
aaacatttggcaataaagtttcttaagattgaatcctgttgccggtcttgcgatgattatcata
taatttctgttgaattacgttaagcatgtaataattaacatgtaatgcatgacgttatttatga
gatgggtttttatgattagagtcccgcaattatacatttaatacgcgatagaaaacaaaatata
gcgcgcaaactaggataaattatcgcgcgcggtgtcatctatgttactagatcgggaattcact
ggccgtcgttttacaacgtcgtgactgggaaaaccctggcgttacccaacttaatcgccttgca
gcacatccccctttcgccagctggcgtaatagcgaagaggcccgcaccgatcgcccttcccaac -continued agttgcgcagcctgaatggcgcccgctcctttcgctttcttcccttcctttctcgccacgttcg
ccggctttccccgtcaagctctaaatcgggggctccctttagggttccgatttagtgctttacg
gcacctcgaccccaaaaaacttgatttgggtgatggttcacgtagtgggccatcgccctgatag
acggtttttcgccctttgacgttggagtccacgttctttaatagtggactcttgttccaaactg
gaacaacactcaaccctatctcgggctattcttttgatttataagggattttgccgatttcgga
accaccatcaaacaggattttcgcctgctggggcaaaccagcgtggaccgcttgctgcaactct
ctcagggccaggcggtgaagggcaatcagctgttgcccgtctcactggtgaaaagaaaaaccac
cccagtacattaaaaacgtccgcaatgtgttattaagttgtctaagcgtcaattt*gtttacacc*
*acaatatatcctgcca*

SEQ ID NO:137 is the nucleic acid sequence of pBI121-HP-GmCPP. Italicized sequences are the right and left border repeats. Underlined sequence is the 35S promoter. Bold sequence is the antisense prenyl protease fragment of *G. max*. Bold and underlined sequence is the *G. max* sense prenyl protease fragment and sequence in upper case is the truncated GUS fragment.

*gtttacccgccaatatatcctgtc*aaacactgatagtttaaactgaaggcgggaaacgacaatc SEQ ID NO:138
tgatcatgagcggagaattaagggagtcacgttatgacccccgccgatgacgcgggacaagccg
ttttacgtttggaactgacagaaccgcaacgttgaaggagccactcagccgcgggtttctggag
tttaatgagctaagcacatacgtcagaaaccattattgcgcgttcaaaagtcgcctaaggtcac
tatcagctagcaaatatttcttgtcaaaaatgctccactgacgttccataaattcccctcggta
tccaattagagtctcatattcactctcaatccaaataatctgcaccggatctggatcgtttcgc
atgattgaacaagatggattgcacgcaggttctccggccgcttgggtggagaggctattcggct
atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg -continued tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggggactctagag gatccccgggttagtcttccttcttatccggttcgtccagcgcggccaatctttcaacaagggg aggatgagaatagtgataagcagagtaccaaggatctgtattcatagctgacagattctcctcc tgtagtttcacaagaccaccgcgtaatccagatgcatatccaagcttcttggcaaagccatcag cctgaaattcaaatgatcggctgactaggttcagaccaaagctgaccaattgctgaagtgggat tacagtatgctgaaatatgatgagcccaatgaggactggctgcgtatcaaacccaaagcttcga tacagatcagctgaatttcgcactagtgtatatcctccaaattgtagaagtgtaagaatctgca tagcaacaaatgtgtacacagtatggttgagcttccagtgtcccaactcatgggcaataacagc aacaatttcctcatcgtctttgcactgttgaattaatgtgtcataagggacaatcctcttgttc ttgaagaatccatacatataggcattgctgtgacttgatcttgtggatccatcgacaacaaata gtttctttaacggatagttgagggaggaagcaagtttctcgattttctccctgagttgaccatc tggaagtggagtgaacttattgaagagtggagctattagtactggataaagggtcatcatcaca atagaaagaccaaacgtaaaaacccaaagatagatggccaagtatggacctcctttctgtacta

-continued ttacaatgattgcagccacaataggtggaccaattattacagaaaggaaaattcctttaagcat gtccctaaagaataaccatggtgtttgcttattaaaaccatgacgggcctcaatcacaaaagtt gagtacagagaaaagggcaaatctgttatctgtgaccaaatcatcagccctgctaagaaggcaa gggtatgcagtatttcattctcagcattgaaaccagctattgtcataaaatctcctgatttctt ccaaaaccagggcaataccccaaagtacaaaattgtagagtctgtcactattgtcacaaactcg tgaacaaaatggaagtggcttttatcaagactataggctctagatttctcaaatttctcttggc tgataacaccctctaaagtctttggaagagtaggaagtttgagggccctatgttgtcgcacatc caagtaagtttcaaaaatgtacattaatatcataaatccgacaacggcttccatgtagggaaac gccatgagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattcactggccgtcgttttacaacgtcgtgactgggaaaacc ctggcgttacccaacttaatcgccttgcagcacatccccctttcgccagctggcgtaatagcga agaggcccgcaccgatcgcccttcccaacagttgcgcagcctgaatggcgcccgctcctttcgc tttcttcccttcctttctcgccacgttcgccggctttccccgtcaagctctaaatcgggggctc cctttagggttccgatttagtgctttacggcacctcgaccccaaaaaacttgatttgggtgatg gttcacgtagtgggccatcgccctgatagacggtttttcgccctttgacgttggagtccacgtt ctttaatagtggactcttgttccaaactggaacaacactcaaccctatctcgggctattctttt gatttataagggattttgccgatttcggaaccaccatcaaacaggattttcgcctgctggggca aaccagcgtggaccgcttgctgcaactctctcagggccaggcggtgaagggcaatcagctgttg cccgtctcactggtgaaaagaaaaaccaccccagtacattaaaaacgtccgcaatgtgttatta agttgtctaagcgtcaattt*gtttacaccacaatatatcctgcca*

SEQ ID NO:138 is the nucleic acid sequence of pBI121-antisense-GmCPP. Italicized sequences are the right and left border repeats. Underlined sequence is the 35S promoter. Sequence in bold is the GmCPP anti-sense sequence.

*gtttacccgccaatatatcctgtc*aaacactgatagtttaaactgaaggcgggaaacgacaatc SEQ ID NO:139 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag -continued ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacattttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt -continued atctctctcagtctctctataaacttagtgagaccctcctctgttttactcacaaatatgcaaa ctagaaaacaatcatcaggaataaagggtttgattacttctattggaaaggactctagaggatc cccgggatggcgtttccctacatggaagccgttgtcggatttatgatattaatgtacatttttg aaacttacttggatgtgcgacaacatagggccctcaaacttcctactcttccaaagactttaga gggtgttatcagccaagagaaatttgagaaatctagagcctatagtcttgataaaagccacttc cattttgttcacgagtttgtgacaatagtgacagactctacaattttgtactttggggtattgc cctggttttggaagaaatcaggagattttatgacaatagctggtttcaatgctgagaatgaaat actgcatacccttgccttcttagcagggctgatgatttggtcacagataacagatttgcccttt tctctgatctcaacttttgtgattgaggcccgtcatggttttaataagcaaacaccatggttat tctttagggacatgcttaaaggaattttcctttctgtaataattggtccacctattgtggctgc aatcattgtaatagtacagaaaggaggtccatacttggccatctatctttgggtttttacgttt ggtctttctattgtgatgatgaccctttatccagtactaatagctccactcttcaataagttca ctccacttccagatggtcaactcagggagaaaatcgagaaacttgcttcctccctcaactatcc gttaaagaaactatttgttgtcgatggatccacaagatcaagtcacagcaatgcctatatgtat ggattcttcaagaacaagaggattgtcccttatgacacattaattcaacagtgcaaagacgatg aggaaattgttgctgttattgcccatgagttgggacactggaagctcaaccatactgtgtacac atttgttgctatgcagattcttacacttctacaatttggaggatatacactagtgcgaaattca gctgatctgtatcgaagctttgggtttgatacgcagccagtcctcattgggctcatcatatttc agcatactgtaatcccacttcagcaattggtcagctttggtctgaacctagtcagccgatcatt tgaatttcaggctgatggctttgccaagaagcttggatatgcatctggattacgcggtggtctt gtgaaactacaggaggagaatctgtcagctatgaatacagatccttggtactctgcttatcact attctcatcctccccttgttgaaagattggccgcgctggacgaaccggataagaaggaagacta agagctcgaatttccccgatcgttcaaacatttggcaataaagtttcttaagattgaatcctgt tgccggtcttgcgatgattatcatataatttctgttgaattacgttaagcatgtaataattaac atgtaatgcatgacgttatttatgagatgggtttttatgattagagtcccgcaattatacattt aatacgcgatagaaaacaaaatatagcgcgcaaactaggataaattatcgcgcgcggtgtcatc tatgttactagatcgggaattcactggccgtcgttttacaacgtcgtgactgggaaaaccctgg cgttacccaacttaatcgccttgcagcacatccccctttcgccagctggcgtaatagcgaagag gcccgcaccgatcgcccttcccaacagttgcgcagcctgaatggcgcccgctcctttcgctttc ttcccttcctttctcgccacgttcgccggctttccccgtcaagctctaaatcgggggctccctt tagggttccgatttagtgctttacggcacctcgaccccaaaaaacttgatttgggtgatggttc acgtagtgggccatcgccctgagagacggtttttcgccctttgacgttggagtccacgttcttt aatagtggactcttgttccaaactggaacaacactcaaccctatctcgggctattcttttgatt tataagggattttgccgatttcggaaccaccatcaaacaggattttcgcctgctggggcaaacc agcgtggaccgcttgctgcaactctctcagggccaggcggtgaagggcaatcagctgttgcccg tctcactggtgaaaagaaaaaccaccccagtacattaaaaacgtccgcaatgtgttattaagtt gtctaagcgtcaattt*gtttacaccacaatatatcctgcca*

SEQ ID NO:139 is the nucleic acid sequence of pRD29A-GmCPP. Italicized sequences are the right and left border repeats. Underlined sequence is the RD29A promoter. Sequence in bold is the GmCPP sense sequence.

*gtttacccgccaatatatcctgtc*caaacactgatagtttaaactgaaggcgggaaacgacaatc SEQ ID NO:140 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcag<u>ggagccatagatgcaattcaatcaaactgaaatttctgcaagaatc</u>

-continued tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacattttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaccggt
tcgtccagcgcggccaatctttcaacaaggggaggatgagaatagtgataagcagagtaccaag
gatctgtattcatagctgacagattctcctcctgtagtttcacaagaccaccgcgtaatccaga
tgcatatccaagcttcttggcaaagccatcagcctgaaattcaaatgatcggctgactaggttc
agaccaaagctgaccaattgctgaagtgggattacagtatgctgaaatatgatgagcccaatga
ggactggctgcgtatcaaacccaaagcttcgatacagatcagctgaatttcgcactagtgtata
tcctccaaattgtagaagtgtaagaatctgcatagcaacaaatgtgtacacagtatggttgagc
ttccagtgtcccaactcatgggcaataacagcaacaatttcctcatcgtctttgcactgttgaa
ttaatgtgtcataagggacaatcctcttgttcttgaagaatccatacatataggcattgctgtg
acttgatcttgtggatccccATCTACCCGCTTCGCGTCGGCATCCGGTCAGTGGCAGTGAAGGG
CGAACAGTTCCTGATTAACCACAAACCGTTCTACTTTACTGGCTTTGGTCGTCATGAAGATGCG
GACTTGCGTGGCAAAGGATTCGATAACGTGCTGATGGTGCACGACCACGCATTAATGGACTGGA
TTGGGGCCAACTCCTACCGTACCTCGCATTACCCTTACGCTGAAGAGATGCTCGACTGGGCAGA
TGAACATGGCATCGTGGTGATTGATGAAACTGCTGCTGTCGGCTTTTCGCTCTCTTTAGGCATT
GGTTTCGAAGCGGGCAACAAGCCGAAAGAACTGTACAGCGAAGAGGCAGTCAACGGGGAAACTC
AGCAAGCGCACTTACAGGCGATTAAAGAGCTGATAGCGCGTGACAAAAACCACCCAAGCGTGGT
GATGTGGAGTATTGCCAACGAACCGGATACCCGTCCGCAAGGTGCACGGGAATATTTCGCGCCA
CTGGCGGAAGCAACGCGTAAACTCGACCCGACGCGTCCGATCACCTGCGTCAATGTAATGTTCT
GCGACGCTCACACCGATACCATCAGCGATCTCTTTGATGTGCTGTGCCTGAACCGTTATTACGG
ATGGTATGTCCAAAGCGGCGATTTGGAAACGGCAGAGAAGGTACTGGAAAAAGAACTTCTGGCC
TGGCAGGAGAAACTGTACACCGACATGTGGAGTGAAGAGTATCAGTGTGCATGGCTGGATATGT
ATCACCGCGTCTTTGATCGCGTCAGCGCCGTCGTCGGTGAACAGGTATGGAATTTCGCCGATTT
TGCGACCTCGCAAGGCATATTGCGCGTTGGCGGTAACAAGAAAGGGATCTTCACTCGCGACCGC
AAACCGAAGTCGGCGGCTTTTCTGCTGCAAAAACGCTGGACTGGCATGAACTTCGGTGAAAAAC
CGCAGCAGGGAGGCAAACAATGAatcaacaactctcctggcgcaccatcgtcggctacagcctc
gggaattgctaccgagctcacaagatcaagtcacagcaatgcctatatgtatggattcttcaag
aacaagaggattgtcccttatgacacattaattcaacagtgcaaagacgatgaggaaattgttg

-continued ctgttattgcccatgagttgggacactggaagctcaaccatactgtgtacacatttgttgctat gcagattcttacacttctacaatttggaggatatacactagtgcgaaattcagctgatctgtat cgaagctttgggtttgatacgcagccagtcctcattgggctcatcatatttcagcatactgtaa tcccacttcagcaattggtcagctttggtctgaacctagtcagccgatcatttgaatttcaggc tgatggctttgccaagaagcttggatatgcatctggattacgcggtggtcttgtgaaactacag gaggagaatctgtcagctatgaatacagatccttggtactctgcttatcactattctcatcctc cccttgttgaaagattggccgcgctggacgaaccgggagctcgaatttccccgatcgttcaaac atttggcaataaagtttcttaagattgaatcctgttgccggtcttgcgatgattatcatataat ttctgttgaattacgttaagcatgtaataattaacatgtaatgcatgacgttatttatgagatg ggtttttatgattagagtcccgcaattatacatttaatacgcgatagaaaacaaaatatagcgc gcaaactaggataaattatcgcgcgcggtgtcatctatgttactagatcgggaattcactggcc gtcgttttacaacgtcgtgactgggaaaaccctggcgttacccaacttaatcgccttgcagcac atccccctttcgccagctggcgtaatagcgaagaggcccgcaccgatcgcccttcccaacagtt gcgcagcctgaatggcgcccgctcctttcgctttcttcccttcctttctcgccacgttcgccgg ctttccccgtcaagctctaaatcgggggctccctttagggttccgatttagtgctttacggcac ctcgaccccaaaaaacttgatttgggtgatggttcacgtagtgggccatcgccctgatagacgg tttttcgccctttgacgttggagtccacgttctttaatagtggactcttgttccaaactggaac aacactcaaccctatctcgggctattcttttgatttataagggattttgccgatttcggaacca ccatcaaacaggattttcgcctgctggggcaaaccagcgtggaccgcttgctgcaactctctca gggccaggcggtgaagggcaatcagctgttgcccgtctcactggtgaaaagaaaaaccacccca gtacattaaaaacgtccgcaatgtgttattaagttgtctaagcgtcaattt*gtttacaccacaa*

*tatatcctgcca*

SEQ ID NO:140 is the nucleic acid sequence of pRD29A-HP-GmCPP. Italicized sequences are the right and left border repeats. Underlined sequence is the RD29A promoter. Sequence in bold is the GmCPP antisense sequence, bold and underlined sequence is the GmCPP sense sequence.

SEQ ID NO:141

*gtttacccgccaatatatcctgtc*aaacactgatagtttaaactgaaggcgggaaacgacaatctgatcatgagcggagaattaagg gagtcacgttatgacccccgccgatgacgcgggacaagccgttttacgtttggaactgacagaaccgcaacgttgaaggagccac tcagccgcgggtttctggagtttaatgagctaagcacatacgtcagaaaccattattgcgcgttcaaaagtcgcctaaggtcactat cagctagcaaatatttcttgtcaaaaatgctccactgacgttccataaattcccctcggtatccaattagagtctcatattcactctcaa tccaaataatctgcaccggatctggatcgtttcgcatgattgaacaagatggattgcacgcaggttctccggccgcttgggtggaga ggctattcggcttgactgggcacaacagacaatcggctgctctgatgccgccgtgttccggctgtcagcgcaggggcgcccggtt ctttttgtcaagaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcaggatctcctgtc atctcaccttgctcctgccgagaaagtatccatcatggctgatgcaatgcggcggctgcatacgcttgatcggctacctgcccattc gaccaccaagcgaaacatcgcatcgagcgagcacgtactcggatggaagccggtcttgtcgatcaggatgatctggacgaagag catcaggggctcgcgccagccgaactgttcgccaggctcaaggcgcgcatgcccgacggcgatgatctcgtcgtgacccatggcg atgcctgcttgccgaatatcatggtggaaaatggccgcttttctggattcatcgactgtggccggctgggtgtggcggaccgctatca

-continued ggacatagcgttggctacccgtgatattgctgaagagcttggcggcgaatgggctgaccgcttcctcgtgctttacggtatcgccgct cccgattcgcagcgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgggacgccggctgg atgatcctccagcgcggggatctcatgctggagttcttcgcccacgggatctctgcggaacaggcggtcgaaggtgccgatatcatt acgacagcaacggccgacaagcacaacgccacgatcctgagcgacaatatgatcgggcccggcgtccacatcaacggcgtcgg cggcgactgcccaggcaagaccgagatgcaccgcgatatcttgctgcgttcggatattttcgtggagttcccgccacagacccgga tgatcccgatcgttcaaacatttggcaataaagtttcttaagattgaatcctgttgccggtcttgcgatgattatcatataatttctgg gaattacgttaagcatgtaataattaacatgtaatgcatgacgttatttatgagatgggtttttatgattagagtcccgcaattatacat ttaatacgcgatagaaaacaaaatatagcgcgcaaactaggataaattatcgcgcgcggtgtcatctatgttactagatcgggcct cctgtcaatgctggcggcggctctggtggtggttctggtggcggctctgagggtggtggctctgagggtggcggttctgagggtggc ggctctgagggaggcggttccggtggtggctctggttccggtgattttgattatgaaaagatggcaaacgctaataagggggctatg accgaaaatgccgatgaaaacgcgctacagtctgacgctaaaggcaaacttgattctgtcgctactgattacggtgctgctatcgat ggtttcattggtgacgtttccggccttgctaatggtaatggtgctactggtgattttgctggctctaattcccaaatggctcaagtcggt gacggtgataattcacctttaatgaataatttccgtcaatatttaccttccctccctcaatcggttgaatgtcgcccttttgtctttggccc aatacgcaaaccgcctctccccgcgcgttggccgattcattaatgcagctggcacgacaggtttcccgactggaaagcgggcagtg agcgcaacgcaattaatgtgagttagctcactcattaggcaccccaggctttacactttatgcttccggctcgtatgugtgtggaatt gtgagcggataacaatttcacacaggaaacagctatgaccatgattacgccaagcttgcatgcctgcaggggagccatagatgcaa ttcaatcaaactgaaatttctgcaagaatctcaaacacggagatctcaaagtttgaaagaaaatttatttcttcgactcaaaacaaa cttacgaaatttaggtagaacttatatacattatattgtaatttttgtaacaaaatgtttttattattattatagaattttactggttaaat taaaaatgaatagaaaaggtgaattaagaggagagaggaggtaaacattttcttctatttttttcatattttcaggataaattattgta aaagtttacaagatttccatttgactagtgtaaatgaggaatattctctagtaagatcattatttcatctacttcttttatcttctaccagt agaggaataaacaatatttagctcctttgtaaatacaaattaattttccttcttgacatcattcaattttaattttacgtataaaataaa agaggaataaacaatatttagctcctttgtaaatacaaattaattttccttcttgacatcattcaattttaattttacgtataaaataaa agatcatacctattagaacgattaaggagaaatacaattcgaatgagaaggatgtgccgtttgttataataaacagccacacgacg taaacgtaaaatgaccacatgatgggccaatagacatggaccgactactaataatagtaagttacattttaggatggaataaatat cataccgacatcagttttgaaagaaaagggaaaaaaagaaaaaataaataaaagatatactaccgacatgagttccaaaaagc aaaaaaaaagatcaagccgacacagacacgcgtagagagcaaaatgactttgacgtcacaccacgaaaacagacgcttcatac gtgtccctttatctctctcagtctctctataaacttagtgagaccctcctctgttttactcacaaatatgcaaactagaaaacaatcatc aggaataaagggtttgattacttctattggaaagactctagaggatccccgggttagtcttccttcttatccggttcgtccagcgcggcc aatctttcaacaaggggaggatgagaatagtgataagcagagtaccaaggatctgtattcatagctgacagattctcctcctgtagtttcacaa gaccaccgcgtaatccagatgcatatccaagcttcttggcaaagccatcagcctgaaattcaaatgatcggctgactaggttcagaccaaag ctgaccaattgctgaagtgggattacagtatgctgaaatatgatgagcccaatgaggactggctgcgtatcaaacccaaagcttcgatacag atcagctgaatttcgcactagtgtatatcctccaaattgtagaagtgtaagaatctgcatagcaacaaatgtgtacacagtatggttgagcttcc agtgtcccaactcatgggcaataacagcaacaatttcctcatcgtctttgcactgttgaattaatgtgtcataagggacaatcctcttgttcttgaa gaatccatacatataggcattgctgtgacttgatcttgtggatccatcgacaacaaatagtttctttaacggatagttgagggaggaagcaagtt tctcgattuctccctgagttgaccatctggaagtggagtgaacttattgaagagtggagctattagtactggataaagggtcatcatcacaata gaaagaccaaacgtaaaaacccaaagatagatggccaagtatggacctcctttctgtactattacaatgaugcagccacaataggtggacc aattattacagaaaggaaaattcctttaagcatgtccctaaagaataaccatggtgtttgcttattaaaaccatgacgggcctcaatcacaaaag ttgagtacagagaaaagggcaaatctgttatctgtgaccaaatcatcagccctgctaagaaggcaagggtatgcagtatttcauctcagcatt gaaaccagctattgtcataaaatctcctgatttcttccaaaaccagggcaataccccaaagtacaaaattgtagagtctgtcactattgtcacaa -continued actcgtgaacaaaatggaagtggcttttatcaagactataggctctagatttctcaaatttctcttggctgataacaccctctaaagtctttggaag agtaggaagtttgagggccctatgttgtcgcacatccaagtaagtttcaaaaatgtacattaatatcataaatccgacaacggcttccatgtag ggaaacgccatgagctcgaatttccccgatcgttcaaacatttggcaataaagtttcttaagattgaatcctgttgccggtcttgcgat gattatcatataatttctgttgaattacgttaagcatgtaataattaacatgtaatgcatgacgttatttatgagatgggtttttatgatt agagtcccgcaattatacatttaatacgcgatagaaaacaaaatatagcgcgcaaactaggataaattatcgcgcgcggtgtcatc tatgttactagatcgggaattcactggccgtcgttttacaacgtcgtgactgggaaaaccctggcgttacccaacttaatcgccttgc agcacatccccctttcgccagctggcgtaatagcgaagaggcccgcaccgatcgcccttcccaacagttgcgcagcctgaatggcg cccgctcctttcgctttcttcccttcctttctcgccacgttcgccggctttccccgtcaagctctaaatcgggggctccctttagggttccg atttagtgcutacggcacctcgaccccaaaaaacttgatttgggtgatggttcacgtagtgggccatcgccctgatagacggtttttc gccctttgacgttggagtccacgttctttaatagtggactcttgttccaaactggaacaacactcaaccctatctcgggctattcttttg atttataagggattttgccgatttcggaaccaccatcaaacaggattttcgcctgctggggcaaaccagcgtggaccgcttgctgca actctctcagggccaggcggtgaagggcaatcagctgttgcccgtctcactggtgaaaagaaaaaccaccccagtacattaaaaa cgtccgcaatgtgttattaagttgtctaagcgtcaattt*gtttacaccacaatatatcctgcca*

SEQ ID NO:141 is the nucleic acid sequence of pRD29A-antisense-GmCPP. Italicized sequences are the right and left border repeats. Underlined sequence is the RD29A promoter. Sequence in bold is the GmCPP antisense sequence.

gtttacccgccaatatatcctgtcaaacactgatagtttaaactgaaggcgggaaacgacaatc SEQ ID NO:142 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc -continued ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagcccacagatggttagagaggcttacgcagcaggtctcatcaagacg
atctacccgagcaataatctccaggaaatcaaataccttcccaagaaggttaaagatgcagtca
aaagattcaggactaactgcatcaagaacacagagaaagatatatttctcaagatcagaagtac
tattccagtatggacgattcaaggcttgcttcacaaaccaaggcaagtaatagagattggagtc
tctaaaaaggtagttcccactgaatcaaaggccatggagtcaaagattcaaatagaggacctaa
cagaactcgccgtaaagactggcgaacagttcatacagagtctcttacgactcaatgacaagaa
gaaaatcttcgtcaacatggtggagcacgacacacttgtctactccaaaaatatcaaagataca
gtctcagaagaccaaagggcaattgagacttttcaacaaagggtaatatccggaaacctcctcg
gattccattgcccagctatctgtcactttattgtgaagatagtggaaaaggaaggtggctccta
caaatgccatcattgcgataaaggaaaggccatcgttgaagatgcctctgccgacagtggtccc
aaagatggacccccacccacgaggagcatcgtggaaaaagaagacgttccaaccacgtcttcaa
agcaagtggattgatgtgatatctccactgacgtaagggatgacgcacaatcccactatccttc
gcaagacccttcctctatataaggaagttcatttcatttggagagaacacggggggactctagag
gatccatggcgattcctttcatggaaaccgtcgttggttttatgatagtgatgtacgtttttga
gacgtatttggatctgaggcaacatactgctctcaagcttcccactctcccaaagactttggtt
ggagtcattagccaagagaagtttgagaaatctcgagcttacagtcttgacaaaagccattttc
actttgttcatgagtttgttactatacttatggactctgcgattctgttctttgggatcttgcc
ttggttttggaagatatctggcggctttctaccaatggtgggactcgatccagagaatgaaatc
ctgcacactctttcattcttggctggtcttatgacatggtcacagatcactgatttgccatttt
ctttgtactcaactttcgtgatcgagtctcggcatgggttcaacaaacaaacaatatggatgtt
cattagggacatgatcaaaggaatactcctctctgtcatacctgcccctcctatcgttgccgca
attattgttatagttcagaaaggaggtccttacctcgccatctatctgtgggcattcatgttta
tcctgtctctagtgatgatgactatataccctgttttgattgcacctcttttcaacaagttcac
tcctcttcctgatggagacctccgggagaagattgagaaacttgcttcttctctaaagtttcct

-continued ctgaagaagctgtttgttgtcgatggatctacaaggtcaagccatagtaatgcttacatgtatg gtttcttcaagaacaaaaggattgttctttatgacacattgattcagcagtgccagaatgagaa tgaaattgtggcggttattgcacacgagctgggacactggaagctgaatcacactacatactcg ttcattgctgttcaaatccttgccttcttgcaatttggaggatacactcttgtcagaaactcca ctgatctcttcaggagttttggttttgatacacaaccagttctcattggtttgatcatatttca gcacactgtaataccacttcaacacctagtaagctttgacctcaaccttgttagtcgagcgttt gagtttcaggctgatgcttttgcagtgaatcttggttatgcaaaggatctacgtcctgccctag tgaagctacaggaagagaacttatcagcgatgaacacagacccattgtactcagcttatcacta ctcacaccctcctcttgtagagaggcttcgagccattgatggagaagacaagaagacagattaa cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatcccccttttcgccagctqgcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:142 is the nucleic acid sequence of pBI121-BnCPP Italicized sequences are the right and left border repeats. Underlined sequence is the 35S promoter. Sequence in bold is the BnCPP antisense sequence.

gtttacccgccaatatatcctgtcaaacactgatagtttaaactgaaggcgggaaacgacaatc   SEQ ID NO:143 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct -continued tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc -continued gcaagacccttcctctatataaggaagttcatttcatttggagagaacacggggactctagac cagtgtcccagctcgtgtgcaataaccgccacaatttcattctcattctggcactgctgaatca atgtgtcataaagaacaatccttttgttcttgaagaaaccatacatgtaagcattactatggct tgaccttgtagatccatcgacaacaaacagcttcttcagaggaaactttagagaagaagcaagt ttctcaatcttctcccggaggtctccatcaggaagaggagtgaacttgttgaaaagaggtgcaa tcaaaacagggtatatagtcatcatcactagagacaggataaacatgaatgcccacagatagat ggcgaggtaaggacctcctttctgaactataacaataattgcggcaacgataggaggggcaggt atgacagagaggagtattcctttgatcatgtccctaatgaacatccatattgtttgtttgttga acccatgccgagactcgatcacgaaagttgagtacaaagaaaatggcaaatcagtgatctgtga ccatgtcataagaccagccaagaatgaaagagtgtgcaggatttcattctctggatcgagtccc accattggtagaaggatccccATCTACCCGCTTCGCGTCGGCATCCGGTCAGTGGCAGTGAAGG

GCGAACAGTTCCTGATTAACCACAAACCGTTCTACTTTACTGGCTTTGGTCGTCATGAAGATGC

GGACTTGCGTGGCAAAGGATTCGATAACGTGCTGATGGTGCACGACCACGCATTAATGGACTGG

ATTGGGGCCAACTCCTACCGTACCTCGCATTACCCTTACGCTGAAGAGATGCTCGACTGGGCAG

ATGAACATGGCATCGTGGTGATTGATGAAACTGCTGCTGTCGGCTTTTCGCTCTCTTTAGGCAT

TGGTTTCGAAGCGGGCAACAAGCCGAAAGAACTGTACAGCGAAGAGGCAGTCAACGGGGAAACT

CAGCAAGCGCACTTACAGGCGATTAAAGAGCTGATAGCGCGTGACAAAAACCACCCAAGCGTGG

TGATGTGGAGTATTGCCAACGAACCGGATACCCGTCCGCAAGGTGCACGGGAATATTTCGCGCC

ACTGGCGGAAGCAACGCGTAAACTCGACCCGACGCGTCCGATCACCTGCGTCAATGTAATGTTC

TGCGACGCTCACACCGATACCATCAGCGATCTCTTTGATGTGCTGTGCCTGAACCGTTATTACG

GATGGTATGTCCAAAGCGGCGATTTGGAAACGGCAGAGAAGGTACTGGAAAAAGAACTTCTGGC

CTGGCAGGAGAAACTGTACACCGACATGTGGAGTGAAGAGTATCAGTGTGCATGGCTGGATATG

TATCACCGCGTCTTTGATCGCGTCAGCGCCGTCGTCGGTGAACAGGTATGGAATTTCGCCGATT

TTGCGACCTCGCAAGGCATATTGCGCGTTGGCGGTAACAAGAAAGGGATCTTCACTCGCGACCG

CAAACCGAAGTCGGCGGCTTTTCTGCTGCAAAAACGCTGGACTGGCATGAACTTCGGTGAAAAA

CCGCAGCAGGGAGGCAAACAATGAatcaacaactctcctggcgcaccatcgtcggctacagcct cgggaattgctaccgagctcttctaccaatggtgggactcgatccagagaatgaaatcctgcac actctttcattcttggctggtcttatgacatggtcacagatgactgatttgccattttctttgt actcaactttcgtgatcgagtctcggcatgggttcaacaaacaaacaatatggatgttcattag ggacatgatcaaaggaatactcctctctgtcatacctgcccctcctatcgttgccgcaattatt gttatagttcagaaaggaggtccttacctcgccatctatctgtgggcattcatgtttatcctgt ctctagtgatgatgactatataccctgttttgattgcacctcttttcaacaagttcactcctct tcctgatggagacctccgggagaagattgagaaacttgcttcttctctaaagtttcctctgaag aagctgtttgttgtcgatggatctacaaggtcaagccatagtaatgcttacatgtatggtttct tcaagaacaaaaggattgttctttatgacacattgattcagcagtgccagaatgagaatgaaat tgtggcggttattgcacacgagctgggacactgggagctcgaatttccccgatcgttcaaacat ttggcaataaagtttcttaagattgaatcctgttgccggtcttgcgatgattatcatataattt ctgttgaattacgttaagcatgtaataattaacatgtaatgcatgacgttatttatgagatggg tttttatgattagagtcccgcaattatacatttaatacgcgatagaaaacaaaatatagcgcgc aaactaggataaattatcgcgcgcggtgtcatctatgttactagatcgggaattcactggccgt -continued cgttttacaacgtcgtgactgggaaaaccctggcgttacccaacttaatcgccttgcagcacat ccccctttcgccagctggcgtaatagcgaagaggcccgcaccgatcgcccttcccaacagttgc gcagcctgaatggcgcccgctcctttcgctttcttcccttcctttctcgccacgttcgccggct ttccccgtcaagctctaaatcgggggctccctttagggttccgatttagtgctttacggcacct cgaccccaaaaaacttgatttgggtgatggttcacgtagtgggccatcgccctgatagacggtt tttcgccctttgacgttggagtccacgttctttaatagtggactcttgttccaaactggaacaa cactcaaccctatctcgggctattcttttgatttataagggattttgccgatttcggaaccacc atcaaacaggattttcgcctgctggggcaaaccagcgtggaccgcttgctgcaactctctcagg gccaggcggtgaagggcaatcagctgttgcccgtctcactggtgaaaagaaaaaccaccccagt acattaaaaacgtccgcaatgtgttattaagttgtctaagcgtcaattt*gtttacaccacaata*

*tatcctgcca*

SEQ ID NO:143 is the nucleic acid sequence of pBI121-HP-BnCPP. Italicized sequences are the right and left border repeats. Underlined sequence is the 35S promoter. Sequence in bold is the BnCPP antisense sequence, bold and underlined sequence is the BnCPP sense fragment and upper case indicates the truncated GUS fragment.

*gtttacccgccaatatatcctgt*caaacactgatagtttaaactgaaggcgggaaacgacaatc SEQ ID NO:144 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc -continued ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccttaatctgtcttcttgtcttctccatcaatggctcgaagcctctctacaagaggagggt gtgagtagtgataagctgagtacaatgggtctgtgttcatcgctgataagttctcttcctgtag cttcactagggcaggacgtagatcctttgcataaccaagattcactgcaaaagcatcagcctga aactcaaacgctcgactaacaaggttgaggtcaaagcttactaggtgttgaagtggtattacag tgtgctgaaatatgatcaaaccaatgagaactggttgtgtatcaaaaccaaaactcctgaagag atcagtggagtttctgacaagagtgtatcctccaaattgcaagaaggcaaggatttgaacagca atgaacgagtatgtagtgtgattcagcttccagtgtcccagctcgtgtgcaataaccgccacaa tttcattctcattctggcactgctgaatcaatgtgtcataaagaacaatccttttgttcttgaa gaaaccatacatgtaagcattactatggcttgaccttgtagatccatcgacaacaaacagcttc ttcagaggaaactttagagaagaagcaagtttctcaatcttctcccggaggtctccatcaggaa gaggagtgaacttgttgaaaagaggtgcaatcaaaacagggtatatagtcatcatcactagaga -continued caggataaacatgaatgcccacagatagatggcgaggtaaggacctcctttctgaactataaca ataattgcggcaacgataggaggggcaggtatgacagagaggagtattcctttgatcatgtccc taatgaacatccatattgtttgtttgttgaacccatgccgagactcgatcacgaaagttgagta caaagaaaatggcaaatcagtgatctgtgaccatgtcataagaccagccaagaatgaaagagtg tgcaggatttcattctctggatcgagtcccaccattggtagaaagccgccagatatcttccaaa accaaggcaagatcccaaagaacagaatcgcagagtccataagtatagtaacaaactcatgaac aaagtgaaaatggcttttgtcaagactgtaagctcgagatttctcaaacttctcttggctaatg actccaaccaaagtctttgggagagtgggaagcttgagagcagtatgttgcctcagatccaaat acgtctcaaaaacgtacatcactatcataaaaccaacgacggtttccatgaaaggaatcgccat cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:144 is the nucleic acid sequence of pBI121-antisense-BnCPP. Italicized sequences are the right and left border repeats. Underlined sequence is the 35S promoter. Sequence in bold is the BnCPP antisense sequence.

*gtttacccgccaatatatcctgtcaaa*cactgatagtttaaactgaaggcgggaaacgacaatc SEQ ID NO:145 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg -continued gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt -continued atctctctcagtctctctataaacttagtgagaccctcctctgttttactcacaaatatgcaaa ctagaaaacaatcatcaggaataaagggtttgattacttctattggaaaggactctagaggatc catggcgattcctttcatggaaaccgtcgttggttttatgatagtgatgtacgtttttgagacg tatttggatctgaggcaacatactgctctcaagcttcccactctcccaaagactttggttggag tcattagccaagagaagtttgagaaatctcgagcttacagtcttgacaaaagccattttcactt tgttcatgagtttgttactatacttatggactctgcgattctgttctttgggatcttgccttgg ttttggaagatatctggcggctttctaccaatggtgggactcgatccagagaatgaaatcctgc acactctttcattcttggctggtcttatgacatggtcacagatcactgatttgccattttcttt gtactcaactttcgtgatcgagtctcggcatgggttcaacaaacaaacaatatggatgttcatt agggacatgatcaaaggaatactcctctctgtcatacctgcccctcctatcgttgccgcaatta ttgttatagttcagaaaggaggtccttacctcgccatctatctgtgggcattcatgtttatcct gtctctagtgatgatgactatataccctgttttgattgcacctcttttcaacaagttcactcct cttcctgatggagacctccgggagaagattgagaaacttgcttcttctctaaagtttcctctga agaagctgtttgttgtcgatggatctacaaggtcaagccatagtaatgcttacatgtatggttt cttcaagaacaaaaggattgttctttatgacacattgattcagcagtgccagaatgagaatgaa attgtggcggttattgcacacgagctgggacactggaagctgaatcacactacatactcgttca ttgctgttcaaatccttgccttcttgcaatttggaggatacactcttgtcagaaactccactga tctcttcaggagttttggttttgatacacaaccagttctcattggtttgatcatatttcagcac actgtaataccacttcaacacctagtaagctttgacctcaaccttgttagtcgagcgtttgagt ttcaggctgatgcttttgcagtgaatcttggttatgcaaaggatctacgtcctgccctagtgaa gctacaggaagagaacttatcagcgatgaacacagacccattgtactcagcttatcactactca caccctcctcttgtagagaggcttcgagccattgatggagaagacaagaagacagattaacccc tcgaatttccccgatcgttcaaacatttggqaataaagtttcttaagattgaatcctgttgccg gtcttgcgatgattatcatataatttctgttgaattacgttaagcatgtaataattaacatgta atgcatgacgttatttatgagatgggtttttatgattagagtcccgcaattatacatttaatac gcgatagaaaacaaaatatagcgcgcaaactaggataaattatcgcgcgcggtgtcatctatgt tactagatcgggaattcactggccgtcgttttacaacgtcgtgactgggaaaaccctggcgtta cccaacttaatcgccttgcagcacatccccctttcgccagctggcgtaatagcgaagaggcccg caccgatcgcccttcccaacagttgcgcagcctgaatggcgcccgctcctttcgctttcttccc ttcctttctcgccacgttcgccggctttccccgtcaagctctaaatcgggggctccctttaggg ttccgatttagtgctttacggcacctcgaccccaaaaaacttgatttgggtgatggttcacgta gtgggccatcgccctgatagacggtttttcgccctttgacgttggagtccacgttctttaatag tggactcttgttccaaactggaacaacactcaaccctatctcgggctattcttttgatttataa gggattttgccgatttcggaaccaccatcaaacaggattttcgcctgctggggcaaaccagcgt ggaccgcttgctgcaactctctcagggccaggcggtgaagggcaatcagctgttgcccgtctca ctggtgaaaagaaaaaccaccccagtacattaaaaacgtccgcaatgtgttattaagttgtcta agcgtcaattt*gtttacaccacaatatatcctgcca*

SEQ ID NO:145 is the nucleic acid sequence of pRD29A-BnCPP. Italicized sequences are the right and left border repeats. Underlined sequence is the RD29A promoter. Sequence in bold is the BnCPP sense sequence.

*gtttacccgccaatatatcctgtc*caaacactgatagtttaaactgaaggcgggaaacgacaatc SEQ ID NO:146
tgatcatgagcggagaattaagggagtcacgttatgacccccgccgatgacgcgggacaagccg
ttttacgtttggaactgacagaaccgcaacgttgaaggagccactcagccgcgggtttctggag
tttaatgagctaagcacatacgtcagaaaccattattgcgcgttcaaaagtcgcctaaggtcac
tatcagctagcaaatatttcttgtcaaaaatgctccactgacgttccataaattcccctcggta
tccaattagagtctcatattcactctcaatccaaataatctgcaccggatctggatcgtttcgc
atgattgaacaagatggattgcacgcaggttctccggccgcttgggtggagaggctattcggct
atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc -continued tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaccagt gtcccagctcgtgtgcaataaccgccacaatttcattctcattctggcactgctgaatcaatgt gtcataaagaacaatccttttgttcttgaagaaaccatacatgtaagcattactatggcttgac cttgtagatccatcgacaacaaacagcttcttcagaggaaactttagagaagaagcaagtttct caatcttctcccggaggtctccatcaggaagaggagtgaacttgttgaaaagaggtgcaatcaa aacagggtatatagtcatcatcactagagacaggataaacatgaatgcccacagatagatggcg aggtaaggacctcctttctgaactataacaataattgcggcaacgataggaggggcaggtatga cagagaggagtattcctttgatcatgtccctaatgaacatccatattgtttgtttgttgaaccc atgccgagactcgatcacgaaagttgagtacaaagaaaatggcaaatcagtgatctgtgaccat gtcataagaccagccaagaatgaaagagtgtgcaggatttcattctctggatcgagtcccacca ttggtagaaggatccccATCTACCCGCTTCGCGTCGGCATCCGGTCAGTGGCAGTGAAGGGCGA

ACAGTTCCTGATTAACCACAAACCGTTCTACTTTACTGGCTTTGGTCGTCATGAAGATGCGGAC

TTGCGTGGCAAAGGATTCGATAACGTGCTGATGGTGCACGACCACGCATTAATGGACTGGATTG

GGGCCAACTCCTACCGTACCTCGCATTACCCTTACGCTGAAGAGATGCTCGACTGGGCAGATGA

ACATGGCATCGTGGTGATTGATGAAACTGCTGCTGTCGGCTTTTCGCTCTCTTTAGGCATTGGT

TTCGAAGCGGGCAACAAGCCGAAAGAACTGTACAGCGAAGAGGCAGTCAACGGGGAAACTCAGC

AAGCGCACTTACAGGCGATTAAAGAGCTGATAGCGCGTGACAAAAACCACCCAAGCGTGGTGAT

GTGGAGTATTGCCAACGAACCGGATACCCGTCCGCAAGGTGCACGGGAATATTTCGCGCCACTG

GCGGAAGCAACGCGTAAACTCGACCCGACGCGTCCGATCACCTGCGTCAATGTAATGTTCTGCG

ACGCTCACACCGATACCATCAGCGATCTCTTTGATGTGCTGTGCCTGAACCGTTATTACGGATG

GTATGTCCAAAGCGGCGATTTGGAAACGGCAGAGAAGGTACTGGAAAAAGAACTTCTGGCCTGG

CAGGAGAAACTGTACACCGACATGTGGAGTGAAGAGTATCAGTGTGCATGGCTGGATATGTATC

ACCGCGTCTTTGATCGCGTCAGCGCCGTCGTCGGTGAACAGGTATGGAATTTCGCCGATTTTGC

GACCTCGCAAGGCATATTGCGCGTTGGCGGTAACAAGAAAGGGATCTTCACTCGCGACCGCAAA

CCGAAGTCGGCGGCTTTTCTGCTGCAAAAACGCTGGACTGGCATGAACTTCGGTGAAAAACCGC

AGCAGGGAGGCAAACAATGAATCAACAACTCTCCTGGCGCACCATCGTCGGCTACAGCCTCGGG

AATTGCTACCGAGCTCttctaccaatggtgggactcgatccagagaatgaaatcctgcacactc

-continued tttcattcttggctggtcttatgacatggtcacagatcactgatttgccattttctttgtactc aactttcgtgatcgagtctcggcatgggttcaacaaacaaacaatatggatgttcattagggac atgatcaaaggaatactcctctctgtcatacctgcccctcctatcgttgccgcaattattgtta tagttcagaaaggaggtccttacctcgccatctatctgtgggcattcatgtttatcctgtctct agtgatgatgactatataccctgttttgattgcacctcttttcaacaagttcactcctcttcct gatggagacctccgggagaagattgagaaacttgcttcttctctaaagtttcctctgaagaagc tgtttgttgtcgatggatctacaaggtcaagccatagtaatgcttacatgtatggtttcttcaa gaacaaaaggattgttctttatgacacattgattcagcagtgccagaatgagaatgaaattgtg gcggttattgcacacgagctgggacactgggagctcgaatttccccgatcgttcaaacatttgg caataaagtttcttaagattgaatcctgttgccggtcttgcgatgattatcatataatttctgt tgaattacgttaagcatgtaataattaacatgtaatgcatgacgttatttatgagatgggtttt tatgattagagtcccgcaattatacatttaatacgcgatagaaaacaaaatatagcgcgcaaac taggataaattatcgcgcgcggtgtcatctatgttactagatcgggaattcactggccgtcgtt ttacaacgtcgtgactgggaaaaccctggcgttacccaacttaatcgccttgcagcacatcccc ctttcgccagctggcgtaatagcgaagaggcccgcaccgatcgcccttcccaacagttgcgcag cctgaatggcgcccgctcctttcgctttcttcccttcctttctcgccacgttcgccggctttcc ccgtcaagctctaaatcgggggctccctttagggttccgatttagtgctttacggcacctcgac cccaaaaaacttgatttgggtgatggttcacgtagtgggccatcgccctgatagacggtttttc gccctttgacgttggagtccacgttctttaatagtggactcttgttccaaactggaacaacact caaccctatctcgggctattcttttgatttataagggattttgccgatttcggaaccaccatca aacaggattttcgcctgctggggcaaaccagcgtggaccgcttgctgcaactctctcagggcca ggcggtgaagggcaatcagctgttgcccgtctcactggtgaaaagaaaaaccaccccagtacat taaaaacgtccgcaatgtgttattaagttgtctaagcgtcaattt*gtttacaccacaatatatc*

*ctgcca*

SEQ ID NO:146 is the nucleic acid sequence of pRD29A-HP-BnCPP. Italicized sequences are the right and left border repeats. Underlined sequence is the RD29A promoter. Sequence in bold is the BnCPP antisense sequence, bold and underlined sequence is BnCPP sense fragment and the upper case sequence represents the truncated GUS fragment.

*gtttacccgcc*aatatatcctgtcaaacactgatagtttaaactgaaggcgggaaacgacaatc SEQ ID NO:147 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg -continued aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcat taatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt -continued aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc cttaatctgtcttcttgtcttctccatcaatggctcgaagcctctctacaagaggagggtgtga gtagtgataagctgagtacaatgggtctgtgttcatcgctgataagttctcttcctgtagcttc actagggcaggacgtagatcctttgcataaccaagattcactgcaaaagcatcagcctgaaact caaacgctcgactaacaaggttgaggtcaaagcttactaggtgttgaagtggtattacagtgtg ctgaaatatgatcaaaccaatgagaactggttgtgtatcaaaaccaaaactcctgaagagatca gtggagtttctgacaagagtgtatcctccaaattgcaagaaggcaaggatttgaacagcaatga acgagtatgtagtgtgattcagcttccagtgtcccagctcgtgtgcaataaccgccacaatttc attctcattctggcactgctgaatcaatgtgtcataaagaacaatccttttgttcttgaagaaa ccatacatgtaagcattactatggcttgaccttgtagatccatcgacaacaaacagcttcttca gaggaaactttagagaagaagcaagtttctcaatcttctcccggaggtctccatcaggaagagg agtgaacttgttgaaaagaggtgcaatcaaaacagggtatatagtcatcatcactagagacagg ataaacatgaatgcccacagatagatggcgaggtaaggacctcctttctgaactataacaataa ttgcggcaacgataggaggggcaggtatgacagagaggagtattcctttgatcatgtccctaat gaacatccatattgtttgtttgttgaacccatgccgagactcgatcacgaaagttgagtacaaa gaaaatggcaaatcagtgatctgtgaccatgtcataagaccagccaagaatgaaagagtgtgca ggatttcattctctggatcgagtcccaccattggtagaaagccgccagatatcttccaaaacca aggcaagatcccaaagaacagaatcgcagagtccataagtatagtaacaaactcatgaacaaag tgaaaatggcttttgtcaagactgtaagctcgagatttctcaaacttctcttggctaatgactc caaccaaagtctttgggagagtgggaagcttgagagcagtatgttgcctcagatccaaatacgt ctcaaaaacgtacatcac tatcataaaaccaacgacggtttccatgaaaggaatcgccatcccc tcgaatttccccgatcgttcaaacatttggcaataaagtttcttaagattgaatcctgttgccg gtcttgcgatgattatcatataatttctgttgaattacgttaagcatgtaataattaacatgta atgcatgacgttatttatgagatgggtttttatgattagagtcccgcaattatacatttaatac gcgatagaaaacaaaatatagcgcgcaaactaggataaattatcgcgcgcggtgtcatctatgt tactagatcgggaattcactggccgtcgttttacaacgtcgtgactgggaaaaccctggcgtta cccaacttaatcgccttgcagcacatccccctttcgccagctggcgtaatagcgaagaggcccg caccgatcgcccttcccaacagttgcgcagcctgaatggcgcccgctcctttcgctttcttccc ttcctttctcgccacgttcgccggctttccccgtcaagctctaaatcgggggctccctttaggg ttccgatttagtgctttacggcacctcgaccccaaaaaacttgatttgggtgatggttcacgta gtgggccatcgccctgatagacggtttttcgccctttgacgttggagtccacgttctttaatag tggactcttgttccaaactggaacaacactcaaccctatctcgggctattcttttgatttataa gggattttgccgatttcggaaccaccatcaaacaggattttcgcctgctggggcaaaccagcgt ggaccgcttgctgcaactctctcagggccaggcggtgaagggcaatcagctgttgcccgtctca ctggtgaaaagaaaaaccaccccagtacattaaaaacgtccgcaatgtgttattaagttgtcta agcgtcaattt*gtttacaccacaatatatcctgcca*

SEQ ID NO:147 is the nucleic acid sequence of pRD29A-antisense-BnCPP. Italicized sequences are the right and left border repeats. Underlined sequence is the RD29A promoter. Sequence in bold is the BnCPP antisense sequence.

*gtttacccgccaatatatcctgtca*aacactgatagtttaaactgaaggcgggaaacgacaatc SEQ ID NO:148 tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa -continued ttaatgtgagttagctcactcattaggcaccccaggctttacactttatgcttccggctcgtat gttgtgtggaattgtgagcggataacaatttcacacaggaaacagctatgaccatgattacgcc aagctgggaaatttttcgccagttctaaatatccggaaacctcttgggatgccattgcccatct atctgtaatttattgacgaaatagacgaaaaggaaggtggctcctataaagcacatcattgcga taacagaaaggccattgttgaagatacctctgctgacattggtccccaagtggaagcaccaccc catgaggagcaccgtggagtaagaagacgttcgagccacgtcgaaaaagcaagtgtgttgatgt agtatctccattgacgtaagggatgacgcacaatccaactatccatcgcaagaccattgctcta tataagaaagttaatatcatttcgagtggccacgctgaggggatccatggcgattcctttcat ggaaaccgtcgttggttttatgatagtgatgtacgtttttgagacgtatttggatctgaggcaa catactgctctcaagcttcccactctcccaaagactttggttggagtcattagccaagagaagt ttgagaaatctcgagcttacagtcttgacaaaagccattttcactttgttcatgagtttgttac tatacttatggactctgcgattctgttctttgggatcttgccttggttttggaagatatctggc ggctttctaccaatggtgggactcgatccagagaatgaaatcctgcacactctttcattcttgg ctggtcttatgacatggtcacagatcactgatttgccattttctttgtactcaactttcgtgat cgagtctcggcatgggttcaacaaacaaacaatatggatgttcattagggacatgatcaaagga atactcctctctgtcatacctgcccctcctatcgttgccgcaattattgttatagttcagaaag gaggtccttacctcgccatctatctgtgggcattcatgtttatcctgtctctagtgatgatgac tatataccctgttttgattgcacctcttttcaacaagttcactcctcttcctgatggagacctc cgggagaagattgagaaacttgcttcttctctaaagtttcctctgaagaagctgtttgttgtcg atggatctacaaggtcaagccatagtaatgcttacatgtatggtttcttcaagaacaaaaggat tgttctttatgacacattgattcagcagtgccagaatgagaatgaaattgtggcggttattgca cacgagctgggacactggaagctgaatcacactacatactcgttcattgctgttcaaatccttg ccttcttgcaatttggaggatacactcttgtcagaaactccactgatctcttcaggagttttgg ttttgatacacaaccagttctcattggtttgatcatatttcagcacactgtaataccacttcaa cacctagtaagctttgacctcaaccttgttagtcgagcgtttgagtttcaggctgatgcttttg cagtgaatcttggttatgcaaaggatctacgtcctgccctagtgaagctacaggaagagaactt atcagcgatgaacacagacccattgtactcagcttatcactactcacaccctcctcttgtagag aggcttcgagccattgatggagaagacaagaagacagattaacccctcgaatttccccgatcgt tcaaacatttggcaataaagtttcttaagattgaatcctgttgccggtcttgcgatgattatca tataatttctgttgaattacgttaagcatgtaataattaacatgtaatgcatgacgttatttat gagatgggtttttatgattagagtcccgcaattatacatttaatacgcgatagaaaacaaaata tagcgcgcaaactaggataaattatcgcgcgcggtgtcatctatgttactagatcgggaattca ctggccgtcgttttacaacgtcgtgactgggaaaaccctggcgttacccaacttaatcgccttg cagcacatccccctttcgccagctggcgtaatagcgaagaggcccgcaccgatcgcccttccca acagttgcgcagcctgaatggcgcccgctcctttcgctttcttcccttcctttctcgccacgtt cgccggctttccccgtcaagctctaaatcgggggctccctttagggttccgatttagtgcttta cggcacctcgaccccaaaaaacttgatttgggtgatggttcacgtagtgggccatcgccctgat agacggtttttcgccctttgacgttggagtccacgttctttaatagtggactcttgttccaaac tggaacaacactcaaccctatctcgggctattcttttgatttataagggattttgccgatttcg gaaccaccatcaaacaggattttcgcctgctggggcaaaccagcgtggaccgcttgctgcaact -continued

```
ctctcagggccaggcggtgaagggcaatcagctgttgcccgtctcactggtgaaaagaaaaacc

accccagtacattaaaaacgtccgcaatgtgttattaagttgtctaagcgtcaatttgtttaca

ccacaatatatcctgcca
```

SEQ ID NO:148 is the nucleic acid sequence of MuA-BnCPP. Italicized sequences are the right and left border repeats. Underlined sequence is the MuA promoter. Sequence in bold is the BnCPP sense sequence.

Example 33

Genomic Southern blot analysis of transgenic *Arabidopsis* was performed using standard techniques known to one skilled in the art. Typically, 10 μg of DNA was electrophoresed in a 0.8% agarose gel and transferred to an appropriate membrane such as Hybond N+ (Amersham Pharmacia Biotech). Pre-hybridization and hybridization conditions were as suggested by the membrane manufacturer, typically at 65° C. The final stringency wash was typically at 1×SSC and 0.1% SDS at 65° C. The NPTII coding region was typically used as the radio-labeled probe in Southern blot analysis.

Example 34

PCR Analysis of Transgenic Plants

PCR was used as a method to confirm the presence of the transgene in all transgenic lines and every construct.. Typical PCR mixtures contained: 1× reaction buffer (10 mM Tris-HCl pH 8.8, 1.5 mM $MgCl_2$,50 mM KCl), dNTP's at 200 μM, 1 pM forward and reverse primer, 2.5U. Taq DNA polymerase, and template plus water to a final volume of 50 μL. Reactions were run at 1 minute 94° C., 1 minute 60° C., 1 minute 72° C., for 30 cycles. Primers used in the analysis pBI121-AtCPP and pBI121-HP-AtCPP transgenic plants were as shown in Table 20. Primers used in the analysis of pRD29A-AtCPP were RD29AP1 (SEQ ID NO:161) and SEQ ID NO:102. Primers used in the analysis of pRD29A-HP-AtCPP transgenic plants were those identified as RD29AP1 (SEQ ID NO:161), SEQ ID NO:103 and SEQ ID NO:103, Nosterm-RV (SEQ ID NO:162).

TABLE 20

| | | |
|---|---|---|
| pBI1211-AtcPP BamFW: | 5'-GCCGACAGTGGTCCCAAAGATGG-3' | (SEQ ID NO:105) |
| p35S-AtcPP SmaRV: | 5'-AAACCCGGGTTAATCTGTCTTCTTGTCTTCTCCA-3' | (SEQ ID NO:102) |
| p35S-HP-AtcPP BamFW: | 5'-CTGGAGCTCTTTTACCGAGGTTGGGCCTTGATCC-3' | (SEQ ID NO:103) |
| p35S-HP-AtcPP SmaRV: | 5'-GCAAGACCGGCAACAGGA-3' | (SEQ ID NO:108) |
| pRD29AP1: | 5'-TTTAAGCTTGGAGCCATAGATGCAATTCAA-3' | (SEQ ID NO:161) |
| pRD29AP1: | 5'-TTTAAGCTTGGAGCCATAGATGCAATTCAA-3' | (SEQ ID NO:161) |
| Nosterm-RV: | 5'-GCAAGACCGGCAACAGGA-3' | (SEQ ID NO:162) |

Figure 27:
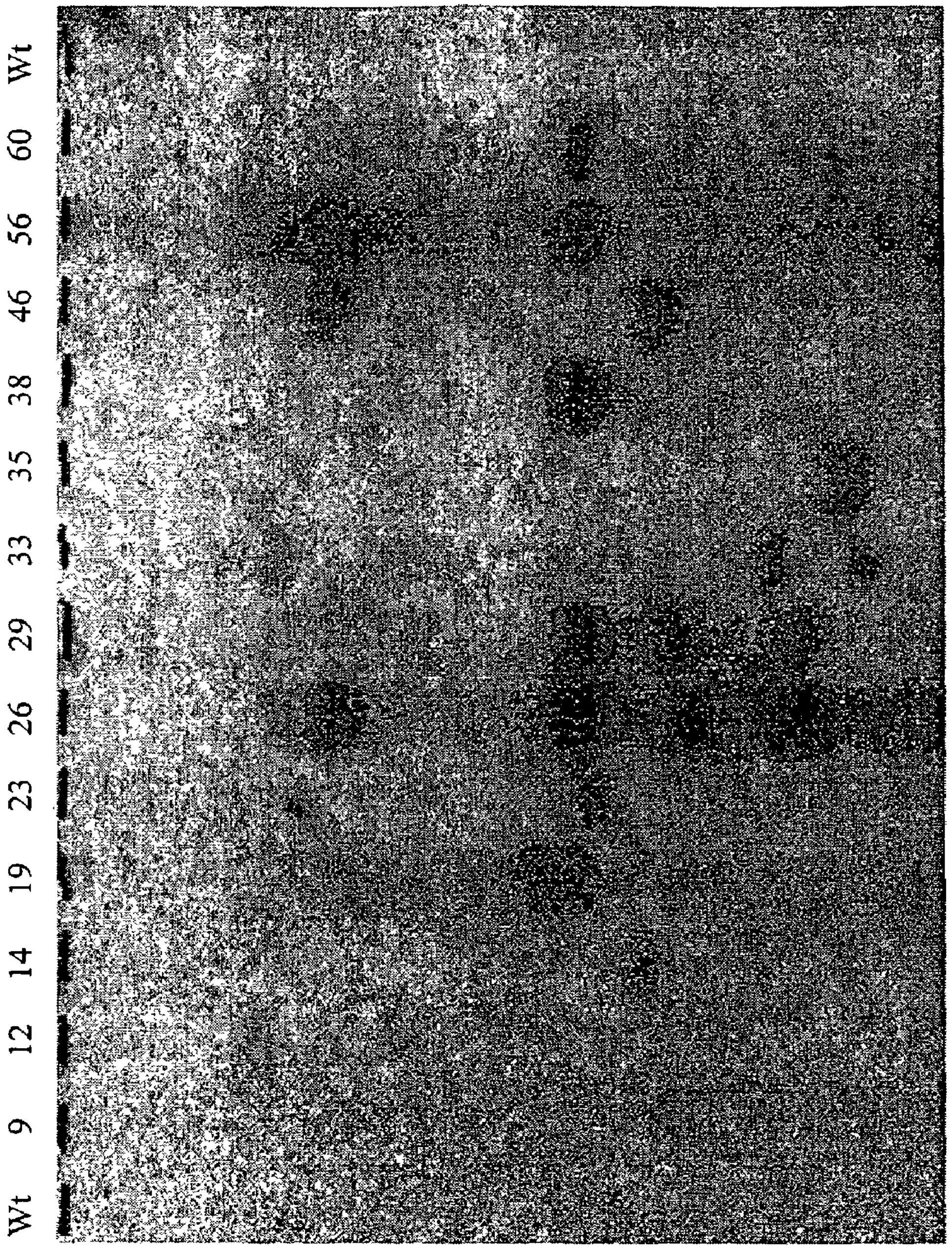
FIG. 27. is a scan of a typical Southern blot of transgenic *Arabidopsis* T1 lines carrying the pBI121-AtCPP construct.

Thirty-seven *Arabidopsis* lines were selected as homozygous pBI121-AtCPP over-expression lines for further examination. FIG. 27 shows a representative blot confirming the presence of the pBI121-AtCPP transgene. Lines were confirmed to be transgenic by PCR analysis using transgene specific primers in the PCR assays.

Figure 28:
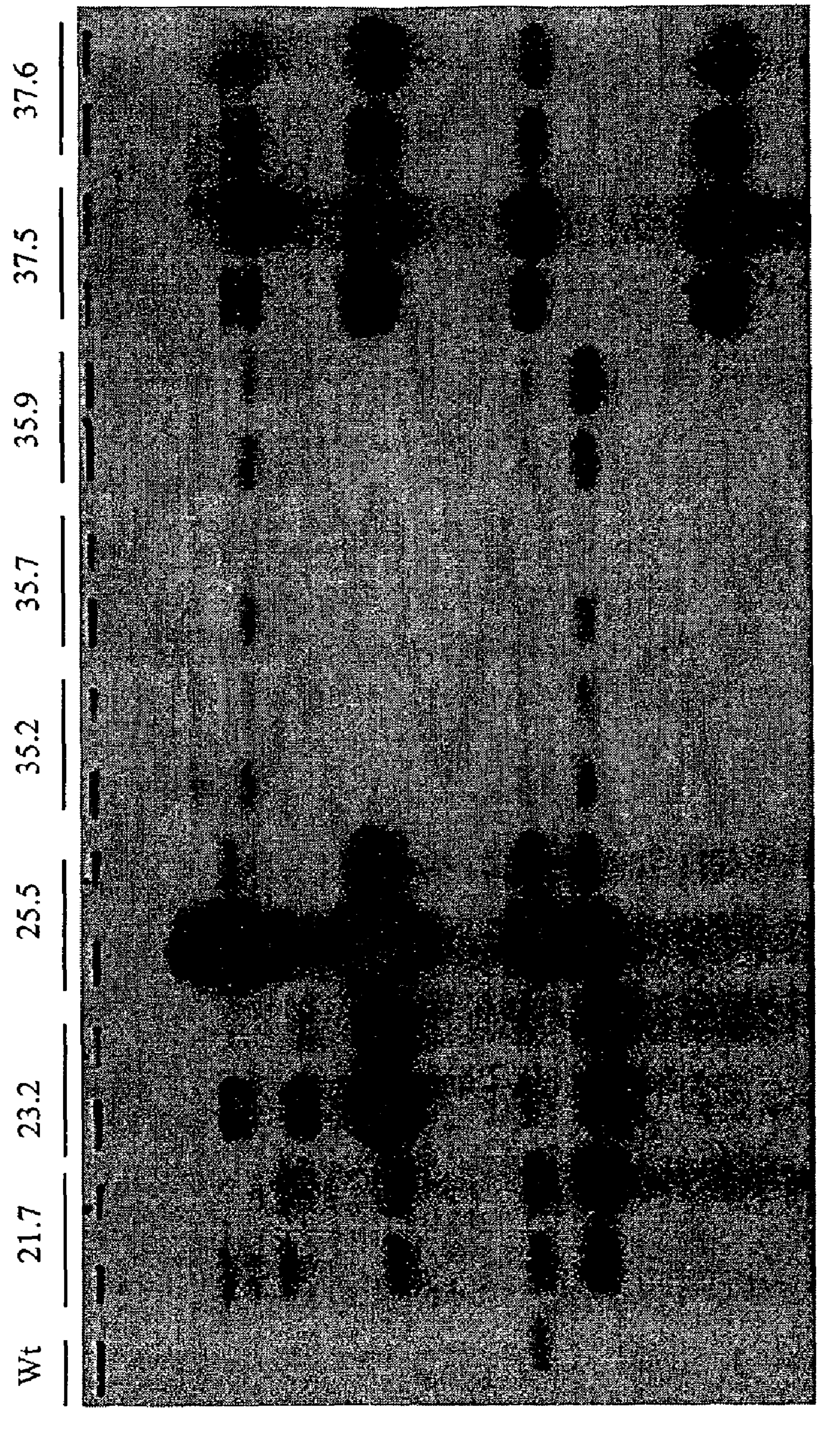
FIG. 28. is a scan of a typical Southern blot of transgenic *Arabidopsis* T3 lines carrying the pBI121-HP-AtCPP construct.

Thirty-three *Arabidopsis* lines were selected as homozygous pBI121-HP-AtCPP hair-pin down-regulation lines for further examination. FIG. 28 shows a representative blot confirming the presence of the pBI121-HP-AtCPP hair-pin construct. All lines were confirmed to be transgenic by PCR analysis using transgene specific primers in the PCR assays.

Figure 29:
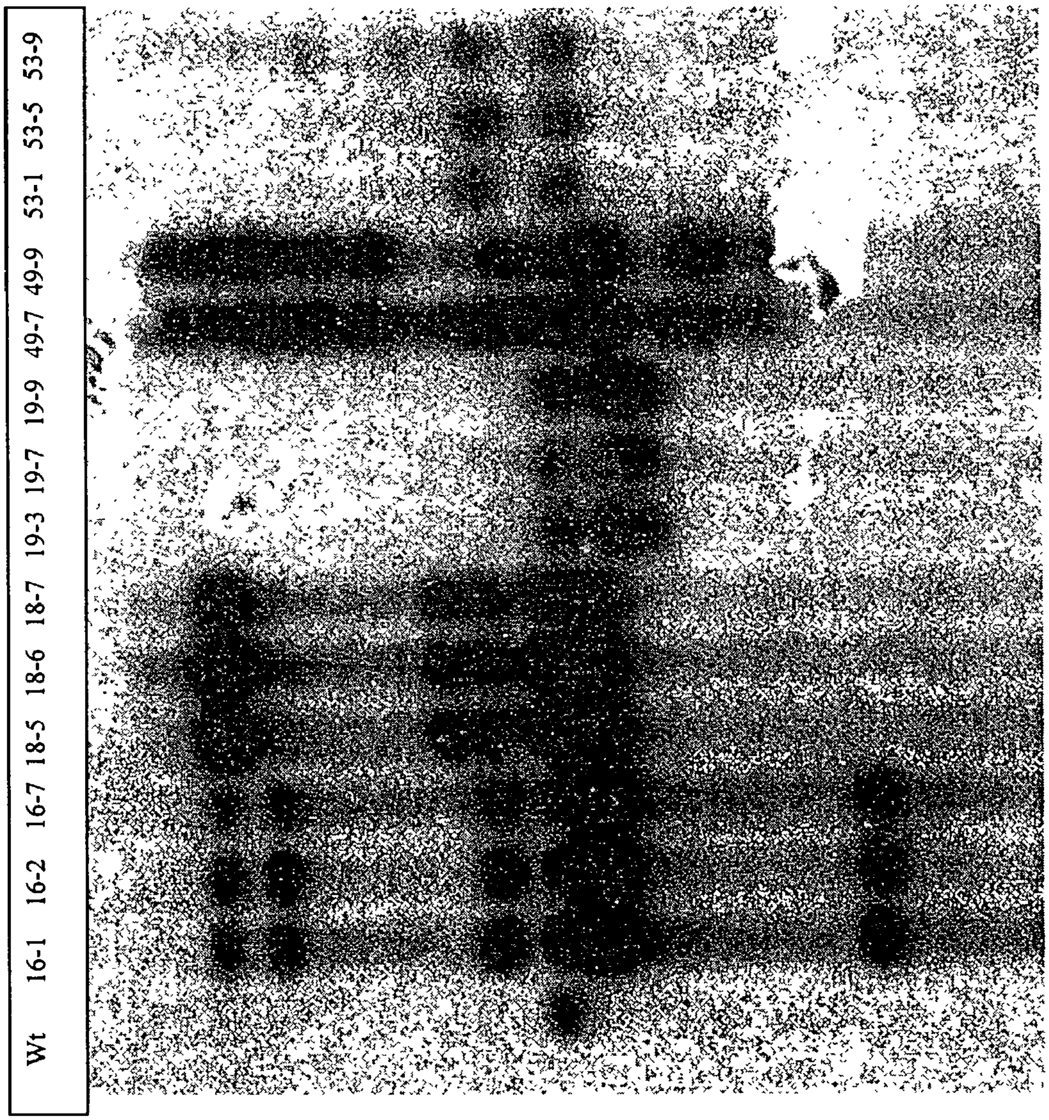
FIG. 29. is a scan of a typical Southern blot of transgenic *Arabidopsis* lines carrying the pRD29A-AtCPP construct.

*Arabidopsis* lines were selected as homozygous pRD29A-AtCPP over-expression lines for firther examination. FIG. 29 shows a representative blot confirming the presence of the pRD29A-AtCPP transgene. Lines were confirmed to be transgenic by PCR analysis using transgene specific primers in the PCR assays.

Figure 30:
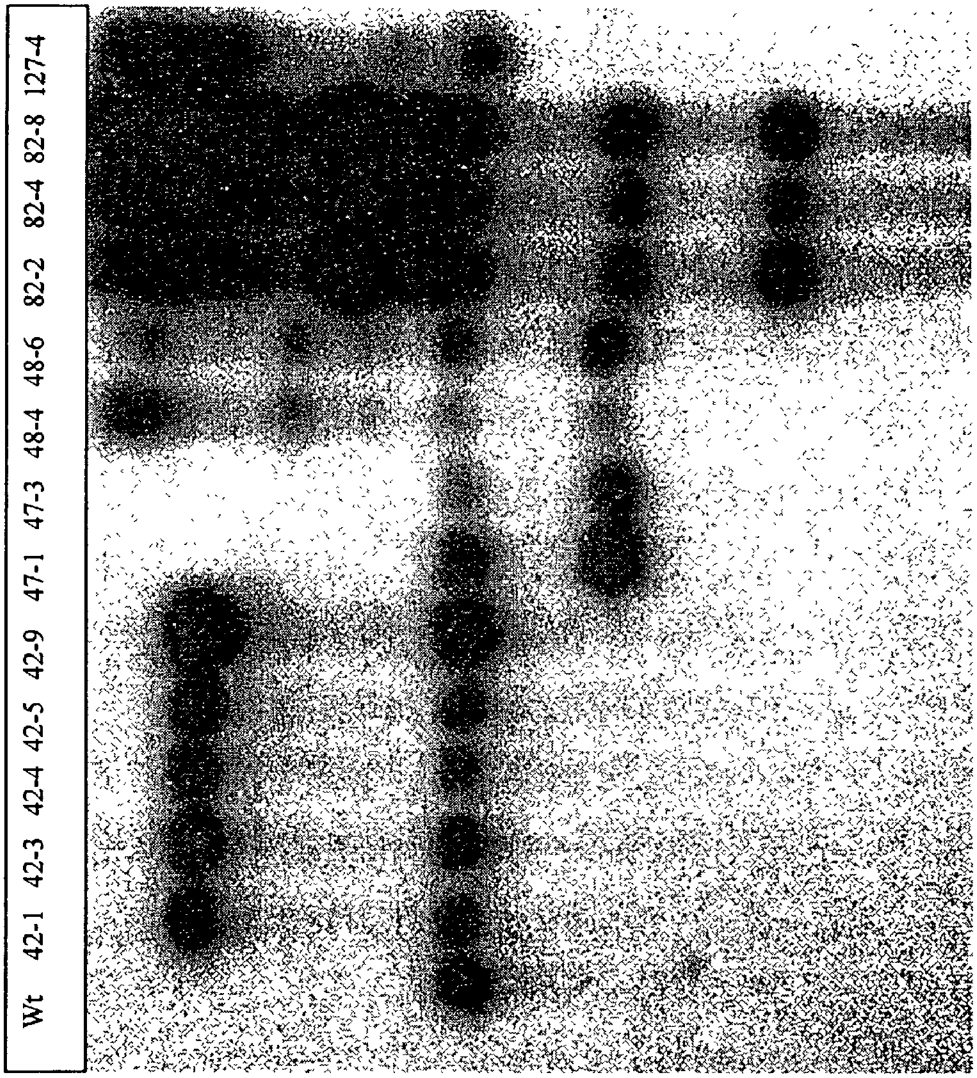
FIG. 30. is a scan of a typical Southern blot of transgenic *Arabidopsis* lines carrying the pRD29A-HP-AtCPP construct.

*Arabidopsis* lines were selected as homozygous pRD29A-HP-AtCPP lines for further examination. FIG. 30 shows a representative blot confirming the presence of the pRD29A-HP-AtCPP transgene. Lines were confirmed to be transgenic by PCR analysis using transgene specific primers in the PCR assays.

Example 35

Northern Analysis of Transgenic Plants

Figure 31:
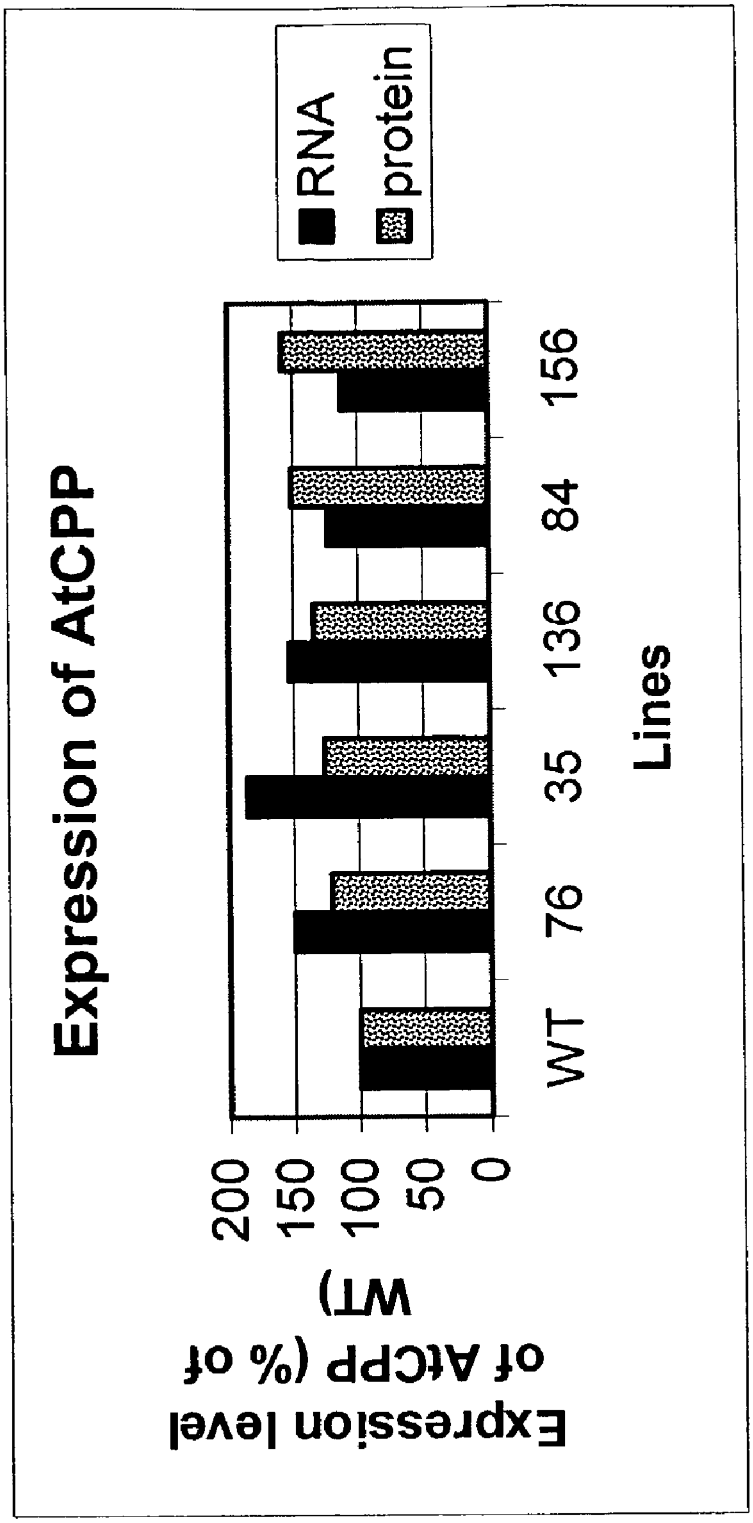
FIG. 31 is an illustration showing the relative expression of AtCPP mRNA transcript (solid bars) and AtCPP protein levels (stippled bars) in several pBI 121-AtCPP transgenic lines.

Total RNA was isolated from developing leaf tissue of 27 35S-AtCPP *Arabidopsis* lines (T3 plants). Approximately 10 μg of total RNA was loaded into each lane. The Northern blot was first probed with $P^{32}$ labeled, single-stranded antisense transcript of AtCPP which detects sense transcript, then stripped and re-probed with cDNA of β-tubulin that was used as a reference. The hybridizing bands of AtCPP and β-tubulin were scanned and quantified using the UN-Scan-It programme (Silk Scientific, Utah, USA), and the ratio of the two hybridizing bands for each sample was obtained. The ratio of the wild type plants was set to 100%, and was compared with those of the transgenic lines. Twenty-one out of twenty-seven lines showed higher expression of AtCPP transcript as compared to the wild type. Values ranged from 104% to 282% of wild type. The results of five lines (35, 84, 76, 136, and 156) of the 21 over-expressing lines is shown in FIG. 31.

Example 36

Production of Polyclonal Antibodies Against AtCPP

Anti-AtCPP antibodies were generated using AtCPP fusion protein over-expressed in *E. coli*. The over-expression vector, pMAL-p2, contains 1175 bp malE gene that is located upstream of AtCPP and encodes a 43 KDa maltose-binding protein (MBP). The 1275 bp BamHI/SmaI DNA fragment of AtCPP was inserted into pMAL-p2 at BamHI and SalI sites. The SalI site was converted into blunt end using Klenow fragment. The resulting fusion protein MBP-AtCPP was then over-expressed in DH5α, and purified by one-step affinity for MBP as described by the manufacturer (New England Biolab). The soluble fraction of the crude bacterial extract containing the MBP-AtCPP fusion protein was loaded to a amylose column (1.5 cm×10.0 cm), and the proteins were eluted with 10 mM maltose in column buffer (50 mM Tris-HCl, pH 7.5, 1 mM EDTA, and 200 mM NaCl). Fractions containing purified MBP-AtCPP fusion protein were pooled, and concentrated with a Centriprep-30 concentrator (Amicon). All purification steps were carried out at 4° C. To generate an antibody, the purified fusion protein was further separated by SDS-PAGE and the Coomassie stained band corresponding to the fusion protein was excised. The identity of the fusion protein was confirmed by Western analysis using anti-MBP antibodies (purchased from New England Biolab). The protein was eluted from the gel slice by electroelution and then emulsified in Ribi adjuvant (Ribi Immunochem) to a final volume of 1 ml. MBP-AtCPP protein was injected into a 3 kg New Zealand rabbit on day 1 and booster injections were given on day 21 and day 35 with 175 μg of the protein each time. High-titer antisera were obtained one week after the final injection.

Example 37

Western Blot Analysis of 35S-AtCPP Transgenic Lines using Anti-AtCPP Antibodies

Western analysis was performed to examine expression level of AtCPP in the transgenic lines compared with that of wild type plants. Anti-Bip antibody, an ER lumenal protein (Stressgen, Victoria, BC, Canada ) was used as a reference. Total proteins were extracted from developing leaf tissue of five $ABA^S$ lines and a wild type control. The antigenic protein bands of AtCPP and Bip were scanned and quantified using the UN-Scan-It programme (Silk Scientific, Utah, USA) and the ratio of the two protein bands for each sample was obtained. The ratio of the wild type plants was set to 100%, and was compared with those of the transgenic lines. Data is presented in FIG. 31 indicating that the AtCPP protein level was increased in the transgenic lines compared to the wild type plants.

Example 38

ABA Sensitivity of Transgenic Seedlings

Approximately 100 seeds were assessed per line per 9 cm plate. Seeds were plated on minimal medium (½ MS) supplemented with no ABA or 1.0 μM ABA. Plates were chilled for 3 days at 4° C. in the dark, and incubated for up to 21 days at 22° C. with 24 hour continuous light. Plates were assessed for germination, cotyledon expansion, true leaf development and seedling vigor. Seedlings were assessed for ABA sensitivity over 21 days of growth at which time sensitive seedlings were arrested at the cotyledon stage, lacked true leaves, and showed inhibition of root growth. Wild type control *Columbia* plants had two to three pairs of true leaves and a well developed root system. Lines were categorized as ABA sensitive ($ABA^S$) if less than 1% of plants looked like control, moderately ABA sensitive ($ABA^{MS}$) if more than 1% but less than 50% of looked like control, or ABA insensitive ($ABA^{Wt}$) if greater than 50% looked like control.

For example, if a plate had 20 healthy seedlings and the control plate had 60 healthy seedlings, the line would be 33% of control and categorized as moderately ABA sensitive.

Figure 32:
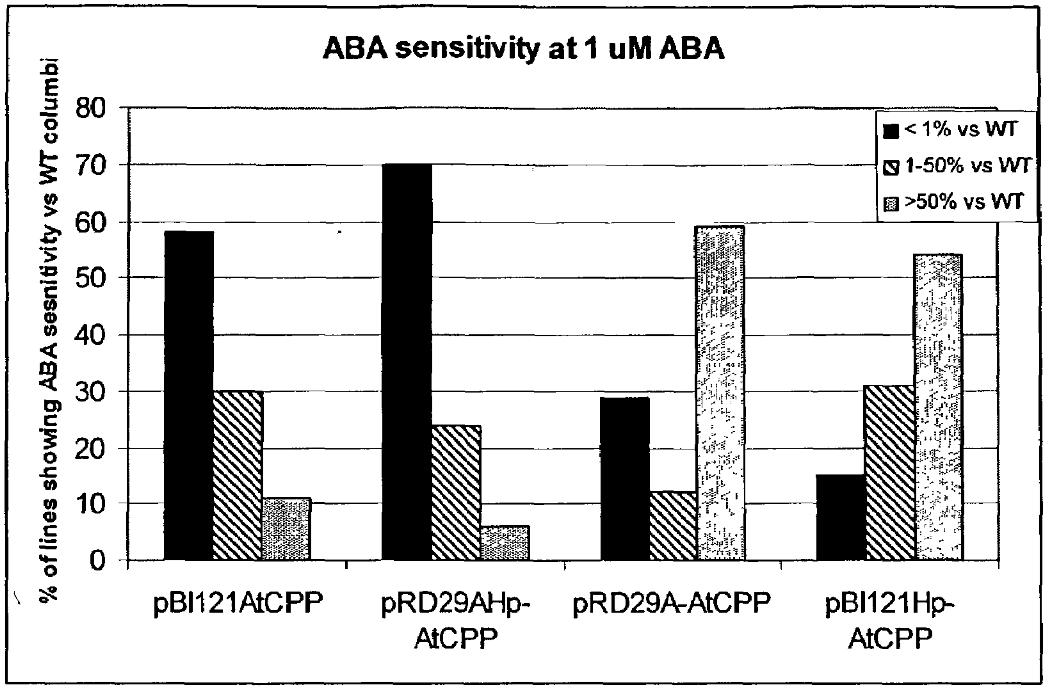
FIG. 32. is a histogram showing the percentage of lines which were categorized as ABA sensitive, moderately ABA sensitive or ABA insensitive. Seedlings were assessed on agar plates containing 1 μM ABA and scored at 21 days growth. Thirty-six lines of the pBI 121-AtCPP over-expression construct were assessed at 21 days by leaf and seedling development. Thirty-two lines of the 35S-HP-AtCPP down-regulation construct were assessed at 21 days for leaf and seedling development. Each line was assessed by plating approximately 100 seeds per plate and the seedlings scored and recorded as the percent insensitive seedlings per plate. Each line was then expressed as a percent of wild type (Wt). Lines were categorized as sensitive (less than 1% of Wt) solid bars, intermediate (1-50% of Wt) diagonally lined or insensitive (greater than 50% of Wt) stippled, based on their relationship to Wt and the percentage of each category plotted as a histogram.
Figure 33:
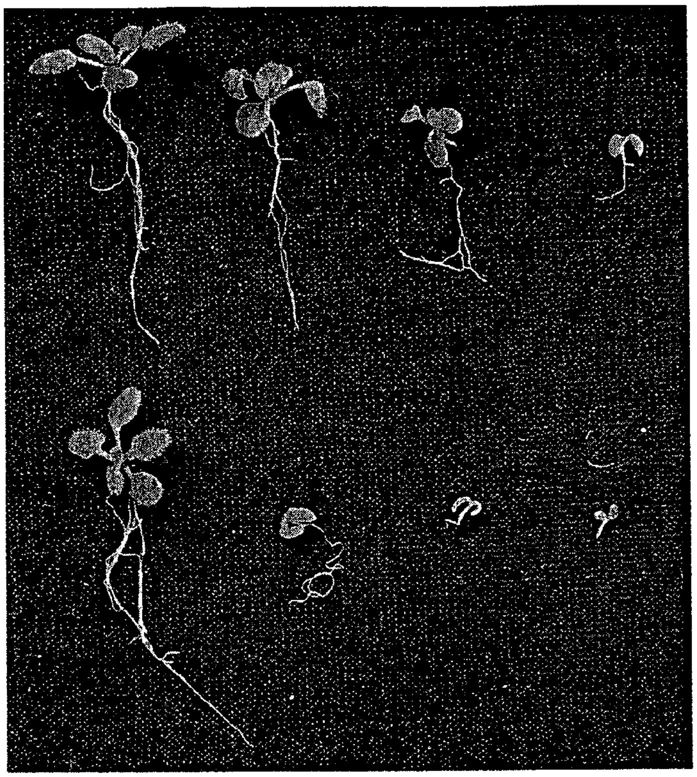
FIG. 33. is an illustration showing the response of wild type and a pRD29A-HP-AtCPP transgenic line to various concentrations of ABA in two week old seedlings.

All four vector constructs (pBI121-AtCPP, pBI121Hp-AtCPP, pRD29AHp-AtCPP, pRD29A-ATCPP) have resulted in transgenic lines of *Arabidopsis* which have increased sensitivity to ABA which is indicative of stress tolerance. The data for all 4 constructs is shown in FIG. 32. Of the lines transformed with the pBI121-AtCPP construct to over-express the AtCPP gene, 58% (21 out of 36) were classified as sensitive and an added 30% (11 out of 36) were classified as moderately sensitive. These lines were tested again in T4 and T5 generations and their ABA sensitivity was still present indicating that ABA sensitivity is an inheritable trait. Of the lines transformed with the pBI121-HP-AtCPP construct to down-regulate the AtCPP gene by double stranded RNA-inhibition, 15% (7 out of 45) were classified as sensitive and 31% (14 out of 45) were classified as moderately sensitive. To illustrate the increased sensitivity of transgenic lines to ABA, FIG. 33 shows the results of germination and seedling development over a range of ABA concentrations. Wild type and pRD29A-HP-AtCPP are compared. Of the lines transformed with pRD29AHp-AtCPP 70% (12 out of 17) showed high sensitivity and 24% (4 out of 17) showed moderate sensitivity to ABA. Of the lines transformed with pRD29A-AtCPP 29% (5 out of 17) showed high sensitivity and 12% (2 out of 17) moderate sensitivity to ABA. Clearly all 4 transgene constructs are altering ABA sensitivity and ABA signal transduction.

Example 39

Drought Experiments

*Arabidopsis* plants were grown five plants per 4" or 3 " pot, in a replicated water-stress experiment. All pots were filled with equal amounts of homogeneous premixed and wetted soil. Plants were grown under 16 hour daylight (150-200 $\mu mol/m^2/s$) at 22° C. and 70% relative humidity. On the day that the first flower opened drought treatment was initiated. First soil water content in each pot was equalized on a weight basis and any further watering of plants was stopped. Daily measurements of soil water content were taken by recording total pot weight. At the end of the drought treatment (6 to 9 days for experiments in 4" pots and 4-5 days for experiments in 3" pots) plants were harvested and shoot dry weights determined. Differences in plant growth were factored into the analysis by expressing water loss on a per gram shoot dry weight basis.

Figure 34:
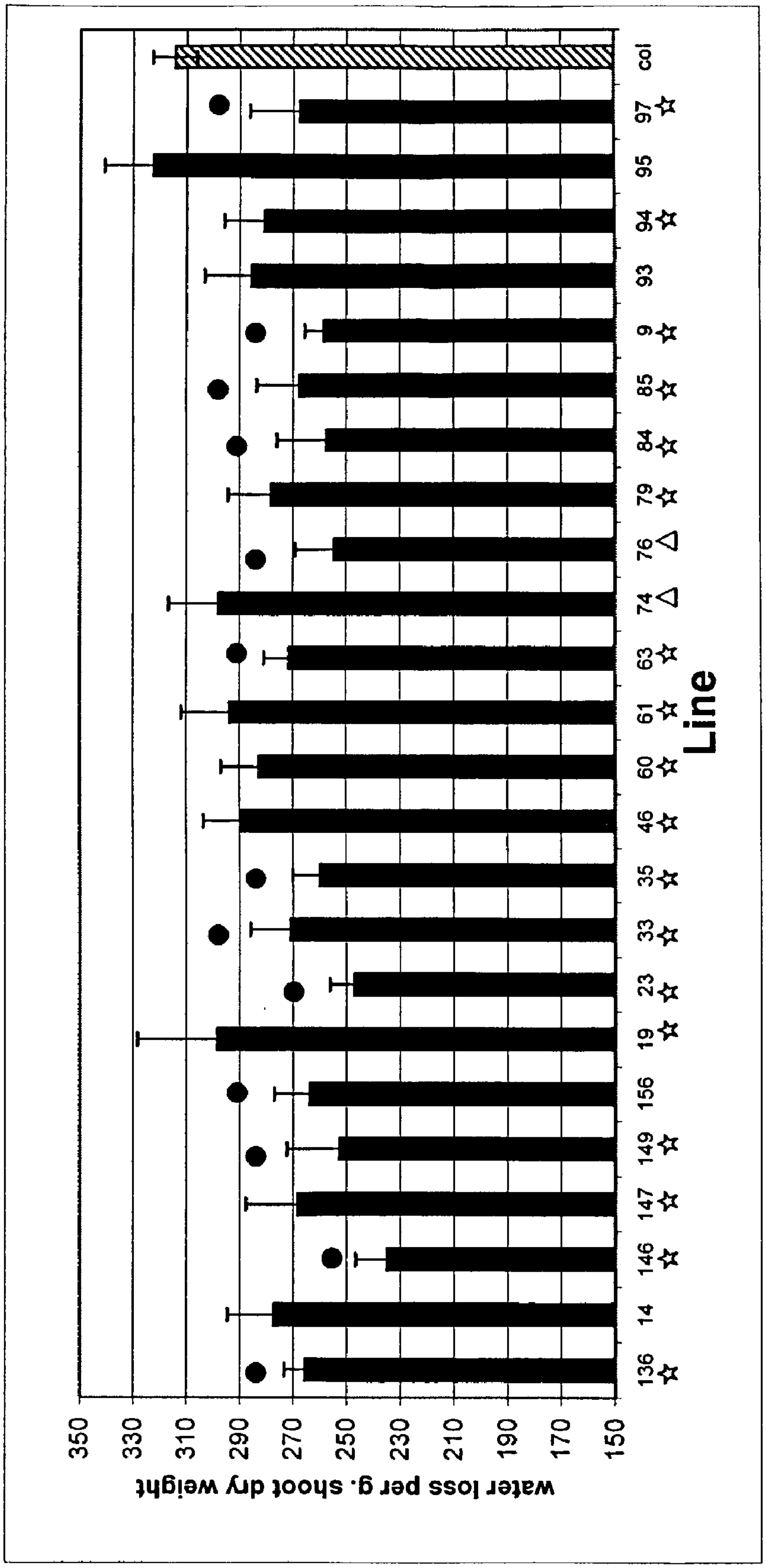
FIG. 34. is a histogram showing the analysis of transgenic plants containing the pBI121-AtCPP over-expression construct, (SEQ ID NO:4). Water loss per gram shoot dry weight after four days of water stress treatment. Lines that are marked with a star are those which were strongly ABA sensitive. Lines marked with a triangle are moderately ABA sensitive. Bars represent means of eight replicates. Lines marked with a filled dot above the bar represents lines which were significantly different from control at a p=0.05 value.

39a) pBI121-AtCPP, Drought Stress Screen:

Analysis of pBI121-AtCPP transgenic lines during water-stress treatment experiments of up to an eight day period, shows a strong trend towards increased soil water content and reduced water loss per gram of shoot biomass. After three days of water-stress treatment most lines had increased soil water content relative to the wild type control with four out of twenty-four lines, 146, 149, 156 and 97, showing a statistically significant difference. The amount of water lost per gram of shoot biomass was lower for all lines except one (95), and thirteen of these lines were significantly different from the wild type *Columbia* control (FIG. 34). All of the lines showing a statistically significant lower water loss per gram shoot biomass also showed an increased ABA sensitivity. There is also a strong trend, for all but one line (95), which is $ABA^{Wt}$, towards greater shoot biomass at the end of the drought stress treatment. Seven of those lines 136, 146, 23, 46, 76, 84 and 9, were statistically significant from control at a p=0.05 value.

39b) pBI121-AtCPP, Water Loss Per Gram Shoot Biomass during Water Stress Treatment:

Lines 35, 76, 95 and a wild type control were grown and placed under a water-stress treatment as above. Plants were harvested at 2 days, 4 days and 6 days of drought treatment. The $ABA^S$ lines, 35 and 76, showed a statistically significant reduction in water-loss relative to shoot dry weight at all three time points (Table 21). Additionally, the two $ABA^S$ transgenic lines had increased shoot biomass, due to increased leaf biomass, and maintained higher soil water contents during drought treatment.

TABLE 21

Water loss (g) per Shoot dry weight (g) after 2, 4 and 6 days of drought-stress treatment. Values in bold indicate statistically significant differences from Columbia.

| | 2 days | | 4 days | | 6 days | |
|---|---|---|---|---|---|---|
| Line | Mean | Std. Error | Mean | Std. Error | Mean | Std. Error |
| 35 | **212.5** | 3.5 | **308.0** | 9.9 | **297.7** | 11.2 |
| 76 | **227.2** | 5.8 | **321.2** | 8.5 | **293.8** | 5.0 |
| 95 | 287.0 | 5.1 | **377.3** | 14.8 | 348.5 | 25.5 |
| Columbia Wild type | 265.3 | 11.8 | 408.2 | 7.7 | 345.9 | 6.7 |

39c) pbBI121-AtCPP, Drought Stress and Shoot Recovery:

Water-stress tolerance and determination of post drought-treatment recovery ability was assessed using 20 of the 24 pBI121-AtCPP transgenic lines. Drought treatment was imposed for 6 days after which the plants were watered and allowed to grow for 6 days. Recovered shoot fresh biomass was then determined. Soil water content of these plants was measured daily during the drought treatment and the results confirm previously seen trends. All ABA sensitive ($ABA^S$) lines that showed a statistically significantly reduction of water loss on a per gram dry weight basis in experiment 39a, continued to show a significant greater soil water content than control plants in this experiment (Table 22). Additionally, Table 22 shows that the recovered shoot fresh biomass after 6 days of drought treatment was significantly greater in all the ABAs lines than *Columbia*.

TABLE 22

Soil water content on day 3 of drought treatment and recovered shoot fresh weight after 6 days of drought treatment (values in bold were significantly different from Columbia at p = 0.05)

| | ABA status | soil water content day 3 | | recovered shoot biomass | |
|---|---|---|---|---|---|
| Line | ABA | Mean (% initial) | Std Error | Mean (g) | Std Error |
| 136 | $ABA^S$ | **46.6** | 1.9 | **4.5** | 0.16 |
| 14 | $ABA^S$ | **50.25** | 0.7 | **4.1** | 0.12 |
| 146 | $ABA^S$ | **45.9** | 2.5 | **4.0** | 0.11 |
| 147 | $ABA^S$ | 45.1 | 1.7 | **4.0** | 0.15 |
| 149 | $ABA^S$ | 45.3 | 1.8 | **3.8** | 0.17 |
| 156 | $ABA^S$ | **47.1** | 1.9 | **4.0** | 0.134 |
| 23 | $ABA^S$ | **49** | 1.4 | **4.0** | 0.17 |
| 33 | $ABA^S$ | **46.9** | 1.6 | **4.3** | 0.14 |
| 35 | $ABA^S$ | 41.7 | 1.7 | **4.0** | 0.11 |
| 46 | $ABA^S$ | 44.8 | 1.7 | **3.8** | 0.09 |
| 63 | $ABA^S$ | **46.3** | 1.4 | **4.0** | 0.19 |
| 76 | $ABA^S$ | **47.8** | 1.0 | **3.9** | 0.17 |
| 79 | $ABA^S$ | 45.4 | 1.1 | **4.1** | 0.09 |
| 84 | $ABA^S$ | **46.8** | 1.9 | **4.1** | 0.16 |
| 85 | $ABA^S$ | 45.3 | 1.9 | **4.0** | 0.12 |
| 9 | $ABA^S$ | 45.2 | 2.1 | **3.9** | 0.12 |
| 93 | $ABA^{wt}$ | 43.5 | 1.2 | 2.8 | 0.07 |
| 94 | $ABA^S$ | **46.9** | 1.5 | **3.9** | 0.13 |
| 97 | $ABA^S$ | **53** | 1.2 | **3.8** | 0.16 |
| 95 | $ABA^{Wt}$ | 41.9 | 1.2 | 2.7 | 0.06 |
| Columbia | $ABA^{Wt}$ | 41.3 | 1.0 | 2.7 | 0.04 |

39d) pBI121-AtCPP, Seed Yield After Drought Stress Treatment:

Seed yield after dought stress during flowering was examined using ten pBI121-AtCPP transgenic lines, eight of which were $ABA^S$. Plants were grown one per 4" pot and were exposed to 9 days of drought treatment as described above. A second group of plants was grown and maintained under well watered conditions as the optimal group. After 9 days of drought treatment plants were re-watered and allowed to continue growth and seed set to maturity. After drought-treatment conditions all eight ABAs lines had increased yields relative to controls, which ranged from 109% to 126% of the *Columbia* (Table 23). Drought-treatment resulted in a reduction of yield in all lines, including controls, relative to plants grown under optimal conditions. Expression of the seed yields obtained from drought-treated group relative to the same line under optimal conditions shows that the transgenics preserve a larger percentage of optimal seed yield than do wild type lines.

TABLE 23

Seed Yield following 9 days drought-treatment

| | ABA status | Seed Yield (g per plant) | | | |
|---|---|---|---|---|---|
| Line | ABA | Mean (g) | Std Error | % Columbia | % Optimal |
| 156 | $ABA^S$ | 0.735 | 0.044 | 126.2 | 83.7 |
| 63 | $ABA^S$ | 0.675 | 0.061 | 116.0 | 71.0 |
| 146 | $ABA^S$ | 0.666 | 0.053 | 114.4 | 72.9 |
| 94 | $ABA^S$ | 0.644 | 0.052 | 110.6 | 68.8 |
| 84 | $ABA^S$ | 0.642 | 0.049 | 110.4 | 61.8 |
| 76 | $ABA^S$ | 0.631 | 0.055 | 108.5 | 66.6 |
| 136 | $ABA^S$ | 0.630 | 0.051 | 108.3 | 74.1 |
| 35 | $ABA^S$ | 0.614 | 0.054 | 105.6 | 74.2 |
| 93 | $ABA^{Wt}$ | 0.567 | 0.041 | 97.5 | 60.0 |
| 95 | $ABA^{Wt}$ | 0.388 | 0.088 | 66.7 | 43.4 |
| Columbia | $ABA^{Wt}$ | 0.582 | 0.060 | 100 | 53.8 |

Figure 35:
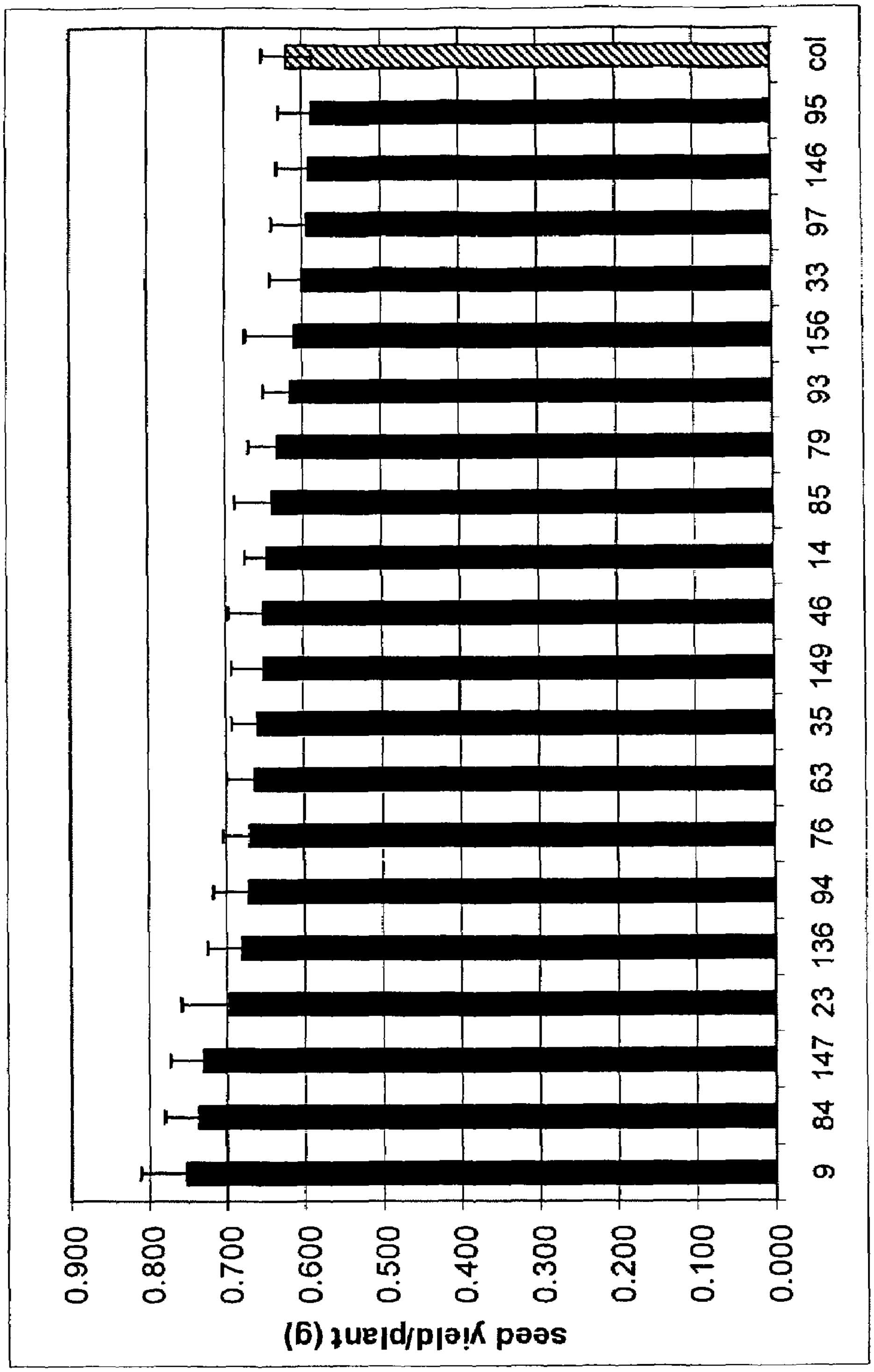
FIG. 35. is a histogram showing seed yield in grams of transgenic *Arabidopsis* lines of pBI121-AtCPP grown under optimal water conditions FIG. 36. is a bar chart showing growth and yield of transgenic *Arabidopsis* lines ofpBI121-AtCPP grown under optimal watering conditions plus a biotic stress condition. Yields as a % of wild type, rosette leaf number, rosette leaf fresh weight and shoot dry weight are plotted.

39e) pBI121-AtCPP, Seed Yield and Growth under Optimal Water Conditions:

The lines evaluated above and a number of additional lines were examined in a growth and yield experiment under optimal, well-watered conditions. Results indicated that the $ABA^S$ lines were shorter at the stage of first open flower, had more rosette leaves, however, by maturity there were no differences in plant height of transgenics and Columbia. Moreover, the $ABA^S$ transgenics showed similar or higher seed yields ranging from 95% to 121% of the wild type control (FIG. 35).

39g) pRD29A-HP-AtCPP Screen for Drought Tolerant Phenotype:

Analysis of 17 transgenic lines identified 7 candidate drought tolerant lines (12, 22, 23, 47, 82, 83, 90) on the basis of higher soil water content and lower water loss per g of shoot dry weight (Table24). All 7 drought tolerant candidate lines showed strong ABA sensitivity and lines that did not show drought tolerance did not show ABA sensitivity.

TABLE 24

Soil water content after 3 days of drought treatment and water lost per g shoot dry weight. Values in bold are statistically different from those of Columbia wild type (p = 0.05)

| Line | ABA status ABA | soil water content day 2 Mean (% initial) | Std Error | water lost in 2 days/g shoot DW Mean (g/g) | Std Error |
|---|---|---|---|---|---|
| 10 | $ABA^S$ | 33.4 | 1.6 | 199.1 | 4.5 |
| 11 | $ABA^S$ | 34.6 | 3.3 | **173.1** | 1.6 |
| 12 | $ABA^S$ | 36.2 | 2.0 | 179.5 | 5.0 |
| 126 | $ABA^{MS}$ | 32.5 | 2.6 | 199.1 | 4.1 |
| 127 | $ABA^{MS}$ | 33.5 | 2.0 | 195.6 | 10.6 |
| 14 | $ABA^S$ | 32.7 | 1.2 | 203 | 4.9 |
| 17 | $ABA^S$ | 29.9 | 1.8 | 200.7 | 7.3 |
| 22 | $ABA^S$ | **39.3** | 2.1 | **170.0** | 3.0 |
| 23 | $ABA^S$ | 35.7 | 1.4 | **174.9** | 2.6 |
| 42 | $ABA^{MS}$ | 28 | 0.7 | 185.4 | 5.8 |
| 47 | $ABA^S$ | 35.9 | 2.2 | 181.2 | 7.7 |
| 7 | $ABA^{Wt}$ | 35 | 1.3 | 201.8 | 5.1 |
| 82 | $ABA^S$ | 36.7 | 2.2 | 178.3 | 4.0 |
| 83 | $ABA^S$ | **40** | 1.4 | 180.7 | 6.9 |
| 9 | $ABA^S$ | 31.4 | 1.4 | 173.8 | 8.7 |
| 90 | $ABA^S$ | **38.2** | 1.3 | **177.6** | 6.2 |
| 93 | $ABA^{Wt}$ | 30.7 | 1.8 | 175.3 | 4.6 |
| Columbia | $ABA^{Wt}$ | 32.1 | 1.2 | 196.9 | 6.2 |

Example 40

Growth Analysis

The growth analysis of most promising constructs has been set up at 3 stages. Eight plants per line were grown in 3" pots with one plant per pot at 22C, 16 hr light,(150-200 $\mu mol/m^2/s$) and 70% RH. Plants were harvested at vegetative growth stage (2 week old seedlings), bolting growth stage (at first open flower) and mid-flowering growth stage (5 to 7 days from first open flower). Also, in some growth experiments additional group of plants was grown in 4" pots (one per pot and 10 plants per line) to maturity for seed yield determinations.

40a) pBI121-AtCPP growth under optimal and biotic stress conditions

The growth and productivity of pBI121-AtCPP transgenic Arabidopsis lines was examined at several stages of development under optimal growth conditions. Although optimal growth conditions were maintained, plants were assessed to be under a degree of stress that was later determined to be a result of the soil properties. Soil analysis found a fungal contaminant that was believed to be responsible for the biotic stress. This stress could be negated by sterilization of the soil prior to use. Eight $ABA^S$ lines, two with normal ABA sensitivity ($ABA^{Wt}$) and a wild type *Columbia* control were analyzed.

Figure 36:
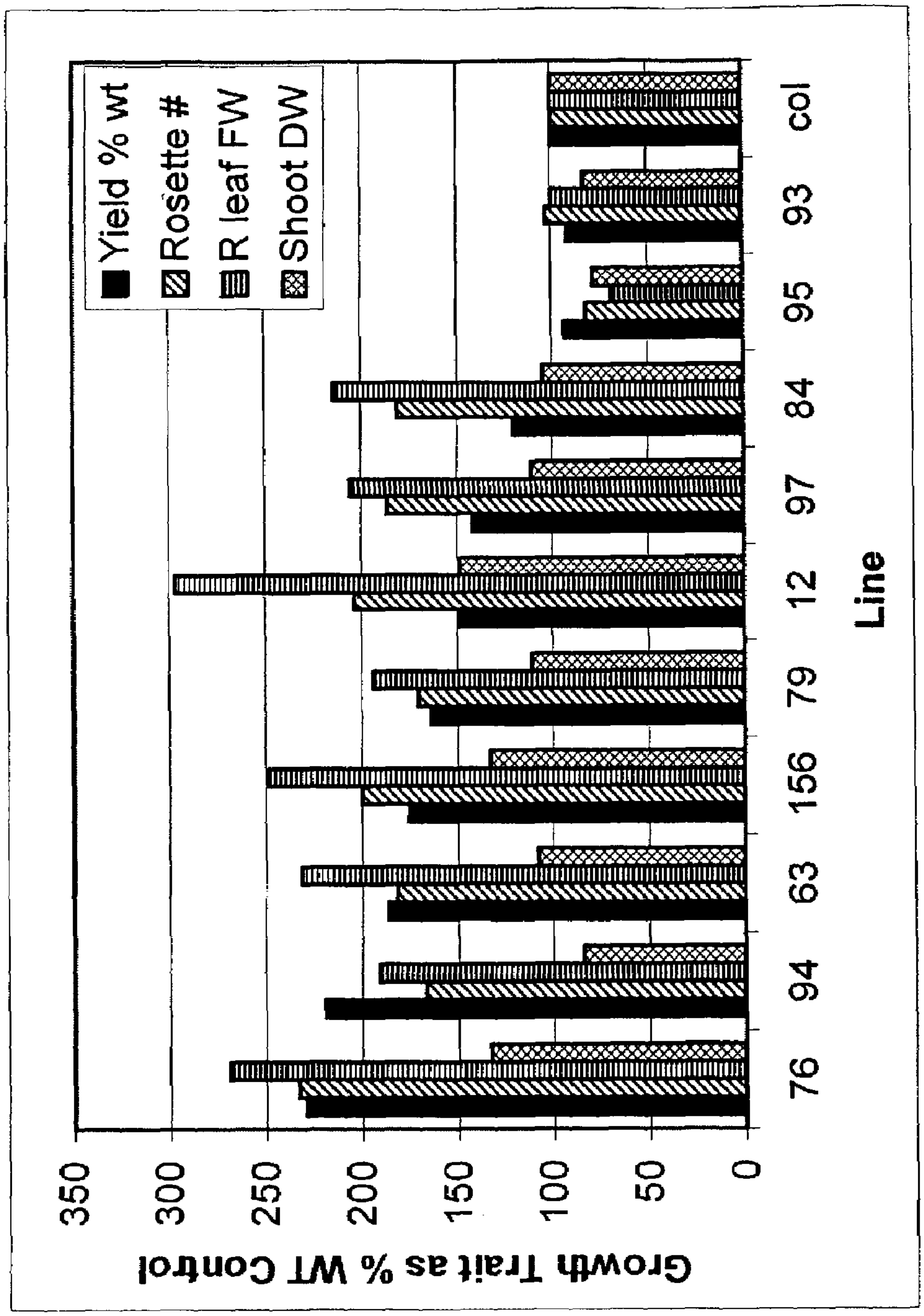
Figure 37:
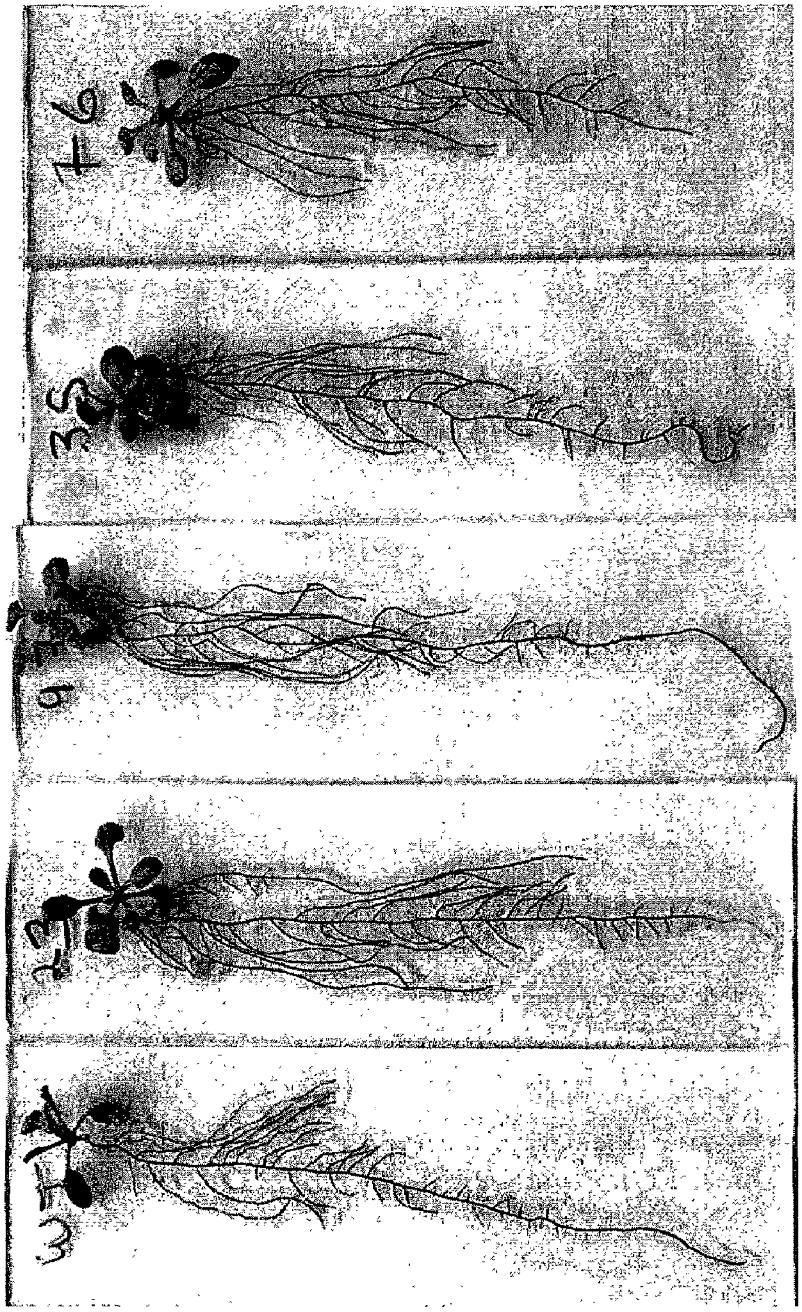
FIG. 37. are photographs showing growth of transgenic *Arabidopsis* lines of pBI121-AtCPP grown on agar plates. Changes to root growth visible.

FIG. 36 presents the results of various growth (from mid-flowering stage) and yield parameters and each trait is expressed as a percentage of the *Columbia* control. The results strongly support an enhanced growth phenotype. This enhanced growth phenotype is present at all growth stages. At the vegetative stage, all $ABA^S$ transgenic plants showed an increase in leaf number relative to that of the wild type with four of the eight lines showing a statistically significant difference. The two $ABA^{Wt}$ lines showed the same or fewer leaves relative to wild type.

At the bolting stage $ABA^S$ transgenics showed an increase in leaf number but plants were shorter at this stage (first open flower) than controls. The shoot fresh weight of transgenics was signicantly increased relative to that of controls, ranging from 80% to 342% of the wild type. The $ABA^S$ transgenics displayed a delay in flowering from one to three days. The $ABA^{Wt}$ transgenics did not show delayed flowering, increased shoot fresh weight or increased height.

At the flowering stage of development the enhanced growth phenotype is maintained (grater leaf number and fresh weight), however, there were no observable differences in plant height indicating that transgenics bolt shorter but reach same final plant height.

Of particular significance is the observation, that under these conditions (biotic stress due to presence of fungi in the soil) yields of the ABAs transgenics were significantly higher, ranging from 120% to 229% of the wild type control. The $ABA^{Wt}$ lines showed similar or slightly reduced yields relative to the *Columbia* control. This finding indicates that $ABA^S$ transgenic lines are affected less by the biotic stress. This observation has been confirmed, where 5 of the drought tolerant lines were grown in contaminated soil to maturity. The seed yields of transgenic lines, even though greatly reduced relative to optimal conditions, were 2.5 to 4.5 fold higher than those of *Columbia* wild type (Table 25).

TABLE 25

Seed yield of pBI121-AtCPP lines grown in contaminated soil. Values in bold indicate statistical differences at p = 0.05

| Line | ABA sensitivity | Seed Yield per plant (g) | % of Columbia |
|---|---|---|---|
| **156** | $ABA^S$ | **0.33 ± 0.04** | 316% |
| **23** | $ABA^S$ | **0.35 ± 0.05** | 336% |
| **76** | $ABA^S$ | **0.31 ± 0.04** | 296% |
| **84** | $ABA^S$ | **0.25 ± 0.33** | 237% |
| **9** | $ABA^S$ | **0.48 ± 0.05** | 455% |
| **Columbia** | $ABA^{Wt}$ | 0.11 ± 0.03 | |

40b) pBI121-AtCPP Early Seedling Growth:

Four $ABA^S$ and one $ABA^{Wt}$ line plus *Columbia* were examined for early seedling growth on agar plates. Twenty seeds were plated in a line on agar plates containing 50% MS with 1% sucrose and vitamins and 6 plates per line were used. Plates were placed on slants, which allowed roots to grow downwards. Root length was measured on 7-day old seedlings and shoot and root biomass determined on 11-day old seedlings. Two of the $ABA^S$ transgenic lines had significantly longer roots and all 4 $ABA^S$ lines had shoot dry weights 114% to 123% of controls and root dry weights of 116% to 151% of controls. As a result, the shoot-biomass to rootbiomass ratios were slightly reduced in transgenics. These results indicate that enhanced growth of these transgenics is evident in the early growth stage, shortly after germination, and the root growth is more enhanced relative to shoot growth. In a different experiment seedlings were pulled out of agar and roots were stained with toluidine blue to show their structure. FIG. 13 shows that transgenic lines had more extensive lateral root system, which would account for greater root biomass.

40c) pRD29A-HP-AtCPP optimal growth characteristics

Figure 38:
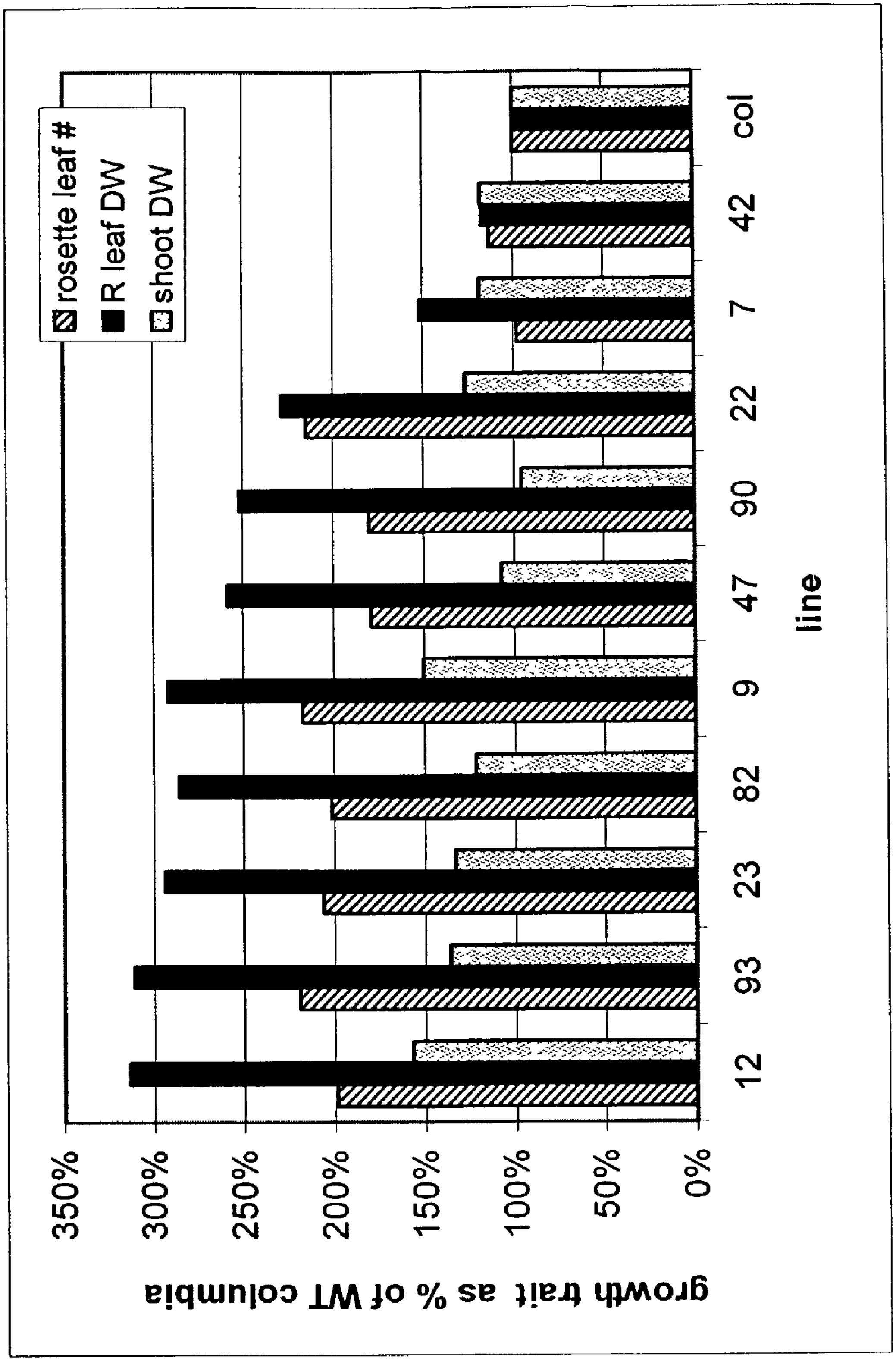
FIG. 38. is a bar chart showing growth of transgenic *Arabidopsis* lines of pRD29A-HP-AtCPP grown under optimal watering conditions. Rosette leaf number, rosette leaf dry weight and shoot dry weight are plotted.

An optimal growth study has been conducted with 10 lines as described before. Vegetative growth data showed that two of the lines (12 and 9) had significantly more leaves and seven of the lines (12, 22, 23, 47, 82, 9) had significantly greater shoot biomass. Bolting data showed that eight of the lines (12, 22, 23, 47, 82, 9, 90, 93) were significantly delayed in flowering by one to two days, and seven of the lines were significantly shorter than *Columbia* at first open flower. All of the lines except 42 and 7 had significantly greater number of rosette leaves and shoot FW and this trend is maintained into the mid-flowering harvest (FIG. 38). The plant height, however, by mid-flowering harvest was not significantly different between the transgenic lines and control. All the lines that showed this enhanced growth also showed drought tolerance and ABA sensitivity.

Example 41

Ultrastructure pBI121-AtCPP

Two of the drought tolerant and $ABA^S$ lines (35 and 76) plus Wt *Columbia* were used to examine stem and root cross-sections for any differences in ultrastructure. Free hand sections of mature stems (plants flowering for 10 days) were obtained from above the first node, stained with toluidine blue and preserved with glycerol. The stems of transgenic plants appeared to have more dense cellular structure and contain one or two more vascular bundles than those of Columbia Wt indicating more enhanced water and nutrient transport system.

Leaf disks were taken and fresh weights determined. Transgenic leaf disks were significantly heavier, 20-24% greater than corresponding wild type controls. This increase is believed to be as a result of a thicker leaf.

Example 42

Cold Stress Experiment pBI121-AtCPP

Four drought tolerant, $ABA^S$ lines (156, 23, 35, 76) and one $ABA^{Wt}$(95) line plus wild type *Columbia* were included in a cold stress study. Plants were grown in 3" pots one per pot) with 10 replicate pots per line at 22C for 10 days (7 days on agar plates and 4 in soil). The cold stress group was moved into 7° C. for 5 days while the optimal group was left at 22C. After 5 days in the cold both cold stress group and the optimal group were harvested for shoot biomass determination. $ABA^S$ and drought tolerant lines had significantly greater shoot biomass than Columbia in both optimal (25 to 39% greater shoot fresh weight) and cold stress groups (18 to 44% greater shoot DW) (Table 26). Results of an eight-- day cold stress showed that differences between the transgenic lines and *Columbia* were even more pronounced (53 to 61% greater shoot fresh weight). This result indicates greater plant vigor and better ability of transgenics to cope with cold stress.

TABLE 26

Shoot fresh weight of optimal and cold stressed (5C for 5d) pBI121-AtCPP. Values in bold indicate statistical difference at p = 0.05

| | | Optimal shoot FW | | Cold stress shoot FW | |
|---|---|---|---|---|---|
| Line | ABA sensitivity | mg | % of Columbia | mg | % of Columbia |
| 156 | $ABA^S$ | **95.4** ± **3.7** | 137% | **23.1 0.7** | 118% |
| 23 | $ABA^S$ | **96.3** ± **3.9** | 139% | **28.3 1.5** | 144% |
| 35 | $ABA^S$ | **87.0** ± **1.7** | 125% | **25.3 1.4** | 130% |
| 76 | $ABA^S$ | **94.7** ± **2.2** | 136% | **27.3 1.5** | 140% |
| 95 | ABAWt | 67 ± 2.4 | 96% | .21.4 1.0 | 109% |
| Columbia | ABAWt | 69 ± 1.9 | | 19.6 1.1 | |

Example 43

Drought Stress under High Temperature pBI121-AtCPP

A drought stress experiment was conducted as described above except that day temperature of 32° C. (16hr) and night temperature of 22° C. (8hr) was maintained. These Temperatures were achieved daily over a 2hr ramping period. Four ABAS and one $ABA^{Wt}$ line plus *Columbia* were included. Plants were monitored daily for water loss and soil water content and after 5 days of drought treatment half of the plants were harvested and the other half was re-water and allowed to recover for four days. Shoots were harvested and shoot fresh weight determined. The results (Table 27) of this experiment showed that previously identified drought tolerant lines maintained their drought tolerant phenotype at high temperature and were able to recover well from the drought stress at high temperature

TABLE 27

Soil water content on day 2 and water lost in 2 days/final shoot dry weight plus recovery shoot FW after 5 days of drought stress at 32 C. day and 22 C. night temperatures. Values in bold indicate significant differences from the Columbia control.

| line | ABA sensitivity | soil water content day 2 | water lost in 2 d/shoot DW | recovered shoot FW (g) |
|---|---|---|---|---|
| 136 | $ABA^S$ | 50.4 ± 1.1 | **485.7** ± 18.5 | **1.30** ± 0.04 |
| 146 | $ABA^S$ | **52.1** ± 1.0 | **504.5** ± 7.9 | **1.15** ± 0.04 |
| 35 | $ABA^S$ | **52.2** ± 0.8 | **502.8** ± 15.8 | **1.19** ± 0.02 |
| 76 | $ABA^S$ | **52.1** ± 0.6 | **435.6** ± 10.5 | **1.11** ± 0.03 |
| 95 | ABAWt | 50.0 ± 0.9 | 518.2 ± 13.0 | 0.86 ± 0.03 |
| Columbia | ABAWt | 48.6 ± 0.6 | 559.7 ± 19.0 | 0.84 ± 0.03 |

Example 44

Heat Stress and Seed Yield pBI121-AtCPP

Two $ABA^S$ lines and one $ABA^{Wt}$ line plus *Columbia* were examined for the effect of heat stess during flowering on the final seed yield. Plants were grown in 4 inch pots (one/pot) as described above and 9 days from first open flower the temperature was ramped from 22 C to 43 C. over 2 hours and plants were kept at 43 C for 2hr. Temperature was then ramped back to 22 C. over 2 hours and plants were grown under optimal conditions until maturity. The seed yields from this experiment are shown in Table 28. One of the drought tolerant lines (35) had significantly greater yield than *Columbia*.

TABLE 28

Seed yield of pBI121-AtCPP lines after two hour 43 C. heat stress 9 days from first open flower. Values in bold are statistically significant from Columbia.

| Line | ABA sensitivity | seed yield (g/plant) | seed yield (% of col.) |
|---|---|---|---|
| 35 | $ABA^S$ | **0.55** ± 0.05 | 347% |
| 76 | $ABA^S$ | 0.24 ± 0.03 | 148% |
| 95 | ABAWt | 0.11 ± 0.02 | 69% |
| Columbia | ABAWt | 0.16 ± 0.03 | |

The effect of heat shock on lines of pBI121-AtCPP at the early flowering stage was assessed. Three $ABA^S$ lines (76, 136, 97) a $ABA^{Wt}$ line (95) and a *Columbia* wild type control were seeded in 128 cell flats, one flat per line. At the early flowering stage flats were exposed to a temperature of 46.8° C. for 50 minutes and then returned to normal growth conditions. Lack of continued growth from main meristems was defined as main meristem death and scored for each line. Data is shown in Table 29.

TABLE 29

Meristem death due to heat shock

| | Line | | | | |
|---|---|---|---|---|---|
| | Wt | 95 | 76 | 136 | 97 |
| % Death | 91 | 97 | 79 | 59 | 18 |

Example 45

Stomata Density Determinations pBI121 AtCPP

Two $ABA^S$ lines (76 and 35) plus *Columbia* were examined for stomata density on the upper and lower leaf surface. Nail polish imprints of the upper and lower epidermis were obtained from a fully expanded leaf #5. These imprints were analyzed under the microscope and the number of stomata per $8.7\times10^{-8}$ $m^2$ were counted. There were no significant differences found between transgenics and *Columbia* in the stomata of the upper or lower epidermis (Table 30). The increases seen in drought tolerance and reduced water loss is not attributable to a reduced number of leaf stomata.

TABLE 30

Stomata numbers per $8.7 \times 10^{-8}$ $m^2$ of abaxial and adaxial epidermis of fully expanded leaf #5 in pBI121AtCPP.

| Line | ABA sensitivity | stomata on upper epidermis | stomata on lower epidermis |
|---|---|---|---|
| 35 | $ABA^S$ | 68 ± 5 | 103 ± 7 |
| 76 | $ABA^S$ | 58 ± 6 | 120 ± 16 |
| Columbia | ABAWt | 57 ± 6 | 116 ± 11 |

Example 46

CPP Consensus Sequences

Also included in the invention is the CPP consensus sequences. The consensus sequences were generated by alignment of the CPP polypeptide and nucleic acid sequences as well as sequences homoiggous using the program BioEdit.

The “x” in the consensus sequence represents any amino acid or nucleotide. Preferably “x” a conservative amino acid or nucleotide substitution. More preferably, “x” is the most amino acid or nucleotide most prevalent at a given position. For example, the amino acid at position 145 of SEQ ID NO: 168 is a proline as it occurs 66% of the time.

```
BASF_AT1   GCCTTGGTTTTGGAAGATGTCTGGAGCTGTTTTACCGAGGTTGGGCCTTGATCCAGAGAA 308
BASF_AT2   GCCTTGGTTTTGGAAGATGTCTGGAGCAGTTTTACCGAGGTTGGGCCTTGATCCAGAGAA 308
BASF-Corn  ----------------------------------------ACGAGGCTGAGTGCTGAGAA 20
BASF-Soy   GCCCTGGTTTTGGAAGAAATCAGGAGATTTTATGACAATAGCTGGTTTCAATGCTGAGAA 540
Consensus  XXXXXXXXXXXXXXXXXXXXXXXXXXXXXXXXXXXXXXXXXXXXGXXTXXXTXCXGAGAA 540

                   550       560       570       580       590       600
           ....|....|....|....|....|....|....|....|....|....|....|....|
BASF_AT1   TGAAATACTGCATACTCTTTCATTCTTGGCTGGTGTTATGACATGGTCACACATCACTGA 368
BASF_AT2   TGAAATACTGCATACTCTTTCATTCTTGGCTGGTGTTATGACATGGTCACAGATCACTGA 368
BASF-Corn  TGAGATAATACACACCCTTGCTTTCTTAGCTGGTTCCATGGTTTGGTCGCAGATTACAGA 80
BASF-Soy   TGAAATACTGCATACCCTTGCCTTCTTAGCAGGCTGATGATTTGGTCACAGATAACAGA 600
Consensus  TGAXATAXTXCAXACXCTTXCXTTCTTXGCXGGXXXXATGXXXTGGTCXCAXATXACXGA 600

                   610       620       630       640       650       660
           ....|....|....|....|....|....|....|....|....|....|....|....|
BASF_AT1   TTTGCCATTTTCTTTGTACTCAACTTTCGTGATCGAGTCTCGGCATGGGTTCAACAAACA 428
BASF_AT2   TTTGCCATTTTCTTTGTACTCAACTTTCGTGATCGAGTCTCGGCATGGGTTCAACAAACA 428
BASF-Corn  CTTGCCGTTCTCTCTCTATTCAACTTTTGTTATAGAGGCTCGACATGGTTTTAACAAGCA 140
BASF-Soy   TTTGCCCTTTTCTCTGTACTCAACTTTTGTGATTGAGGCCCGTCATGGTTTTAATAAGCA 660
Consensus  XTTGCCXTTXTCTXTXTAXTCAACTTTXGTXATXGAGXCXCGXCATGGXTTXAAXAAXCA 660

                   670       680       690       700       710       720
           ....|....|....|....|....|....|....|....|....|....|....|....|
BASF_AT1   AACAATATGGATGTTCATTAGGGACATGATCAAAGGAACATTCCTCTCTGTCATACTAGG 488
BASF_AT2   AACAATATGGATGTTCATTAGGGACATGATCAAAGGAACATTCCTCTCTGTCATACTAGG 488
BASF-Corn  AACTATATGGCTCTTCATTAGGGATATGATCAAAGGAATTTTACTATCCATGATATTGGG 200
BASF-Soy   AACACCATGGTTATTCTTTAGGGACATGCTTAAAGGAATTTTCCTTTCCGTAATAATTGG 720
Consensus  AACXXXATGGXTXTTCXTTAGGGAXATGXTXAAAGGAAXXTTXCTXTCXXTXATAXTXGG 720

                   730       740       750       760       770       780
           ....|....|....|....|....|....|....|....|....|....|....|....|
BASF_AT1   CCCACCCATTGTTGCCGCGATAATTTTCATAGTCCAGAAAGGAGGTCCTTATCTTGCCAT 548
BASF_AT2   CCCACCCATTGTTGCTGCGATAATTTTCATAGTCCAGAAAGGAGGTCCTTATCTTGCCAT 548
BASF-Corn  GCCACCAATCGTGGCTGCTATCATCTACATAGTACAGATTGGAGGACCTTACCTGGCTAT 260
BASF-Soy   TCCACCTATTGTGGCTGCAATCATTGTAATAGTACAGAAAGGAGGTCCATACTTGGCCAT 780
Consensus  XCCACCXATXGTXGCXGCXATXATXXXXATAGTXCAGAXXGGAGGXCCXTAXXTXGCXAT 780

                   790       800       810       820       830       840
           ....|....|....|....|....|....|....|....|....|....|....|....|
BASF_AT1   CTATCTGTGGGCATTCATGTTTATCCTGTCTCTAGTGATGATGACTATATACCCGGTCTT 608
BASF_AT2   CTATCTGTGGGCATTCATGTTTATCCTGTCTCTAGTGATGATGACTATATACCCGGTCTT 608
BASF-Corn  ATATCTCTGGGGTTTTATGTTTGTATTAGCTCTACTGATGATGACAATATACCCCATTGT 320
BASF-Soy   CTATCTTTGGGTTTTTACGTTTGGTCTTTCTATTGTGATGATGACCCTTTATCCAGTACT 840
Consensus  XTATCTXTGGGXXTTXAXGTTTXXXXTXXCTXTXXTGATGATGACXXTXTAXCCXXTXXT 840

                   850       860       870       880       890       900
           ....|....|....|....|....|....|....|....|....|....|....|....|
BASF_AT1   GATAGCACCGCTCTTCAACAAGTTCACTCCTCTTCCAGATGGAGACCTCCGGGAGAAGAT 668
BASF_AT2   GATAGCACCGCTCTTCAACAAGTTCACTCCTCTTCCAGATGGAGACCTCCGGGAGAAGAT 668
BASF-Corn  GATAGCTCCTCTGTTCAACAAGTTCACTCCTCTTCCTGAAGGAGTCCTCAGGGAAAAAAT 380
BASF-Soy   AATAGCTCCACTCTTCAATAAGTTCACTCCACTTCCAGATGGTCAACTCAGGGAGAAAAT 900
Consensus  XATAGCXCCXCTXTTCAAXAAGTTCACTCCXCTTCCXGAXGGXXXXCTCXGGGAXAAXAT 900

                   910       920       930       940       950       960
           ....|....|....|....|....|....|....|....|....|....|....|....|
BASF_AT1   TGAGAAACTTGCTTCTTCTCTAAAGTTTCCTTTGAAGAAGCTGTTTGTTGTCGATGGATC 728
BASF_AT2   TGAGAAACTTGCTTCTTCTCTAAAGTTTCCTTTGAAGAAGCTGTTTGTTGTCGATGGATC 728
BASF-Corn  AGAGAAGCTGGCAGCTTCCCTCAAGTTTCCTTTGAAAAAGCTTTTCGTGGTAGATGGGTC 440
BASF-Soy   CGAGAAACTTGCTTCCTCCCTCAACTATCCGTTAAAGAAACTATTTGTTGTCGATGGATC 960
Consensus  XGAGAAXCTXGCXXCXTCXCTXAAXTXTCCXTTXAAXAAXCTXTTXGTXGTXGATGGXTC 960

                   970       980       990      1000      1010      1020
           ....|....|....|....|....|....|....|....|....|....|....|....|
BASF_AT1   TACAAGGTCAAGCCATAGCAATGCTTACATGTATGGTTTCTTTAAGAACAAAAGGATTGT 788
BASF_AT2   TACAAGGTCAAGCCATAGCAATGCTTACATGTATGGTTTCTTTAAGAACAAAAGGATTGT 788
BASF-Corn  TACCAGATCAAGCCACAGTAATGCCTACATGTATGGTTTTTTCAAGAACAAGCGCATAGT 500
BASF-Soy   CACAAGATCAAGTCACAGCAATGCCTATATGTATGGATTCTTCAAGAACAAGAGGATTGT 1020
Consensus  XACXAGXTCAAGXCAXAGXAATGCXTAXATGTATGGXTTXTTXAAGAACAAXXGXATXGT 1020

                  1030      1040      1050      1060      1070      1080
```

```
           ....|....|....|....|....|....|....|....|....|....|....|....|
BASF_AT1   TCTTTATGATACGTTGATTCAGCAGTGCAAGAATGAGGATGAAATTGTGGCGGTTATTGC 848
BASF_AT2   TCTTTATGATACGTTGATTCAGCAGTGCAAGAATGAGGATGAAATTGTGGCGGTTATTGC 848
BASF-Corn  ACTCTATGACACATTGATTCAGCAGTGTAGCAATGAGGATGAGATAGTTTCTGTTATAGC 560
BASF-Soy   CCTTTATGACACATTAATTCAACAGTGCAAAGACGATGAGGAAATTGTTGCTGTTATTGC 1080
Consensus  XCTXTATGAXACXTTXATTCAXCAGTGXAXXXAXGAXGAXGAXATXGTXXCXGTTATXGC 1080

                    1090      1100      1110      1120      1130      1140
           ....|....|....|....|....|....|....|....|....|....|....|....|
BASF_AT1   ACACGAGCTTGGACATTGGAAACTGAATCACACTACATACTCGTTCATTGCAGTTCAAAT 908
BASF_AT2   ACACGAGCTTGGACATTGGAAACTGAATCACACTACATACTCGTTCATTGCAGTTCAAAT 908
BASF-Corn  ACATGAACTTGGACACTGGAAACTCAATCATACTGTCTATTGCTTTGTAGCTGTCCAGCT 620
BASF-Soy   CCATGAGTTGGGACACTGGAAGCTCAACCATACTGTGTACACATTTGTTGCTATGCAGAT 1140
Consensus  XCAXGAXXTXGGACAXTGGAAXCTXAAXCAXACTXXXTAXXCXTTXXTXGCXXTXCAXXT 1140

                    1150      1160      1170      1180      1190      1200
           ....|....|....|....|....|....|....|....|....|....|....|....|
BASF_AT1   CCTTGCCTTCTTACAATTTGGAGGATACACTCTTGTCAGAAACTCCACTGATCTCTTCAG 968
BASF_AT2   CCTTGCCTTCTTACAATTTGGAGGATACACTCTTGTCAGAAACTCCACTGATCTCTTCAG 968
BASF-Corn  GCTTATGTTTCTTCAATTTGGAGGATATACTCTAGTAAGGAGCTCCAAAGATCTATTTGG 680
BASF-Soy   TCTTACACTTCTACAATTTGGAGGATATACACTAGTGCGAAATTCAGCTGATCTGTATCG 1200
Consensus  XCTTXXXXTXXTXCAATTTGGAGGATAXACXCTXGTXXGXAXXTCXXXXGATCTXTXXXG 1200

                    1210      1220      1230      1240      1250      1260
           ....|....|....|....|....|....|....|....|....|....|....|....|
BASF_AT1   GAGTTTCGGATTTGATACACAGCCTGTTCTCATTGGTTTGATCATATTTCAGCACACTGT 1028
BASF_AT2   GAGTTTCGGATTTGATACACAGCCTGTTCTCATTGGTTTGATCATATTTCAGCACACTGT 1028
BASF-Corn  AAGTTTTGGCTTCAAGGACCAGCCAGTAATAATTGGATTGATCATTTTCCCGCACACCAT 740
BASF-Soy   AAGCTTTGGGTTTGATACGCAGCCAGTCCTCATTGGGCTCATCATATTTCAGCATACTGT 1260
Consensus  XAGXTTXGGXTTXXAXXXXCAGCCXGTXXTXATTGGXXTXATCATXTTXCXGCAXACXXT 1260

                    1270      1280      1290      1300      1310      1320
           ....|....|....|....|....|....|....|....|....|....|....|....|
BASF_AT1   AATACCACTGCAACATCCAGTAAGCTTTGGCCTCAACCTTGTTAGTCGAGCGTTTGAGTT 1088
BASF_AT2   AATACCACTGCAACATCTAGTAAGCTTTGGCCTGAACCTCGTTAGTCGAGCGTTTGAGTT 1088
BASF-Corn  AATACCCATCCAACACCTTCTGAGCTTTCGCCTGAACCTTGTCAGCAGAGCATTTGAATT 800
BASF-Soy   AATCCCACTTCAGCAATTGGTCAGCTTTGGTCTGAACCTAGTCAGCCGATCATTTGAATT 1320
Consensus  AATXCCXXTXCAXCAXXXXXTXAGCTTTXGXCTXAACCTXGTXAGXXGAXCXTTTGAXTT 1320

                    1330      1340      1350      1360      1370      1380
           ....|....|....|....|....|....|....|....|....|....|....|....|
BASF_AT1   TCAGGCTGATGCTTTTGCTGTGAAGCTTGGCTATGCAAAAGATCTTCGTCCTACTCTAGT 1148
BASF_AT2   TCAGGCTGATGCTTTTGCTGTGAAGCTTGGCTATGCAAAAGATCTTCGTCCTGCTCTAGT 1148
BASF-Corn  TCAGGCTGATGCCTTTGCCAAGAACCTTGGATATGCCCCTCAGCTCCGAGCAGCCCTTGT 860
BASF-Soy   TCAGGCTGATGGCTTTGCCAAGAAGCTTGGATATGCATCTGGATTACGCGGTGGTCTTGT 1380
Consensus  TCAGGCTGATGXXTTTGCXXXGAAXCTTGGXTATGCXXXXXXXXTXCGXXXXXXXCTXGT 1380

                    1390      1400      1410      1420      1430      1440
           ....|....|....|....|....|....|....|....|....|....|....|....|
BASF_AT1   GAAACTACAGGAAGAGAACTTATCAGCAATGAATACTGATCCATTGTACTCAGCTTATCA 1208
BASF_AT2   GAAACTACAGGAAGAGAACTTATCAGCAATGAAAACTGATCTATTGTACTCAGCTTATCA 1208
BASF-Corn  TAAACTACAGGAGGAGAACTTGTCTGCGATGAACACCGATCCTTGGTATTCGGCATATCA 920
BASF-Soy   GAAACTACAGGAGGAGAATCTGTCAGCTATGAATACAGATCC-TTGCTCGTGCCG----- 1434
Consensus  XAAACTACAGGAXGAGAAXXTXTCXGCXATGAAXACXGATCXXTXGXXXXXXXCXXXXXX 1440

                    1450      1460      1470      1480      1490      1500
           ....|....|....|....|....|....|....|....|....|....|....|....|
BASF_AT1   CTACTCACATCCTCCTCTTGTTGAAAGGCTTCGAGCCATTGATGGAGAAGACAAGAAGAC 1268
BASF_AT2   CTACTCACATCCTCCTCTTGTTGAAAGGCTTCGAGCCATTGATGGAGAAGACAAGAAGAC 1268
BASF-Corn  CTACTCCCACCCACCACTCGTCGAGAGGCTGCAAGCTTTGGAAGATTCAGACGACAAAAA 980
BASF-Soy   ------------------------------------------------------------ 1434
Consensus  XXXXXXXXXXXXXXXXXXXXXXXXXXXXXXXXXXXXXXXXXXXXXXXXXXXXXXXXXXXX 1500

                    1510      1520      1530      1540      1550      1560
           ....|....|....|....|....|....|....|....|....|....|....|....|
BASF_AT1   AGATTAA----------------------------------------------------- 1275
BASF_AT2   AGATTAA----------------------------------------------------- 1275
BASF-Corn  AGAAGATTAGTCGATCCTTGTATGAGGTTTACATATGGATTTTTCCCTGCCACATGCACA 1040
BASF-Soy   ------------------------------------------------------------ 1434
Consensus  XXXXXXXXXXXXXXXXXXXXXXXXXXXXXXXXXXXXXXXXXXXXXXXXXXXXXXXXXXXX 1560
```

```
                 1570      1580      1590      1600      1610      1620
             ....|....|....|....|....|....|....|....|....|....|....|....|
BASF_AT1     ------------------------------------------------------------ 1275
BASF_AT2     ------------------------------------------------------------ 1275
BASF-Corn    CCGATTCAGTGCTTGGATGGTGAGGGTTTTGACATAGGAGTGTTGTCAAAGCTTTAGAGT 1100
BASF-Soy     ------------------------------------------------------------ 1434
Consensus    XXXXXXXXXXXXXXXXXXXXXXXXXXXXXXXXXXXXXXXXXXXXXXXXXXXXXXXXXXXX 1620

                 1630      1640      1650      1660      1670      1680
             ....|....|....|....|....|....|....|....|....|....|....|....|
BASF_AT1     ------------------------------------------------------------ 1275
BASF_AT2     ------------------------------------------------------------ 1275
BASF-Corn    GCATCTTTCGGTCAGGTGCAACAGCCTTTCGGTCATTGAGACATATAAGCGAATTAGCTA 1160
BASF-Soy     ------------------------------------------------------------ 1434
Consensus    XXXXXXXXXXXXXXXXXXXXXXXXXXXXXXXXXXXXXXXXXXXXXXXXXXXXXXXXXXXX 1680

                 1690      1700      1710      1720      1730      1740
             ....|....|....|....|....|....|....|....|....|....|....|....|
BASF_AT1     ------------------------------------------------------------ 1275
BASF_AT2     ------------------------------------------------------------ 1275
BASF-Corn    TTAAAAAAAACAGAACTGTTGCATCAAAAAAAAAAAAAAAAAAAGAAACAAAAAAAAAAA 1220
BASF-Soy     ------------------------------------------------------------ 1434
Consensus    XXXXXXXXXXXXXXXXXXXXXXXXXXXXXXXXXXXXXXXXXXXXXXXXXXXXXXXXXXXX 1740

                 1750      1760      1770      1780      1790      1800
             ....|....|....|....|....|....|....|....|....|....|....|....|
BASF_AT1     ------------------------------------------------------------ 1275
BASF_AT2     ------------------------------------------------------------ 1275
BASF-Corn    AAAAAAAAAAAAGAAAAAAAAAAAAAAAAAAAAAGTGCTCTGCGTTGTTACCACTGCTTG 1280
BASF-Soy     ------------------------------------------------------------ 1434
Consensus    XXXXXXXXXXXXXXXXXXXXXXXXXXXXXXXXXXXXXXXXXXXXXXXXXXXXXXXXXXXX 1800

                 1810      1820
             ....|....|....|....|.
BASF_AT1     --------------------- 1275
BASF_AT2     --------------------- 1275
BASF-Corn    CCCTATAGTGATCGTATCAGA 1301
BASF-Soy     --------------------- 1434
Consensus    XXXXXXXXXXXXXXXXXXXXX 1821
```

Table 32. ClustalW Analysis of BASF Amino Acids

1) BASF_AT1 (SEQ ID NO:117)
2) BASF_AT2 (SEQ ID NO:119)
3) BASF-Corn (SEQ ID NO:121)
4) BASF-Soy (SEQ ID NO:123)
5) Consensus (SEQ ID NO:164)

```
                        10        20        30        40        50        60
                ....|....|....|....|....|....|....|....|....|....|....|....|
BASF_AT1        MAIPFMETVVGFMIVMYIFETYLDLRQLTALKLPTLPKTLVGVISQEKFEKSRAYSLDKS 60
BASF_AT2        MAIPFMETVVGFMIVMYIFETYLDLRQLTALKLPTLPKTLVGVISQEKFEKSRAYSLDKS 60
BASF-Corn       ------------------------------------------------------------ 1
BASF-Soy        MAFPYMEAVVGFMILMYIFETYLDVRQHRALKLPTLPKTLEGVISQEKFEKSRAYSLDKS 60
Consensus BASF  XXXXXXXXXXXXXXXXXXXXXXXXXXXXXXXXXXXXXXXXXXXXXXXXXXXXXXXXXXXX 60

                        70        80        90       100       110       120
                ....|....|....|....|....|....|....|....|....|....|....|....|
BASF_AT1        YFHFVHEFVTILMDSAILFFGILPWFWKMSGAVLPRLGLDPENEILHTLSFLAGVMTWSH 120
BASF_AT2        YFHFVHEFVTILMDSAILFFGILPWFWKMSGAVLPRLGLDPENEILHTLSFLAGVMTWSQ 120
BASF-Corn       ------------------------------------TRLSAENEIIHTLAFLAGSMVWSQ 24
BASF-Soy        HFHFVHEFVTIVTDSTILYFGVLPWFWKKSGDFMTIAGFNAENEILHTLAFLAGLMIWSQ 120
Consensus BASF  XXXXXXXXXXXXXXXXXXXXXXXXXXXXXXXXXXXXXXXXXENEIXHTLXFLAGXMXWSX 120
```

```
                          130       140       150       160       170       180
                  ....|....|....|....|....|....|....|....|....|....|....|....|
BASF_AT1          ITDLPFSLYSTFVIESRHGFNKQTIWMFIRDMIKGTFLSVILGPPIVAAIIFIVQKGGPY 180
BASF_AT2          ITDLPFSLYSTFVIESRHGFNKQTIWMFIRDMIKGTFLSVILGPPIVAAIIFIVQKGGPY 180
BASF-Corn         ITDLPFSLYSTFVIEARHGFNKQTIWLFIRDMIKGILLSMILGPPIVAAIIYIVQIGGPY 84
BASF-Soy          ITDLPFSLYSTFVIEARHGFNKQTPWLFFRDMLKGIFLSVIIGPPIVAAIIVIVQKGGPY 180
Consensus BASF    ITDLPFSLYSTFVIEXRHGFNKQTXWXFXRDMXKGXXLSXIXGPPIVAAIIXIVQXGGPY 180

                          190       200       210       220       230       240
                  ....|....|....|....|....|....|....|....|....|....|....|....|
BASF_AT1          LAIYLWAFMFILSLVMMTIYPVLIAPLFNKFTPLPDGDLREKIEKLASSLKFPLKKLFVV 240
BASF_AT2          LAIYLWAFMFILSLVMMTIYPVLIAPLFNKFTPLPDGDLREKIEKLASSLKFPLKKLFVV 240
BASF-Corn         LAIYLWGFMFVLALLMMTIYPIVIAPLFNKFTPLPEGVLREKIEKLAASLKFPLKKLFVV 144
BASF-Soy          LAIYLWVFTFGLSIVMMTLYPVLIAPLFNKFTPLPDGQLREKIEKLASSLNYPLKKLFVV 240
Consensus BASF    LAIYLWXFXFXLXXXMMTXYPXXIAPLFNKFTPLPXGXLREKIEKLAXSLXXPLKKLFVV 240

                          250       260       270       280       290       300
                  ....|....|....|....|....|....|....|....|....|....|....|....|
BASF_AT1          DGSTRSSHSNAYMYGFFKNKRIVLYDTLIQQCKNEDEIVAVIAHELGHWKLNHTTYSFIA 300
BASF_AT2          DGSTRSSHSNAYMYGFFKNKRIVLYDTLIQQCKNEDEIVAVIAHELGHWKLNHTTYSFIA 300
BASF-Corn         DGSTRSSHSNAYMYGFFKNKRIVLYDTLIQQCSNEDEIVSVIAHELGHWKLNHTVYSFVA 204
BASF-Soy          DGSTRSSHSNAYMYGFFKNKRIVLYDTLIQQCKDDEEIVAVIAHELGHWKLNHTVYTFVA 300
Consensus BASF    DGSTRSSHSNAYMYGFFKNKRIVLYDTLIQQCXXXXEIVXVIAHELGHWKLNHTXYXFXA 300

                          310       320       330       340       350       360
                  ....|....|....|....|....|....|....|....|....|....|....|....|
BASF_AT1          VQILAFLQFGGYTLVRNSTDLFRSFGFDTQPVLIGLIIFQHTVIPLQHPVSFGLNLVSRA 360
BASF_AT2          VQILAFLQFGGYTLVRNSTDLFRSFGFDTQPVLIGLIIFQHTVIPLQHLVSFGLNLVSRA 360
BASF-Corn         VQLLMFLQFGGYTLVRSSKDLFGSFGFKDQPVIIGLIIFPHTIIPIQHLLSFRLNLVSRA 264
BASF-Soy          MQILTLLQFGGYTLVRNSADLYRSFGFDTQPVLIGLIIFQHTVIPLQQLVSFGLNLVSRS 360
Consensus BASF    XQXLXXLQFGGYTLVRXSXDLXXSFGFXXQPVXIGLIIFXHTXIPXQXXXSFXLNLVSRX 360

                          370       380       390       400       410       420
                  ....|....|....|....|....|....|....|....|....|....|....|....|
BASF_AT1          FEFQADAFAVKLGYAKDLRPTLVKLQEENLSAMNTDPLYSAYHYSHPPLVERLRAIDGED 420
BASF_AT2          FEFQADAFAVKLGYAKDLRPALVKLQEENLSAMKTDLLYSAYHYSHPPLVERLRAIDGED 420
BASF-Corn         FEFQADAFAKNLGYAPQLRAALVKLQEENLSAMNTDPWYSAYHYSHPPLVERLQALEDSD 324
BASF-Soy          FEFQADGFAKKLGYASGLRGGLVKLQEENLSAMNTDPCSC-------------------- 400
Consensus BASF    FEFQADXFAXXLGYAXXLRXXLVKLQEENLSAMXTDXXXXXXXXXXXXXXXXXXXXXXXX 420

                          430       440       450       460       470       480
                  ....|....|....|....|....|....|....|....|....|....|....|....|
BASF_AT1          KKTD-------------------------------------------------------- 424
BASF_AT2          KKTD-------------------------------------------------------- 424
BASF-Corn         DKKEDSILVGLHMDFSLPHAHRFSAWMVRVLTECCQSFRVHLSVRCNSLSVIETYKRISY 384
BASF-Soy          ------------------------------------------------------------ 400
Consensus BASF    XXXXXXXXXXXXXXXXXXXXXXXXXXXXXXXXXXXXXXXXXXXXXXXXXXXXXXXXXXXX 480

                          490       500       510       520       530       540
                  ....|....|....|....|....|....|....|....|....|....|....|....|
BASF_AT1          ------------------------------------------------------------ 424
BASF_AT2          ------------------------------------------------------------ 424
BASF-Corn         KKQNCCIKKKKKKETKKKKKKKKKKKKKKKVLCVVTTACPIVIVS--------------- 429
BASF-Soy          ------------------------------------------------------------ 400
Consensus BASF    XXXXXXXXXXXXXXXXXXXXXXXXXXXXXXXXXXXXXXXXXXXXX--------------- 525

                          550       560       570       580       590       600
                  ....|....|....|....|....|....|....|....|....|....|....|....|
BASF_AT1          ------------------------------------------------------------ 424
BASF_AT2          ------------------------------------------------------------ 424
BASF-Corn         ------------------------------------------------------------ 429
BASF-Soy          ------------------------------------------------------------ 400
Consensus BASF    ------------------------------------------------------------ 525

                          610       620       630       640       650       660
                  ....|....|....|....|....|....|....|....|....|....|....|....|
BASF_AT1          ------------------------------------------------------------ 424
BASF_AT2          ------------------------------------------------------------ 424
BASF-Corn         ------------------------------------------------------------ 429
BASF-Soy          ------------------------------------------------------------ 400
Consensus BASF    ------------------------------------------------------------ 525
```

```
                          670       680       690       700       710       720
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                          730       740       750       760       770       780
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                          790       800       810       820       830       840
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                          850       860       870       880       890       900
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                          910       920       930       940       950       960
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                          970       980       990      1000      1010      1020
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                         1030      1040      1050      1060      1070      1080
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                         1090      1100      1110      1120      1130      1140
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
Consensus BASF     ------------------------------------------------------------ 525

                         1150      1160      1170      1180      1190      1200
                   ....|....|....|....|....|....|....|....|....|....|....|....|
BASF_AT1           ------------------------------------------------------------ 424
BASF_AT2           ------------------------------------------------------------ 424
BASF-Corn          ------------------------------------------------------------ 429
BASF-Soy           ------------------------------------------------------------ 400
```

```
Consensus BASF  ------------------------------------------------------------ 525

                          1210      1220      1230      1240      1250      1260
                ....|....|....|....|....|....|....|....|....|....|....|....|
BASF_AT1        ------------------------------------------------------------ 424
BASF_AT2        ------------------------------------------------------------ 424
BASF-Corn       ------------------------------------------------------------ 429
BASF-Soy        ------------------------------------------------------------ 400
Consensus BASF  ------------------------------------------------------------ 525

                          1270      1280      1290      1300      1310      1320
                ....|....|....|....|....|....|....|....|....|....|....|....|
BASF_AT1        ------------------------------------------------------------ 424
BASF_AT2        ------------------------------------------------------------ 424
BASF-Corn       ------------------------------------------------------------ 429
BASF-Soy        ------------------------------------------------------------ 400
Consensus BASF  ------------------------------------------------------------ 525

                          1330      1340      1350      1360      1370      1380
                ....|....|....|....|....|....|....|....|....|....|....|....|
BASF_AT1        ------------------------------------------------------------ 424
BASF_AT2        ------------------------------------------------------------ 424
BASF-Corn       ------------------------------------------------------------ 429
BASF-Soy        ------------------------------------------------------------ 400
Consensus BASF  ------------------------------------------------------------ 525
```

Table 33. ClustalW Analysis of Generic Nucleic Acids 1) afc1 (SEQ ID NO:124)
2) AT4g01320 (SEQ ID NO:126)
3) AF007269 (SEQ ID NO:128)
4) Consensus (SEQ ID NO:165)

```
                   10        20        30        40        50        60
           ....|....|....|....|....|....|....|....|....|....|....|....|
afc1       ------------------------------------------------------------ 1
AT4g01320  ------------------------------------------------------------ 1
AF007269   ATGGCGATTCCTTTCATGGAAACCGTCGTGGGTAAGCTTCAAAACCTTTTTCTGAGACAT 60
Consensus  XXXXXXXXXXXXXXXXXXXXXXXXXXXXXXXXXXXXXXXXXXXXXXXXXXXXXXXXXXXX 60

                   70        80        90       100       110       120
           ....|....|....|....|....|....|....|....|....|....|....|....|
afc1       ------------------------------------------------------------ 1
AT4g01320  ------------------------------------------------------------ 1
AF007269   TTTACTATCCTGTTTCACTCATCGTATTTCGTTTTTGTTTGGGTTTTGCTTTCTGTGTTG 120
Consensus  XXXXXXXXXXXXXXXXXXXXXXXXXXXXXXXXXXXXXXXXXXXXXXXXXXXXXXXXXXXX 120

                  130       140       150       160       170       180
           ....|....|....|....|....|....|....|....|....|....|....|....|
afc1       ------------------------------------------------------------ 1
AT4g01320  ------------------------------------------------------------ 1
AF007269   TGTGTGTTGAGATTCCATGACTCGTTTGTTTCATATACCATCGTCTCTGCTTCTCGTTTC 180
Consensus  XXXXXXXXXXXXXXXXXXXXXXXXXXXXXXXXXXXXXXXXXXXXXXXXXXXXXXXXXXXX 180

                  190       200       210       220       230       240
           ....|....|....|....|....|....|....|....|....|....|....|....|
afc1       ------------------------------------------------------------ 1
AT4g01320  ------------------------------------------------------------ 1
AF007269   TAAATTTTGTTCTTTTCTAATAGTGCGTACCTTGATCTGAGGTTTTATTACTCCTACTAG 240
Consensus  XXXXXXXXXXXXXXXXXXXXXXXXXXXXXXXXXXXXXXXXXXXXXXXXXXXXXXXXXXXX 240

                  250       260       270       280       290       300
           ....|....|....|....|....|....|....|....|....|....|....|....|
afc1       ------------------------------------------------------------ 1
AT4g01320  ------------------------------------------------------------ 1
```

```
AF007269   TTTCTTGTCTTACTCGTGCGTTTGATTTGATTTGAGCTTATGTGATTTCATCATCTCTTC 300
Consensus  XXXXXXXXXXXXXXXXXXXXXXXXXXXXXXXXXXXXXXXXXXXXXXXXXXXXXXXXXXXX 300

                  310       320       330       340       350       360
           ....|....|....|....|....|....|....|....|....|....|....|....|
afc1       ------------------------------------------------------------ 1
AT4g01320  ------------------------------------------------------------ 1
AF007269   CTCGGTTTTAGAATGTACGGAGCTTCTCTGTTAACCAAAATCTAGGATTTGGGAAGAAAA 360
Consensus  XXXXXXXXXXXXXXXXXXXXXXXXXXXXXXXXXXXXXXXXXXXXXXXXXXXXXXXXXXXX 360

                  370       380       390       400       410       420
           ....|....|....|....|....|....|....|....|....|....|....|....|
afc1       ------------------------------------------------------------ 1
AT4g01320  ------------------------------------------------------------ 1
AF007269   GTCGGAGTCTTTTTTTTCCTCATTCCCGATTGGAAATTGAGAATCTTGAAATTTTTCTTT 420
Consensus  XXXXXXXXXXXXXXXXXXXXXXXXXXXXXXXXXXXXXXXXXXXXXXXXXXXXXXXXXXXX 420

                  430       440       450       460       470       480
           ....|....|....|....|....|....|....|....|....|....|....|....|
afc1       ------------------------------------------------------------ 1
AT4g01320  ------------------------------------------------------------ 1
AF007269   GTTCAAGTCATACAGCTTGAGGTTTTGGGTTTTCTTGTCAGGGTATTATTATGTTCGTGA 480
Consensus  XXXXXXXXXXXXXXXXXXXXXXXXXXXXXXXXXXXXXXXXXXXXXXXXXXXXXXXXXXXX 480

                  490       500       510       520       530       540
           ....|....|....|....|....|....|....|....|....|....|....|....|
afc1       ------------------------------------------------------------ 1
AT4g01320  ------------------------------------------------------------ 1
AF007269   CTGCAACTAGAGTTTTCTGGAGTTTTTTGAAATGGGTTTTGTGTTGTGGAACCGTATGTG 540
Consensus  XXXXXXXXXXXXXXXXXXXXXXXXXXXXXXXXXXXXXXXXXXXXXXXXXXXXXXXXXXXX 540

                  550       560       570       580       590       600
           ....|....|....|....|....|....|....|....|....|....|....|....|
afc1       ------------------------------------------------------------ 1
AT4g01320  ------------------------------------------------------------ 1
AF007269   AATGTTGCATCAAAACTCTTTCAGTGCTCCAATGTTTCCATCAGTAGTCAGCACAAGAGA 600
Consensus  XXXXXXXXXXXXXXXXXXXXXXXXXXXXXXXXXXXXXXXXXXXXXXXXXXXXXXXXXXXX 600

                  610       620       630       640       650       660
           ....|....|....|....|....|....|....|....|....|....|....|....|
afc1       ------------------------------------------------------------ 1
AT4g01320  ------------------------------------------------------------ 1
AF007269   TCTTTTTATATCTGGTTGATCAAAAAAGTAGATGATGTTATTGAATTTTCAGTGATGGAG 660
Consensus  XXXXXXXXXXXXXXXXXXXXXXXXXXXXXXXXXXXXXXXXXXXXXXXXXXXXXXXXXXXX 660

                  670       680       690       700       710       720
           ....|....|....|....|....|....|....|....|....|....|....|....|
afc1       ---------------------------------ATGGCGATTCCT--TTCATGGAAACCG 25
AT4g01320  ---------------------------------ATGGCGATTCCT--TTCATGGAAACCG 25
AF007269   TATCTGTTGTTGTGGCATTTAGAGTAGATTCGTATTTCATCTTCTGTTTTATTCTTTTTC 720
Consensus  XXXXXXXXXXXXXXXXXXXXXXXXXXXXXXXXXATXXCXXXTXCTXXTTXATXXXXXXXX 720

                  730       740       750       760       770       780
           ....|....|....|....|....|....|....|....|....|....|....|....|
afc1       TCGTGGGTTTTATGATAGTGATGTACATTTTTGAGACGTATTTGGATCTGAGGCAACTCA 85
AT4g01320  TCGTGGGTTTTATGATAGTGATGTACATTTTTGAGACGTATTTGGATCTGAGGCAACTCA 85
AF007269   TTACAGGTTTTATGATAGTGATGTACATTTTTGAGACGTATTTGGATCTGAGGCAACTCA 780
Consensus  TXXXXGGTTTTATGATAGTGATGTACATTTTTGAGACGTATTTGGATCTGAGGCAACTCA 780

                  790       800       810       820       830       840
           ....|....|....|....|....|....|....|....|....|....|....|....|
afc1       CTGCTCTCAAGCTTCCAACTCTCCCGAAAACCTTGGTTGGTGTAATTAGCCAAGAGAAGT 145
AT4g01320  CTGCTCTCAAGCTTCCAACTCTCCCGAAAACCTTGGTTGGTGTAATTAGCCAAGAGAAGT 145
AF007269   CTGCTCTCAAGCTTCCAACTCTCCCGAAAACCTTGGTTGGTGTAATTAGCCAAGAGAAGT 840
Consensus  CTGCTCTCAAGCTTCCAACTCTCCCGAAAACCTTGGTTGGTGTAATTAGCCAAGAGAAGT 840

                  850       860       870       880       890       900
           ....|....|....|....|....|....|....|....|....|....|....|....|
afc1       TTGAGAAATCACGAGCATACAG-------------------------------------- 167
AT4g01320  TTGAGAAATCACGAGCATACAGG------------------------------------- 168
AF007269   TTGAGAAATCACGAGCATACAGTCTTGACAAAAGGTTTCGTCTTGATCATATTTATATCA 900
```

```
Consensus  TTGAGAAATCACGAGCATACAGXXXXXXXXXXXXXXXXXXXXXXXXXXXXXXXXXXXXXX 900

                  910       920       930       940       950       960
           ....|....|....|....|....|....|....|....|....|....|....|....|
afc1       ------------------------------------------TCTTGACAAA---AGCTA 182
AT4g01320  -------------------------GATATCATCACTGAGAACTTTAATATATGCAGCTA 203
AF007269   TTTTAGTTTTTTATAATTGCCAGGGGATATCATCACTGAGAACTTTAATATATGCAGCTA 960
Consensus  XXXXXXXXXXXXXXXXXXXXXXXXXXXXXXXXXXXXXXXXXXXXTTXAXAXAXXXAGCTA 960

                  970       980       990      1000      1010      1020
           ....|....|....|....|....|....|....|....|....|....|....|....|
afc1       TTTTCACTTTGTTCATGAGTTTGTAACTATACTTATGGACTCTGCAATTTTGTTCTTTGG 242
AT4g01320  TTTTCACTTTGTTCATGAGTTTGTAACTATACTTATGGACTCTGCAATTTTGTTCTTTGG 263
AF007269   TTTTCACTTTGTTCATGAGTTTGTAACTATACTTATGGACTCTGCAATTTTGTTCTTTGG 1020
Consensus  TTTTCACTTTGTTCATGAGTTTGTAACTATACTTATGGACTCTGCAATTTTGTTCTTTGG 1020

                 1030      1040      1050      1060      1070      1080
           ....|....|....|....|....|....|....|....|....|....|....|....|
afc1       GATCTTGCCTTGGTTTTGGAAG-------------------------------------- 264
AT4g01320  GATCTTGCCTTGGTTTTGGAAG-------------------------------------- 285
AF007269   GATCTTGCCTTGGTTTTGGAAGGTACATATCTGGTTTCGGTATACAGTATCTCATTTTGA 1080
Consensus  GATCTTGCCTTGGTTTTGGAAGXXXXXXXXXXXXXXXXXXXXXXXXXXXXXXXXXXXXXX 1080

                 1090      1100      1110      1120      1130      1140
           ....|....|....|....|....|....|....|....|....|....|....|....|
afc1       ------------------------------------------------ATGTCTGGAGCT 276
AT4g01320  ------------------------------------------------ATGTCTGGAGCT 297
AF007269   ATATAGAGTTGTTACATTACAATTGTAAAGTTTTCATTTTTACCTTAGATGTCTGGAGCT 1140
Consensus  XXXXXXXXXXXXXXXXXXXXXXXXXXXXXXXXXXXXXXXXXXXXXXXXATGTCTGGAGCT 1140

                 1150      1160      1170      1180      1190      1200
           ....|....|....|....|....|....|....|....|....|....|....|....|
afc1       GTTTTACCGAGGTTGGGCCTTGATCCAGAGAATGAAATACTGCATACTCTTTCATTCTTG 336
AT4g01320  GTTTTACCGAGGTTGGGCCTTGATCCAGAGAATGAAATACTGCATACTCTTTCATTCTTG 357
AF007269   GTTTTACCGAGGTTGGGCCTTGATCCAGAGAATGAAATACTGCATACTCTTTCATTCTTG 1200
Consensus  GTTTTACCGAGGTTGGGCCTTGATCCAGAGAATGAAATACTGCATACTCTTTCATTCTTG 1200

                 1210      1220      1230      1240      1250      1260
           ....|....|....|....|....|....|....|....|....|....|....|....|
afc1       GCTGGTGTTATGACATGGTCACAG------------------------------------ 360
AT4g01320  GCTGGTGTTATGACATGGTCACAG------------------------------------ 381
AF007269   GCTGGTGTTATGACATGGTCACAGGTGTTCCAAATAAACCCCTTCATATAGTCCTATACG 1260
Consensus  GCTGGTGTTATGACATGGTCACAGXXXXXXXXXXXXXXXXXXXXXXXXXXXXXXXXXXXX 1260

                 1270      1280      1290      1300      1310      1320
           ....|....|....|....|....|....|....|....|....|....|....|....|
afc1       ------------------------------------------------------------ 360
AT4g01320  ------------------------------------------------------------ 381
AF007269   TTTAGCATCAAAATATCTATTTTCTTAAGATAATAATATTTCTTTTATATTCTGATGCAG 1320
Consensus  XXXXXXXXXXXXXXXXXXXXXXXXXXXXXXXXXXXXXXXXXXXXXXXXXXXXXXXXXXXX 1320

                 1330      1340      1350      1360      1370      1380
           ....|....|....|....|....|....|....|....|....|....|....|....|
afc1       ATCACTGATTTGCCATTTTCTTTGTACTCAACTTTCGTGATCGAGTCTCGGCATGGGTTC 420
AT4g01320  ATCACTGATTTGCCATTTTCTTTGTACTCAACTTTCGTGATCGAGTCTCGGCATGGGTTC 441
AF007269   ATCACTGATTTGCCATTTTCTTTGTACTCAACTTTCGTGATCGAGTCTCGGCATGGGTTC 1380
Consensus  ATCACTGATTTGCCATTTTCTTTGTACTCAACTTTCGTGATCGAGTCTCGGCATGGGTTC 1380

                 1390      1400      1410      1420      1430      1440
           ....|....|....|....|....|....|....|....|....|....|....|....|
afc1       AACAAA------------------------------------------------------ 426
AT4g01320  AACAAA------------------------------------------------------ 447
AF007269   AACAAAGTATGTCGTATTTCCAACACTACCTTGTGACTTACGTTTTTTATCAGAGATGT 1440
Consensus  AACAAAXXXXXXXXXXXXXXXXXXXXXXXXXXXXXXXXXXXXXXXXXXXXXXXXXXXXXX 1440

                 1450      1460      1470      1480      1490      1500
           ....|....|....|....|....|....|....|....|....|....|....|....|
afc1       --------------------------------CAAACAATATGGATGTTCATTAGGGACA 454
AT4g01320  --------------------------------CAAACAATATGGATGTTCATTAGGGACA 475
AF007269   GGATTAAATTTGCTTCTAAATTCTGTTGACAGCAAACAATATGGATGTTCATTAGGGACA 1500
Consensus  XXXXXXXXXXXXXXXXXXXXXXXXXXXXXXXXCAAACAATATGGATGTTCATTAGGGACA 1500
```

```
                 1510      1520      1530      1540      1550      1560
             ....|....|....|....|....|....|....|....|....|....|....|....|
afc1         TGATCAAAGGAACATTCCTCTCTGTCATACTAGGCCCACCCATTGTTGCTGCGATAATTT 514
AT4g01320    TGATCAAAGGAACATTCCTCTCTGTCATACTAGGCCCACCCATTGTTGCTGCGATAATTT 535
AF007269     TGATCAAAGGAACATTCCTCTCTGTCATACTAGGCCCACCCATTGTTGCTGCGATAATTT 1560
Consensus    TGATCAAAGGAACATTCCTCTCTGTCATACTAGGCCCACCCATTGTTGCTGCGATAATTT 1560

                 1570      1580      1590      1600      1610      1620
             ....|....|....|....|....|....|....|....|....|....|....|....|
afc1         TCATAGTCCAG------------------------------------------------- 525
AT4g01320    TCATAGTCCAG------------------------------------------------- 546
AF007269     TCATAGTCCAGGTTTGATGATTCTGGATTCATCTTATTTCTGAGTTTTTCACATGGATGA 1620
Consensus    TCATAGTCCAGXXXXXXXXXXXXXXXXXXXXXXXXXXXXXXXXXXXXXXXXXXXXXXXXX 1620

                 1630      1640      1650      1660      1670      1680
             ....|....|....|....|....|....|....|....|....|....|....|....|
afc1         ------------------------------------------------------------ 525
AT4g01320    ------------------------------------------------------------ 546
AF007269     CTATTCTCCATTGAGTGTGAGCTTCAAAGTTTTTAGTTTTCGTGTTAAAAATTTAAAATT 1680
Consensus    XXXXXXXXXXXXXXXXXXXXXXXXXXXXXXXXXXXXXXXXXXXXXXXXXXXXXXXXXXXX 1680

                 1690      1700      1710      1720      1730      1740
             ....|....|....|....|....|....|....|....|....|....|....|....|
afc1         ------------------------------------AAAGGAGGTCCTTATCTTGCCATC 549
AT4g01320    ------------------------------------AAAGGAGGTCCTTATCTTGCCATC 570
AF007269     TGCTTCTCTGAGCATGAAGTTTCTATCTTTTTCCAGAAAGGAGGTCCTTATCTTGCCATC 1740
Consensus    XXXXXXXXXXXXXXXXXXXXXXXXXXXXXXXXXXXXAAAGGAGGTCCTTATCTTGCCATC 1740

                 1750      1760      1770      1780      1790      1800
             ....|....|....|....|....|....|....|....|....|....|....|....|
afc1         TATCTGTGGGCATTCATGTTTATCCTGTCTCTAGTGATGATGACTATATACCCGGTCTTG 609
AT4g01320    TATCTGTGGGCATTCATGTTTATCCTGTCTCTAGTGATGATGACTATATACCCGGTCTTG 630
AF007269     TATCTGTGGGCATTCATGTTTATCCTGTCTCTAGTGATGATGACTATATACCCGGTCTTG 1800
Consensus    TATCTGTGGGCATTCATGTTTATCCTGTCTCTAGTGATGATGACTATATACCCGGTCTTG 1800

                 1810      1820      1830      1840      1850      1860
             ....|....|....|....|....|....|....|....|....|....|....|....|
afc1         ATAGCACCGCTCTTCAACAAGTTCACTCCT------------------------------ 639
AT4g01320    ATAGCACCGCTCTTCAACAAGTTCACTCCT------------------------------ 660
AF007269     ATAGCACCGCTCTTCAACAAGTTCACTCCTGTGTGTATTTCTGTCATGGCCATTTTACAA 1860
Consensus    ATAGCACCGCTCTTCAACAAGTTCACTCCTXXXXXXXXXXXXXXXXXXXXXXXXXXXXXX 1860

                 1870      1880      1890      1900      1910      1920
             ....|....|....|....|....|....|....|....|....|....|....|....|
afc1         ------------------------------------------------------------ 639
AT4g01320    ------------------------------------------------------------ 660
AF007269     TTCACTGCTTGTTTGCATATGTTGTTACCAGACAATATAATCTCCCGCTTTTTTATGGCT 1920
Consensus    XXXXXXXXXXXXXXXXXXXXXXXXXXXXXXXXXXXXXXXXXXXXXXXXXXXXXXXXXXXX 1920

                 1930      1940      1950      1960      1970      1980
             ....|....|....|....|....|....|....|....|....|....|....|....|
afc1         ----CTTCCAGATGGAGACCTCCGGGAGAAGATTGAGAAACTTGCTTCTTCTCTAAAGTT 695
AT4g01320    ----CTTCCAGATGGAGACCTCCGGGAGAAGATTGAGAAACTTGCTTCTTCTCTAAAGTT 716
AF007269     ATAGCTTCCAGATGGAGACCTCCGGGAGAAGATTGAGAAACTTGCTTCTTCTCTAAAGTT 1980
Consensus    XXXXCTTCCAGATGGAGACCTCCGGGAGAAGATTGAGAAACTTGCTTCTTCTCTAAAGTT 1980

                 1990      2000      2010      2020      2030      2040
             ....|....|....|....|....|....|....|....|....|....|....|....|
afc1         TCCTTTGAAGAAGCTGTTTGTTGTCGATGGATCTACAAGGTCAAGCCATAGCAATG---- 751
AT4g01320    TCCTTTGAAGAAGCTGTTTGTTGTCGATGGATCTACAAGGTCAAGCCATAGCAATG---- 772
AF007269     TCCTTTGAAGAAGCTGTTTGTTGTCGATGGATCTACAAGGTCAAGCCATAGCAATGTGAG 2040
Consensus    TCCTTTGAAGAAGCTGTTTGTTGTCGATGGATCTACAAGGTCAAGCCATAGCAATGXXXX 2040

                 2050      2060      2070      2080      2090      2100
             ....|....|....|....|....|....|....|....|....|....|....|....|
afc1         ------------------------------------------------------------ 751
AT4g01320    ------------------------------------------------------------ 772
AF007269     AAGCTTGAGATCTCTTCCTACCTACTTTACTCTAGTTTACCATTAGAAGCTTACGTATCT 2100
Consensus    XXXXXXXXXXXXXXXXXXXXXXXXXXXXXXXXXXXXXXXXXXXXXXXXXXXXXXXXXXXX 2100
```

```
                2110      2120      2130      2140      2150      2160
            ....|....|....|....|....|....|....|....|....|....|....|....|
afc1        ----------------CTTACATGTATGGTTTCTTTAAGAACAAAAGGATTGTTCTTTAT  795
AT4g01320   ----------------CTTACATGTATGGTTTCTTTAAGAACAAAAGGATTGTTCTTTAT  816
AF007269    TGTTACATCATACAGGCTTACATGTATGGTTTCTTTAAGAACAAAAGGATTGTTCTTTAT  2160
Consensus   XXXXXXXXXXXXXXXXCTTACATGTATGGTTTCTTTAAGAACAAAAGGATTGTTCTTTAT  2160

                2170      2180      2190      2200      2210      2220
            ....|....|....|....|....|....|....|....|....|....|....|....|
afc1        GATACGTTGATTCAGCAG------------------------------------------  813
AT4g01320   GATACGTTGATTCAGCAG------------------------------------------  834
AF007269    GATACGTTGATTCAGCAGGTACTGTGACTCTTGATGCTTCAAACGAGCTATACTCACATT  2220
Consensus   GATACGTTGATTCAGCAGXXXXXXXXXXXXXXXXXXXXXXXXXXXXXXXXXXXXXXXXXX  2220

                2230      2240      2250      2260      2270      2280
            ....|....|....|....|....|....|....|....|....|....|....|....|
afc1        --------------------------------------------TGCAAGAATGAGGATG  829
AT4g01320   --------------------------------------------TGCAAGAATGAGGATG  850
AF007269    TCTGTTTCTGGTTCTGAAACATAACATAATCTTCTATTGTGCAGTGCAAGAATGAGGATG  2280
Consensus   XXXXXXXXXXXXXXXXXXXXXXXXXXXXXXXXXXXXXXXXXXXXTGCAAGAATGAGGATG  2280

                2290      2300      2310      2320      2330      2340
            ....|....|....|....|....|....|....|....|....|....|....|....|
afc1        AAATTGTGGCGGTTATTGCACACGAGCTTGGACATTGGAAACTGAATCACACTACATACT  889
AT4g01320   AAATTGTGGCGGTTATTGCACACGAGCTTGGACATTGGAAACTGAATCACACTACATACT  910
AF007269    AAATTGTGGCGGTTATTGCACACGAGCTTGGACATTGGAAACTGAATCACACTACATACT  2340
Consensus   AAATTGTGGCGGTTATTGCACACGAGCTTGGACATTGGAAACTGAATCACACTACATACT  2340

                2350      2360      2370      2380      2390      2400
            ....|....|....|....|....|....|....|....|....|....|....|....|
afc1        CGTTCATTGCAGTTCAA-------------------------------------------  906
AT4g01320   CGTTCATTGCAGTTCAA-------------------------------------------  927
AF007269    CGTTCATTGCAGTTCAAGTGAGGCTCAACCGACAGTTCAAAAACTTACTCACATCTACAT  2400
Consensus   CGTTCATTGCAGTTCAAXXXXXXXXXXXXXXXXXXXXXXXXXXXXXXXXXXXXXXXXXXX  2400

                2410      2420      2430      2440      2450      2460
            ....|....|....|....|....|....|....|....|....|....|....|....|
afc1        ---------------------------------------------------ATCCTTGCC  915
AT4g01320   ---------------------------------------------------ATCCTTGCC  936
AF007269    TTCACTTAAGAAATCATGTCTTATGACCCTCTCTCAATGTTTTGCTTGCAGATCCTTGCC  2460
Consensus   XXXXXXXXXXXXXXXXXXXXXXXXXXXXXXXXXXXXXXXXXXXXXXXXXXXATCCTTGCC  2460

                2470      2480      2490      2500      2510      2520
            ....|....|....|....|....|....|....|....|....|....|....|....|
afc1        TTCTTACAATTTGGAGGATACACTCTTGTCAGAAACTCCACTGATCTCTTCAGGAGTTTC  975
AT4g01320   TTCTTACAATTTGGAGGATACACTCTTGTCAGAAACTCCACTGATCTCTTCAGGAGTTTC  996
AF007269    TTCTTACAATTTGGAGGATACACTCTTGTCAGAAACTCCACTGATCTCTTCAGGAGTTTC  2520
Consensus   TTCTTACAATTTGGAGGATACACTCTTGTCAGAAACTCCACTGATCTCTTCAGGAGTTTC  2520

                2530      2540      2550      2560      2570      2580
            ....|....|....|....|....|....|....|....|....|....|....|....|
afc1        GGATTTGATACACAGCCTGTTCTCATTGGTTTGATCATATTTCAG---------------  1020
AT4g01320   GGATTTGATACACAGCCTGTTCTCATTGGTTTGATCATATTTCAG---------------  1041
AF007269    GGATTTGATACACAGCCTGTTCTCATTGGTTTGATCATATTTCAGGTTTGTTATTTTTGC  2580
Consensus   GGATTTGATACACAGCCTGTTCTCATTGGTTTGATCATATTTCAGXXXXXXXXXXXXXXX  2580

                2590      2600      2610      2620      2630      2640
            ....|....|....|....|....|....|....|....|....|....|....|....|
afc1        ------------------------------------------------------------  1020
AT4g01320   ------------------------------------------------------------  1041
AF007269    CTTTTGACACTAATCTAATGAATCAAGGATGGATTAAGAAAAAAAAACTCTAAACCTTTG  2640
Consensus   XXXXXXXXXXXXXXXXXXXXXXXXXXXXXXXXXXXXXXXXXXXXXXXXXXXXXXXXXXXX  2640

                2650      2660      2670      2680      2690      2700
            ....|....|....|....|....|....|....|....|....|....|....|....|
afc1        ---------------------------CACACTGTAATACCACTGCAACATCTAGTAAGC  1053
AT4g01320   ---------------------------CACACTGTAATACCACTGCAACATCTAGTAAGC  1074
AF007269    GTTATATCTCCTGTCTGATTATCACAGCACACTGTAATACCACTGCAACATCTAGTAAGC  2700
Consensus   XXXXXXXXXXXXXXXXXXXXXXXXXXXCACACTGTAATACCACTGCAACATCTAGTAAGC  2700

                2710      2720      2730      2740      2750      2760
```

```
           ....|....|....|....|....|....|....|....|....|....|....|....|
afc1       TTTGGCCTGAACCTCGTTAGTCGAGCGTTTGAGTTTCAGG-------------------- 1093
AT4g01320  TTTGGCCTGAACCTCGTTAGTCGAGCGTTTGAGTTTCAGG-------------------- 1114
AF007269   TTTGGCCTGAACCTCGTTAGTCGAGCGTTTGAGTTTCAGGTACCATCTTACAATCCCTCA 2760
Consensus  TTTGGCCTGAACCTCGTTAGTCGAGCGTTTGAGTTTCAGGXXXXXXXXXXXXXXXXXXXX 2760

                2770      2780      2790      2800      2810      2820
           ....|....|....|....|....|....|....|....|....|....|....|....|
afc1       ------------------------------------------------------------ 1093
AT4g01320  ------------------------------------------------------------ 1114
AF007269   AGATCCAACCATAGTTTCTTTATTGCAATGGCAGCCTCATCTACTAATCTGAGTTAACGT 2820
Consensus  XXXXXXXXXXXXXXXXXXXXXXXXXXXXXXXXXXXXXXXXXXXXXXXXXXXXXXXXXXXX 2820

                2830      2840      2850      2860      2870      2880
           ....|....|....|....|....|....|....|....|....|....|....|....|
afc1       ------------CTGATGCTTTTGCCGTGAAGCTTGGCTATGCAAAAGATCTTCGTCCTG 1141
AT4g01320  ------------CTGATGCTTTTGCTGTGAAGCTTGGCTATGCAAAAGATCTTCGTCCTG 1162
AF007269   TCCTTTTGCAGGCTGATGCTTTTGCTGTGAAGCTTGGCTATGCAAAAGATCTTCGTCCTG 2880
Consensus  XXXXXXXXXXXXCTGATGCTTTTGCXGTGAAGCTTGGCTATGCAAAAGATCTTCGTCCTG 2880

                2890      2900      2910      2920      2930      2940
           ....|....|....|....|....|....|....|....|....|....|....|....|
afc1       CTCTAGTGAAACTACAGG------------------------------------------ 1159
AT4g01320  CTCTAGTGAAACTACAGGTCAGAGAAGATAACAACAGAACACAAACTGTTACCTCAATTT 1222
AF007269   CTCTAGTGAAACTACAGGTCAGAGAAGATAACAACAGAACACAAACTGTTACCTCAATTT 2940
Consensus  CTCTAGTGAAACTACAGGXXXXXXXXXXXXXXXXXXXXXXXXXXXXXXXXXXXXXXXXXX 2940

                2950      2960      2970      2980      2990      3000
           ....|....|....|....|....|....|....|....|....|....|....|....|
afc1       ------------------------------------------AAGAGAACTTATCAGCAA 1177
AT4g01320  GTGTCACACACTTAAATGGATTTTTTGTTGGGATTTTGCAGGAAGAGAACTTATCAGCAA 1282
AF007269   GTGTCACACACTTAAATGGATTTTTTGTTGGGATTTTGCAGGAAGAGAACTTATCAGCAA 3000
Consensus  XXXXXXXXXXXXXXXXXXXXXXXXXXXXXXXXXXXXXXXXXXAAGAGAACTTATCAGCAA 3000

                3010      3020      3030      3040      3050      3060
           ....|....|....|....|....|....|....|....|....|....|....|....|
afc1       TGAACACTGATCCATTGCACTCAGCTTATCACTACTCACATCCTCCTCTTGTTGAAAGGC 1237
AT4g01320  TGAACACTGATCCATTGTACTCAGCTTATCACTACTCACATCCTCCTCTTGTTGAAAGGC 1342
AF007269   TGAACACTGATCCATTGTACTCAGCTTATCACTACTCACATCCTCCTCTTGTTGAAAGGC 3060
Consensus  TGAACACTGATCCATTGXACTCAGCTTATCACTACTCACATCCTCCTCTTGTTGAAAGGC 3060

                3070      3080      3090
           ....|....|....|....|....|....|....|...
afc1       TTCGAGCCATTGATGGAGAAGACAAGAAGACAGATTAA 1275
AT4g01320  TTCGAGCCATTGATGGAGAAGACAAGAAGACAGATTAA 1380
AF007269   TTCGAGCCATTGATGGAGAAGACAAGAAGACAGATTAA 3098
Consensus  TTCGAGCCATTGATGGAGAAGACAAGAAGACAGATTAA 3098
```

Table 34. ClustalW Analysis of Generic Amino Acids 1) afc1 (SEQ ID NO:125)
2) AT4g01320 (SEQ ID NO:127)
3) AF007269 (SEQ ID NO:129)
4) Consensus (SEQ ID NO:166)

```
                         10        20        30        40        50        60
                 ....|....|....|....|....|....|....|....|....|....|....|....|
afc1             MAIPFMETVVGFMIVMYIFETYLDLRQLTALKLPTLPKTLVGVISQEKFEKSRAYS--LD 58
AT4g01320        MAIPFMETVVGFMIVMYIFETYLDLRQLTALKLPTLPKTLVGVISQEKFEKSRAYRDIIT 60
AF007269         MAIPFMETVVGFMIVMYIFETYLDLRQLTALKLPTLPKTLT------------------- 41
Consensus Publi  MAIPFMETVVGFMIVMYIFETYLDLRQLTALKLPTLPKTLXXXXXXXXXXXXXXXXXXXX 60

                         70        80        90       100       110       120
                 ....|....|....|....|....|....|....|....|....|....|....|....|
afc1             K-----SYFHFVHEFVTILMDSAILFFGILPWFWKMSGAVLPRLGLDPENEILHTLSFLA 113
```

```
AT4g01320        ENFNICSYFHFVHEFVTILMDSAILFFGILPWFWKMSGAVLPRLGLDPENEILHTLSFLA 120
AF007269         -------------------------------------------------------T---- 42
Consensus Publi  XXXXXXXXXXXXXXXXXXXXXXXXXXXXXXXXXXXXXGXXXXXXXXXXXXXXXXXXXXXX 120

                      130       140       150       160       170       180
                 ....|....|....|....|....|....|....|....|....|....|....|....|
afc1             GVMTWSQITDLPFSLYSTFVIESRHGFNKQTIWMFIRDMIKGTFLSVILGPPIVAAIIFI 173
AT4g01320        GVMTWSQITDLPFSLYSTFVIESRHGFNKQTIWMFIRDMIKGTFLSVILGPPIVAAIIFI 180
AF007269         ---------DLPFSLYSTFVIESRHGFNKQTIWMFIRDMIKGTFLSVILGPPIVAAIIFI 93
Consensus Publi  XXXXXXXXXXXXXXXXXXXXXXXXXXXXXXXXXXXXXXXXXXXXXXXXXXXXXXXXXXXX 180

                      190       200       210       220       230       240
                 ....|....|....|....|....|....|....|....|....|....|....|....|
afc1             VQKGGPYLAIYLWAFMFILSLVMMTIYPVLIAPLFNKFTPLPDGDLREKIEKLASSLKFP 233
AT4g01320        VQKGGPYLAIYLWAFMFILSLVMMTIYPVLIAPLFNKFTPLPDGDLREKIEKLASSLKFP 240
AF007269         VQKGGPYLAIYLWAFMFILSLVMMTIYPVLIAPLFNKFTPLPDGDLREKIEKLASSLKFP 153
Consensus Publi  XXXXXXXXXXXXXXXXXXXXXXXXXXXXXXXXXXXXXXXXXXXXXXXXXXXXXXXXXXXX 240

                      250       260       270       280       290       300
                 ....|....|....|....|....|....|....|....|....|....|....|....|
afc1             LKKLFVVDGSTRSSHSNAYMYGFFKNKRIVLYDTLIQQCKNEDEIVAVIAHELGHWKLNH 293
AT4g01320        LKKLFVVDGSTRSSHSNAYMYGFFKNKRIVLYDTLIQQCKNEDEIVAVIAHELGHWKLNH 300
AF007269         LKKLFVVDGSTRSSHSNAYMYGFFKNKRIVLYDTLIQQCKNEDEIVAVIAHELGHWKLNH 213
Consensus Publi  XXXXXXXXXXXXXXXXXXXXXXXXXXXXXXXXXXXXXXXXXXXXXXXXXXXXXXXXXXXX 300

                      310       320       330       340       350       360
                 ....|....|....|....|....|....|....|....|....|....|....|....|
afc1             TTYSFIAVQILAFLQFGGYTLVRNSTDLFRSFGFDTQPVLIGLIIFQHTVIPLQHLVSFG 353
AT4g01320        TTYSFIAVQILAFLQFGGYTLVRNSTDLFRSFGFDTQPVLIGLIIFQHTVIPLQHLVSFG 360
AF007269         TTYSFIAV--------------------------------------QHTVIPLQHLVSFG 235
Consensus Publi  XXXXXXXXXXXXXXXXXXXXLXRXXXXXXXXXXXXXXXXXXXXIXXQHXVXXXXXLVSXX 360

                      370       380       390       400       410       420
                 ....|....|....|....|....|....|....|....|....|....|....|....|
afc1             LNLVSRAFEFQADAFAVKLGYAKDLRPALVKLQ--------------------------- 386
AT4g01320        LNLVSRAFEFQADAFAVKLGYAKDLRPALVKLQVREDNNRTQTVTSICVTHLNGFFVGIL 420
AF007269         LNLVSRAFEFQADAFAVKLGYAKDLRPALVKLQVREDNNRTQT----------------- 278
Consensus Publi  XXXXXXAFXXXXXXXXXXXXXXXXLXXXXXXXXXXXXXXXXXXXXXXXXXXXXXXXXGXX 420

                      430       440       450       460       470       480
                 ....|....|....|....|....|....|....|....|....|....|....|....|
afc1             -EENLSAMNTDPLHSAYHYSHPPLVERLRAIDGEDKKTD--------------------- 424
AT4g01320        QEENLSAMNTDPLYSAYHYSHPPLVERLRAIDGEDKKTD--------------------- 459
AF007269         -EENLSAMNTDPLYSAYHYSHPPLVERLRAIDGEDKKTD--------------------- 316
Consensus Publi  XXXXLSAMNTDPLYSAYHYSHPPLVERLRAIDGEDKKTD--------------------- 480
```

Table 35. ClustalW Analysis of PPI Nucleic Acids

1) PPI-AtCPP (SEQ ID NO:97)
2) PPI-BnCPP (SEQ ID NO:109)
3) PPI-SoyCPP (SEQ ID NO:112)
4) Consensus (SEQ ID NO:167)

```
                   10        20        30        40        50        60
            ....|....|....|....|....|....|....|....|....|....|....|....|
PPI-AtCPP   ATGGCGATTCCTTTCATGGAAACCGTCGTGGGTTTTATGATAGTGATGTACATTTTTGAG 60
PPI-BnCPP   ATGGCGATTCCTTTCATGGAAACCGTCGTTGGTTTTATGATAGTGATGTACGTTTTTGAG 60
PPI-SoyCPP  ATGGCGTTTCCCTACATGGAAGCCGTTGTCGGATTTATGATATTAATGTACATTTTTGAA 60
Consensus   ATGGCGXTTCCXTXCATGGAAXCCGTXGTXGGXTTTATGATAXTXATGTACXTTTTTGAX 60

                   70        80        90       100       110       120
            ....|....|....|....|....|....|....|....|....|....|....|....|
PPI-AtCPP   ACGTATTTGGATCTGAGGCAACTCACTGCTCTCAAGCTTCCAACTCTCCCGAAAACCTTG 120
PPI-BnCPP   ACGTATTTGGATCTGAGGCAACATACTGCTCTCAAGCTTCCCACTCTCCCAAAGACTTTG 120
PPI-SoyCPP  ACTTACTTGGATGTGCGACAACATAGGGCCCTCAAACTTCCTACTCTTCCAAAGACTTTA 120
Consensus   ACXTAXTTGGATXTGXGXCAACXXAXXGCXCTCAAXCTTCCXACTCTXCCXAAXACXTTX 120
```

```
                 130       140       150       160       170       180
PPI-AtCPP  GTTGGTGTAATTAGCCAAGAGAAGTTTGAGAAATCACGAGCATACAGTCTTGACAAAAGC 180
PPI-BnCPP  GTTGGAGTCATTAGCCAAGAGAAGTTTGAGAAATCTCGAGCTTACAGTCTTGACAAAAGC 180
PPI-SoyCPP GAGGGTGTTATCAGCCAAGAGAAATTTGAGAAATCTAGAGCCTATAGTCTTGATAAAAGC 180
Consensus  GXXGGXGTXATXAGCCAAGAGAAXTTTGAGAAATCXXGAGCXTAXAGTCTTGAXAAAAGC 180

                 190       200       210       220       230       240
PPI-AtCPP  TATTTTCACTTTGTTCATGAGTTTGTAACTATACTTATGGACTCTGCAATTTTGTTCTTT 240
PPI-BnCPP  CATTTTCACTTTGTTCATGAGTTTGTTACTATACTTATGGACTCTGCGATTCTGTTCTTT 240
PPI-SoyCPP CACTTCCATTTTGTTCACGAGTTTGTGACAATAGTGACAGACTCTACAATTTTGTACTTT 240
Consensus  XAXTTXCAXTTTGTTCAXGAGTTTGTXACXATAXTXAXXGACTCTXCXATTXTGTXCTTT 240

                 250       260       270       280       290       300
PPI-AtCPP  GGGATCTTGCCTTGGTTTTGGAAGATGTCTGGAGCTGTTTTACCGAGGTTGGGCCTTGAT 300
PPI-BnCPP  GGGATCTTGCCTTGGTTTTGGAAGATATCTGGCGGCTTTCTACCAATGGTGGGACTCGAT 300
PPI-SoyCPP GGGGTATTGCCCTGGTTTTGGAAGAAATCAGGAGATTTTATGACAATAGCTGGTTTCAAT 300
Consensus  GGGXTXTTGCCXTGGTTTTGGAAGAXXTCXGGXGXXXTTXTXXCXAXXXXXGGXXTXXAT 300

                 310       320       330       340       350       360
PPI-AtCPP  CCGGAGAATGAAATACTGCATACTCTTTCATTCTTGGCTGGTGTTATGACATGGTCACAG 360
PPI-BnCPP  CCAGAGAATGAAATCCTGCACACTCTTTCATTCTTGGCTGGTCTTATGACATGGTCACAG 360
PPI-SoyCPP GCTGAGAATGAAATACTGCATACCCTTGCCTTCTTAGCAGGGCTGATGATTTGGTCACAG 360
Consensus  XCXGAGAATGAAATXCTGCAXACXCTTXCXTTCTTXGCXGGXXTXATGAXXTGGTCACAG 360

                 370       380       390       400       410       420
PPI-AtCPP  ATCACTGATTTGCCATTTTCTTTGTACTCAACTTTCGTGATCGAGTCTCGGCATGGGTTC 420
PPI-BnCPP  ATCACTGATTTGCCATTTTCTTTGTACTCAACTTTCGTGATCGAGTCTCGGCATGGGTTC 420
PPI-SoyCPP ATAACAGATTTGCCCTTTTCTCTGTACTCAACTTTTGTGATTGAGGCCCGTCATGGTTTT 420
Consensus  ATXACXGATTTGCCXTTTTCTXTGTACTCAACTTTXGTGATXGAGXCXCGXCATGGXTTX 420

                 430       440       450       460       470       480
PPI-AtCPP  AACAAACAAACAATATGGATGTTCATTAGGGACATGATCAAAGGAACATTCCTCTCTGTC 480
PPI-BnCPP  AACAAACAAACAATATGGATGTTCATTAGGGACATGATCAAAGGAATACTCCTCTCTGTC 480
PPI-SoyCPP AATAAGCAAACACCATGGTTATTCTTTAGGGACATGCTTAAAGGAATTTTCCTTTCTGTA 480
Consensus  AAXAAXCAAACAXXATGGXTXTTCXTTAGGGACATGXTXAAAGGAAXXXTCCTXTCTGTX 480

                 490       500       510       520       530       540
PPI-AtCPP  ATACTAGGCCCACCCATTGTTGCTGCGATAATTTTCATAGTCCAGAAAGGAGGTCCTTAT 540
PPI-BnCPP  ATACCTGCCCCTCCTATCGTTGCCGCAATTATTGTTATAGTTCAGAAAGGAGGTCCTTAG 540
PPI-SoyCPP ATAATTGGTCCACCTATTGTGGCTGCAATCATTGTAATAGTACAGAAAGGAGGTCCATAC 540
Consensus  ATAXXXGXXCCXCCXATXGTXGCXGCXATXATTXTXATAGTXCAGAAAGGAGGTCCXTAX 540

                 550       560       570       580       590       600
PPI-AtCPP  CTTGCCATCTATCTGTGGGCATTCATGTTTATCCTGTCTCTAGTGATGATGACTATATAC 600
PPI-BnCPP  CTCGCCATCTATCTGTGGGCATTCATGTTTATCCTGTCTCTAGTGATGATGACTATATAC 600
PPI-SoyCPP TTGGCCATCTATCTTTGGGTTTTTACGTTTGGTCTTTCTATTGTGATGATGACCCTTTAT 600
Consensus  XTXGCCATCTATCTXTGGGXXTTXAXGTTTXXXCTXTCTXTXGTGATGATGACXXTXTAX 600

                 610       620       630       640       650       660
PPI-AtCPP  CCGGTCTTGATAGCACCGCTCTTCAACAAATTCACTCCTCTTCCAGATGGAGACCTCCGG 660
PPI-BnCPP  CCTGTTTTGATTGCACCTCTTTTCAACAAGTTCACTCCTCTTCCTGATGGAGACCTCCGG 660
PPI-SoyCPP CCAGTACTAATAGCTCCACTCTTCAATAAGTTCACTCCACTTCCAGATGGTCAACTCAGG 660
Consensus  CCXGTXXTXATXGCXCCXCTXTTCAAXAAXTTCACTCCXCTTCCXGATGGXXAXCTCXGG 660

                 670       680       690       700       710       720
PPI-AtCPP  GAGAAGATTGAGAAACTTGCTTCTTCCCTAAAGTTTCCTTTGAAGAAGCTGTTTGTTGTC 720
PPI-BnCPP  GAGAAGATTGAGAAACTTGCTTCTTCTCTAAAGTTTCCTCTGAAGAAGCTGTTTGTTGTC 720
PPI-SoyCPP GAGAAAATCGAGAAACTTGCTTCCTCCCTCAACTATCCGTTAAAGAAACTATTTGTTGTC 720
Consensus  GAGAAXATXGAGAAACTTGCTTCXTCXCTXAAXTXTCCXXTXAAGAAXCTXTTTGTTGTC 720

                 730       740       750       760       770       780
```

```
PPI-AtCPP    GATGGATCTACAAGGTCAAGCCATAGCAATGCTTACATGTATGGTTTCTTTAAGAACAAA 780
PPI-BnCPP    GATGGATCTACAAGGTCAAGCCATAGTAATGCTTACATGTATGGTTTCTTCAAGAACAAA 780
PPI-SoyCPP   GATGGATCCACAAGATCAAGTCACAGCAATGCCTATATGTATGGATTCTTCAAGAACAAG 780
Consensus    GATGGATCXACAAGXTCAAGXCAXAGXAATGCXTAXATGTATGGXTTCTTXAAGAACAAX 780

                       790       800       810       820       830       840
PPI-AtCPP    AGGATTGTTCTTTATGATACGTTGATTCAGCAGTGCAAGAATGAGGATGAAATTGTGGCG 840
PPI-BnCPP    AGGATTGTTCTTTATGACACATTGATTCAGCAGTGCCAGAATGAGAATGAAATTGTGGCG 840
PPI-SoyCPP   AGGATTGTCCCTTATGACACATTAATTCAACAGTGCAAAGACGATGAGGAAATTGTTGCT 840
Consensus    AGGATTGTXCXTTATGAXACXTTXATTCAXCAGTGCXAXXAXGAXXAXGAAATTGTXGCX 840

                       850       860       870       880       890       900
PPI-AtCPP    GTTATTGCACACGAGCTTGGACATTGGAAACTGAATCACACTACATACTCGTTCATTGCA 900
PPI-BnCPP    GTTATTGCACACGAGCTGGGACACTGGAAGCTGAATCACACTACATACTCGTTCATTGCT 900
PPI-SoyCPP   GTTATTGCCCATGAGTTGGGACACTGGAAGCTCAACCATACTGTGTACACATTTGTTGCT 900
Consensus    GTTATTGCXCAXGAGXTXGGACAXTGGAAXCTXAAXCAXACTXXXTACXCXTTXXTTGCX 900

                       910       920       930       940       950       960
PPI-AtCPP    GTTCAAATCCTTGCCTTCTTACAATTTGGAGGATACACTCTTCTCAGAAACTCCACTGAT 960
PPI-BnCPP    GTTCAAATCCTTGCCTTCTTGCAATTTGGAGGATACACTCTTGTCAGAAACTCCACTGAT 960
PPI-SoyCPP   ATGCAGATTCTTACACTTCTACAATTTGGAGGATATACACTAGTGCGAAATTCAGCTGAT 960
Consensus    XTXCAXATXCTTXCXXTXXTXCAATTTGGAGGATAXACXCTXXTXXGAAAXTCXXCTGAT 960

                       970       980       990      1000      1010      1020
PPI-AtCPP    CTCTTCAGGAGTTTCGGATTTGATACACAGCCTGTTCTCATTGGTTTGATCATATTTCAG 1020
PPI-BnCPP    CTCTTCAGGAGTTTTGGTTTTGATACACAACCAGTTCTCATTGGTTTGATCATATTTCAG 1020
PPI-SoyCPP   CTGTATCGAAGCTTTGGGTTTGATACGCAGCCAGTCCTCATTGGGCTCATCATATTTCAG 1020
Consensus    CTXTXXXGXAGXTTXGGXTTTGATACXCAXCCXGTXCTCATTGGXXTXATCATATTTCAG 1020

                      1030      1040      1050      1060      1070      1080
PPI-AtCPP    CACACTGTAATACCACTGCAACATCTAGTAAGCTTTGGCCTGAACCTCGTTAGTCGAGCG 1080
PPI-BnCPP    CACACTGTAATACCACTTCAACACCTAGTAAGCTTTGACCTCAACCTTGTTAGTCGAGCG 1080
PPI-SoyCPP   CATACTGTAATCCCACTTCAGCAATTGGTCAGCTTTGGTCTGAACCTAGTCAGCCGATCA 1080
Consensus    CAXACTGTAATXCCACTXCAXCAXXTXGTXAGCTTTGXXCTXAACCTXGTXAGXCGAXCX 1080

                      1090      1100      1110      1120      1130      1140
PPI-AtCPP    TTTGAGTTTCAGGCTGATGCTTTTGCTGTGAAGCTTGACTATGCAAAAGATCTTCGTCCT 1140
PPI-BnCPP    TTTGAGTTTCAGGCTGATGCTTTTGCAGTGAATCTTGGTTATGCAAAGGATCTACGTCCT 1140
PPI-SoyCPP   TTTGAATTTCAGGCTGATGGCTTTGCCAAGAAGCTTGGATATGCATCTGGATTACGCGGT 1140
Consensus    TTTGAXTTTCAGGCTGATGXXTTTGCXXXGAAXCTTGXXTATGCAXXXGXXXTXCGXXXT 1140

                      1150      1160      1170      1180      1190      1200
PPI-AtCPP    GCTCTAGTGAAACTACAGGAAGAGAACTTATCAACAATGAACACTGATCCATTGTACTCA 1200
PPI-BnCPP    GCCCTAGTGAAGCTACAGGAAGAGAACTTATCAGCGATGAACACAGACCCATTGTACTCA 1200
PPI-SoyCPP   GGTCTTGTGAAACTACAGGAGGAGAATCTGTCAGCTATGAATACAGATCCTTGGTACTCT 1200
Consensus    GXXCTXGTGAAXCTACAGGAXGAGAAXXTXTCAXCXATGAAXACXGAXCCXTXGTACTCX 1200

                      1210      1220      1230      1240      1250      1260
PPI-AtCPP    GCTTATCACTACTCACATCCTCCTCTTGTTGAAAGGCTTCGAGCCACTGATGGAGAAGAC 1260
PPI-BnCPP    GCTTATCACTACTCACACCCTCCTCTTGTAGAGAGGCTTCGAGCCATTGATGGAGAAGAC 1260
PPI-SoyCPP   GCTTATCACTATTCTCATCCTCCCCTTGTTGAAAGATTGGCCGCGCTGGACGAACCGGAT 1260
Consensus    GCTTATCACTAXTCXCAXCCTCCXCTTGTXGAXAGXXTXXXXGCXXXXGAXGXAXXXGAX 1260

                      1270
PPI-AtCPP    AAGAAGACAGATTAA 1275
PPI-BnCPP    AAGAAGACAGATTAA 1275
PPI-SoyCPP   AAGAAGGAAGACTAA 1275
Consensus    AAGAAGXXAGAXTAA 1275
```

Table 36. ClustalW Analysis of PPI Amino Acids

1) PPI-AtCPP (SEQ ID NO:98)
2) PPI-BnCPP (SEQ ID NO:110)
3) PPI-SoyCPP (SEQ ID NO:113)
4) Consensus (SEQ ID NO:168)

```
                           10        20        30        40        50        60
                   ....|....|....|....|....|....|....|....|....|....|....|....|
PPI-AtCPP          MAFPYMEAVVGFMILMYIFETYLDVRQHRALKLPTLPKTLEGVISQEKFEKSRAYSLDKS  60
PPI-BnCPP          MAIPEMETVVGFMIVMYVFETYLDLRQHTALKLPTLPKTLVGVISQEKFEKSRAYSLDKS  60
PPI-SoyCPP         MAFPYMEAVVGFMILMYIFETYLDVRQHRALKLPTLPKTLEGVISQEKFEKSRAYSLDKS  60
Consensus PPI      MAXPXMEXVVGFMIXMYXFETYLDXRQHXALKLPTLPKTLXGVISQEKFEKSRAYSLDKS  60

                           70        80        90       100       110       120
                   ....|....|....|....|....|....|....|....|....|....|....|....|
PPI-AtCPP          HFHFVHEFVTIVTDSTILYFGVLPWFWKKSGDFMTIAGFNAENEILHTLAFLAGLMIWSQ  120
PPI-BnCPP          HFHFVHEFVTILMDSAILFFGILPWFWKISGGFLPMVGLDPENEILHTLSFLAGLMTWSQ  120
PPI-SoyCPP         HFHFVHEFVTIVTDSTILYFGVLPWFWKKSGDFMTIAGFNAENEILHTLAFLAGLMIWSQ  120
Consensus PPI      HFHFVHEFVTIXXDSXILXFGXLPWFWKXSGXFXXXXGXXXENEILHTLXFLAGLMXWSQ  120

                          130       140       150       160       170       180
                   ....|....|....|....|....|....|....|....|....|....|....|....|
PPI-AtCPP          ITDLPFSLYSTFVIEARHGFNKQTPWLFFRDMLKGIFLSVIIGPPIVAAIIVIVQKGGPY  180
PPI-BnCPP          ITDLPFSLYSTFVIESRHGFNKQTIWMFIRDMIKGILLSVIPAPPIVAAIIVIVQKGGPY  180
PPI-SoyCPP         ITDLPFSLYSTFVIEARHGFNKQTPWLFFRDMLKGIFLSVIIGPPIVAAIIVIVQKGGPY  180
Consensus PPI      ITDLPFSLYSTFVIEXRHGFNKQTXWXFXRDMXKGIXLSVIXXPPIVAAIIVIVQKGGPY  180

                          190       200       210       220       230       240
                   ....|....|....|....|....|....|....|....|....|....|....|....|
PPI-AtCPP          LAIYLWVFTFGLSIVMMTLYPVLIAPLFNKFTPLPDGQLREKIEKLASSLNYPLKKLFVV  240
PPI-BnCPP          LAIYLWAFMFILSLVMMTIYPVLIAPLFNKFTPLPDGDLREKIEKLASSLKFPLKKLFVV  240
PPI-SoyCPP         LAIYLWVFTFGLSIVMMTLYPVLIAPLFNKFTPLPDGQLREKIEKLASSLNYPLKKLFVV  240
Consensus PPI      LAIYLWXFXFXLSXVMMTXYPVLIAPLFNKFTPLPDGXLREKIEKLASSLXXPLKKLFVV  240

                          250       260       270       280       290       300
                   ....|....|....|....|....|....|....|....|....|....|....|....|
PPI-AtCPP          DGSTRSSHSNAYMYGFFKNKRIVPYDTLIQQCKDDEEIVAVIAHELGHWKLNHTVYTFVA  300
PPI-BnCPP          DGSTRSSHSNAYMYGFFKNKRIVLYDTLIQQCQNENEIVAVIAHELGHWKLNHTTYSFIA  300
PPI-SoyCPP         DGSTRSSHSNAYMYGFFKNKRIVPYDTLIQQCKDDEEIVAVIAHELGHWKLNHTVYTFVA  300
Consensus PPI      DGSTRSSHSNAYMYGFFKNKRIVXYDTLIQQCXXXXEIVAVIAHELGHWKLNHTXYXFXA  300

                          310       320       330       340       350       360
                   ....|....|....|....|....|....|....|....|....|....|....|....|
PPI-AtCPP          MQILTLLQFGGYTLVRNSADLYRSFGFDTQPVLIGLIIFQHTVIPLQQLVSFGLNLVSRS  360
PPI-BnCPP          VQILAFLQFGGYTLVRNSTDLFRSFGFDTQPVLIGLIIFQHTVIPLQHLVSFDLNLVSRA  360
PPI-SoyCPP         MQILTLLQFGGYTLVRNSADLYRSFGFDTQPVLIGLIIFQHTVIPLQQLVSFGLNLVSRS  360
Consensus PPI      XQILXXLQFGGYTLVRNSXDLXRSFGFDTQPVLIGLIIFQHTVIPLQXLVSFXLNLVSRX  360

                          370       380       390       400       410       420
                   ....|....|....|....|....|....|....|....|....|....|....|....|
PPI-AtCPP          FEFQADGFAKKLGYASGLRGGLVKLQEENLSAMNTDPWYSAYHYSHPPLVERLAALDEPD  420
PPI-BnCPP          FEFQADAFAVNLGYAKDLRPALVKLQEENLSAMNTDPLYSAYHYSHPPLVERLRAIDGED  420
PPI-SoyCPP         FEFQADGFAKKLGYASGLRGGLVKLQEENLSAMNTDPWYSAYHYSHPPLVERLAALDEPD  420
Consensus PPI      FEFQADXFAXXLGYAXXLRXXLVKLQEENLSAMNTDPXYSAYHYSHPPLVERLXAXDXXD  420

                          430       440       450       460       470       480
                   ....|....|....|....|....|....|....|....|....|....|....|....|
PPI-AtCPP          KKED--------------------------------------------------------  424
PPI-BnCPP          KKTD--------------------------------------------------------  424
PPI-SoyCPP         KKED--------------------------------------------------------  424
Consensus PPI      KKXD                                                          480
```

Table 37. ClustalW Analysis of PPI/Generic Nucleic Acids

1) PPI-AtCPP (SEQ ID NO:97)
2) PPI-BnCPP (SEQ ID NO:109)
3) PPI-SoyCPP (SEQ ID NO:112)
4) afc1 (SEQ ID NO:124)
5) AT4g01320 (SEQ ID NO:126)
6) AF007269 (SEQ ID NO:128)
6) Consensus (SEQ ID NO:170)

```
                        10        20        30        40        50        60        70
                ....|....|....|....|....|....|....|....|....|....|....|....|....|....|
PPI-AtCPP NA    ----------------------------------------------------------------------
PPI-BnCPP       ----------------------------------------------------------------------
PPI-SoyCPP      ----------------------------------------------------------------------
afc1            ----------------------------------------------------------------------
AT4g01320       ----------------------------------------------------------------------
AF007269        ATGGCGATTCCTTTCATGGAAACCGTCGTGGGTAAGCTTCAAAACCTTTTTCTGAGACATTTTACTATCC
Consensus       ----------------------------------------------------------------------

                        80        90       100       110       120       130       140
                ....|....|....|....|....|....|....|....|....|....|....|....|....|....|
PPI-AtCPP NA    ----------ATGGCGTTTCCCTACATGGAAGCCGTTGTCGGATTTATGATATTAATGTACATTTTTGAA
PPI-BnCPP       ----------------------------------------------------------------------
PPI-SoyCPP      ----------ATGGCGTTTCCCTACATGGAAGCCGTTGTCGGATTTATGATATTAATGTACATTTTTGAA
afc1            ----------------------------------------------------------------------
AT4g01320       ----------------------------------------------------------------------
AF007269        TGTTTCACTCATCGTATTTCGTTTTTGTTTGGGTTTTGCTTTCTGTGTTGTGTGTGTTGAGATTCCATGA
Consensus       ----------ATGGCGATTCCTTTCATGGAAACCGTCGT-GGTTTTATGATAT--ATGTACATTTTTGAA

                       150       160       170       180       190       200       210
                ....|....|....|....|....|....|....|....|....|....|....|....|....|....|
PPI-AtCPP NA    ACTTACTTGGATG-TGCGACAACATAGGGCCCTCAAACTTCCTACTCTTCCAAAGACTTTAGAGGGTGTT
PPI-BnCPP       ----------------------------------------------------------------------
PPI-SoyCPP      ACTTACTTGGATG-TGCGACAACATAGGGCCCTCAAACTTCCTACTCTTCCAAAGACTTTAGAGGGTGTT
afc1            ----------------------------------------------------------------------
AT4g01320       ----------------------------------------------------------------------
AF007269        -CTCGTTTGTTTCATATACCATCGTCTCTGCTTCTCGTTTCTAAATTTTGTTCTTTTCTAATAGTGCGTA
Consensus       --CTATTTGGAT----TGGCAACATG----CCTCAA--CTTCCACTCTCC---AAACTTGGTGGTGTAT-

                       220       230       240       250       260       270       280
                ....|....|....|....|....|....|....|....|....|....|....|....|....|....|
PPI-AtCPP NA    ATCAGCCAAGAGAAATTTGAGAAATCTAGAGCCTATAGTCTTGATAAAAGCCACTTCCATTTTGTTCACG
PPI-BnCPP       ----------------------------------------------------------------------
PPI-SoyCPP      ATCAGCCAAGAGAAATTTGAGAAATCTAGAGCCTATAGTCTTGATAAAAGCCACTTCCATTTTGTTCACG
afc1            ----------------------------------------------------------------------
AT4g01320       ----------------------------------------------------------------------
AF007269        CCTTGATCTGAGGTTTTATTACTCCTACTAGTTTCTTGTCTTACTCGTG--CGTTT-GATTTGATTTGAG
Consensus       ---AGCCAAGAGAAGTTTGAGAAATCTGAG--CTACAGTCTTGAAAAAG--CATT--CATTT-GTTCA-G

                       290       300       310       320       330       340       350
                ....|....|....|....|....|....|....|....|....|....|....|....|....|....|
PPI-AtCPP NA    AGTTTGTGACAATAGTGACAGACTCTACAATTTTGTACTTTGGGGTATTGCCCTGGTTTTGGAA-----G
PPI-BnCPP       ----------------------------------------------------------------------
PPI-SoyCPP      AGTTTGTGACAATAGTGACAGACTCTACAATTTTGTACTTTGGGGTATTGCCCTGGTTTTGGAA-----G
afc1            ----------------------------------------------------------------------
AT4g01320       ----------------------------------------------------------------------
AF007269        CTTATGTGA-TTTCATCATCTCTTCCTCGGTTTTAGAATGTACGGAGCTTCTCTGTTAACCAAAATCTAG
Consensus       AGTTTGTA--CATAGT--TAGACTCT-CAATTTTGT-CTTTGGG---TTTGCCTGGTTTTGGAA-----G

                       360       370       380       390       400       410       420
                ....|....|....|....|....|....|....|....|....|....|....|....|....|....|
PPI-AtCPP NA    AAATCAGGAGATTTTATGACAATAGCTGGTTTCAATGCTGAGAATGAAATACTGCATACCCTTGCCTTCT
PPI-BnCPP       ----------------------------------------------------------------------
```

```
PPI-SoyCPP     AAATCAGGAGATTTTATGACAATAGCTGGTTTCAATGCTGAGAATGAAATACTGCATACCCTTGCCTTCT
afc1           ----------------------------------------------------------------------
AT4g01320      ----------------------------------------------------------------------
AF007269       GATTTGGGAAGAAAAGTCGGAGTCTTTTTTTTCCTCATTCCCGATTGGAAATTGAGAATCTTGAAATTTT
Consensus      AT-TCGGG---TTTTGCAA------TTGGT-----CATCGAGAATGAAAT-CTGCATACC-TT--CTTCT

                        430       440       450       460       470       480       490
               ....|....|....|....|....|....|....|....|....|....|....|....|....|....|
PPI-AtCPP NA   TAGCAGGGCTGATGATTTGGTCACAGATAACAGATTTGCCCTTTTCTCTGTACTCAACTTTT-----GTG
PPI-BnCPP      ----------------------------------------------------------------------
PPI-SoyCPP     TAGCAGGGCTGATGATTTGGTCACAGATAACAGATTTGCCCTTTTCTCTGTACTCAACTTTT-----GTG
afc1           ----------------------------------------------------------------------
AT4g01320      ----------------------------------------------------------------------
AF007269       TCTTTGTTCAAGTCATACAGCTTGAGGTTTTGGGTTTTCTTGTCAGGGTATTATTATGTTCGTGACTGCA
Consensus      T-GCGGT----ATGAT--GGTCACAGATA--CGATTTGCCTTTTCTT--GTACTCAACTTT------GTG

                        500       510       520       530       540       550       560
               ....|....|....|....|....|....|....|....|....|....|....|....|....|....|
PPI-AtCPP NA   ATTGAGGCCCGTCATGGTTTTAATAAGCAAACAC--CATGGTTATTCTTTAGGGACATGCTTAAAGGAAT
PPI-BnCPP      ----------------------------------------------------------------------
PPI-SoyCPP     ATTGAGGCCCGTCATGGTTTTAATAAGCAAACAC--CATGGTTATTCTTTAGGGACATGCTTAAAGGAAT
afc1           ----------------------------------------------------------------------
AT4g01320      ----------------------------------------------------------------------
AF007269       ACTAGAGTTTTCTGGAGTTTTTTGAAATGGGTTTTGTGTTGTGGAACCGTATGTGAATGTTGCATCAAAA
Consensus      AT--GAGTCCG-CATGGTTAAAACAAACA-------CATGGTT---TCTTAGGGACATG--TAAAGGAAT

                        570       580       590       600       610       620       630
               ....|....|....|....|....|....|....|....|....|....|....|....|....|....|
PPI-AtCPP NA   TTTCCTTTCTGTAATAATTGGTCCACCTATTGTGGCTGCAA------TCATTGTAA-TAGTACAGAAAGG
PPI-BnCPP      ----------------------------------------------------------------------
PPI-SoyCPP     TTTCCTTTCTGTAATAATTGGTCCACCTATTGTGGCTGCAA------TCATTGTAA-TAGTACAGAAAGG
afc1           ----------------------------------------------------------------------
AT4g01320      ----------------------------------------------------------------------
AF007269       CTCTTTCAGTGCTCCAATGTTTCCATCAGTAGTCAGCACAAGAGATCTTTTTATATCTGGTTGATCAAAA
Consensus      TTCCTTCTGTATA------G--CC-CCTATTGTG-CTGCAA------T-ATTGTA--TAGT-CAGAAAGG

                        640       650       660       670       680       690       700
               ....|....|....|....|....|....|....|....|....|....|....|....|....|....|
PPI-AtCPP NA   AGGTCCATA--CTTGGCCATCTATCTTTGGGTTTTTACGTTTGGTCTTTCTATTGTGATGATGACCCTTT
PPI-BnCPP      --------------------------------------------------------------------AT
PPI-SoyCPP     AGGTCCATA--CTTGGCCATCTATCTTTGGGTTTTTACGTTTGGTCTTTCTATTGTGATGATGACCCTTT
afc1           --------------------------------------------------------------------AT
AT4g01320      --------------------------------------------------------------------AT
AF007269       AAGTAGATGATGTTATTGAATTTTCAGTGATGGAGTATCTGTTGTTGTGGCATTTAGAGTAGATTCGTAT
Consensus      AGGTCC-----TATG-CCATCTATCTTGGG---------TTTAGTTTTCTTCTTGTGATGATGACC--TT

                        710       720       730       740       750       760       770
               ....|....|....|....|....|....|....|....|....|....|....|....|....|....|
PPI-AtCPP NA   ATCCAGTACTA-ATAGCTCCACTCTTCAATAAGTTCACTCCACT--TCCAGATGGTCAACTCAGGGAGAA
PPI-BnCPP      GGCGATTCCT--TTCATGGAAACCGTCGTTGGTTTTATGATAGTGATGTACGTTTTGAGACGTATTTGG
PPI-SoyCPP     ATCCAGTACTA-ATAGCTCCACTCTTCAATAAGTTCACTCCACT--TCCAGATGGTCAACTCAGGGAGAA
afc1           GGCGATTCCT--TTCATGGAAACCGTCGTGGGTTTTATGATAGTGATGTACATTTTGAGACGTATTTGG
AT4g01320      GGCGATTCCT--TTCATGGAAACCGTCGTGGGTTTTATGATAGTGATGTACATTTTGAGACGTATTTGG
AF007269       TTCATCTTCTGTTTTATTCTTTTTCTTACAGGTTTTATGATAGTGATGTACATTTTGAGACGTATTTGG
Consensus      A-CC--------GTTATGCCCCTCTTCAA-AAGTTCACTCC-CT--TCCAGATGG---ACTC-GGGAGAA

                        780       790       800       810       820       830       840
               ....|....|....|....|....|....|....|....|....|....|....|....|....|....|
PPI-AtCPP NA   AATCGAGA-AACTTGCTTCCTCCCT-CAACTATCCGTTAAAGAAACTATTTGTTGTCGATGGATCCACAA
PPI-BnCPP      ATCTGAGGCAACTATACTGCTCTCAAGCTTCCCACTCTCCCAAAGACT-TTGGTTGGAG-TCATTAGCCAA
PPI-SoyCPP     AATCGAGA-AACTTGCTTCCTCCCT-CAACTATCCGTTAAAGAAACTATTTGTTGTCGATGGATCCACAA
afc1           ATCTGAGGCAACTCACTGCTCTCAAGCTTCCAACTCTCCCGAAAACC-TTGGTTGGTG-TAATTAGCCAA
AT4g01320      ATCTGAGGCAACTCACTGCTCTCAAGCTTCCAACTCTCCCGAAAACC-TTGGTTGGTG-TAATTAGCCAA
AF007269       ATCTGAGGCAACTCACTGCTCTCAAGCTTCCAACTCTCCCGAAAACC-TTGGTTGGTG-TAATTAGCCAA
Consensus      A--TGAGA-AACTTGCTTCTCCT----A---ATTCCTTAAG--AACTATTTGTTGTCGATGGATC-ACAA

                        850       860       870       880       890       900       910
               ....|....|....|....|....|....|....|....|....|....|....|....|....|....|
PPI-AtCPP NA   GATCAAGTCACAGCAATGCCTATATGTATGGATTCTTCAAGAACAAGAGGATTGTCC---CTTATGACAC
PPI-BnCPP      G-AGAAGTTTGAGAAATCTCGA-GCTTACAG---------------------------------------
PPI-SoyCPP     GATCAAGTCACAGCAATGCCTATATGTATGGATTCTTCAAGAACAAGAGGATTGTCC---CTTATGACAC
```

```
afc1         G-AGAAGTTTGAGAAATCACGA-GCATACAG---------------------------------------
AT4g01320    G-AGAAGTTTGAGAAATCACGA-GCATACAG---------------------------------------
AF007269     G-AGAAGTTTGAGAAATCACGA-GCATACAGTCTTGACAAAAGGTTTCGTCTTGATCATATTTATATCAT
Consensus    G-TCAAG-CATAG-AATGCTAA--TGTATGG--TTCTTAAGAACAA-AGGATTGTC-----TTATGACAC

                    920       930       940       950       960       970       980
             ....|....|....|....|....|....|....|....|....|....|....|....|....|....|
PPI-AtCPP NA ATTAATTC-------------AACAGTGCAAAGAC-GATGAGGAAATTGTTG-CTGTTATTGCCCATGAG
PPI-BnCPP    ----------------------------------------TCTTGACAAA---AGCCATTTTCACTTTG
PPI-SoyCPP   ATTAATTC-------------AACAGTGCAAAGAC-GATGAGGAAATTGTTG-CTGTTATTGCCCATGAG
afc1         ----------------------------------------TCTTGACAAA---AGCTATTTTCACTTTG
AT4g01320    ------------------------GGATATCATCACTGAGAACTTTAATATATGCAGCTATTTTCACTTTG
AF007269     TTTAGTTTTTTATAATTGCCAGGGGATATCATCACTGAGAACTTTAATATATGCAGCTATTTTCACTTTG
Consensus    ATTATTC---------------ACAGTGCAA--------GAAGAAATTGTG---CGTTATTGCC---AGA

                    990      1000      1010      1020      1030      1040      1050
             ....|....|....|....|....|....|....|....|....|....|....|....|....|....|
PPI-AtCPP NA TTGGGACACTGCAAGCTCAACCATACTGTGTACACATTTGTTGCTATGCAGATTCTTACACTTCTACAAT
PPI-BnCPP    TTCATGAGTTTGTTACTATA-CTTATGGACTCTGCGAT-TCTGTTCTTTGGGATCTTGC----CTTGGTT
PPI-SoyCPP   TTGGGACACTGCAAGCTCAACCATACTGTGTACACATTTGTTGCTATGCAGATTCTTACACTTCTACAAT
afc1         TTCATGAGTTTGTAACTATA-CTTATGGACTCTGCAAT-TTTGTTCTTTGGGATCTTGC----CTTGGTT
AT4g01320    TTCATGAGTTTGTAACTATA-CTTATGGACTCTGCAAT-TTTGTTCTTTGGGATCTTGC----CTTGGTT
AF007269     TTCATGAGTTTGTAACTATA-CTTATGGACTCTGCAAT-TTTGTTCTTTGGGATCTTGC----CTTGGTT
Consensus    GTGGGACACTGCAA-------CTAACAACTTACACATT-ATTGCTTC----AATCTT----CTTTACAAT

                   1060      1070      1080      1090      1100      1110      1120
             ....|....|....|....|....|....|....|....|....|....|....|....|....|....|
PPI-AtCPP NA TTGGAGGATATACACTAGTGCGAAATTCAGCTGATCTGTATCGAAGCTTTGGGTTTGATACGCAGCCAGT
PPI-BnCPP    TTGGAAG---------------------------------------------------------------
PPI-SoyCPP   TTGGAGGATATACACTAGTGCGAAATTCAGCTGATCTGTATCGAAGCTTTGGGTTTGATACGCAGCCAGT
afc1         TTGGAAG---------------------------------------------------------------
AT4g01320    TTGGAAG---------------------------------------------------------------
AF007269     TTGGAAGGTACATATCTGGTTTCGGTATACAGTATCT-CATTTTGAATATAGAGTTGTTACATTACAA--
Consensus    TTGGAGGATACAC-CTAGTG--AAATCC---TGATCT----TGAG----TTGGTTTGATAC-CAGCCG--

                   1130      1140      1150      1160      1170      1180      1190
             ....|....|....|....|....|....|....|....|....|....|....|....|....|....|
PPI-AtCPP NA CCTCATTGGGCTCATCATATTTCAGCATACTGTAATCCCACTTCAGCAATTGGTCAGCTTTGGTCT---G
PPI-BnCPP    --------------------------ATATCTGGCGGC-TTTCTACCAA-TGGTGGGACTCGATCCAGAG
PPI-SoyCPP   CCTCATTGGGCTCATCATATTTCAGCATACTGTAATCCCACTTCAGCAATTGGTCAGCTTTGGTCT---G
afc1         --------------------------ATGTCTGGAGCT-GTTTTACCGA-GGTTGGGCCTTGATCCAGAG
AT4g01320    --------------------------ATGTCTGGAGCT-GTTTTACCGA-GGTTGGGCCTTGATCCAGAG
AF007269     TTGTAAAGTTTCATTTTTACCTTAGATGTCTGGAGCT-GTTTTACCGA-GGTTGGGCCTTGATCCAGAG
Consensus    TCTCATTGG---TATCATATTTCAGCATACTGTAATCC-ACTTCA-----CATGTAGCTTTGCT------

                   1200      1210      1220      1230      1240      1250      1260
             ....|....|....|....|....|....|....|....|....|....|....|....|....|....|
PPI-AtCPP NA AACCTAGTCAGCCGATCATTTGAATTTCAGGCTGATGGCTTTGCCAAGAAGCTTGGATATGCATCTGGAT
PPI-BnCPP    AATGAAATCCTGCACACTCTTTCATTCTTGGCTGGTC-TTATGACATGGTCACAG---------------
PPI-SoyCPP   AACCTAGTCAGCCGATCATTTGAATTTCAGGCTGATGGCTTTGCCAAGAAGCTTGGATATGCATCTGGAT
afc1         AATGAAATACTGCATACTCTTTCATTCTTGGCTGGTG-TTATGACATGGTCACAG---------------
AT4g01320    AATGAAATACTGCATACTCTTTCATTCTTGGCTGGTG-TTATGACATGGTCACAG---------------
AF007269     AATGAAATACTGCATACTCTTTCATTCTTGGCTGGTG-TTATGACATGGTCACAGGTGTTCCAAATAAAC
Consensus    AACCTG------TAGCGACTTTGATTTCAGGCTGATG-CTTTGC---GAAGCTTGG-TATGCAGTCGG--

                   1270      1280      1290      1300      1310      1320      1330
             ....|....|....|....|....|....|....|....|....|....|....|....|....|....|
PPI-AtCPP NA TACGCGGTG--GTCTTGTGAAACTACAGGAGGAGAATCTGTCAGCT----ATGAATACAGATCCTTGGTA
PPI-BnCPP    ----------------------------------------------------------------------
PPI-SoyCPP   TACGCGGTG--GTCTTGTGAAACTACAGGAGGAGAATCTGTCAGCT----ATGAATACAGATCCTTGGTA
afc1         ----------------------------------------------------------------------
AT4g01320    ----------------------------------------------------------------------
AF007269     CCCTTCATATAGTCCTATACGTTTAGCATCAAAATATCTATTTTCTTAAGATAATAATATTTCTTTTATA
Consensus    --T--------GTCTAGTGAA-CTACAGGAGAGAA---TGTCAGC-----ATGAA-ACAGATCCTTG-TA

                   1340      1350      1360      1370      1380      1390      1400
             ....|....|....|....|....|....|....|....|....|....|....|....|....|....|
PPI-AtCPP NA CTCT---GCTTATCACTATTCTCATCCTCCCCT-----TGTTGAAAGATTGGCCGCGCTGGACGAA----
PPI-BnCPP    -----------ATCACTGATTTGCCATTTTCTTTG---TACTCAACTTTCG-------TGATCGAG----
PPI-SoyCPP   CTCT---GCTTATCACTATTCTCATCCTCCCCT-----TGTTGAAAGATTGGCCGCGCTGGACGAA----
afc1         -----------ATCACTGATTTGCCATTTTCTTTG---TACTCAACTTTCG-------TGATCGAG----
```

```
AT4g01320     -----------ATCACTGATTTGCCATTTTCTTTG---TACTCAACTTTCG-------TGATCGAG----
AF007269      TTCTGATGCAGATCACTGATTTGCCATTTTCTTTG---TACTCAACTTTCG-------TGATCGAG----
Consensus     CTC----GCTTATCACTATCCACCTCCCTTGTGAAAGATGCTGAGAGAAAGAAGAGATAATCTAAATTCT

                        1410      1420      1430      1440      1450      1460      1470
              ....|....|....|....|....|....|....|....|....|....|....|....|....|....|
PPI-AtCPP NA  --CCGGATAAGAAGGAAGACTAA-----------------------------------------------
PPI-BnCPP     --TCTCGGCATGGGTTCAACAAA-----------------------------------------------
PPI-SoyCPP    --CCGGATAAGAAGGAAGACTAA-----------------------------------------------
afc1          --TCTCGGCATGGGTTCAACAAA-----------------------------------------------
AT4g01320     --TCTCGGCATGGGTTCAACAAA-----------------------------------------------
AF007269      --TCTCGGCATGGGTTCAACAAAGTATGTCGTATTTCCAACACTACCTTGTGACTTACGTTTTTTTATCA
Consensus     TTCCTTTTCATGGAGGTAACAAAGTATGTCGTATTTCCAACACTACCTTGTGACTTACGTTTTTTTATCA

                        1480      1490      1500      1510      1520      1530      1540
              ....|....|....|....|....|....|....|....|....|....|....|....|....|....|
PPI-AtCPP NA  ----------------------------------------------------------------------
PPI-BnCPP     ---------------------------------------CAAACAATATGGATGTTCATTAGGGACATGA
PPI-SoyCPP    ----------------------------------------------------------------------
afc1          ---------------------------------------CAAACAATATGGATGTTCATTAGGGACATGA
AT4g01320     ---------------------------------------CAAACAATATGGATGTTCATTAGGGACATGA
AF007269      GAGATGTGGATTAAATTTGCTTCTAAATTCTGTTGACAGCAAACAATATGGATGTTCATTAGGGACATGA
Consensus     GAGATGTGGATTAAATTTGCTTCTAAATTCTGTTGACAGCAAACAATATGGATGTTCATTAGGGACATGA

                        1550      1560      1570      1580      1590      1600      1610
              ....|....|....|....|....|....|....|....|....|....|....|....|....|....|
PPI-AtCPP NA  ----------------------------------------------------------------------
PPI-BnCPP     TCAAAGGAATACTCCTCTCTGTCATACCTGCCCCTCCTATCGTTGGCGCAATTATTGTTATAGTTCAG--
PPI-SoyCPP    ----------------------------------------------------------------------
afc1          TCAAAGGAACATTCCTCTCTGTCATACTAGGCCCACCCATTGTTGCTGCGATAATTTTCATAGTCCAG--
AT4g01320     TCAAAGGAACATTCCTCTCTGTCATACTAGGCCCACCCATTGTTGCTGCGATAATTTTCATAGTCCAG--
AF007269      TCAAAGGAACATTCCTCTCTGTCATACTAGGCCCACCCATTGTTGCTGCGATAATTTTCATAGTCCAGGT
Consensus     TCAAAGGAACATTCCTCTCTGTCATACTAGGCCCACCCATTGTTGCTGCGATAATTTTCATAGTCCAGGT

                        1620      1630      1640      1650      1660      1670      1680
              ....|....|....|....|....|....|....|....|....|....|....|....|....|....|
PPI-AtCPP NA  ----------------------------------------------------------------------
PPI-BnCPP     ----------------------------------------------------------------------
PPI-SoyCPP    ----------------------------------------------------------------------
afc1          ----------------------------------------------------------------------
AT4g01320     ----------------------------------------------------------------------
AF007269      TTGATGATTCTGGATTCATCTTATTTCTGAGTTTTTCACATGGATGACTATTCTCCATTGAGTGTGAGCT
Consensus     TTGATGATTCTGGATTCATCTTATTTCTGAGTTTTTCACATGGATGACTATTCTCCATTGAGTGTGAGCT

                        1690      1700      1710      1720      1730      1740      1750
              ....|....|....|....|....|....|....|....|....|....|....|....|....|....|
PPI-AtCPP NA  ----------------------------------------------------------------------
PPI-BnCPP     ----------------------------------------------------------------------
PPI-SoyCPP    ----------------------------------------------------------------------
afc1          ----------------------------------------------------------------------
AT4g01320     ----------------------------------------------------------------------
AF007269      TCAAAGTTTTTAGTTTTCGTGTTAAAAATTTAAAATTTGCTTCTCTGAGCATGAAGTTTCTATCTTTTTC
Consensus     TCAAAGTTTTTAGTTTTCGTGTTAAAAATTTAAAATTTGCTTCTCTGAGCATGAAGTTTCTATCTTTTTC

                        1760      1770      1780      1790      1800      1810      1820
              ....|....|....|....|....|....|....|....|....|....|....|....|....|....|
PPI-AtCPP NA  ----------------------------------------------------------------------
PPI-BnCPP     ---AAAGGAGGTCCTTACCTCGCCATCTATCTGTGGGCATTCATGTTTATCCTGTCTCTAGTGATGATGA
PPI-SoyCPP    ----------------------------------------------------------------------
afc1          ---AAAGGAGGTCCTTATCTTGCCATCTATCTGTGGGCATTCATGTTTATCCTGTCTCTAGTGATGATGA
AT4g01320     ---AAAGGAGGTCCTTATCTTGCCATCTATCTGTGGGCATTCATGTTTATCCTGTCTCTAGTGATGATGA
AF007269      CAGAAAGGAGGTCCTTATCTTGCCATCTATCTGTGGGCATTCATGTTTATCCTGTCTCTAGTGATGATGA
Consensus     CAGAAAGGAGGTCCTTATCTTGCCATCTATCTGTGGGCATTCATGTTTATCCTGTCTCTAGTGATGATGA

                        1830      1840      1850      1860      1870      1880      1890
              ....|....|....|....|....|....|....|....|....|....|....|....|....|....|
PPI-AtCPP NA  ----------------------------------------------------------------------
PPI-BnCPP     CTATATACCCTGTTTTGATTGCACCTCTTTTCAACAAGTTCACTCCT-----------------------
PPI-SoyCPP    ----------------------------------------------------------------------
afc1          CTATATACCCGGTCTTGATAGCACCGCTCTTCAACAAGTTCACTCCT-----------------------
AT4g01320     CTATATACCCGGTCTTGATAGCACCGCTCTTCAACAAGTTCACTCCT-----------------------
```

```
AF007269      CTATATACCCGGTCTTGATAGCACCGCTCTTCAACAAGTTCACTCCTGTGTGTATTTCTGTCATGGCCAT
Consensus     CTATATACCCGGTCTTGATAGCACCGCTCTTCAACAAGTTCACTCCTGTGTGTATTTCTGTCATGGCCAT

                         1900      1910      1920      1930      1940      1950      1960
                    ....|....|....|....|....|....|....|....|....|....|....|....|....|....|
PPI-AtCPP NA  ----------------------------------------------------------------------
PPI-BnCPP     ----------------------------------------------------------------------
PPI-SoyCPP    ----------------------------------------------------------------------
afc1          ----------------------------------------------------------------------
AT4g01320     ----------------------------------------------------------------------
AF007269      TTTACAATTCACTGCTTGTTTGCATATGTTGTTACCAGACAATATAATCTCCCGCTTTTTTATGGCTATA
Consensus     TTTACAATTCACTGCTTGTTTGCATATGTTGTTACCAGACAATATAATCTCCCGCTTTTTTATGGCTATA

                         1970      1980      1990      2000      2010      2020      2030
                    ....|....|....|....|....|....|....|....|....|....|....|....|....|....|
PPI-AtCPP NA  ----------------------------------------------------------------------
PPI-BnCPP     -CTTCCTGATGGAGACCTCCGGGAGAAGATTGAGAAACTTGCTTCTTCTCTAAAGTTTCCTCTGAAGAAG
PPI-SoyCPP    ----------------------------------------------------------------------
afc1          -CTTCCAGATGGAGACCTCCGGGAGAAGATTGAGAAACTTGCTTCTTCTCTAAAGTTTCCTTTGAAGAAG
AT4g01320     -CTTCCAGATGGAGACCTCCGGGAGAAGATTGAGAAACTTGCTTCTTCTCTAAAGTTTCCTTTGAAGAAG
AF007269      GCTTCCAGATGGAGACCTCCGGGAGAAGATTGAGAAACTTGCTTCTTCTCTAAAGTTTCCTTTGAAGAAG
Consensus     GCTTCCAGATGGAGACCTCCGGGAGAAGATTGAGAAACTTGCTTCTTCTCTAAAGTTTCCTTTGAAGAAG

                         2040      2050      2060      2070      2080      2090      2100
                    ....|....|....|....|....|....|....|....|....|....|....|....|....|....|
PPI-AtCPP NA  ----------------------------------------------------------------------
PPI-BnCPP     CTGTTTGTTGTCGATGGATCTACAAGGTCAAGCCATAGTAATG--------------------------
PPI-SoyCPP    ----------------------------------------------------------------------
afc1          CTGTTTGTTGTCGATGGATCTACAAGGTCAAGCCATAGCAATG--------------------------
AT4g01320     CTGTTTGTTGTCGATGGATCTACAAGGTCAAGCCATAGCAATG--------------------------
AF007269      CTGTTTGTTGTCGATGGATCTACAAGGTCAAGCCATAGCAATGTGAGAAGCTTGAGATCTCTTCCTACCT
Consensus     CTGTTTGTTGTCGATGGATCTACAAGGTCAAGCCATAGCAATGTGAGAAGCTTGAGATCTCTTCCTACCT

                         2110      2120      2130      2140      2150      2160      2170
                    ....|....|....|....|....|....|....|....|....|....|....|....|....|....|
PPI-AtCPP NA  ----------------------------------------------------------------------
PPI-BnCPP     ------------------------------------------------CTTACATGTATGGTTTC
PPI-SoyCPP    ----------------------------------------------------------------------
afc1          ------------------------------------------------CTTACATGTATGGTTTC
AT4g01320     ------------------------------------------------CTTACATGTATGGTTTC
AF007269      ACTTTACTCTAGTTTACCATTAGAAGCTTACGTATCTTGTTACATCATACAGGCTTACATGTATGGTTTC
Consensus     ACTTTACTCTAGTTTACCATTAGAAGCTTACGTATCTTGTTACATCATACAGGCTTACATGTATGGTTTC

                         2180      2190      2200      2210      2220      2230      2240
                    ....|....|....|....|....|....|....|....|....|....|....|....|....|....|
PPI-AtCPP NA  ----------------------------------------------------------------------
PPI-BnCPP     TTCAAGAACAAAAGGATTGTTCTTTATGACACATTGATTCAGCAG-------------------------
PPI-SoyCPP    ----------------------------------------------------------------------
afc1          TTTAAGAACAAAAGGATTGTTCTTTATGATACGTTGATTCAGCAG-------------------------
AT4g01320     TTTAAGAACAAAAGGATTGTTCTTTATGATACGTTGATTCAGCAG-------------------------
AF007269      TTTAAGAACAAAAGGATTGTTCTTTATGATACGTTGATTCAGCAGGTACTGTGACTCTTGATGCTTCAAA
Consensus     TTTAAGAACAAAAGGATTGTTCTTTATGATACGTTGATTCAGCAGGTACTGTGACTCTTGATGCTTCAAA

                         2250      2260      2270      2280      2290      2300      2310
                    ....|....|....|....|....|....|....|....|....|....|....|....|....|....|
PPI-AtCPP NA  ----------------------------------------------------------------------
PPI-BnCPP     ------------------------------------------------------TGCCAGAAT
PPI-SoyCPP    ----------------------------------------------------------------------
afc1          ------------------------------------------------------TGCAAGAAT
AT4g01320     ------------------------------------------------------TGCAAGAAT
AF007269      CGAGCTATACTCACATTTCTGTTTCTGGTTCTGAAACATAACATAATCTTCTATTGTGCAGTGCAAGAAT
Consensus     CGAGCTATACTCACATTTCTGTTTCTGGTTCTGAAACATAACATAATCTTCTATTGTGCAGTGCAAGAAT

                         2320      2330      2340      2350      2360      2370      2380
                    ....|....|....|....|....|....|....|....|....|....|....|....|....|....|
PPI-AtCPP NA  ----------------------------------------------------------------------
PPI-BnCPP     GAGAATGAAATTGTGGCGGTTATTGCACACGAGCTGGGACACTGGAAGCTGAATCACACTACATACTCGT
PPI-SoyCPP    ----------------------------------------------------------------------
afc1          GAGGATGAAATTGTGGCGGTTATTGCACACGAGCTTGGACATTGGAAACTGAATCACACTACATACTCGT
AT4g01320     GAGGATGAAATTGTGGCGGTTATTGCACACGAGCTTGGACATTGGAAACTGAATCACACTACATACTCGT
AF007269      GAGGATGAAATTGTGGCGGTTATTGCACACGAGCTTGGACATTGGAAACTGAATCACACTACATACTCGT
```

```
Consensus      GAGGATGAAATTGTGGCGGTTATTGCACACGAGCTTGGACATTGGAAACTGAATCACACTACATACTCGT

                        2390      2400      2410      2420      2430      2440      2450
               ....|....|....|....|....|....|....|....|....|....|....|....|....|....|
PPI-AtCPP NA   ----------------------------------------------------------------------
PPI-BnCPP      TCATTGCTGTTCAA--------------------------------------------------------
PPI-SoyCPP     ----------------------------------------------------------------------
afc1           TCATTGCAGTTCAA--------------------------------------------------------
AT4g01320      TCATTGCAGTTCAA--------------------------------------------------------
AF007269       TCATTGCAGTTCAAGTGAGGCTCAACCGACAGTTCAAAAACTTACTCACATCTACATTTCACTTAAGAAA
Consensus      TCATTGCAGTTCAAGTGAGGCTCAACCGACAGTTCAAAAACTTACTCACATCTACATTTCACTTAAGAAA

                        2460      2470      2480      2490      2500      2510      2520
               ....|....|....|....|....|....|....|....|....|....|....|....|....|....|
PPI-AtCPP NA   ----------------------------------------------------------------------
PPI-BnCPP      --------------------------------------ATCCTTGCCTTCTTGCAATTTGGAGGATACAC
PPI-SoyCPP     ----------------------------------------------------------------------
afc1           --------------------------------------ATCCTTGCCTTCTTACAATTTGGAGGATACAC
AT4g01320      --------------------------------------ATCCTTGCCTTCTTACAATTTGGAGGATACAC
AF007269       TCATGTCTTATGACCCTCTCTCAATGTTTTGCTTGCAGATCCTTGCCTTCTTACAATTTGGAGGATACAC
Consensus      TCATGTCTTATGACCCTCTCTCAATGTTTTGCTTGCAGATCCTTGCCTTCTTACAATTTGGAGGATACAC

                        2530      2540      2550      2560      2570      2580      2590
               ....|....|....|....|....|....|....|....|....|....|....|....|....|....|
PPI-AtCPP NA   ----------------------------------------------------------------------
PPI-BnCPP      TCTTGTCAGAAACTCCACTGATCTCTTCAGGAGTTTTGGTTTTGATACACAACCAGTTCTCATTGGTTTG
PPI-SoyCPP     ----------------------------------------------------------------------
afc1           TCTTGTCAGAAACTCCACTGATCTCTTCAGGAGTTTCGGATTTGATACACAGCCTGTTCTCATTGGTTTG
AT4g01320      TCTTGTCAGAAACTCCACTGATCTCTTCAGGAGTTTCGGATTTGATACACAGCCTGTTCTCATTGGTTTG
AF007269       TCTTGTCAGAAACTCCACTGATCTCTTCAGGAGTTTCGGATTTGATACACAGCCTGTTCTCATTGGTTTG
Consensus      TCTTGTCAGAAACTCCACTGATCTCTTCAGGAGTTTCGGATTTGATACACAGCCTGTTCTCATTGGTTTG

                        2600      2610      2620      2630      2640      2650      2660
               ....|....|....|....|....|....|....|....|....|....|....|....|....|....|
PPI-AtCPP NA   ----------------------------------------------------------------------
PPI-BnCPP      ATCATATTTCAG----------------------------------------------------------
PPI-SoyCPP     ----------------------------------------------------------------------
afc1           ATCATATTTCAG----------------------------------------------------------
AT4g01320      ATCATATTTCAG----------------------------------------------------------
AF007269       ATCATATTTCAGGTTTGTTATTTTTGCCTTTTGACACTAATCTAATGAATCAAGGATGGATTAAGAAAAA
Consensus      ATCATATTTCAGGTTTGTTATTTTTGCCTTTTGACACTAATCTAATGAATCAAGGATGGATTAAGAAAAA

                        2670      2680      2690      2700      2710      2720      2730
               ....|....|....|....|....|....|....|....|....|....|....|....|....|....|
PPI-AtCPP NA   ----------------------------------------------------------------------
PPI-BnCPP      --------------------------------------------CACACTGTAATACCACTTCAACACCT
PPI-SoyCPP     ----------------------------------------------------------------------
afc1           --------------------------------------------CACACTGTAATACCACTGCAACATCT
AT4g01320      --------------------------------------------CACACTGTAATACCACTGCAACATCT
AF007269       AAAACTCTAAACCTTTGGTTATATCTCCTGTCTGATTATCACAGCACACTGTAATACCACTGCAACATCT
Consensus      AAAACTCTAAACCTTTGGTTATATCTCCTGTCTGATTATCACAGCACACTGTAATACCACTGCAACATCT

                        2740      2750      2760      2770      2780      2790      2800
               ....|....|....|....|....|....|....|....|....|....|....|....|....|....|
PPI-AtCPP NA   ----------------------------------------------------------------------
PPI-BnCPP      AGTAAGCTTTGACCTCAACCTTGTTAGTCGAGCGTTTGAGTTTCAGG-----------------------
PPI-SoyCPP     ----------------------------------------------------------------------
afc1           AGTAAGCTTTGGCCTGAACCTCGTTAGTCGAGCGTTTGAGTTTCAGG-----------------------
AT4g01320      AGTAAGCTTTGGCCTGAACCTCGTTAGTCGAGCGTTTGAGTTTCAGG-----------------------
AF007269       AGTAAGCTTTGGCCTGAACCTCGTTAGTCGAGCGTTTGAGTTTCAGGTACCATCTTACAATCCCTCAAGA
Consensus      AGTAAGCTTTGGCCTGAACCTCGTTAGTCGAGCGTTTGAGTTTCAGGTACCATCTTACAATCCCTCAAGA

                        2810      2820      2830      2840      2850      2860      2870
               ....|....|....|....|....|....|....|....|....|....|....|....|....|....|
PPI-AtCPP NA   ----------------------------------------------------------------------
PPI-BnCPP      ---------------------------------------------------------------------C
PPI-SoyCPP     ----------------------------------------------------------------------
afc1           ---------------------------------------------------------------------C
AT4g01320      ---------------------------------------------------------------------C
AF007269       TCCAACCATAGTTTCTTTATTGCAATGGCAGCCTCATCTACTAATCTGAGTTAACGTTCCTTTTGCAGGC
Consensus      TCCAACCATAGTTTCTTTATTGCAATGGCAGCCTCATCTACTAATCTGAGTTAACGTTCCTTTTGCAGGC
```

```
                 2880      2890      2900      2910      2920      2930      2940
             ....|....|....|....|....|....|....|....|....|....|....|....|....|....|
PPI-AtCPP NA ----------------------------------------------------------------------
PPI-BnCPP    TGATGCTTTTGCAGTGAATCTTGGTTATGCAAACGATCTACGTCCTGCCCTAGTGAAGCTACAGG-----
PPI-SoyCPP   ----------------------------------------------------------------------
afc1         TGATGCTTTTGCCGTGAAGCTTGGCTATGCAAAAGATCTTCGTCCTGCTCTAGTGAAACTACAGG-----
AT4g01320    TGATGCTTTTGCTGTGAAGCTTGGCTATGCAAAAGATCTTCGTCCTGCTCTAGTGAAACTACAGGTCAGA
AF007269     TGATGCTTTTGCTGTGAAGCTTGGCTATGCAAAAGATCTTCGTCCTGCTCTAGTGAAACTACAGGTCAGA
Consensus    TGATGCTTTTGCTGTGAAGCTTGGCTATGCAAAAGATCTTCGTCCTGCTCTAGTGAAACTACAGGTCAGA

                 2950      2960      2970      2980      2990      3000      3010
             ....|....|....|....|....|....|....|....|....|....|....|....|....|....|
PPI-AtCPP NA ----------------------------------------------------------------------
PPI-BnCPP    ----------------------------------------------------------------------
PPI-SoyCPP   ----------------------------------------------------------------------
afc1         ----------------------------------------------------------------------
AT4g01320    GAAGATAACAACAGAACACAAACTGTTACCTCAATTTGTGTCACACACTTAAATGGATTTTTTGTTGGGA
AF007269     GAAGATAACAACAGAACACAAACTGTTACCTCAATTTGTGTCACACACTTAAATGGATTTTTTGTTGGGA
Consensus    GAAGATAACAACAGAACACAAACTGTTACCTCAATTTGTGTCACACACTTAAATGGATTTTTTGTTGGGA

                 3020      3030      3040      3050      3060      3070      3080
             ....|....|....|....|....|....|....|....|....|....|....|....|....|....|
PPI-AtCPP NA ----------------------------------------------------------------------
PPI-BnCPP    ------A---AGAGAACTTATCAGCGATGAACACAGACCCATTGTACTCAGCTTATCACTACTCACACCC
PPI-SoyCPP   ----------------------------------------------------------------------
afc1         ------A---AGAGAACTTATCAGCAATGAACACTGATCCATTGCACTCAGCTTATCACTACTCACATCC
AT4g01320    TTTTGCAGGAAGAGAACTTATCAGCAATGAACACTGATCCATTGTACTCAGCTTATCACTACTCACATCC
AF007269     TTTTGCAGGAAGAGAACTTATCAGCAATGAACACTGATCCATTGTACTCAGCTTATCACTACTCACATCC
Consensus    TTTTGCAGGAAGAGAACTTATCAGCAATGAACACTGATCCATTGTACTCAGCTTATCACTACTCACATCC

                 3090      3100      3110      3120      3130
             ....|....|....|....|....|....|....|....|....|....|....|.
PPI-AtCPP NA --------------------------------------------------------
PPI-BnCPP    TCCTCTTGTAGAGAGGCTTCGAGCCATTGATGGAGAAGACAAGAAGACAGATTAA-
PPI-SoyCPP   --------------------------------------------------------
afc1         TCCTCTTGTTGAAAGGCTTCGAGCCATTGATGGAGAAGACAAGAAGACAGATTAAA
AT4g01320    TCCTCTTGTTGAAAGGCTTCGAGCCATTGATGGAGAAGACAAGAAGACAGATTAAR
AF007269     TCCTCTTGTTGAAAGGCTTCGAGCCATTGATGGAGAAGACAAGAAGACAGATTAA-
Consensus    TCCTCTTGTTGAAAGGCTTCGAGCCATTGATGGAGAAGACAAGAAGACAGATTAA-
```

Table XX. ClustalW Analysis of PPI/Generic Nucleic Acids

1) PPI-AtCPP (SEQ ID NO:97)
2) PPI-BnCPP (SEQ ID NO:109)
3) PPI-SoyCPP (SEQ ID NO:112)
4) afc1 (SEQ ID NO:124)
5) AT4g01320 (SEQ ID NO:126)
6) AF007269 (SEQ ID NO:128)
6) Consensus (SEQ ID NO:170)

```
                   10        20        30        40        50        60        70
             ....|....|....|....|....|....|....|....|....|....|....|....|....|....|
PPI-AtCPP NA ----------------------------------------------------------------------
PPI-BnCPP    ----------------------------------------------------------------------
PPI-SoyCPP   ----------------------------------------------------------------------
afc1         ----------------------------------------------------------------------
AT4g01320    ----------------------------------------------------------------------
AF007269     ATGGCGATTCCTTTCATGGAAACCGTCGTGGGTAAGCTTCAAAACCTTTTTCTGAGACATTTTACTATCC
```

Table 38. ClustalW Analysis of PPI/Generic Amino Acids

1) PPI-AtCPP (SEQ ID NO:98)
2) PPI-BnCPP (SEQ ID NO:110)

3) PPI-SoyCPP (SEQ ID NO:113)
4) afc1 (SEQ ID NO:125)
5) AT4g01320 (SEQ ID NO:127)
6) AF007269 (SEQ ID NO:129)
7) Consensus Gener (SEQ ID NO:169)

```
                           10        20        30        40        50        60
                   ....|....|....|....|....|....|....|....|....|....|....|....|
PPI-AtCPP          MAFPYMEAVVGFMILMYIFETYLDVRQHRALKLPTLPKTLEGVISQEKFEKSRAYS--LD  58
PPI-BnCPP          MAIPFMETVVGFMIVMYVFETYLDLRQHTALKLPTLPKTLVGVISQEKFEKSRAYS--LD  58
PPI-SoyCPP         MAFPYMEAVVGFMILMYIFETYLDVRQHRALKLPTLPKTLEGVISQEKFEKSRAYS--LD  58
afc1               MAIPFMETVVGFMIVMYIFETYLDLRQLTALKLPTLPKTLVGVISQEKFEKSRAYS--LD  58
AT4g01320          MAIPFMETVVGFMIVMYIFETYLDLRQLTALKLPTLPKTLVGVISQEKFEKSRAYRDIIT  60
AF007269           MAIPFMETVVGFMIVMYIFETYLDLRQLTALKLPTLPKTLV-------------------  41
Consensus Gener    MAXPXMEXVVGFMIXMYXFETYLDXRQXXALKLPTLPKTLXXXXXXXXXXXXXXXXXXXX  60

                           70        80        90       100       110       120
                   ....|....|....|....|....|....|....|....|....|....|....|....|
PPI-AtCPP          KS-----HFHFVHEFVTIVTDSTILYFGVLPWFWKKSGDFMTIAGFNAENEILHTLAFLA 113
PPI-BnCPP          KS-----HFHFVHEFVTILMDSAILFFGILPWFWKISGGFIPMVGLDPENEILHTLSFLA 113
PPI-SoyCPP         KS-----HFHFVHEFVTIVTDSTILYFGVLPWFWKKSGDFMTIAGFNAENEILHTLAFLA 113
afc1               KS-----YFHFVHEFVTILMDSAILFFGILPWFWKMSGAVLPRLGLDPENEILHTLSFLA 113
AT4g01320          ENFNICSYFHFVHEFVTILMDSAILFFGILPWFWKMSGAVLPRLGLDPENEILHTLSFLA 120
AF007269           ------------------------------------------------------------  41
Consensus Gener    XXXXXXXXXXXXXXXXXXXXXXXXXXXXXXXXXXXXXXXXXXXXXXXXXXXXXXXXXXXX 120

                          130       140       150       160       170       180
                   ....|....|....|....|....|....|....|....|....|....|....|....|
PPI-AtCPP          GLMIWSQITDLPFSLYSTFVIEARHGFNKQTPWLFFRDMLKGIFLSVIIGPPIVAAIIVI 173
PPI-BnCPP          GLMTWSQITDLPFSLYSTFVIESRHGFNKQTIWMFIRDMIKGILLSVIPAPPIVAAIIVI 173
PPI-SoyCPP         GLMIWSQITDLPFSLYSTFVIEARHGFNKQTPWLFFRDMLKGIFLSVIIGPPIVAAIIVI 173
afc1               GVMTWSQITDLPFSLYSTFVIESRHGFNKQTIWMFIRDMIKGTFLSVILGPPIVAAIIFI 173
AT4g01320          GVMTWSQITDLPFSLYSTFVIESRHGFNKQTIWMFIRDMIKGTFLSVILGPPIVAAIIFI 180
AF007269           --------TDLPFSLYSTFVIESRHGFNKQTIWMFIRDMIKGTFLSVILGPPIVAAIIFI  93
Consensus Gener    XXXXXXXXTDLPFSLYSTFVIEXRHGFNKQTXWXFXRDMXKGXXLSVIXXPPIVAAIIXI 180

                          190       200       210       220       230       240
                   ....|....|....|....|....|....|....|....|....|....|....|....|
PPI-AtCPP          VQKGGPYLAIYLWVFTFGLSIVMMTLYPVLIAPLFNKFTPLPDGQLREKIEKLASSLNYP 233
PPI-BnCPP          VQKGGPYLAIYLWAFMFILSLVMMTIYPVLIAPLFNKFTPLPDGDLREKIEKLASSLKFP 233
PPI-SoyCPP         VQKGGPYLAIYLWVFTFGLSIVMMTLYPVLIAPLFNKFTPLPDGQLREKIEKLASSLNYP 233
afc1               VQKGGPYLAIYLWAFMFILSLVMMTIYPVLIAPLFNKFTPLPDGDLREKIEKLASSLKFP 233
AT4g01320          VQKGGPYLAIYLWAFMFILSLVMMTIYPVLIAPLFNKFTPLPDGDLREKIEKLASSLKFP 240
AF007269           VQKGGPYLAIYLWAFMFILSLVMMTIYPVLIAPLFNKFTPLPDGDLREKIEKLASSLKFP 153
Consensus Gener    VQKGGPYLAIYLWXFXFXLSXVMMTXYPVLIAPLFNKFTPLPDGXLREKIEKLASSLXXP 240

                          250       260       270       280       290       300
                   ....|....|....|....|....|....|....|....|....|....|....|....|
PPI-AtCPP          LKKLFVVDGSTRSSHSNAYMYGFFKNKRIVPYDTLIQQCKDDEEIVAVIAHELGHWKLNH 293
PPI-BnCPP          LKKLFVVDGSTRSSHSNAYMYGFFKNKRIVLYDTLIQQCQNENEIVAVIAHELGHWKLNH 293
PPI-SoyCPP         LKKLFVVDGSTRSSHSNAYMYGFFKNKRIVPYDTLIQQCKDDEEIVAVIAHELGHWKLNH 293
afc1               LKKLFVVDGSTRSSHSNAYMYGFFKNKRIVLYDTLIQQCKNEDEIVAVIAHELGHWKLNH 293
AT4g01320          LKKLFVVDGSTRSSHSNAYMYGFFKNKRIVLYDTLIQQCKNEDEIVAVIAHELGHWKLNH 300
AF007269           LKKLFVVDGSTRSSHSNAYMYGFFKNKRIVLYDTLIQQCKNEDEIVAVIAHELGHWKLNH 213
Consensus Gener    LKKLFVVDGSTRSSHSNAYMYGFFKNKRIVXYDTLIQQCXXXXEIVAVIAHELGHWKLNH 300

                          310       320       330       340       350       360
                   ....|....|....|....|....|....|....|....|....|....|....|....|
PPI-AtCPP          TVYTFVAMQILTLLQFGGYTLVRNSADLYRSFGFDTQPVLIGLIIFQHTVIPLQQLVSFG 353
PPI-BnCPP          TTYSFIAVQILAFLQFGGYTLVRNSTDLFRSFGFDTQPVLIGLIIFQHTVIPLQHLVSFD 353
PPI-SoyCPP         TVYTFVAMQILTLLQFGGYTLVRNSADLYRSFGFDTQPVLIGLIIFQHTVIPLQQLVSFG 353
afc1               TTYSFIAVQILAFLQFGGYTLVRNSTDLFRSFGFDTQPVLIGLIIFQHTVIPLQHLVSFG 353
AT4g01320          TTYSFIAVQILAFLQFGGYTLVRNSTDLFRSFGFDTQPVLIGLIIFQHTVIPLQHLVSFG 360
AF007269           TTYSFIAV--------------------------------------QHTVIPLQHLVSFG 235
Consensus Gener    TXYXFXAXXXXXXXXXXXXXXXXXXXXXXXXXXXXXXXXXXXXXXXQHTVIPLQXLVSFX 360

                          370       380       390       400       410       420
                   ....|....|....|....|....|....|....|....|....|....|....|....|
PPI-AtCPP          LNLVSRSFEFQADGFAKKLGYASGLRGGLVKLQ--------------------------- 386
```

```
PPI-BnCPP        LNLVSRAFEFQADAFAVNLGYAKDLRPALVKLQ---------------------------  386
PPI-SoyCPP       LNLVSRSFEFQADGFAKKLGYASGLRGGLVKLQ---------------------------  386
afc1             LNLVSRAFEFQADAFAVKLGYAKDLRPALVKLQ---------------------------  386
AT4g01320        LNLVSRAFEFQADAFAVKLGYAKDLRPALVKLQVREDNNRTQTVTSICVTHLNGFFVGIL  420
AF007269         LNLVSRAFEFQADAFAVKLGYAKDLRPALVKLQVREDNNRTQT-----------------  278
Consensus Gener  LNLVSRXFEFQADXFAXXLGYAXXLRXXLVKLQXXXXXXXXXXXXXXXXXXXXXXXXXXX  420

                         430         440         450
                 ....|....|....|....|....|....|....|....
PPI-AtCPP        -EENLSAMNTDPWYSAYHYSHPPLVERLAALDEPDKKED  424
PPI-BnCPP        -EENLSAMNTDPLYSAYHYSHPPLVERLRAIDGEDKKTD  424
PPI-SoyCPP       -EENLSAMNTDPWYSAYHYSHPPLVERLAALDEPDKKED  424
afc1             -EENLSAMNTDPLHSAYHYSHPPLVERLRAIDGEDKKTD  424
AT4g01320        QEENLSAMNTDPLYSAYHYSHPPLVERLRAIDGEDKKTD  459
AF007269         -EENLSAMNTDPLYSAYHYSHPPLVERLRAIDGEDKKTD  316
Consensus Gener  XEENLSAMNTDPXXSAYHYSHPPLVERLXAXDXXDKKXD  459
```

```
Zea mays-FT-A     FRSLFLGGLAAM[illegible]GWDVTTEALL[illegible]NAQLGSP[illegible]RYLKGLY[illegible]GGNNLLL[illegible]EGEIS[illegible]F[illegible]-ANDWTC
Soy1-FT-A         TRSLFLGGL[illegible]AMSEE[illegible]LTTIFA[illegible]YEG[illegible]SSHPYLRGLY[illegible]GE[illegible]T[illegible]PD[illegible]SSVCLF[illegible]-[illegible]TKENY
Soy2-FT-A         TRSIFLANL[illegible]AMSR[illegible]LNTI[illegible]YE[illegible]SSHPYLRGLY[illegible]GE[illegible]T[illegible]PD[illegible]SS[illegible]LF[illegible]-[illegible]KENY
Triticum-FT-A     [illegible]RSLILAGLAAM[illegible]EDD[illegible]VEALL[illegible]VNA[illegible]ESP[illegible]RYLRGLY[illegible]DGNNLL[illegible]AENEI[illegible]DA[illegible]LF[illegible]-NKDWTC

                            290       300       310       320       330       340       350
                  ....|....|....|....|....|....|....|....|....|....|....|....|....|....|
BnA-12            [illegible]ALSTLLLDLL[illegible]DG[illegible]EN[illegible]HK[illegible]SVK[illegible]ANE[illegible]P---[illegible]TN---------------[illegible]NLV[illegible]CR[illegible]A
At-FT-A           [illegible]ALSTILLDLLGDG[illegible]TN[illegible]HK[illegible]SVR[illegible]ANE[illegible]P---[illegible]TN---------------LANLY[illegible]GR[illegible]A
PPI-Soy-FTA       [illegible]ALST[illegible]F[illegible]Y[illegible]NEDI[illegible]D[illegible]TADM---DKQDLDD[illegible]EKGEQQNLN[illegible]RN[illegible]CSIL[illegible]KQ[illegible]T
Pea-FT-A          [illegible]ALSTLLLD[illegible]SASV[illegible]NEDF[illegible]LQIL---IKQ--DS[illegible]----------[illegible]IT[illegible]CSIL[illegible]V
Tomato-FT-A       H[illegible]RF[illegible]HD[illegible]SQ[illegible]LKSAVDV[illegible]TPQSC---SPD-------------LA[illegible]TKK[illegible]CSIL[illegible]HA[illegible]VK
RiceFT-A          [illegible]L[illegible]QI[illegible]SDELKGT[illegible]KNSDPEAD[illegible]AVDA--[illegible]----------D[illegible]TA[illegible]QKC[illegible]I
Zea mays-FT-A     [illegible]L[illegible]SDGL[illegible]STEGTI[illegible]SSHP---[illegible]TADD--[illegible]----------P[illegible]AAV[illegible]C[illegible]QKC[illegible]AV
Soy1-FT-A         [illegible]LST[illegible]F[illegible]Y[illegible]NEDI[illegible]D[illegible]TADM---DKQDLDD[illegible]EKGEQQNLN[illegible]RN[illegible]CSI[illegible]KQ[illegible]T
Soy2-FT-A         [illegible]I[illegible]F[illegible]Y[illegible]NBDI[illegible]D[illegible]TADM---[illegible]KQDLDD[illegible]EKGEQQNLN[illegible]RN[illegible]CSI[illegible]KQ[illegible]T
Triticum-FT-A     [illegible]AL[illegible]FL[illegible]DL[illegible]RM[illegible]SN[illegible]LKGT[illegible]ENS[illegible]P---[illegible]TGHA--[illegible]----------[illegible]VAV[illegible]QKC[illegible]I

                            360       370
                  ....|....|....|....|....|....
BnA-12            [illegible]A[illegible]L------------------------
At-FT-A           [illegible]A[illegible]K[illegible]TVAAI----------------
PPI-Soy-FTA       [illegible]I[illegible]R[illegible]P---------------------
Pea-FT-A          [illegible]V[illegible]R[illegible]PQAA------------------
Tomato-FT-A       [illegible]N[illegible]M[illegible]RVQLLQSQNAERLANLSVQE
RiceFT-A          [illegible]S[illegible]YR[illegible]T[illegible]SSQT------------------
Zea mays-FT-A     [illegible]S[illegible]F[illegible]DT[illegible]SQIS------------------
Soy1-FT-A         [illegible]I[illegible]F[illegible]R[illegible]PLSA------------------
Soy2-FT-A         [illegible]I[illegible]R[illegible]PLSA------------------
Triticum-FT-A     [illegible]S[illegible]YD[illegible]T[illegible]SS--------------------
```

Table 10C. ClustalW Nucleic Acid Analysis of FT Beta Subunits

1) PPI-BnFTb; FT3 (SEQ ID NO:14)
2) era1 (SEQ ID NO:178)
3) Wiggum (SEQ ID NO:80)
4) PPI-Soy-FTB; FT5 (SEQ ID NO:40)
5) DuP-Soy-FTB (SEQ ID NO:81)
6) PPI-Corn-FTB; FT6 (SEQ ID NO:43)
7) DuP-Corn-FTB (SEQ ID NO:82)
8) Pea-FT-B (SEQ ID NO:83)
9) Tomato (SEQ ID NO:84)
10) Tobacco (SEQ ID NO:85)

```
                          10        20        30        40        50        60        70
                  ....|....|....|....|....|....|....|....|....|....|....|....|....|....|
PPI-BnFTb         ----------------------------------------------------------------------
era1              ----------------------------------------------------------------------
Wiggum            ATGCCAGTAGTAACCCGCTTGATTCGTTTGAAGTGTGTAGGGCTCAGACTTGACCGGAGTGGACTCAATC
PPI-Soy-FTB       ----------------------------------------------------------------------
DuP-Soy-FTB       ----------------------------------------------------------------------
PPI-Corn-FTB      ----------------------------------------------------------------------
DuP-Corn-FTB      ----------------------------------------------------------------------
Pea FT-B          ----------------------------------------------------------------------
Tomato            ---------------------------------------------------GTAAACGAGCGTTGATTT
Tobacco           ----------------------------------------------------------------------

                          80        90       100       110       120       130       140
                  ....|....|....|....|....|....|....|....|....|....|....|....|....|....|
PPI-BnFTb         ----------------------------------------------------------------------
era1              ----------------------------------------------------------------------
Wiggum            GGCGAATCTGTCACGGAGGACACGGGGAATCAACGCGGCGGAGAGTGATGGAAGAGCTTTCAAGCCTAGC
PPI-Soy-FTB       ----------------------------------------------------------------------
DuP-Soy-FTB       ----------------------------------------------------------------------
```

```
                 1330       1340       1350       1360       1370       1380
            ....|....|....|....|....|....|....|....|....|....|....|....|
PPI-BnFTb   CTAGATTT---------------------------------------------------- 1110
era1        TCGAGTTCTTCTTTAAAGCAGCATGACCCGTTGTTGCTAATGTATGGGAAACCCCAAACA 1249
PPI-Soy-FTB ------------------------------------------------------------ 1135
PPI-Corn-FTB ----------------------------------------------------------- 1245
Consensus           ---------------------------------------------------- 797

                 1390       1400       1410       1420
            ....|....|....|....|....|....|....|....|.
PPI-BnFTb   ----------------------------------------- 1110 (SEQ ID NO:14)
era1        TAAGAGTTTCCGTAGTGTTGTAACTTGTAAGATTTCAAAAG 1290 (SEQ ID NO:178)
PPI-Soy-FTB ----------------------------------------- 1135 (SEQ ID NO:40)
PPI-Corn-FTB ---------------------------------------- 1245 (SEQ ID NO:43)
Consensus   ----------------------------------------- 797  (SEQ ID NO:97)
```

Example

Cloning, Vector Construction and Over-expression of AtFT-B Sequences in *Arabidopsis* Produces a Dominant-negative Phenotype Farnesyltransferase is a heterodimer formed by its α- and β-subunits and its activity relies on the proper dimerization between these subunits. Increased ABA sensitivity can be achieved by the over-expression of a non-full-length form of AtFTB (SEQ ID NO:1) in *Arabidopsis*. In the corollary experiment, over-expression of the full-length AtFTB failed to alter the ABA sensitivity. These results suggest that the phenotype of enhanced ABA response is likely the result of dominant-negative effect of the truncated form AtFTB. The truncated AtFTB maybe nonfunctional or possess limited finctionality in vivo as compared to a full length endogenous subunit. However. The reduction of Ft activity results in enhanced ABA sensitivity.

Cloning

The farnesyltransferase sequence described by SEQ ID NO:1 was cloned into an appropriate vector under the transcriptional control of the 35S CaMV promoter (pBI121 derived vector) in the sense orientation for expression in plant cells. This vector was designated ΔN90AtFTB and designated SEQ ID NO:79. The protein encoded by SEQ ID NO:1 has been determined to lack the 5' 270 nucleotides, and therefore does not code for the 5' terminal 90 amino acids. The full length farnesyltransferase sequence was obtained using the primer pair identified by SEQ ID NO:86 and SEQ ID NO:171 and methodology as described elsewhere in this document. The resulting sequence, identified as SEQ ID NO:172 was cloned into an appropriate vector under the transcriptional control of the 35S CaMV promoter (pBI121 derived vector) in the sense orientation for expression in plant cells. This vector was designated pBI121-AtFTB, SEQ ID NO:173. The protein encoded by SEQ ID NO:172 has been determined to represent the full length polypeptide.

*Agrobacterum*-Mediated Transformation, Transgenic Line Selection and ABA Test.

*Agrobacterium* strain GV3101 carrying the binary constructs described above were transformed into *Arabidopsis thaliana* via *agrobacterium*-mediated floral dipping transformation. Transformed *Arabidopsis* lines (T1) were selected on Murashige/Skoog (Sigma) plates containing kanamycin (50 μg/μl). Kanamycin-resistant seedlings were then transferred to soil. The subsequent T2 seeds were harvested from individual transgenic lines for ABA tests.

Northern Blot Analysis.

Total RNA was isolated from two-week-old T2 *Arabidopsis* plants of the pBI121-ΔN90AtFTB, as well as from wild-type *Columbia* and era1mutant plants. After separated in the agarose gel, RNA was transferred onto the nitrocellulose membrane and was hybridized with the $^{32}$P-labelled ΔN90AtFTB DNA probe.

Over-Expression of pBI121-ΔN90AtFTB, not pBI121-AtFTB Resulted in Enhanced ABA Sensitivity:

Transgenic plants were selected and advanced to the second generation. T2 seeds of these two constructs were subjected to ABA test using 0.0, 0.25, 0.5 and 1.0 μM ABA in minimum MS-agarose plates. Of the fifteen pBI121-ΔN90AtFTB lines ten showed an enhanced ABA sensitivity phenotype. At 0.5 μM ABA, the seeds would germinate, however, the development of the seedlings for these 10 lines were retarded or arrested, showing a typical ABA hypersensitive response. In contrast, of the fifteen pBI121-AtFTB transgenic lines, all but one line showed normal wild-type like ABA response to seed germination and seedling development.

Northern blot analysis indicated that in the transgenic lines of pBI121-ΔN90AtFTB, the expression levels were higher than the endogenous AtFTB transcript level as depicted by the wild-type control. This indicates the ABA hypersensitive phenotype of these transgenic lines is unlikely due to transcriptional co-suppression. The enhanced ABA response correlates with the results of other methods of AtFTB down-regulation, such as anti-sense and RNAi, hairpin constructs. It is possible that the observed ABA hypersensitive response in ΔN90AtFTB transgenic lines are due to a dominant negative effect. The high transcript levels of ΔN90AtFTB should produce an abundance of the truncated form of AtFTB which may bind to the endogenous AtFTA and result in competitive inhibition of AtFTase activity.

Further support for the interaction of truncated FT-B with endogenous FT-A comes from a yeast two-hybrid interaction experiment. Use of the ΔN90AtFTB cDNA as bait, identified interacting clones the majority of which were found to encode FT-A.

pBI121-ΔN90AtFTB Truncated FT-B Vector

*gtttacccgccaatatatcctgt*caaacactgatagtttaaactgaaggcgggaaacgacaatctgatcatgagcgg SEQ ID agaattaagggagtcacgttatgacccccgccgatgacgcgggacaagccgttttacgtttggaactgacagaaccg NO:79 caacgttgaaggagccactcagccgcgggtttctggagtttaatgagctaagcacatacgtcagaaaccattattgc gcgttcaaaagtcgcctaaggtcactatcagctagcaaatatttcttgtcaaaaatgctccactgacgttccataaa ttcccctcggtatccaattagagtctcatattcactctcaatccaaataatctgcaccggatctggatcgtttcgca tgattgaacaagatggattgcacgcaggttctccggccgcttgggtggagaggctattcggctatgactgggcacaa cagacaatcggctgctctgatgccgccgtgttccggctgtcagcgcaggggcgcccggttctttttgtcaagaccga cctgtccggtgccctgaatgaactgcaggacgaggcagcgcggctatcgtggctggccacgacgggcgttccttgcg cagctgtgctcgacgttgtcactgaagcgggaagggactggctgctattgggcgaagtgccggggcaggatctcctg tcatctcaccttgctcctgccgagaaagtatccatcatggctgatgcaatgcggcggctgcatacgcttgatccggc -continued tacctgcccattcgaccaccaagcgaaacatcgcatcgagcgagcacgtactcggatggaagccggtcttgtcgatc aggatgatctggacgaagagcatcaggggctcgcgccagccgaactgttcgccaggctcaaggcgcgcatgcccgac ggcgatgatctcgtcgtgacccatggcgatgcctgcttgccgaatatcatggtggaaaatggccgcttttctggatt catcgactgtggccggctgggtgtggcggaccgctatcaggacatagcgttggctacccgtgatattgctgaagagc ttggcggcgaatgggctgaccgcttcctcgtgctttacggtatcgccgctcccgattcgcagcgcatcgccttctat cgccttcttgacgagttcttctgagcgggactctggggttcgaaatgaccgaccaagcgacgcccaacctgccatca cgagatttcgattccaccgccgccttctatgaaaggttgggcttcggaatcgttttccgggacgccggctggatgat cctccagcgcggggatctcatgctggagttcttcgcccacgggatctctgcggaacaggcggtcgaaggtgccgata tcattacgacagcaacggccgacaagcacaacgccacgatcctgagcgacaatatgatcgggcccggcgtccacatc aacggcgtcggcggcgactgcccaggcaagaccgagatgcaccgcgatatcttgctgcgttcggatattttcgtgga gttcccgccacagacccggatgatccccgatcgttcaaacatttggcaataaagtttcttaagattgaatcctgttg ccggtcttgcgatgattatcatataatttctgttgaattacgttaagcatgtaataattaacatgtaatgcatgacg ttatttatgagatgggtttttatgattagagtcccgcaattatacatttaatacgcgatagaaaacaaaatatagcg cgcaaactaggataaattatcgcgcgcggtgtcatctatgttactagatcgggcctcctgtcaatgctggcggcggc tctggtggtggttctggtggcggctctgagggtggtggctctgagggtggcggttctgagggtggcggctctgaggg aggcggttccggtggtggctctggttccggtgattttgattatgaaaagatggcaaacgctaataagggggctatga ccgaaaatgccgatgaaaacgcgctacagtctgacgctaaaggcaaacttgattctgtcgctactgattacggtgct gctatcgatggtttcattggtgacgtttccggccttgctaatggtaatggtgctactggtgattttgctggctctaa ttcccaaatggctcaagtcggtgacggtgataattcacctttaatgaataatttccgtcaatatttaccttccctcc ctcaatcggttgaatgtcgcccttttgtctttggcccaatacgcaaaccgcctctccccgcgcgttggccgattcat taatgcagctggcacgacaggtttcccgactggaaagcgggcagtgagcgcaacgcaattaatgtgagttagctcac tcattaggcaccccaggctttacactttatgcttccggctcgtatgttgtgtggaattgtgagcggataacaatttc acacaggaaacagctatgaccatgattacgccaagcttgcatgcctgcagcccacagatggttagagaggcttacgc agcaggtctcatcaagacgatctacccgagcaataatctccaggaaatcaaataccttcccaagaaggttaaagatg cagtcaaaagattcaggactaactgcatcaagaacacagagaaagatatatttctcaagatcagaagtactattcca gtatggacgattcaaggcttgcttcacaaaccaaggcaagtaatagagattggagtctctaaaaaggtagttcccac tgaatcaaaggccatggagtcaaagattcaaatagaggacctaacagaactcgccgtaaagactggcgaacagttca tacagagtctcttacgactcaatgacaagaagaaaatcttcgtcaacatggtggagcacgacacacttgtctactcc aaaaatatcaaagatacagtctcagaagaccaaagggcaattgagacttttcaacaaagggtaatatccggaaacct cctcggattccattgcccagctatctgtcactttattgtgaagatagtggaaaaggaaggtggctcctacaaatgcc atcattgcgataaaggaaaggccatcgttgaagatgcctctgccgacagtggtcccaaagatggacccccacccacg aggagcatcgtggaaaaagaagacgttccaaccacgtcttcaaagcaagtggattgatgtgatatctccactgacgt aagggatgacgcacaatcccactatccttcgcaagacccttcctctatataaggaagttcatttcatttggagagaaca cggggactctagaGGATCCgtccggaattcccgggtcgacccacgcgtccgggagattcagcgagataagcaattggattatctg atgaaaggcttaaggcagcttggtccgcagttttcttccttagatgctaatcgaccttggctttgttactggattcttcattcaatagctttgct tggggagactgtggatgatgaattagaaagcaatgccattgacttccttggacgctgccagggctctgaaggtggatacggtggtggtcctggc caacttccacatcttgcaactacttatgctgcagtgaatgcacttgttactttaggaggtgacaaagccctttcttcaattaatagagaaaaaatg tcttgtttttaagacggatgaaggatacaagtggaggtttcaggatgcatgatatgggagaaatggatgttcgtgcatgctacactgcaatttc ggttgcaagcatcctaaatattatggatgatgaactcacccagggcctaggagattacatcttgagttgccaaacttatgaaggtggcattgga ggggaacctggctccgaagctcacggtgggtatacctactgtggtttggctgctatgattttaatcaatgaggtcgaccgtttgaatttggattc -continued attaatgaattgggctgtacatcgacaaggagtagaaatgggatttcaaggtaggacgaacaaattggtcgatggttgctacacattttggca ggcagccccttgtgttctactacaaagattatattcaaccaatgatcatgacgttcatggatcatcacatatatcagaagggacaaatgaagaa catcatgctcatgatgaagatgaccttgaagacagtgatgatgatgatgattctgatgaggacaacgatgaagattcagtgaatggtcacaga atccatcatacatccacctacattaacaggagaatgcaactggtttttgatagcctcggcttgcagagatatgtactcttgtgctctaagatccct gacggtggattcagagacaagccgaggaaaccccgtgacttctaccacacatgttactgcctgagcggcttgtctgtggctcagcacgctt ggttaaaagacgaggacactcctccctttgactcgcgacattatgggtggctactcgaatctccttgaacctgttcaacttcttcacaacattgtc atggatcagtataatgaagctatcgagttcttctttaaagcagcatgaGGATCCctcgaatttccccgatcgttcaaacatttg gcaataaagtttcttaagattgaatcctgttgccggtcttgcgatgattatcatataatttctgttgaattacgtta agcatgtaataattaacatgtaatgcatgacgttatttatgagatgggtttttatgattagagtcccgcaattatac atttaatacgcgatagaaaacaaaatatagcgcgcaaactaggataaattatcgcgcgcggtgtcatctatgttact agatcgggaattcactggccgtcgttttacaacgtcgtgactgggaaaaccctggcgttacccaacttaatcgcctt gcagcacatccccctttcgccagctggcgtaatagcgaagaggcccgcaccgatcgcccttcccaacagttgcgcag cctgaatggcgcccgctcctttcgctttcttcccttcctttctcgccacgttcgccggctttccccgtcaagctcta aatcgggggctccctttagggttccgatttagtgctttacggcacctcgaccccaaaaaacttgatttgggtgatgg ttcacgtagtgggccatcgccctgatagacggtttttcgccctttgacgttggagtccacgttctttaatagtggac tcttgttccaaactggaacaacactcaaccctatctcgggctattcttttgatttataagggattttgccgatttcg gaaccaccatcaaacaggattttcgcctgctggggcaaaccagcgtggaccgcttgctgcaactctctcagggccag gcggtgaagggcaatcagctgttgcccgtctcactggtgaaaagaaaaaccaccccagtacattaaaaacgtccgca atgtgttattaagttgtctaagcgtcaattt*gtttacaccacaatatatcctgcca*

SEQ ID NO:86 FORWARD Primer SacI site 5' aaaCCCGG-Gatgccagtagtaacccgc 3'

SEQ ID NO:171 REV Primer BamHI site 5' aaaggatcctcat-gctgctttaaagaagaactcgat 3'

Full length FT-B cccgggatgccagtagtaacccgcttgattcgtttgaagtgtgtagggctcagacttgaccggagtggactcaatcg SEQ ID NO:172 gcgaatctgtcacggaggacacggggaatcaacgcggcggagagtgatggaagagctttcaagcctaaccgtgagtc agcgcgagcaatttctggtggagaacgatgtgttcgggatctataattacttcgacgccagcgacgtttctactcaa aaatacatgatggagattcagcgagataagcaattggattatctgatgaaaggcttaaggcagcttggtccgcagtt ttcttccttagatgctaatcgaccttggctttgttactggattcttcattcaatagctttgcttggggagactgtgg atgatgaattagaaagcaatgccattgacttccttggacgctgccagggctctgaaggtggatacggtggtggtcct ggccaacttccacatcttgcaactacttatgctgcagtgaatgcacttgttactttaggaggtgacaaagccctttc ttcaattaatagagaaaaaatgtcttgtttttaagacggatgaaggatacaagtggaggtttcaggatgcatgata tgggagaaatggatgttcgtgcatgctacactgcaatttcggttgcaagcatcctaaatattatggatgatgaactc acccagggcctaggagattacatcttgagttgccaaacttatgaaggtggcattggaggggaacctggctccgaagc tcacggtgggtatacctactgtggtttggctgctatgattttaatcaatgaggtcgaccgtttgaatttggattcat taatgaattgggctgtacatcgacaaggagtagaaatgggatttcaaggtaggacgaacaaattggtcgatggttgc tacacattttggcaggcagccccttgtgttctactacaaagattatattcaaccaatgatcatgacgttcatggatc atcacatatatcagaagggacaaatgaagaacatcatgctcatgatgaagatgaccttgaagacagtgatgatgatg atgattctgatgaggacaacgatgaagattcagtgaatggtcacagaatccatcatacatccacctacattaacagg agaatgcaactggtttttgatagcctcggcttgcagagatatgtactcttgtgctctaagatccctgacggtggatt -continued cagagacaagccgaggaaaccccgtgacttctaccacacatgttactgcctgagcggcttgtctgtggctcagcacg cttggttaaaagacgaggacactcctcctttgactcgcgacattatgggtggctactcgaatctccttgaacctgtt caacttcttcacaacattgtcatggatcagtataatgaagctatcgagttcttctttaaagcagcatgaggatcc Full Length FT-B amino acid sequence encoded by SEQ ID NO:172

MPVVTRLIRLKCVGLRLDRSGLNRRICHGGHGESTRRRVMEELSSLTVSQREQFLVENDVFGIYNYFDASDVSTQKY SEQ ID NO:177

MMEIQRDKQLDYLMKGLRQLGPQFSSLDANRPWLCYWILHSIALLGETVDDELESNAIDFLGRCQGSEGGYGGGPGQ

LPHLATTYAAVNALVTLGGDKALSSINREKMSCFLRRMKDTSGGFRMHDMGEMDVRACYTAISVASILNIMDDELTQ

GLGDYILSCQTYEGGIGGEPGSEAHGGYTYCGLAAMILINEVDRLNLDSLMNWAVHRQGVEMGFQGRTNKLVDGCYT

FWQAAPCVLLQRLYSTNDHDVHGSSHISEGTNEEHHAHDEDDLEDSDDDDDSDEDNDEDSVNGHRIHHTSTYINRRM

QLVFDSLGLQRYVLLCSKIPDGGFRDKPRKPRDFYHTCYCLSGLSVAQHAWLKDEDTPPLTRDIMGGYSNLLEPVQL

LHNIVMDQYNEAIEFFFKAA pBI121-AtFTB (Full length vector Over-expression)

SEQ ID NO:173

*gtttacccgccaatatatcctgtc*aaacactgatagtttaaactgaaggcgggaaacgacaatctgatcatgagcgg agaattaagggagtcacgttatgacccccgccgatgacgcgggacaagccgttttacgtttggaactgacagaaccg caacgttgaaggagccactcagccgcgggtttctggagtttaatgagctaagcacatacgtcagaaaccattattgc gcgttcaaaagtcgcctaaggtcactatcagctagcaaatatttcttgtcaaaaatgctccactgacgttccataaa ttcccctcggtatccaattagagtctcatattcactctcaatccaaataatctgcaccggatctggatcgtttcgca tgattgaacaagatggattgcacgcaggttctccggccgcttgggtggagaggctattcggctatgactgggcacaa cagacaatcggctgctctgatgccgccgtgttccggctgtcagcgcaggggcgcccggttctttttgtcaagaccga cctgtccggtgccctgaatgaactgcaggacgaggcagcgcggctatcgtggctggccacgacgggcgttccttgcg cagctgtgctcgacgttgtcactgaagcgggaagggactggctgctattgggcgaagtgccggggcaggatctcctg tcatctcaccttgctcctgccgagaaagtatccatcatggctgatgcaatgcggcggctgcatacgcttgatccggc tacctgcccattcgaccaccaagcgaaacatcgcatcgagcgagcacgtactcggatggaagccggtcttgtcgatc aggatgatctggacgaagagcatcaggggctcgcgccagccgaactgttcgccaggctcaaggcgcgcatgcccgac ggcgatgatctcgtcgtgacccatggcgatgcctgcttgccgaatatcatggtggaaaatggccgcttttctggatt catcgactgtggccggctgggtgtggcggaccgctatcaggacatagcgttggctacccgtgatattgctgaagagc ttggcggcgaatgggctgaccgcttcctcgtgctttacggtatcgccgctcccgattcgcagcgcatcgccttctat cgccttcttgacgagttcttctgagcgggactctggggttcgaaatgaccgaccaagcgacgcccaacctgccatca cgagatttcgattccaccgccgccttctatgaaaggttgggcttcggaatcgttttccgggacgccggctggatgat cctccagcgcggggatctcatgctggagttcttcgcccacgggatctctgcggaacaggcggtcgaaggtgccgata tcattacgacagcaacggccgacaagcacaacgccacgatcctgagcgacaatatgatcgggcccggcgtccacatc aacggcgtcggcggcgactgcccaggcaagaccgagatgcaccgcgatatcttgctgcgttcggatattttcgtgga gttcccgccacagacccggatgatccccgatcgttcaaacatttggcaataaagtttcttaagattgaatcctgttg ccggtcttgcgatgattatcatataatttctgttgaattacgttaagcatgtaataattaacatgtaatgcatgacg ttatttatgagatgggtttttatgattagagtcccgcaattatacatttaatacgcgatagaaaacaaaatatagcg cgcaaactaggataaattatcgcgcgcggtgtcatctatgttactagatcgggcctcctgtcaatgctggcggcggc tctggtggtggttctggtggcggctctgagggtggtggctctgagggtggcggttctgagggtggcggctctgaggg aggcggttccggtggtggctctggttccggtgattttgattatgaaaagatggcaaacgctaataagggggctatga ccgaaaatgccgatgaaaacgcgctacagtctgacgctaaaggcaaacttgattctgtcgctactgattacggtgct -continued gctatcgatggtttcattggtgacgtttccggccttgctaatggtaatggtgctactggtgattttgctggctctaa ttcccaaatggctcaagtcggtgacggtgataattcacctttaatgaataatttccgtcaatatttaccttccctcc ctcaatcggttgaatgtcgcccttttgtctttggcccaatacgcaaaccgcctctccccgcgcgttggccgattcat taatgcagctggcacgacaggtttcccgactggaaagcgggcagtgagcgcaacgcaattaatgtgagttagctcac tcattaggcaccccaggctttacactttatgcttccggctcgtatgttgtgtggaattgtgagcggataacaatttc acacaggaaacagctatgaccatgattacgccaagcttgcatgcctgcagcccacagatggttagagaggcttacgc agcaggtctcatcaagacgatctacccgagcaataatctccaggaaatcaaataccttcccaagaaggttaaagatg cagtcaaaagattcaggactaactgcatcaagaacacagagaaagatatatttctcaagatcagaagtactattcca gtatggacgattcaaggcttgcttcacaaaccaaggcaagtaatagagattggagtctctaaaaaggtagttcccac tgaatcaaaggccatggagtcaaagattcaaatagaggacctaacagaactcgccgtaaagactggcgaacagttca tacagagtctcttacgactcaatgacaagaagaaaatcttcgtcaacatggtggagcacgacacacttgtctactcc aaaaatatcaaagatacagtctcagaagaccaaagggcaattgagacttttcaacaaagggtaatatccggaaacct cctcggattccattgcccagctatctgtcactttattgtgaagatagtggaaaaggaaggtggctcctacaaatgcc atcattgcgataaaggaaaggccatcgttgaagatgcctctgccgacagtggtcccaaagatggacccccacccacg aggagcatcgtggaaaaagaagacgttccaaccacgtcttcaaagcaagtggattgatgtgatatctccactgacgt aagggatgacgcacaatcccactatccttcgcaagacccttcctctatataaggaagttcatttcatttggagagaacacgg gggactctagaggatccCCCGGGatgccagtagtaacccgcttgattcgtttgaagtgtgtagggctcagacttgaccggagtggactcaatcggcgaat ctgtcacggaggacacggggaatcaacgcggcggagagtgatggaagagctttcaagcctaaccgtgagtcagcgcgagcaatttctggtggagaacgat gtgttcgggatctataattacttcgacgccagcgacgttctactcaaaaatacatgatggagattcagcgagataagcaattggattatctgatgaaagg ctttaaggcagcttggtccgcagttttcttccttagatgctaatcgaccttggctttgttactggattcttcattcaatagctttgcttggggagactgt ggatgatgaattagaaagcaatgccattgacttccttggacgctgccagggctctgaaggtggatacggtggtggtcctggccaacttccacatcttgca actacttatgctgcagtgaatgcacttgttactttaggaggtgacaaagccctttcttcaattaatagagaaaaaatgtcttgtttttaagacggatga aggatacaagtggaggtttcaggatgcatgatatgggagaaatggatgttcgtgcatgctacactgcaatttcggttgcaagcatcctaaatattatgga tgatgaactcacccagggcctaggagattacatcttgagttgccaaacttatgaaggtggcattggaggggaacctggctccgaagctcacggtgggtat acctactgtggtttggctgctatgattttaatcaatgaggtcgaccgtttgaatttggattcattaatgaattgggctgtacatcgacaaggagtagaaa tgggatttcaaggtaggacgaacaaattggtcgatggttgctacacattttggcaggcagccccttgtgttctactacaaagattatattcaaccaatga tcatgacgttcatggatcatcacatatatcagaagggacaaatgaagaccatcatgctcatgatgaagatgaccttgaagacagtgatgatgatgatgat tctgatgaggacaacgatgaagattcagtgaatggtcacagaatccatcatacatccacctacattaacaggagaatgcaactggtttttgatagcctcg gcttgcagagatatgtactcttgtgctctaagatccctgacggtggattcagagacaagccgaggaaaccccgtgacttctaccacacatgttactgcct gagcggcttgtctgtggctcagcacgcttggttaaaagacgaggacactcctcctttgactcgcgacattatgggtggctactcgaatctccttgaacct gttcaacttcttcacaacattgtcatggatcagtataatgaagtatcgagttcttctttaaagcagcatgaGGATCCctcgaatttccccgatcgttcaa acatttggcaataaagtttcttaagattgaatcctgttgccggtcttgcgatgattatcatataatttctgttgaattacgttaagcatgtaataattaa catgtaatgcatgacgttatttatgagatgggtttttatgattagagtcccgcaattatacatttaatacgcgatagaaaacaaaatatagcgcg caaactaggataaattatcgcgcgcggtgtcatctatgttactagatcgggaattcactggccgtcgttttacaacg tcgtgactgggaaaaccctggcgttacccaacttaatcgccttgcagcacatccccctttcgccagctggcgtaata gcgaagaggcccgcaccgatcgcccttcccaacagttgcgcagcctgaatggcgcccgctcctttcgctttcttccc ttcctttctcgccacgttcgccggctttccccgtcaagctctaaatcgggggctccctttagggttccgatttagtg ctttacggcacctcgaccccaaaaaacttgatttgggtgatggttcacgtagtgggccatcgccctgatagacggtt tttcgccctttgacgttggagtccacgttctttaatagtggactcttgttccaaactggaacaacactcaaccctat ctcgggctattcttttgatttataagggattttgccgatttcggaaccaccatcaaacaggattttcgcctgctggg -continued

```
gcaaaccagcgtggaccgcttgctgcaactctctcagggccaggcggtgaagggcaatcagctgttgcccgtctcac

tggtgaaaagaaaaaccaccccagtacattaaaaacgtccgcaatgtgttattaagttgtctaagcgtcaatttgtt

tacaccacaatatatcctgcca
```

Example 48

Cloning and Transformation of Isoprenylcysteine Carboxyl Methyltransferase

The *Arabidopsis* isoprenylcysteine carboxyl methyltransferase (ICMT) sequence was obtained by RT-PCR amplification using the protocol described above. The sequence was produced using the primer pair identified by SEQ ID NO:174 (5'-aaaggatccatgacagagatcttcagtgacacca-3') and SEQ ID NO:175 (5'-aaagagctctcagttcacaaatggaacaccaga-3'). The sequence is identical to that reported by Accession number AB007648, GI:10177821 (December 2000).

The isolated sequence was used to generate plant transformation vectors designed either to express the encoded protein or down-regulate expression. The vectors were used to transform *Arabidopsis* by the flower dipping method described elsewhere. Transformed plants were selected and propagated. Molecular and physiological analysis of the transgenic lines can be performed as detailed in other examples. Such analysis can include; molecular studies such as PCR, Southern, Northern and Western analysis; physiological analysis such as; growth studies, tolerance to environmental stress (drought, salt, heat, cold,) tolerance to biotic stress, nutritional stress, as well as biochemical analysis.

Eisenmann, D. M. and Kim, S. K. (1994). Signal transduction and cell fate specification during *Caenorhabditis elegans* vulval development. Curr. Opin. Genet. Dev. 4:508-516.

Ellington, A. (1987). Preparation and Analysis of DNA. In Current Protocols in Molecular Biology F. Ausubel et al. eds. (Boston, Greene). pp 2.0.1-2.12.5.

Goodman, L E, Perou, C M, Fujiyama, A, Tamanoi, F (1988) Yeast 4:271

Haughn, G. and Somerville C. R. (1986). Sulfonylurea-resistant mutants of *Arabidopsis thaliana*. Mol. Gen. Genet. 204:430-434.

Koornneef, M, Reuling, G and Karssen, C M (1984) The isolation and characterization of abscisic acid-insensitive mutants of *Arabidopsis thaliana*. Physiol. Plant. 61:377-383.

Leung, J, Bouvier-Durand, M, Morris, P-C, Guerrier, D, Chefdor, F, and Giraudat, J (1994) *Arabidopsis* ABA-response gene ABI1: features of a calcium-modulated protein phosphatase. Science 264:1448-1452.

Meyer, K, Leube, M P, and Grill, E (1994) A protein phosphatase 2C involved in ABA signal transduction in *Arabidopsis thaliana*. Science 264:1452-1455.

```
atgacagagatcttcagtgacaccagcatcagacagttatctcaaatgctactatcactaatcttcttccacatatccgaatacattctagccatc   SEQ ID

accattcacggagcatcaaacgtaactcttagttcgcttttaatcaccaagcattacgctttagcaatgcttctgtcgcttctcgaatacctaacg   NO:176

gagattatcctcttcccggggctgaaacaacactggtgggtcagcaactttggactcataatgatcatcgttggggaaatcatcaggaaggc

agcgataataacagcgggaagatcgttcactcacctcataaagatcaactacgaagagcatcacgggcttgtgactcatggtgtgtatagac

taatgaggcatccaagttactgcggttttctcatctggtcggtcgggacacaagttatgctctgtaaccccgtttcagcagttgcgttcgcggtt

gtcgtgtggcggtttttgctcagagaataccgtacgaggagtattttctgaatcagtttttggggtacagtatctagagtatgcagagagtgtt

gcctctggtgttccatttgtgaactga
```

REFERENCES

Baskin, J M and Baskin, C C (1971) Can J Bot 50:277.

Chandler, P M and Robertson, M (1994) Gene expression regulated by abscisic acid and its relationship to stress tolerance. Ann Rev Plant Physiol and Plant Mol Biol 45:113-141.

Chen, W-J, Anders, D A, Goldstein, J L, Russell, D W, Brown, M S (1991) Cell 66:327

Cutler, S, Ghassemian, M, Bonetta, D, Cooney, S, McCourt, P (1996) A protein farnesyl transferase involved in abscisic acid signal transduction in *Arabidopsis.* Science 273: 1239-1241.

Dellaporta, S. L., Wood, J. and Hicks, J. B. (1983). A plant DNA mini-preparation: version II. Plant Mol. Biol. Rep. 1:19-21.

Randall, S K, Marshall, M S, Crowell, D N (1993) Protein isoprenylation in suspension-cultured tobacco cells. Plant Cell 5:433-442.

Reid, J B, and Howell, S H (1995) The function of hormones in plant growth and development. In Plant Hormones Physiology, Biochemistry and Molecular Biology. 2nd ed. P. Davies ed. (Dortrecht Kluwer) pp. 448-485.

Sambrook, J., E. F. Fritsch and Maniatis, T. (1989). Molecular Cloning: A Laboratory Manual, Second edition (Cold Spring Harbor, N.Y.: Cold Spring Harbor Laboratory Press)

Schafer, W R, and Rine, J (1992) Protein Prenylation: Genes, Enzymes, Targets and Functions. Ann Rev Genet 30:209-237.

Shirley, B W, Hanley, S, Goodman, H M (1992) Plant Cell 4: 333

Verwoerd, T. C., Dekker, B. M. M. and Hoekema, A. (1989). A small-scale procedure for the rapid isolation of plant RNA's. Nucleic Acids Research 17:2362.

Yang, Z, Cramer, C L, and Watson, J C (1993) Protein farnesyl transferase in plants. Plant Physiology 101:667-674.

All citations in this application to materials and methods are hereby incorporated by reference.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of producing a drought tolerant plant comprising:

a) providing a nucleic acid construct comprising a promoter operably linked to a nucleic acid that inhibits farnesyltransferase beta activity;

b) inserting said nucleic construct into a vector;

c) transforming a plant, tissue culture, or a plant cell with the vector to obtain a plant, tissue culture or a plant cell with decreased farnesyltransferase beta activity;

d) growing said plant or regenerating a plant from said tissue culture or plant cell, wherein a drought tolerant plant is produced.

2. The method of claim 1, wherein said promoter is a constitutive promoter, an ABA inducible promoter, a tissue specific promoter or a guard cell specific promoter.

3. A drought tolerant transgenic plant produced by the method claim 1 or 2.

4. A transgenic seed produced by the transgenic plant of claim 3, wherein said seed produces a drought tolerant plant.

* * * * *